US007365174B2

(12) United States Patent
Miura et al.

(10) Patent No.: US 7,365,174 B2
(45) Date of Patent: Apr. 29, 2008

(54) AZALIDE AND AZALACTAM DERIVATIVES AND METHOD FOR PRODUCING THE SAME

(75) Inventors: Tomoaki Miura, Kanagawa (JP); Kenichi Kanemoto, Kanagawa (JP); Satomi Natsume, Tokyo (JP); Naoto Ohkura, Tokyo (JP); Yumiko Fujihira, Kanagawa (JP); Takashi Watanabe, Kanagawa (JP); Hideki Fushimi, Kanagawa (JP); Kunio Atsumi, Tokyo (JP); Keiichi Ajito, Kanagawa (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 10/569,063

(22) PCT Filed: Aug. 20, 2004

(86) PCT No.: PCT/JP2004/012323

§ 371 (c)(1), (2), (4) Date: Sep. 28, 2006

(87) PCT Pub. No.: WO2005/019238

PCT Pub. Date: Mar. 3, 2005

(65) Prior Publication Data

US 2007/0042974 A1 Feb. 22, 2007

(30) Foreign Application Priority Data

Aug. 22, 2003 (JP) ............................ 2003-208407

(51) Int. Cl.
*C07H 17/08* (2006.01)

(52) U.S. Cl. ....................... 536/7.1; 536/7.4; 536/18.2; 536/123.13; 536/4.1

(58) Field of Classification Search ................ 536/7.4, 536/7.1
See application file for complete search history.

(56) References Cited

U.S. PATENT DOCUMENTS

| | | | |
|---|---|---|---|
| 4,328,334 | A | 5/1982 | Kobrehel et al. |
| 4,474,768 | A | 10/1984 | Bright |
| 4,517,359 | A | 5/1985 | Kobrehel et al. |
| 5,332,807 | A | 7/1994 | Waddell et al. |
| 2006/0014742 | A1 | 1/2006 | Asaki et al. |

FOREIGN PATENT DOCUMENTS

| | | |
|---|---|---|
| EP | 0515141 | 5/1992 |
| EP | 0410433 | 2/1996 |
| EP | 0735041 | 10/1996 |
| JP | 57-088193 | 6/1982 |
| JP | 5-208990 | 8/1993 |
| JP | 8-269078 | 10/1996 |
| JP | 2003-502338 | 1/2003 |
| WO | 94/15617 | 7/1994 |
| WO | 99/36419 | 7/1999 |
| WO | 00/77016 | 12/2000 |
| WO | 01/38326 | 5/2001 |
| WO | 02/38568 | 5/2002 |
| WO | 02/064607 | 8/2002 |
| WO | 03/014136 | 2/2003 |
| WO | 2004/002963 | 1/2004 |

OTHER PUBLICATIONS

Marshall et al. "Synthesis of a C22-34 Subunit of the Immunosuppressant FK-506", Journal of Organic Chemistry, 1995, vol. 60, pp. 7230-7237.

(Continued)

*Primary Examiner*—Elli Peselev
(74) *Attorney, Agent, or Firm*—Greenblum & Bernstein, P.L.C.

(57) ABSTRACT

Compounds represented by the general formula (1) or pharmaceutically acceptable salts thereof, effective in the prevention and/or treatment of infections with microbes: (1) (a) wherein $R_1$ is hydrogen or straight-chain $C_{1-6}$ alkylcarbonyl; $R_2$ is hydrogen or $C_{1-6}$ alkylcarbonyl; $R_3$ is hydrogen, $C_{1-6}$ alkyl, $C_{1-6}$ alkylcarbonyl, $C_{1-6}$ alkenyl, $C_{2-6}$ alkenylcarbonyl, $C_{2-6}$ alkynyl, or an Ar—B— group (wherein Ar is aryl or a heterocyclic group; and B is $C_{1-6}$ alkyl, $C_{1-6}$ alkylcarbonyl, $C_{2-6}$ alkenyl, $C_{2-6}$ alkenylcarbonyl, or $C_{2-6}$ alkynyl); $R_5$, $R_6$, $R_7$ and $R_8$ are each hydrogen, $C_{1-6}$ alkyl, $C_{2-6}$ alkenyl, $C_{2-6}$ alkynyl, or an Ar—B'— group (wherein B' is $C_{1-6}$ alkyl, $C_{2-6}$ alkenyl, or $C_{2-6}$ alkynyl); X is oxygen or —$NR_4$— (wherein $R_4$ is hydrogen, $C_{1-6}$ alkyl or $C_{1-6}$ alkyl which may be substituted with Ar); and $R_{4'}$ is hydrogen or a group represented by the general formula (a) (wherein $R_{3''}$ and $R_{4''}$ are each hydrogen or straight-chain or branched $C_{1-6}$ alkylcarbonyl)

(1)

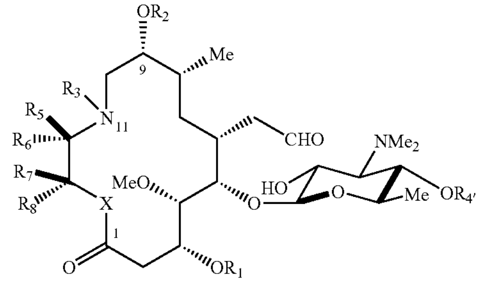

(a)

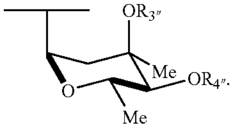

41 Claims, No Drawings

OTHER PUBLICATIONS

Shiina et al. "A Novel and Efficient Macrolactonization of ω-Hydroxycarboxylic Acids Using 2-Methyl-6-nitrobenzoic Anhydride (MNBA)", Tetrahedron Letters, 2002, vol. 43, pp. 7535-7539.
Djokić et al., "Erythromycin Series. Part 11. Ring Expansion of Erythromycin A Oxime by the Beckmann Rearrangement," Journal of the Chemical Society-Perkin Transactions I, pp. 1881-1890 (1986).
Bright et al., "Synthesis, In Vitro and In Vivo Activity of Novel 9-Deoxo-9a-Aza-9a-Homeorythromycin A Derivatives; A New Class of Macrolide Antibiotics, The Azalides," The Journal of Antibiotics, vol. 41, No. 8, pp. 1029-1047 (1988).
Sakakibara et al., "Acyl Derivatives of 16-Membered Macrolides," The Journal of Antibiotics, vol. 34, No. 8, pp. 1001-1010 (1981).
Sakakibara et al., "Acyl Derivatives of 16-Membered Macrolides," The Journal of Antibiotics, vol. 34, No. 8, pp. 1011-1018 (1981).
Omoto et al., "Modifications of a Macrolide Antibiotic Midecamycin (SF-837)," The Journal of Antibiotics, vol. 29, No. 5, pp. 536-548 (1976).
Kawaharajo et al., "In Vitro and In Vivo Antibacterial Activity of 9,3"-Di-*0*-Acetyl Midecamycin (MOM), A New Macrolide Antibiotic," The Journal of Antibiotics, vol. 34, No. 4, pp. 436-442 (1981).
Cabri et al., "Recent Developments and New Perspectives in the Heck Reaction," Accounts of Chemical Research, vol. 28, No. 1, pp. 2-7 (1995).
Littke et al., "A Versatile Catalyst for Heck Reactions of Aryl Chlorides and Aryl Bromides under Mild Conditions," Journal of the American Chemical Society, vol. 123, No. 29, pp. 6989-7000 (2001).
Chatterjee et al., "A General Model for Selectivity in Olefin Cross Metathesis," Journal of the American Chemical Society, vol. 125, No. 37, pp. 11360-11370 (2003).
Chatterjee et al., "Synthesis of Trisubstituted Alkenes via Olefin Cross-Metathesis," Organic Letters, vol. 1, No. 11, pp. 1751-1753 (1999).
Sonogashira et al., "A Convenient Synthesis of Acetylenes: Catalytic Substitutions of Acetylenic Hydrogen with Bromoalkenes, Iodoarenes, and Bromopyridines," Tetrahedron Letters, vol. 16, No. 50, pp. 4467-4470 (1975).
Takahashi et al., "A Convenient Synthesis of Ethynylarenes and Diethynylarenes," Synthesis, pp. 627-630 (1980).
Soheili et al., "Efficient and General Protocol for the Copper-Free Sonogashira Coupling of Aryl Bromides at Room Temperature," Organic Letters, vol. 5, No. 22, pp. 4191-4194 (2003).
Ohshiro et al., "Synthesis of Optical Active Proline," Yakugaku Zasshi, vol. 87, No. 10, pp. 1184-1188 (1967).
Zymalkowski et al., "Zur Chemie des Chinolin-carbaldehyds-(3)," Justus Liebigs Annalen der Chemie, vol. 699, pp. 98-106 (1966).
Hamada et al., "Syntheses of Nitrogen-containing Heterocyclic Compounds. XXI. Syntheses of Naphthyridines by Improved One-Step Process," Yakugaku Zasshi, vol. 94, No. 10, pp. 1328-1334 (1974).
Choi-Sledeski et al., "Sulfonamidopyrrolidinone Factor Xa Inhibitors: Potency and Selectivity Enhancements via P-1 and P-4 Optimization," Journal of the Medicinal Chemistry, vol. 42, No. 18, pp. 3572-3587 (1999).
Karig et al., "Synthesis and Nicotinic Binding of Novel Phenyl Derivatives of UB-165. Identifying Factors Associated with α7 Selectivity," Bioorganic & Medical Chemistry Letters, vol. 13, pp. 2825-2828 (2003).
Karig et al., "C-H Activation and Palladium Migration within Biaryls under Heck Reaction Conditions," Organic Letters, vol. 4, No. 18, pp. 3115-3118 (2002).
Goto et al., "Revision of Minimum Inhibitory Concentration (MIC) Measurement Law," Chemotherapy, vol. 29, No. 1, pp. 76-79 (1981).

AZALIDE AND AZALACTAM DERIVATIVES AND METHOD FOR PRODUCING THE SAME

RELATED APPLICATIONS

The present application is a National Stage of PCT/JP2004/12323, filed Aug. 20, 2004, and which claims priority of Japanese Application No. 2003-208407, filed Aug. 22, 2003.

1. Technical Field

The present invention relates to novel 14- to 16-membered ring azalide derivatives and azalactam derivatives effective against gram positive and gram negative bacteria. The present invention also relates to synthetic intermediates for preparation thereof and method for producing the same.

2. Background Art

Macrolide antibiotics generally have low toxicity and can be orally administered, and therefore they are a class of clinically important antibacterial agents in the filed of therapeutic treatment of bacterial infectious diseases. Macrolide antibiotics are roughly classified into 14-membered ring macrolides and 16-membered ring macrolides according to the number of ring-constituting atoms in the lactone ring moiety which is an aglycone (non-saccharide moiety). As a chemically modified antibacterial agent, azithromycin as a commercially available 15-membered ring macrolide is known (U.S. Pat. Nos. 4,474,768 and 4,517,359), in which a nitrogen atom is introduced into the lactone ring. For azithromycin, the ketone in the 9-position of erythromycin, a 14-membered ring macrolide, is converted into an oxime, and then an imino ether obtained by the Beckmann rearrangement is reduced to introduce the nitrogen atom (J. Chem. Soc. Perkin Trans. I, 1881, 1986; J. Antibiotics, 41, 1029, 1988). The macrolide derivatives containing a nitrogen atom as a ring-constituting atom of the lactone ring are presently known as azalides. The aforementioned azithromycin has characteristic kinetics in vivo as compared to those of the other macrolides, and has a feature of being effective to some gram negative bacteria.

Other than azithromycin, some reports about compounds having the azalide structure are known. However, as positions of a nitrogen atom present in the lactone ring, only three kinds of positions are known. Specifically, only azalides in which a nitrogen atom is present at the 9th, 10th or 12th position counted counterclockwise from the 1-carbonyl group of the lactone have been reported.

As azalides derived from 16-membered ring macrolides, 8-aza-8a-homotylosin derivatives and 9a-aza-9a-homotylosin derivatives have been reported, which are synthesized from 9-ketoxime derivatives of tylosins by using a ring expanding reaction based on the Beckmann rearrangement in a similar manner to the preparation of azithromycin (European Patent Nos. 410433 and 410433). These derivatives are 17-membered ring azalides, in which a nitrogen atom is present at the 9th or 10th position relative to the carbonyl group of the lactone at the 1-position, as in the aforementioned azalides derived from 14-membered ring macrolides.

However, no azalide or azalactam derived from a 16-membered ring macrolide has been reported which is obtained by a method other than the Beckmann rearrangement.

Among 16-membered ring macrolides, those having been clinically used so far are only leucomycin antibiotics including derivatives thereof. As for the leucomycin antibiotics, many groups including the Kitasato Institute, Toyo Jozo Co., Ltd. (at that time) and the applicant's firm have conducted researches for improvement of efficacy thereof, and rokitamycin (J. Antibiotics, 34, 1001, 1981; J. Antibiotics, 34, 1011, 1981), miokamycin (J. Antibiotics, 29, 536, 1976, J. Antibiotics, 34, 436, 1981) and the like have been launched in the market.

DISCLOSURE OF THE INVENTION

Conventional leucomycin 16-membered ring macrolides are effective mainly against gram positive bacteria. However, their antibacterial activity against gram negative bacteria remain unimproved, and developments of macrolides effective against gram negative bacteria are desired.

The macrolide antibiotics are useful in the treatment of bacterial infectious diseases in mammals including human, and examples include the aforementioned azithromycin, rokitamycin, miokamycin, and the like.

Azithromycin as explained in detail above was found on the basis of the new structural conversion using erythromycin as a starting material. Therefore, a novel structural conversion by using a 16-membered ring macrolide as a starting material has been desired.

As for the azalides, methods are reported in which an amine is generated by a ring opening reaction of the erythromycin structure, and then a 13- to 15-membered ring azalide is prepared via a coupling of the amine with an appropriate aldehyde and successive re-cyclization reaction, or the oxygen atom of the lactone moiety as the aglycone is converted to a nitrogen atom to prepare a 13- to 15-membered ring azalactam into which two nitrogen atoms are introduced into the ring (International Patent Publication WO94/15617). A method is also reported in which an aldehyde is generated by an oxidative cleavage reaction of the erythromycin structure, and the resultant is subjected to a coupling with an appropriate amine and then re-cyclization to prepare an azalide or azalactam (International Patent Publication WO03/014136).

However, no azalide or azalactam derived from a leucomycin 16-membered ring macrolide has been reported. Further, no report is made about a method of constructing the azalide fundamental structure using a leucomycin 16-membered ring macrolide as a starting material by first carrying out ring opening of the aglycone using the conjugated double bond at the 10- to 13-positions as a target of the reaction and then carrying out re-cyclization.

As for the tylosin class of 16-membered ring macrolides, a report about 17-membered ring azalides is made as described above. The leucomycin 16-membered ring macrolides have been generally used as medicaments for humans. However, tylosins are used only as animal drugs.

Therefore, the inventors of the present invention conducted various researches on novel azalide and azalactam derivatives having a nitrogen atom in the lactone ring which are derived from leucomycin 16-membered ring macrolides.

The inventors of the present invention used leucomycin macrolides as starting materials, placing the focus on the conjugated double bond at the 10- to 13-positions of the lactone ring thereof, to prepare novel dialdehyde intermediates by oxidative cleavage of the double bond, which had not been reported before the time, and converted the dialdehyde intermediates into aldehyde-carboxylic acid intermediates. Further, they successfully constructed the azalide and azalactam fundamental structures by a reductive coupling reaction using amines, and a subsequent re-cyclization reaction. They also successfully provided novel 14- to 16-membered ring azalide and azalactam derivatives by applying the aforementioned technique, in which various side chains were introduced on the ring-constituting atoms newly introduced into the aglycone, i.e., on the 11-nitrogen atom or oxygen atom or the other nitrogen atom.

As a result, they found that these compounds had a superior antibacterial activity compared with the leucomycin analogues as the starting materials, and thus achieved the present invention.

The compounds provided by the present invention have a nitrogen atom at the 11th position counted counterclockwise from the 1-carbonyl group of the lactone ring, which azalides have not yet been reported so far.

The present invention thus provides:

(1) A compound represented by the following general formula (1) or a pharmaceutically acceptable salt thereof:

(1)

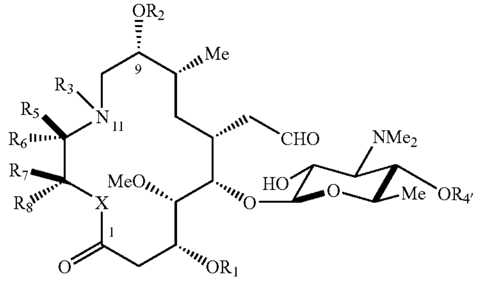

[wherein:

$R_1$ represents hydrogen atom, or a linear C1-6 alkylcarbonyl group, $R_2$ represents hydrogen atom, or a C1-6 alkylcarbonyl group, $R_3$ represents hydrogen atom, a C1-6 alkyl group, a C1-6 alkylcarbonyl group, a C1-6 alkenyl group, a C2-6 alkenylcarbonyl group, a C2-6 alkynyl group, or an Ar—B— group (wherein Ar represents an aryl group, or a heterocyclic group, and B represents a C1-6 alkyl group, a C1-6 alkylcarbonyl group, a C2-6 alkenyl group, a C2-6 alkenylcarbonyl group, or a C2-6 alkynyl group), $R_5$, $R_6$, $R_7$, and $R_8$ may be the same or different, and represent hydrogen atom, a C1-6 alkyl group, a C2-6 alkenyl group, a C2-6 alkynyl group, or an Ar—B'— group (wherein Ar has the same meaning as that defined above, and B' represents a C1-6 alkyl group, a C2-6 alkenyl group, or a C2-6 alkynyl group), X represents oxygen atom, or an —$NR_4$— group (wherein $R_4$ represents hydrogen atom, a C1-6 alkyl group, or a C1-6 alkyl group which may be substituted with an Ar group (wherein Ar has the same meaning as that defined above)), and $R_{4'}$ represents hydrogen atom, or a group represented by the following formula (a):

(a)

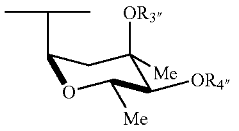

(wherein $R_{3''}$ and $R_{4''}$ may be the same or different, and represent hydrogen atom, or a linear or branched C1-6 alkylcarbonyl group)].

According to preferred embodiments of the present invention, the following inventions are provided:

(2) The compound or a pharmaceutically acceptable salt thereof according to (1), wherein $R_3$ represents a C1-6 alkyl group, a C2-6 alkenyl group, or an Ar—B— group (wherein Ar represents an aryl group, or a heterocyclic group, and B represents a C1-6 alkyl group, a C1-6 alkylcarbonyl group, a C2-6 alkenyl group, or a C2-6 alkenylcarbonyl group);

(3) The compound or a pharmaceutically acceptable salt thereof according to (1), wherein $R_1$ is a linear C1-6 alkylcarbonyl group, $R_2$ is a C1-6 alkylcarbonyl group, $R_3$ is a C1-6 alkyl group, a C2-6 alkenyl group, or an Ar—B— group (wherein Ar represents an aryl group, or a heterocyclic group, and B represents a C1-6 alkyl group, a C1-6 alkylcarbonyl group, a C2-6 alkenyl group, or a C2-6 alkenylcarbonyl group), $R_5$ and $R_6$ are hydrogen atoms, one of $R_7$ and $R_8$ is hydrogen atom, the other is hydrogen atom, a C1-6 alkyl group, a C2-6 alkenyl group, a C2-6 alkynyl group, or an Ar—B'— group (wherein Ar has the same meaning as that defined above, and B' represents a C1-6 alkyl group, a C2-6 alkenyl group, or a C2-6 alkynyl group), X is oxygen atom, or an —$NR_4$— group (wherein $R_4$ represents hydrogen atom, a C1-6 alkyl group, or a C1-6 alkyl group which may be substituted with an Ar group (wherein Ar has the same meaning as that defined above)), and $R_{4'}$ is a group represented by the following formula (a)

(a)

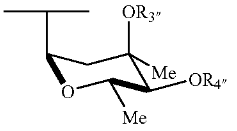

(wherein $R_{3''}$ and $R_{4''}$ may be the same or different, and represent hydrogen atom, or a linear or branched C1-6 alkylcarbonyl group);

(4) The compound or a pharmaceutically acceptable salt thereof according to (1), wherein $R_3$ is methyl group, or 4-phenylbutyl group:

(5) The compound or a pharmaceutically acceptable salt thereof according to (1), wherein $R_7$ and $R_8$ may be the same or different, and represent hydrogen atom, or methyl group;

(6) The compound or a pharmaceutically acceptable salt thereof according to (1), wherein X is an —$NR_4$— group, and $R_4$ is hydrogen atom, methyl group, or 4-phenylbutyl group;

(7) The compound or a pharmaceutically acceptable salt thereof according to any one of (1) to (5), wherein X is oxygen atom; and (8) The compound or a pharmaceutically acceptable salt thereof according to (1), wherein $R_3$ is methyl group, or 4-phenylbutyl group, $R_7$ and $R_8$ represent hydrogen atom, or methyl group, X is oxygen atom, or an —$NR_4$— group, and $R_4$ is hydrogen atom, methyl group, or 4-phenylbutyl group.

From another aspect, the present invention provides:

(9) A compound represented by the following general formula (2) or a pharmaceutically acceptable salt thereof:

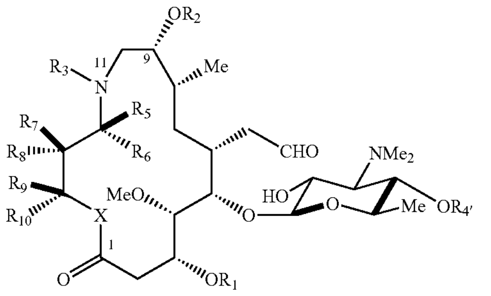

(2)

[wherein:

$R_1$ represents hydrogen atom, or a linear C1-6 alkylcarbonyl group, $R_2$ represents hydrogen atom, or a C1-6 alkylcarbonyl group, $R_3$ represents hydrogen atom, a C1-6 alkyl group, a C1-6 alkylcarbonyl group, a C2-6 alkenyl group, a C2-6 alkenylcarbonyl group, a C2-6 alkynyl group, or an Ar—B— group (wherein Ar represents an aryl group, or a heterocyclic group, and B represents a C1-6 alkyl group, a C1-6 alkylcarbonyl group, a C2-6 alkenyl group, a C2-6 alkenylcarbonyl group, or a C2-6 alkynyl group), $R_5$, $R_6$, $R_9$ and $R_{10}$ may be the same or different, and represent hydrogen atom, a C1-6 alkyl group, a C2-6 alkenyl group, a C2-6 alkynyl group, or an Ar—B'— group (wherein Ar has the same meaning as that defined above, and B' represents a C1-6 alkyl group, a C2-6 alkenyl group, or a C2-6 alkynyl group), $R_7$ and $R_8$ may be the same or different, and represent hydrogen atom, hydroxyl group, a C1-6 alkyl group, a C2-6 alkenyl group, a C2-6 alkynyl group, or an Ar—B'— group (wherein Ar has the same meaning as that defined above, and B' represents a C1-6 alkyl group, a C2-6 alkenyl group, or a C2-6 alkynyl group), X represents oxygen atom, or an —$NR_4$— group (wherein $R_4$ represents hydrogen atom, a C1-6 alkyl group, or an Ar—B"— group (wherein Ar has the same meaning as that defined above, and B" represents a C1-6 alkyl group)), and $R_{4'}$ represents hydrogen atom, or a group represented by the following formula (a)

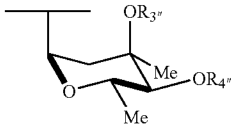

(a)

(wherein $R_{3''}$ and $R_{4''}$ may be the same or different, and represent hydrogen atom, or a linear or branched C1-6 alkylcarbonyl group), provided that a compound wherein X is oxygen atom, $R_5$, $R_6$, $R_7$, $R_8$ and $R_9$ are hydrogen atoms, and $R_{10}$ is methyl group is excluded].

According to preferred embodiments of the aforementioned invention, the following inventions are provided:

(10) The compound or a pharmaceutically acceptable salt thereof according to (9), wherein $R_3$ is a C1-6 alkyl group, a C2-6 alkenyl group, or an Ar—B— group (wherein Ar represents an aryl group, or a heterocyclic group, and B represents a C1-6 alkyl group, or a C2-6 alkenyl group), and $R_5$, $R_6$, $R_7$, $R_8$, $R_9$, and $R_{10}$ may be the same or different, and represent hydrogen atom, a C1-6 alkyl group, a C2-6 alkenyl group, or an Ar—B'— group (wherein Ar has the same meaning as that defined above, and B' represents a C1-6 alkyl group, or a C2-6 alkenyl group);

(11) The compound or a pharmaceutically acceptable salt thereof according to (9), wherein $R_3$ is a C1-6 alkyl group, a C2-6 alkenyl group, or an Ar—B— group (wherein Ar represents an aryl group, or a heterocyclic group, and B represents a C1-6 alkyl group, or a C2-6 alkenyl group), $R_5$, $R_6$, $R_7$, and $R_8$ are hydrogen atoms, one of $R_9$ and $R_{10}$ is hydrogen atom, and the other is hydrogen atom, a C1-6 alkyl group, a C2-6 alkenyl group, or an Ar—B'— group (wherein Ar has the same meaning as that defined above, and B' represents a C1-6 alkyl group, or a C2-6 alkenyl group);

(12) The compound or a pharmaceutically acceptable salt thereof according to (9), wherein $R_1$ is a linear C1-6 alkylcarbonyl group, $R_2$ is hydrogen atom, and $R_{3''}$ and $R_{4''}$ may be the same or different, and represent a linear or branched C1-6 alkylcarbonyl group;

(13) The compound or a pharmaceutically acceptable salt thereof according to (9), wherein $R_1$ is a linear C1-6 alkylcarbonyl group, $R_2$ is hydrogen atom, $R_3$ is hydrogen atom, and $R_{4''}$ is a linear or branched C1-6 alkylcarbonyl group;

(14) The compound or a pharmaceutically acceptable salt thereof according to (9), wherein $R_1$, $R_2$, and $R_{3''}$ are hydrogen atoms, and $R_{4''}$ is hydrogen atom, or a linear or branched C1-6 alkylcarbonyl group;

(15) The compound or a pharmaceutically acceptable salt thereof according to (9), wherein $R_{4'}$ is hydrogen atom;

(16) The compound or a pharmaceutically acceptable salt thereof according to (9), wherein X is —NH— group;

(17) The compound or a pharmaceutically acceptable salt thereof according to (9), wherein X is oxygen atom;

(18) The compound or a pharmaceutically acceptable salt thereof according to (9), wherein $R_3$ is methyl group, 4-phenylbutyl group, or 3-(quinolin-4-yl)propyl group;

(19) The compound or a pharmaceutically acceptable salt thereof according to (9), wherein one of $R_9$ and $R_{10}$ is hydrogen atom, and the other is hydrogen atom, methyl group, 3-(quinolin-4-yl)propyl group, trans-3-(quinolin-4-yl)-2-propenyl group, trans-3-(quinolin-4-yl)-1-propenyl group, 3-(quinolin-3-yl)propyl group, or trans-3-(quinolin-3-yl)-2-propenyl group; and

(20) The compound or a pharmaceutically acceptable salt thereof according to (9), wherein $R_3$ is methyl group, 4-phenylbutyl group, or 3-(quinolin-4-yl)propyl group, $R_5$, $R_6$, $R_7$, and $R_8$ are hydrogen atoms, one of $R_9$ and $R_{10}$ is hydrogen atom, the other is hydrogen atom, methyl group, 3-(quinolin-4-yl)propyl group, trans-3-(quinolin-4-yl)-2-propenyl group, trans-3-(quinolin-4-yl)-1-propenyl group, 3-(quinolin-3-yl)propyl group, or trans-3-(quinolin-3-yl)-2-propenyl group, and X is oxygen atom, or —NH— group.

From another aspect, the present invention provides:

(21) A compound represented by the following general formula (3) or a pharmaceutically acceptable salt thereof:

(3)

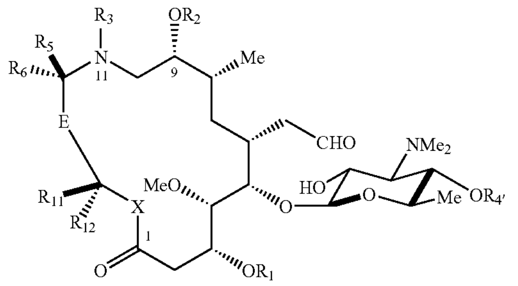

[wherein:

$R_1$ represents hydrogen atom, or a linear C1-6 alkylcarbonyl group, $R_2$ represents hydrogen atom, or acetyl group, $R_3$ represents hydrogen atom, a C1-6 alkyl group, a C1-6 alkylcarbonyl group, a C2-6 alkenyl group, a C2-6 alkenylcarbonyl group, a C2-6 alkynyl group, or an Ar—B— group (wherein Ar represents an aryl group, or a heterocyclic group, and B represents a C1-6 alkyl group, a C1-6 alkylcarbonyl group, a C2-6 alkenyl group, a C2-6 alkenylcarbonyl group, or a C2-6 alkynyl group), when E is a group represented by the following formula (b), (b)

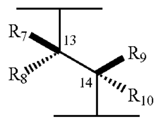

one of $R_5$, $R_6$, $R_7$, $R_8$, $R_5$, $R_{10}$, $R_{11}$ and $R_{12}$ represents hydrogen atom, a C1-6 alkyl group, a C2-6 alkenyl group, a C2-6 alkynyl group, or an Ar—B'— group (wherein Ar has the same meaning as that defined above, and B' represents a C1-6 alkyl group, a C2-6 alkenyl group, or a C2-6 alkynyl group), another represents hydrogen atom, hydroxyl group, or a C1-6 alkyl group, and all the remaining groups represent hydrogen atom, when E is a group represented by the following formula (c), (c)

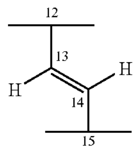

one of $R_5$, $R_6$, $R_{11}$ and $R_{12}$ represents hydrogen atom, a C1-6 alkyl group, a C2-6 alkenyl group, a C2-6 alkynyl group, or an Ar—B'— group (wherein Ar has the same meaning as that defined above, and B' represents a C1-6 alkyl group, a C2-6 alkenyl group, or a C2-6 alkynyl group), another represents hydrogen atom, or a C1-6 alkyl group, and all the remaining groups represent hydrogen atom, X represents oxygen atom, or an —$NR_4$— group (wherein $R_4$ represents hydrogen atom, a C1-6 alkyl group, or Ar—B"— group (wherein Ar has the same meaning as that defined above, and B" represents a C1-6 alkyl group)), and $R_{4'}$ represents hydrogen atom, or a group represented by the following formula (a)

(a)

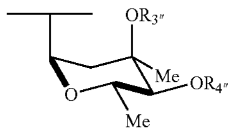

(wherein $R_{3''}$ and $R_{4''}$ may be the same or different, and represent hydrogen atom, or a linear or branched C1-6 alkylcarbonyl group)].

According to preferred embodiments of the aforementioned invention, the following inventions are provided:

(22) The compound or a pharmaceutically acceptable salt thereof according to (21), wherein $R_3$ is a C1-6 alkyl group, a C2-6 alkenyl group, or an Ar—B— group (wherein Ar represents an aryl group, or a heterocyclic group, and B represents a C1-6 alkyl group, or a C2-6 alkenyl group), when E is a group represented by the following formula (b), (b)

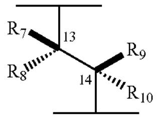

one of $R_5$, $R_6$, $R_7$, $R_8$, $R_9$, $R_{10}$, $R_{11}$ and $R_{12}$ is hydrogen atom, a C1-6 alkyl group, a C2-6 alkenyl group, or an Ar—B'— group (wherein Ar has the same meaning as that defined above, and B' represents a C1-6 alkyl group, a C2-6 alkenyl group, or a C2-6 alkynyl group), another is hydrogen atom, or a C1-6 alkyl group, and all the remaining groups are hydrogen atoms, and when E is a group represented by the following formula (c), (c)

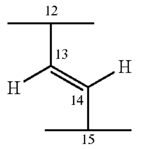

one of $R_5$, $R_6$, $R_{11}$ and $R_{12}$ is hydrogen atom, a C1-6 alkyl group, a C2-6 alkenyl group, or an Ar—B'— group (wherein Ar has the same meaning as that defined above, and B' represents a C1-6 alkyl group, or a C2-6 alkenyl group), another is hydrogen atom, or a C1-6 alkyl group, and all the remaining groups are hydrogen atoms;

(23) The compound or a pharmaceutically acceptable salt thereof according to (21), wherein E is a group represented by the following formula (b),

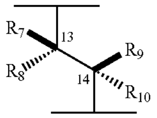

(b)

$R_5$, $R_6$, $R_9$, $R_{10}$, $R_{11}$ and $R_{12}$ are hydrogen atoms, one of $R_7$ and $R_8$ represents hydrogen atom, a C1-6 alkyl group, a C2-6 alkenyl group, or an Ar—B'— group (wherein Ar has the same meaning as that defined above, and B' represents a C1-6 alkyl group, or a C2-6 alkenyl group), and all the remaining groups are hydrogen atom;

(24) The compound or a pharmaceutically acceptable salt thereof according to (21), wherein E is a group represented by the following formula (b),

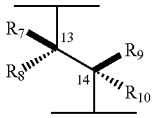

(b)

$R_5$, $R_6$, $R_7$, $R_8$, $R_9$ and $R_{10}$ are hydrogen atoms, one of $R_{11}$ and $R_{12}$ is hydrogen atom, a C1-6 alkyl group, a C2-6 alkenyl group, or an Ar—B'— group (wherein Ar has the same meaning as that defined above, and B' represents a C1-6 alkyl group, a C2-6 alkenyl group, or a C2-6 alkynyl group), and the other is hydrogen atom;

(25) The compound or a pharmaceutically acceptable salt thereof according to (21), wherein E is a group represented by the following formula (c),

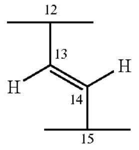

(c)

$R_5$ and $R_6$ are hydrogen atoms, one of $R_{11}$ and $R_{12}$ is hydrogen atom, a C1-6 alkyl group, a C2-6 alkenyl group, or an Ar—B'— group (wherein Ar has the same meaning as that defined above, and B' represents a C1-6 alkyl group, or a C2-6 alkenyl group), and the other is hydrogen atom;

(26) The compound or a pharmaceutically acceptable salt thereof according to (21), wherein $R_1$ is a linear C1-6 alkylcarbonyl group, $R_2$ is hydrogen atom, or acetyl group, and $R_{3''}$ and $R_{4''}$ may be the same or different, and represent a linear or branched C1-6 alkylcarbonyl group;

(27) The compound or a pharmaceutically acceptable salt thereof according to (21), wherein $R_1$ is a linear C1-6 alkylcarbonyl group, $R_2$ is hydrogen atom, or acetyl group, $R_{3''}$ is hydrogen atom, and $R_{4''}$ is a linear or branched C1-6 alkylcarbonyl group;

(28) The compound or a pharmaceutically acceptable salt thereof according to (21), wherein $R_1$, $R_2$ and $R_{3''}$ are hydrogen atoms, and $R_{4''}$ is hydrogen atom, or a linear or branched C1-6 alkylcarbonyl group;

(29) The compound or a pharmaceutically acceptable salt thereof according to (21), wherein $R_1$ is hydrogen atom, $R_2$ is hydrogen atom, or acetyl group, and $R_{3''}$ and $R_{4''}$ may be the same or different, and represent hydrogen atom, or a linear or branched C1-6 alkylcarbonyl group;

(30) The compound or a pharmaceutically acceptable salt thereof according to (21), wherein $R_{4'}$ is hydrogen atom;

(31) The compound or a pharmaceutically acceptable salt thereof according to (21), wherein X is —NH— group;

(32) The compound or a pharmaceutically acceptable salt thereof according to (21), wherein X is oxygen atom;

(33) The compound or a pharmaceutically acceptable salt thereof according to (21), wherein $R_3$ is methyl group, 4-phenylbutyl group, or 3-(quinolin-4-yl)propyl group;

(34) The compound or a pharmaceutically acceptable salt thereof according to (21), wherein one of $R_7$ and $R_8$ is hydrogen atom, and the other is hydrogen atom, 3-(quinolin-4-yl)propyl group, trans-3-(quinolin-4-yl)-1-propenyl group, cis-3-(quinolin-4-yl)-1-propenyl group, 3-(1-methyl-1,2,3,4-tetrahydroquinolin-4-yl)propyl group, trans-3-(quinolin-3-yl)-1-propenyl group, cis-3-(quinolin-3-yl)-1-propenyl group, trans-3-(quinolin-6-yl)-1-propenyl group, trans-3-(quinolin-8-yl)-1-propenyl group, trans-3-(isoquinolin-4-yl)-1-propenyl group, trans-3-(naphthalen-2-yl)-2-propenyl group, or 5-(quinolin-3-yl)pentyl group;

(35) The compound or a pharmaceutically acceptable salt thereof according to (21), wherein one of $R_{11}$ and $R_{12}$ is hydrogen atom, and the other is hydrogen atom, methyl group, 2-propenyl group, 3-(quinolin-4-yl)propyl group, trans-3-(quinolin-4-yl)-2-propenyl group, 3-(quinolin-3-yl)propyl group, trans-3-(quinolin-3-yl)-2-propenyl group, trans-3-(quinolin-6-yl)-2-propenyl group, trans-3-(pyridin-3-yl)-2-propenyl group, trans-3-(naphthalen-2-yl)-2-propenyl group, trans-3-phenyl-2-propenyl group, trans-3-(naphthalen-1-yl)-2-propenyl group, trans-3-(2-fluoro-4-((R)-5-(hydroxymethyl)oxazolidin-2-on-3-yl)phenyl)-2-propenyl group, trans-3-(6-nitroquinolin-3-yl)-2-propenyl group, trans-3-(6-cyanoquinolin-3-yl)-2-propenyl group, trans-3-(1,8-naphthyridin-3-yl)-2-propenyl group, trans-3-(phenanthren-9-yl)-2-propenyl group, trans-3-(benzothiophen-3-yl)-2-propenyl group, trans-3-(benzo[c][[1,2,5]oxadiazol-5-yl)-2-propenyl group, trans-3-(4-(1H-pyrazol-1-yl)phenyl)-2-propenyl group, trans-3-(2-fluoro-4-(1H-tetrazol-1-yl)phenyl)-2-propenyl group, trans-3-(4-(isoxazol-5-yl)phenyl)-2-propenyl group, trans-3-(4-(pyridin-3-yl)phenyl)-2-propenyl group, trans-3-(4-(pyridin-4-yl)phenyl)-2-propenyl group, trans-3-(4-(pyridin-2-yl)phenyl)-2-propenyl group, trans-3-(4-fluoro-3-(1H-pyrazol-1-yl)phenyl)-2-propenyl group, trans-3-(3-(2-methylthiazol-4-yl)phenyl)-2-propenyl group, trans-3-(3-biphenyl)-2-propenyl group, trans-3-(3-(pyridin-3-yl)phenyl)-2-propenyl group, trans-3-(3-(pyridin-4-yl)phenyl)-2-propenyl group, trans-3-(3-(1H-imidazol-1-yl)phenyl)-2-propenyl group, trans-3-(3-(pyrimidin-5-yl)phenyl)-2-propenyl group, trans-3-(5-phenylpyridin-3-yl)-2-propenyl group, trans-3-(3-(1H-1,2,4-triazol-1-yl)phenyl)-2-propenyl group, trans-3-(3-(pyridin-2-yl)phenyl)-2-propenyl group, trans-3-(5-(pyridin-3-yl)pyridin-3-yl)-2-propenyl group, trans-3-(2-(pyridin-3-yl)phenyl)-2-propenyl group, trans-3-(4-(4-morpholinesulfonyl)phenyl)-2-propenyl group, trans-3-(4-(6-methylpyridazin-3-yloxy)phenyl)-2-propenyl group, trans-3-(5-benzoylpyridin-3-yl)-2-propenyl group, trans-3-(5-phenoxypyridin-3-yl)-2-propenyl group, trans-3-(5-phenylthiopyridin-3-yl)-2-propenyl group, trans-3-(5-phenylaminopyridin-3-yl)-2-propenyl group, trans-3-(3-cyano-4-fluorophenyl)-2-propenyl group, trans-3-(4-hydroxyphenyl)-2-propenyl group, trans-3-(5-aminocarbonylpyridin-3-yl)-2-propenyl group, trans-3-(5-diethylaminocarbonylpyridin-3-yl)-2-propenyl group, trans-3-(5-(N,O-dimethylhydroxyaminocarbonyl)pyridin-3-yl)-2-propenyl group, trans-3-(isoquinolin-4-yl)-2-propenyl group, 3-(naphthalen-2-yl)-2-propynyl group, 3-(quinolin-3-yl)-2-propynyl group, cis-3-(quinolin-3-yl)-2-propenyl group, 2-(quinolin-3-yl) ethyl group, 4-(quinolin-3-yl)butyl group, 4-(naphthalen-2-yl)butyl group, 5-(quinolin-3-yl)pentyl group, or 5-(naphthalen-2-yl)pentyl group; and

(36) The compound or a pharmaceutically acceptable salt thereof according to (21), wherein $R_3$ is methyl group, 4-phenylbutyl group, or 3-(quinolin-4-yl)propyl group, $R_5$ and $R_6$ are hydrogen atoms, $R_7$ and $R_8$ represent hydrogen atom, 3-(quinolin-4-yl)propyl group, trans-3-(quinolin-4-yl)-1-propenyl group, cis-3-(quinolin-4-yl)-1-propenyl group, 3-(1-methyl-1,2,3,4-tetrahydroquinolin-4-yl)propyl group, trans-3-(quinolin-3-yl)-1-propenyl group, cis-3-(quinolin-3-yl)-1-propenyl group, trans-3-(quinolin-6-yl)-1-propenyl group, trans-3-(quinolin-8-yl)-1-propenyl group, trans-3-(isoquinolin-4-yl)-1-propenyl group, trans-3-(naphthalen-2-yl)-2-propenyl group, or 5-(quinolin-3-yl)pentyl group, $R_9$ and $R_{10}$ are hydrogen atoms, $R_{11}$ and $R_{12}$ represents hydrogen atom, methyl group, 2-propenyl group, 3-(quinolin-4-yl)propyl group, trans-3-(quinolin-4-yl)-2-propenyl group, 3-(quinolin-3-yl)propyl group, trans-3-(quinolin-3-yl)-2-propenyl group, trans-3-(quinolin-6-yl)-2-propenyl group, trans-3-(pyridin-3-yl)-2-propenyl group, trans-3-(naphthalen-2-yl)-2-propenyl group, trans-3-phenyl-2-propenyl group, trans-3-(naphthalen-1-yl)-2-propenyl group, trans-3-(2-fluoro-4-((R)-5-(hydroxymethyl)oxazolidin-2-on-3-yl) phenyl)-2-prop enyl group, trans-3-(6-nitroquinolin-3-yl)-2-propenyl group, trans-3-(6-cyanoquinolin-3-yl)-2-propenyl group, trans-3-(1,8-naphthyridin-3-yl)-2-propenyl group, trans-3-(phenanthren-9-yl)-2-propenyl group, trans-3-(benzothiophen-3-yl)-2-propenyl group, trans-3-(benzo[c][1,2,5]oxadiazol-5-yl)-2-propenyl group, trans-3-(4-(1H-pyrazol-1-yl)phenyl)-2-propenyl group, trans-3-(2-fluoro-4-(1H-tetrazol-1-yl)phenyl)-2-propenyl group, trans-3-(4-(isoxazol-5-yl)phenyl)-2-propenyl group, trans-3-(4-(pyridin-3-yl)phenyl)-2-propenyl group, trans-3-(4-(pyridin-4-yl)phenyl)-2-propenyl group, trans-3-(4-(pyridin-2-yl)phenyl)-2-propenyl group, trans-3-(4-fluoro-3-(1H-pyrazol-1-yl)phenyl)-2-propenyl group, trans-3-(3-(2-methylthiazol-4-yl)phenyl)-2-propenyl group, trans-3-(3-biphenyl)-2-propenyl group, trans-3-(3-(pyridin-3-yl)phenyl)-2-propenyl group, trans-3-(3-(pyridin-4-yl)phenyl)-2-propenyl group, trans-3-(3-(1H-imidazol-1-yl)phenyl)-2-propenyl group, trans-3-(3-(pyrimidin-5-yl)phenyl)-2-propenyl group, trans-3-(5-phenylpyridin-3-yl)-2-propenyl group, trans-3-(3-(1H-1,2,4-triazol-1-yl)phenyl)-2-propenyl group, trans-3-(3-(pyridin-2-yl)phenyl)-2-propenyl group, trans-3-(5-(pyridin-3-yl)pyridin-3-yl)-2-propenyl group, trans-3-(2-(pyridin-3-yl)phenyl)-2-propenyl group, trans-3-(4-(4-morpholinesulfonyl)phenyl)-2-propenyl group, trans-3-(4-(6-methylpyridazin-3-yloxy)phenyl)-2-propenyl group, trans-3-(5-benzoylpyridin-3-yl)-2-propenyl group, trans-3-(5-phenoxypyridin-3-yl)-2-propenyl group, trans-3-(5-phenylthiopyridin-3-yl)-2-propenyl group, trans-3-(5-phenylaminopyridin-3-yl)-2-propenyl group, trans-3-(3-cyano-4-fluorophenyl)-2-propenyl group, trans-3-(4-hydroxyphenyl)-2-propenyl group, trans-3-(5-aminocarbonylpyridin-3-yl)-2-propenyl group, trans-3-(5-diethylaminocarbonylpyridin-3-yl)-2-propenyl group, trans-3-(5-(N,O-dimethylhydroxyaminocarbonyl)pyridin-3-yl)-2-propenyl group, trans-3-(isoquinolin-4-yl)-2-propenyl group, 3-(naphthalen-2-yl)-2-propynyl group, 3-(quinolin-3-yl)-2-propynyl group, cis-3-(quinolin-3-yl)-2-propenyl group, 2-(quinolin-3-yl) ethyl group, 4-(quinolin-3-yl)butyl group, 4-(naphthalen-2-yl)butyl group, 5-(quinolin-3-yl)pentyl group, or 5-(naphthalen-2-yl)pentyl group, and X is oxygen atom, or —NH— group.

From another aspect, the present invention further provides:

(37) A compound represented by the following general formula (4) or a pharmaceutically acceptable salt thereof:

(4)

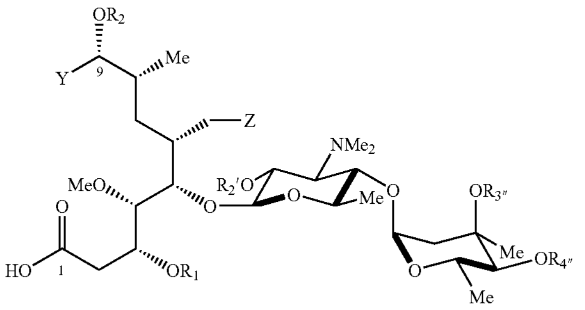

[wherein:

$R_1$ represents hydrogen atom, or a linear C1-6 alkylcarbonyl group, $R_2$ represents hydrogen atom, a C1-6 alkylcarbonyl group, or a silyl type protective group, $R_{3''}$ and $R_{4''}$ may be the same or different, and represent hydrogen atom, or a linear or branched C1-6 alkylcarbonyl group, $R_{2'}$ represents hydrogen atom, a linear C1-6 alkylcarbonyl group, a silyl type protective group, or benzyloxycarbonyl group, Z represents a —CH($OR_{13}$)$_2$ group (wherein $R_{13}$ represents a C1-6 alkyl group), or a group represented by the following formula (d)

(d)

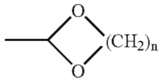

(wherein n represents an integer of 2 or 3), and

Y represents formyl group, or hydroxymethyl group].

According to a preferred embodiment of the aforementioned invention, provided is:

(38) The compound or a pharmaceutically acceptable salt thereof according to (37), wherein $R_2$ is a C1-6 alkylcarbonyl group, $R_{2'}$ is hydrogen atom, or a linear C1-6 alkylcarbonyl group, Z is —$CH(OCH_3)_2$ group, and Y is formyl group.

The present invention further provides:

(39) A method for producing a compound represented by the aforementioned general formula (1), (2) or (3) or a pharmaceutically acceptable salt thereof, which comprises the step of cyclizing a compound represented by the aforementioned general formula (4) or a pharmaceutically acceptable salt thereof.

According to a preferred embodiment of this invention, provided is:

(40) The method according to (39), wherein the compound represented by the aforementioned general formula (1), (2) or (3) or a pharmaceutically acceptable salt thereof is the compound or a pharmaceutically acceptable salt thereof according to any one of (2) to (8), (10) to (20) and (22) to (36).

From another aspect, the present invention provides:

(41) A medicament comprising the compound or a pharmaceutically acceptable salt thereof according to any one of (1) to (36) as an active ingredient; and

(42) The medicament according to (41), which is an antibacterial agent.

The compound or a pharmaceutically acceptable salt thereof of the present invention can be administered to a mammal including human requiring a prophylactic and/or therapeutic treatment of bacterial infection.

The present invention thus provides:

(43) A method for a prophylactic and/or therapeutic treatment of a bacterial infectious disease, which comprises the step of administering a prophylactically and/or therapeutically effective amount of a substance selected from compounds represented by the aforementioned general formula (1), (2) or (3) and pharmaceutically acceptable salts thereof to a mammal including human.

The present invention also provides:

(44) Use of a substance selected from compounds represented by the aforementioned general formula (1), (2) or (3) and pharmaceutically acceptable salts thereof for the manufacture of the aforementioned medicament.

BEST MODE FOR CARRYING OUT THE INVENTION

Hereafter, the present invention will be explained in detail.

In the specification, the azalide means a compound represented by the general formula (1) (2), or (3) which contains a lactone ring having a nitrogen atom at the 11-position as an aglycone (non-saccharide moiety).

In the specification, the azalactam means a compound represented by the general formula (1) (2), or (3) which contains a lactam ring having a nitrogen atom at the 11-position as an aglycone (non-saccharide moiety).

In the specification, Me means methyl group.

In the specification, the alkyl group and an alkyl moiety of a substituent containing the alkyl moiety (for example, an alkoxyl group, an alkylcarbonyl group and the like) is preferably a C1-6 alkyl unless otherwise specifically indicated, and group may be a linear, branched or cyclic alkyl such as methyl, ethyl, propyl, butyl, pentyl, hexyl, isopropyl, isobutyl, tert-butyl, isopentyl, neopentyl, tert-pentyl, cyclopropyl, cyclobutyl and cyclopentyl, or an alkyl group consisting of a combination thereof, preferably a linear or branched alkyl group, unless otherwise indicated. More preferred examples are methyl, ethyl, propyl, butyl, pentyl, hexyl, cyclopropylmethyl, and the like.

The alkyl group and an alkyl moiety of a substituent containing the alkyl moiety (for example, an alkoxyl group, an alkylcarbonyl group and the like) may optionally be substituted with hydroxyl group.

The alkenyl or alkynyl group, or an alkenyl or alkynyl moiety of a substituent containing the moiety is preferably C2-6 unless otherwise specifically indicated, and the group may be a linear, branched or cyclic alkenyl or alkynyl such as vinyl, 1-propenyl, 2-propenyl, isopropenyl, 1-butenyl, 2-butenyl, 1-propynyl, 2-propynyl, propargyl, 1-butynyl, 1-pentynyl and 2-butynyl, or alkenyl or alkynyl consisting of a combination thereof, preferably a linear or branched alkenyl or alkynyl group. Number and position of double bond or triple bond contained in the alkenyl and alkynyl moiety are not particularly limited, and double bond in the alkenyl moiety may be in cis-configuration or trans-configuration.

More preferable examples include linear groups such as 1-propenyl, 2-propenyl, 2-butenyl and 2-propynyl, and double bond may be in cis-configuration or trans-configuration.

In the specification, the aryl group means a group derived from a 6- to 14-membered aromatic ring (monocyclic to tricyclic) not containing hetero atoms, such as phenyl group, 1-naphthyl group, 2-naphthyl group and 9-phenanthryl group. The 6- to 14-membered aryl group has 6 to 14 carbon atoms in the ring system. The 6- to 14-membered aryl group may be substituted optionally with 1 to 5 substituents selected from a halogen atom, hydroxyl group, nitro group, cyano group, trifluoromethyl group, a C1-6 alkyl group, a C1-6 acyl group, a C1-6 alkyloxycarbonyl group, a C1-6 acyloxy group, dimethylamino group, diethylamino group, a C1-6 alkoxyl group, a 6- to 10-membered aryl group (examples include phenyl group, 1-naphthyl group, 2-naphthyl group and the like, wherein bonding position is not particularly limited), a 5- to 10-membered heterocyclic group (examples include 1-imidazolyl group, 2-pyridyl group, 3-pyridyl group, 4-pyridyl group, 3-quinolinyl group, 4-quinolinyl group, 6-quinolinyl group, 8-quinolinyl group, 4-isoquinolinyl group, benzimidazolyl group, (R)-5-(hydroxymethyl)oxazolidin-2-one group, 1-pyrazolyl group, 1-tetrazolyl group, 5-isoxazolyl group, 2-methyl-4-thiazolyl group, 5-pyrimidinyl group, 1,2,4-triazolyl group, and the like, wherein bonding position is not particularly limited), 6-methylpyridazin-3-yloxy group and 4-morpholinesulfonyl group.

The aryl group may preferably be substituted with one substituent selected from fluorine atom, nitro group, methoxy group, dimethylamino group, hydroxyl group, phenyl group, 1-imidazolyl group, 1-pyrazolyl group, 1-tetrazolyl group, 5-isoxazolyl group, 2-methyl-4-thiazolyl group, 5-pyrimidinyl group, 1,2,4-triazolyl group, 2-pyridyl group, 3-pyridyl group and 4-pyridyl group.

In the specification, the heterocyclic group means, unless otherwise specifically indicated, an aromatic or aliphatic 5- to 10-membered heterocyclic group (monocyclic or bicyclic) containing 1 to 4 hetero atoms selected from oxygen atom, sulfur atom and nitrogen atom, such as 1-imidazolyl group, 4-imidazolyl group, 2-pyridyl group, 3-pyridyl group, 4-pyridyl group, 3-quinolinyl group, 4-quinolinyl group, 6-quinolinyl group, 8-quinolinyl group, 4-isoquinolinyl group, 1,8-naphthyridin-3-yl group, 2-benzimidazolyl group, 2-benzothiazolyl group, 1-methyl-1,2,3,4-tetrahydroquinolin-4-yl group, 3-quinoxalinyl group, 6-quinoxalinyl group, 6-benzothiazolyl group, 2-benzoxazolyl group, 5-benzoxazolyl group, 5-benzofuryl group, 5-benzothienyl group, 5-benzimidazole group, 3-benzothienyl group, 3,4-dihydro-1H-[1,8]naphthyridin-2-on-6-yl group, 5-benzo[c][1,2,5]oxadiazolyl group, (R)-5-(hydroxymethyl)oxazolidin-2-one group, 1-pyrazolyl group, 1-tetrazolyl group, 5-isoxazolyl group, 4-thiazolyl group, 5-pyrimidinyl group, and 1,2,4-triazolyl group (wherein bonding position is not particularly limited to these examples). The 5- to 10-membered heterocyclic ring contains 5 to 10 atoms in the ring system. The 5- to 10-membered aromatic heterocyclic group may be substituted optionally with 1 to 3 substituents selected from a halogen atom, hydroxyl group, nitro group, cyano group, trifluoromethyl group, a C1-6 alkyl group, a C1-6 alkylcarbonyl group, a C1-6 alkyloxycarbonyl group, a C1-6 acyloxy group, dimethylamino group, diethylamino group, a C1-6 alkoxyl groups, an arylcarbonyl group, an aryloxy group, an arylthio group, an arylamino group, aminocarbonyl group which may be substituted and a heterocyclic group (as described above).

The heterocyclic ring may preferably be substituted with one substituent selected from 1-imidazolyl group, 4-(pyridin-3-yl)-1-imidazolyl group, 3-pyridyl group, 3-quinolinyl group, 4-quinolinyl group, 6-quinolinyl group, 8-quinolinyl group, 4-isoquinolinyl group, 6-quinoxalinyl group, 1,8-naphthyridin-3-yl group, 6-nitroquinolin-3-yl group, 6-cyanoquinolin-3-yl group, 2-benzothiazolyl group, 6-benzothiazolyl group, 5-benzofuryl group, 5-benzothienyl group, 3-benzothienyl group, 1-methyl-1,2,3,4-tetrahydroquinolin-4-yl group, 3,4-dihydro-1H-[1,8]naphthyridin-2-on-6-yl group, 5-benzo[c][1,2,5]oxadiazolyl group, (R)-5-(hydroxymethyl)oxazolidin-2-one group, 1-pyrazolyl group, 1-tetrazolyl group, 5-isoxazolyl group, 2-methyl-4-thiazolyl group, 5-pyrimidinyl group, 1,2,4-triazolyl group, 5-phenylpyridin-3-yl group, 5-(pyridin-3-yl)pyridin-3-yl group, 5-benzoylpyridin-3-yl group, 5-phenoxypyridin-3-yl group, 5-phenylthiopyridin-3-yl group, 5-phenylaminopyridin-3-yl group, 5-aminocarbonylpyridin-3-yl group, 5-diethylaminocarbonylpyridin-3-yl group and 5-(N,O-dimethylhydroxylaminocarbonyl)pyridin-3-yl group.

In the specification, the acyl group or an acyl moiety of a substituent containing the acyl moiety (for example, an acyloxy group such as acetoxy group) means, unless otherwise specifically indicated, a linear or branched C1-5 alkylcarbonyl group, such as formyl group, acetyl group, propionyl group, butyryl group, isobutyryl group, valeryl group and isovaleryl group. Preferred examples include acetyl group, propionyl group, n-butyryl group, isobutyryl group, isovaleryl group, and the like.

In the specification, the silyl type protective group means a readily removable group well known in the field which can protect hydroxyl group and be selectively removed, such as trimethylsilyl group, triethylsilyl group, tert-butyldimethylsilyl group, tert-butyldiphenylsilyl group, and the like. Preferred examples include trimethylsilyl group, tert-butyldimethylsilyl group, and the like.

In the specification, the ether type protective group means a readily removable group well known in this field which can protect hydroxyl group and be selectively removed, such as ethoxyethyl group. Preferred examples include ethoxyethyl group, and the like.

In the specification, the acetal type protective group means, unless otherwise specifically indicated, a readily removable group well known in this field which can protect formyl group and be selectively removed, for example, non-cyclic acetals such as dimethyl acetal, diethyl acetal and diisopropyl acetal, and cyclic acetals such as ethylene acetal and propylene acetal. Preferred examples include dimethyl acetal group, and the like.

As for the aforementioned protective groups, those skilled in the art can choose a suitable protective group by referring to, for example, "Protective Groups in Organic Syntheses, Ed. by P. G. M. Wuts and T. Green, 3rd edition, 1999, John Wiley & Sons, and the like. As for introduction and elimination of a protective group, methods described in, for example, "Handbook of Reagents for Organic Synthesis", Ed. by L. A. Paquette, 4 volumes in total, 1999, John Wiley & Sons, and the like can be referred to.

In the specification, the halogen atom means, unless otherwise specifically indicated, an atom selected from fluorine, chlorine, bromine and iodine atoms. Preferred examples include fluorine atom, chlorine atom and bromine atom.

In the specification, the halomethyl group means a methyl group one of which hydrogen atom is replaced with a halogen atom. Preferred examples include chloromethyl group, and the like.

The compounds of the present invention in which X is oxygen atom in the general formulas can be produced via the seven steps shown in Preparation Scheme 1 mentioned below. Unless otherwise specifically indicated, $R_1$ to $R_3$, $R_{13}$, $R_{3''}$ and $R_{4''}$ mentioned in the preparation scheme mentioned below have the same meanings as those defined above, A represents a straight C2-4 alkylene chain which may be substituted with hydroxyl group, a C1-6 alkyl group, a C2-6 alkenyl group, a C2-6 alkynyl group, or an Ar—B' group (wherein Ar and B' have the same meanings as defined above), provided that the alkylene chain may contain one double bond in a C4 chain. The preparation methods are divided into the first to seventh steps shown in Preparation Scheme 1, each of which will be explained in detail.

Preparation Scheme 1
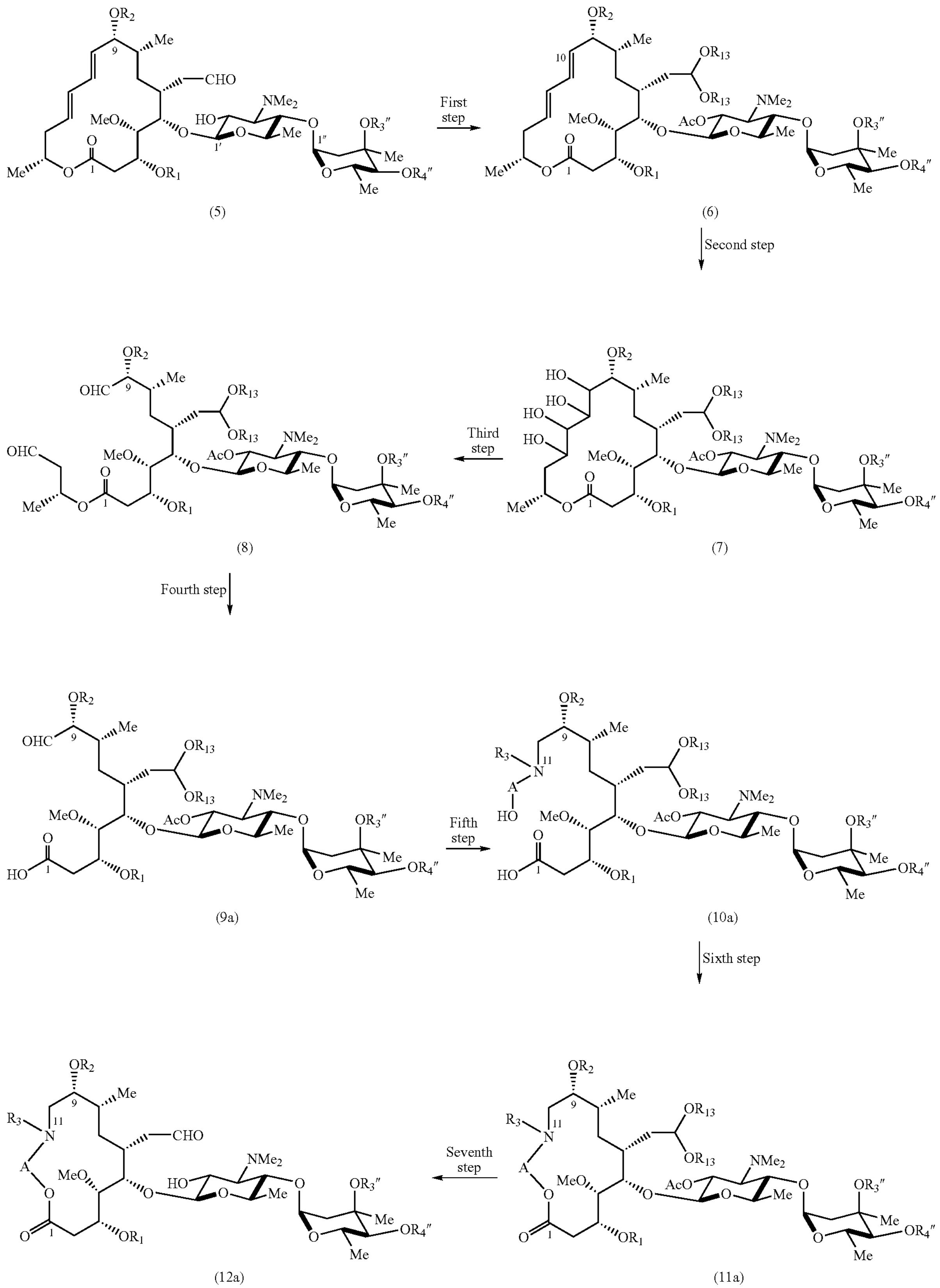
(5) (6) (7) (8) (9a) (10a) (11a) (12a)
+

-continued

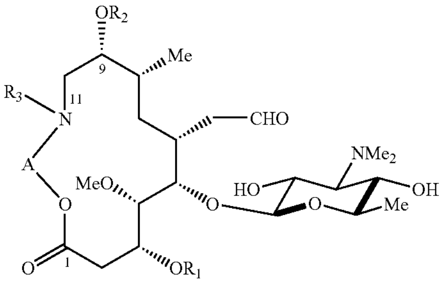

(13a)

First, the method for preparing the compounds represented by the formula (6) by using a compound represented by the formula (5) as a starting material will be explained.

The modification of the 9-hydroxyl group of the starting material represented by the formula (5) with an acyl group can be selectively progressed by a reaction with an acid halide in methylene chloride solvent in the presence of pyridine. The solvent used in this reaction may be, besides methylene chloride, an aprotic solvent such as chloroform, benzene, toluene and xylene. The base is preferably an organic base such as pyridine, and preferably used in an amount of 1 to 10 equivalents. As the acylation reagent, 1 to 5 equivalents of an acid halide is preferably used. The reaction progresses at a temperature in the range of 0 to 50° C., and the reaction time may be 0.5 to 24 hours.

If the subsequent modification of the formyl group with an acetal type protective group is performed in, for example, methyl orthoformate solvent or a mixed solvent of methyl orthoformate and methanol in the presence of an organic acid, the reaction progresses in a good yield. As the acid used, an organic acid such as paratoluenesulfonic acid and camphorsulfonic acid can be employed. Preferably, 1 to 3 equivalents of pyridinium p-toluenesulfonate (PPTS) may be used. As the solvent, methyl orthoformate, which also serves as the reagent, or a mixed solvent of methyl orthoformate and methanol is preferably used in an amount of 10 times (V/W) to 60 times (V/W). The reaction progresses in a sufficient yield at a temperature in the range of 20 to 80° C., and the reaction time may be 1 hour to 6 days.

When an acetal type protective group other than dimethyl acetal, i.e., $R_{13}$ is methyl group, is introduced into a compound represented by the general formula (6), the modification can be similarly carried out by using, for example, a mixed solvent of ethyl orthoformate and ethanol, a mixed solvent of isopropyl orthoformate and isopropanol, a mixed solvent of ethylene glycol and benzene, or a mixed solvent of propylene glycol and benzene, instead of the mixed solvent of methyl orthoformate and methanol.

The successive modification of the 2'-hydroxyl group in the mycaminose moiety with acetyl group can be progressed quantitatively, for example, in an acetonitrile solvent by a reaction using acetic anhydride. The solvent used for this reaction may also be an aprotic solvent such as methylene chloride and chloroform, and as the acetylating agent, 1 to 5 equivalents of acetic anhydride may be preferably used. The reaction progresses in a good yield at a temperature in the range of 20 to 60° C., and the reaction time may be 1 to 48 hours.

The second step of preparing the compounds represented by the formula (7) will be explained. The second step can be carried out by a reaction using N-methylmorpholine N-oxide as a co-oxidizing agent with a compound represented by the formula (6), for example, in a mixed solvent of acetone and water in the presence of a catalytic amount of a metal oxidizing agent. The metal oxidizing agent used may be potassium osmate(VI) dihydrate. Preferably, 0.05 to 1 equivalent of osmium tetraoxide may be used. As the co-oxidizing agent, a chlorate such as sodium chlorate, silver chlorate and barium chlorate, hydrogen peroxide, tert-butyl hydroperoxide, and the like may be used in the presence or absence of trimethylamine N-oxide, potassium hexacyanoferrate (III), or a quarternary ammonium salt such as tetraethylammonium acetate. Preferably, 1 to 5 equivalents of N-methylmorpholine N-oxide may be used. The solvent may be, besides the mixed solvent of acetone and water, acetonitrile, tetrahydrofuran, methylene chloride, tert-butyl alcohol, diethyl ether, tert-butyl alcohol, a mixed solvent of tert-butyl alcohol and water, a mixed solvent of tetrahydrofuran and water, or the like, and the reaction progresses at a temperature in the range of 0 to 50° C. The reaction time may be 5 hours to 3 days.

The third step of preparing the compounds represented by the formula (8) will be explained. The third step can be carried out by a reaction of a compound represented by the formula (7) using lead tetraacetate as an oxidizing agent in benzene in the presence of an inorganic base.

The oxidizing agent used for this reaction may be a peroxy acid such as sodium metaperiodate, active manganese dioxide, pyridinium chlorochlomate or the like. Preferably, 1 to 5 equivalents of lead tetraacetate may be used. As the solvent used for the reaction with lead tetraacetate, an aprotic solvent such as benzene, toluene, xylene and methylene chloride is preferred. The solvent used for the reaction with a peroxy acid such as metaperiodic acid may also be water, a mixed solvent of ether and water, or a mixed solvent of methylene chloride and water. As the base in this reaction, 1 to 15 equivalents of an inorganic base such as sodium hydrogencarbonate, sodium carbonate, potassium hydrogencarbonate and potassium carbonate may be preferably used. The reaction progresses at a temperature in the range of 0 to 50° C., and the reaction time may be 5 minutes to 24 hours. The compound represented by the formula (8) provided by this reaction can be used for the following fourth step without purification.

The method for preparing the compounds represented by the general formula (4) wherein Y is a group other than formyl group (Y is hydroxymethyl group) will be described below.

By subjecting a compound represented by the formula (8) to reduction using, for example, sodium borohydride in an ethanol solvent, the compound in which Y is hydroxymethyl group is provided.

The reducing agent used for this reaction may be lithium borohydride, lithium aluminum hydride, sodium triacetoxyborohydride, sodium cyanoborohydride, zinc borohydride, or the like. Preferably, 0.5 to 2 equivalents of sodium borohydride may be used. The solvent used for the reaction may be, besides ethanol, a lower alcohol such as methanol and isopropanol, acetonitrile, tetrahydrofuran, methylene chloride, 1,2-dichloroethane, or the like.

The fourth step of preparing the compounds represented by the formula (9a) will be explained. This compound is provided by allowing a base to react on a compound represented by the formula (8) in, for example, acetonitrile.

The base used in this reaction may be 1,5-diazabicyclo[4.3.0]-nonan-5-ene, 1,4-diazabicyclo[2.2.2]-octane, 4-dimethylaminopyridine, or the like. Preferably, 1 to 5 equivalents of 1,8-diazabicyclo[5.4.0]-undecan-7-ene may be used. The solvent may be, besides acetonitrile, a lower alcohol such as methanol, ethanol and isopropanol, tetrahydrofuran, methylene chloride, ethyl acetate, or the like, and the solvent may be used in an amount of 1 times (V/W) to 100 times (V/W) based on the amount of the compound represented by the formula (8). The reaction progresses at a temperature in the range of 0 to 50° C., and the reaction time may be 1 hour to 48 hours.

The compounds represented by the formula (9a) can also be provided by treating a compound represented by the formula (8) with magnesium sulfate in benzene.

As the solvent in this reaction, benzene, as well as methylene chloride, chloroform, diethyl ether, ethyl acetate, or the like may be used.

The fifth step of preparing the compounds represented by the formula (10a) will be explained. These compounds can be provided by adding an appropriate amine to a compound represented by the formula (9a) in, for example, dimethylformamide, in the presence of molecular sieve, stirring the mixture at 0 to 50° C. for 1 to 24 hours, and performing reductive amination using sodium borohydride as a reducing agent.

The appropriate amine used in this reaction is $R_3NHAOH$, wherein $R_3$ and A have the same meanings as those defined above.

Preferred examples of $R_3NHAOH$ include (−)-(R)-1-(4-phenylbutylamino)-2-propanol, (R)-1-methylamino-2-propanol, 3-(4-phenylbutylamino)propanol, (−)-(R)—N-(4-hydroxypentyl)-N-(4-phenylbutyl)amine, trans-(4-phenylbutylamino)-3-penten-2-ol, 7-methylamino-1-hepten-4-ol, (−)-(S)-7-methylamino-1-hepten-4-ol, 3-methylaminomethyl-5-hexenol, (−)-(R)—N-(4-hydroxypentyl)-N-(3-(quinolin-4-yl)propyl)amine, (R)-7-methylamino-1-hepten-4-ol, (R)-7-(methylamino)hept-1-yn-4-ol, (S)-6-methylamino-1-(quinolin-3-yl)hexan-3-ol, and the like.

The reducing agent used in this reaction may be sodium triacetoxyborohydride, sodium cyanoborohydride, or the like. Preferably, 1 to 5 equivalents of sodium borohydride may be used. The aforementioned amine may be in the form of a salt with an inorganic acid such as hydrochloric acid or an organic acid such as acetic acid, and preferably used in an amount of 0.8 to 7 equivalents. The molecular sieve is preferably used in an amount of 1 time (W/W) to 10 times (W/W) based on the amount of the compound represented by the formula (9a). The solvent may be, dimethylformamide, as well as a lower alcohol such as methanol, ethanol and isopropanol, acetonitrile, tetrahydrofuran, methylene chloride, or the like, and preferably used in an amount of 1 time (V/W) to 50 times (V/W) based on the amount of the compound represented by the formula (9a). The reaction progresses at a temperature in the range of 0 to 50° C., and the reaction time may be 0.5 hour to 24 hours.

The compounds represented by the formula (10a) can also be prepared by the following method. The compounds can be provided by adding acetic acid and an appropriate amine to a compound represented by the formula (9a), for example, in ethanol in the presence of molecular sieve, and performing reductive amination using sodium cyanoborohydride as a reducing agent.

The reducing agent used in this reaction may be sodium triacetoxyborohydride, sodium cyanoborohydride, or the like. Preferably, 1 to 10 equivalents of sodium cyanoborohydride may be used. The aforementioned amine may be in the form of a salt with an inorganic acid such as hydrochloric acid or an organic acid such as acetic acid, and preferably used in an amount of 0.8 to 7 equivalents. The acid to be added may be hydrochloric acid or the like. Preferably, 1 to 30 equivalents of acetic acid may be used. The solvent may be, ethanol, as well as a lower alcohol such as methanol and isopropanol, dimethylformamide, acetonitrile, tetrahydrofuran, methylene chloride, 1,2-dichloroethane, or the like, and preferably used in an amount of 1 time (V/W) to 50 times (V/W) based on the amount of the compound represented by the formula (9a). The reaction progresses at a temperature in the range of 0 to 50° C., and the reaction time may be 0.5 hour to 48 hours.

The sixth step of preparing the compounds represented by the formula (11a) will be explained. A compound represented by the formula (10a) is added with 2,4,6-trichlorobenzoyl chloride, for example, in tetrahydrofuran in the presence of triethylamine, and stirred at 0 to 50° C. for 1 to 24 hours to prepare a mixed acid anhydride. By adding dropwise the mixed acid anhydride prepared above to a solution of 4-dimethylaminopyridine in toluene over 5 minutes to 3 hours at 0 to 50° C. to perform a cyclization reaction, the desired compounds are provided.

The solvent used in the preparation of the mixed acid anhydride may be methylene chloride, toluene, benzene, or the like. Preferably, tetrahydrofuran may be used in an amount of 5 to 50 times (V/W) based on the amount of the compound represented by the formula (10a). Triethylamine is preferably used in an amount of 1 to 5 equivalents. The aforementioned amine may be in the form of a salt with an inorganic acid such as hydrochloric acid or an organic acid such as acetic acid, and is preferably used in an amount of 1 to 5 equivalents. 2,4,6-Trichlorobenzoyl chloride is preferably used in an amount of 1 to 2 equivalents. 4-Dimethylaminopyridine used in the subsequent cyclization reaction is preferably used in an amount of 1 to 5 equivalents. As the solvent, benzene as well as toluene may be used, and the solvent is preferably used in an amount of 50 to 300 times (V/W) based on the amount of the compound represented by the formula (10a). The reaction progresses at a temperature in the range of 0 to 80° C., and the reaction time may be 0.5 to 24 hours.

The compounds represented by the formula (11a) can also be prepared by the following method. For example, by slowly adding dropwise a solution of a compound represented by the formula (10a) in tetrahydrofuran to a solution of 2-methyl-6-nitrobenzoic anhydride and 4-dimethylaminopyridine in tetrahydrofuran to carry out a cyclization reaction, the desired compounds are provided.

As the base in this reaction, 4-dimethylaminopyridine 1-oxide, 4-pyrrolidinopyridine 1-oxide or the like alone may be used in an amount of 2 to 5 equivalents, or in addition to 2 to 5 equivalents of triethylamine, 0.1 to 0.5 equivalent of 4-dimethylaminopyridine, 4-dimethylaminopyridine 1-oxide, 4-pyrrolidinopyridine, 4-pyrrolidinopyridine 1-oxide or the like may be used. Preferably, 2 to 5 equivalents of 4-dimethylaminopyridine may be used. 2-Methyl-6-nitrobenzoic anhydride is preferably used in an amount of 1 to 2 equivalents. The solvent may be methylene chloride, tetrahydrofuran, toluene, benzene, or the like. Preferably, methylene chloride or tetrahydrofuran may be used in an amount of 10 to 600 times (V/W) based on the amount of the compound represented by the formula (10a). The solution of a compound represented by the formula (10a) in methylene chloride or tetrahydrofuran may be added dropwise over 20 minutes to 20 hours at 0 to 50° C., and after the addition, the reaction progresses at a temperature in the range of 0 to 50° C. The reaction time may be 0.5 to 24 hours.

The compounds of the formula (11a) wherein $R_{3''}$ represents propionyl group, and $R_{4''}$ represents an acyl group are also obtained in the following manner.

By reacting a compound of the formula (11a) wherein $R_{3''}$ is a hydrogen atom, and $R_{4''}$ is propionyl group, which is obtained by the aforementioned cyclization reaction, with an acid anhydride in pyridine, the rearrangement of the propionyl group of $R_{4''}$ to $R_{3''}$ occurs and then an acyl group (acyl group derived from the acid anhydride) is newly introduced into $R_{4''}$.

The acid anhydride used in this reaction is preferably used in an amount of 10 to 50 equivalents. Pyridine used as the solvent is preferably employed in an amount of 1 to 30 times (V/W) based on the amount of the compound represented by the formula (11a) wherein $R_{3''}$ is hydrogen atom, and $R_{4''}$ is propionyl group. The reaction progresses at a temperature in the range of 60 to 120° C., and the reaction time may be 5 hours to 100 hours.

Finally, the seventh step of preparing the novel compounds represented by the formula (12a) or (13a) will be explained. The deprotection for the 2'-acetyl group in the mycaminose moiety of the compounds represented by the formula (11a) progresses in methanol or a mixed solvent of methanol and water. The reaction progresses at a temperature in the range of 0 to 80° C., and the reaction time may be 12 hours to 10 days. When $R_2$ in the compounds represented by the formula (11a) is acetyl group, $R_2$ can be removed simultaneously with the deacetylation of the 2'-position, depending on the reaction conditions.

Subsequently, the acetal type protective group in the compound of the formula (11a) is removed by a reaction with difluoroacetic acid in a mixed solvent of acetonitrile and water to obtain a compound represented by the formula (12a) or (13a). When $R_{3''}$ is a hydrogen atom in the compounds of the formula (11a), these compounds can be converted into the compounds represented by the formula (12a) and/or the compounds represented by the formula (13a), and by extending the reaction time or raising the concentration of the acid used, said compounds can be converted selectively into the compounds represented by the formula (13a). The equivolume mixed solution of acetonitrile and water used as the solvent is preferably employed in an amount of 10 to 300 times (V/W) based on the amount of the compound represented by the formula (11a). As the acid, monofluoroacetic acid, trifluoroacetic acid, acetic acid, hydrochloric acid, or the like may be used. Preferably, 1 to 100 equivalents of difluoroacetic acid may be used. The reaction progresses at a temperature in the range of 0 to 50° C., and the reaction time may be 1 hour to 10 days.

The compounds of the present invention wherein X is —$NR_4$— in the general formulas can be prepared via four steps shown in Preparation Scheme 2 mentioned below. $R_1$ to $R_4$, $R_{13}$, $R_{3''}$, $R_{4''}$ and A mentioned in the following preparation scheme have the same meanings as those defined above, unless otherwise specifically indicated. These preparation methods are divided into the first to fourth steps shown in Preparation Scheme 2, and the details of the methods will be explained for each step.

Preparation Scheme 2

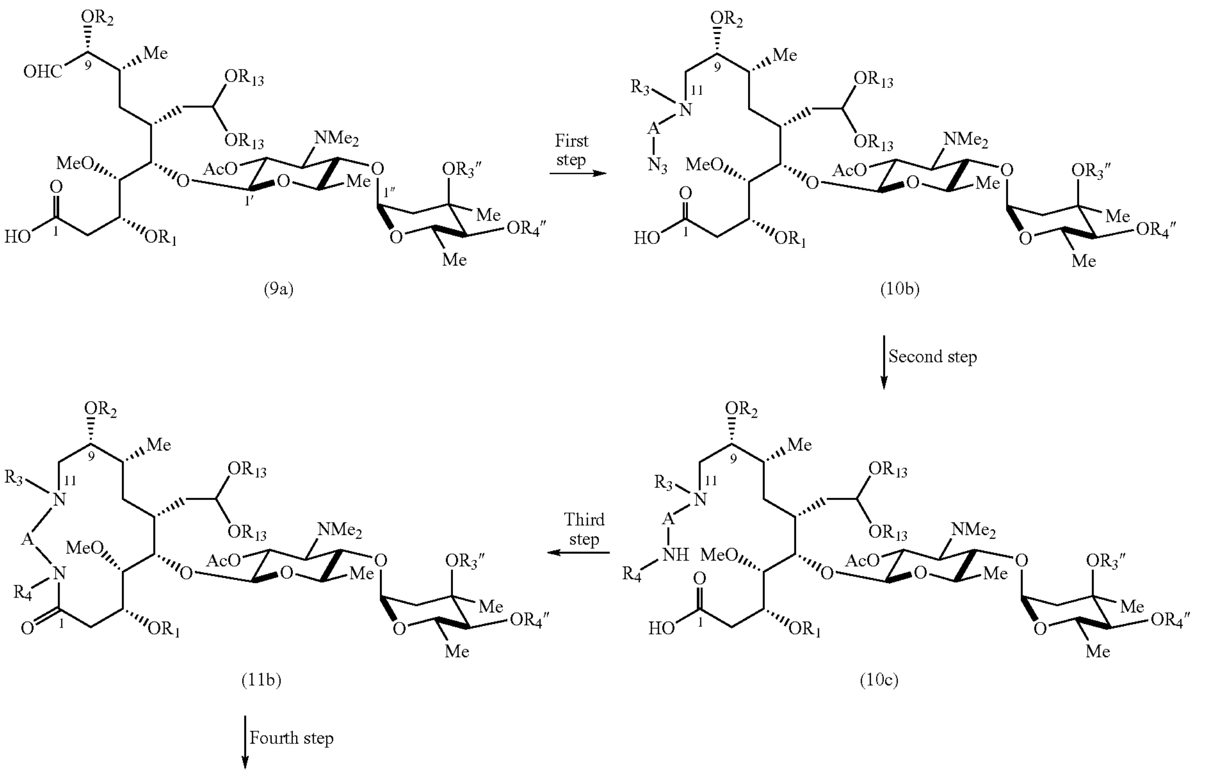

(9a) (10b) (11b) (10c)

-continued

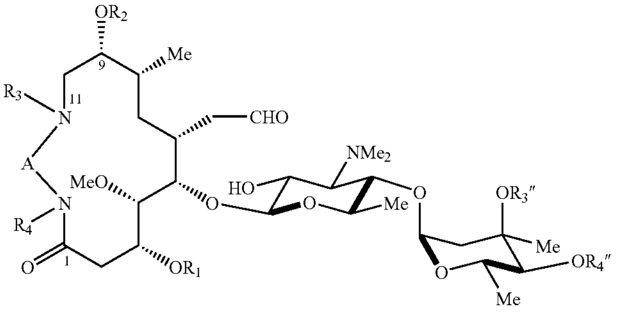

(12b)

+

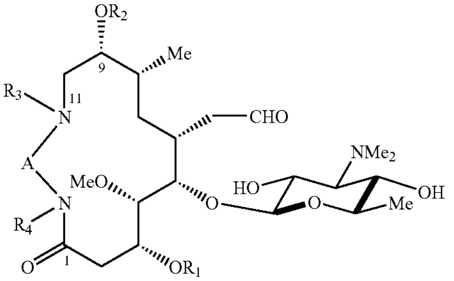

(13b)

The first step of preparing the compounds represented by the formula (10b) will be explained. These compounds are provided by carrying out reductive amination using an amine having an azide for a compound represented by the formula (9a) as in the fifth step shown in Preparation Scheme 1.

The amine having an azide used in this reaction is represented as $R_3NAN_3$, wherein and $R_3$ and A have the same meanings as those defined above.

Preferred examples of $R_3NAN_3$ include N-(2-azidoethyl)-N-(4-phenylbutyl)amine, (R)—N-(2-azidopropyl)-N-(4-phenylbutyl)amine, N-(2-azidoethyl)-N-methylamine, (+)-(R)—N-(2-azidopropyl)-N-(4-methoxybenzyl)amine, (−)-(S)—N-(2-azidopropyl)-N-(4-methoxybenzyl)amine, N-(3-azidopropyl)-N-(4-phenylbutyl)amine, N-(3-azidobutyl)-N-(4-phenylbutyl)amine, N-(3-azidobutyl)-N-(4-methoxybenzyl)amine, N-(3-azido-5-hexenyl)-N-methylamine, N-(3-azidopropyl)-N-(4-methoxybenzyl) amine, N-(4-azidobutyl)-N-(4-phenylbutyl)amine, N-(4-azidopentyl)-N-methylamine, and the like.

The second step of preparing the compounds represented by the formula (10c) will be explained. These compounds can be provided by performing a reduction reaction, for example, using trimethylphosphine in a mixed solvent of acetonitrile and water, for a compound represented by the formula (10b). These compounds can be N-alkylated as required.

The phosphine reagent in this reaction may be tributylphosphine or the like. Preferably, 1 to 10 equivalents of triphenylphosphine or trimethylphosphine may be used. Trimethylphosphine can be used after dissolution in toluene or the like. The solvent may be, a mixed solvent of acetonitrile and water, as well as a mixed solvent of tetrahydrofuran and water, a mixed solvent of dioxane and water, or the like, and the solvent may be preferably used in an amount of 5 to 100 times (V/W) based on the amount of the compound represented by the formula (10b). The reaction progresses at a temperature in the range of 0 to 100° C., and the reaction time may be 1 hour to 3 days.

The third step of preparing the compounds represented by the formula (11b) will be explained. These compounds can be provided by carrying out a cyclization reaction, for example, using diphenylphosphoryl azide in dimethylformamide in the presence of a base for a compound represented by the formula (10c).

The diphenylphosphoryl azide in this reaction is preferably used in an amount of 1 to 5 equivalents. The base may be an organic base such as triethylamine and diisopropylethylamine. Preferably, sodium hydrogencarbonate may be used in an amount of 1 to 20 equivalents. The solvent may be dimethylformamide, as well as tetrahydrofuran, 1,2-dimethoxyethane, or the like, and the solvent may be preferably used in an amount of 30 to 250 times (V/W) based on the amount of the compound represented by the formula (10c). The reaction progresses at a temperature in the range of 0 to 50° C., and the reaction time may be 1 to 48 hours.

Finally, the fourth step of preparing the compounds represented by the formula (12b) or (13b) will be explained. These compounds can be synthesized by deprotection for the acetyl group at the 2'-position of the mycaminose moiety in a compound represented by the formula (11b), followed by elimination of the acetal type protective group, as in the seventh step in Preparation Scheme 1.

In the deprotection for the 2'-acetyl group, when $R_1$ is propionyl group, $R_2$ is acetyl group, and $R_{4''}$ is propionyl group in the compound represented by the formula (11b), $R_1$, $R_2$ or $R_{4''}$ may be removed simultaneously with the deacetylation at the 2'-position, depending on the reaction conditions.

Where an alkyl group containing Ar (Ar has the same meaning as that defined above) is introduced beforehand into the amine used in the fifth step in Preparation Scheme 1 or the first step in Preparation Scheme 2, and the resultant is subjected to a cyclization reaction according to the preparation method shown in Preparation Scheme 1 or 2, it is possible to prepare the compounds represented by the formula (15a) or formula (16a) as shown in Preparation Scheme 3, and the compounds represented by the formula (15b) or (16b) as shown in Preparation Scheme 4. As shown in Preparation Schemes 3 and 4, it is also possible to convert the amine into the compounds represented by the formula (15a), (16a), (15b), or (16b) by introducing the Ar group (Ar group has the same meaning as that defined above) after the cyclization. The compounds represented by the formula (15a) or (16a) can be prepared via the two steps shown in Preparation Scheme 3 mentioned below. $R_1$ to $R_3$, $R_{13}$, $R_{3''}$, $R_{4''}$, X and Ar mentioned in the following Preparation Schemes have the same meanings as those defined above, unless otherwise specifically indicated. These preparation methods are divided into the first and second steps shown in Preparation Scheme 3, and the details of the methods will be explained for each step.

Preparation Scheme 3

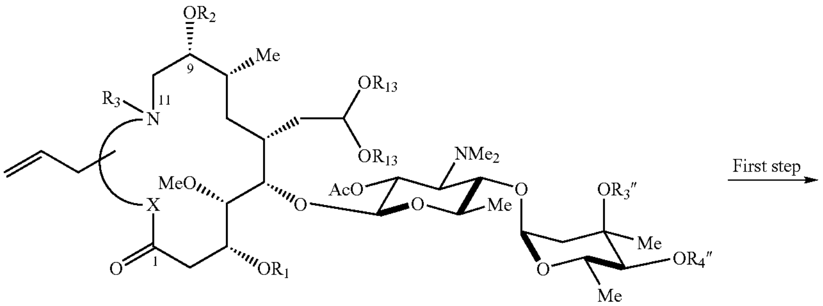

(14a)

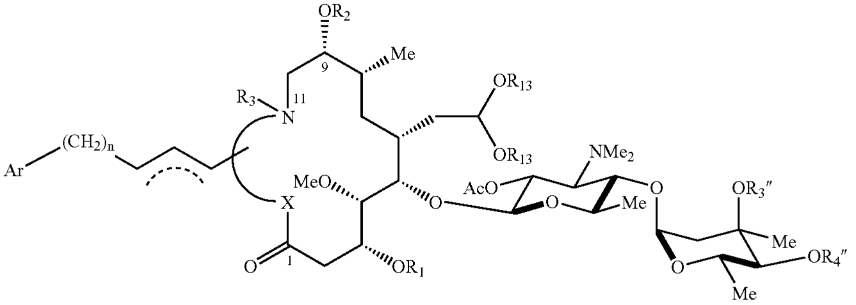

(15a)

Second step

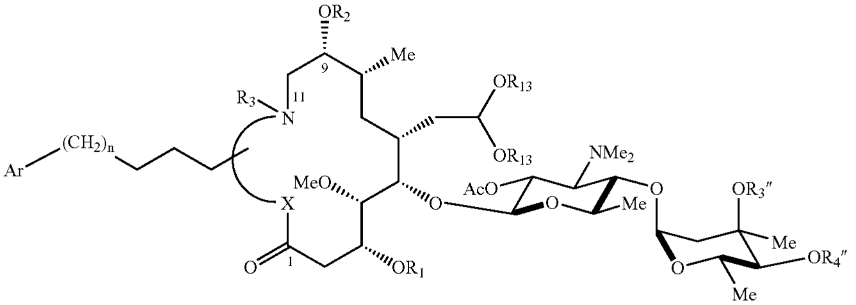

(16a)

n = 0-2

Preparation Scheme 4

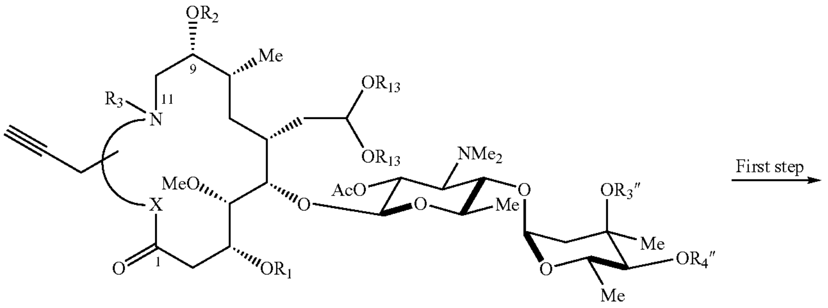

(14b)

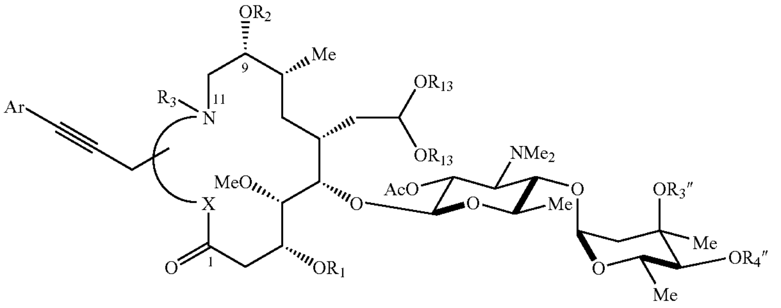

(15b)

Second step

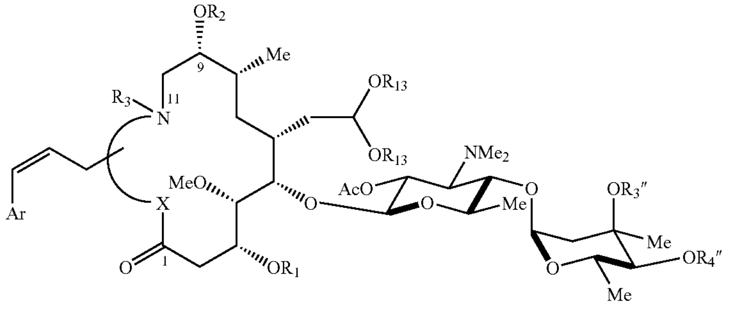

(16b)

The first step of preparing the compounds represented by the formula (15a) will be explained. These compounds (n=0) are provided by performing the Heck reaction (Acc. Chem. Res., 1995, 28, 2-7; J. Am. Chem. Soc., 2001, 123, 6989-7000) using a palladium catalyst in the presence of a halogen compound, suitable base and phosphine ligand for a compound represented by the formula (14a) prepared according to the first step to sixth step of Preparation Scheme 1 or the first step to third step of Preparation Scheme 2.

A palladium catalyst that can be used for the usual Heck reaction such as tetrakis(triphenylphosphine)palladium(0) and palladium(II) chloride can be used for this reaction. Preferably, palladium(II) acetate or tris(dibenzylideneacetone)-dipalladium(0) may be used in an amount of 0.05 to 0.6 equivalent. The base to be used may be sodium carbonate, cesium carbonate, or the like. Preferably, triethylamine, dicyclohexylmethylamine, or sodium hydrogencarbonate may be used in an amount of 1 to 5 equivalents. As the phosphine ligand to be used, a ligand that can be used for the usual Heck reaction such as 1,3-bis(diphenylphosphino)propane, 1,4-bis-(diphenylphosphino)butane, and 1,1'-bis-(diphenylphosphino)ferrocene can be used, and 2-(di-tert-butylphosphino)biphenyl, tri-o-tolylphosphine, or tri-tert-butylphosphine is preferably used in an amount of 0.1 to 1.5 equivalents. When tetrabutylammonium chloride is used as an additive, it is not necessary to use the phosphine ligand. The halogen compound to be used is a compound having a halogen atom on an appropriate aryl group or heterocyclic ring ("aryl group or heterocyclic ring" mentioned herein has the same meaning as Ar mentioned above), and is preferably used in an amount of 1 to 10 equivalents. The halogen atom may be chlorine atom or iodine atom. Bromine atom is preferred. The solvent may be tetrahydrofuran, dimethyl sulfoxide, 1-methyl-2-pyrrolidone, or the like. Preferably, acetonitrile, 1,4-dioxane, or dimethylformamide may be used in an amount of 1 to 50 times (V/W) based on the amount of the compound represented by the formula (14a). The reaction progresses at a temperature in the range of 10 to 130° C., and the reaction time may be 0.5 hour to 10 days.

In this reaction, besides usual products in the Heck reaction, products wherein a double bond of the usual products is rearranged to the adjacent position may sometimes be produced.

The compounds represented by the formula (15a) (n=1, 2) can also be provided by subjecting a compound represented by the formula (14a) to the olefin cross metathesis reaction with an olefin compound using a metal catalyst (J. Am. Chem. Soc., 2003, 125, 11360-11370; Org. Lett., 1999, 1, 1751-1753).

For this reaction, a metal catalyst that can be used for ordinary cross metathesis reactions such as (benzylidene) bis(trichlorohexylphosphine)ruthenium(IV) dichloride, and 2,6-diisopropylphenylimidoneophylidene molybdenum(VI) bis(hexafluoro-t-butoxide) can be used. Preferably, tricyclohexylphosphine[1,3-bis(2,4,6-trimethylphenyl)-4,5-dihydroimidazol-2-ylidene][benzylidene]ruthenium(IV) dichloride may be used in an amount of 0.05 to 0.6 equivalent. The olefin compound used may preferably have 2-propenyl group or 3-butenyl group on an appropriate aryl group or heterocyclic ring ("aryl group or heterocyclic ring" mentioned herein has the same meaning as Ar mentioned above), and be used in an amount of 1 to 5 equivalents. The solvent may be benzene, toluene, or the like, and preferably ethylene chloride may be used in an amount of 10 to 50 times (V/W) based on the amount of the compound represented by the formula (14a). The reaction progresses at a temperature in the range of 30 to 130° C., and the reaction time may be 1 hour to 2 days.

The second step of preparing the compounds represented by the formula (16a) will be explained. These compound are provided by subjecting a compound represented by the formula (15a) to catalytic hydrogen reduction.

The catalyst used for this reaction may be palladium black, palladium hydroxide, or the like. Preferably, palladium carbon (Pd—C) may be used in an amount of 5 to 80% (W/W) based on the raw material. As the solvent, a single solvent of a lower alcohol such as methanol, ethanol and isopropanol, dioxane, water, acetonitrile, tetrahydrofuran, ethyl acetate, or the like may be used, or a mixed solvent consisting of a combination of these may be used. The reaction progresses at a temperature in the range of 0 to 50° C. under a hydrogen atmosphere of 1 to 5 atm, and the reaction time may be 1 to 48 hours.

In this reaction, a part of the heterocyclic ring existing in the molecule may be reduced in addition to the reduction of the double bond. A secondary amine may be produced in the heterocyclic ring in the reaction. The resulting secondary amine moiety can be converted into a tertiary amine by, for example, a reductive alkylation reaction using formalin or an appropriate aldehyde in ethanol in the presence of acetic acid.

The reducing agent in this reaction may be sodium triacetoxyborohydride or the like. Preferably, sodium cyanoborohydride may be used in an amount of 1 to 5 equivalents. Formalin or aldehyde used may preferably be employed in an amount of 1 to 5 equivalents, and acetic acid is preferably used in an amount of 1 to 10 equivalents. The solvent may be, ethanol, as well as a lower alcohol such as methanol and isopropanol, acetonitrile, tetrahydrofuran, dimethylformamide, 1,2-dichloroethane, dioxane, water, or the like. The reaction progresses at a temperature in the range of 0 to 50° C., and the reaction time may be 0.5 to 24 hours.

The compounds represented by the formula (15b) or (16b) can be prepared via the two steps shown in Preparation Scheme 4 mentioned above. Unless otherwise specifically indicated, $R_1$ to $R_3$, $R_{13}$, $R_{3'''}$, $R_{4'''}$, X and Ar mentioned in the Preparation Scheme mentioned above have the same meanings as those defined above. These preparation methods are divided into the first and second steps shown in Preparation Scheme 4, and the details of the methods will be explained for each step. The first step of preparing the compounds represented by the formula (15b) will be explained. These compounds are provided by subjecting a compound represented by the formula (14b) prepared according to the first to sixth steps of Preparation Scheme 1 or the first to third steps of Preparation Scheme 2 to the Sonogashira reaction with a halogen compound using a palladium catalyst in the presence of suitable base and additive (Tetrahedron Lett., 1975, 16, 4467-4470; Synthesis, 1980, 627-630; Org. Lett., 2003, 5, 4191-4194).

For this reaction, a palladium catalyst that can be used for the usual Sohogasira reaction such as palladium(II) acetate, bis(benzonitrile)-dichloropalladium(II) and dichlorobis (triphenylphosphine)palladium(II) can be used. Preferably, allylpalladium chloride dimer may be used in an amount of 0.05 to 0.6 equivalent. The base used may be diisopropylamine, triethylamine, dicyclohexylmethylamine, diisopropylmethylamine, piperidine, or the like. Preferably, 1,4-diazabicyclo[2.2.2.]octane may be used in an amount of 1 to 5 equivalents. Depending on the conditions, copper iodide(I) used for the usual Sonogashira reaction as an additive may be used in an amount of 0.1 to 1.2 equivalents. When a catalyst not having a phosphine ligand such as palladium(II) acetate and allylpalladium chloride dimmer is used, a phosphine ligand such as triphenylphosphine is preferably used, and tri-t-butylphosphine is preferably used in an amount of 0.1 to 1.5 equivalents. The halide used may preferably have a halogen atom on a suitable aromatic ring or heterocyclic ring, and preferably be used in an amount of 1 to 10 equivalents. The halogen atom may be chlorine atom or iodine atom. Bromine atom is preferred. The solvent may be 1,4-dioxane, dimethylformamide, tetrahydrofuran, benzene, or the like. Preferably, acetonitrile may be used in an amount of 1 to 50 times (V/W) based on the amount of the compound represented by the formula (14b). The reaction progresses at a temperature in the range of 20 to 90° C., and the reaction time may be 1 hour to 10 days.

The second step of preparing the compounds represented by the formula (16b) will be explained. These compounds are provided by subjecting a compound represented by the formula (15b) to catalytic hydrogen reduction.

As the catalyst used for this reaction, palladium/calcium carbonate deactivated with lead acetate (Lindlar catalyst) is preferably used in an amount of 10 to 120% (W/W) based on the amount of the compound represented by the formula (15b). As the solvent, 1,4-dioxane may be used as a single solvent, or may be used as a mixed solvent with water. The reaction progresses at a temperature in the range of 20 to 50° C. under a hydrogen atmosphere of 1 to 5 atm, and the reaction time may be 1 hour to 6 days.

The compounds represented by the formula (15a), (16a), (15b) or (16b) prepared according to the methods of Preparation Schemes 3 and 4 can be converted into the compounds represented by the formulas (12a) and/or (13a), or by the formulas (12b) and/or (13b) by using the same method as the method of the seventh step of Preparation Scheme 1 or the fourth step of Preparation Scheme 2.

It is also possible to prepare the compounds represented by the formula (11e) having various substituents as $R_3$ as shown in Preparation Scheme 5 by introducing $R_3$ ($R_3$ has the same meaning as that defined above) beforehand into the amine used in the fifth step of Preparation Scheme 1 or the first step of Preparation Scheme 2, and subjecting the resultant to a cyclization reaction according to the methods shown in Preparation Scheme 1 or 2, and as shown in a Preparation Scheme 5, it is also possible to perform cyclization to prepare a compound represented by the formula (11c) introduced with para-methoxybenzyl group as a protective group, then remove the para-methoxybenzyl group as deprotection, and convert the resultant into a compound represented by the formula (11e) by newly introducing $R_3$. $R_1$ to $R_3$, $R_{13}$, $R_{3''}$, $R_{4''}$, A and X mentioned in the following Preparation Scheme have the same meanings as those defined above, unless otherwise specifically indicated. These preparation methods are divided into the first and second steps shown in Preparation Scheme 5, and the details of the methods will be explained for each step.

Scheme 1 or the first to third steps of Preparation Scheme 2 by catalytic hydrogen reduction.

The catalyst used for this reaction may be palladium black, palladium hydroxide, or the like. Preferably, palladium/carbon may be used in an amount of 10 to 150% (W/W) based on the amount of the compound represented by the formula (11c). As the solvent, a single solvent of a lower alcohol such as methanol, ethanol and isopropanol, dioxane, water, acetonitrile, tetrahydrofuran, or the like may be used, or a mixed solvent consisting of a combination of these may be used. Ethyl acetate is preferably used. The reaction progresses at a temperature in the range of 0 to 50° C., and the reaction time may be 5 hours to 3 days.

The second step of preparing the compounds represented by the formula (11e) will be explained. These compounds Preparation Scheme 5

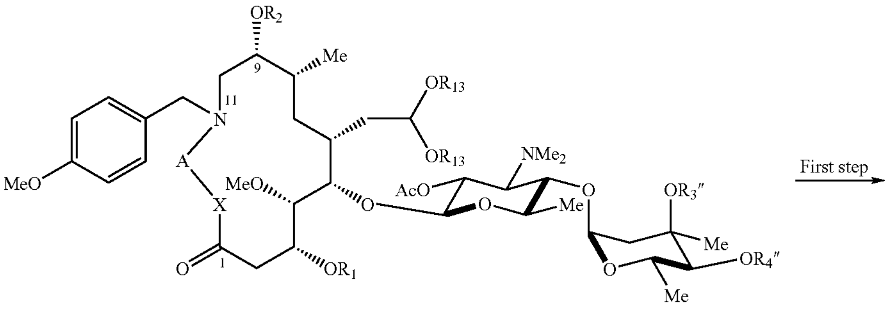

(11c)

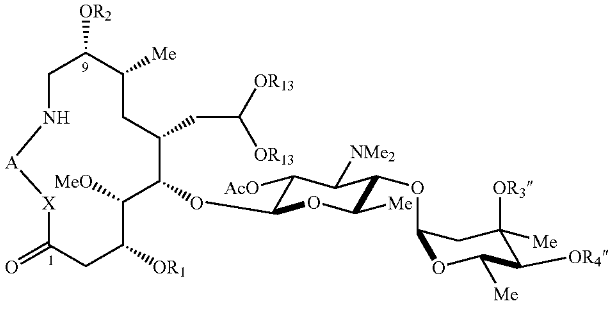

(11d)

Second step

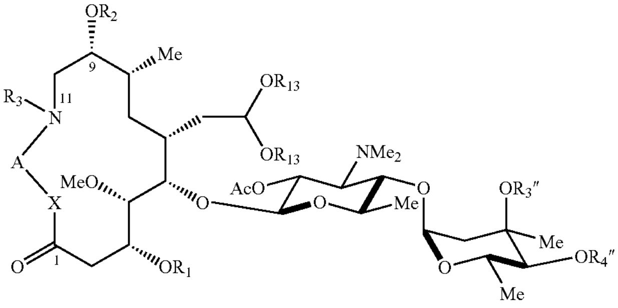

(11e)

The first step of preparing the compounds represented by the formula (11d) will be explained. These compounds are provided by removing 4-methoxybenzyl group at the 11-position in a compound represented by the formula (11c) prepared according to the first to sixth steps of Preparation are provided by subjecting a compound represented by the formula (11d) to a reductive alkylation reaction, which is performed by adding a suitable aldehyde in ethanol in the presence of acetic acid and using sodium cyanoborohydride as a reducing agent.

The reducing agent used in this reaction may be sodium triacetoxyborohydride, sodium borohydride, or the like. Preferably, sodium cyanoborohydride may be used in an amount of 1 to 10 equivalents. The aforementioned aldehyde is preferably used in an amount of 1 to 2 equivalents, and the acid added may be hydrochloric acid, or the like. Preferably, acetic acid may be used in an amount of 1 to 10 equivalents. The solvent may be ethanol, as well as a lower alcohol such as methanol and isopropanol, acetonitrile, tetrahydrofuran, methylene chloride, 1,2-dichloroethane, or the like. The reaction progresses at a temperature in the range of 0 to 50° C., and the reaction time may be 0.5 to 48 hours.

The compounds represented by the formula (11e) prepared according to the methods of Preparation Scheme 5 can be converted into the compounds represented by the formulas (12a) and/or (13a), or by the formulas (12b) and/or (13b) by using the same method as the seventh step of Preparation Scheme 1, or the fourth step of Preparation Scheme 2.

As for the methods of preparing the aldehyde-carboxylic acid represented by the formula (9a) via the dialdehyde represented by the formula (8), both of the method wherein the dialdehyde represented by the formula (8) mentioned in Preparation Scheme 1 is purified and the method wherein said dialdehyde is not purified fall within the scope of the present invention.

The methods for preparing the compounds of the present invention are not limited to the methods explained above or the methods specifically described in the examples, and the compounds prepared by any methods also fall within the scope of the present invention. For example, it should be understood that any compounds fall within the scope of the present invention which are obtainable by syntheses, preparations, extractions and purifications based on the aforementioned general explanations and specific explanations in the examples with modifications by known means.

The compounds of the present invention form salts with various bases or acids, and this property is used for manufacture of pure substances and forms for supply as medicaments. More specifically, in the manufacture, they can be solubilized in a polar solvent such as water by acidification, for example, and isolated by extraction and purification as a form of a salt having favorable physicochemical properties. For use as medicaments, the compounds may be in a form of a pharmaceutically acceptable salt. As an active ingredient of the medicament of the present invention, a substance in any forms mentioned above may be used.

Forms of the salts formable by the compounds of the present invention are not particularly limited. A form of a pharmaceutically acceptable salt of the compound is preferred.

For example, examples of base addition salt include lithium salts, sodium salts, potassium salts, magnesium salts, calcium salts, salts with ammonia or an appropriate non-toxic amine, C1-6 alkylamine (triethylamine and the like) salts, C1-6 alkanolamine (diethanolamine, triethanolamine and the like) salts, procaine salts, cyclohexylamine (dicyclohexylamine and the like) salts, benzylamine (N-methylbenzylamine, N-ethylbenzylamine, N-benzyl-β-phenethylamine, N,N-dibenzylethylenediamine, dibenzylamine and the like) salts, heterocyclic amine (morpholine, N-ethylpyridine, and the like) salts, and the like.

Examples of acid addition salts include, for example, hydrogen halide acid (hydrofluoric acid, hydrochloric acid, hydrobromic acid, hydroiodic acid and the like) salts, inorganic acid (sulfuric acid, nitric acid, phosphoric acid, perchloric acid, carbonic acid and the like) salts, carboxylic acid (acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, malic acid and the like) salts, amino acid (alginic acid, aspartic acid, glutamic acid and the like) salts, organic acid (methanesulfonic acid, para-toluenesulfonic acid and the like) salts, and the like.

As for forms of solvates formable by the compounds of the present invention, types of solvents are not particularly limited, and examples include, for example, water; alcohols such as methanol, ethanol and isopropanol; ethers such as tetrahydrofuran, and the like.

The compounds of the present invention have two or more asymmetric carbons, and the configurations thereof are as shown in the aforementioned general formulas (the configurations in the formulas represent absolute configurations, and the indications of the configurations are according to those ordinarily used). In addition to the asymmetric carbons shown in the general formulas (1) to (16), the compounds of the present invention may sometimes have asymmetric carbon(s) in substituents. Arbitrary stereoisomers (optical isomers, diastereoisomers) based on the asymmetric carbon(s) existing in substituents and arbitrary mixtures thereof (racemates, mixtures of diastereomers) all fall within the scope of the present invention. Besides the compounds represented by the general formula (1), (2), (3) or (4) in free forms or salts thereof, arbitrary hydrates and solvates thereof also fall within the scope of the present invention.

A substance selected from the group consisting of the compounds of the present invention, pharmaceutically acceptable salts thereof, and solvates thereof can be administered to human or animals orally or parenterally (for example, intravenous injection, intramuscular injection, subcutaneous administration, intraperitoneal administration, rectal administration, transdermal administration).

The medicament of the present invention which comprises the aforementioned substance as an active ingredient is prepared in a form of a suitable pharmaceutical composition depending on a route of administration. The medicament of the present invention can be prepared as a pharmaceutical composition, for example, as injections such as intravenous injection and intramuscular injection, oral agents such as capsules, tablets, granules, powders, pills, subtilized granules, and troches, agents for rectal administration, greasy suppository, aqueous suppository, and the like.

These pharmaceutical compositions can be prepared in a conventional manner by using one or more kinds of pharmaceutical additives ordinarily used, for example, excipients, fillers, binders, wetting agents, disintegrating agents, surfactants, lubricants, dispersing agents, buffering agent, preservatives, dissolving aids, antiseptics, flavoring agents, soothing agents, stabilizers, and the like.

Examples of the excipients include, for example, lactose, fructose, glucose, cornstarch, sorbit, crystalline cellulose and the like, examples of the disintegrating agents include, for example, starch, sodium arginate, gelatin, calcium carbonate, calcium citrate, dextrin, magnesium carbonate, synthetic magnesium silicate and the like, examples of the binders include, for example, methylcellulose and salts thereof, ethylcellulose, gum arabic, gelatin, hydroxypropylcellulose, polyvinylpyrrolidone and the like, examples of the lubricants include, for example, talc, magnesium stearate, polyethylene glycol, hydrogenated vegetable oil and the like, and examples of the other additives include, for example, syrup, vaseline, glycerol, ethanol, propylene glycol, citric acid, sodium chloride, sodium sulfite, sodium phosphate and the like A content of the active ingredient in the pharmaceutical composition may differ depending on a form of the composition. The content may generally be about 10 to 95% by weight, preferably 30 to 80% by weight, of a total weight of the pharmaceutical composition.

A dose is suitably determined considering a route of administration, age and sexuality of a patient, type of a disease, severity of symptoms and the like. The dose may generally be about 1 to 3000 mg, preferably 10 to 2000 mg, per day for an adult, and the aforementioned dose can be administered at one time or several times as divided portions in one day.

EXAMPLES

Hereafter, the present invention will be explained more specifically by referring to the following examples. However, the scope of the present invention is not limited by the following examples.

Reference Example 1

Preparation Method of (−)-(R)-1-(4-phenylbutylamino)-2-propanol

In an amount of 700 mg of 4-phenylbutyl aldehyde and 532 mg of (−)-(R)-1-amino-2-propanol were dissolved in 21 ml of tetrahydrofuran, added with 700 mg of Molecular Sieve 3A, and stirred at room temperature for 19.5 hours. The reaction mixture was added with 179 mg of sodium borohydride, stirred at room temperature for 3 hours, then further added with 70 mg of sodium borohydride, and stirred at room temperature for 5 hours. By using 30 ml of chloroform, the reaction mixture was filtered through a Cerite layer, then the filtrate was added with 30 ml of 10% aqueous ammonium chloride, and the organic layer and the aqueous layer were separated. The aqueous layer was extracted with 30 ml of chloroform, and then the organic layers were combined and washed once with 30 ml of saturated brine. The organic layer was dried over anhydrous sodium sulfate, and then filtered. The filtrate was concentrated under reduced pressure, and the resulting residue was purified by silica gel column chromatography (chloroform/methanol/aqueous ammonia (20:1:0.1 to 10:1:0.1)) to obtain 235 mg of the title compound.

Physicochemical Properties of this Compound (1) Molecular formula: $C_{13}H_{21}NO$ (2) Mass spectrum (FAB): m/z 208 $(M+H)0^+$ (3) Specific rotation: $[\alpha]_D^{21}$ −30° (c1.0, $CHCl_3$)

(4) $^1H$ NMR spectrum (300 MHz, $CDCl_3$) δ (ppm): 1.14 (d, 3-H), 1.46-1.72 (m, $C_6H_5CH_2(CH_2)_2CH_2$), 2.02 (br s, OH), 2.37 (dd, 1-H), 2.55-2.72 (m, $C_6H_5CH_2(CH_2)_2CH_2$ and 1-H), 3.74 (ddq, 2-H), 7.14-7.23 (m, $C_6H_5$), 7.24-7.33 (m, $C_6H_5$).

Reference Example 2

Preparation Method of (R)-1-methylamino-2-propanol (a) In an amount of 246 mg of (R)-1-amino-2-propanol was dissolved in 5 ml of 1,4-dioxane, added with 722 ml of 5 N aqueous sodium hydroxide, then added with 345 μl of ethyl chloroformate, and stirred at room temperature for 30 minutes. The reaction mixture was added with water, and extracted with ethyl acetate, and the organic layer was dried over anhydrous magnesium sulfate, and then filtered. The filtrate was concentrated under reduced pressure to obtain 465 mg of (R)-1-ethoxycarbonylamino-2-propanol.

Physicochemical Properties of this Compound (1) Molecular formula: $C_6H_{13}NO_3$ (2) Mass spectrum (FAB): m/z 148 $(M+H)^+$ (3) $^1H$ NMR spectrum (400 MHz, $CDCl_3$) δ (ppm): 1.16 (d, 3-H), 1.21 (t, $CO_2CH_2CH_3$), 2.50 (br s, 2-OH), 3.02 (m, 1-H), 3.29 (m, 1-H), 3.38 (m, 2-H), 4.09 (q, $CO_2CH_2CH_3$), 5.12 (br s, NH).

(b) In an amount of 29.7 mg of the compound of Reference Example 2(a) was dissolved in 594 μl of tetrahydrofuran, added with 15.3 mg of lithium aluminum hydride under ice cooling, and stirred at 65° C. for 2 hours. The reaction mixture was further added with 15.3 mg of lithium aluminum hydride, and stirred at 70° C. for 1 hour and 30 minutes. Then, the reaction mixture was returned to room temperature, successively added with 45 μl of water, 45 μl of 15% aqueous sodium hydroxide and 135 μl of water, and stirred until the reaction mixture became white. The reaction mixture was filtered through a Cerite layer, and then the filtrate was concentrated under reduced pressure to obtain 25.5 mg of the title compound.

Physicochemical Properties of this Compound (1) Molecular formula: $C_4H_{11}NO$ (2) Mass spectrum (ES): m/z 90 $(M+H)^+$ (3) $^1H$ NMR spectrum (400 MHz, $CDCl_3$) δ (ppm): 1.09 (d, 3-H), 2.60 (s, $NCH_3$), 2.81 (dd, 1-H), 2.97 (dd, 1-H), 3.95 (m, 2-H).

Reference Example 3

Preparation Method of N-(2-azidoethyl)-N-(4-phenylbutyl)amine (a) In a volume of 2 ml of 2-aminoethanol was dissolved in a mixed solvent of 150 ml of tetrahydrofuran and 150 ml of water, and added with 10 ml of 5 N aqueous sodium hydroxide and 10.8 g of di-tert-butyl dicarbonate, and the mixture was stirred at room temperature for 4.5 hours. The reaction mixture was adjusted to pH 7 by using 5 N hydrochloric acid, and then added with 300 ml of ethyl acetate, and the organic layer and the aqueous layer were separated. The aqueous layer was extracted twice with 50 ml of ethyl acetate, and then the organic layers were combined, and washed with 200 ml of 25% brine. The organic layer was dried over anhydrous sodium sulfate, and then filtered. The filtrate was concentrated under reduced pressure, and the resulting residue was purified by silica gel column chromatography (hexane/ethyl acetate (1:2)) to obtain 4.68 g of 2-(tert-butoxycarbonylamino)ethanol.

Physicochemical Properties of this Compound (1) Molecular formula: $C_7H_{15}NO_3$ (2) $^1H$ NMR spectrum (300 MHz, $CDCl_3$) δ (ppm): 1.45 (s, $(CH_3)_3C$), 3.30 (dt, 2-H), 3.71 (dt, 1-H), 2.28 (br s, OH), 4.92 (br s, NH).

(b) In an amount of 4.68 g of the compound of Reference Example 3(a) was dissolved in 140 ml of methylene chloride under argon atmosphere, and added with 6.1 ml of diisopropylethylamine and 2.8 ml of methanesulfonyl chloride under ice cooling, and the mixture was stirred for 1 hour. The reaction mixture was washed with 70 ml of water, the aqueous layer was extracted twice with 30 ml of ethyl acetate, and then the organic layers were combined, and washed with 100 ml of 25% brine. The organic layer was dried over anhydrous sodium sulfate, and then filtered. The filtrate was concentrated under reduced pressure, and the resulting residue was purified by silica gel column chromatography (hexane/ethyl acetate (1:1)) to obtain 7.01 g of methanesulfonic acid 2-(tert-butoxycarbonylamino)ethyl ester.

Physicochemical Properties of this Compound (1) Molecular formula: $C_8H_{17}NO_5S$ (2) $^1H$ NMR spectrum (300 MHz, $CDCl_3$) δ (ppm): 1.45 (s, $(CH_3)_3C$), 3.04 (s, $CH_3SO_3$), 3.48 (dt, 2-H), 4.29 (t, 1-H), 4.91 (br s, NH).

(c) In an amount of 7.01 g of the compound of Reference Example 3(b) was dissolved in 200 ml of N,N-dimethylformamide under argon atmosphere, and added with 2.35 g of sodium azide, and the mixture was stirred at 50° C. for 2.5 hours. The reaction mixture was diluted with 400 ml of ethyl acetate, and successively washed twice with 200 ml of water and once with 200 ml of 25% brine. The organic layer was dried over anhydrous sodium sulfate, and then filtered. The filtrate was concentrated under reduced pressure, and the resulting residue was purified by silica gel column chromatography (hexane/ethyl acetate (4:1)) to obtain 3.13 g of N-(2-azidoethyl)-N-tert-butoxycarbonylamine.

Physicochemical Properties of this Compound (1) Molecular formula: $C_7H_{14}N_4O_2$ (2) $^1H$ NMR spectrum (300 MHz, $CDCl_3$) δ (ppm): 1.45 (s, $(CH_3)_3C$), 3.30 (dt, 1-H), 3.42 (t, 2-H), 4.81 (br s, NH).

(d) In an amount of 3.13 g of the compound of Reference Example 3(c) was dissolved in 32 ml of 1,4-dioxane, added with 6.5 ml of 4 N hydrochloric acid/1,4-dioxane solution, and stirred at room temperature for 20 hours. The reaction mixture was further added with 2.2 ml of 4 N hydrochloric acid/1,4-dioxane solution, and stirred at room temperature for 52 hours. The precipitates were taken by filtration, washed with ethyl acetate, and then dried under reduced pressure to obtain 1.97 g of 2-azidoethylamine hydrochloride.

Physicochemical Properties of this Compound (1) Molecular formula: $C_2H_6N_4$ (2) $^1H$ NMR spectrum (300 MHz, $D_2O$) δ (ppm): 2.85 (t, 1-H), 3.39 (t, 2-H), 4.48 (s, $NH_2$).

(e) In an amount of 0.50 g of phenylbutylaldehyde was dissolved in 16 ml of methanol, added with 0.97 ml of acetic acid, 0.62 g of the compound of Reference Example 3(d), and 88 mg of sodium cyanoborohydride under ice cooling, and the reaction mixture was stirred for 19 hours and 30 minutes with warming to room temperature. The reaction mixture was concentrated under reduced pressure, and the residue was added with 20 ml of ethyl acetate, and washed with 20 ml of 8% aqueous sodium hydrogencarbonate. The aqueous layer was extracted twice with 5 ml of ethyl acetate, and the organic layers were combined, and washed with 20 ml of 25% brine. The organic layer was dried over anhydrous sodium sulfate, and then filtered. The filtrate was concentrated under reduced pressure, and the resulting residue was purified by silica gel column chromatography (chloroform/methanol (30:1)) to obtain 360 mg of the title compound.

Physicochemical Properties of this Compound (1) Molecular formula: $C_{12}H_{18}N_4$ (2) $^1H$ NMR spectrum (300 MHz, $CDCl_3$) δ (ppm): 1.71 (m, $C_6H_5CH_2(CH_2)_2CH_2$), 1.82 (m, $C_6H_5CH_2(CH_2)_2CH_2$), 2.65 (t, $C_6H_5CH_2$), 2.94 (t, $C_6H_5$ $(CH_2)_3CH_2$), 3.01 (t, $CH_2CH_2N_3$), 3.78 (t, $CH_2CH_2N_3$), 7.18 (m, $C_6H_5$), 7.28 (m, $C_6H_5$).

Reference Example 4

Preparation Method of (R)—N-(2-azidopropyl)-N-(4-phenylbutyl)amine (a) In the same manner as in Reference Example 3(a), 6.00 g of (S)-1-(tert-butoxycarbonylamino)-2-propanol was obtained from 2.00 g of (S)-(+)-1-amino-2-propanol.

Physicochemical Properties of this Compound (1) Molecular formula: $C_7H_{17}NO_3$ (2) $^1H$ NMR spectrum (300 MHz, $CDCl_3$) δ (ppm): 1.18 (d, 3-H), 1.45 (s, $(CH_3)_3C$), 2.28 (br s, OH), 3.00 (ddd, 1-H), 3.27 (ddd, 1-H), 3.91 (m, 2-H), 4.91 (br s, NH).

(b) In the same manner as in Reference Example 3(b), 8.93 g of (S)-methanesulfonic acid 2-(tert-butoxycarbonylamino)-1-methylethyl ester was obtained from 6.00 g of the compound of Reference Example 4(a).

Physicochemical Properties of this Compound (1) Molecular formula: $C_9H_{19}NO_5S$ (2) $^1H$ NMR spectrum (300 MHz, $CDCl_3$) δ (ppm): 1.41 (d, 1-$CH_3$), 1.45 (s, $(CH_3)_3C$), 3.03 (s, $CH_3SO_3$), 3.22 (m, 2-H), 3.44 (m, 1-H).

(c) In the same manner as in Reference Example 3(c), 6.06 g of (R)—N-(2-azidopropyl)-N-tert-butoxycarbonylamine was obtained from 8.93 g of the compound of Reference Example 4(b).

Physicochemical Properties of this Compound (1) Molecular formula: $C_8H_{16}N_4O_2$ (2) $^1H$ NMR spectrum (300 MHz, $CDCl_3$) δ (ppm): 1.25 (d, 3-H), 1.45 (s, $(CH_3)_3C$), 2.97 (m, 1-H), 3.29 (m, 1-H), 3.67 (br s, OH), 4.81 (br s, NH).

(d) In the same manner as in Reference Example 3(d), 3.54 g of (R)-2-azidopropylamine hydrochloride was obtained from 6.06 g of the compound of Reference Example 4(c).

Physicochemical Properties of this Compound (1) Molecular formula: $C_3H_8N_4$ (2) $^1H$ NMR spectrum (300 MHz, $D_2O$) δ (ppm): 1.04 (d, 3-H), 2.60 (dd, 1-H), 2.80 (ddd, 1-H), 3.62 (m, 2-H).

(e) In the same manner as in Reference Example 3(e), 70.0 mg of the title compound was obtained from 101 mg of the compound of Reference Example 4(d).

Physicochemical Properties of this Compound (1) Molecular formula: $C_{13}H_{20}N_4$ (2) $^1H$ NMR spectrum (300 MHz, $CDCl_3$) δ (ppm): 1.26 (d, 3-H), 1.53 (m, $C_6H_5CH_2(CH_2)_2CH_2$), 1.66 (m, $C_6H_5CH_2(CH_2)_2CH_2$), 2.62 (m, $C_6H_5CH_2(CH_2)_2CH_2$ and $CH_2CHN_3$), 3.65 (ddq, $CH_2CHN_3$), 7.17 (m, $C_6H_5$), 7.28 (m, $C_6H_5$).

Reference Example 5

Preparation Method of N-(2-azidoethyl)-N-methylamine hydrochloride (a) In the same manner as in Reference Example 3(a), 6.30 g of 2-(N-tert-butoxycarbonyl-N-methylamino)ethanol was obtained from 3.00 ml of 2-(methylamino)ethanol.

Physicochemical Properties of this Compound (1) Molecular formula: $C_8H_{17}NO_3$ (2) $^1H$ NMR spectrum (300 MHz, $CDCl_3$) δ (ppm): 1.47 (s, $(CH_3)_3C$), 2.84 (br s, OH), 2.92 (s, $NCH_3$), 3.40 (t, 2-H), 3.75 (q, 2-H).

(b) In the same manner as in Reference Example 3(b), 8.57 g of methanesulfonic acid 2-(N-tert-butoxycarbonyl-N-methylamino)ethyl ester was obtained from 6.30 g of the compound of Reference Example 5(a).

Physicochemical Properties of this Compound (1) Molecular formula: $C_9H_{19}NO_5S$ (2) $^1H$ NMR spectrum (300 MHz, $CDCl_3$) δ (ppm): 1.47 (s, $(CH_3)_3C$), 2.95 (s, $NCH_3$), 3.02 (s, $CH_3SO_3$), 3.55 (m, 2-H), 4.32 (br s, 1-H).

(c) In the same manner as in Reference Example 3(c), 2.52 g of N-(2-azidoethyl)-N-tert-butoxycarbonyl-N-methylamine was obtained from 8.57 g of the compound of Reference Example 5(b).

Physicochemical Properties of this Compound (1) Molecular formula: $C_8H_{16}N_4O_2$ (2) $^1H$ NMR spectrum (300 MHz, $CDCl_3$) δ (ppm): 1.47 (s, $(CH_3)_3C$), 2.93 (s, $NCH_3$), 3.40 (m, $CH_2CH_2N_3$).

(d) In the same manner as in Reference Example 3(d), except that 4 N hydrochloric acid/ethyl acetate solution was used instead of 4 N hydrochloric acid/1,4-dioxane solution, 1.06 g of the title compound was obtained from 2.52 g of the compound of Reference Example 5(c).

Reference Example 6

Preparation Method of (+)-(R)—N-(2-azidopropyl)-N-(4-methoxybenzyl)amine

In the same manner as in Reference Example 3(e), except that p-anisaldehyde was used instead of 4-phenylbutylaldehyde, 414 mg of the title compound was obtained from 400 mg of the compound of Reference Example 4(d).

Physicochemical Properties of this Compound (1) Molecular formula: $C_{11}H_{16}N_4O$ (2) Mass spectrum (FAB): m/z 221 $(M+H)^+$ (3) Specific rotation: $[\alpha]_D^{19}$+41° (c1.1, $CHCl_3$)

(4) $^1H$ NMR spectrum (300 MHz, $CDCl_3$) δ (ppm): 1.24 (d, 3-H), 2.64 (dd, 1-H), 2.76 (dd, 1-H), 3.64 (ddq, 2-H), 3.73 (s, $C_6H_4CH_2$), 3.79 (s, $OCH_3$), 6.86 (d, $C_6H_4$), 7.23 (d, $C_6H_4$).

Reference Example 7

Preparation Method of (−)-(S)—N-(2-azidopropyl)-N-(4-methoxybenzyl)amine (a) In the same manner as in Reference Example 3(a), 3.66 g of (−)-(R)-1-amino-2-propanol was used to obtain 8.58 g of (R)-1-(tert-butoxycarbonylamino)-2-propanol.

Physicochemical Properties of this Compound (1) Molecular formula: $C_7H_{17}NO_3$ (2) Mass spectrum (FAB): m/z 176 $(M+H)^+$ (3) $^1H$ NMR spectrum (300 MHz, $CDCl_3$) δ (ppm): 1.18 (d, 3-H), 1.45 (s, $(CH_3)_3C$), 2.62 (br s, OH), 3.00 (ddd, 1-H), 3.26 (ddd, 1-H), 3.90 (m, 2-H), 5.01 (br s, NH).

(b) In the same manner as in Reference Example 3(b), (R)-methanesulfonic acid 2-(tert-butoxycarbonylamino)-1-methylethyl ester was obtained from 8.58 g of the compound of Reference Example 7(a). From this compound, 8.96 g of (S)—N-(2-azidopropyl)-N-tert-butoxycarbonylamine was obtained in the same manner as in Reference Example 3(c).

Physicochemical Properties of this Compound (1) Molecular formula: $C_8H_{16}N_4O_2$ (2) $^1H$ NMR spectrum (300 MHz, $CDCl_3$) δ (ppm): 1.25 (d, 3-H), 1.45 (s, $(CH_3)_3C$), 2.98 (m, 1-H), 3.31 (m, 1-H), 3.67 (m, 2-H), 4.87 (br s, NH).

(c) In the same manner as in Reference Example 3(d), except that 4 N hydrochloric acid/ethyl acetate solution was used instead of 4 N hydrochloric acid/1,4-dioxane solution, 4.44 g of (S)-2-azidopropylamine hydrochloride was obtained from 8.96 g of the compound of Reference Example 7(b).

Physicochemical Properties of this Compound (1) Molecular formula: $C_3H_8N_4$ (2) Mass spectrum (FAB): m/z 101 $(M+H)^+$ (3) $^1H$ NMR spectrum (300 MHz, $D_2O$) δ (ppm): 1.15 (d, 3-H), 2.71 (dd, 1-H), 2.92 (dd, 1-H), 3.73 (m, 2-H), 4.48 (br s, $NH_2$).

(d) In the same manner as in Reference Example 3(e), 684 mg of the title compound was obtained from 600 mg of the compound of Reference Example 7(c).

Physicochemical Properties of this Compound (1) Molecular formula: $C_{11}H_{16}N_4O$ (2) Mass spectrum (FAB): m/z 221 $(M+H)^+$ (3) Specific rotation: $[\alpha]_D^{19}$ −38° (c1.1, $CHCl_3$)

(4) $^1H$ NMR spectrum (300 MHz, $CDCl_3$) δ (ppm): 1.26 (d, 3-H), 2.59 (dd, 1-H), 2.70 (dd, 1-H), 3.76 (ddt, 2-H), 3.79 (s, $OCH_3$), 3.81 (s, $C_6H_4CH_2$), 6.87 (d, $C_6H_4$), 7.28 (d, $C_6H_4$).

Reference Example 8

Preparation Method of 3-(4-phenylbutylamino)propanol

In the same manner as in Reference Example 3(e), 374 mg of the title compound was obtained from 1.2 ml of 3-aminopropanol.

Physicochemical Properties of this Compound (1) Molecular formula: $C_{13}H_{21}NO$ (2) $^1H$ NMR spectrum (300 MHz, $CDCl_3$) δ (ppm): 1.56-1.74 (m, $C_6H_5CH_2(CH_2)_2CH_2$), 1.79 (quint, 2-H), 2.64 (t, $C_6H_5CH_2$), 2.77 (t, $C_6H_5CH_2(CH_2)_2CH_2$), 2.99 (t, 3-H), 3.82 (t, 1-H), 7.14-7.22 (m, $C_6H_5$), 7.24-7.31 (m, $C_6H_5$).

Reference Example 9

Preparation Method of N-(3-azidopropyl)-N-(4-phenylbutyl)amine (a) In the same manner as in Reference Example 3(a), 7.78 g of 3-(N-tert-butoxycarbonylamino)propanol was obtained from 3.00 ml of 3-amino-1-propanol.

Physicochemical Properties of this Compound (1) Molecular formula: $C_8H_{17}NO_3$ (2) $^1H$ NMR spectrum (300 MHz, $CDCl_3$) δ (ppm): 1.45 (s, $(CH_3)_3C$), 1.66 (quint, 2-H), 3.91 (t, OH), 3.29 (dt, 3-H), 3.27 (dt, 1-H), 4.74 (br s, NH).

(b) In the same manner as in Reference Example 3(b), 12.5 g of methanesulfonic acid 3-(tert-butoxycarbonylamino) propyl ester was obtained from 7.78 g of the compound of Reference Example 9(a).

Physicochemical Properties of this Compound (1) Molecular formula: $C_9H_{19}NO_5S$ (2) $^1$H NMR spectrum (300 MHz, $CDCl_3$) δ (ppm): 1.44 (s, $(CH_3)_3C$), 1.94 (quint, 2-H), 3.04 (s, $CH_3SO_3$), 3.27 (dt, 3-H), 4.30 (t, 1-H), 4.72 (br s, NH).

(c) In the same manner as in Reference Example 3(c), 8.29 g of N-(3-azidopropyl)-N-tert-butoxycarbonylamine was obtained from 12.5 g of the compound of Reference Example 9(b).

Physicochemical Properties of this Compound (1) Molecular formula: $C_8H_{16}N_4O_2$ (2) $^1$H NMR spectrum (300 MHz, $CDCl_3$) δ (ppm): 1.45 (s, $(CH_3)_3C$), 1.77 (quint, 2-H), 3.22 (dt, 1-H), 3.36 (t, 3-H), 4.63 (br s, NH).

(d) In the same manner as in Reference Example 3(d), except that 4 N hydrochloric acid/ethyl acetate solution was used instead of 4 N hydrochloric acid/1,4-dioxane solution, 6.30 g of N-(3-azidopropyl)amine hydrochloride was obtained from 8.29 g of the compound of Reference Example 9(c).

(e) In the same manner as in Reference Example 3(e), 560 mg of the title compound was obtained from 744 mg of the compound of Reference Example 9(d).

Physicochemical Properties of this Compound (1) Molecular formula: $C_{13}H_{20}N_4$ (2) $^1$H NMR spectrum (300 MHz, $CDCl_3$) δ (ppm): 1.62 (m, $C_6H_5CH_2(CH_2)_2CH_2$), 1.85 (quint, $CH_2CH_2CH_2N_3$), 2.56 (m, $C_6H_5CH_2$), 2.68 (m, $C_6H_5CH_2(CH_2)_2CH_2$), 2.74 (t, $CH_2CH_2CH_2N_3$), 3.33 (t, $CH_2CH_2CH_2N_3$), 6.16 (br s, NH), 7.08-7.13 (m, $C_6H_5$), 7.18-7.23 (m, $C_6H_5$).

Reference Example 10

Preparation Method of N-(3-azidobutyl)-N-(4-phenylbutyl) amine (a) In the same manner as in Reference Example 3(b), except that triethylamine was used instead of diisopropylethylamine, 9.30 g of 3-methanesulfonyloxybutyric acid ethyl ester was obtained from 5.00 g of 3-hydroxybutyric acid ethyl ester.

Physicochemical Properties of this Compound (1) Molecular formula: $C_6H_{12}O_5S$ (2) $^1$H NMR spectrum (300 MHz, $CDCl_3$) δ (ppm): 1.44 (d, 4-H), 2.52 (dd, 2-H), 2.73 (dd, 2-H), 2.97 (s, $CH_3SO_3$), 3.65 (s, $COOCH_3$), 5.07 (ddq, 3-H).

(b) In the same manner as in Reference Example 3(c), 4.11 g of 3-azidobutyric acid ethyl ester was obtained from 9.30 g of the compound of Reference Example 10(a).

Physicochemical Properties of this Compound (1) Molecular formula: $C_5H_9N_3O_2$ (2) $^1$H NMR spectrum (300 MHz, $CDCl_3$) δ (ppm): 1.25 (d, 4-H), 2.37 (dd, 2-H), 2.46 (dd, 2-H), 3.65 (s, $COOCH_3$), 3.90 (ddq, 3-H).

(c) In an amount of 100 mg of the compound of Reference Example 10(b) was dissolved in 5 ml of methylene chloride under argon atmosphere, added with 0.76 ml of a solution of diisobutylalminum hydride in toluene at −78° C., and stirred for 1 hour. The reaction mixture was added with 2 drops of methanol, diluted with 100 ml of diethyl ether, and then warmed to room temperature. The reaction mixture was added with 100 ml of saturated Rochelle salt aqueous solution, and stirred for 1 hour, and then the organic layer and the aqueous layer were separated. The aqueous layer was extracted twice with 20 ml of diethyl ether, and then the organic layers were combined, and washed with 100 ml of 25% brine. The organic layer was dried over anhydrous sodium sulfate, and then filtered. The filtrate was concentrated under reduced pressure to obtain 3-azidobutylaldehyde.

(d) The compound of Reference Example 10(c) was dissolved in 4 ml of 1,2-dichloroethane, added with 0.4 ml of acetic acid, 0.17 ml of 4-phenylbutylamine, and 189 mg of sodium triacetoxyborohydride under ice cooling, and stirred 16 hours with warming the reaction mixture to room temperature. The reaction mixture was added with 10 ml of ethyl acetate, and washed with 5 ml of 8% aqueous sodium hydrogencarbonate, and then the aqueous layer was extracted twice with ethyl acetate. The organic layers were combined, washed with 100 ml of 25% brine, dried over anhydrous sodium sulfate, and then filtered. The filtrate was concentrated under reduced pressure, and the resulting residue was purified by silica gel column chromatography (chloroform/methanol (10:1)) to obtain 36.1 mg of the title compound.

Physicochemical Properties of this Compound (1) Molecular formula: $C_{14}H_{22}N_4$ (2) $^1$H NMR spectrum (300 MHz, $CDCl_3$) δ (ppm): 1.21 (d, $CH(CH_3)N_3$), 1.61 (m, $C_6H_5CH_2(CH_2)_2CH_2$), 1.69 (m, $CH_2CH_2CH(CH_3)N_3$), 2.52-2.68 (m, $C_6H_5CH_2(CH_2)_2CH_2$), 2.70 (m, $CH_2CH_2CH(CH_3)N_3$), 3.52 (br dq., $CH_2CH_2CH(CH_3)N_3$), 5.13 (br s, NH), 7.08-7.12 (m, $C_6H_5$), 7.17-7.23 (m, $C_6H_5$).

Reference Example 11

Preparation Method of N-(3-azidobutyl)-N-(4-methoxybenzyl)amine

In the same manner as in Reference Example 10(d), except that 4-methoxybenzylamine was used instead of 4-phenylbutylamine, 648 mg of the title compound was obtained from the compound of Reference Example 10(c) synthesized by using 2.00 g of the compound of Reference Example 10(b).

Physicochemical Properties of this Compound (1) Molecular formula: $C_{12}H_{18}N_4O$ (2) $^1$H NMR spectrum (300 MHz, $CDCl_3$) δ (ppm): 1.20 (d, $CH(CH_3)N_3$), 1.59 (m., $CH_2CH_2CH(CH_3)N_3$), 2.64 (t, $CH_2CH_2CH(CH_3)N_3$), 3.52 (br dq., $CH_2CH_2CH(CH_3)N_3$), 3.75 (s., $OCH_3$), 4.29 (d, $C_6H_4CH_2$), 5.60 (br s, NH), 6.79 (dd, $C_6H_4$), 7.15 (dd, $C_6H_4$).

Reference Example 12

Preparation Method of N-(3-azido-5-hexenyl)-N-methylamine (a) In the same manner as in Reference Example 2(a), 7.10 g of 3-ethoxycarbonylaminopropanol was obtained from 8.00 ml of 3-aminopropanol.

Physicochemical Properties of this Compound (1) Molecular formula: $C_6H_{13}NO_3$ (2) $^1$H NMR spectrum (300 MHz, $CDCl_3$) δ (ppm): 1.17 (t, $COOCH_2CH_3$), 1.63 (quint, 2-H), 2.59 (t, OH), 3.27 (q, 3-H), 3.61 (q, 1-H), 4.05 (q., $COOCH_2CH_3$), 4.83 (br s, NH).

(b) In the same manner as in Reference Example 2(b), 3.37 g of 3-(N-methylamino)propanol was obtained from 7.10 g of the compound of Reference Example 12(a).

Physicochemical Properties of this Compound (1) Molecular formula: $C_4H_{11}NO$ (2) $^1$H NMR spectrum (300 MHz, $CDCl_3$) δ (ppm): 1.62 (quint, 2-H), 2.35 (s, $NCH_3$), 2.77 (t, 3-H), 3.74 (t, 1-H).

(c) In the same manner as in Reference Example 3(a), 5.12 g of 3-(N-tert-butoxycarbonyl-N-methylamino)propanol was obtained from 3.37 g of the compound of Reference Example 12(b).

Physicochemical Properties of this Compound (1) Molecular formula: $C_9H_{19}NO_3$ (2) $^1$H NMR spectrum (300 MHz, $CDCl_3$) δ (ppm): 1.40 (s, $(CH_3)_3C$), 1.61 (m, 2-H), 2.76 (s, $NCH_3$), 3.32 (m, 3-H), 3.47 (m, 1-H).

(d) In a volume of 24 ml of methylene chloride cooled to −78° C. was added with 1 ml of oxalyl chloride and 1.7 ml of dimethyl sulfoxide, stirred for 20 minutes, then added with a solution of 1.11 g of the compound of Reference Example 12(c) in 7 ml of methylene chloride and 6.6 ml of triethylamine, stirred at −78° C. for 40 minutes, and further stirred at room temperature for 40 minutes. The reaction mixture was diluted with 50 ml of ethyl acetate, and washed with 30 ml of water. The aqueous layer was extracted twice with 10 ml of ethyl acetate, and the organic layers were combined, and washed with 30 ml of 25% brine. The organic layer was dried over anhydrous sodium sulfate, and then filtered. The filtrate was concentrated under reduced pressure, and the resulting residue was purified by silica gel column chromatography (hexane/ethyl acetate (3:1)) to obtain 1.08 g of 3-(N-tert-butoxycarbonyl-N-methylamino) propionaldehyde.

Physicochemical Properties of this Compound (1) Molecular formula: $C_9H_{17}NO_3$ (2) $^1$H NMR spectrum (300 MHz, $CDCl_3$) δ (ppm): 1.38 (s, $(CH_3)_3C$), 2.61 (d t, 2-H), 2.80 (s, $NCH_3$), 3.47 (t, 3-H), 9.73 (t, 1-H).

(e) In an amount of 4.92 g of the compound of Reference Example 12(d) was dissolved in 148 ml of tetrahydrofuran under argon atmosphere, then cooled to −78° C., added with a solution of allyl magnesium bromide in 32 ml of tetrahydrofuran, and stirred for 1.5 hours. The reaction mixture was diluted with 200 ml of ethyl acetate, and washed with 100 ml of saturated aqueous ammonium chloride. The aqueous layer was extracted twice with 30 ml of ethyl acetate, and the organic layers were combined, and washed with 100 ml of 25% brine. The organic layer was dried over anhydrous sodium sulfate, and then filtered. The filtrate was concentrated under reduced pressure, and the resulting residue was purified by silica gel column chromatography (hexane/ethyl acetate (3:1)) to obtain 3.21 g of 6-(N-tert-butoxycarbonyl-N-methylamino)-1-hexen-4-ol.

Physicochemical Properties of this Compound (1) Molecular formula: $C_{12}H_{23}NO_3$ (2) $^1$H NMR spectrum (300 MHz, $CDCl_3$) δ (ppm): 1.39 (s, $(CH_3)_3C$), 1.60 (m, 5-H), 2.18 (m, 3-H), 2.76 (s, $NCH_3$), 3.47 (m, 6-H), 5.04 (m, 1-H), 5.78 (m, 2-H).

(f) In the same manner as in Reference Example 3(b), 2.82 g of 6-(N-tert-butoxycarbonyl-N-methylamino)-4-methanesulfonyloxy-1-hexene was obtained from 2.03 g of the compound of Reference Example 12(e).

Physicochemical Properties of this Compound (1) Molecular formula: $C_{13}H_{25}NO_5S$ (2) $^1$H NMR spectrum (300 MHz, $CDCl_3$) δ (ppm): 1.39 (s, $(CH_3)_3C$), 1.86 (dt, 5-H), 2.45 (m, 3-H), 2.78 (s, $NCH_3$), 2.96 (s, $CH_3SO_3$), 3.28 (br t, 6-H), 4.66 (quint, 4-H), 5.11 (m, 1-H), 5.71 (ddt, 2-H).

(g) In the same manner as in Reference Example 3(c), 1.63 g of 4-azido-6-(N-tert-butoxycarbonyl-N-methylamino)-1-hexene was obtained from 2.82 g of the compound of Reference Example 12(f).

Physicochemical Properties of this Compound (1) Molecular formula: $C_{12}H_{22}N_4O_2$ (2) $^1$H NMR spectrum (300 MHz, $CDCl_3$) δ (ppm): 1.39 (s, $(CH_3)_3C$), 1.64 (m, 5-H), 2.29 (dd, 3-H), 2.78 (s, $NCH_3$), 3.24 (br t, 6-H), 3.26 (m, 4-H), 5.10 (m, 1-H), 5.74 (dd t, 2-H).

(h) In the same manner as in Reference Example 3(d), 1.63 g of the compound of Reference Example 12(g) was reacted by using 4 N hydrochloric acid/ethyl acetate solution instead of 4 N hydrochloric acid/1,4-dioxane solution, and then the reaction mixture was concentrated. The resulting residue was purified by silica gel column chromatography (chloroform/methanol/aqueous ammonia (5:1:0.1)) to obtain 938 mg of the title compound.

Physicochemical Properties of this Compound (1) Molecular formula: $C_7H_{14}N_4$ (2) $^1$H NMR spectrum (300 MHz, $CDCl_3$) δ (ppm): 1.64 (m, 5-H), 2.27 (dd, 3-H), 2.38 (s, $NCH_3$), 2.63 (m, 6-H), 3.42 (m, 4-H), 5.09 (m, 1-H), 5.75 (dd t, 2-H).

Reference Example 13

Preparation Method of N-(3-azidopropyl)-N-(4-methoxybenzyl)amine

In the same manner as in Reference Example 3(e), except that 4-methoxybenzaldehyde was used instead of phenylbutylaldehyde, 1.51 g of the title compound was obtained from 1.09 g of the compound of Reference Example 9(d).

Physicochemical Properties of this Compound (1) Molecular formula: $C_{11}H_{16}N_4O$ (2) Mass spectrum (FAB): m/z 221 $(M+H)^+$ (3) $^1$H NMR spectrum (300 MHz, $CDCl_3$) δ (ppm): 1.77 (dt, $N_3CH_2CH_2$), 2.71 (t, $C_6H_4CH_2$), 3.37 (t, $N_3CH_2$), 3.72 (m, $N_3(CH_2)_2CH_2$), 3.80 (s, $OCH_3$), 6.86 (d, $C_6H_4$), 7.23 (d, $C_6H_4$).

Reference Example 14

Preparation Method of (−)-(R)—N-(4-hydroxypentyl)-N-(4-phenylbutyl)amine (a) In an amount of 2.86 g of (R)-2-tert-butyldimethylsilyloxypropionaldehyde (J. Org. Chem, 60, 7230 (1995)) was dissolved in 85 ml of benzene, added with 5.09 g of triphenylphosphoranilideneacetaldehyde, and stirred at 80° C. for 24 hours. The reaction mixture was concentrated under reduced pressure, and the resulting residue was purified by silica gel column chromatography (hexane/chloroform (1:1 to 1:2)) to obtain 2.52 g of (−)-(4$R_2$E)-4-tert-butyldimethylsilyloxy-2-pentenal.

Physicochemical Properties of this Compound (1) Molecular formula: $C_{11}H_{22}O_2Si$ (2) Specific rotation: $[\alpha]_D^{19}$ −17° (c1.5, $CHCl_3$)

(3) $^1H$ NMR spectrum (300 MHz, $CDCl_3$) δ (ppm): 0.08 and 0.09 (s, $Si(CH_3)_2$), 0.92 (s, $(CH_3)_3C$), 1.32 (d, 5-H), 4.58 (m, 4-H), 6.28 (ddd, 3-H), 6.81 (dd, 2-H), 9.59 (d, 1-H).

(b) In an amount of 1.83 g of the compound of Reference Example 14(a) was dissolved in 28 ml of methanol, added with 388 mg of sodium borohydride, and stirred at room temperature for 1 hours and 30 minutes. The reaction mixture was concentrated under reduced pressure, and then added with 60 ml of diethyl ether and 40 ml of 10% aqueous ammonium chloride, and the organic layer and the aqueous layer were separated. The organic layer was successively washed with 40 ml of water, and 40 ml of saturated brine, dried over anhydrous sodium sulfate, and then filtered. The filtrate was concentrated under reduced pressure, and the resulting residue was purified by silica gel column chromatography (hexane/ethyl acetate (5:1)) to obtain 1.69 g of (−)-(4$R_2$E)-4-tert-butyldimethylsilyloxy-2-pentenol.

Physicochemical Properties of this Compound (1) Molecular formula: $C_{11}H_{24}O_2Si$ (2) Mass spectrum (FAB): m/z 216 $(M)^+$ (3) Specific rotation: $[\alpha]_D^{25}$ −3.7° (c1.0, $CHCl_3$)

(4) $^1H$ NMR spectrum (300 MHz, $CDCl_3$) δ (ppm): 0.06 and 0.07 (each s, $Si(CH_3)_2$), 0.91 (s, $(CH_3)_3C$), 1.23 (d, 5-H), 1.30 (t, OH), 4.15 (t, 1-H), 4.34 (dq, 4-H), 5.68-5.85 (m, 2-H and 3-H).

(c) In an amount of 600 mg of the compound of Reference Example 14(b) was dissolved in 14 ml of ethyl acetate, and added with 6.3 mg of 10% Pd—C catalyst suspended in 2 ml of ethyl acetate. The reaction vessel was purged with hydrogen, the reaction mixture was stirred at room temperature for 1 hour, and then the catalyst was removed by filtration. The filtrate was concentrated under reduced pressure, and the resulting residue was purified by silica gel column chromatography (chloroform/ethyl acetate (30:1)) to obtain 1.69 g of (−)-(R)-4-tert-butyldimethylsilyloxypentanol.

Physicochemical Properties of this Compound (1) Molecular formula: $C_{11}H_{26}O_2Si$ (2) Mass spectrum (TSP): m/z 219 $(M+H)^+$ (3) Specific rotation: $[\alpha]_D^{21}$ −14° (c0.47, $CHCl_3$)

(4) $^1H$ NMR spectrum (300 MHz, $CDCl_3$) δ (ppm): 0.07 (s, $Si(CH_3)_2$), 0.90 (s, $(CH_3)_3C$), 1.16 (d, 5-H), 1.49-1.58 (m, 2-H), 1.59-1.70 (m, 3-H), 2.09 (br s, OH), 3.64 (m, 1-H), 3.90 (ddq, 4-H).

(d) In the same manner as in Reference Example 12(d), 390 mg of (R)-4-tert-butyldimethylsilyloxypentanal was obtained from 435 mg of the compound of Reference Example 14(c).

Physicochemical Properties of this Compound (1) Molecular formula: $C_{11}H_{24}O_2Si$ (2) $^1H$ NMR spectrum (300 MHz, $CDCl_3$) δ (ppm): 0.05 and 0.06 (each s, $Si(CH_3)_2$), 0.89 (s, $(CH_3)_3C$), 1.16 (d, 5-H), 1.65-1.87 (m, 3-H), 2.50 (dt, 2-H), 3.88 (ddq, 4-H), 9.79 (t, 1-H).

(e) In the same manner as in Reference Example 1, except that 1.3 ml of 4-phenylbutylamine was used instead of (−)-(R)-1-aminopropan-2-ol, and dimethylformamide was used instead of tetrahydrofuran, 525 mg of (−)-(R)—N-(4-tert-butyldimethylsilyloxypentyl)-N-(4-phenylbutyl)amine was obtained from 449 mg of the compound of Reference Example 14(d).

Physicochemical Properties of this Compound (1) Molecular formula: $C_{21}H_{39}NOSi$ (2) Mass spectrum (FAB): m/z 350 $(M+H)^+$ (3) Specific rotation: $[\alpha]_D^{23}$ −7.5° (c1.0, $CHCl_3$)

(4) $^1H$ NMR spectrum (300 MHz, $CDCl_3$) δ (ppm): 0.05 (s, $Si(CH_3)_2$), 0.89 (s, $(CH_3)_3C$), 1.13 (d, $CH_3CH$), 1.35-1.72 (m, $C_6H_5CH_2(CH_2)_2CH_2$ and $CH_2CH_2CH_2NH$), 2.54-2.68 (m, $CH_2NHCH_2$ and $C_6H_5CH_2$), 3.80 (ddq, CH), 7.14-7.22 (m, $C_6H_5$), 7.24-7.32 (m, $C_6H_5$).

(f) In an amount of 525 mg of the compound of Reference Example 14(e) was dissolved in 3 ml of tetrahydrofuran, added with 2.3 ml of a 1 M solution of tetrabutylammonium fluoride in tetrahydrofuran, and stirred at room temperature for 48 hours. The reaction mixture was concentrated under reduced pressure, and then added with 60 ml of chloroform and 60 ml of water, and the organic layer and the aqueous layer were separated. The aqueous layer was saturated with sodium chloride, and extracted twice with 30 ml of chloroform, and the organic layers were combined, dried over anhydrous sodium sulfate, and then filtered. The filtrate was concentrated under reduced pressure, and the resulting residue was purified by silica gel column chromatography (chloroform/methanol/aqueous ammonia (20:1:0.1)), and then further purified by silica gel column chromatography (chloroform/methanol/aqueous ammonia (15:1:0.1)) to obtain 100 mg of the title compound.

Physicochemical Properties of this Compound (1) Molecular formula: $C_{15}H_{25}NO$ (2) Mass spectrum (FAB): m/z 236 $(M+H)^+$ (3) Specific rotation: $[\alpha]_D^{19}$ −20° (c1.0, $CHCl_3$)

(4) $^1H$ NMR spectrum (300 MHz, $CDCl_3$) δ (ppm): 1.17 (d, $CH_3CH$), 1.34-1.83 (m, $C_6H_5CH_2(CH_2)_2CH_2$ and $CH_2CH_2CH_2NH$), 2.47-2.83 (m, $CH_2NHCH_2$ and $C_6H_5CH_2$), 3.72 (ddq, CH), 7.13-7.21 (m, $C_6H_5$), 7.23-7.31 (m, $C_6H_5$).

Reference Example 15

Preparation Method of trans-(4-phenylbutylamino)-3-penten-2-ol (a) In the same manner as in Reference Example 3(b), 1.55 g of trans-methanesulfonic acid 4-tert-butyldimethylsilyloxy-2-pentenyl ester was obtained from 1.20 g of trans-4-tert-butyldimethylsilyloxypentan-2-en-1-ol, which was obtained from 2-tert-butyldimethylsilyloxypropionaldehyde in the same manner as in Reference Example 14(a) and (b).

Physicochemical Properties of this Compound (1) Molecular formula: $C_{12}H_{26}O_4SSi$ (2) Mass spectrum (FAB): m/z 295 $(M+H)^+$ (3) $^1H$ NMR spectrum (300 MHz, $CDCl_3$) δ (ppm): 0.07 and 0.08 (each s, $Si(CH_3)_2$), 0.91 (s, $(CH_3)_3C$), 1.23 (d, 5-H), 3.02 (s, $CH_3SO_2$), 4.36 (ddq, 4-H), 4.73 (d, 1-H), 5.79 (ddt, 2-H), 5.93 (dd, 3-H).

(b) In an amount of 1.55 g of the compound Reference Example 15(a) was dissolved in 23 ml of dimethylformamide, added with 411 mg of sodium azide, and stirred at room temperature for 3 hours. The reaction mixture was added with 100 ml of diethyl ether, successively washed twice with 60 ml of water and twice with 60 ml of saturated brine, dried over anhydrous magnesium sulfate, and then filtered. The filtrate was concentrated under reduced pressure, and the resulting residue was purified by silica gel column chromatography (hexane/diethyl ether (10:1)) to obtain 0.943 g of trans-1-azido-4-tert-butyldimethylsilyloxy-2-pentene.

Physicochemical Properties of this Compound (1) Molecular formula: $C_{11}H_{23}N_3OSi$ (2) $^1H$ NMR spectrum (300 MHz, $CDCl_3$) δ (ppm): 0.07 and 0.08 (each s, $Si(CH_3)_2$), 0.91 (s, $(CH_3)_3C$), 1.24 (d, 5-H), 3.75 (d, 1-H), 4.36 (ddq, 4-H), 5.69 (ddt, 2-H), 5.81 (dd, 3-H).

(c) In an amount of 718 mg of the compound of Reference Example 15(b) was dissolved in 11 ml of acetonitrile/water (9:1), added with 930 mg of triphenylphosphine, and stirred at room temperature for 27 hours. The reaction mixture was concentrated under reduced pressure, and the resulting residue was purified by silica gel column chromatography (chloroform/methanol/aqueous ammonia (30:1:0.1 to 20:1:0.1)) to obtain 398 mg of trans-4-tert-butyldimethylsilyloxy-2-pentenylamine.

Physicochemical Properties of this Compound (1) Molecular formula: $C_{11}H_{25}NOSi$ (2) Mass spectrum (FAB): m/z 216 $(M+H)^+$ (3) $^1H$ NMR spectrum (300 MHz, $CDCl_3$) δ (ppm): 0.07 and 0.08 (each s, $Si(CH_3)_2$), 0.91 (s, $(CH_3)_3C$), 1.21 (d, 5-H), 3.30 (d, 1-H), 4.32 (ddq, 4-H), 5.59 (dd, 3-H), 5.71 (ddt, 2-H).

(d) In the same manner as in Reference Example 1, except that 1.3 ml of 4-phenylbutylamine was used instead of (−)-(R)-1-aminopropan-2-ol, and dimethylformamide was used instead of tetrahydrofuran, 15 mg of N-(trans-4-tert-butyldimethylsilyloxy-2-pentenyl)-N-(4-phenylbutyl)amine was obtained from 30 mg of the compound of Reference Example 15(d).

Physicochemical Properties of this Compound (1) Molecular formula: $C_{21}H_{37}NOSi$ (2) Mass spectrum (EI): m/z 347 (M)+

(3) $^1H$ NMR spectrum (300 MHz, $CDCl_3$) δ (ppm): 0.06 and 0.07 (each s, $Si(CH_3)_2$), 0.90 (s, $(CH_3)_3C$), 1.21 (d, $CH_3CH$), 1.54 and 1.67 (each quint, $C_6H_5CH_2(CH_2)_2CH_2$), 2.63 and 2.64 (each t, $C_6H_5CH_2(CH_2)_2CH_2$), 3.21 (d, $CH_2NH$), 4.30 (dq, $CH_3CH$), 5.56-5.72 (m, CH═CH), 7.15-7.22 (m, $C_6H_5$), 7.24-7.32 (m, $C_6H_5$).

Further, besides the aforementioned method, N-(trans-4-tert-butyldimethylsilyloxy-2-pentenyl)-N-(4-phenylbutyl)amine was prepared by the method described below.

(e) In an amount of 262 mg of the compound of Reference Example 15(c) and 285 mg of 4-phenylbutyl bromide were dissolved in 8 ml of ethanol, added with 202 mg of potassium carbonate and 547 mg of sodium iodide, and stirred at 70° C. for 28 hours. The reaction mixture was filtered, and then the filtrate was concentrated under reduced pressure. The resulting residue was added with 10 ml of saturated brine, and extracted three times with 20 ml of chloroform. The organic layer was dried over anhydrous sodium sulfate, and filtered, and then the filtrate was concentrated under reduced pressure. The resulting residue was purified by silica gel column chromatography (chloroform/methanol (50:1 to 10:1)) to obtain 47 mg of N-(trans-4-tert-butyldimethylsilyloxy-2-pentenyl)-N-(4-phenylbutyl)amine.

(f) In an amount of 148 mg of the compound of Reference Example 15(d) was dissolved in 4.5 ml of methylene chloride, added with 0.5 ml of trifluoroacetic acid, and stirred at room temperature for 6 hours. The reaction mixture was concentrated under reduced pressure, then added with 3 ml of 2 N hydrochloric acid, and washed twice with 10 ml of diethyl ether. The aqueous layer was made alkaline with potassium carbonate and potassium hydroxide, then added with 20 ml of water and 20 ml of saturated brine, and extracted 4 times with 25 ml of chloroform. The organic layer was dried over anhydrous sodium sulfate, and then filtered. The filtrate was concentrated under reduced pressure to obtain 83 mg of the title compound.

Physicochemical Properties of this Compound (1) Molecular formula: $C_{15}H_{23}NO$ (2) Mass spectrum (EI): m/z 233 (M)+

(3) $^1H$ NMR spectrum (300 MHz, $CDCl_3$) δ (ppm): 1.24 (d, $CH_3CH$), 1.68 and 1.84 (each quint, $C_6H_5CH_2(CH_2)_2CH_2$), 2.63 and 2.87 (each t, $C_6H_5CH_2(CH_2)_2CH_2$), 3.45 (d, $CH_2NH$), 4.31 (dq, $CH_3CH$), 5.81-5.97 (m, CH═CH), 7.17 (t, $C_6H_5$), 7.26 (t, $C_6H_5$).

Reference Example 16

Preparation Method of 7-methylamino-1-hepten-4-ol (a) In an amount of 25.5 g of 4-aminobutanol was dissolved in 255 ml of a mixed solvent of acetone/water (3:1). Under ice cooling, the mixture was added with 43.5 g of potassium carbonate, added dropwise with 27.6 ml of ethyl chloroformate over 13 minutes, and then stirred for 2 hours. The reaction mixture was added with 100 ml of water, and extracted with 100 ml of ethyl acetate, and then the organic layer was washed with saturated brine. The organic layer was dried over anhydrous magnesium sulfate, and then filtered. The filtrate was concentrated under reduced pressure to obtain 45.3 g of 4-ethoxycarbonylaminobutanol.

Physicochemical Properties of this Compound (1) Molecular formula: $C_7H_{15}NO_3$ (2) Mass spectrum (FAB): m/z 162 $(M+H)^+$ (3) $^1H$ NMR spectrum (400 MHz, $CDCl_3$) δ (ppm): 1.17 (t, $CO_2CH_2CH_3$), 1.43-1.56 (m, $CH_2CH_2CH_2CH_2$), 3.15 (q, 4-H), 3.61 (dt, 1-H), 4.04 (q, $CO_2CH_2CH_3$), 4.69 (br s, NH).

(b) In the same manner as in Reference Example 2(b), 23.1 g of 4-methylaminobutanol was obtained from 46.1 g of the compound of Reference Example 16(a). From 23.1 g of this compound, 45.5 g of 4-(N-tert-butoxycarbonyl-N-methylamino)butanol was obtained in the same manner as in Reference Example 3(a).

Physicochemical Properties of this Compound (1) Molecular formula: $C_{10}H_{21}NO_3$ (2) Mass spectrum (FAB): m/z 204 $(M+H)^+$ (3) $^1H$ NMR spectrum (400 MHz, $CDCl_3$) δ (ppm): 1.43 (s, $(CH_3)_3C$), 1.48-1.68 (m, $CH_2CH_2CH_2CH_2$), 2.82 (s, $NCH_3$), 3.23 (t, 4-H), 3.65 (t, 1-H).

(c) In the same manner as in Reference Example 12(d), 29.6 g of 4-(N-tert-butoxycarbonyl-N-methylamino)butanal was obtained from 45.5 g of the compound of Reference Example 16(b).

Physicochemical Properties of this Compound (1) Molecular formula: $C_{10}H_{19}NO_3$ (2) Mass spectrum (FAB): m/z 202 $(M+H)^+$ (3) $^1H$ NMR spectrum (400 MHz, $CDCl_3$) δ (ppm): 1.42 (s, $(CH_3)_3C$), 1.77-1.86 (m, $CH_2CH_2CH_2$), 2.44 (t, 2-H), 2.81 (s, $NCH_3$), 3.23 (t, 4-H), 9.76 (s, CHO).

(d) In the same manner as in Reference Example 12(e), 8.5 g of 7-(N-tert-butoxycarbonyl-N-methylamino)-1-hepten-4-ol was obtained from 18.1 g of the compound of Reference Example 16(c).

Physicochemical Properties of this Compound (1) Molecular formula: $C_{13}H_{25}NO_3$ (2) Mass spectrum (FAB): m/z 244 $(M+H)^+$ (3) $^1H$ NMR spectrum (400 MHz, $CDCl_3$) δ (ppm): 1.42 (s, $(CH_3)_3C$), 1.50-1.72 (m, $CH_2CH_2CH_2CH_2$), 2.13 (ddd, 3-H), 2.22-2.32 (m, 3-H), 2.81 (s, $NCH_3$), 3.19 (t, 7-H), 3.59-3.37 (m, 4-H), 5.11 (d, 1-H). 5.73-5.86 (m, 2-H).

(e) In the same manner as in Reference Example 3(d), 847 mg of the title compound was obtained from 1.56 g of the compound of Reference Example 16(d).

Physicochemical Properties of this Compound (1) Molecular formula: $C_8H_{17}NO$ (2) Mass spectrum (ES): m/z 144 $(M+H)^+$

Reference Example 17

Preparation Method of (−)-(S)-7-methylamino-1-hepten-4-ol (a) In an amount of 3.0 g of (S)-5-amino-2-hydroxypentanoic acid (YAKUGAKU ZASSHI, Vol 87, 1184-1188 (1967)) was dissolved in 15 ml of a mixed solvent of dioxane/water (1:1), successively added with 6.28 ml of triethylamine, and 5.69 ml of di-tert-butyl dicarbonate, and stirred at room temperature for 4 hours. The reaction mixture was added with saturated aqueous sodium hydrogencarbonate, and washed with ethyl acetate, and then the aqueous layer was adjusted to pH 3 with 1 N hydrochloric acid. The aqueous layer was extracted with ethyl acetate, and the organic layer was dried over anhydrous magnesium sulfate, and filtered. Then, the filtrate was concentrated under reduced pressure to obtain 5.58 g of (S)-5-tert-butoxycarbonylamino -2-hydroxypentanoic acid.

Physicochemical Properties of this Compound (1) Molecular formula: $C_{10}H_{19}NO_5$ (2) Mass spectrum (FAB): m/z 234 $(M+H)^+$ (3) Specific rotation: $[\alpha]_D^{27}$ +2° (c1.2, $CHCl_3$)

(4) $^1H$ NMR spectrum (400 MHz, $CDCl_3$) δ (ppm): 1.42 (s, $(CH_3)_3C$), 1.52-1.92 (m, 3-H and 4-H), 3.15 (br s, 5-H), 4.25 (br s, 2-H), 4.81 (br s, NH), 6.17 (br s, NH).

(b) In the same manner as in Reference Example 2(b), 1.85 g of (S)-5-methylaminopentane-1,2-diol was obtained from 3.83 g of the compound of Reference Example 17(a).

Physicochemical Properties of this Compound (1) Molecular formula: $C_6H_{15}NO_2$ (2) Mass spectrum (FAB): m/z 134 $(M+H)^+$ (c) In an amount of 1.85 g of the compound of Reference Example 17(b) was dissolved in a mixed solvent of dioxane/water (2:1), successively added with 6.88 ml of triethylamine, and 7.18 g of di-tert-butyl dicarbonate, and stirred at room temperature for 4 hours. The reaction mixture was added with 20% aqueous ammonium chloride, and extracted with ethyl acetate, and the organic layer was concentrated. The resulting residue was dissolved in 30 ml of a mixed solvent of methanol/water (2:1), and added with 4.7 g of granular potassium hydroxide, and disappearance of the compound of which hydroxyl group was protected with tert-butoxycarbonyl group was confirmed. The reaction mixture was added with 3 ml of 28% aqueous ammonia, and extracted with ethyl acetate, and then the organic layer was concentrated under reduced pressure. The resulting residue was purified by silica gel column chromatography (chloroform/methanol (20:1)) to obtain 832 mg of (S)-5-(N-tert-butoxycarbonyl-N-methylamino)pentane-1,2-diol.

Physicochemical Properties of this Compound (1) Molecular formula: $C_{11}H_{23}NO_4$ (2) Mass spectrum (FAB): m/z 234 $(M+H)^+$ (3) $^1H$ NMR spectrum (400 MHz, $CDCl_3$) δ (ppm): 1.30-1.38 (m, 4-H), 1.39 (s, $(CH_3)_3C$), 1.51-1.66 (m, 3-H), 2.77 (s, $NCH_3$), 3.05-3.32 (m, 5-H), 3.37 (dd, 1-H), 3.55 (dd, 1-H), 3.61-3.72 (m, 2-H).

(d) In an amount of 832 mg of the compound of Reference Example 17(c) was dissolved in 8.3 ml of methylene chloride, successively added with 17.7 mg of dibutyltin oxide, 497 μl of triethylamine, and 680 mg of p-toluenesulfonyl chloride, and stirred at room temperature for 9 hours. The reaction mixture was filtered, and the filtrate was added with water, and then extracted with chloroform. The organic layer was concentrated, and the resulting residue was purified by silica gel column chromatography (hexane/ethyl acetate (3:2)) to obtain 993 mg of (S)-5-(N-tert-butoxycarbonyl-N-methylamino)-1-(p-toluenesulfonyloxy)-2-pentanol.

Physicochemical Properties of this Compound (1) Molecular formula: $C_8H_{29}NO_6S$ (2) Mass spectrum (FAB): m/z 388 $(M+H)^+$ (3) $^1H$ NMR spectrum (400 MHz, $CDCl_3$) δ (ppm): 1.37 (s, $(CH_3)_3C$), 1.48-1.63 (m, 3-H and 4-H), 2.39 (s, $CH_3C_6H_4$), 2.74 (s, $NCH_3$), 3.10 (br s, 5-H), 3.75-3.85 (m, 1-H), 3.88-3.97 (m, 2-H), 7.29 (d, $C_6H_4$), 7.73 (d, $C_6H_4$).

(e) In an amount of 993 mg of the compound of Reference Example 17(d) was dissolved in 6.1 ml of methanol, added with 3.84 ml of a 2 N solution of sodium methoxide in methanol, and stirred at room temperature for 40 minutes. The reaction mixture was added with 20% aqueous ammonium chloride, and extracted with ethyl acetate, and then the organic layer was concentrated under reduced pressure. The resulting residue was purified by silica gel column chromatography (hexane/ethyl acetate (2:1)) to obtain 475 mg of (−)-(S)—N-tert-butoxycarbonyl-N-(4,5-epoxypentyl)-N-methylamine.

Physicochemical Properties of this Compound (1) Molecular formula: $C_{11}H_{21}NO_3$ (2) Mass spectrum (FAB): m/z 216 $(M+H)^+$ (3) Specific rotation: $[\alpha]_D^{23}$ −5.3 (c1.0, $CHCl_3$)

(4) $^1H$ NMR spectrum (400 MHz, $CDCl_3$) δ (ppm): 1.38 (s, $(CH_3)_3C$), 1.48-1.69 (m, 3-H and 4-H), 2.42 (dd, 5-H), 2.70 (t, 5-H), 2.78 (s, $NCH_3$), 2.84-2.90 (m, 4-H), 3.19 (t, 1-H).

(f) A suspension of copper(I) cyanide (522 mg) in tetrahydrofuran (13 ml) was cooled to −40° C., added dropwise with 12 ml of a 0.97 M solution of vinyl magnesium bromide in tetrahydrofuran over 5 minutes, and then stirred for 30 minutes. The reaction mixture was added dropwise with a solution of 418 mg of the compound of Reference Example 17(e) in tetrahydrofuran (3.7 ml) over 5 minutes, and then further stirred at −30 to −20° C. for 3 hours. The reaction mixture was added with 45 ml of a mixture of 28% aqueous ammonia/20% aqueous ammonium chloride (3:1), and stirred until the aqueous layer became transparent in blue. The aqueous layer was extracted with ethyl acetate, and the organic layer was dried over anhydrous magnesium sulfate, and then filtered. The filtrate was concentrated under reduced pressure, and the resulting residue was purified by silica gel column chromatography (hexane/ethyl acetate (2:1)) to obtain 440 mg of (−)-(S)-7-(N-tert-butoxycarbonyl-N-methylamino)-1-hepten-4-ol.

Physicochemical Properties of this Compound (1) Molecular formula: $C_{13}H_{25}NO_3$ (2) Mass spectrum (FAB): m/z 244 $(M+H)^+$ (3) Specific rotation: $[\alpha]_D^{21}$ −7.4 (c1.5, $CHCl_3$)

(4) $^1H$ NMR spectrum (400 MHz, $CDCl_3$) δ (ppm): 1.42 (s, $(CH_3)_3C$), 1.50-1.72 (m, $CH_2CH_2CH_2CH_2$), 2.13 (ddd, 3-H), 2.22-2.32 (m, 3-H), 2.81 (s, $NCH_3$), 3.19 (t, 7-H), 3.59-3.37 (m, 4-H), 5.11 (d, 1-H). 5.73-5.86 (m, 2-H).

(g) In the same manner as in Reference Example 3(d), 229 mg of the title compound was obtained from 440 mg of the compound of Reference Example 17(f).

Physicochemical Properties of this Compound (1) Molecular formula: $C_8H_{17}NO$ (2) Mass spectrum (ES): m/z 144 $(M+H)^+$ (3) Specific rotation: $[\alpha]_D^{20}$ −8.7° (c1.2, MeOH)

Reference Example 18

Preparation Method of 3-methylaminomethyl-5-hexenol (a) In an amount of 112 mg of 3-allyldihydrofuran-2-one (WO99/36419) was dissolved in 1 ml of 1,2-dimethoxyethane, added with 1.2 ml of 28% aqueous ammonia, and stirred at room temperature for 17 hours. The reaction mixture was concentrated under reduced pressure to obtain 130 mg of 1-(2-hydroxyethyl)-3-butenecarboxamide.

Physicochemical Properties of this Compound (1) Molecular formula: $C_7H_{13}NO_2$ (2) Mass spectrum (EI): m/z 145 (M)+

(3) $^1H$ NMR spectrum (300 MHz, $CDCl_3$) δ (ppm): 1.78 (m, $HOCH_2CH_2$), 2.21 (m, 2-H), 2.40 (m, 2-H), 2.47 (m, 1-H), 3.68 (m, $HOCH_2CH_2$), 5.05 (dd, 4-H), 5.09 (dd, 4-H), 5.76 (m, 3-H), 5.92 (br d, $NH_2$).

(b) In the same manner as in Reference Example 2(b), 90 mg of 3-aminomethyl-5-hexenol was obtained from 130 mg of the compound of Reference Example 18(a).

Physicochemical Properties of this Compound (1) Molecular formula: $C_7H_{15}NO$ (2) Mass spectrum (FAB): m/z 130 $(M+H)^+$ (3) $^1H$ NMR spectrum (300 MHz, $CDCl_3$) δ (ppm): 1.37-1.75 (m, 2-H and 3-H), 2.01 (m, 4-H), 2.44 (dd, 3-$CH_2$), 2.82 (dd, 3-$CH_2$), 3.51 (m, 1-H), 3.63 (m, 1-H), 4.97 (dd, 1H), 4.93-5.02 (dd, 6-H), 5.72 (m, 5-H).

(c) In the same manner as in Reference Example 3(a), 2.27 g of 3-(tert-butoxycarbonylaminomethyl)-5-hexenol was obtained as a crude product from 1.28 g of the compound of Reference Example 18(b).

Physicochemical Properties of this Compound (1) Molecular formula: $C_{12}H_{23}NO_3$ (2) Mass spectrum (FAB): m/z 230 $(M+H)^+$ (3) $^1H$ NMR spectrum (300 MHz, $CDCl_3$) δ (ppm): 1.43 (s, $C(CH_3)_3$), 1.45-1.81 (m, 2-H and 3-H), 2.05 (t, 4-H), 3.11 (dd, 3-$CH_2$), 3.71 (m, 1-H), 5.00-5.09 (m, 6-H), 5.77 (m, 5-H).

(d) In the same manner as in Reference Example 2(b), 1.34 g of the title compound was obtained from 2.27 g of the compound of Reference Example 18(c).

Physicochemical Properties of this Compound (1) Molecular formula: $C_8H_{17}NO$ (2) Mass spectrum (FAB): m/z 144 $(M+H)^+$ (3) $^1H$ NMR spectrum (300 MHz, $CDCl_3$) δ (ppm): 1.45 (m, 2-H), 1.57 (m, 3-H), 1.76 (m, 2-H), 2.02 (m, 4-H), 2.33 (dd, 3-$CH_2$), 2.39 (s, $NCH_3$), 2.65 (dd, 3-$CH_2$), 3.46 (ddd, $HOCH_2$), 3.65 (ddd, $HOCH_2$), 5.00 (m, 1-H), 5.73 (m, 2-H).

Reference Example 19

Preparation Method of N-(4-azidobutyl)-N-(4-phenylbutyl)amine (a) In the same manner as in Reference Example 3(a), 7.16 g of 4-(N-tert-butoxycarbonylamino)butanol was obtained from 3.00 ml of 4-amino-1-butanol.

Physicochemical Properties of this Compound (1) Molecular formula: $C_9H_{19}NO_3$ (2) $^1H$ NMR spectrum (300 MHz, $CDCl_3$) δ (ppm): 1.37 (s, $(CH_3)_3C$), 1.47-1.58 (m, 2-H and 3-H), 3.09 (m, 4-H), 3.60 (dt, 1-H), 4.52 (br s, NH).

(b) In the same manner as in Reference Example 3(b), 12.2 g of methanesulfonic acid 4-(tert-butoxycarbonylamino)butyl ester was obtained from 7.16 g of the compound of Reference Example 19(a).

Physicochemical Properties of this Compound (1) Molecular formula: $C_{10}H_{21}NO_5S$ (2) $^1H$ NMR spectrum (300 MHz, $CDCl_3$) δ (ppm): 1.37 (s, $(CH_3)_3C$), 1.54 (m, 3-H), 1.72 (m, 2-H), 2.94 (s, $CH_3SO_3$), 3.10 (dt, 4-H), 4.18 (t, 1-H), 4.48 (br s, NH).

(c) In the same manner as in Reference Example 3(c), 7.95 g of unpurified N-(4-azidobutyl)-N-tert-butoxycarbonylamine was obtained from 12.2 g of the compound of Reference Example 19(b).

Physicochemical Properties of this Compound (1) Molecular formula: $C_9H_{18}N_4O_2$ (2) $^1H$ NMR spectrum (300 MHz, $CDCl_3$) δ (ppm): 1.37 (s, $(CH_3)_3C$), 1.42-1.62 (m, 2-H and 3-H), 3.08 (dt, 1-H), 3.23 (t, 4-H), 4.47 (br s, NH).

(d) In the same manner as in Reference Example 3(d), except that 4 N hydrochloric acid/ethyl acetate solution was used instead of 4 N hydrochloric acid/1,4-dioxane solution, 3.96 g of 4-azidobutylamine was obtained from 7.95 g of the compound of Reference Example 19(c). From 781 mg of this compound, 550 mg of the title compound was obtained in the same manner as in Reference Example 3(e).

Physicochemical Properties of this Compound (1) Molecular formula: $C_{14}H_{22}N_4$ (2) $^1H$ NMR spectrum (300 MHz, $CDCl_3$) δ (ppm): 1.50-1.67 (m, $C_6H_5CH_2(CH_2)_2CH_2$ and $CH_2CH_2CH_2N_3$), 2.56 (m, $C_6H_5CH_2$), 2.60-2.70 (m, $CH_2NHCH_2$), 3.21 (t, $CH_2CH_2CH_2N_3$), 5.10 (br s, NH), 7.08-7.12 (m, $C_6H_5$), 7.17-7.23 (m, $C_6H_5$).

Reference Example 20

Preparation Method of N-(4-azidopentyl)-N-methylamine (a) In the same manner as in Reference Example 12(e), except that a solution of methyl magnesium bromide in tetrahydrofuran was used instead of the solution of allyl magnesium bromide in tetrahydrofuran, 360 mg of 5-(N-tert-butoxycarbonyl-N-methyl)amino-2-pentanol was obtained from 374 mg of the compound of Reference Example 16(c).

Physicochemical Properties of this Compound (1) Molecular formula: $C_{11}H_{23}NO_3$ (2) $^1$H NMR spectrum (300 MHz, $CDCl_3$) δ (ppm): 1.12 (d, 1-H), 1.30-1.60 (m, 3-H and 4-H), 1.38 (s, $(CH_3)_3C$), 2.76 (s, $NCH_3$), 3.14 (t, 5-H), 3.75 (m, 2-H).

(b) In the same manner as in Reference Example 3(b), 646 mg of methanesulfonic acid 4-(N-tert-butoxycarbonyl-N-methyl)amino-1-methylbutyl ester was obtained from 391 mg of the compound of Reference Example 20(a).

Physicochemical Properties of this Compound (1) Molecular formula: $C_{12}H_{25}NO_5S$ (2) $^1$H NMR spectrum (300 MHz, $CDCl_3$) δ (ppm): 1.36 (d, 1-$CH_3$), 1.38 (s, $(CH_3)_3C$), 1.45-1.64 (m, 2-H and 3-H), 2.77 (s, $NCH_3$), 2.94 (s, $CH_3SO_3$), 3.19 (m, 4-H), 4.77 (m, 1-H).

(c) In the same manner as in Reference Example 3(c), 523 mg of N-(4-azidopentyl)-N-tert-butoxycarbonyl-N-methylamine was obtained from 646 mg of the compound of Reference Example 20(b).

Physicochemical Properties of this Compound (1) Molecular formula: $C_{11}H_{22}N_4O_2$ (2) $^1$H NMR spectrum (300 MHz, $CDCl_3$) δ (ppm): 1.19 (d, 1-H), 1.38 (s, $(CH_3)_3C$), 1.32-1.67 (m, 3-H and 4-H), 2.77 (s, $NCH_3$), 3.14 (br t, 5-H), 3.40 (m, 2-H).

(d) In the same manner as in Reference Example 5(d), the title compound was obtained from the compound of Reference Example 20(c). This compound was used in the reaction of Example 65(a) without purification.

Reference Example 21

Preparation Method of (−)-(R)—N-(4-hydroxypentyl)-N-(3-(quinolin-4-yl)propyl)amine (a) In the same manner as in Reference Example 3(b), except that triethylamine was used instead of diisopropylethylamine, 1.35 g of methanesulfonic acid (R)-4-tert-butyldimethylsilyloxypentyl ester was obtained from 1 g of the compound of Reference Example 14(c).

Physicochemical Properties of this Compound (1) Molecular formula: $C_{12}H_{28}O_4SSi$ (2) Mass spectrum (FAB): m/z 297 $(M+H)^+$ (3) $^1$H NMR spectrum (300 MHz, $CDCl_3$) δ (ppm): 0.06 and 0.07 (s, $Si(CH_3)_2$), 0.89 (s, $(CH_3)_3C$), 1.15 (d, 5-H), 1.53 (m, 3-H), 1.82 (m, 2-H), 3.01 (s, $CH_3SO_3$), 3.85 (ddq, 4-H), 4.25 (t, 1-H).

(b) In the same manner as in Reference Example 3(c), 1.35 g of (R)-(5-azidopentan-2-yloxy)(tert-butyl)dimethylsilane was obtained from 1.35 g of the compound of Reference Example 21(a).

Physicochemical Properties of this Compound (1) Molecular formula: $C_{11}H_{25}N_3OSi$ (2) Mass spectrum (ES): m/z 244 $(M+H)^+$ (3) $^1$H NMR spectrum (300 MHz, $CDCl_3$) δ (ppm): 0.06 and 0.07 (s, $Si(CH_3)_2$), 0.90 (s, $(CH_3)_3C$), 1.15 (d, 1-H), 1.50 (m, 4-H), 1.66 (m, 3-H), 3.28 (t, 5-H), 3.83 (ddq, 2-H).

(c) In the same manner as in Reference Example 14(c), except that ethanol was used instead of ethyl acetate, 933 mg of (R)—N-(4-tert-butyldimethylsilyloxypentyl)amine was obtained from 1.07 g of the compound of Reference Example 21(b).

Physicochemical Properties of this Compound (1) Molecular formula: $C_{11}H_{27}NOSi$ (2) Mass spectrum (ES): m/z 218 $(M+H)^+$ (3) $^1$H NMR spectrum (300 MHz, $CDCl_3$) δ (ppm): 0.06 (s, $Si(CH_3)_2$), 0.90 (s, $(CH_3)_3C$), 1.14 (d, 5-H), 1.36-1.60 (m, 2-H and 3-H), 2.69 (t, 1-H), 3.81 (ddq, 4-H).

(d) In the same manner as in Reference Example 1, except that 3-(quinolin-4-yl)propanal was used instead of 4-phenylbutylaldehyde, 152 mg of N—((R)-4-tert-butyldimethylsilyloxypentyl)-N-(3-(quinolin-4-yl)propyl)amine was obtained from 211 mg of the compound of Reference Example 21(c).

Physicochemical Properties of this Compound (1) Molecular formula: $C_{23}H_{38}N_2OSi$ (2) Mass spectrum (FAB): m/z 387 $(M+H)^+$ (3) $^1$H NMR spectrum (300 MHz, $CDCl_3$) δ (ppm): 0.05 (each s, $Si(CH_3)_2$), 0.89 (s, $(CH_3)_3C$), 1.14 (d, $\underline{CH_3}CH$), 1.32-1.66 (m, $CH\underline{(CH_2)_2}$), 1.96 (m, quinoline —$CH_2\underline{CH_2}$), 2.62 (t, $CH(CH_2)_2\underline{CH_2}$), 2.74 (t, quinoline-$(CH_2)_2\underline{CH_2}$), 3.14 (br dd, quinoline-$CH_2$), 3.81 (ddq, CH), 7.26 (d, quinoline), 7.56 (ddd, quinoline), 7.71 (ddd, quinoline), 8.07 (dd, quinoline), 8.12 (dd, quinoline), 8.82 (d, quinoline).

(e) In an amount of 148 mg of the compound of Reference Example 21(d) was added with 4.5 ml of methylene chloride and dissolved therein, added with 300 μl of trifluoroacetic acid, and stirred at room temperature for 4 hours. The reaction mixture was added with 5 ml of water and 4 ml of 1 N aqueous sodium hydroxide, and extracted 4 times with 10 ml of chloroform. The organic layer was dried over anhydrous sodium sulfate, and filtered, and then the filtrate was concentrated under reduced pressure. The resulting residue was purified by silica gel column chromatography (chloroform/methanol (20:1) to chloroform/methanol/aqueous ammonia (10:1:0.1)) to obtain 94 mg of the title compound.

Physicochemical Properties of this Compound (1) Molecular formula: $C_{17}H_{24}N_2O$ (2) Mass spectrum (FAB): m/z 273 $(M+H)^+$ (3) Specific rotation: $[\alpha]_D^{25}$ −15° (c0.56, $CHCl_3$)

(4) $^1$H NMR spectrum (300 MHz, $CDCl_3$) δ (ppm): 1.18 (d, $\underline{CH_3}CH$), 1.34-1.48 (m, $CHCH_2\underline{CH_2}$), 1.75 (m, $CH\underline{CH_2}$), 1.98 (m, quinoline-$CH_2\underline{CH_2}$), 2.57 (m, $CH(CH_2)_2\underline{CH_2}$), 2.76 (t, quinoline-$(CH_2)_2\underline{CH_2}$), 3.13 (br t, quinoline-$\underline{CH_2}$), 3.74 (m, CH), 7.24 (d, quinoline), 7.56 (ddd, quinoline), 7.70 (ddd, quinoline), 8.04 (dd, quinoline), 8.12 (dd, quinoline), 8.80 (d, quinoline).

Reference Example 22

Preparation Method of (R)-7-methylamino-1-hepten-4-ol (a) In an amount of 15.3 g of (R)-5-amino-2-hydroxypentanoic acid, which was synthesized from (D)-ornithine hydrochloride according to the method described in YAKUGAKU ZASSHI (Vol 87, (1967), 1184-1188), was dissolved in 150 ml of a mixed solvent of acetone/water (1:1), added dropwise simultaneously with 45.8 ml of 5 N aqueous sodium hydroxide and 11 ml of ethyl chloroformate under ice cooling over 40 minutes, and stirred under the same condition for 1 hour. The reaction system was washed with ethyl acetate, then the aqueous layer was adjusted to pH 1 by slowly adding 10 N hydrochloric acid, and extracted with ethyl acetate, and the organic layer was dried over anhydrous magnesium sulfate, and filtered. Then, the filtrate was concentrated under reduced pressure to obtain 24.4 g of crude (R)-5-ethoxycarbonylamino-2-hydroxypentanoic acid.

Physicochemical Properties of this Compound
(1) Molecular formula: $C_8H_{15}NO_5$
(2) Mass spectrum (FAB): m/z 206 $(M+H)^+$
(3) Specific rotation: $[\alpha]_D^{20}$ −4.1° (c1.51, $CHCl_3$)
(4) $^1H$ NMR spectrum (400 MHz, $CDCl_3$) δ (ppm): 1.25 (t, $COCH_2CH_3$), 1.50-2.00 (m, 3-H and 4-H), 3.22 (br s, 5-H), 4.12 (q, $COCH_2CH_3$), 4.25 (m, 2-H), 5.07 (s, NH).

(b) In the same manner as in Reference Example 2(b), 13.0 g of (R)-5-methylaminopentan-1,2-diol was obtained from 24.4 g of the compound of Reference Example 22(a).

(c) In the same manner as in Reference Example 17(c), 13.7 g of (R)-5-(N-tert-butoxycarbonyl-N-methylamino)pentan-1,2-diol was obtained from 13.0 g of the compound of Reference Example 22(b).

Physicochemical Properties of this Compound
(1) Molecular formula: $C_{11}H_{23}NO_4$
(2) Mass spectrum (FAB): m/z 234 $(M+H)^+$
(3) Specific rotation: $[\alpha]_D^{20}$ 5.7° (c0.66, $CHCl_3$)

(d) In the same manner as in Reference Example 17(d), 16.9 g of (R)-5-(N-tert-butoxycarbonyl-N-methylamino)-1-(p-toluenesulfonyloxy)-2-pentanol was obtained from 13.7 g of the compound of Reference Example 22(c).

Physicochemical Properties of this Compound
(1) Molecular formula: $C_{18}H_{29}NO_6S$
(2) Mass spectrum (FAB): m/z 388 $(M+H)^+$
(3) Specific rotation: $[\alpha]_D^{21}$ −3.7 (c1.07, $CHCl_3$)

(e) In the same manner as in Reference Example 17(e), 8.14 g of (R)—N-tert-butoxycarbonyl-N-(4,5-epoxypentyl)-N-methylamine was obtained from 16.9 g of the compound of Reference Example 22(d).

Physicochemical Properties of this Compound
(1) Molecular formula: $C_{11}H_{21}NO_3$
(2) Mass spectrum (FAB): m/z 216 $(M+H)^+$
(3) Specific rotation: $[\alpha]_D^{21}$ −5.9° (c1.35, $CHCl_3$)

(f) In the same manner as in Reference Example 17(f), 2.17 g of (R)-7-(N-tert-butoxycarbonyl-N-methylamino)-1-hepten-4-ol was obtained from 2.56 g of the compound of Reference Example 22(e).

Physicochemical Properties of this Compound
(1) Molecular formula: $C_{11}H_{21}NO_3$
(2) Mass spectrum (FAB): m/z 216 $(M+H)^+$
(3) Specific rotation: $[\alpha]_D^{21}$ 5.9° (c1.35, $CHCl_3$)

(g) In an amount of 2.17 g of the compound of Reference Example 22(f) was dissolved in 10.9 ml of dioxane, successively added with 10.9 ml of a 4 N solution of hydrochloric acid in dioxane, and stirred at room temperature for 2 hours. The reaction system was concentrated as it was under reduced pressure, the concentrate was desalted by using DOWEX 50W—X2 (H form) produced by Muromachi Technos Co., Ltd, eluted with 28% aqueous ammonia/methanol (1:7), and the eluate was concentrated under reduced pressure to obtain 1.03 g of the title compound. This compound was used as it was in the following step without further purification.

Physicochemical Properties of this Compound
(1) Molecular formula: $C_8H_{17}NO$
(2) Mass spectrum (ES): m/z 144 $(M+H)^+$
(3) Specific rotation: $[\alpha]_D^{24}$ 9.8° (c1.16, $CHCl_3$)

Reference Example 23

Preparation Method of (R)-7-(methylamino)hept-1-yn-4-ol (a) In an amount of 524 mg of the compound of Reference Example 22(e) was dissolved in 5 ml of dimethyl sulfoxide, added with 269 mg of lithium acetylide ethylenediamine complex at room temperature, and stirred under the same condition for 2 hours. The reaction mixture was added with saturated aqueous ammonium chloride, and extracted with ethyl acetate, and the organic layer was concentrated under reduced pressure. The resulting residue was purified by silica gel column chromatography (hexane/ethyl acetate (3:1 to 1:1)) to obtain 517 mg of (R)-7-(N-tert-butoxycarbonyl-N-methylamino)hept-1-yn-4-ol.

Physicochemical Properties of this Compound
(1) Molecular formula: $C_{13}H_{23}NO_3$
(2) Mass spectrum (FAB): m/z 242 $(M+H)^+$
(3) Specific rotation: $[\alpha]_D^2$ −6.5° (c1.06, $CHCl_3$)
(4) $^1H$ NMR spectrum (400 MHz, $CDCl_3$) δ (ppm): 1.45 (s, $C(CH_3)_3$), 1.48-1.73 (m, 3-H, 5-H and 6-H), 2.05 (s, 1-H), 2.30-2.38 (t, 3-H), 2.38-2.48 (m, 3-H), 2.84 (s, $NCH_3$), 3.22 (br t, 7-H), 3.79 (m, 4-H).

(b) In the same manner as in Reference Example 22(g), 245 mg of the title compound was obtained from 517 mg of the compound of Reference Example 23(a). This compound was used as it was in the following step without further purification.

Physicochemical Properties of this Compound
(1) Molecular formula: $C_8H_{15}NO$
(2) Mass spectrum (FAB): m/z 242 $(M+H)^+$ Reference Example 24

Preparation Method of 3-bromo-6-cyanoquinoline

In an amount of 37.8 mg of 6-cyanoquinoline (Justus Liebigs Ann. Chem., 1966, 699, 98-106) was dissolved in 1 ml of carbon tetrachloride, added with 13 μl of bromine, and then stirred under reflux. After 2 hours, the reaction mixture was added with 20 μl of pyridine, and further stirred for 23 hours under reflux. The reaction mixture was concentrated under reduced pressure, and the resulting residue was purified by silica gel column chromatography (hexane/ethyl acetate (4:1)) to obtain 34.8 mg of the title compound.

Physicochemical Properties of this Compound (1) Molecular formula: $C_{10}H_5BrN_2$ (2) Mass spectrum (EI): m/z 232 $(M)^+$ (3) $^1H$ NMR spectrum (300 MHz, $CDCl_3$) δ (ppm): 7.88 (dd, quinoline), 8.16 (d, quinoline), 8.19 (d, quinoline), 8.39 (dd, quinoline), 9.04 (d, quinoline).

Reference Example 25

Preparation Method of 4-(3-bromophenyl)pyridine

In an amount of 1.0 g of 4-bromopyridine hydrochloride was added with 5.2 ml of 1 N aqueous sodium hydroxide, and extracted three times with 10 ml of methylene chloride. The organic layer was dried over anhydrous sodium sulfate, and then filtered, and the filtrate was concentrated at 0° C. under reduced pressure to obtain 4-bromopyridine. Without purification, this compound was dissolved in 23 ml of tetrahydrofuran under argon atmosphere, added with 4 ml of a 1.58 M solution of n-butyllithium in hexane at −78° C., stirred for 25 minutes, then added with 5.2 ml of a 1 M solution of zinc chloride in diethyl ether, then warmed to room temperature over 2 hours or more, added with 60 mg of tetrakis(triphenylphosphine)palladium dissolved in 7.5 ml of tetrahydrofuran and 0.68 ml of 1-bromo-3-iodobenzene, and further stirred for 92 hours. The reaction mixture was concentrated under reduced pressure, and then added with 100 ml of ethyl acetate, and the organic layer was successively washed with 45 ml of 10% aqueous ammonia, and 50 ml of saturated brine. The organic layer was dried over anhydrous sodium sulfate, and then filtered. The filtrate was concentrated under reduced pressure, and the resulting residue was purified by silica gel column chromatography (hexane/ethyl acetate (4:1 to 3:1)) to obtain 127 mg of the title compound.

Physicochemical Properties of this Compound (1) Molecular formula: $C_{11}H_8BrN$ (2) Mass spectrum (FAB): m/z 234 $(M+H)^+$ (3) $^1H$ NMR spectrum (300 MHz, $CDCl_3$) δ (ppm): 7.36 (t, $C_6H_4$), 7.46 (d, pyridine), 7.56 (m, $C_6H_4$), 7.77 (s, $C_6H_4$), 8.68 (d, pyridine).

Reference Example 26

Preparation Method of 1-(3-bromophenyl)-1H-imidazole

In an amount of 400 mg of imidazole was dissolved in 7.5 ml of dimethyl sulfoxide under argon atmosphere, added with 255 mg of 60% sodium hydride, and stirred at room temperature. After 1 hour, the reaction mixture was added with 0.8 ml of 3-bromofluorobenzene, and stirred at 140° C. for 21 hours. The reaction mixture was diluted with 50 ml of ethyl acetate, and washed with 20 ml of saturated brine. The organic layer was dried over anhydrous sodium sulfate, and then filtered. The filtrate was concentrated under reduced pressure, and the resulting residue was purified by silica gel column chromatography (hexane/ethyl acetate (3:1 to 1:1)) to obtain 1.1 g of the title compound.

Physicochemical Properties of this Compound (1) Molecular formula: $C_9H_7BrN_2$ (2) Mass spectrum (FAB): m/z 223 $(M+H)^+$ (3) $^1H$ NMR spectrum (300 MHz, $CDCl_3$) δ (ppm): 7.22 (s, imidazole), 7.27 (m, imidazole), 7.35 (m, $C_6H_4$), 7.51 (m, $C_6H_4$), 7.57 (m, $C_6H_4$), 7.85 (s, imidazole).

Reference Example 27

Preparation Method of 5-(3-bromophenyl)pyrimidine

In the same manner as in Reference Example 25, except that 0.8 g of 5-bromopyridine was used instead of 4-bromopyrimidine, 177 mg of the title compound was obtained.

Physicochemical Properties of this Compound (1) Molecular formula: $C_{10}H_7BrN_2$ (2) Mass spectrum (EI): m/z 234 $(M)^+$ (3) $^1H$ NMR spectrum (300 MHz, $CDCl_3$) δ (ppm): 7.41 (dt, $C_6H_4$), 7.52 (m, $C_6H_4$), 7.61 (m, $C_6H_4$), 7.74 (m, $C_6H_4$), 8.94 (d, pyrimidine), 9.24 (d, pyrimidine).

Reference Example 28

Preparation Method of 2-(3-bromophenyl)pyridine

In the same manner as in Reference Example 25, except that a solution of tert-butyllithium in n-pentane was used instead of n-butyllithium, and 0.63 ml of 2-bromopyridine was used instead of 4-bromopyridine, 845 mg of the title compound was obtained.

Physicochemical Properties of this Compound (1) Molecular formula: $C_{11}H_8BrN$ (2) Mass spectrum (EI): m/z 233 $(M)^+$ (3) $^1H$ NMR spectrum (300 MHz, $CDCl_3$) δ (ppm): 7.25 (ddd, pyridine), 7.33 (m, $C_6H_4$), 7.53 (ddd, $C_6H_4$), 7.69 (ddd, pyridine), 7.75 (ddd, pyridine), 7.90 (ddd, $C_6H_4$), 8.17 (dd, $C_6H_4$), 8.69 (ddd, pyridine).

Reference Example 29

Preparation Method of 3-bromo-5-(phenylthio)pyridine

In a volume of 268 μl of thiophenol was dissolved in 8 ml of dimethylformamide, added with 62.6 mg of sodium hydride at room temperature, and stirred for 1 hour. The reaction system was added with 618 mg of 3,5-dibromopyridine, heated to 130° C., and stirred under the same condition for 6.5 hours. The reaction system was added with saturated aqueous ammonium chloride, and extracted with ethyl acetate, and the organic layer was concentrated under reduced pressure. The resulting residue was purified by silica gel column chromatography (hexane/ethyl acetate (50:1 to 7:1)) to obtain 403 mg of the title compound.

Physicochemical Properties of this Compound (1) Molecular formula: $C_{11}H_8BrNS$ (2) Mass spectrum (EI): m/z 266 $(M)^+$ (3) $^1H$ NMR spectrum (400 MHz, $CDCl_3$) δ (ppm): 7.39 (m, $C_6H_5$), 7.44 (m, $C_6H_5$), 7.64 (t, pyridine), 8.39 (d, pyridine), 8.47 (d, pyridine).

Reference Example 30

Preparation Method of 3-bromo-5-phenoxypyridine

In the same manner as in Reference Example 29, 245 mg of the title compound was obtained from 223 mg of phenol.

Physicochemical Properties of this Compound (1) Molecular formula: $C_{11}H_8BrNO$ (2) Mass spectrum (EI): m/z 250 $(M)^+$ (3) $^1$H NMR spectrum (400 MHz, $CDCl_3$) δ (ppm): 7.05 (d, $C_6H_5$), 7.22 (t, pyridine), 7.41 (m, $C_6H_5$), 8.33 (d, pyridine), 8.40 (d, pyridine).

Reference Example 31

Preparation method of 5-bromo-N-phenylpyridine-3-amine

In an amount of 107 mg of tris(dibenzylideneacetone) dipalladium was dissolved in 11 ml of toluene, successively added with 225 mg of sodium tert-butoxide, 555 mg of 3,5-dibromopyridine, and 107 μl of aniline, and stirred at 80° C. for 2 hours. The reaction system was added with saturated aqueous ammonium chloride, and extracted with ethyl acetate, and the organic layer was dried over anhydrous magnesium sulfate, and filtered. Then, the filtrate was concentrated under reduced pressure, and the resulting residue was purified by NH silica gel column chromatography (hexane/acetone (4:1)), and then purified again by preparative TLC (chloroform/methanol (10:1)) to obtain 11.7 mg of the title compound.

Physicochemical Properties of this Compound (1) Molecular formula: $C_{11}H_9BrN_2$ (2) Mass spectrum (FAB): m/z 249 $(M+H)^+$ (3) $^1$H NMR spectrum (400 MHz, $CDCl_3$) δ (ppm): 5.78 (s, NH), 7.07 (t, $C_6H_5$), 7.11 (d, $C_6H_5$), 7.34 (dt, $C_6H_5$), 7.52 (t, pyridine), 8.17 (d, pyridine), 8.25 (d, pyridine).

Reference Example 32

Preparation Method of 5-bromopyridine-3-carboxamide

In an amount of 555 mg of 5-bromonicotinoyl chloride was dissolved in 5.5 ml of tetrahydrofuran, added with 768 μl of 28% aqueous ammonia under ice cooling, stirred for 40 minutes, then warmed to room temperature, and further stirred at room temperature for 20 minutes. The reaction system was added with 15% brine, and extracted with tetrahydrofuran, and the organic layer was dried over anhydrous magnesium sulfate, and filtered. Then, the filtrate was concentrated under reduced pressure until about half amount of crystals were deposited, and added with ethyl acetate until the deposition of crystals was terminated, and the crystals were taken by filtration to obtain 374 mg of the title compound.

Physicochemical Properties of this Compound (1) Molecular formula: $C_6H_5BrN_2O$ (2) Mass spectrum (FAB): m/z 202 $(M+H)^+$ (3) $^1$H NMR spectrum (400 MHz, DMSO-d6) δ (ppm): 8.01 (br s, $NH_2$), 8.49 (br s, $NH_2$), 8.69 (t, pyridine), 9.11 (d, pyridine), 9.25 (d, pyridine).

Reference Example 33

Preparation Method of 5-bromo-N,N-diethylpyridine-3-carboxamide

In the same manner as in Reference Example 32, except that diethylamine was used instead of 28% aqueous ammonia, 514 mg of the title compound was obtained from 506 mg of 5-bromonicotinoyl chloride. For purification, silica gel column chromatography (hexane/ethyl acetate (4:1 to 1:1)) was used.

Physicochemical Properties of this Compound (1) Molecular formula: $C_{10}H_{13}BrN_2O$ (2) Mass spectrum (FAB): m/z 258 $(M+H)^+$ (3) $^1$H NMR spectrum (400 MHz, $CDCl_3$) δ (ppm): 1.16 (br t, $N(CH_2CH_3)_2$), 1.26 (br t, $N(CH_2CH_3)_2$), 3.27 (br q, $N(CH_2CH_3)_2$), 3.56 (br q, $N(CH_2CH_3)_2$), 7.87 (t, pyridine), 8.55 (d, pyridine), 8.74 (d, pyridine).

Reference Example 34

Preparation method of 5-bromo-N-methoxy-N-methylpyridine-3-carboxamide

In an amount of 1.03 g of 5-bromonicotinoyl chloride was dissolved in 10 ml of tetrahydrofuran, successively added with 1.95 ml of triethylamine, and 1.37 g of N,O-dimethylhydroxylamine hydrochloride at room temperature, and stirred under the same condition for 2 hours. The reaction system was added with saturated aqueous ammonium chloride, and extracted with ethyl acetate, and the organic layer was dried over anhydrous magnesium sulfate, and filtered. Then, the filtrate was concentrated under reduced pressure, and the resulting residue was purified by silica gel column chromatography (hexane/ethyl acetate (3:1 to 1:1)) to obtain 795 mg of the title compound.

Physicochemical Properties of this Compound (1) Molecular formula: $C_8H_9BrN_2O_2$ (2) Mass spectrum (EI): m/z 245 $(M)^+$ (3) $^1$H NMR spectrum (300 MHz, $CDCl_3$) δ (ppm): 3.40 (s, $N(CH_3)OCH_3$), 3.50 (s, $N(CH_3)OCH_3$), 8.18 (t, pyridine), 8.76 (d, pyridine), 8.87 (d, pyridine).

Reference Example 35

Preparation Method of 5-bromopyridin-3-ylphenyl ketone

In an amount of 245 mg of the compound of Reference Example 34 was dissolved in 4.9 ml of tetrahydrofuran, added with 1.07 ml of a 0.94 N solution of phenyllithium in hexane under ice cooling, and stirred under the same condition for 3.5 hours. The reaction system was adjusted to pH 1 by adding 1 N hydrochloric acid, and washed with ethyl acetate, and then the aqueous layer was neutralized by adding saturated aqueous sodium hydrogencarbonate, and extracted with ethyl acetate. The organic layer was dried over anhydrous magnesium sulfate, and filtered. Then, the filtrate was concentrated under reduced pressure, and the resulting residue was purified by silica gel column chromatography (hexane/ethyl acetate (6:1)) to obtain 136 mg of the title compound.

Physicochemical Properties of this Compound (1) Molecular formula: $C_{12}H_8BrNO$ (2) Mass spectrum (EI): m/z 262 $(M)^+$ (3) $^1$H NMR spectrum (300 MHz, $CDCl_3$) δ (ppm): 7.54 (t, $C_6H_5$), 7.67 (tt, $C_6H_5$), 7.81 (dd, $C_6H_5$), 8.26 (t, pyridine), 8.88 (d, pyridine), 8.89 (d, pyridine).

Reference Example 36

Preparation Method of (S)-6-methylamino-1-(quinolin-3-yl)hexane-3-ol (a) In a volume of 148 μl of diisopropylamine was dissolved in 1.5 ml of tetrahydrofuran, added with 669 μl of a 1.58 M solution of n-butyllithium in hexane under ice cooling, stirred for 30 minutes, added with 92 μl of hexamethylphosphoric triamide, and further stirred for 15 minutes. This reaction mixture was added to 750 μl of a solution of 151 mg of 3-methylquinoline in tetrahydrofuran under ice cooling, and stirred under the same condition for 30 minutes. This ice-cooled solution was added to 750 μl of a solution of 114 mg of the compound of Reference Example 22(e) in tetrahydrofuran at room temperature, and stirred under the same condition for 21.5 hours. The reaction system was added with saturated aqueous ammonium chloride, and extracted with ethyl acetate, and the organic layer was concentrated under reduced pressure. The resulting residue was purified by silica gel column chromatography (hexane/acetone (3:1 to 1:1)) to obtain 72 mg of (S)-6-(N-tert-butoxycarbonyl-N-methylamino)-1-(quinolin-3-yl)hexane-3-ol.

Physicochemical Properties of this Compound (1) Molecular formula: $C_{21}H_{30}N_2O_3$ (2) Mass spectrum (FAB): m/z 359 $(M+H)^+$ (3) Specific rotation: $[\alpha]_D^{18}$ −11° (c1.81, $CHCl_3$)

(4) $^1H$ NMR spectrum (400 MHz, $CDCl_3$) δ (ppm): 1.45 (s, $C(CH_3)_3$), 1.57-1.92 (m, 2-H, 4-H and 5-H), 2.83 (s, $NCH_3$), 2.88 (dt, 1-H), 2.99 (dt, 1-H), 3.20 (br s, 6-H), 3.70 (m, 3-H), 7.52 (ddd, quinoline), 7.66 (ddd, quinoline), 7.76 (br d, quinoline), 7.95 (d, quinoline), 8.07 (br d, quinoline), 8.79 (d, quinoline).

(b) In the same manner as in Reference Example 22(g), 68.9 mg of the title compound was obtained from 103 mg of the compound of Reference Example 36(a). This compound was used as it was in the following step without further purification.

Physicochemical Properties of this Compound (1) Molecular formula: $C_{16}H_{22}N_2O$ (2) Mass spectrum (FAB): m/z 259 $(M+H)^+$ Reference Example 37

Preparation Method of 3-allylquinoline

In an amount of 24.8 mg of copper(I) iodide was added with 9 ml of diethyl ether and 343.5 μl of 3-bromoquinoline, then added dropwise with 1.6 ml of a 1.57 M solution of n-butyllithium in hexane at −78° C., and stirred at −78° C. for 30 minutes. This reaction mixture was added with 71.4 μl of allyl bromide, stirred at −78° C. for 30 minutes, then warmed to 0° C., added with 20 ml of saturated aqueous ammonium chloride, diluted with 20 ml of ethyl acetate, and successively washed twice with 20 ml of saturated aqueous ammonium chloride and once with 20 ml of saturated brine. The organic layer was dried over anhydrous magnesium sulfate, and then filtered. The filtrate was concentrated under reduced pressure, and the resulting residue was purified by silica gel column chromatography (dichloromethane to ethyl acetate/hexane (1:1)) to obtain 130 mg of the title compound.

Physicochemical Properties of this Compound (1) Molecular formula: $C_{12}H_{11}N$ (2) Mass spectrum (FAB): m/z 170 $(M+H)^+$ (3) $^1H$ NMR spectrum (300 MHz, $CDCl_3$) δ (ppm): 3.58 (d, $CH_2CH{=}CH_2$), 5.16 (dd, $CH{=}CH_2$), 5.17 (dd, $CH{=}CH_2$), 6.03 (ddt, $CH{=}CH_2$), 7.52 (dd, quinoline), 7.65 (ddd, quinoline), 7.77 (d, quinoline), 7.93 (d, quinoline), 8.08 (d, quinoline), 8.77 (d, quinoline)

Reference Example 38

Preparation method of 2-allylnaphthalene

In an amount of 515.8 mg of 2-naphthaleneethanol was added with 30 ml of methylene chloride and dissolved therein, added with 6.3 ml of dimethyl sulfoxide, 2.5 ml of triethylamine, and 1.4 g of sulfur trioxide/pyridine complex, stirred at room temperature for 2 hours, then added with 50 ml of water, and extracted with 50 ml of ethyl acetate, and the organic layer was successively washed with 30 ml of saturated aqueous ammonium chloride, and 30 ml of saturated brine. The organic layer was dried over anhydrous sodium sulfate, and then filtered, and the filtrate was concentrated under reduced pressure to obtain 511 mg of 2-(naphthalen-2-yl)acetaldehyde.

In an amount of 1.7 g of methyltriphenylphosphonium bromide was added with 25 ml of tetrahydrofuran and dissolved therein, and added with 4.4 ml of a 1.0 M solution of sodium (bistrimethylsilyl)amide in tetrahydrofuran under ice cooling, and this reaction mixture was stirred for 15 minutes under ice cooling, then added dropwise with 511 mg of 2-(naphthalen-2-yl)acetaldehyde dissolved in 5 ml of tetrahydrofuran under ice cooling, and stirred at room temperature for 40 minutes. The reaction mixture was added with 2 ml of acetone, and then diluted with 30 ml of ethyl acetate, and the organic layer was successively washed once with 50 ml of water, and once with 50 ml of saturated brine. The organic layer was dried over anhydrous sodium sulfate, and then filtered. The filtrate was concentrated under reduced pressure, and the resulting residue was purified by silica gel column chromatography (hexane) to obtain 212 mg of the title compound.

Physicochemical Properties of this Compound (1) Molecular formula: $C_{13}H_{12}$ (2) $^1H$ NMR spectrum (300 MHz, $CDCl_3$) δ (ppm): 3.56 (d, $CH_2CH{=}CH_2$), 5.13 (d, $CH{=}CH_2$), 5.15 (dd, $CH{=}CH_2$), 6.06 (ddt, $CH{=}CH_2$), 7.33 (dd, naphthalene), 7.44 (m, naphthalene), 7.63 (s, naphthalene), 7.78 (dd, naphthalene)

Reference Example 39

Preparation Method of 3-(3-butenyl)quinoline (a) In an amount of 10.2 g of 3-bromoquinoline was stirred together with 7 ml of methyl acrylate, 110 mg of palladium (II) acetate, 599 mg of tri-o-tolylphosphine, and 29 ml of triethylamine at 100° C. for 17 hours in a sealed tube. The reaction mixture was diluted with 300 ml of chloroform, and successively washed with 250 ml of saturated brine, and 250 ml of saturated aqueous ammonium chloride. The organic layer was dried over anhydrous sodium sulfate, and then filtered, and the filtrate was concentrated under reduced pressure. The resulting residue was dissolved in 80 ml of chloroform, added with 200 ml of hexane under ice cooling, and stirred for 30 minutes. The precipitates were taken by filtration, washed with hexane, and then dried under reduced pressure to obtain 8.0 g of methyl (E)-3-(quinolin-3-yl) acrylate.

Physicochemical Properties of this Compound (1) Molecular formula: $C_{13}H_{11}NO_2$ (2) $^1H$ NMR spectrum (300 MHz, $CDCl_3$) δ (ppm): 3.85 (s, $CO_2CH_3$), 6.67 (d, CH═CH), 7.59 (ddd, quinoline), 7.76 (ddd, quinoline), 7.85 (d, CH═CH), 7.86 (dd, quinoline), 8.11 (br d, quinoline), 8.25 (dd, quinoline), 9.09 (s, quinoline).

(b) In an amount of 200 mg of the compound of Reference Example 39(a) was dissolved in 6 ml of 1,4-dioxane, and added with 41 mg of 10% Pd—C catalyst. The reaction vessel was purged with hydrogen, and the reaction mixture was stirred at room temperature for 8 hours. The reaction mixture was filtered through a Celite layer, and washed with methanol, and the filtrate was concentrated under reduced pressure. The resulting residue was purified by silica gel column chromatography (hexane/ethyl acetate (5:1)) to obtain 161 mg of methyl 3-(quinolin-3-yl)propionate.

Physicochemical Properties of this Compound (1) Molecular formula: $C_{13}H_{13}NO_2$ (2) $^1H$ NMR spectrum (300 MHz, $CDCl_3$) δ (ppm): 2.74 (t, $CH_2$), 3.14 (t, $CH_2$), 3.67 (s, $CO_2CH_3$), 7.51 (ddd, quinoline), 7.66 (ddd, quinoline), 7.76 (br d, quinoline), 7.95 (d, quinoline), 8.07 (br d, quinoline), 8.79 (d, quinoline).

(c) In an amount of 76.3 mg of the compound of Reference Example 39(b) was dissolved in 4 ml of toluene under argon atmosphere, added with 0.76 ml of a 1 M solution of diisobutylalminum hydride in toluene at −78° C., and stirred for 1.5 hours. The reaction mixture was added dropwise with 5 drops of methanol, added with 50 ml of diethyl ether and 50 ml of saturated aqueous sodium potassium tartrate, and stirred at room temperature for 1 hour. The aqueous layer was extracted twice with 10 ml of diethyl ether, and the organic layers were combined, and washed with 30 ml of saturated brine. The organic layer was dried over anhydrous sodium sulfate, and then filtered. The filtrate was concentrated under reduced pressure, and the resulting residue was purified by silica gel column chromatography (hexane/ethyl acetate (1:1)) to obtain 60.2 mg of 3-(quinolin-3-yl)propionaldehyde.

Physicochemical Properties of this Compound (1) Molecular formula: $C_{12}H_{11}NO$ (2) $^1H$ NMR spectrum (300 MHz, $CDCl_3$) δ (ppm): 2.88 (dt, $CH_2$), 3.11 (t, $CH_2$), 7.50 (dt, quinoline), 7.65 (dt, quinoline), 7.74 (dd, quinoline), 7.92 (d, quinoline), 8.06 (d, quinoline), 8.77 (d, quinoline), 9.83 (t, CHO).

(d) In an amount of 240.3 mg of methyltriphenylphosphonium bromide was dissolved in 3 ml of tetrahydrofuran under argon atmosphere, added with 0.62 ml of a 1 M solution of sodium bis(trimethylsilyl)amide in tetrahydrofuran under ice cooling, and stirred for 20 minutes. The reaction mixture was added dropwise with a solution of 60.2 mg of the compound of Reference Example 39(c) dissolved in 3 ml of tetrahydrofuran, and further stirred for 1 hour under ice cooling. The reaction mixture was diluted with 15 ml of ethyl acetate, successively washed with 5 ml of saturated aqueous ammonium chloride, and 5 ml of saturated brine, and the organic layer was dried over anhydrous sodium sulfate, and then filtered. The filtrate was concentrated under reduced pressure, and the resulting residue was purified by silica gel column chromatography (hexane/ethyl acetate (3:1)) to obtain 51.7 mg of the title compound.

Physicochemical Properties of this Compound (1) Molecular formula: $C_{13}H_{13}N$ (2) $^1H$ NMR spectrum (300 MHz, $CDCl_3$) δ (ppm): 2.47 (q, $CH_2$), 2.89 (t, $CH_2$), 5.00-5.09 (m, $CH_2$), 5.86 (tq, CH), 7.51 (t, quinoline), 7.65 (dt, quinoline), 7.75 (d, quinoline), 7.91 (d, quinoline), 8.08 (d, quinoline), 8.78 (d, quinoline).

Reference Example 40

Preparation method of 2-(3-butenyl)naphthalene

In an amount of 198 mg of 2-(bromomethyl)naphthalene, and 24.8 mg of copper(I) iodide were added with 9 ml of diethyl ether, added dropwise with 1.3 ml of a solution of allyl magnesium bromide in diethyl ether at −45° C., stirred at −45° C. for 3 hours, then further added with 1.3 ml of a 1.0 M solution of allyl magnesium bromide in diethyl ether, and further stirred at −45° C. for 3 hours. The reaction mixture was added with 20 ml of saturated aqueous ammonium chloride, warmed to room temperature, then diluted with 20 ml of ethyl acetate, and successively washed once with 20 ml of saturated aqueous ammonium chloride, and once with 20 ml of saturated brine. The organic layer was dried over anhydrous sodium sulfate, and then filtered. The filtrate was concentrated under reduced pressure, and the resulting residue was purified by silica gel column chromatography (hexane) to obtain 79.2 mg of the title compound.

Physicochemical Properties of this Compound (1) Molecular formula: $C_{14}H_{14}$ (2) $^1H$ NMR spectrum (300 MHz, $CDCl_3$) δ (ppm): 2.48 (dt, $\underline{CH_2}CH_2$ CH═$CH_2$), 2.88 (t, $CH_2\underline{CH_2}$CH═$CH_2$), 5.00 (dd, CH═$CH_2$), 5.08 (dd, CH═$CH_2$), 5.90 (ddt, CH═$CH_2$), 7.35 (dd, naphthalene), 7.44 (m, naphthalene), 7.63 (s, naphthalene), 7.79 (dd, naphthalene).

Example 1

Preparation method of (3R$_4$S,5S,6R8R9R)-9-acetoxy-5-[2-O-acetyl-4-O-(3-O-acetyl-2,6-dideoxy-3-C-methyl-4-O-propionyl-α-L-ribo-hexopyranosyl)-3,6-dideoxy-3-dimethylamino-β-D-glucopyranosyl]-6-(2,2-dimethoxyethyl)-4-methoxy-8-methyl-10-oxo-3-propionyloxydecanoic acid (compound represented by the formula (4) wherein $R_1$ is propionyl group, $R_2$ is acetyl group, $R_2$ is acetyl group, $R_{3''}$ is acetyl group, $R_{4''}$ is propionyl group, Y is formyl group, and Z is dimethoxymethyl group)

(a) In an amount of 64.2 g of 9,3"-di-O-acetylmidecamycin 18-dimethyl acetal (WO02/64607) was added with 610 ml of acetonitrile and dissolved therein, added with 7.8 ml of acetic anhydride, and stirred at 40° C. for 24 hours. The reaction mixture was concentrated under reduced pressure, and then added with 660 ml of ethyl acetate, and the organic layer was successively washed twice with 300 ml of aqueous saturated sodium hydrogencarbonate, and 300 ml of saturated brine. The organic layer was dried over anhydrous sodium sulfate, and then filtered. The filtrate was concentrated under reduced pressure to obtain 67.0 g of 9,2',3"-tri-O-acetylmidecamycin 18-dimethyl acetal (compound represented by the formula (6) mentioned in Preparation Scheme 1 wherein $R_1$ is propionyl group, $R_2$ is acetyl group, $R_{13}$ is methyl group, $R_{3''}$ is acetyl group, and $R_{4''}$ is propionyl group).

In an amount of 20.0 g of this compound was added with 500 ml of acetone and 77 ml of water, dissolved therein, added with 9.5 ml of N-methylmorpholine N-oxide and 19.5 ml of 4% osmium tetraoxide aqueous solution, and stirred at room temperature. After 20 hours, the reaction mixture was added with 2.4 ml of N-methylmorpholine N-oxide, and further stirred for 4.5 hours. The reaction mixture was concentrated under reduced pressure, and then added with 600 ml of ethyl acetate, and the organic layer was successively washed with 200 ml of water, 300 ml of 5% aqueous sodium thiosulfate, and 300 ml of saturated brine. The organic layer was dried over anhydrous sodium sulfate, and filtered, and then the filtrate was concentrated under reduced pressure. The resulting residue was roughly purified by silica gel column chromatography (chloroform/methanol (25:1 to 15:1)), and the resulting roughly purified product was further purified by silica gel column chromatography (chloroform/ethyl acetate/methanol (30:30:1 to 25:25:1)) to obtain 8.46 g of 9,2',3"-tri-O-acetyl-10,11,12,13-tetrahydroxymidecamycin 18-dimethyl acetal (compound represented by the formula (7) mentioned in Preparation Scheme 1 wherein $R_1$ is propionyl group, $R_2$ is acetyl group, $R_{13}$ is methyl group, $R_{3''}$ is acetyl group, and $R_{4''}$ is propionyl group).

Physicochemical Properties of this Compound (1) Molecular formula: $C_{49}H_{83}NO_{23}$ (2) Mass spectrum (FAB): m/z 1054 $(M+H)^+$ (3) Specific rotation: $[\alpha]_D^{21}$ −81° (c1.0, $CHCl_3$)

(4) $^1H$ NMR spectrum (300 MHz, $CDCl_3$) δ (ppm): 0.96 (d, 19-H), 1.07 (d, 6"-H), 1.13 (t, 3-$OCOCH_2CH_3$), 1.19 (t, 4"-$OCOCH_2CH_3$), 1.20 (d, 6'-H), 1.27 (d, 16-H), 1.41 (s, 3"-$CH_3$), 1.50 (br dd, 14-H), 1.68 (dd, 2"-Hax), 1.88 (br dd, 17-H), 2.03 (s, 9-$OCOCH_3$), 2.04 (s, 3"-$OCOCH_3$), 2.17 (s, 2'-$OCOCH_3$), 2.35 (m, 8-H), 2.44 (s, 3'-$N(CH_3)_2$), 2.60 (t, 3'-H), 2.73 (dd, 2-H), 3.15 (t, 4'-H), 3.18 (s, 18-$OCH_3$), 3.20 (d, 2"-Heq), 3.22 (s, 18-$OCH_3$), 3.27 (dq, 5'-H), 3.39 (br d, 4-H), 3.57 (s, 4-$OCH_3$), 3.63 (m, 12-H), 3.83 (br d, 5-H), 3.91 (dd, 10-H), 4.09 (br t, 13-H), 4.38 (dd, 18-H), 4.48 (dq, 5"-H), 4.57 (d, 4"-H), 4.70 (d, 1'-H), 4.82 (d, 1"-H), 4.96 (dd, 2'-H), 5.02 (m, 9-H), 5.04 (m, 15-H), 5.34 (br d, 3-H).

(b) In an amount of 30 mg of the compound of Example 1(a) was dissolved in 1 ml of benzene, added with 18 mg of sodium carbonate, and then added with 29 mg of lead tetraacetate as 5 of divided portions over 20 minutes. The reaction mixture was stirred at room temperature for 1 hour, and then the supernatant was transferred to a separating funnel. The residue was added with 5 ml of benzene, and the supernatant was transferred to a separating funnel, and then the same procedure was repeated three times. The separating funnel was added with 10 ml of water and 15 ml of saturated aqueous sodium hydrogencarbonate to wash the organic layer. The organic layer was further washed with 15 ml of saturated brine, dried over anhydrous sodium sulfate, and then filtered. The filtrate was concentrated under reduced pressure, and the resulting residue was purified by preparative TLC (hexane/acetone (2:3)) to obtain 6.5 mg of (−)-(1R)-1-methyl-3-oxopropyl (3R4S,5S,6R8R9R)-9-acetoxy-5-[2-O-acetyl-4-O-(3-O-acetyl-2,6-dideoxy-3-C-methyl-4-O-propionyl-α-L-ribo-hexopyranosyl)-3,6-dideoxy-3-dimethylamino-β-D-glucopyranosyl]-6-(2,2-dimethoxyethyl)-4-methoxy-8-methyl-10-oxo-3-propionyloxydecanoate (compound represented by the formula (8) mentioned in Preparation Scheme 1 wherein $R_1$ is propionyl group, $R_2$ is acetyl group, $R_{13}$ is methyl group, $R_{3''}$ is acetyl group, and $R_{4''}$ is propionyl group).

Physicochemical Properties of this Compound (1) Molecular formula: $C_{47}H_{77}NO_{21}$ (2) Mass spectrum (FAB): m/z 992 $(M+H)^+$ (3) Specific rotation: $[\alpha]_D^{25}$ −69° (c0.78, $CHCl_3$)

(4) $^1H$ NMR spectrum (300 MHz, $CDCl_3$) δ (ppm): 1.05 (d, 8-$CH_3$), 1.08 (d, 6"-H), 1.14 (t, 3-$OCOCH_2CH_3$), 1.20 (t, 4"-$OCOCH_2CH_3$), 1.21 (d, 6'-H), 1.33 (d, $OCH(CH_3)CH_2CHO$), 1.42 (s, 3"-$CH_3$), 1.68 (dd, 2"-Hax), 1.85 (m, 6-H), 2.03 (s, 3"-$OCOCH_3$), 2.07 (s, 2'-$OCOCH_3$), 2.20 (s, 9-$OCOCH_3$), 2.36, 2.37 (2xq, 4"-$OCOCH_2CH_3$), 2.44 (s, 3'-$N(CH_3)_2$), 2.62 (t, 3'-H), 2.64 (br d, 2-H), 2.76 (dd, 2-H), 3.17 (t, 4'-H), 3.19 (s, $CH(OCH_3)_2$), 3.23 (d, 2"-Heq), 3.26 (s, $CH(OCH_3)_2$), 3.46 (dd, 4-H), 3.52 (s, 4-$OCH_3$), 3.82 (br d, 5-H), 4.48 (dq, 5"-H), 4.58 (d, 4"-H), 4.66 (d, 1'-H), 4.81 (d, 1"-H), 4.92 (br d, 9-H), 4.96 (dd, 2'-H), 5.27 (br dd, 3-H), 5.39 (ddq, $OCH(CH_3)CH_2CHO$), 9.59 (d, 10-H), 9.75 (dd, $OCH(CH_3)CH_2CHO$).

(c) In an amount of 3.20 g of the compound of Example 1(b) was added with 64 ml of acetonitrile, dissolved therein, added with 720 μl of 1,8-diazabicyclo[5.4.0]-undecene, and stirred at room temperature for 5 hours. The reaction mixture was concentrated under reduced pressure, and then added with 100 ml of chloroform, and the organic layer was washed with 100 ml of saturated brine. The organic layer was separated, and then the aqueous layer was extracted with 50 ml of chloroform. The organic layer was dried over anhydrous sodium sulfate, and filtered, and then the filtrate was concentrated under reduced pressure. The resulting residue was purified by silica gel column chromatography (chloroform/methanol (50:1 to 30:1)) to obtain 755 mg of the title compound.

Physicochemical Properties of this Compound (1) Molecular formula: $C_{43}H_{71}NO_{20}$ (2) Mass spectrum (FAB): m/z 922 $(M+H)^+$ (3) $^1H$ NMR spectrum (300 MHz, $CDCl_3$) δ (ppm): 1.03 (d, 8-$CH_3$), 1.07 (d, 6"-H), 1.14 (t, 3-$OCOCH_2CH_3$), 1.20 (d, 6'-H), 1.20 (t, 4"-$OCOCH_2CH_3$), 1.42 (s, 3"-$CH_3$), 1.51 (m, 6-$CH_2$), 1.68 (dd, 2"-Hax), 1.86 (m, 6-$CH_2$), 2.03 (s, 3"-$OCOCH_3$), 2.06 (s, 2'-$OCOCH_3$), 2.15 (m, 8-H), 2.20 (s, 9-$OCOCH_3$), 2.43 (s, 3'-$N(CH_3)_2$), 2.62 (t, 3'-H), 2.69 (dd, 2-H), 2.83 (dd, 2-H), 3.13 (t, 4'-H), 3.18 (s, $CH(OCH_3)_2$), 3.19 (d, 2"-Heq), 3.26 (s, $CH(OCH_3)_2$), 3.48 (br d, 4-H), 3.55 (s, 4-$OCH_3$), 3.83 (br d, 5-H), 4.44 (dd, $CH(OCH_3)_2$), 4.49 (dq, 5"-H), 4.57 (d, 4"-H), 4.66 (d, 1"-H), 4.81 (d, 1"-H), 4.87 (d, 9-H), 5.24 (br dd, 3-H), 9.56 (s, 10-H).

Preparation Scheme 6

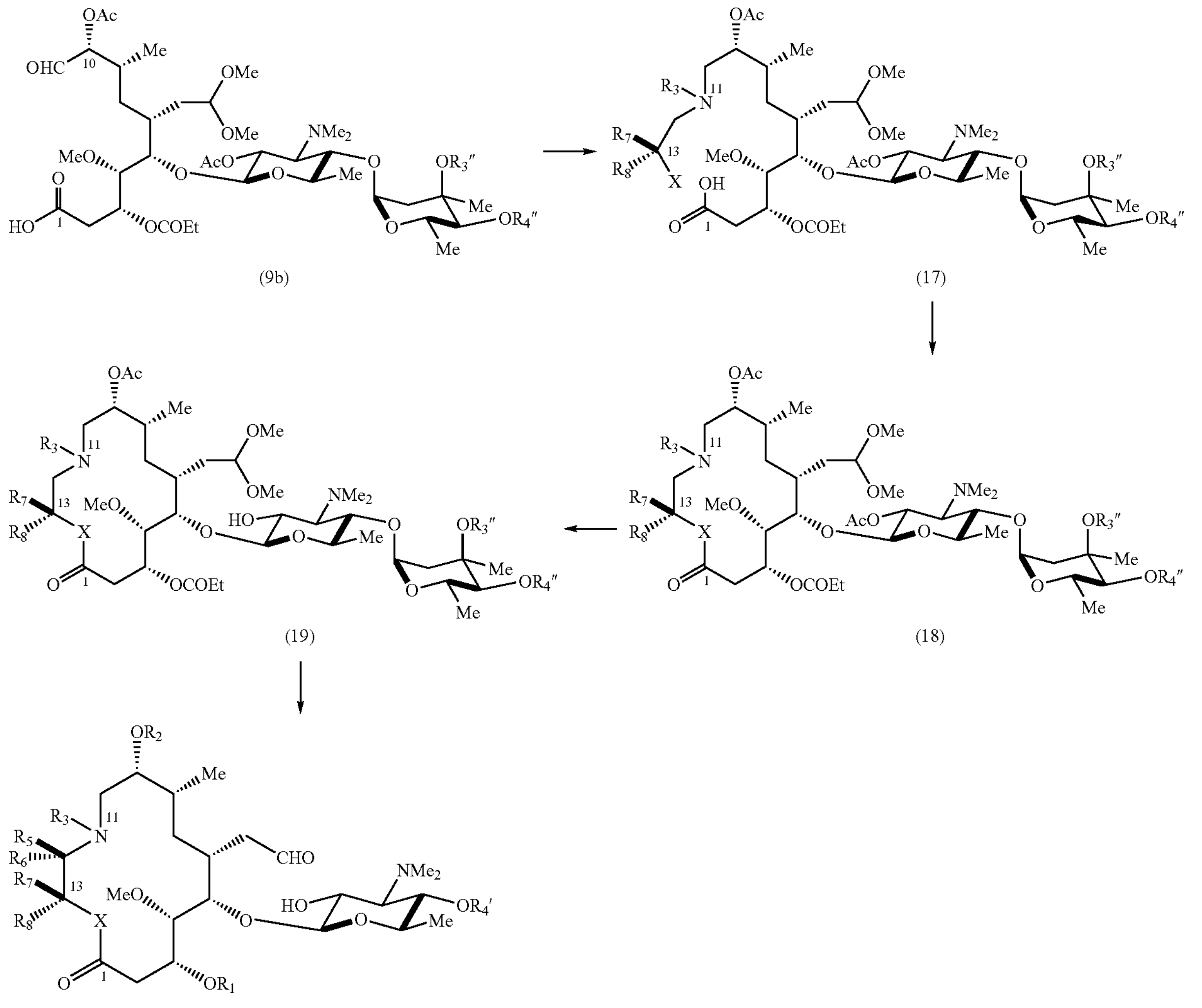

(9b) (17) (18) (19) (1)

Example 2

Preparation method of the compound represented by the formula (1) wherein $R_1$ is propionyl group, $R_2$ is acetyl group, $R_3$ is 4-phenylbutyl group, $R_5$, $R_6$, $R_7$ are hydrogen atoms, $R_8$ is methyl group, $R_{4'}$ is a group represented by the formula (a), $R_{3''}$ is acetyl group, $R_{4''}$ is propionyl group, and X is oxygen atom (a) In an amount of 400 mg of the compound of Example 1 and 135 mg of the compound of Reference Example 1 were dissolved in 1 ml of dimethylformamide, added with 800 mg of Molecular Sieve 3A, and 250 μl of acetic acid, and stirred at room temperature for 5 hours. The reaction mixture was added with 16.5 mg of sodium borohydride, and further stirred at room temperature for 2 hours and 30 minutes. The reaction mixture was filtered through Cerite by using 100 ml of ethyl acetate, and then the filtrate was successively washed twice with 30 ml of water, and twice with 30 ml of saturated brine. The organic layer was dried over anhydrous sodium sulfate, and then filtered. The filtrate was concentrated under reduced pressure, and the resulting residue was purified by silica gel column chromatography (chloroform/methanol (80:1 to 30:1)) to obtain 240 mg of an amine compound (compound represented by the formula (17) mentioned in Preparation Scheme 6 wherein $R_3$ is 4-phenylbutyl group, $R_7$ is hydrogen atom, $R_8$ is methyl group, $R_{3''}$ is acetyl group, $R_{4''}$ is propionyl group, and X is hydroxyl group).

Physicochemical Properties of this Compound (1) Molecular formula: $C_{56}H_{92}N_2O_20$ (2) Mass spectrum (FAB): m/z 1113 $(M+H)^+$ (3) Specific rotation: $[\alpha]_D^{19}$ −75° (c1.0, $CHCl_3$)

(4) $^1H$ NMR spectrum (300 MHz, $CDCl_3$) δ (ppm): 0.86 (d, 8-$CH_3$), 1.07 (d, 6"-H), 1.16 (t, 3-$OCOCH_2CH_3$), 1.17 (d, $CH(CH_3)OH$), 1.19 (t, 4"-$OCOCH_2CH_3$), 1.19 (d, 6'-H), 1.41 (s, 3"-$CH_3$), 1.66 (dd, 2"-Hax), 1.90 (m, 8-H), 1.96 (s, 3"-$OCOCH_3$), 2.03 (s, 9-$OCOCH_3$), 2.23 (s, 2'-$OCOCH_3$), 2.42 (s, 3'-$N(CH_3)_2$), 2.61 (t, 3'-H), 2.89 (dd, 2-H), 3.12 (t, 4'-H), 3.19 (d, 2"-Heq), 3.22 (s, $CH(OCH_3)_2$), 3.26 (s, $CH(OCH_3)_2$), 3.53 (s, 4-$OCH_3$), 3.61 (br d, 4-H), 3.88 (br d, 5-H), 4.10 (m, $CH(CH_3)OH$), 4.50 (dq, 5"-H), 4.56 (d, 4"-H), 4.71 (d, 1'-H), 4.80 (d, 1"-H), 4.95 (dd, 2'-H), 5.16 (br dd, 9-H), 5.38 (br s, 3-H), 7.12-7.33 (m, $C_6H_5$).

(b) In an amount of 132 mg of the compound of Example 2(a) was dissolved in 3.5 ml of tetrahydrofuran, added with 33 μl of triethylamine and 22 μl of 2,4,6-trichlorobenzoyl chloride, and stirred at room temperature for 2 hours. This reaction mixture was added dropwise to a solution of 21.7 mg of 4-dimethylaminopyridine dissolved in 23 ml of toluene over 30 minutes under ice cooling. The mixture was further stirred for 1 hour under ice cooling, then added with 30 ml of water, and extracted with 30 ml of ethyl acetate, and the organic layer was successively washed with 30 ml of water, 30 ml of saturated aqueous sodium hydrogencarbonate, and 30 ml of saturated brine. The organic layer was dried over anhydrous sodium sulfate, and then filtered, and the filtrate was concentrated under reduced pressure. The resulting residue was purified by silica gel column chromatography (chloroform/ethyl acetate (15:1 to 5:1)), and further purified by preparative TLC (chloroform/ethyl acetate (2:1)) to obtain 26 mg of a cyclized compound (compound represented by the formula (18) mentioned in Preparation Scheme 6 wherein $R_3$ is 4-phenylbutyl group, $R_7$ is hydrogen atom, $R_8$ is methyl group, $R_{3''}$ is acetyl group, $R_{4''}$ is propionyl group, and X is oxygen atom).

Physicochemical Properties of this Compound (1) Molecular formula: $C_{56}H_{90}N_2O_{19}$ (2) Mass spectrum (FAB): m/z 1095 $(M+H)^+$ (3) Specific rotation: $[\alpha]_D^{20}$ −66° (c0.7, $CHCl_3$)

(4) $^1$H NMR spectrum (300 MHz, $CDCl_3$) δ (ppm): 0.75 (m, 7-H), 0.92 (d, 8-$CH_3$), 1.07 (d, 6"-H), 1.14 (t, 3-$OCOCH_2CH_3$), 1.19 (t, 4"-$OCOCH_2CH_3$), 1.21 (d, 6'-H), 1.22 (d, 13-$CH_3$), 1.42 (s, 3"-$CH_3$), 1.68 (dd, 2"-Hax), 2.02 (s, 3"-$OCOCH_3$), 2.04 (s, 9-$OCOCH_3$), 2.08 (s, 2'-$OCOCH_3$), 2.44 (s, 3'-$N(CH_3)_2$), 2.81 (dd, 12-H), 2.96 (dd, 2-H), 3.13 (m, 4'-H), 3.14 (s, $CH(OCH_3)_2$), 3.20 (d, 2"-Heq), 3.25 (s, $CH(OCH_3)_2$), 3.27 (m, 5'-H), 3.57 (s, 4-$OCH_3$), 3.71 (br d, 4-H), 3.86 (br d, 5-H), 4.45 (m, $CH(OCH_3)_2$), 4.47 (dq, 5"-H), 4.57 (d, 4"-H), 4.71 (d, 1'-H), 4.81 (d, 1"-H), 4.84 (m, 9-H), 4.98 (dd, 2'-H), 5.07 (m, 13-H), 5.18 (br d, 3-H), 7.05-7.36 (m, $C_6H_5$).

(c) In an amount of 25 mg of the compound of Example 2(b) was added with 1 ml of methanol, dissolved therein, and stirred at room temperature for 5 hours. The reaction mixture was concentrated under reduced pressure, and the resulting residue was purified by preparative TLC (chloroform/methanol (30:1)) to obtain 22 mg of a 2'-deacetylated compound (compound represented by the formula (19) mentioned in Preparation Scheme 6 wherein $R_3$ is 4-phenylbutyl group, $R_7$ is hydrogen atom, $R_8$ is methyl group, $R_{3''}$ is acetyl group, $R_{4''}$ is propionyl group, and X is oxygen atom).

Physicochemical Properties of this Compound (1) Molecular formula: $C_{54}H_{88}N_2O_{18}$ (2) Mass spectrum (FAB): m/z 1053 $(M+H)^+$ (3) Specific rotation: $[\alpha]_D^{20}$ −52° (c0.8, $CHCl_3$)

(4) $^1$H NMR spectrum (300 MHz, $CDCl_3$) δ (ppm): 0.88 (m, 7-H), 0.94 (d, 8-$CH_3$), 1.09 (d, 6"-H), 1.14 (t, 3-$OCOCH_2CH_3$), 1.20 (t, 4"-$OCOCH_2CH_3$), 1.21 (d, 6'-H), 1.24 (d, 13-$CH_3$), 1.42 (s, 3"-$CH_3$), 1.70 (dd, 2"-Hax), 1.84 (m, 6-H), 2.02 (s, 3"-$OCOCH_3$), 2.04 (s, 9-$OCOCH_3$), 2.56 (s, 3'-$N(CH_3)_2$), 2.61 (t, $C_6H_5(CH_2)_4$), 2.76 (dd, 12-H), 2.89 (dd, 10-H), 2.96 (dd, 2-H), 3.15 (s, $CH(OCH_3)_2$), 3.23 (d, 2"-Heq), 3.26 (s, $CH(OCH_3)_2$), 3.40 (dd, 2'-H), 3.65 (s, 4-$OCH_3$), 3.78 (br d, 4-H), 3.89 (br d, 5-H), 4.45 (dd, $CH(OCH_3)_2$), 4.51 (d, 1'-H), 4.52 (dq, 5"-H), 4.59 (d, 4"-H), 4.86 (d, 1"-H), 4.95 (m, 9-H), 5.08 (m, 13-H), 5.21 (m, 3-H), 7.05-7.37 (m, $C_6H_5$).

(d) In an amount of 29 mg of the compound of Example 2(c) was added with 1.2 ml of a equivolume mixed solvent of acetonitrile/water, and 52 μl of difluoroacetic acid, and stirred at room temperature for 25 hours and 30 minutes. The reaction mixture was diluted with 25 ml of chloroform, and washed with 15 ml of saturated aqueous sodium hydrogencarbonate. The organic layer was further successively washed with 15 ml of saturated aqueous sodium hydrogencarbonate, and 15 ml of saturated brine, dried over anhydrous sodium sulfate, and then filtered. The filtrate was concentrated under reduced pressure, and the resulting residue was purified by preparative TLC (chloroform/methanol (25:1)) to obtain 22 mg of the title compound.

Physicochemical Properties of this Compound (1) Molecular formula: $C_{52}H_{82}N_2O_{17}$ (2) Mass spectrum (FAB): m/z 1007 $(M+H)^+$ (3) Specific rotation: $[\alpha]_D^{20}$ −61° (c0.6, $CHCl_3$)

(4) $^1$H NMR spectrum (300 MHz, $CDCl_3$) δ (ppm): 0.93 (d, 8-$CH_3$), 1.10 (d, 6"-H), 1.15 (d, 6'-H), 1.18 (t, 3-$OCOCH_2CH_3$), 1.19 (t, 4"-$OCOCH_2CH_3$), 1.24 (d, 13-$CH_3$), 1.42 (s, 3"-$CH_3$), 1.55 (quint, $C_6H_5(CH_2)_4$), 1.71 (dd, 2"-Hax), 1.76 (m, 8-H), 2.01 (s, 3"-$OCOCH_3$), 2.04 (s, 9-$OCOCH_3$), 2.24 (dd, 6-$CH_2$), 2.37 (dd, 10-H), 2.56 (s, 3'-$N(CH_3)_2$), 2.61 (t, $C_6H_5(CH_2)_4$), 2.72 (dd, 12-H), 2.88 (dd, 10-H), 2.99 (dd, 2-H), 3.05 (dd, 6-$CH_2$), 3.23 (m, 4'-H), 3.23 (m, 5'-H), 3.23 (d, 2"-Heq), 3.35 (dd, 2'-H), 3.64 (s, 4-$OCH_3$), 3.87 (br s, 4-H), 3.87 (br s, 5-H), 4.43 (d, 1'-H), 4.50 (dq, 5"-H), 4.59 (d, 4"-H), 4.87 (d, 1"-H), 4.93 (m, 9-H), 5.07 (br dq, 13-H), 5.36 (br d, 3-H), 7.05-7.36 (m, $C_6H_5$), 9.63 (s, CHO).

Example 3

Preparation method of the compound represented by the formula (1) wherein $R_1$ is propionyl group, $R_2$ is acetyl group, $R_3$ is methyl group, $R_5$, $R_6$ and $R_7$ are hydrogen atoms, $R_8$ is methyl group, $R_{4'}$ is a group represented by the formula (a), $R_{3''}$ is acetyl group, $R_{4''}$ is propionyl group, and X is oxygen atom (a) In the same manner as in Example 2(a), except that the compound of Reference Example 2 was used instead of the compound of Reference Example 1, 239 mg of an amine compound (compound represented by the formula (17) mentioned in Preparation Scheme 6 wherein $R_3$ is methyl group, $R_7$ is hydrogen atom, $R_8$ is methyl group, $R_{3''}$ is acetyl group, $R_{4''}$ is propionyl group, and X is hydroxyl group) was obtained from 391 mg of the compound of Example 1.

Physicochemical Properties of this Compound (1) Molecular formula: $C_{47}H_{82}N_2O_20$ (2) Mass spectrum (FAB): m/z 995 $(M+H)^+$ (3) Specific rotation: $[\alpha]_D^{26}$ −94° (c1.2, $CHCl_3$)

(4) $^1$H NMR spectrum (300 MHz, $CDCl_3$) δ (ppm): 0.86 (d, 8-$CH_3$), 1.05 (d, 6"-H), 1.16 (t, 3-$OCOCH_2CH_3$), 1.17 (d, 6'-H), 1.17 (t, 4"-$OCOCH_2CH_3$), 1.22 (d, 13-$CH_3$), 1.39 (s, 3"-$CH_3$), 1.43 (dd, 6-$CH_2$), 1.65 (dd, 2"-Hax), 1.72 (d, 7-H), 2.01 (s, 3"-$OCOCH_3$), 2.03 (s, 9-$OCOCH_3$), 2.03 (s, 2"-$OCOCH_3$), 2.41 (s, 3'-$N(CH_3)_2$), 2.57 (t, 3'-H), 2.61 (d, 10-H), 2.68 (s, 11-$NCH_3$), 2.90 (dd, 2-H), 3.03 (dd, 12-H), 3.08 (dd, 2-H), 3.14 (d, 2"-Heq), 3.20 (s, $CH(OCH_3)_2$), 3.24 (s, $CH(OCH_3)_2$), 3.50 (br d, 4-H), 3.53 (s, 4-$OCH_3$), 3.88 (br d, 5-H), 4.15 (m, 13-H), 4.46 (dq, 5"-H), 4.47 (dd, $CH(OCH_3)_2$), 4.54 (d, 4"-H), 4.70 (d, 1'-H), 4.78 (d, 1"-H), 4.93 (dd, 2'-H), 5.16 (dd, 9-H), 5.34 (br d, 3-H).

(b) In the same manner as in Example 2(b), 53 mg of a cyclized compound (compound represented by the formula (18) mentioned in Preparation Scheme 6 wherein $R_3$ is methyl group, $R_7$ is hydrogen atom, $R_8$ is methyl group, $R_{3''}$ is acetyl group, $R_{4''}$ is propionyl group, and X is oxygen atom) was obtained from 239 mg of the compound of Example 3(a).

Physicochemical Properties of this Compound (1) Molecular formula: $C_{47}H_{80}N_2O_{19}$ (2) Mass spectrum (FAB): m/z 977 $(M+H)^+$ (3) Specific rotation: $[\alpha]_D^{27}$ −78° (c1.0, $CHCl_3$)

(4) $^1H$ NMR spectrum (300 MHz, $CDCl_3$) δ (ppm): 0.90 (d, 8-$CH_3$), 1.05 (d, 6"-H), 1.17 (t, 3-$OCOCH_2CH_3$), 1.17 (t, 4"-$OCOCH_2CH_3$), 1.18 (d, 6'-H), 1.21 (d, 13-$CH_3$), 1.40 (s, 3"-$CH_3$), 1.48 (m, 6-$CH_2$), 1.66 (dd, 2"-Hax), 2.00 (s, 3"-$OCOCH_3$), 2.03 (s, 9-$OCOCH_3$), 2.05 (s, 2'-$OCOCH_3$), 2.19 (s, 11-$NCH_3$), 2.27 (d, 12-H), 2.42 (s, 3'-$N(CH_3)_2$), 2.49 (dd, 2-H), 2.61 (t, 3'-H), 2.66 (dd, 12-H), 2.95 (dd, 2H), 3.13 (s, $CH(OCH_3)_2$), 3.32 (m, 5'-H), 3.58 (s, 4-$OCH_3$), 3.37 (d, 4-H), 3.85 (br d, 5-H), 4.44 (dq, 5"-H), 4.45 (dd, $CH(OCH_3)_2$), 4.55 (d, 4"-H), 4.69 (d, 1'-H), 4.80 (d, 1"-H), 4.84 (dd, 9-H), 4.96 (dd, 2'-H), 5.10 (m, 13-H), 5.10 (d, 3-H).

(c) In the same manner as in Example 2(c), 47 mg of a 2'-deacetylated compound (compound represented by the formula (19) mentioned in Preparation Scheme 6 wherein $R_3$ is methyl group, $R_7$ is hydrogen atom, $R_9$ is methyl group, $R_{3''}$ is acetyl group, $R_{4''}$ is propionyl group, and X is oxygen atom) was obtained from 52 mg of the compound of Example 3(b).

Physicochemical Properties of this Compound (1) Molecular formula: $C_{45}H_{78}N_2O_{18}$ (2) Mass spectrum (ES): m/z 935 $(M+H)^+$ (3) Specific rotation: $[\alpha]_D^{28}$ −52° (c0.83, $CHCl_3$)

(4) $^1H$ NMR spectrum (300 MHz, $CDCl_3$) δ (ppm): 0.92 (d, 8-$CH_3$), 1.17 (d, 6"-H), 1.18 (t, 3-$OCOCH_2CH_3$), 1.18 (t, 4"-$OCOCH_2CH_3$), 1.20 (d, 6'-H), 1.22 (d, 13-$CH_3$), 1.40 (s, 3"-$CH_3$), 1.68 (dd, 2"-Hax), 2.10 (s, 3"-$OCOCH_3$), 2.03 (s, 9-$OCOCH_3$), 2.19 (s, 11-$NCH_3$), 2.35 (t, 3'-H), 2.54 (s, 3'-$N(CH_3)_2$), 2.65 (dd, 12-H), 2.96 (dd, 2-H), 3.16 (s, $CH(OCH_3)_2$), 3.17 (m, 4'-H), 3.17 (m, 5'-H), 3.17 (d, 2"-Heq), 3.24 (s, $CH(OCH_3)_2$), 3.43 (br s, 2'-H), 3.66 (s, 4-$OCH_3$), 3.76 (br d, 4-H), 3.90 (br d, 5-H), 4.44 (dd, $CH(OCH_3)_2$), 4.50 (d, 1'-H), 4.52 (dq, 5"-H), 4.57 (d, 4"-H), 4.88 (d, 1"-H), 4.91 (m, 9-H), 5.14 (m, 13-H), 5.14 (br t, 3-H).

(d) In the same manner as in Example 2(d), 37 mg of the title compound was obtained from 47 mg of the compound of Example 3(c).

Physicochemical Properties of this Compound (1) Molecular formula: $C_{43}H_{72}N_2O_{17}$ (2) Mass spectrum (FAB): m/z 889 $(M+H)^+$ (3) Specific rotation: $[\alpha]_D^{26}$ −61° (c0.94, $CHCl_3$)

(4) $^1H$ NMR spectrum (300 MHz, $CDCl_3$) δ (ppm): 0.89 (d, 8-$CH_3$), 1.07 (d, 6"-H), 1.13 (d, 6'-H), 1.16 (t, 3-$OCOCH_2CH_3$), 1.17 (t, 4"-$OCOCH_2CH_3$), 1.23 (d, 13-$CH_3$), 1.40 (s, 3"-$CH_3$), 1.68 (dd, 2"-Hax), 1.99 (s, 3"-$OCOCH_3$), 2.02 (s, 9-$OCOCH_3$), 2.18 (s, 11-$NCH_3$), 2.28 (br d, 6-$CH_2$), 2.37 (t, 3'-H), 2.54 (s, 3'-$N(CH_3)_2$), 2.63 (dd, 12-H), 3.00 (dd, 2-H), 3.08 (dd, 6-$CH_2$), 3.20 (m, 4'-H), 3.20 (m, 5'-H), 3.20 (d, 2"-Heq), 3.36 (d, 2'-H), 3.65 (s, 4-$OCH_3$), 4.40 (d, 1'-H), 4.48 (dq, 5"-H), 4.57 (d, 4"-H), 4.84 (d, 1"-H), 4.91 (m, 9-H), 5.14 (m, 13-H), 5.27 (br dd, 3-H), 9.59 (s, CHO).

Example 4

Preparation method of the compound represented by the formula (1) wherein $R_1$ is propionyl group, $R_2$ is acetyl group, $R_3$ is 4-phenylbutyl group, $R_5$, $R_6$, $R_7$ and $R_5$ are hydrogen atoms, $R_{4'}$ is a group represented by the formula (a), $R_{3''}$ is acetyl group, $R_4$ is propionyl group, and X is NH group (a) In an amount of 135.5 mg of the compound of Example 1 was dissolved in 6.5 ml of ethanol under argon atmosphere, and added with 70 μl of acetic acid, 49.2 mg of the compound of Reference Example 3, and 4.1 mg of sodium cyanoborohydride under ice cooling, and the mixture was warmed to room temperature, and stirred for 21 hours. The reaction mixture was diluted with 13 ml of ethyl acetate, and washed with 8% aqueous sodium hydrogencarbonate. The aqueous layer was extracted twice with 3 ml of ethyl acetate, and the organic layers were combined, and washed with 10 ml of 25% brine. The organic layer was dried over anhydrous sodium sulfate, and then filtered. The filtrate was concentrated under reduced pressure, and the resulting residue was purified by silica gel column chromatography (chloroform/methanol (30:1)) to obtain 84.1 mg of an azide compound (compound represented by the formula (17) mentioned in Preparation Scheme 6 wherein $R_3$ is 4-phenylbutyl, $R_7$ and $R_8$ are hydrogen atoms, $R_{3''}$ is acetyl group, $R_{4''}$ is propionyl group, and X is azido group).

Physicochemical Properties of this Compound (1) Molecular formula: $C_{55}H_{89}N_5O_{19}$ (2) Mass spectrum (FAB): m/z 1124 $(M+H)^+$ (3) Specific rotation: $[\alpha]_D^{18}$ −64° (c1.0, $CHCl_3$)

(4) $^1H$ NMR spectrum (300 MHz, $CDCl_3$) δ (ppm): 0.87 (d, 8-$CH_3$), 1.07 (d, 6"-H), 1.16 (t, 3-$OCOCH_2CH_3$), 1.19 (t, 4"-$OCOCH_2CH_3$), 1.20 (d, 6'-H), 1.31 (m, 7-H), 1.41 (s, 3"-$CH_3$), 1.49 (m, 6-$CH_2$), 1.67 (dd, 2"-Hax), 1.90 (m, 6-$CH_2$), 2.00 (s, 3"-$OCOCH_3$), 2.03 (s, 9-$OCOCH_3$), 2.03 (s, 2'-$OCOCH_3$), 2.43 (s, 3'-$N(CH_3)_2$), 2.62 (t, 3'-H), 2.74 (dd, 2-H), 2.83 (m, 12-H), 3.13 (t, 4'-H), 3.19 (d, 2"-Heq), 3.22 (s, $CH(OCH_3)_2$), 3.26 (s, $CH(OCH_3)_2$), 3.53 (s, 4-$OCH_3$), 3.44 (br d, 4-H), 3.55 (m, 13-H), 3.88 (br d, 5-H), 4.50 (dq, 5"-H), 4.57 (d, 4"-H), 4.69 (d, 1'-H), 4.80 (d, 1"-H), 4.96 (dd, 2'-H), 7.12-7.33 (m, $C_6H_5$).

(b) In an amount of 84.1 mg of the compound of Example 4(a) was dissolved in 5 ml of tetrahydrofuran and 0.5 ml of water, added with 98.5 mg of triphenylphosphine, and stirred at 60° C. for 35 hours and 30 minutes. The reaction mixture was concentrated under reduced pressure, and the resulting residue was purified by silica gel column chromatography (chloroform/methanol (40:1 to 10:1)) to obtain 43.2 mg of an azide-reduced compound (compound represented by the formula (17) mentioned in Preparation Scheme 6 wherein $R_3$ is 4-phenylbutyl, $R_7$ and $R_8$ are hydrogen atoms, $R_{3''}$ is acetyl group, $R_{4''}$ is propionyl group, and X is amino group).

Physicochemical Properties of this Compound (1) Molecular formula: $C_{55}H_{91}N_3O_{19}$ (2) Mass spectrum (FAB): m/z 1098 $(M+H)^+$ (3) Specific rotation: $[\alpha]_D^{20}$ −82° (c1.0, $CHCl_3$)

(4) $^1H$ NMR spectrum (300 MHz, $CDCl_3$) δ (ppm): 0.95 (d, 8-$CH_3$), 1.07 (d, 6"-H), 1.11 (t, 3-$OCOCH_2CH_3$), 1.18 (d, 6'-H), 1.19 (t, 4"-$OCOCH_2CH_3$), 1.41 (s, 3"-$CH_3$), 1.67 (dd, 2"-Hax), 2.00 (s, 3"-$OCOCH_3$), 2.01 (s, 2'-$OCOCH_3$), 2.03 (s, 9-$OCOCH_3$), 2.43 (s, 3'-$N(CH_3)_2$), 2.61 (t, 3'-H), 3.13 (s, $CH(OCH_3)_2$), 3.19 (d, 2"-Heq), 3.24 (s, $CH(OCH_3)_2$), 3.55 (s, 4-$OCH_3$), 3.60 (br d, 4-H), 3.84 (br d, 5-H), 4.50 (dq, 5"-H), 4.57 (d, 4"-H), 4.71 (d, 1'-H), 4.80 (d, 1"-H), 4.96 (dd, 2'-H), 5.14 (br dd, 3-H), 7.12-7.33 (m, $C_6H_5$).

(c) In an amount of 43.2 mg of the compound of Example 4(b) was dissolved in 9 ml of dimethylformamide under argon atmosphere, added with 58.6 mg of sodium hydrogencarbonate, and 30 μl of diphenylphosphoryl azide under ice cooling, and the mixture was warmed to room temperature, and stirred for 19 hours. The reaction mixture was diluted with 20 ml of ethyl acetate, and washed twice with 10 ml of water, and once with 10 ml of 25% brine. The organic layer was dried over anhydrous sodium sulfate, and then filtered. The filtrate was concentrated under reduced pressure, and the resulting residue was purified by silica gel column chromatography (ethyl acetate) to obtain 40.8 mg of a cyclized compound (compound represented by the formula (18) mentioned in Preparation Scheme 6 wherein $R_3$ is 4-phenylbutyl, $R_7$ and $R_8$ are hydrogen atoms, $R_{3''}$ is acetyl group, $R_{4''}$ is propionyl group, and X is NH group).

Physicochemical Properties of this Compound (1) Molecular formula: $C_{55}H_{89}N_3O_{18}$ (2) Mass spectrum (FAB): m/z 1080 $(M+H)^+$ (3) Specific rotation: $[\alpha]_D^{20}$ −47° (c0.43, $CHCl_3$)

(4) $^1H$ NMR spectrum (300 MHz, $CDCl_3$) δ (ppm): 0.88 (d, 8-$CH_3$), 1.07 (d, 6"-H), 1.15 (t, 3-$OCOCH_2CH_3$), 1.19 (t, 4"-$OCOCH_2CH_3$), 1.20 (d, 6'-H), 1.42 (s, 3"-$CH_3$), 1.67 (dd, 2"-Hax), 1.77 (m, 8-H), 1.88 (m, 6-$CH_2$), 2.01 (s, 3"-$OCOCH_3$), 2.02 (s, 9-$OCOCH_3$), 2.02 (s, 2'-$OCOCH_3$), 2.43 (s, 3'-$N(CH_3)_2$), 2.93 (m, 13-H), 3.13 (s, $CH(OCH_3)_2$), 3.19 (d, 2"-Heq), 3.25 (s, $CH(OCH_3)_2$), 3.69 (s, 4-$OCH_3$), 3.93 (br d, 5-H), 4.50 (dq, 5"-H), 4.57 (d, 4"-H), 4.73 (d, 1'-H), 4.80 (d, 1"-H), 4.95 (dd, 2'-H), 5.05 (br dd, 3-H), 6.49 (br s, NH), 7.05-7.36 (m, $C_6H_5$).

(d) In the same manner as in Example 2(c), 27 mg of a deacetyled compound (compound represented by the formula (19) mentioned in Preparation Scheme 6 wherein $R_3$ is 4-phenylbutyl group, $R_7$ and $R_8$ are hydrogen atoms, $R_{3''}$ is acetyl group, $R_{4''}$ is propionyl group, and X is NH group) was obtained from 41 mg of the compound of Example 4(c).

Physicochemical Properties of this Compound (1) Molecular formula: $C_{53}H_{87}N_3O_{17}$ (2) Mass spectrum (FAB): m/z 1038 $(M+H)^+$ (3) Specific rotation: $[\alpha]_D^{19}$ −38° (c0.41, $CHCl_3$)

(4) $^1H$ NMR spectrum (300 MHz, $CDCl_3$) δ (ppm): 0.89 (d, 8-$CH_3$), 1.09 (d, 6"-H), 1.15 (t, 3-$OCOCH_2CH_3$), 1.20 (t, 4"-$OCOCH_2CH_3$), 1.21 (d, 6'-H), 1.42 (s, 3"-$CH_3$), 1.69 (dd, 2"-Hax), 1.80 (m, 8-H), 2.02 (s, 9-$OCOCH_3$), 2.02 (s, 3"-$OCOCH_3$), 2.54 (s, 3'-$N(CH_3)_2$), 3.16 (s, $CH(OCH_3)_2$), 3.22 (d, 2"-Heq), 3.27 (s, $CH(OCH_3)_2$), 3.41 (dd, 2'-H), 3.46 (br d, 4-H), 3.67 (m, 13-H), 3.73 (s, 4-$OCH_3$), 3.95 (br d, 5-H), 4.59 (d, 4"-H), 4.80 (m, 9-H), 4.85 (d, 1"-H), 5.07 (br d, 3-H), 6.42 (br s, NH), 7.05-7.37 (m, $C_6H_5$).

(e) In the same manner as in Example 2(d), 21 mg of the title compound was obtained from 26 mg of the compound of Example 4(d).

Physicochemical Properties of this Compound (1) Molecular formula: $C_{51}H_{81}N_3O_{16}$ (2) Mass spectrum (FAB): m/z 992 $(M+H)^+$ (3) Specific rotation: $[\alpha]_D^{18}$ −47° (c0.34, $CHCl_3$)

(4) $^1H$ NMR spectrum (300 MHz, $CDCl_3$) δ (ppm): 0.86 (d, 8-$CH_3$), 1.09 (d, 6"-H), 1.14 (d, 6'-H), 1.19 (t, 3-$OCOCH_2CH_3$), 1.20 (t, 4"-$OCOCH_2CH_3$), 1.42 (s, 3"-$CH_3$), 1.69 (dd, 2"-Hax), 1.83 (m, 8-H), 2.01 (s, 9-$OCOCH_3$), 2.01 (s, 3"-$OCOCH_3$), 2.55 (s, 3'-$N(CH_3)_2$), 3.00 (m, 13-H), 3.07 (m, 6-$CH_2$), 3.22 (d, 2"-Heq), 3.34 (dd, 2'-H), 3.49 (br d, 4-H), 3.58 (m, 13-H), 3.73 (s, 4-$OCH_3$), 3.92 (br d, 5-H), 4.45 (d, 1'-H), 4.52 (dq, 5"-H), 4.59 (d, 4"-H), 4.78 (m, 9-H), 4.85 (d, 1"-H), 5.13 (br d, 3-H), 6.42 (br s, NH), 7.05-7.36 (m, $C_6H_5$), 9.63 (s, CHO).

Example 5

Preparation method of the compound represented by the formula (1) wherein $R_1$ is propionyl group, $R_2$ is acetyl group, $R_3$ is 4-phenylbutyl group, $R_5$, $R_6$ and $R_7$ are hydrogen atoms, $R_8$ is methyl group, $R_{4'}$ is a group represented by the formula (a), $R_{3''}$ is acetyl group, $R_{4''}$ is propionyl group, and X is NH group (a) In the same manner as in Example 4(a), except that 11.6 mg of the compound of Reference Example 4 was used instead of the compound of Reference Example 3, 19.0 mg of an azide compound (compound represented by the formula (17) mentioned in Preparation Scheme 6 wherein $R_{3''}$ is 4-phenylbutyl group, $R_7$ is hydrogen atom, $R_8$ is methyl group, $R_{3''}$ is acetyl group, $R_{4''}$ is propionyl group, and X is azido group) was obtained from 29.5 mg of the compound of Example 1.

Physicochemical Properties of this Compound (1) Molecular formula: $C_{56}H_{91}N_5O_{19}$ (2) Mass spectrum (FAB): m/z 1138 $(M+H)^+$ (3) Specific rotation: $[\alpha]_D^{20}$ −80° (c1.0, $CHCl_3$)

(4) $^1H$ NMR spectrum (300 MHz, $CDCl_3$) δ (ppm): 0.88 (d, 8-$CH_3$), 1.07 (d, 6"-H), 1.14 (t, 3-$OCOCH_2CH_3$), 1.20 (d, 6'-H), 1.22 (t, 4"-$OCOCH_2CH_3$), 1.41 (s, 3"-$CH_3$), 1.50 (br dd, 6-$CH_2$), 1.67 (dd, 2"-Hax), 1.80 (m, 8-H), 1.90 (m, 6-$CH_2$), 2.00 (s, 3"-$OCOCH_3$), 2.01 (s, 9-$OCOCH_3$), 2.03 (s, 2'-$OCOCH_3$), 2.43 (s, 3'-$N(CH_3)_2$), 2.76 (d, 2-H), 2.91 (d, 2-H), 3.12 (t, 4'-H), 3.19 (d, 2"-Heq), 3.20 (s, $CH(OCH_3)_2$), 3.26 (s, $CH(OCH_3)_2$), 3.53 (br d, 4-H), 3.54 (s, 4-$OCH_3$), 3.87 (br d, 5-H), 3.93 (m, 13-H), 4.50 (dq, 5"-H), 4.57 (d, 4"-H), 4.69 (d, 1'-H), 4.80 (d, 1"-H), 4.96 (dd, 2'-H), 5.04 (br dd, 9-H), 5.17 (br dd, 3-H), 7.15-7.20 (m, $C_6H_5$), 7.25-7.30 (m, $C_6H_5$).

(b) In the same manner as in Example 4(b), 11.5 mg of an azide-reduced compound (compound represented by the formula (17) mentioned in Preparation Scheme 6 wherein $R_3$ is 4-phenylbutyl group, $R_7$ is hydrogen atom, $R_8$ is methyl group, $R_{3''}$ is acetyl group, $R_{4''}$ is propionyl group, and X is amino group) was obtained from 18.3 mg of the compound of Example 5(a).

Physicochemical Properties of this Compound (1) Molecular formula: $C_{56}H_{93}N_3O_{19}$ (2) Mass spectrum (FAB): m/z 1112 $(M+H)^+$ (3) Specific rotation: $[\alpha]_D^{24}$ −81° (c0.46, $CHCl_3$)

(4) $^1H$ NMR spectrum (300 MHz, $CDCl_3$) δ (ppm): 0.96 (d, 8-$CH_3$), 1.07 (d, 6"-H), 1.11 (t, 3-$OCOCH_2CH_3$), 1.18 (d, 6'-H), 1.28 (d, 13-$CH_3$), 1.19 (t, 4"-$OCOCH_2CH_3$), 1.41 (s, 3"-$CH_3$), 1.68 (dd, 2"-Hax), 1.85 (m, 6-$CH_2$), 2.00 (s, 3"-$OCOCH_3$), 2.01 (s, 2'-$OCOCH_3$), 2.02 (s, 9-$OCOCH_3$), 2.43 (s, 3'-$N(CH_3)_2$), 2.52 (dd, 2-H), 2.70 (dd, 2-H), 3.12 (s, $CH(OCH_3)_2$), 3.24 (s, $CH(OCH_3)_2$), 3.18 (d, 2"-Heq), 3.56 (s, 4-$OCH_3$), 4.48 (dq, 5"-H), 4.57 (d, 4"-H), 4.71 (d, 1'-H), 4.80 (d, 1"-H), 4.96 (dd, 2'-H), 5.12 (br dd, 3-H), 7.15-7.19 (m, $C_6H_5$), 7.25-7.30 (m, $C_6H_5$).

(c) In the same manner as in Example 4(c), 37.1 mg of a cyclized compound (compound represented by the formula (18) mentioned in Preparation Scheme 6 wherein $R_3$ is 4-phenylbutyl group, $R_7$ is hydrogen atom, $R_8$ is methyl group, $R_{3''}$, is acetyl group, $R_{4''}$ is propionyl group, and X is NH group) was obtained from 45.1 mg of the compound of Example 5(b).

Physicochemical Properties of this Compound
(1) Molecular formula: $C_{56}H_{91}N_3O_{18}$
(2) Mass spectrum (FAB): m/z 1094 $(M+H)^+$ (d) In the same manner as in Example 2(c), 5.0 mg of a deacetyled compound (compound represented by the formula (19) mentioned in Preparation Scheme 6 wherein $R_3$ is 4-phenylbutyl group, $R_7$ is hydrogen atom, $R_8$ is methyl group, $R_{3''}$ is acetyl group, $R_{4''}$ is propionyl group, and X is NH group) was obtained from 10.4 mg of the compound of Example 5(c).

Physicochemical Properties of this Compound
(1) Molecular formula: $C_{54}H_{89}N_3O_{17}$
(2) Mass spectrum (FAB): m/z 1052 $(M+H)^+$
(3) Specific rotation: $[\alpha]_D^{20}$ −50° (c0.32, $CHCl_3$)
(4) $^1$H NMR spectrum (300 MHz, $CDCl_3$) δ (ppm): 0.89 (d, 8-$CH_3$), 1.09 (d, 6"-H), 1.16 (t, 3-$OCOCH_2CH_3$), 1.20 (t, 4"-$OCOCH_2CH_3$), 1.21 (d, 6'-H), 1.24 (d, 13-$CH_3$), 1.42 (s, 3"-$CH_3$), 1.69 (dd, 2"-Hax), 1.82 (m, 8-H), 2.02 (s, 9-$OCOCH_3$), 2.02 (s, 3"-$OCOCH_3$), 2.54 (s, 3'-$N(CH_3)_2$), 3.21 (s, $CH(OCH_3)_2$), 3.22 (d, 2"-Heq), 3.27 (s, $CH(OCH_3)_2$), 3.44 (dd, 2'-H), 3.68 (s, 4-$OCH_3$), 3.89 (br d, 5-H), 4.49 (d, 1'-H), 4.59 (d, 4"-H), 4.85 (d, 1"-H), 5.14 (br dd, 3-H), 6.33 (br s, NH), 7.15-7.20 (m, $C_6H_5$), 7.25-7.35 (m, $C_6H_5$).

(e) In the same manner as in Example 2(d), 15.4 mg of the title compound was obtained from 17.4 mg of the compound of Example 5(d).

Physicochemical Properties of this Compound
(1) Molecular formula: $C_{52}H_{83}N_3O_{16}$
(2) Mass spectrum (FAB): m/z 1006 $(M+H)^+$
(3) Specific rotation: $[\alpha]_D^{18}$ −58° (c0.39, $CHCl_3$)
(4) $^1$H NMR spectrum (300 MHz, $CDCl_3$) δ (ppm): 0.89 (d, 8-$CH_3$), 1.09 (d, 6"-H), 1.14 (d, 6'-H), 1.19 (t, 3-$OCOCH_2CH_3$), 1.19 (t, 4"-$OCOCH_2CH_3$), 1.24 (d, 13-$CH_3$), 1.42 (s, 3"-$CH_3$), 1.70 (dd, 2"-Hax), 1.85 (m, 8-H), 2.02 (s, 9-$OCOCH_3$), 2.02 (s, 3"-$OCOCH_3$), 2.30 (dd, 6-$CH_2$), 2.55 (s, 3'-$N(CH_3)_2$), 3.09 (dd, 6-$CH_2$), 3.22 (d, 2"-Heq), 3.38 (dd, 2'-H), 3.55 (ddq, 13-H), 3.64 (s, 4-$OCH_3$), 3.79 (br d, 4-H), 3.88 (br d, 5-H), 4.41 (d, 1'-H), 4.51 (dq, 5"-H), 4.59 (d, 4"-H), 4.85 (d, 1"-H), 5.26 (m, 3-H), 6.35 (br s, NH), 7.16-7.20 (m, $C_6H_5$), 7.23-7.30 (m, $C_6H_5$), 9.63 (s, CHO).

Example 6

Preparation method of the compound represented by the formula (1) wherein $R_1$ is propionyl group, $R_2$ is acetyl group, $R_3$ is 4-phenylbutyl group, $R_5$, $R_6$, $R_7$ and $R_8$ are hydrogen atoms, $R_{4'}$ is a group represented by the formula (a), $R_{3''}$ is acetyl group, $R_{4''}$ is propionyl group, X is —$NR_4$— group, and $R_4$ is methyl group (a) In an amount of 19.9 mg of the compound of Example 4(a) was dissolved in 1 ml of methylene chloride under argon atmosphere, and added with 9.8 mg of triphenylphosphine, and the mixture was stirred at room temperature for 23 hours. The reaction mixture was added with 3.0 mg of paraformaldehyde, and further stirred for 8 hours. The reaction mixture was diluted with 1.3 ml of ethanol, added with 7.0 mg of sodium borohydride under ice cooling, and stirred for 2 hours. The reaction mixture was diluted with 5 ml of ethyl acetate, washed with 5 ml of 8% aqueous sodium hydrogencarbonate, and then the aqueous layer was extracted twice with 2 ml of ethyl acetate. The organic layers were combined, and washed with 5 ml of 25% brine. The organic layer was dried over anhydrous sodium sulfate, and then filtered. The filtrate was concentrated under reduced pressure, and the resulting residue was purified by preparative TLC (chloroform/methanol (5:1)) to obtain 3.0 mg of a methylated compound (compound represented by the formula (17) mentioned in Preparation Scheme 6 wherein $R_3$ is 4-phenylbutyl, $R_7$ and $R_8$ are hydrogen atoms, $R_{3''}$ is acetyl group, $R_{4''}$ is propionyl group, and X is $NHCH_3$ group).

Physicochemical Properties of this Compound
(1) Molecular formula: $C_{56}H_{93}N_3O_{19}$
(2) Mass spectrum (FAB): m/z 1112 $(M+H)^+$
(3) Specific rotation: $[\alpha]_D^{21}$ −31° (c0.35, $CHCl_3$)
(4) $^1$H NMR spectrum (300 MHz, $CDCl_3$) δ (ppm): 0.96 (d, 8-$CH_3$), 1.07 (d, 6"-H), 1.14 (t, 3-$OCOCH_2CH_3$), 1.18 (d, 6'-H), 1.19 (t, 4"-$OCOCH_2CH_3$), 1.41 (s, 3"-$CH_3$), 1.67 (dd, 2"-Hax), 1.85 (m, 6-$CH_2$), 2.00 (s, 3"-$OCOCH_3$), 2.01 (s, 9-$OCOCH_3$), 2.02 (s, 2'-$OCOCH_3$), 2.43 (s, 3'-$N(CH_3)_2$), 2.62 (s, $NHCH_3$), 3.12 (t, 4'-H), 3.18 (d, 2"-Heq), 3.21 (s, $CH(OCH_3)_2$), 3.26 (s, $CH(OCH_3)_2$), 3.53 (s, 4-$OCH_3$), 3.54 (br d, 4-H), 3.80 (br d, 5-H), 4.41 (dd, $CH(OCH_3)_2$), 4.49 (dq, 5"-H), 4.57 (d, 4"-H), 4.69 (d, 1'-H), 4.80 (d, 1"-H), 4.85 (br dd, 9-H), 4.96 (dd, 2'-H), 5.17 (br dd, 3-H), 7.15-7.22 (m, $C_6H_5$), 7.26-7.31 (m, $C_6H_5$).

(b) In the same manner as in Example 4(c), 19.5 mg of a cyclized compound (compound represented by the formula (18) mentioned in Preparation Scheme 6 wherein $R_3$ is 4-phenylbutyl group, $R_7$ and $R_8$ are hydrogen atoms, $R_{3''}$ is acetyl group, $R_{4''}$ is propionyl group, and X is $NCH_3$ group) was obtained from 18.7 mg of the compound of Example 6(a).

Physicochemical Properties of this Compound
(1) Molecular formula: $C_{56}H_{91}N_3O_{18}$
(2) Mass spectrum (FAB): m/z 1094 $(M+H)^+$
(3) $^1$H NMR spectrum (300 MHz, $CDCl_3$) δ (ppm): 0.80 (br dd, 7-H), 0.84 (d, 8-$CH_3$), 1.00 (d, 6"-H), 1.08 (t, 3-$OCOCH_2CH_3$), 1.12 (t, 4"-$OCOCH_2CH_3$), 1.13 (d, 6'-H), 1.34 (s, 3"-$CH_3$), 1.60 (dd, 2"-Hax), 1.75 (m, 6-$CH_2$), 1.91 (s, 3"-$OCOCH_3$), 1.97 (s, 9-$OCOCH_3$), 1.98 (s, 2'-$OCOCH_3$), 2.39 (s, 3'-$N(CH_3)_2$), 2.76 (dd, 2-H), 3.04 (s, $CH(OCH_3)_2$), 3.12 (d, 2"-Heq), 3.17 (s, $CH(OCH_3)_2$), 3.24 (s, $NCH_3$), 3.29 (br d, 4-H), 3.72 (s, 4-$OCH_3$), 3.84 (br d, 5-H), 4.17 (m, 13-H), 4.43 (dq, 5"-H), 4.50 (d, 4"-H), 4.69 (d, 1'-H), 4.75 (d, 1"-H), 4.89 (dd, 2'-H), 4.96 (br d, 3-H), 7.08-7.13 (m, $C_6H_5$), 7.18-7.21 (m, $C_6H_5$).

(c) In the same manner as in Example 2(c), 11.2 mg of a deacetyled compound (compound represented by the formula (19) mentioned in Preparation Scheme 6 wherein $R_3$ is 4-phenylbutyl group, $R_7$ and $R_8$ are hydrogen atoms, $R_{3''}$ is acetyl group, $R_{4''}$ is propionyl group, and X is $NCH_3$ group) was obtained from 21.7 mg of the compound of Example 6(b).

Physicochemical Properties of this Compound
(1) Molecular formula: $C_{54}H_{89}N_3O_{17}$
(2) Mass spectrum (FAB): m/z 1052 $(M+H)^+$
(3) Specific rotation: $[\alpha]_D^{22}$ −34° (c0.34, $CHCl_3$)
(4) $^1$H NMR spectrum (300 MHz, $CDCl_3$) δ (ppm): 0.65 (br dd, 7-H), 0.84 (d, 8-$CH_3$), 1.02 (d, 6"-H), 1.09 (t, 3-OCOCH$_2$CH$_3$), 1.12 (t, 4"-OCOCH$_2$CH$_3$), 1.14 (d, 6'-H), 1.35 (s, 3"-CH$_3$), 1.62 (dd, 2"-Hax), 1.71 (br dd, 7-H), 1.80 (m, 8-H), 1.95 (s, 9-OCOCH$_3$), 1.98 (s, 3"-OCOCH$_3$), 2.47 (s, 3'-N(CH$_3$)$_2$), 2.73 (dd, 2-H), 3.08 (s, CH(OCH$_3$)$_2$), 3.15 (d, 2"-Heq), 3.19 (s, CH(OCH$_3$)$_2$), 3.24 (s, NCH$_3$), 3.34 (dd, 2'-H), 3.40 (br d, 4-H), 3.79 (s, 4-OCH$_3$), 3.87 (br d, 5-H), 4.18 (m, 13-H), 4.48 (d, 1'-H), 4.44 (dq, 5"-H), 4.52 (d, 4"-H), 4.58 (br dd, 9-H), 4.78 (d, 1"-H), 5.00 (br dd, 3-H), 7.08-7.12 (m, C$_6$H$_5$), 7.18-7.23 (m, C$_6$H$_5$).

(d) In the same manner as in Example 2(d), 9.3 mg of the title compound was obtained from 11.2 mg of the compound of Example 6(c).

Physicochemical Properties of this Compound (1) Molecular formula: $C_{52}H_{83}N_3O_6$ (2) Mass spectrum (FAB): m/z 1006 $(M+H)^+$ (3) Specific rotation: $[\alpha]_D^{24}$ −45° (c0.25, CHCl$_3$)

(4) $^1$H NMR spectrum (300 MHz, CDCl$_3$) δ (ppm): 0.59 (m, 7-H), 0.82 (d, 8-CH$_3$), 1.02 (d, 6"-H), 1.05 (d, 6'-H), 1.12 (t, 3-OCOCH$_2$CH$_3$), 1.14 (t, 4"-OCOCH$_2$CH$_3$), 1.35 (s, 3"-CH$_3$), 1.62 (dd, 2"-Hax), 1.74 (m, 7-H), 1.94 (s, 9-OCOCH$_3$), 1.98 (s, 3"-OCOCH$_3$), 2.08 (d, 6-CH$_2$), 2.48 (s, 3'-N(CH$_3$)$_2$), 3.02 (dd, 6-CH$_2$), 3.15 (d, 2"-Heq), 3.24 (s, NCH$_3$), 3.28 (dd, 2'-H), 3.44 (br d, 4-H), 3.78 (s, 4-OCH$_3$), 3.86 (br d, 5-H), 4.17 (m, 13-H), 4.41 (d, 1'-H), 4.44 (dq, 5"-H), 4.52 (d, 4"-H), 4.61 (br dd, 9-H), 4.77 (d, 1"-H), 5.10 (br dd, 3-H), 7.08-7.11 (m, C$_6$H$_5$), 7.19-7.23 (m, C$_6$H$_5$), 9.53 (s, CHO).

Example 7

Preparation method of the compound represented by the formula (1) wherein R$_1$ is propionyl group, R$_2$ is acetyl group, R$_3$ is methyl group, R$_5$, R$_6$, R$_7$ and R$_8$ are hydrogen atoms, R$_{4'}$ is a group represented by the formula (a), R$_{3''}$ is acetyl group, R$_4$ is propionyl group, and X is NH group (a) In the same manner as in Example 4(a), except that the compound of Reference Example 5 was used instead of the compound of Reference Example 3, 79.9 mg of an azide compound (compound represented by the formula (17) mentioned in Preparation Scheme 6 wherein R$_3$ is methyl group, R$_7$ and R$_8$ are hydrogen atoms, R$_{3''}$ is acetyl group, R$_{4''}$ is propionyl group, and X is azido group) was obtained from 152 mg of the compound of Example 1.

Physicochemical Properties of this Compound (1) Molecular formula: $C_{46}H_{79}N_5O_{19}$ (2) Mass spectrum (FAB): m/z 1006 $(M+H)^+$ (3) Specific rotation: $[\alpha]_D^{22}$ −61° (c0.53, CHCl$_3$)

(4) $^1$H NMR spectrum (300 MHz, CDCl$_3$) δ (ppm): 0.80 (d, 8-CH$_3$), 0.99 (d, 6"-H), 1.08 (t, 3-OCOCH$_2$CH$_3$), 1.11 (t, 4"-OCOCH$_2$CH$_3$), 1.12 (d, 6'-H), 1.33 (s, 3"-CH$_3$), 1.44 (m, 6-CH$_2$), 1.59 (dd, 2"-Hax), 1.95 (s, 3"-OCOCH$_3$), 1.96 (s, 9-OCOCH$_3$), 1.97 (s, 2'-OCOCH$_3$), 2.09 (s, NCH$_3$), 2.35 (s, 3'-N(CH$_3$)$_2$), 2.54 (t, 3'-H), 3.05 (t, 4'-H), 3.11 (d, 2"-Heq), 3.14 (s, CH(OCH$_3$)$_2$), 3.18 (s, CH(OCH$_3$)$_2$), 3.32 (br d, 4-H), 3.47 (s, 4-OCH$_3$), 3.54 (m, 13-H), 3.82 (br d, 5-H), 4.41 (dq, 5"-H), 4.49 (d, 4"-H), 4.62 (d, 1'-H), 4.72 (d, 1"-H), 4.88 (dd, 2'-H), 4.97 (br dd, 9-H), 5.04 (br dd, 3-H).

(b) In an amount of 60.1 mg of the compound of Example 7(a) was dissolved in 4 ml of ethanol under argon atmosphere, and added with 105 μl of acetic acid, and 60 mg of 10% Pd—C catalyst, the reaction vessel was purged with hydrogen, and the reaction mixture was stirred at room temperature for 3 hours. The reaction mixture was filtered through a Celite layer, and washed with ethyl acetate, the filtrate was concentrated under reduced pressure, and the resulting residue was dissolved in 50 ml of ethyl acetate. The organic layer was washed with 40 ml of 8% aqueous sodium hydrogencarbonate, and extracted twice with 10 ml of ethyl acetate, and the organic layers were combined, and washed with 40 ml of 25% brine. The organic layer was dried over anhydrous sodium sulfate, and then filtered. The filtrate was concentrated under reduced pressure, and the resulting residue was purified by preparative TLC (chloroform/methanol (5:1)) to obtain 17.8 mg of an azide-reduced compound (compound represented by the formula (17) mentioned in Preparation Scheme 6 wherein R$_3$ is methyl group, R$_7$ and R$_8$ are hydrogen atoms, R$_{3''}$ is acetyl group, R$_{4''}$ is propionyl group, and X is amino group).

Physicochemical Properties of this Compound (1) Molecular formula: $C_{46}H_{81}N_3O_{19}$ (2) Mass spectrum (FAB): m/z 980 $(M+H)^+$ (3) Specific rotation: $[\alpha]_D^{22}$ −78° (c0.40, CHCl$_3$)

(4) $^1$H NMR spectrum (300 MHz, CDCl$_3$) δ (ppm): 0.86 (d, 8-CH$_3$), 1.00 (d, 6"-H), 1.04 (t, 3-OCOCH$_2$CH$_3$), 1.12 (d, 6'-H), 1.12 (t, 4"-OCOCH$_2$CH$_3$), 1.34 (s, 3"-CH$_3$), 1.49 (m, 6-CH$_2$), 1.60 (dd, 2"-Hax), 1.73 (m, 6-CH$_2$), 1.94 (s, 3"-OCOCH$_3$), 1.96 (s, 2'-OCOCH$_3$), 1.99 (s, 9-OCOCH$_3$), 2.21 (s, NCH$_3$), 2.36 (s, 3'-N(CH$_3$)$_2$), 3.06 (t, 4'-H), 3.06 (s, CH(OCH$_3$)$_2$), 3.12 (d, 2"-Heq), 3.17 (s, CH(OCH$_3$)$_2$), 3.49 (s, 4-OCH$_3$), 3.50 (br d, 4-H), 3.79 (br d, 5-H), 4.41 (dq, 5"-H), 4.49 (d, 4"-H), 4.65 (d, 1'-H), 4.73 (d, 1"-H), 4.89 (dd, 2'-H), 5.07 (br dd, 3-H).

(c) In the same manner as in Example 4(c), 26.2 mg of a cyclized compound (compound represented by the formula (18) mentioned in Preparation Scheme 6 wherein R$_3$ is methyl group, R$_7$ and R$_8$ are hydrogen atoms, R$_{3''}$ is acetyl group, R$_{4''}$ is propionyl group, and X is NH group) was obtained from 22.5 mg of the compound of Example 7(b).

Physicochemical Properties of this Compound (1) Molecular formula: $C_{46}H_{79}N_3O_{18}$ (2) Mass spectrum (FAB): m/z 962 $(M+H)^+$ (3) $^1$H NMR spectrum (300 MHz, CDCl$_3$) δ (ppm): 0.81 (d, 8-CH$_3$), 1.00 (d, 6"-H), 1.08 (t, 3-OCOCH$_2$CH$_3$), 1.12 (t, 4"-OCOCH$_2$CH$_3$), 1.13 (d, 6'-H), 1.34 (s, 3"-CH$_3$), 1.50 (m, 8-H), 1.60 (dd, 2"-Hax), 1.95 (s, 3"-OCOCH$_3$), 1.96 (s, 9-OCOCH$_3$), 1.97 (s, 2'-OCOCH$_3$), 2.13 (s, NCH$_3$), 2.36 (s, 3'-N(CH$_3$)$_2$), 2.54 (t, 3'-H), 2.63 (t, 2-H), 3.05 (t, 4'-H), 3.07 (s, CH(OCH$_3$)$_2$), 3.12 (d, 2"-Heq), 3.17 (s, CH(OCH$_3$)$_2$), 3.21 (t, 5'-H), 3.28 (br d, 4-H), 3.62 (s, 4-OCH$_3$), 3.65 (m, 13-H), 3.87 (br d, 5-H), 4.41 (dq, 5"-H), 4.50 (d, 4"-H), 4.66 (d, 1'-H), 4.73 (d, 1"-H), 4.89 (dd, 2'-H), 4.94 (br dd, 3-H), 6.31 (br s, NH).

(d) In the same manner as in Example 2(c), 13.9 mg of a deacetyled compound (compound represented by the formula (19) mentioned in Preparation Scheme 6 wherein R$_3$ is methyl group, R$_7$ and R$_8$ are hydrogen atoms, R$_{3''}$ is acetyl group, R$_{4''}$ is propionyl group, and X is NH group) was obtained from 26.2 mg of the compound of Example 7(c).

Physicochemical Properties of this Compound (1) Molecular formula: $C_{44}H_{77}N_3O_{17}$ (2) Mass spectrum (FAB): m/z 920 $(M+H)^+$ (3) Specific rotation: $[\alpha]_D^{25}$ −44° (c0.70, CHCl$_3$)

(4) $^1$H NMR spectrum (300 MHz, CDCl$_3$) δ (ppm): 0.83 (d, 8-CH$_3$), 1.02 (d, 6"-H), 1.08 (t, 3-OCOCH$_2$CH$_3$), 1.13 (t, 4"-OCOCH$_2$CH$_3$), 1.14 (d, 6'-H), 1.35 (s, 3"-CH$_3$), 1.38 (m, 6-CH$_2$), 1.62 (dd, 2"-Hax), 1.81 (m, 6-CH$_2$), 1.81 (m, 8-H), 1.97 (s, 3"-OCOCH$_3$), 1.99 (s, 9-OCOCH$_3$), 2.14 (s, NCH$_3$), 2.48 (s, 3'-N(CH$_3$)$_2$), 2.53 (dd, 10-H), 2.66 (dd, 2-H), 2.90

(m, 13-H), 3.11 (s, $CH(OCH_3)_2$), 3.15 (d, 2"-Heq), 3.20 (s, $CH(OCH_3)_2$), 3.35 (dd, 2'-H), 3.40 (br d, 4-H), 3.66 (s, 4-$OCH_3$), 3.89 (br d, 5-H), 4.52 (d, 4"-H), 4.78 (d, 1"-H), 4.97 (br dd, 3-H), 6.35 (br s, NH).

(e) In the same manner as in Example 2(d), 11.9 mg of the title compound was obtained from 13.9 mg of the compound of Example 7(d).

Physicochemical Properties of this Compound (1) Molecular formula: $C_{42}H_{71}N_3O_{16}$ (2) Mass spectrum (FAB): m/z 874 $(M+H)^+$ (3) Specific rotation: $[\alpha]_D^{26}$ −55° (c0.60, $CHCl_3$)

(4) $^1H$ NMR spectrum (300 MHz, $CDCl_3$) δ (ppm): 0.80 (d, 8-$CH_3$), 0.96 (m, 7-H), 1.01 (d, 6"-H), 1.06 (d, 6'-H), 1.12 (t, 3-$OCOCH_2CH_3$), 1.12 (t, 4"-$OCOCH_2CH_3$), 1.34 (s, 3"-$CH_3$), 1.40 (m, 7-H), 1.62 (dd, 2"-Hax), 1.86 (m, 8-H), 1.93 (s, 9-$OCOCH_3$), 1.96 (s, 3"-$OCOCH_3$), 2.13 (s, $NCH_3$), 2.20 (dd, 10-H), 2.48 (s, 3'-$N(CH_3)_2$), 2.68 (dd, 2-H), 2.93 (m, 13-H), 3.00 (dd, 6-$CH_2$), 3.15 (d, 2"-Heq), 3.27 (dd, 2'-H), 3.34 (br d, 4-H), 3.58 (m, 13-H), 3.65 (s, 4-$OCH_3$), 3.84 (br d, 5-H), 4.38 (d, 1'-H), 4.43 (dq, 5"-H), 4.51 (d, 4"-H), 4.75 (br dd, 9-H), 4.78 (d, 1"-H), 5.04 (br d, 3-H), 6.34 (br s, NH), 9.55 (s, CHO).

Example 8

Preparation method of the compound represented by the formula (1) wherein $R_1$ is propionyl group, $R_2$ is acetyl group, $R_3$ is methyl group, $R_5$, $R_6$ and $R_7$ are hydrogen atoms, $R_8$ is methyl group, $R_{4'}$ is a group represented by the formula (a), $R_{3''}$ is acetyl group, $R_{4''}$ is propionyl group, and X is NH group (a) In the same manner as in Example 4(a), except that the compound of Reference Example 6 was used instead of the compound of Reference Example 3, 16 mg of an azide compound (compound represented by the formula (17) mentioned in Preparation Scheme 6 wherein $R_3$ is 4-methoxybenzyl group, $R_7$ is hydrogen atom, $R_8$ is methyl group, $R_3$ is acetyl group, $R_{4''}$ is propionyl group, and X is azido group) was obtained from 50 mg of the compound of Example 1.

Physicochemical Properties of this Compound (1) Molecular formula: $C_{54}H_{87}N_5O_{20}$ (2) Mass spectrum (FAB): m/z 1126 $(M+H)^+$ (3) Specific rotation: $[\alpha]_D^{21}$ −59° (c1.2, $CHCl_3$)

(4) $^1H$ NMR spectrum (300 MHz, $CDCl_3$) δ (ppm): 0.82 (d, 8-$CH_3$), 1.07 (d, 6"-H), 1.11 (t, 3-$OCOCH_2CH_3$), 1.18 (t, 4"-$OCOCH_2CH_3$), 1.19 (d, 6'-H), 1.24 (d, 13-$CH_3$), 1.40 (s, 3"-$CH_3$), 1.67 (dd, 2"-Hax), 1.88 (m, 8-H), 2.01 (s, 3"-$OCOCH_3$), 2.03 (s, 9-$OCOCH_3$), 2.08 (s, 2'-$OCOCH_3$), 2.43 (s, 3'-$N(CH_3)_2$), 3.15 (s, $CH(OCH_3)_2$), 3.19 (d, 2"-Heq), 3.24 (s, $CH(OCH_3)_2$), 3.53 (s, 4-$OCH_3$), 3.73 (m, 13-H), 3.80 (s, $C_6H_4$—$OCH_3$), 4.48 (dq, 5"-H), 4.55 (d, 4"-H), 4.57 (d, 1'-H), 4.79 (d, 1"-H), 4.96 (dd, 2'-H), 5.01 (br dd, 9-H), 5.19 (br s, 3-H), 6.85 (d, $C_6H_4$), 7.23 (d, $C_6H_4$).

(b) In the same manner as in Example 4(b), 75 mg of an azide-reduced compound (compound represented by the formula (17) mentioned in Preparation Scheme 6 wherein $R_3$ is 4-methoxybenzyl group, $R_7$ is hydrogen atom, $R_8$ is methyl group, $R_{3''}$ is acetyl group, $R_{4''}$ is propionyl group, and X is amino group) was obtained from 120 mg of the compound of Example 8(a).

Physicochemical Properties of this Compound (1) Molecular formula: $C_{54}H_{89}N_3O_{20}$ (2) Mass spectrum (FAB): m/z 1100 $(M+H)^+$ (3) Specific rotation: $[\alpha]_D^{21}$ −63° (c0.6, $CHCl_3$)

(4) $^1H$ NMR spectrum (300 MHz, $CDCl_3$) δ (ppm): 0.92 (d, 8-$CH_3$), 1.06 (d, 6"-H), 1.11 (t, 3-$OCOCH_2CH_3$), 1.20 (d, 6'-H), 1.21 (t, 4"-$OCOCH_2CH_3$), 1.41 (s, 3"-$CH_3$), 1.66 (dd, 2"-Hax), 2.02 (s, 3"-$OCOCH_3$), 2.12 (s, 9-$OCOCH_3$), 2.18 (s, 2'-$OCOCH_3$), 2.43 (s, 3'-$N(CH_3)_2$), 3.09 (s, $CH(OCH_3)_2$), 3.14 (s, $CH(OCH_3)_2$), 3.14 (d, 2"-Heq), 3.30 (m, 13-H), 3.62 (s, 4-$OCH_3$), 3.90 (dd, 12-H), 4.50 (dq, 5"-H), 4.56 (d, 4"-H), 4.77 (d, 1'-H), 4.79 (d, 1"-H), 4.97 (dd, 2'-H), 5.23 (br dd, 9-H), 5.29 (br d, 3-H), 6.74 (d, $C_6H_4$), 7.09 (d, $C_6H_4$).

(c) In the same manner as in Example 4(c), 98 mg of a cyclized compound (compound represented by the formula (18) mentioned in Preparation Scheme 6 wherein $R_3$ is 4-methoxybenzyl group, $R_7$ is hydrogen atom, $R_8$ is methyl group, $R_{3''}$ is acetyl group, $R_{4''}$ is propionyl group, and X is NH group) was obtained from 83 mg of the compound of Example 8(b).

Physicochemical Properties of this Compound (1) Molecular formula: $C_{54}H_{87}N_3O_{19}$ (2) Mass spectrum (FAB): m/z 1082 $(M+H)^+$ (3) Specific rotation: $[\alpha]_D^{22}$ −47° (c1.0, $CHCl_3$)

(4) $^1H$ NMR spectrum (300 MHz, $CDCl_3$) δ (ppm): 0.83 (d, 8-$CH_3$), 1.05 (d, 6"-H), 1.16 (d, 6'-H), 1.18 (t, 3-$OCOCH_2CH_3$), 1.20 (t, 4"-$OCOCH_2CH_3$), 1.40 (s, 3"-$CH_3$), 1.51 (m, 6-H), 1.65 (dd, 2"-Hax), 1.91 (m, 8H), 1.99 (s, 3"-$OCOCH_3$), 2.00 (s, 9-$OCOCH_3$), 2.00 (s, 2'-$OCOCH_3$), 2.41 (s, 3'-$N(CH_3)_2$), 3.12 (t, 4'-H), 3.14 (s, $CH(OCH_3)_2$), 3.24 (s, $CH(OCH_3)_2$), 3.26 (m, 5'-H), 3.42 (br d, 4-H), 3.72 (s, 4-$OCH_3$), 3.80 (s, $C_6H_4$—$OCH_3$), 3.99 (br d, 5-H), 4.48 (dq, 5"-H), 4.55 (d, 4"-H), 4.68 (dd, $CH(OCH_3)_2$), 4.76 (d, 1'-H), 4.78 (d, 1"-H), 4.84 (br dd, 9-H), 4.95 (dd, 2'-H), 5.02 (br d, 3-H), 6.06 (br d, NH), 6.91 (d, $C_6H_4$), 7.31 (d, $C_6H_4$).

(d) In an amount of 55 mg of the compound of Example 8(c) was added with 2 ml of 1,4-dioxane, dissolved therein, and added with 12 mg of 10% Pd—C catalyst. The reaction vessel was purged with hydrogen, and the reaction mixture was stirred at room temperature for 9 hours, further added with 12 mg of 10% Pd—C catalyst, and stirred at room temperature for 28 hours. After the catalyst was removed by filtration, the filtrate was washed with ethyl acetate, and concentrated under reduced pressure, and the resulting residue was purified by preparative TLC (chloroform/methanol (10:1)) to obtain 37 mg of a reduced compound (compound represented by the formula (18) mentioned in Preparation Scheme 6 wherein $R_3$ and $R_7$ are hydrogen atoms, $R_8$ is methyl group, $R_{3''}$ is acetyl group, $R_{4''}$ is propionyl group, and X is NH group).

Physicochemical Properties of this Compound (1) Molecular formula: $C_{46}H_{79}N_3O_{18}$ (2) Mass spectrum (FAB): m/z 962 $(M+H)^+$ (3) Specific rotation: $[\alpha]_D^{24}$ −43° (c1.0, $CHCl_3$)

(4) $^1H$ NMR spectrum (300 MHz, $CDCl_3$) δ (ppm): 0.82 (d, 8-$CH_3$), 1.05 (d, 6"-H), 1.14 (d, 13-$CH_3$), 1.12 (t, 3-$OCOCH_2CH_3$), 1.14 (t, 4"-$OCOCH_2CH_3$), 1.19 (d, 6'-H), 1.40 (s, 3"-$CH_3$), 1.65 (dd, 2"-Hax), 1.91 (m, 8H), 2.00 (s, 3"-$OCOCH_3$), 2.02 (s, 9-$OCOCH_3$), 2.03 (s, 2'-$OCOCH_3$), 2.41 (s, 3'-$N(CH_3)_2$), 3.11 (s, $CH(OCH_3)_2$), 3.11 (t, 4'-H), 3.22 (s, $CH(OCH_3)_2$), 3.25 (m, 5'-H), 3.45 (br d, 4-H), 3.74 (s, 4-$OCH_3$), 3.95 (br d, 5-H), 3.95 (m, 13-H), 4.47 (dq, 5"-H), 4.55 (d, 4"-H), 4.73 (d, 1'-H), 4.78 (d, 1"-H), 4.85 (br dd, 9-H), 4.86 (br d, 3-H), 4.93 (dd, 2'-H), 6.52 (br d, NH).

(e) In an amount of 40 mg of the compound of Example 8(d) and 19 μl of 37% formaldehyde aqueous solution were dissolved in 2 ml of ethanol, added with 19 μl of acetic acid under ice cooling, and stirred for 30 minutes. The reaction mixture was added with 5.3 mg of sodium cyanoborohydride, and further stirred for 2 hours and 30 minutes under ice cooling. The reaction mixture was diluted with 20 ml of ethyl acetate, successively washed with 20 ml of saturated aqueous sodium hydrogencarbonate, and twice with 30 ml of saturated brine. The organic layer was dried over anhydrous sodium sulfate, and then filtered. The filtrate was concentrated under reduced pressure, and the resulting residue was purified by preparative TLC (chloroform/methanol (10:1)) to obtain 40 mg of an N-methylated compound (compound represented by the formula (18) mentioned in Preparation Scheme 6 wherein $R_3$ is methyl group, $R_7$ is hydrogen atom, $R_8$ is methyl group, $R_{3''}$ is acetyl group, $R_{4''}$ is propionyl group, and X is NH group).

Physicochemical Properties of this Compound (1) Molecular formula: $C_{47}H_{81}N_3O_{18}$ (2) Mass spectrum (FAB): m/z 976 $(M+H)^+$ (3) Specific rotation: $[\alpha]_D^{23}$ −32° (c1.0, $CHCl_3$)

(4) $^1H$ NMR spectrum (300 MHz, $CDCl_3$) δ (ppm): 0.82 (d, 8-$CH_3$), 1.05 (d, 6"-H), 1.12 (t, 3-$OCOCH_2CH_3$), 1.14 (t, 4"-$OCOCH_2CH_3$), 1.14 (d, 13-H), 1.18 (d, 6'-H), 1.35 (m, 6-H), 1.40 (s, 3"-$CH_3$), 1.77 (m, 6-$CH_2$), 1.65 (dd, 2"-Hax), 1.77 (m, 6-$CH_2$), 2.00 (s, 3"-$OCOCH_3$), 2.01 (s, 9-$OCOCH_3$), 2.01 (s, 2'-$OCOCH_3$), 2.23 (s, $NCH_3$), 2.41 (s, 3'-$N(CH_3)_2$), 3.11 (s, $CH(OCH_3)_2$), 3.11 (t, 4'-H), 3.23 (s, $CH(OCH_3)_2$), 3.27 (m, 5'-H), 3.42 (br d, 4-H), 3.69 (s, 4-$OCH_3$), 3.93 (br d, 5-H), 4.09 (m, 13-H), 4.47 (dq, 5"-H), 4.55 (d, 4"-H), 4.58 (dd, $CH(OCH_3)_2$), 4.73 (d, 1'-H), 4.78 (d, 1"-H), 4.87 (br dd, 9-H), 4.94 (br d, 3-H), 4.94 (dd, 2'-H), 6.08 (br d, NH).

(f) In the same manner as in Example 2(c), 32 mg of a deacetyled compound (compound represented by the formula (19) mentioned in Preparation Scheme 6 wherein $R_3$ is methyl group, $R_7$ is hydrogen atom, $R_8$ is methyl group, $R_{3''}$ is acetyl group, $R_{4''}$ is propionyl group, and X is NH group) was obtained from 39 mg of the compound of Example 8(e).

Physicochemical Properties of this Compound (1) Molecular formula: $C_{45}H_{79}N_3O_{17}$ (2) Mass spectrum (FAB): m/z 934 $(M+H)^+$ (3) Specific rotation: $[\alpha]_D^{25}$ −2° (c0.8, $CHCl_3$)

(4) $^1H$ NMR spectrum (300 MHz, $CDCl_3$) δ (ppm): 0.86 (d, 8-$CH_3$), 1.07 (d, 6"-H), 1.13 (d, 13-$CH_3$), 1.14 (t, 3-$OCOCH_2CH_3$), 1.19 (t, 4"-$OCOCH_2CH_3$), 1.19 (d, 6'-H), 1.41 (s, 3"-$CH_3$), 1.67 (dd, 2"-Hax), 1.80 (m, 8-H), 2.01 (s, 3"-$OCOCH_3$), 2.01 (s, 9-$OCOCH_3$), 2.24 (s, $NCH_3$), 2.53 (s, 3'-$N(CH_3)_2$), 3.16 (s, $CH(OCH_3)_2$), 3.17 (m, 4'-H), 3.23 (m, 5'-H), 3.26 (s, $CH(OCH_3)_2$), 3.43 (dd, 2'-H), 3.51 (br d, 4-H), 3.73 (s, 4-$OCH_3$), 3.95 (br d, 5-H), 4.51 (d, 1'-H), 4.52 (m, 5"-H), 4.53 (d, 4"-H), 4.82 (d, 1"-H), 4.87 (m, 9-H), 4.97 (br d, 3-H), 6.17 (br d, NH).

(g) In the same manner as in Example 2(d), 28 mg of the title compound was obtained from 32 mg of the compound of Example 8(f).

Physicochemical Properties of this Compound (1) Molecular formula: $C_{43}H_{73}N_3O_{16}$ (2) Mass spectrum (FAB): m/z 888 $(M+H)^+$ (3) Specific rotation: $[\alpha]_D^{26}$ −27° (c0.5, $CHCl_3$)

(4) $^1H$ NMR spectrum (300 MHz, $CDCl_3$) δ (ppm): 0.83 (d, 8-$CH_3$), 1.07 (d, 6"-H), 1.14 (d, 13-$CH_3$), 1.16 (t, 3-$OCOCH_2CH_3$), 1.18 (t, 4"-$OCOCH_2CH_3$), 1.18 (d, 6'-H), 1.40 (s, 3"-$CH_3$), 1.67 (dd, 2"-Hax), 1.79 (m, 8-H), 1.99 (s, 3"-$OCOCH_3$), 2.01 (s, 9-$OCOCH_3$), 2.24 (s, $NCH_3$), 2.53 (s, 3'-$N(CH_3)_2$), 2.95 (dd, 6-$CH_2$), 3.18 (m, 4'-H), 3.18 (m, 5'-H), 3.20 (d, 2"-Heq), 3.35 (dd, 2'-H), 3.53 (br d, 4-H), 3.74 (s, 4-$OCH_3$), 3.91 (br d, 5-H), 4.01 (m, 13-H), 4.02 (d, 1'-H), 4.49 (dq, 5"-H), 4.57 (d, 4"-H), 4.82 (m, 9-H), 4.83 (d, 1"-H), 5.03 (br d, 3-H), 6.27 (br d, NH), 9.63 (s, CHO).

Example 9

Preparation method of the compound represented by the formula (1) wherein $R_1$ is propionyl group, $R_2$ is acetyl group, $R_3$ is methyl group, $R_5$, $R_6$ and $R_8$ are hydrogen atoms, $R_7$ is methyl group, $R_{4'}$ is a group represented by the formula (a), $R_{3''}$ is acetyl group, $R_{4''}$ is propionyl group, and X is NH group (a) In the same manner as in Example 4(a), except that the compound of Reference Example 7 was used instead of the compound of Reference Example 3, 471 mg of an azide compound (compound represented by the formula (17) mentioned in Preparation Scheme 6 wherein $R_3$ is 4-methoxybenzyl group, $R_7$ is methyl group, $R_8$ is hydrogen atom, $R_{3''}$ is acetyl group, $R_{4''}$ is propionyl group, and X is azido group) was obtained from 862 mg of the compound of Example 1.

Physicochemical Properties of this Compound (1) Molecular formula: $C_{54}H_{87}N_5O_{20}$ (2) Mass spectrum (FAB): m/z 1126 $(M+H)^+$ (3) Specific rotation: $[\alpha]_D^{22}$ −77° (c0.9, $CHCl_3$)

(4) $^1H$ NMR spectrum (300 MHz, $CDCl_3$) δ (ppm): 0.85 (d, 8-$CH_3$), 1.05 (d, 6"-H), 1.12 (d, 13-$CH_3$), 1.12 (t, 3-$OCOCH_2CH_3$), 1.17 (d, 6'-H), 1.18 (t, 4"-$OCOCH_2CH_3$), 1.40 (s, 3"-$CH_3$), 1.48 (m, 6-H), 1.56 (m, 6-$CH_2$), 1.87 (m, 6-$CH_2$), 1.66 (dd, 2"-Hax), 1.74 (m, 8-H), 1.99 (s, 3"-$OCOCH_3$), 2.01 (s, 9-$OCOCH_3$), 2.07 (s, 2'-$OCOCH_3$), 2.40 (s, 3'-$N(CH_3)_2$), 2.62 (t, 3'-H), 3.10 (t, 4'-H), 3.16 (s, $CH(OCH_3)_2$), 3.22 (m, 5'-H), 3.24 (s, $CH(OCH_3)_2$), 3.50 (dd, 4-H), 3.52 (s, 4-$OCH_3$), 3.65 (m, 13-H), 3.78 (s, $C_6H_4$—$OCH_3$), 3.79 (br d, 5-H), 4.48 (dq, 5"-H), 4.55 (d, 4"-H), 4.65 (d, 1'-H), 4.79 (d, 1"-H), 4.94 (dd, 2'-H), 5.03 (br dd, 9-H), 5.18 (br dd, 3-H), 6.84 (d, $C_6H_4$), 7.25 (d, $C_6H_4$).

(b) In the same manner as in Example 4(b), 172 mg of an azide-reduced compound (compound represented by the formula (17) mentioned in Preparation Scheme 6 wherein $R_3$ is 4-methoxybenzyl group, $R_7$ is methyl group, $R_8$ is hydrogen atom, $R_{3''}$ is acetyl group, $R_{4''}$ is propionyl group, and X is amino group) was obtained from 470 mg of the compound of Example 9(a).

Physicochemical Properties of this Compound (1) Molecular formula: $C_{54}H_{89}N_3O_{20}$ (2) Mass spectrum (FAB): m/z 1100 $(M+H)^+$ (3) Specific rotation: $[\alpha]_D^{24}$ −92° (c0.9, $CHCl_3$)

(4) $^1H$ NMR spectrum (300 MHz, $CDCl_3$) δ (ppm): 0.87 (d, 8-$CH_3$), 1.05 (d, 6"-H), 1.08 (t, 3-$OCOCH_2CH_3$), 1.17 (t, 4"-$OCOCH_2CH_3$), 1.18 (s, 3"-$CH_3$), 1.27 (d, 6'-H), 1.40 (s, 3"-H), 1.65 (dd, 2"-Hax), 1.89 (s, 3"-$OCOCH_3$), 2.00 (s, 9-$OCOCH_3$), 2.01 (s, 2'-$OCOCH_3$), 2.42 (s, 3'-$N(CH_3)_2$), 2.63 (t, 3'-H), 3.07 (s, $CH(OCH_3)_2$), 3.11 (m, 4'-H), 3.17 (d, 2"-Heq), 3.21 (s, $CH(OCH_3)_2$), 3.23 (m, 5'-H), 3.57 (s, 4-$OCH_3$), 3.71 (m, 13-H), 3.78 (s, $C_6H_4$—$OCH_3$), 4.46 (dq, 5"-H), 4.55 (d, 4"-H), 4.70 (d, 1'-H), 4.78 (d, 1"-H), 4.95 (dd, 2'-H), 4.95 (m, 9-H), 5.24 (br dd, 3-H), 6.83 (d, $C_6H_4$), 7.09 (d, $C_6H_4$).

(c) In the same manner as in Example 4(c), 155 mg of a cyclized compound (compound represented by the formula (18) mentioned in Preparation Scheme 6 wherein $R_3$ is 4-methoxybenzyl group, $R_7$ is methyl group, $R_8$ is hydrogen atom, $R_{3''}$ is acetyl group, $R_{4''}$ is propionyl group, and X is NH group) was obtained from 172 mg of the compound of Example 9(b).

Physicochemical Properties of this Compound (1) Molecular formula: $C_{54}H_{87}N_3O_{19}$ (2) Mass spectrum (FAB): m/z 1082 $(M+H)^+$ (3) Specific rotation: $[\alpha]_D^{26}$ −77° (c0.5, $CHCl_3$)

(4) $^1$H NMR spectrum (300 MHz, $CDCl_3$) δ (ppm): 0.72 (d, 8-$CH_3$), 1.05 (d, 6"-H), 1.16 (d, 13-$CH_3$), 1.17 (t, 3-$OCOCH_2CH_3$), 1.19 (d, 6'-H), 1.20 (t, 4"-$OCOCH_2CH_3$), 1.40 (s, 3"-$CH_3$), 1.65 (dd, 2"-Hax), 1.86 (m, 8-H), 2.01 (s, 3"-$OCOCH_3$), 2.02 (s, 9-$OCOCH_3$), 2.03 (s, 2'-$OCOCH_3$), 2.42 (s, 3'-$N(CH_3)_2$), 3.16 (s, $CH(OCH_3)_2$), 3.24 (s, $CH(OCH_3)_2$), 3.01 (d, 3"-Heq), 3.65 (s, 4-$OCH_3$), 3.79 (s, $C_6H_4$—$OCH_3$), 4.48 (dq, 5"-H), 4.55 (d, 4"-H), 4.71 (d, 1'-H), 4.79 (d, 1"-H), 4.87 (br dd, 9-H), 4.96 (dd, 2'-H), 5.13 (br d, 3-H), 6.40 (br s, NH), 6.90 (d, $C_6H_4$), 7.25 (d, $C_6H_4$).

(d) In the same manner as in Example 8(d), 78 mg of an amine compound (compound represented by the formula (18) mentioned in Preparation Scheme 6 wherein $R_3$ is hydrogen atom, $R_7$ is methyl group, $R_8$ is hydrogen atom, $R_{3''}$ is acetyl group, $R_{4''}$ is propionyl group, and X is NH group) was obtained from 155 mg of the compound of Example 9(c).

Physicochemical Properties of this Compound (1) Molecular formula: $C_{46}H_{79}N_3O_{18}$ (2) Mass spectrum (FAB): m/z 962 $(M+H)^+$ (3) Specific rotation: $[\alpha]_D^{24}$ −66° (c1.2, $CHCl_3$)

(4) $^1$H NMR spectrum (300 MHz, $CDCl_3$) δ (ppm): 0.89 (d, 8-$CH_3$), 1.05 (d, 6"-H), 1.16 (d, 13-$CH_3$), 1.17 (t, 3-$OCOCH_2CH_3$), 1.20 (t, 4"-$OCOCH_2CH_3$), 1.20 (d, 6'-H), 1.40 (s, 3"-$CH_3$), 1.65 (dd, 2"-Hax), 1.89 (m, 8-H), 2.01 (s, 3"-$OCOCH_3$), 2.05 (s, 9-$OCOCH_3$), 2.05 (s, 2'-$OCOCH_3$), 2.41 (s, 3'-$N(CH_3)_2$), 2.61 (t, 3'-H), 3.23 (s, $CH(OCH_3)_2$), 3.23 (s, $CH(OCH_3)_2$), 3.46 (s, 4-$OCH_3$), 4.46 (m, $CH(OCH_3)_2$), 4.47 (dq, 5"-H), 4.55 (d, 4"-H), 4.61 (d, 1'-H), 4.79 (d, 1"-H), 4.84 (m, 9-H), 4.89 (br dd, 3-H), 4.96 (dd, 2'-H).

(e) In the same manner as in Example 8(e), 20 mg of an N-methylated compound (compound represented by the formula (18) mentioned in Preparation Scheme 6 wherein $R_3$ and $R_7$ are methyl groups, $R_8$ is hydrogen atom, $R_{3''}$ is acetyl group, $R_{4''}$ is propionyl group, and X is NH group) was obtained from 31 mg of the compound of Example 9(d).

Physicochemical Properties of this Compound (1) Molecular formula: $C_{47}H_{81}N_3O_{18}$ (2) Mass spectrum (FAB): m/z 976 $(M+H)^+$ (3) Specific rotation: $[\alpha]_D^{26}$ −66° (c1.0, $CHCl_3$)

(4) $^1$H NMR spectrum (300 MHz, $CDCl_3$) δ (ppm): 0.85 (d, 8-$CH_3$), 1.05 (d, 6"-H), 1.14 (t, 3-$OCOCH_2CH_3$), 1.16 (d, 6'-H), 1.18 (t, 4"-$OCOCH_2CH_3$), 1.18 (d, 13-H), 1.40 (s, 3"-$CH_3$), 1.66 (dd, 2"-Hax), 1.72 (m, 6-H), 1.87 (m, 8-H), 2.02 (s, 3"-$OCOCH_3$), 2.02 (s, 9-$OCOCH_3$), 2.02 (s, 2'-$OCOCH_3$), 2.15 (s, $NCH_3$), 2.42 (s, 3'-$N(CH_3)_2$), 2.60 (t, 3'-H), 3.13 (t, 4'-H), 3.18 (d, 2"-Heq), 3.24 (s, $CH(OCH_3)_2$), 3.62 (s, 4-$OCH_3$), 4.50 (dq, 5"-H), 4.55 (d, 4"-H), 4.66 (d, 1'-H), 4.79 (d, 1"-H), 4.87 (m, 9-H), 4.94 (br dd, 3-H), 5.00 (dd, 2'-H), 6.26 (br s, NH).

(f) In the same manner as in Example 2(c), 13 mg of a deacetyled compound (compound represented by the formula (19) mentioned in Preparation Scheme 6 wherein $R_3$ and $R_7$ are methyl groups, $R_8$ is hydrogen atom, $R_{3''}$ is acetyl group, $R_{4''}$ is propionyl group, and X is NH group) was obtained from 20 mg of the compound of Example 9(e).

Physicochemical Properties of this Compound (1) Molecular formula: $C_{45}H_{79}N_3O_{17}$ (2) Mass spectrum (FAB): m/z 934 $(M+H)^+$ (3) Specific rotation: $[\alpha]_D^{24}$ −56° (c0.6, $CHCl_3$)

(4) $^1$H NMR spectrum (300 MHz, $CDCl_3$) δ (ppm): 0.88 (d, 8-$CH_3$), 1.07 (d, 6"-H), 1.15 (t, 3-$OCOCH_2CH_3$), 1.18 (t, 4"-$OCOCH_2CH_3$), 1.20 (d, 6'-H), 1.23 (d, 13-$CH_3$), 1.40 (s, 3"-$CH_3$), 1.68 (dd, 2"-Hax), 1.91 (m, 8-H), 2.01 (s, 3"-$OCOCH_3$), 2.02 (s, 9-$OCOCH_3$), 2.17 (s, $NCH_3$), 2.53 (s, 3'-$N(CH_3)_2$), 2.67 (dd, 2-H), 3.21 (s, $CH(OCH_3)_2$), 3.26 (s, $CH(OCH_3)_2$), 3.67 (s, 4-$OCH_3$), 3.45 (dd, 2'-H), 4.49 (dq, 5"-H), 4.51 (d, 1'-H), 4.57 (d, 4"-H), 4.83 (d, 1"-H), 4.90 (m, 9-H), 5.09 (m, 3-H), 6.18 (br d, NH).

(g) In the same manner as in Example 2(d), 11 mg of the title compound was obtained from 13 mg of the compound of Example 9(f).

Physicochemical Properties of this Compound (1) Molecular formula: $C_{43}H_{73}N_3O_{16}$ (2) Mass spectrum (FAB): m/z 888 $(M+H)^+$ (3) Specific rotation: $[\alpha]_D^{23}$ −66° (c0.5, $CHCl_3$)

(4) $^1$H NMR spectrum (300 MHz, $CDCl_3$) δ (ppm): 0.88 (d, 8-$CH_3$), 1.08 (d, 6"-H), 1.13 (d, 6'-H), 1.16 (t, 3-$OCOCH_2CH_3$), 1.21 (t, 4"-$OCOCH_2CH_3$), 1.26 (d, 13-$CH_3$), 1.41 (s, 3"-$CH_3$), 1.68 (dd, 2"-Hax), 1.94 (m, 8-H), 2.00 (s, 3"-$OCOCH_3$), 2.02 (s, 9-$OCOCH_3$), 2.18 (s, 11-$CH_3$), 2.54 (s, 3'-$N(CH_3)_2$), 2.71 (dd, 2-H), 3.07 (dd, 6-$CH_2$), 3.19 (m, 5'-H), 3.21 (m, 4'-H), 3.38 (dd, 2'-H), 3.65 (s, 4-$OCH_3$), 4.39 (d, 1'-H), 4.50 (dq, 5"-H), 4.57 (d, 4"-H), 4.84 (d, 1"-H), 4.88 (m, 9-H), 5.22 (br d, 3-H), 6.27 (br d, NH), 9.63 (s, CHO).

Example 10

Preparation method of the compound represented by the formula (1) wherein $R_1$ is propionyl group, $R_2$ is acetyl group, $R_3$ is methyl group, $R_5$, $R_6$, $R_7$ and $R_8$ are hydrogen atoms, $R_{4'}$ is a group represented by the formula (a), $R_{3''}$ is acetyl group, $R_{4''}$ is propionyl group, X is —$NR_4$— group, and $R_4$ is 4-phenylbutyl group (a) In the same manner as in Example 4(a), 18 mg of a 4-phenylbutyl compound (compound represented by the formula (17) mentioned in Preparation Scheme 6 wherein $R_3$ is methyl group, $R_7$ and $R_8$ are hydrogen atoms, $R_{3''}$ is acetyl group, $R_{4''}$ is propionyl group, and X is 4-phenylbutylamino group) was obtained from 66 mg of the compound of Example 7(b).

Physicochemical Properties of this Compound (1) Molecular formula: $C_{56}H_{93}N_3O_{19}$ (2) Mass spectrum (FAB): m/z 1112 $(M+H)^+$ (3) Specific rotation: $[\alpha]_D^{23}$ −54° (c0.6, $CHCl_3$)

(4) $^1$H NMR spectrum (300 MHz, $CDCl_3$) δ (ppm): 0.93 (d, 8-$CH_3$), 1.06 (d, 6"-H), 1.14 (t, 3-$OCOCH_2CH_3$), 1.15 (d, 6'-H), 1.18 (t, 4"-$OCOCH_2CH_3$), 1.40 (s, 3"-$CH_3$), 1.65 (dd, 2"-Hax), 2.00 (s, 3"-$OCOCH_3$), 2.00 (s, 9-$OCOCH_3$), 2.01 (s, 2'-$OCOCH_3$), 2.22 (s, $NCH_3$), 2.42 (s, 3'-$N(CH_3)_2$), 3.21 (s, $CH(OCH_3)_2$), 3.25 (s, $CH(OCH_3)_2$), 3.50 (br d, 4-H), 3.52 (s, 4-$OCH_3$), 3.80 (br d, 5-H), 4.41 (dd, $CH(OCH_3)_2$), 4.49 (dq, 5"-H), 4.55 (d, 4"-H), 4.68 (d, 1'-H), 4.79 (d, 1"-H), 4.91 (br dd, 9-H), 4.95 (dd, 2'-H), 5.17 (br dd, 3-H), 7.17 (d, $C_6H_5$), 7.26 (d, $C_6H_5$).

(b) In the same manner as in Example 4(c), 192 mg of a cyclized compound (compound represented by the formula (18) mentioned in Preparation Scheme 6 wherein $R_3$ is methyl group, $R_7$ and $R_8$ are hydrogen atoms, $R_{3''}$ is acetyl group, $R_{4''}$ is propionyl group, and X is $C_6H_5(CH_2)_4N$ group) was obtained from 18 mg of the compound of Example 10(a).

Physicochemical Properties of this Compound (1) Molecular formula: $C_{56}H_{91}N_3O_{18}$ (2) Mass spectrum (FAB): m/z 1094 $(M+H)^+$ (3) $^1H$ NMR spectrum (300 MHz, $CDCl_3$) δ (ppm): 0.88 (d, 8-$CH_3$), 1.04 (d, 6"-H), 1.12 (t, 3-$OCOCH_2CH_3$), 1.16 (s, 6'-$CH_3$), 1.17 (t, 4"-$OCOCH_2CH_3$), 1.39 (s, 3"-H), 1.65 (dd, 2"-Hax), 1.98 (s, 3"-$OCOCH_3$), 2.00 (s, 9-$OCOCH_3$), 2.01 (s, 2'-$OCOCH_3$), 2.41 (s, 3'-$N(CH_3)_2$), 2.62 (t, 3'-H), 3.09 (s, $CH(OCH_3)_2$), 3.21 (s, $CH(OCH_3)_2$), 3.36 (br d, 4-H), 3.79 (s, 4-$OCH_3$), 3.88 (br d, 5-H), 4.46 (m, $CH(OCH_3)_2$), 4.47 (dq, 5"-H), 4.54 (d, 4"-H), 4.73 (d, 1'-H), 4.77 (d, 1"-H), 4.94 (dd, 2'-H), 4.99 (br dd, 3-H), 7.23 (d, $C_6H_5$), 7.36 (d, $C_6H_5$).

(c) In the same manner as in Example 2(c), 17 mg of a deacetyled compound (compound represented by the formula (19) mentioned in Preparation Scheme 6 wherein $R_3$ is methyl group, $R_7$ and $R_8$ are hydrogen atoms, $R_{3''}$ is acetyl group, $R_{4''}$ is propionyl group, and X is $C_6H_5(CH_2)_4N$ group) was obtained from 33 mg of the compound of Example 10(b).

Physicochemical Properties of this Compound (1) Molecular formula: $C_{54}H_{79}N_3O_{17}$ (2) Mass spectrum (FAB): m/z 1052 $(M+H)^+$ (3) Specific rotation: $[\alpha]_D^{22}$ −19° (c0.8, $CHCl_3$)

(4) $^1H$ NMR spectrum (300 MHz, $CDCl_3$) δ (ppm): 0.90 (d, 8-$CH_3$), 1.08 (d, 6"-H), 1.14 (t, 3-$OCOCH_2CH_3$), 1.19 (t, 4"-$OCOCH_2CH_3$), 1.20 (d, 6'-H), 1.41 (s, 3"-$CH_3$), 2.01 (s, 3"-$OCOCH_3$), 2.04 (s, 9-$OCOCH_3$), 2.22 (s, $NCH_3$), 2.40 (t, 3'-H), 2.54 (s, 3'-$N(CH_3)_2$), 2.63 (dd, 2-H), 2.74 (br d, 2-H), 3.15 (s, $CH(OCH_3)_2$), 3.21 (d, 2"-Heq), 3.25 (s, $CH(OCH_3)_2$), 3.27 (dq, 5'-H), 3.43 (dd, 2'-H), 3.84 (s, 4-$OCH_3$), 4.70 (dd, $CH(OCH_3)_2$), 4.52 (dq, 5"-H), 4.53 (d, 1'-H), 4.58 (d, 4"-H), 4.69 (br dd, 9-H), 4.83 (d, 1"-H), 4.99 (br dd, 3-H), 7.14-7.28 (m, $C_6H_5$), 7.30-7.41 (m, $C_6H_5$).

(d) In the same manner as in Example 2(d), 11 mg of the title compound was obtained from 16 mg of the compound of Example 10(c).

Physicochemical Properties of this Compound (1) Molecular formula: $C_{52}H_{83}N_3O_{16}$ (2) Mass spectrum (FAB): m/z 1006 $(M+H)^+$ (3) Specific rotation: $[\alpha]_D^{23}$ −50° (c0.3, $CHCl_3$)

(4) $^1H$ NMR spectrum (300 MHz, $CDCl_3$) δ (ppm): 0.72 (m, 7-H), 0.87 (d, 8-$CH_3$), 1.08 (d, 6"-H), 1.11 (d, 6'-H), 1.18 (t, 3-$OCOCH_2CH_3$), 1.19 (t, 4"-$OCOCH_2CH_3$), 1.41 (s, 3"-$CH_3$), 1.67 (dd, 2"-Hax), 1.78 (m, 8-H), 2.00 (s, 3"-$OCOCH_3$), 2.04 (s, 9-$OCOCH_3$), 2.22 (s, $NCH_3$), 2.41 (t, 3'-H), 2.54 (s, 3'-$N(CH_3)_2$), 2.65 (t, $C_6H_5(CH_2)_3CH_2$), 2.74 (dd, 2-H), 3.10 (dd, 6-$CH_2$), 3.15 (m, 4'-H), 3.20 (m, 5'-H), 3.55 (dd, 2'-H), 3.49 (br d, 4-H), 3.84 (s, 4-$OCH_3$), 3.92 (br d, 5-H), 4.47 (d, 1'-H), 4.51 (dq, 5"-H), 4.58 (d, 4"-H), 4.71 (br dd, 9-H), 4.83 (d, 1"-H), 5.09 (br dd, 3-H), 7.13-7.21 (m, $C_6H_5$), 7.22-7.30 (m, $C_6H_5$), 9.58 (s, CHO).

Preparation Scheme 7

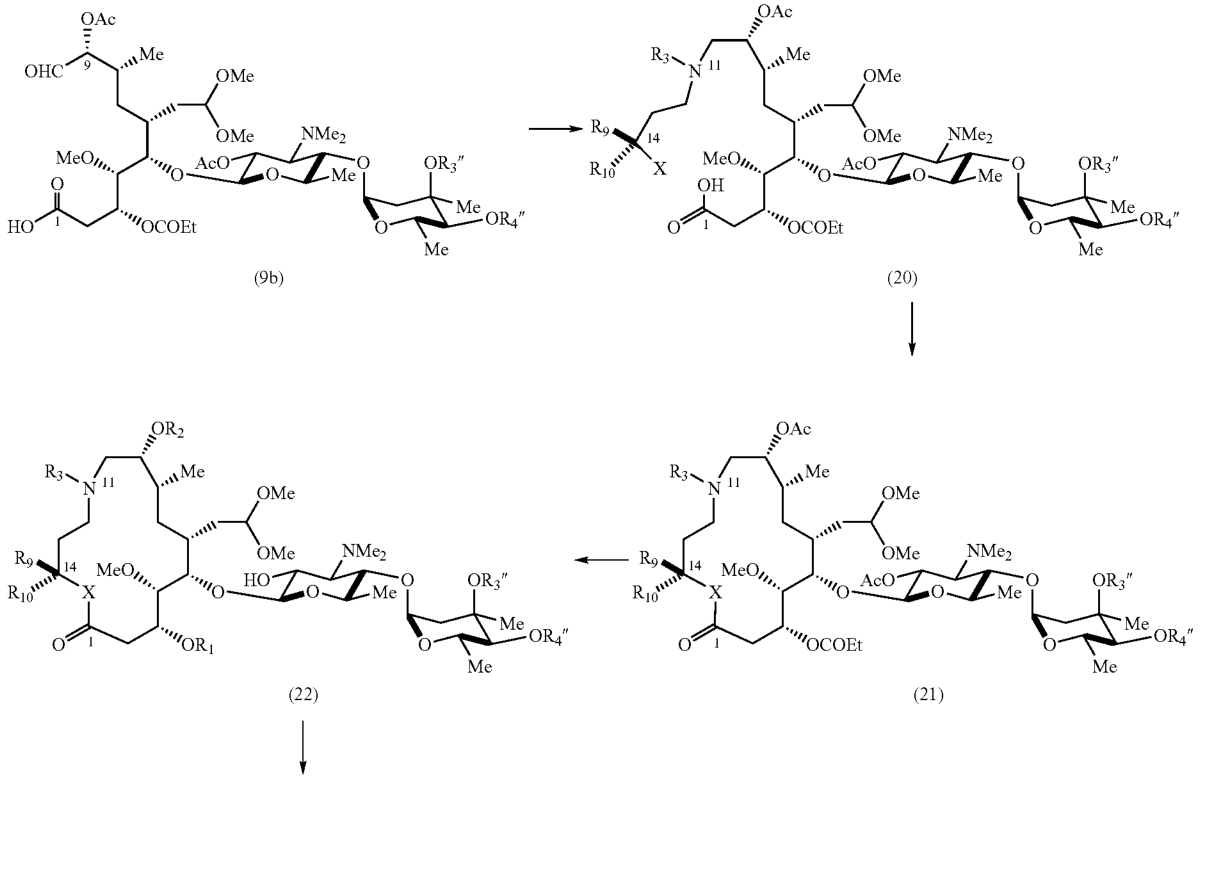

(9b) (20) (21) (22)

-continued

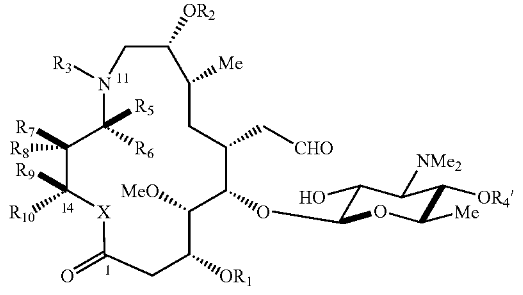

(2)

Example 11

Preparation method of the compound represented by the formula (2) wherein $R_1$ is propionyl group, $R_2$ is acetyl group, $R_3$ is 4-phenylbutyl group, $R_5$, $R_6$, $R_7$, $R_8$, $R_9$ and $R_{10}$ are hydrogen atoms, $R_{4'}$ is a group represented by the formula (a), $R_{3''}$ is acetyl group, $R_{4''}$ is propionyl group, and X is oxygen atom (a) In the same manner as in Example 2(a), except that the compound of Reference Example 8 was used instead of the compound of Reference Example 1, 157 mg of an amine compound (compound represented by the formula (20) mentioned in Preparation Scheme 7 wherein $R_3$ is 4-phenylbutyl group, $R_9$ and $R_{10}$ are hydrogen atoms, $R_{3''}$ is acetyl group, $R_{4''}$ is propionyl group, and X is hydroxyl group) was obtained from 200 mg of the compound of Example 1.

Physicochemical Properties of this Compound (1) Molecular formula: $C_{56}H_{92}N_2O_{20}$ (2) Mass spectrum (FAB): m/z 1113 $(M+H)^+$ (3) Specific rotation: $[\alpha]_D^{23}$ −66° (c0.65, $CHCl_3$)

(4) $^1H$ NMR spectrum (300 MHz, $CDCl_3$) δ (ppm): 0.87 (d, 8-$CH_3$), 1.03 (br dd, 7-H), 1.07 (d, 6"-H), 1.15 (t, 3-$OCOCH_2CH_3$), 1.19 (d, 6'-H), 1.20 (t, 4"-$OCOCH_2CH_3$), 1.30 (m, 7-H), 1.42 (s, 3"-$CH_3$), 1.66 (dd, 2"-Hax), 1.85 (m, 8-H), 1.98 (s, 3"-$OCOCH_3$), 2.03 (s, 9-$OCOCH_3$), 2.03 (s, 2'-$OCOCH_3$), 2.43 (s, 3'-$N(CH_3)_2$), 2.62 (t, 3'-H), 2.88 (dd, 2-H), 3.12 (t, 4'-H), 3.19 (d, 2"-Heq), 3.20 (s, $CH(OCH_3)_2$), 3.26 (s, $CH(OCH_3)_2$), 3.54 (br d, 4-H), 3.57 (s, 4-$OCH_3$), 3.88 (br d, 5-H), 4.49 (dq, 5"-H), 4.53 (dd, $CH(OCH_3)_2$), 4.57 (d, 4"-H), 4.72 (d, 1'-H), 4.80 (d, 1"-H), 4.95 (dd, 2'-H), 5.24 (br dd, 9-H), 5.32 (br d, 3-H), 7.12-7.34 (m, $C_6H_5$).

(b) In the same manner as in Example 2(b), 13 mg of a cyclized compound (compound represented by the formula (21) mentioned in Preparation Scheme 7 wherein $R_3$ is 4-phenylbutyl group, $R_9$ and $R_{10}$ are hydrogen atoms, $R_{3''}$ is acetyl group, $R_{4''}$ is propionyl group, and X is oxygen atom) was obtained from 30 mg of the compound of Example 11(a).

Physicochemical Properties of this Compound (1) Molecular formula: $C_{56}H_{90}N_2O_{19}$ (2) Mass spectrum (FAB): m/z 1095 $(M+H)^+$ (3) Specific rotation: $[\alpha]_D^{19}$ −85° (c1.0, $CHCl_3$)

(4) $^1H$ NMR spectrum (300 MHz, $CDCl_3$) δ (ppm): 0.91 (d, 8-$CH_3$), 1.07 (d, 6"-H), 1.15 (t, 3-$OCOCH_2CH_3$), 1.20 (t, 4"-$OCOCH_2CH_3$), 1.20 (d, 6'-H), 1.42 (s, 3"-$CH_3$), 1.68 (dd, 2"-Hax), 1.99 (s, 3"-$OCOCH_3$), 2.02 (s, 9-$OCOCH_3$), 2.04 (s, 2'-$OCOCH_3$), 2.44 (s, 3'-$N(CH_3)_2$), 2.62 (t, 3'-H), 2.74 (dd, 2-H), 2.86 (dd, 2-H), 3.12 (s, $CH(OCH_3)_2$), 3.15 (t, 4'-H), 3.19 (d, 2"-Heq), 3.25 (s, $CH(OCH_3)_2$), 3.27 (m, 5'-H), 3.36 (br d, 4-H), 3.53 (s, 4-$OCH_3$), 3.95 (br d, 5-H), 4.08 (m, 14-H), 4.41 (m, 14-H), 4.48 (m, 5"-H), 4.57 (d, 4"-H), 4.67 (d, 1'-H), 4.77 (m, 9-H), 4.81 (d, 1"-H), 4.97 (dd, 2'-H), 5.17 (m, 3-H), 7.14-7.31 (m, $C_6H_5$).

(c) In the same manner as in Example 2(c), 24 mg of 9-acetoxyazalide (compound represented by the formula (22) mentioned in Preparation Scheme 7 wherein $R_1$ is propionyl group, $R_2$ is acetyl group, $R_3$ is 4-phenylbutyl group, $R_9$ and $R_{10}$ are hydrogen atoms, $R_{3''}$ is acetyl group, $R_{4''}$ is propionyl group, and X is oxygen atom), and 19 mg of 9-hydroxyazalide (compound represented by the formula (22) mentioned in Preparation Scheme 7 wherein $R_1$ is propionyl group, $R_2$ is hydrogen atom, $R_3$ is 4-phenylbutyl group, $R_9$ and $R_{10}$ are hydrogen atoms, $R_{3''}$ is acetyl group, $R_{4''}$ is propionyl group, and X is oxygen atom) were obtained from 84 mg of the compound of Example 11(b).

Physicochemical Properties of 9-acetoxyazalide (1) Molecular formula: $C_{54}H_{88}N_2O_{18}$ (2) Mass spectrum (FAB): m/z 1053 $(M+H)^+$ (3) Specific rotation: $[\alpha]_D^{20}$ −60° (c1.0, $CHCl_3$)

(4) $^1H$ NMR spectrum (300 MHz, $CDCl_3$) δ (ppm): 0.92 (d, 8-$CH_3$), 1.09 (d, 6"-H), 1.15 (t, 3-$OCOCH_2CH_3$), 1.20 (t, 4"-$OCOCH_2CH_3$), 1.21 (d, 6'-H), 1.42 (s, 3"-$CH_3$), 1.47 (quint, $C_6H_5(CH_2)_4$), 1.59 (quint, $C_6H_5(CH_2)_4$), 1.70 (dd, 2"-Hax), 2.00 (s, 3"-$OCOCH_3$), 2.02 (s, 9-$OCOCH_3$), 2.55 (s, 3'-$N(CH_3)_2$), 2.61 (t, $C_6H_5(CH_2)_4$), 2.75 (dd, 2-H), 2.89 (dd, 2-H), 3.15 (s, $CH(OCH_3)_2$), 3.23 (d, 2"-Heq), 3.27 (s, $CH(OCH_3)_2$), 3.42 (dd, 2'-H), 3.47 (br d, 4-H), 3.61 (s, 4-$OCH_3$), 3.94 (br d, 5-H), 4.09 (m, 14-H), 4.39 (m, 14-H), 4.47 (d, 1'-H), 4.48 (dd, $CH(OCH_3)_2$), 4.56 (m, 5"-H), 4.59 (d, 4"-H), 4.81 (m, 9-H), 4.86 (d, 1"-H), 5.21 (m, 3-H), 7.14-7.29 (m, $C_6H_5$).

Physicochemical Properties of 9-hydroxyazalide (1) Molecular formula: $C_{52}H_{86}N_2O_{17}$ (2) Mass spectrum (FAB): m/z 1011 $(M+H)^+$ (3) Specific rotation: $[\alpha]_D^{20}$ −51° (c1.0, $CHCl_3$)

(4) $^1H$ NMR spectrum (300 MHz, $CDCl_3$) δ (ppm): 0.93 (d, 8-$CH_3$), 1.07 (d, 6"-H), 1.12 (t, 3-$OCOCH_2CH_3$), 1.18 (t, 4"-$OCOCH_2CH_3$), 1.19 (d, 6'-H), 1.40 (s, 3"-$CH_3$), 1.68 (dd, 2"-Hax), 2.00 (s, 3"-$OCOCH_3$), 2.53 (s, 3'-$N(CH_3)_2$), 2.64 (dd, 2-H), 2.81 (dd, 2-H), 3.09 (s, $CH(OCH_3)_2$), 3.20 (m, 5'-H), 3.21 (d, 2"-Heq), 3.24 (m, 4'-H), 3.24 (s, $CH(OCH_3)_2$), 3.39 (dd, 2'-H), 3.50 (br d, 4-H), 3.62 (s, 4-$OCH_3$), 3.90 (br d, 5-H), 4.10 (m, 14-H), 4.28 (m, 14-H), 4.48 (dd, $CH(OCH_3)_2$), 4.48 (d, 1'-H), 4.54 (m, 5"-H), 4.57 (d, 4"-H), 4.84 (d, 1"-H), 5.23 (m, 3-H), 7.12-7.30 (m, $C_6H_5$).

(d) In the same manner as in Example 2(d), 22 mg of the title compound was obtained from 30 mg of 9-acetoxyazalide of Example 11(c).

Physicochemical Properties of this Compound (1) Molecular formula: $C_{52}H_{82}N_2O_{17}$ (2) Mass spectrum (FAB): m/z 1007 $(M+H)^+$ (3) Specific rotation: $[\alpha]_D^{19}$ −67° (c0.67, $CHCl_3$)

(4) $^1H$ NMR spectrum (300 MHz, $CDCl_3$) δ (ppm): 0.91 (d, 8-$CH_3$), 1.08 (d, 6"-H), 1.13 (d, 6'-H), 1.16 (t, 3-$OCOCH_2CH_3$), 1.18 (t, 4"-$OCOCH_2CH_3$), 1.40 (s, 3"-$CH_3$), 1.69 (dd, 2"-Hax), 1.99 (s, 3"-$OCOCH_3$), 1.99 (s, 9-$OCOCH_3$), 2.04 (m, 6-H), 2.34 (dd, 6-$CH_2$), 2.54 (s, 3'-$N(CH_3)_2$), 2.70 (dd, 2-H), 2.87 (dd, 2-H), 2.93 (dd, 6-$CH_2$), 3.20 (m, 4'-H), 3.20 (m, 5'-H), 3.21 (d, 2"-Heq), 3.32 (dd, 2'-H), 3.51 (dd, 4-H), 3.61 (s, 4-$OCH_3$), 3.90 (br d, 5-H), 4.10 (m, 14-H), 4.32 (m, 14-H), 4.41 (d, 1'-H), 4.49 (dq, 5"-H), 4.57 (d, 4"-H), 4.79 (m, 9-H), 4.85 (d, 1"-H), 5.36 (m, 3-H), 7.14-7.29 (m, $C_6H_5$), 9.62 (s, CHO).

Example 12

Preparation method of the compound represented by the formula (2) wherein $R_1$ is propionyl group, $R_2$ is hydrogen atom, $R_3$ is 4-phenylbutyl group, $R_5$, $R_6$, $R_7$, $R_5$, $R_5$ and $R_{10}$ are hydrogen atoms, $R_{4'}$ is a group represented by the formula (a), $R_{3''}$ is acetyl group, $R_{4''}$ is propionyl group, and X is oxygen atom In the same manner as in Example 2(d), 16 mg of the title compound was obtained from 23 mg of 9-hydroxyazalide of Example 11(c).

Physicochemical Properties of this Compound (1) Molecular formula: $C_{50}H_{80}N_2O_{16}$ (2) Mass spectrum (FAB): m/z 965 $(M+H)^+$ (3) Specific rotation: $[\alpha]_D^{20}$ −65° (c0.52, $CHCl_3$)

(4) $^1H$ NMR spectrum (300 MHz, $CDCl_3$) δ (ppm): 0.96 (d, 8-$CH_3$), 0.98 (br dd, 7-H), 1.08 (d, 6"-H), 1.12 (d, 6'-H), 1.16 (t, 3-$OCOCH_2CH_3$), 1.18 (t, 4"-$OCOCH_2CH_3$), 1.40 (s, 3"-$CH_3$), 1.68 (dd, 2"-Hax), 1.99 (s, 3"-$OCOCH_3$), 2.54 (s, 3'-$N(CH_3)_2$), 2.82 (dd, 2-H), 2.96 (dd, 6-$CH_2$), 3.20 (m, 4'-H), 3.20 (m, 5'-H), 3.21 (d, 2"-Heq), 3.33 (dd, 2'-H), 3.45 (br d, 9-H), 3.53 (br d, 4-H), 3.62 (s, 4-$OCH_3$), 3.88 (br d, 5-H), 4.14 (m, 14-H), 4.25 (m, 14-H), 4.42 (d, 1'-H), 4.50 (dq, 5"-H), 4.57 (d, 4"-H), 4.84 (d, 1"-H), 5.37 (m, 3-H), 7.14-7.29 (m, $C_6H_5$), 9.63 (s, CHO).

Example 13

Preparation method of the compound represented by the formula (2) wherein $R_1$ is propionyl group, $R_2$ is hydrogen atom, $R_3$ is 4-phenylbutyl group, $R_5$, $R_6$, $R_7$, $R_5$, $R_5$ and $R_{10}$ are hydrogen atoms, $R_{4'}$ is a group represented by the formula (a), $R_{3''}$ is acetyl group, $R_{4''}$ is propionyl group, and X is NH group)

(a) In the same manner as in Example 4(a), except that the compound of Reference Example 9 was used instead of the compound of Reference Example 3, 950 mg of an azide compound (compound represented by the formula (20) mentioned in Preparation Scheme 7 wherein $R_3$ is 4-phenylbutyl group, $R_9$ and $R_{10}$ are hydrogen atoms, $R_{3''}$ is acetyl group, $R_{4''}$ is propionyl group, and X is azido group) was obtained from 1.10 g of the compound of Example 1.

Physicochemical Properties of this Compound (1) Molecular formula: $C_{56}H_{91}N_5O_{19}$ (2) Mass spectrum (FAB): m/z 1138 $(M+H)^+$ (3) Specific rotation: $[\alpha]_D^{24}$ −62° (c0.48, $CHCl_3$)

(4) $^1H$ NMR spectrum (300 MHz, $CDCl_3$) δ (ppm): 0.86 (d, 8-$CH_3$), 1.07 (d, 6"-H), 1.16 (t, 3-$OCOCH_2CH_3$), 1.19 (t, 4"-$OCOCH_2CH_3$), 1.20 (d, 6'-H), 1.41 (s, 3"-$CH_3$), 1.48 (m, 6-$CH_2$), 1.67 (dd, 2"-Hax), 2.00 (s, 3"-$OCOCH_3$), 2.03 (s, 9-$OCOCH_3$), 2.03 (s, 2'-$OCOCH_3$), 2.43 (s, 3'-$N(CH_3)_2$), 2.57 (dd, 2-H), 3.12 (t, 4'-H), 3.19 (d, 2"-Heq), 3.23 (s, $CH(OCH_3)_2$), 3.26 (s, $CH(OCH_3)_2$), 3.38 (t, 14-H), 3.46 (br d, 4-H), 3.54 (s, 4-$OCH_3$), 3.89 (br d, 5-H), 4.49 (dq, 5"-H), 4.57 (d, 4"-H), 4.70 (d, 1'-H), 4.80 (d, 1"-H), 4.96 (dd, 2'-H), 7.15-7.22 (m, $C_6H_5$), 7.26-7.31 (m, $C_6H_5$).

(b) In the same manner as in Example 7(b), 39.9 mg of an azide-reduced compound (compound represented by the formula (20) mentioned in Preparation Scheme 7 wherein $R_3$ is 4-phenylbutyl group, $R_9$ and $R_{10}$ are hydrogen atoms, $R_{3''}$ is acetyl group, $R_{4''}$ is propionyl group, and X is amino group) was obtained from 100 mg of the compound of Example 13(a).

Physicochemical Properties of this Compound (1) Molecular formula: $C_{56}H_{93}N_3O_{19}$ (2) Mass spectrum (FAB): m/z 1112 $(M+H)^+$ (3) Specific rotation: $[\alpha]_D^{22}$ −72° (c0.87, $CHCl_3$)

(4) $^1H$ NMR spectrum (300 MHz, $CDCl_3$) δ (ppm): 0.85 (d, 8-$CH_3$), 1.00 (d, 6"-H), 1.04 (t, 3-$OCOCH_2CH_3$), 1.12 (d, 6'-H), 1.12 (t, 4"-$OCOCH_2CH_3$), 1.34 (s, 3"-$CH_3$), 1.60 (dd, 2"-Hax), 1.77 (m, 6-$CH_2$), 1.95 (s, 3"-$OCOCH_3$), 1.99 (s, 9-$OCOCH_3$), 2.01 (s, 2'-$OCOCH_3$), 2.36 (s, 3'-$N(CH_3)_2$), 2.48 (dd, 2-H), 2.67 (dd, 2-H), 3.05 (s, $CH(OCH_3)_2$), 3.12 (d, 2"-Heq), 3.18 (s, $CH(OCH_3)_2$), 3.49 (s, 4-$OCH_3$), 3.58 (br d, 4-H), 3.79 (br d, 5-H), 4.41 (m, 5"-H), 4.50 (d, 4"-H), 4.68 (d, 1'-H), 4.73 (d, 1"-H), 4.89 (dd, 2'-H), 7.08-7.12 (m, $C_6H_5$), 7.18-7.23 (m, $C_6H_5$).

(c) In the same manner as in Example 4(c), 37.7 mg of a cyclized compound (compound represented by the formula (21) mentioned in Preparation Scheme 7 wherein $R_3$ is 4-phenylbutyl group, $R_9$ and $R_{10}$ are hydrogen atoms, $R_{3''}$ is acetyl group, $R_{4''}$ is propionyl group, and X is NH group) was obtained from 39.9 mg of the compound of Example 13(b).

Physicochemical Properties of this Compound (1) Molecular formula: $C_{56}H_{91}N_3O_{18}$ (2) Mass spectrum (FAB): m/z 1094 $(M+H)^+$ (3) Specific rotation: $[\alpha]_D^{21}$ −83° (c0.39, $CHCl_3$)

(4) $^1H$ NMR spectrum (300 MHz, $CDCl_3$) δ (ppm): 0.82 (d, 8-$CH_3$), 0.93 (br dd, 7-H), 1.00 (d, 6"-H), 1.05 (t, 3-$OCOCH_2CH_3$), 1.12 (d, 6'-H), 1.12 (t, 4"-$OCOCH_2CH_3$), 1.34 (s, 3"-$CH_3$), 1.60 (dd, 2"-Hax), 1.77 (m, 6-$CH_2$), 1.89 (s, 3"-$OCOCH_3$), 1.95 (s, 9-$OCOCH_3$), 1.97 (s, 2'-$OCOCH_3$), 2.36 (s, 3'-$N(CH_3)_2$), 2.76 (m, 14-H), 2.96 (s, $CH(OCH_3)_2$), 3.06 (t, 4'-H), 3.13 (d, 2"-Heq), 3.16 (s, $CH(OCH_3)_2$), 3.19 (dq, 5'-H), 3.31 (br d, 4-H), 3.58 (s, 4-$OCH_3$), 3.88 (br d, 5-H), 4.41 (dq, 5"-H), 4.50 (d, 4"-H), 4.64 (d, 1'-H), 4.73 (d, 1"-H), 4.88 (dd, 2'-H), 4.98 (br d, 3-H), 7.07-7.12 (m, $C_6H_5$), 7.17-7.22 (m, $C_6H_5$).

(d) In the same manner as in Example 2(c), 26.2 mg of 9-hydroxyazalactam (compound represented by the formula (22) mentioned in Preparation Scheme 7 wherein $R_1$ is propionyl group, $R_2$ is hydrogen atom, $R_3$ is 4-phenylbutyl group, $R_5$ and $R_{10}$ are hydrogen atoms, $R_{3''}$ is acetyl group, $R_{4''}$ is propionyl group, and X is NH group), and 19.4 mg of 9-acetoxyazalactam (compound represented by the formula (22) mentioned in Preparation Scheme 7 wherein $R_1$ is propionyl group, $R_2$ is acetyl group, $R_3$ is 4-phenylbutyl group, $R_9$ and $R_{10}$ are hydrogen atoms, $R_{3''}$ is acetyl group, $R_{4''}$ is propionyl group, and X is NH group) were obtained from 141 mg of the compound of Example 13(c).

Physicochemical Properties of 9-hydroxyazalactam (1) Molecular formula: $C_{52}H_{87}N_3O_{16}$ (2) Mass spectrum (FAB): m/z 1010 $(M+H)^+$ (3) Specific rotation: $[\alpha]_D^{25}$ −68° (c0.35, $CHCl_3$)

(4) $^1H$ NMR spectrum (300 MHz, $CDCl_3$) δ (ppm): 0.80 (d, 8-$CH_3$), 1.02 (d, 6"-H), 1.06 (t, 3-$OCOCH_2CH_3$), 1.12 (t, 4"-$OCOCH_2CH_3$), 1.13 (d, 6'-H), 1.25 (m, 7-H), 1.35 (s, 3"-$CH_3$), 1.62 (dd, 2"-Hax), 1.94 (s, 3"-$OCOCH_3$), 2.47 (s, 3'-$N(CH_3)_2$), 2.54 (t, $C_6H_5(CH_2)_4$), 2.72 (dd, 2-H), 3.02 (s, $CH(OCH_3)_2$), 3.14 (t, 4'-H), 3.15 (d, 2"-Heq), 3.18 (s, $CH(OCH_3)_2$), 3.33 (dd, 2'-H), 3.49 (dd, 4-H), 3.65 (m, 14-H), 3.70 (s, 4-$OCH_3$), 3.88 (br d, 5-H), 4.45 (d, 1'-H), 4.49 (dq, 5"-H), 4.51 (d, 4"-H), 4.78 (d, 1"-H), 4.83 (br d, 3-H), 6.53 (dd, NH), 7.07-7.12 (m, $C_6H_5$), 7.17-7.22 (m, $C_6H_5$).

Physicochemical Properties of 9-acetoxyazalactam (1) Molecular formula: $C_{54}H_{89}N_3O_{17}$ (2) Mass spectrum (FAB): m/z 1052 $(M+H)^+$ (3) Specific rotation: $[\alpha]_D^{25}$ −69° (c0.32, $CHCl_3$)

(4) $^1H$ NMR spectrum (300 MHz, $CDCl_3$) δ (ppm): 0.83 (d, 8-$CH_3$), 0.94 (br dd, 7-H), 1.02 (d, 6"-H), 1.06 (t, 3-$OCOCH_2CH_3$), 1.20 (t, 4"-$OCOCH_2CH_3$), 1.30 (d, 6'-H), 1.35 (s, 3"-$CH_3$), 1.62 (dd, 2"-Hax), 1.91 (s, 3"-$OCOCH_3$), 1.95 (s, 9-$OCOCH_3$), 2.48 (s, 3'-$N(CH_3)_2$), 2.53 (t, $C_6H_5(CH_2)_4$), 2.65 (dd, 2-H), 2.80 (m, 14-H), 3.00 (s, $CH(OCH_3)_2$), 3.15 (t, 4'-H), 3.16 (d, 2"-Heq), 3.18 (s, $CH(OCH_3)_2$), 3.31 (dd, 2'-H), 3.38 (dd, 4-H), 3.52 (m, 14-H), 3.62 (s, 4-$OCH_3$), 3.89 (br d, 5-H), 4.40 (dd, $CH(OCH_3)_2$), 4.44 (d, 1'-H), 4.45 (dq, 5"-H), 4.51 (d, 4"-H), 4.70 (br d, 9-H), 4.78 (d, 1"-H), 5.02 (br d, 3-H), 6.94 (br s, NH), 7.07-7.12 (m, $C_6H_5$), 7.17-7.21 (m, $C_6H_5$).

(e) In the same manner as in Example 2(d), 23.7 mg of the title compound was obtained from 26.2 mg of 9-hydroxyazalactam of Example 13(d).

Physicochemical Properties of this Compound (1) Molecular formula: $C_{50}H_{81}N_3O_{15}$ (2) Mass spectrum (FAB): m/z 964 $(M+H)^+$ (3) Specific rotation: $[\alpha]_D^{24}$ −81° (c0.36, $CHCl_3$)

(4) $^1H$ NMR spectrum (300 MHz, $CDCl_3$) δ (ppm): 0.81 (d, 8-$CH_3$), 0.93 (br dd, 7-H), 1.01 (d, 6"-H), 1.06 (d, 6'-H), 1.11 (t, 3-$OCOCH_2CH_3$), 1.12 (t, 4"-$OCOCH_2CH_3$), 1.23 (m, 7-H), 1.34 (s, 3"-$CH_3$), 1.62 (dd, 2"-Hax), 1.84 (m, 6-H), 1.93 (s, 3"-$OCOCH_3$), 2.16 (m, 10-H), 2.27 (dd, 2-H), 2.48 (s, 3'-$N(CH_3)_2$), 2.54 (t, $C_6H_5(CH_2)_4$), 2.74 (dd, 2-H), 2.93 (dd, 6-$CH_2$), 3.14 (d, 2"-Heq), 3.28 (dd, 2'-H), 3.39 (d, 9-H), 3.54 (dd, 4-H), 3.69 (s, 4-$OCH_3$), 3.83 (br d, 5-H), 4.38 (d, 1'-H), 4.43 (dq, 5"-H), 4.51 (d, 4"-H), 4.77 (d, 1"-H), 4.91 (br d, 3-H), 6.65 (dd, NH), 7.07-7.12 (m, $C_6H_5$), 7.17-7.22 (m, $C_6H_5$), 9.58 (s, CHO).

Example 14

Preparation method of the compound represented by the formula (2) wherein $R_1$ is propionyl group, $R_2$ is acetyl group, $R_3$ is 4-phenylbutyl group, $R_5$, $R_6$, $R_7$, $R_8$, $R_9$ and $R_{10}$ are hydrogen atoms, $R_{4'}$ is a group represented by the formula (a), $R_3$ is acetyl group, $R_{4''}$ is propionyl group, and X is NH group In the same manner as in Example 2(d), 16.2 mg of the title compound was obtained from 19.4 mg of 9-acetoxyazalactam of Example 13(d).

Physicochemical Properties of this Compound (1) Molecular formula: $C_{52}H_{83}N_3O_{16}$ (2) Mass spectrum (FAB): m/z 1006 $(M+H)^+$ (3) $^1H$ NMR spectrum (300 MHz, $CDCl_3$) δ (ppm): 0.81 (d, 8-$CH_3$), 1.02 (d, 6"-H), 1.07 (d, 6'-H), 1.10 (t, 3-$OCOCH_2CH_3$), 1.12 (t, 4"-$OCOCH_2CH_3$), 1.34 (s, 3"-$CH_3$), 1.62 (dd, 2"-Hax), 1.73 (m, 13-H), 1.91 (s, 9-$OCOCH_3$), 1.93 (s, 3"-$OCOCH_3$), 2.48 (s, 3'-$N(CH_3)_2$), 2.68 (dd, 2-H), 2.88 (dd, 6-$CH_2$), 3.15 (d, 2"-Heq), 3.25 (dd, 2'-H), 3.45 (dd, 4-H), 3.58 (m, 14-H), 3.63 (s, 4-$OCH_3$), 3.86 (br d, 5-H), 4.39 (d, 1'-H), 4.43 (dq, 5"-H), 4.51 (d, 4"-H), 4.69 (br d, 9-H), 4.78 (d, 1"-H), 5.05 (br d, 3-H), 7.07-7.13 (m, $C_6H_5$), 7.17-7.21 (m, $C_6H_5$), 9.57 (s, CHO).

Example 15

Preparation method of the compound represented by the formula (2) wherein $R_1$ is propionyl group, $R_2$ is hydrogen atom, $R_3$ is 4-phenylbutyl group, $R_5$, $R_6$, $R_7$ and $R_8$ are hydrogen atoms, one of $R_9$ and $R_{10}$ is methyl group, the other is hydrogen atom, $R_{4'}$ is a group represented by the formula (a), $R_{3''}$ is acetyl group, $R_{4''}$ is propionyl group, and X is NH group (a) In the same manner as in Example 4(a), except that 366 mg of the compound of Reference Example 10 was used instead of the compound of Reference Example 3, 540 mg of an azide compound (compound represented by the formula (20) mentioned in Preparation Scheme 7 wherein $R_3$ is 4-phenylbutyl group, one of $R_9$ and $R_{10}$ is methyl group, the other is hydrogen atom, $R_{3''}$ is acetyl group, $R_{4''}$ is propionyl group, and X is azido group) was obtained as an about 1:1 mixture (measured according to intensities of specific signals) from 882 mg of the compound of Example 1.

Physicochemical Properties of this Compound (1) Molecular formula: $C_{57}H_{93}N_5O_{19}$ (2) Mass spectrum (FAB): m/z 1152 $(M+H)^+$ (3) Specific rotation: $[\alpha]_D^{25}$ −60° (c0.53, $CHCl_3$)

(4) $^1H$ NMR spectrum (300 MHz, $CDCl_3$) δ (ppm): 0.78 (d, 8-$CH_3$), 0.99 (d, 6"-H), 1.09 (t, 3-$OCOCH_2CH_3$), 1.12 (t, 4"-$OCOCH_2CH_3$), 1.12 (d, 6'-H), 1.22 and 1.22 (each d, 14-$CH_3$), 1.34 (s, 3"-$CH_3$), 1.59 (dd, 2"-Hax), 1.90 and 1.93 (each s, 9-$OCOCH_3$), 1.96 (s, 3"-$OCOCH_3$), 2.35 (s, 3'-$N(CH_3)_2$), 3.05 (t, 4'-H), 3.11 (d, 2"-Heq), 3.16 (s, $CH(OCH_3)_2$), 3.19 (s, $CH(OCH_3)_2$), 3.39 (dd, 4-H), 3.46 and 3.48 (each s, 4-$OCH_3$), 3.81 (br d, 5-H), 4.41 (dq, 5"-H), 4.49 (d, 4"-H), 4.61 and 4.64 (each d, 1'-H), 4.73 (d, 1"-H), 4.88 (dd, 2'-H), 7.07-7.14 (m, $C_6H_5$), 7.19-7.24 (m, $C_6H_5$).

(b) In the same manner as in Example 7(b), 221 mg of an azide-reduced compound (compound represented by the formula (20) mentioned in Preparation Scheme 7 wherein $R_3$ is 4-phenylbutyl group, one of $R_9$ and $R_{10}$ is methyl group, the other is hydrogen atom, $R_{3''}$ is acetyl group, $R_{4''}$ is propionyl group, and X is amino group) was obtained as an about 1:1 mixture (measured according to intensities of specific signals) from 431 mg of the compound of Example 15(a).

Physicochemical Properties of this Compound (1) Molecular formula: $C_{57}H_{95}N_3O_{19}$ (2) Mass spectrum (FAB): m/z 1126 $(M+H)^+$ (3) Specific rotation: $[\alpha]_D^{23}$ −620 (c1.0, $CHCl_3$)

(4) $^1H$ NMR spectrum (300 MHz, $CDCl_3$) δ (ppm): 0.84 (d, 8-$CH_3$), 0.99 (d, 6"-H), 1.03 and 1.03 (each t, 3-$OCOCH_2CH_3$), 1.11 (d, 6'-H), 1.12 (t, 4"-$OCOCH_2CH_3$), 1.16 and 1.25 (each d, 14-$CH_3$), 1.34 (s, 3"-$CH_3$), 1.59 (dd, 2"-Hax), 1.65 (m, 8-H), 1.78 (m, 6-$CH_2$), 1.94 (s, 3"-$OCOCH_3$), 1.98 and 2.02 (each s, 9-$OCOCH_3$), 2.03 and 2.10 (each s, 2'-$OCOCH_3$), 2.35 (s, 3'-$N(CH_3)_2$), 2.53 (t, 3'-H), 3.04 (t, 4'-H), 3.05 (s, $CH(OCH_3)_2$), 3.11 (d, 2"-Heq), 3.17 (s, $CH(OCH_3)_2$), 3.46 and 3.63 (each br d, 4-H), 3.51 and 3.54 (each s, 4-$OCH_3$), 3.78 (br d, 5-H), 4.41 (dq, 5"-H), 4.49 (d, 4"-H), 4.69 (d, 1'-H), 4.72 (d, 1"-H), 5.08 and 5.21 (each br d, 9-H), 5.14 and 5.23 (each br dd, 2'-H), 4.89 (dd, 2'-H), 7.07-7.12 (m, $C_6H_5$), 7.17-7.22 (m, $C_6H_5$).

(c) In the same manner as in Example 4(c), 73.4 mg of an isomer A (compound represented by the formula (21) mentioned in Preparation Scheme 7 wherein $R_3$ is 4-phenylbutyl group, one of $R_9$ and $R_{10}$ is methyl group, the other is hydrogen atom, $R_{3''}$ is acetyl group, $R_{4''}$ is propionyl group, and X is NH group), and 89.0 mg of an isomer B (compound represented by the formula (21) mentioned in Preparation Scheme 7 wherein $R_3$ is 4-phenylbutyl group, one of $R_9$ and $R_{10}$ is methyl group, the other is hydrogen atom, $R_{3''}$ is acetyl group, $R_{4''}$ is propionyl group, and X is NH group, provided that the substituents $R_9$ and $R_{10}$ are exchanged compared with the isomer A) were obtained from 221 mg of the compound of Example 15(b).

Physicochemical properties of the isomer A (1) Molecular formula: $C_{57}H_{93}N_3O_{18}$ (2) Mass spectrum (FAB): m/z 1108 $(M+H)^+$ (3) Specific rotation: $[\alpha]_D^{26}$ −71° (c0.52, $CHCl_3$)

(4) $^1H$ NMR spectrum (300 MHz, $CDCl_3$) δ (ppm): 0.82 (d, 8-$CH_3$), 0.99 (d, 6"-H), 1.06 (t, 3-$OCOCH_2CH_3$), 1.12 (d, 6'-H), 1.12 (t, 4"-$OCOCH_2CH_3$), 1.19 (d, 14-$CH_3$), 1.34 (s, 3"-$CH_3$), 1.59 (dd, 2"-Hax), 1.90 (s, 3"-$OCOCH_3$), 1.94 (s, 9-$OCOCH_3$), 1.94 (s, 2'-$OCOCH_3$), 2.36 (s, 3'-$N(CH_3)_2$), 2.53 (t, 3'-H), 3.00 (s, $CH(OCH_3)_2$), 3.05 (t, 4'-H), 3.12 (d, 2"-Heq), 3.17 (s, $CH(OCH_3)_2$), 3.20 (dq, 5'-H), 3.27 (br d, 4-H), 3.45 (m, 14-H), 3.51 (s, 4-$OCH_3$), 3.84 (br d, 5-H), 4.40 (dq, 5"-H), 4.49 (d, 4"-H), 4.61 (d, 1'-H), 4.68 (br d, 9-H), 4.73 (d, 1"-H), 4.88 (dd, 2'-H), 5.02 (br dd, 3-H), 7.06-7.11 (m, $C_6H_5$), 7.16-7.21 (m, $C_6H_5$), 7.30 (br s, NH).

Physicochemical Properties of the Isomer B (1) Molecular formula: $C_{57}H_{93}N_3O_{18}$ (2) Mass spectrum (FAB): m/z 1108 $(M+H)^+$ (3) Specific rotation: $[\alpha]_D^{24}$ −76° (c0.67, $CHCl_3$)

(4) $^1H$ NMR spectrum (300 MHz, $CDCl_3$) δ (ppm): 0.80 (d, 8-$CH_3$), 1.00 (d, 6"-H), 1.06 (t, 3-$OCOCH_2CH_3$), 1.07 (d, 14-$CH_3$), 1.12 (d, 6'-H), 1.12 (t, 4"-$OCOCH_2CH_3$), 1.19 (br dd, 7-H), 1.34 (s, 3"-$CH_3$), 1.59 (dd, 2"-Hax), 1.88 (s, 3"-$OCOCH_3$), 1.95 (s, 9-$OCOCH_3$), 1.98 (s, 2'-$OCOCH_3$), 2.36 (s, 3'-$N(CH_3)_2$), 2.53 (t, $C_6H_5(CH_2)_4$), 2.54 (t, 3'-H), 2.67 (dd, 2-H), 2.95 (s, $CH(OCH_3)_2$), 3.05 (t, 4'-H), 3.12 (d, 2"-Heq), 3.16 (s, $CH(OCH_3)_2$), 3.21 (dq, 5'-H), 3.34 (br d, 4-H), 3.65 (s, 4-$OCH_3$), 3.91 (br d, 5-H), 3.97 (m, 14-H), 4.40 (dq, 5"-H), 4.49 (d, 4"-H), 4.65 (d, 1'-H), 4.73 (d, 1"-H), 4.75 (br d, 9-H), 4.86 (br d, 3-H), 4.88 (dd, 2'-H), 6.55 (d, NH), 7.07-7.11 (m, $C_6H_5$), 7.17-7.22 (m, $C_6H_5$).

(d) In the same manner as in Example 2(c), 54.3 mg of a deacetyled compound (compound represented by the formula (22) mentioned in Preparation Scheme 7 wherein $R_1$ is propionyl group, $R_2$ is hydrogen atom, $R_3$ is 4-phenylbutyl group, one of $R_9$ and $R_{10}$ is methyl group, the other is hydrogen atom, $R_{3''}$ is acetyl group, $R_{4''}$ is propionyl group, and X is NH group) was obtained from 71.2 mg of the isomer A of Example 15(c).

Physicochemical Properties of this Compound (1) Molecular formula: $C_{53}H_{89}N_3O_{16}$ (2) Mass spectrum (FAB): m/z 1024 $(M+H)^+$ (3) Specific rotation: $[\alpha]_D^{25}$ −56° (c0.41, $CHCl_3$)

(4) $^1H$ NMR spectrum (300 MHz, $CDCl_3$) δ (ppm): 0.82 (d, 8-$CH_3$), 0.93 (br dd, 7-H), 1.01 (d, 6"-H), 1.07 (t, 3-$OCOCH_2CH_3$), 1.12 (t, 4"-$OCOCH_2CH_3$), 1.13 (d, 6'-H), 1.17 (d, 14-$CH_3$), 1.34 (s, 3"-$CH_3$), 1.62 (dd, 2"-Hax), 1.84 (br dd, 6-$CH_2$), 1.94 (s, 3"-$OCOCH_3$), 2.47 (s, 3'-$N(CH_3)_2$), 3.11 (s, $CH(OCH_3)_2$), 3.14 (d, 2"-Heq), 3.19 (s, $CH(OCH_3)_2$), 3.35 (dd, 2'-H), 3.57 (s, 4-$OCH_3$), 3.79 (br d, 5-H), 4.37 (d, 1'-H), 4.45 (dq, 5"-H), 4.51 (d, 4"-H), 4.77 (d, 1"-H), 5.04 (m, 3-H), 7.08-7.12 (m, $C_6H_5$), 7.17-7.22 (m, $C_6H_5$).

(e) In the same manner as in Example 2(d), 46.6 mg of the title compound was obtained from 54.3 mg of the compound of Example 15(d).

Physicochemical Properties of this Compound (1) Molecular formula: $C_{51}H_{83}N_3O_{15}$ (2) Mass spectrum (FAB): m/z 978 $(M+H)^+$ (3) Specific rotation: $[\alpha]_D^{25}$ −61° (c0.47, $CHCl_3$)

(4) $^1H$ NMR spectrum (300 MHz, $CDCl_3$) δ (ppm): 0.84 (d, 8-$CH_3$), 1.02 (d, 6"-H), 1.07 (d, 6'-H), 1.10 (t, 3-$OCOCH_2CH_3$), 1.12 (t, 4"-$OCOCH_2CH_3$), 1.21 (d, 14-$CH_3$), 1.35 (s, 3"-$CH_3$), 1.45 (m, 8-H), 1.62 (dd, 2"-Hax), 1.80 (m, 13-H), 1.93 (s, 3"-$OCOCH_3$), 2.48 (s, 3'-$N(CH_3)_2$), 2.92 (dd, 6-$CH_2$), 3.15 (d, 2"-Heq), 3.28 (dd, 2'-H), 3.50 (m, 14-H), 3.57 (s, 4-$OCH_3$), 3.80 (dd, 5-H), 4.36 (d, 1'-H), 4.43 (dq, 5"-H), 4.51 (d, 4"-H), 4.78 (d, 1"-H), 5.10 (m, 3-H), 6.65 (dd, NH), 7.08-7.12 (m, $C_6H_5$), 7.18-7.23 (m, $C_6H_5$), 9.58 (s, CHO).

Example 16

Preparation method of the compound represented by the formula (2) wherein $R_1$ is propionyl group, $R_2$ is hydrogen atom, $R_3$ is 4-phenylbutyl group, $R_5$, $R_6$, $R_7$ and $R_8$ are hydrogen atoms, one of $R_9$ and $R_{10}$ is methyl group, the other is hydrogen atom, $R_{4'}$ is a group represented by the formula (a), $R_{3''}$ is acetyl group, $R_{4''}$ is propionyl group, and X is NH group, provided that the substituents $R_9$ and $R_{10}$ are exchanged compared with the compound of Example 15

(a) In the same manner as in Example 2(c), 72.9 mg of a deacetyled compound (compound represented by the formula (22) mentioned in Preparation Scheme 7 wherein $R_1$ is propionyl group, $R_2$ is hydrogen atom, $R_3$ is 4-phenylbutyl group, one of $R_9$ and $R_{10}$ is methyl group, the other is hydrogen atom, $R_{3''}$ is acetyl group, $R_{4''}$ is propionyl group, and X is NH group, provided that the substituents $R_9$ and $R_{10}$ are exchanged compared with the compound of Example 15(d)) was obtained from 89.0 mg of the isomer B of Example 15(c).

Physicochemical Properties of this Compound (1) Molecular formula: $C_{53}H_{89}N_3O_{16}$ (2) Mass spectrum (FAB): m/z 1024 $(M+H)^+$ (3) Specific rotation: $[\alpha]_D^{27}$ −59° (c0.69, $CHCl_3$)

(4) $^1H$ NMR spectrum (300 MHz, $CDCl_3$) δ (ppm): 0.79 (d, 8-$CH_3$), 0.93 (br dd, 7-H), 1.02 (d, 6"-H), 1.06 (t, 3-$OCOCH_2CH_3$), 1.08 (d, 14-$CH_3$), 1.12 (t, 4"-$OCOCH_2CH_3$), 1.13 (d, 6'-H), 1.23 (br dd, 7-H), 1.35 (s, 3"-$CH_3$), 1.62 (dd, 2"-Hax), 1.95 (s, 3"-$OCOCH_3$), 2.47 (s, 3'-$N(CH_3)_2$), 2.55 (t, $C_6H_5(CH_2)_4$), 2.74 (dd, 2-H), 3.02 (s, $CH(OCH_3)_2$), 3.13 (t, 4'-H), 3.15 (d, 2"-Heq), 3.19 (s, $CH(OCH_3)_2$), 3.30 (br d, 9-H), 3.35 (dd, 2'-H), 3.54 (dd, 4-H), 3.72 (s, 4-$OCH_3$), 3.89 (br d, 5-H), 3.97 (m, 14-H), 4.44 (d, 1'-H), 4.45 (dq, 5"-H), 4.51 (d, 4"-H), 4.78 (d, 1"-H), 4.81 (br d, 3-H), 6.04 (br d, NH), 7.08-7.12 (m, $C_6H_5$), 7.18-7.23 (m, $C_6H_5$).

(b) In the same manner as in Example 2(d), 63.5 mg of the title compound was obtained from 72.9 mg of the compound of Example 16(a).

Physicochemical Properties of this Compound (1) Molecular formula: $C_{51}H_{83}N_3O_{15}$ (2) Mass spectrum (FAB): m/z 978 $(M+H)^+$ (3) Specific rotation: $[\alpha]_D^{26}$ −77° (c0.68, $CHCl_3$)

(4) $^1H$ NMR spectrum (300 MHz, $CDCl_3$) δ (ppm): 0.81 (d, 8-$CH_3$), 0.93 (br dd, 7-H), 1.02 (d, 6"-H), 1.07 (d, 14-$CH_3$), 1.07 (d, 6'-H), 1.12 (t, 3-$OCOCH_2CH_3$), 1.12 (t, 4"-$OCOCH_2CH_3$), 1.26 (br dd, 7-H), 1.34 (s, 3"-$CH_3$), 1.62 (dd, 2"-Hax), 1.78 (m, 13-H), 1.84 (m, 6-H), 1.93 (s, 3"-$OCOCH_3$), 2.48 (s, 3'-$N(CH_3)_2$), 2.55 (t, $C_6H_5(CH_2)_4$), 2.76 (dd, 2-H), 2.93 (dd, 6-$CH_2$), 3.14 (m, 4'-H), 3.14 (m, 5'-H), 3.15 (d, 2"-Heq), 3.30 (dd, 2'-H), 3.58 (dd, 4-H), 3.51 (s, 4-$OCH_3$), 3.83 (br d, 5-H), 3.98 (m, 14-H), 4.37 (d, 1'-H), 4.44 (dq, 5"-H), 4.51 (d, 4"-H), 4.78 (d, 1"-H), 4.90 (br d, 3-H), 6.13 (br d, NH), 7.08-7.12 (m, $C_6H_5$), 7.18-7.23 (m, $C_6H_5$), 9.58 (s, CHO).

Example 17

Preparation method of the compound represented by the formula (2) wherein $R_1$ is propionyl group, $R_2$ is hydrogen atom, $R_3$ is methyl group, $R_5$, $R_6$, $R_7$, $R_8$ are hydrogen atoms, one of $R_9$ and $R_{10}$ is methyl group, the other is hydrogen atom, $R_{4'}$ is a group represented by the formula (a), $R_{3''}$ is acetyl group, $R_{4''}$ is propionyl group, and X is NH group (a) In the same manner as in Example 4(a), except that the compound of Reference Example 11 was used instead of the compound of Reference Example 3, 14.5 mg of an azide compound (compound represented by the formula (20) mentioned in Preparation Scheme 7 wherein $R_3$ is 4-methoxybenzyl group, one of $R_9$ and $R_{10}$ is methyl group, the other is hydrogen atom, $R_{3''}$ is acetyl group, $R_{4''}$ is propionyl group, and X is azido group) was obtained as an about 1:1 mixture (measured according to intensities of specific signals) from 31.5 mg of the compound of Example 1.

Physicochemical Properties of this Compound (1) Molecular formula: $C_{55}H_{89}N_5O_{20}$ (2) Mass spectrum (FAB): m/z 1140 $(M+H)^+$ (3) Specific rotation: $[\alpha]_D^{25}$ −58° (c0.98, $CHCl_3$)

(4) $^1H$ NMR spectrum (300 MHz, $CDCl_3$) δ (ppm): 0.76 and 0.78 (each d, 8-$CH_3$), 1.00 (d, 6"-H), 1.08 (t, 3-$OCOCH_2CH_3$), 1.12 (t, 4"-$OCOCH_2CH_3$), 1.34 (s, 3"-$CH_3$), 1.38 (m, 6-$CH_2$), 1.59 (dd, 2"-Hax), 1.94 (s, 9-$OCOCH_3$), 1.96 (s, 3"-$OCOCH_3$), 1.97 (s, 2'-$OCOCH_3$), 2.35 (s, 3'-$N(CH_3)_2$), 2.54 (t, 3'-H), 3.05 (t, 4'-H), 3.11 (d, 2"-Heq), 3.14 (s, $CH(OCH_3)_2$), 3.19 (s, $CH(OCH_3)_2$), 3.40 (br d, 4-H), 3.44 and 3.45 (each s, 4-$OCH_3$), 3.72 (s, $C_6H_4CH_2$), 3.79 (br d, 5-H), 4.41 (dq, 5"-H), 4.49 (d, 4"-H), 4.61 (d, 1'-H), 4.73 (d, 1"-H), 4.87 (dd, 2'-H), 5.09 (m, 3-H), 5.09 (m, 9-H), 6.81 (d, $C_6H_4$), 7.24 and 7.27 (each d, $C_6H_4$).

(b) In an amount of 14.5 mg of the compound of Example 17(a) was dissolved in 0.73 ml of methylene chloride under argon atmosphere, added with 75 μl of a 0.52 M solution of trimethylphosphine in toluene, and stirred at room temperature for 7 hours. The reaction mixture was added with 1 ml of tetrahydrofuran and 0.15 ml of water, and further stirred at 60° C. for 2 hours. The reaction mixture was concentrated under reduced pressure, and the resulting residue was purified by preparative TLC (chloroform/methanol (10:1)) to obtain 11.4 mg of an azide-reduced compound (compound represented by the formula (20) mentioned in Preparation Scheme 7 wherein $R_3$ is 4-methoxybenzyl group, one of $R_9$ and $R_{10}$ is methyl group, the other is hydrogen atom, $R_{3''}$ is acetyl group, $R_{4''}$ is propionyl group, and X is amino group) as an about 1:1 mixture (measured according to intensities of specific signals).

Physicochemical Properties of this Compound (1) Molecular formula: $C_{55}H_{91}N_3O_{20}$ (2) Mass spectrum (FAB): m/z 1114 $(M+H)^+$ (3) Specific rotation: $[\alpha]_D^{25}$ −55° (c0.64, $CHCl_3$)

(4) $^1H$ NMR spectrum (300 MHz, $CDCl_3$) δ (ppm): 0.87 (d, 8-$CH_3$), 0.99 (d, 6"-H), 1.03 (t, 3-$OCOCH_2CH_3$), 1.12 (t, 4"-$OCOCH_2CH_3$), 1.13 (d, 6'-H), 1.34 (s, 3"-$CH_3$), 1.59 (dd, 2"-Hax), 1.68 (m, 8-H), 1.81 (br dd, 6-$CH_2$), 1.95 (s, 3"-$OCOCH_3$), 1.99 and 2.03 (each s, 9-$OCOCH_3$), 2.12 and 2.24 (each s, 2'-$OCOCH_3$), 2.36 (s, 3'-$N(CH_3)_2$), 2.54 (t, 3'-H), 3.03 and 3.04 (each s, $CH(OCH_3)_2$), 3.12 (d, 2"-Heq), 3.18 and 3.19 (each s, $CH(OCH_3)_2$), 3.54 (br d, 4-H), 3.58 and 3.67 (each s, 4-$OCH_3$), 3.72 (s, $C_6H_4CH_2$), 3.80 (br d, 5-H), 4.41 (dq, 5"-H), 4.49 (d, 4"-H), 4.73 (d, 1"-H), 4.89 and 4.93 (each dd, 2'-H), 5.17 and 5.27 (each br dd, 3-H), 5.32 and 5.47 (each br d, 9-H), 6.74 and 6.76 (each d, $C_6H_4$), 6.94 and 7.03 (each d, $C_6H_4$).

(c) In the same manner as in Example 4(c), 55.9 mg of an isomer A (compound represented by the formula (21) mentioned in Preparation Scheme 7 wherein $R_3$ is 4-methoxybenzyl group, one of $R_9$ and $R_{10}$ is methyl group, the other is hydrogen atom, $R_{3''}$ is acetyl group, $R_{4''}$ is propionyl group, and X is NH group), and 53.4 mg of an isomer B (compound represented by the formula (21) mentioned in Preparation Scheme 7 wherein $R_3$ is 4-methoxybenzyl group, one of $R_9$ and $R_{10}$ is methyl group, the other is hydrogen atom, $R_{3''}$ is acetyl group, $R_{4''}$ is propionyl group, and X is NH group, provided that the substituents $R_9$ and $R_{10}$ are exchanged compared with the isomer A) were obtained from 148 mg of the compound of Example 17(b).

Physicochemical Properties of the Isomer A (1) Molecular formula: $C_{55}H_{89}N_3O_{19}$ (2) Mass spectrum (FAB): m/z 1096 $(M+H)^+$ (3) Specific rotation: $[\alpha]_D^{26}$ −77° (c0.55, $CHCl_3$)

(4) $^1H$ NMR spectrum (300 MHz, $CDCl_3$) δ (ppm): 0.72 (d, 8-$CH_3$), 1.00 (d, 14-$CH_3$), 1.00 (d, 6"-H), 1.07 (t, 3-$OCOCH_2CH_3$), 1.12 (d, 6'-H), 1.12 (t, 4"-$OCOCH_2CH_3$), 1.34 (s, 3"-$CH_3$), 1.60 (dd, 2"-Hax), 1.92 (s, 3"-$OCOCH_3$), 1.95 (s, 9-$OCOCH_3$), 1.98 (s, 2'-$OCOCH_3$), 2.36 (s, 3'-$N(CH_3)_2$), 2.54 (t, 3'-H), 2.68 (dd, 2-H), 2.96 (s, $CH(OCH_3)_2$), 3.05 (t, 4'-H), 3.12 (d, 2"-Heq), 3.16 (s, $CH(OCH_3)_2$), 3.24 (d, $C_6H_4CH_2$), 3.36 (br d, 4-H), 3.58 (d, $C_6H_4CH_2$), 3.66 (s, 4-$OCH_3$), 3.73 (s, $C_6H_4$—$OCH_3$), 3.92 (br d, 5-H), 4.00 (m, 14-H), 4.41 (dq, 5"-H), 4.49 (d, 4"-H), 4.66 (d, 1'-H), 4.73 (d, 1"-H), 4.87 (m, 3-H), 6.64 (br d, NH), 6.75 (d, $C_6H_5$), 7.12 (d, $C_6H_5$).

Physicochemical Properties of the Isomer B (1) Molecular formula: $C_{55}H_{89}N_3O_{19}$ (2) Mass spectrum (FAB): m/z 1096 $(M+H)^+$ (3) Specific rotation: $[\alpha]_D^{26}$ −80° (c0.52, $CHCl_3$)

(4) $^1H$ NMR spectrum (300 MHz, $CDCl_3$) δ (ppm): 0.77 (d, 8-$CH_3$), 1.00 (d, 6"-H), 1.07 (t, 3-$OCOCH_2CH_3$), 1.12 (t, 4"-$OCOCH_2CH_3$), 1.13 (d, 6'-H), 1.19 (d, 14-$CH_3$), 1.34 (s, 3"-$CH_3$), 1.60 (dd, 2"-Hax), 1.80 (m, 6-$CH_2$), 1.92 (s, 3"-$OCOCH_3$), 1.95 (s, 9-$OCOCH_3$), 1.95 (s, 2'-$OCOCH_3$), 2.36 (s, 3'-$N(CH_3)_2$), 2.54 (t, 3'-H), 2.64 (dd, 2-H), 3.00 (s, $CH(OCH_3)_2$), 3.06 (t, 4'-H), 3.12 (d, 2"-Heq), 3.17 (s, $CH(OCH_3)_2$), 3.19 (dq, 5'-H), 3.29 (br d, 4-H), 3.32 (d, $C_6H_4CH_2$), 3.46 (d, $C_6H_4CH_2$), 3.54 (s, 4-$OCH_3$), 3.72 (s, $C_6H_4$-$OCH_3$), 3.86 (br d, 5-H), 4.41 (dq, 5"-H), 4.49 (d, 4"-H), 4.62 (d, 1'-H), 4.73 (d, 1"-H), 4.75 (m, 9-H), 4.89 (dd, 2'-H), 5.08 (br dd, 3-H), 6.76 (d, $C_6H_5$), 7.03 (br s, NH), 7.12 (d, $C_6H_5$).

(d) In the same manner as in Example 8(d), 40.1 mg of an amine compound (compound represented by the formula (21) mentioned in Preparation Scheme 7 wherein $R_3$ is hydrogen atom, one of $R_9$ and $R_{10}$ is methyl group, the other is hydrogen atom, $R_{3''}$ is acetyl group, $R_{4''}$ is propionyl group, and X is NH group) was obtained from 55.9 mg of the isomer A of Example 17(c).

Physicochemical Properties of this Compound (1) Molecular formula: $C_{47}H_{81}N_3O_{18}$ (2) Mass spectrum (FAB): m/z 976 $(M+H)^+$ (3) Specific rotation: $[\alpha]_D^{27}$ −57° (c0.56, $CHCl_3$)

(4) $^1H$ NMR spectrum (300 MHz, $CDCl_3$) δ (ppm): 0.81 (d, 8-$CH_3$), 1.00 (d, 6"-H), 1.07 (t, 3-$OCOCH_2CH_3$), 1.09 (d, 14-$CH_3$), 1.12 (t, 4"-$OCOCH_2CH_3$), 1.13 (d, 6'-H), 1.30 (m, 7-H), 1.35 (s, 3"-$CH_3$), 1.50 (br dd, 6-$CH_2$), 1.60 (dd, 2"-Hax), 1.95 (s, 3"-$OCOCH_3$), 1.99 (s, 9-$OCOCH_3$), 2.36 (s, 3'-$N(CH_3)_2$), 2.54 (t, 3'-H), 2.69 (dd, 2-H), 3.03 (s, $CH(OCH_3)_2$), 3.04 (t, 4'-H), 3.12 (d, 2"-Heq), 3.17 (s, $CH(OCH_3)_2$), 3.44 (br d, 4-H), 3.62 (s, 4-$OCH_3$), 3.90 (br d, 5-H), 4.16 (m, 14-H), 4.41 (dq, 5"-H), 4.50 (d, 4"-H), 4.66 (d, 1'-H), 4.73 (d, 1"-H), 4.83 (m, 3-H), 4.89 (dd, 2'-H), 6.99 (br d, NH).

(e) In the same manner as in Example 8(e), 16.3 mg of a methylated compound (compound represented by the formula (21) mentioned in Preparation Scheme 7 wherein $R_3$ is methyl group, one of $R_9$ and $R_{10}$ is methyl group, the other is hydrogen atom, $R_{3''}$ is acetyl group, $R_{4''}$ is propionyl group, and X is NH group) was obtained from 40.1 mg of the compound of Example 17(d).

Physicochemical Properties of this Compound (1) Molecular formula: $C_{48}H_{83}N_3O_{18}$ (2) Mass spectrum (FAB): m/z 990 $(M+H)^+$ (3) Specific rotation: $[\alpha]_D^{26}$ −75° (c0.82, $CHCl_3$)

(4) $^1H$ NMR spectrum (300 MHz, $CDCl_3$) δ (ppm): 0.81 (d, 8-$CH_3$), 1.00 (d, 6"-H), 1.07 (t, 3-$OCOCH_2CH_3$), 1.08 (d, 14-$CH_3$), 1.12 (t, 4"-$OCOCH_2CH_3$), 1.13 (d, 6'-H), 1.34 (s, 3"-$CH_3$), 1.48 (br dd, 6-$CH_2$), 1.60 (dd, 2"-Hax), 1.95 (s, 3"-$OCOCH_3$), 1.98 (s, 9-$OCOCH_3$), 2.37 (s, 3'-$N(CH_3)_2$), 2.54 (t, 3'-H), 2.68 (dd, 2-H), 2.99 (s, $CH(OCH_3)_2$), 3.06 (t, 4'-H), 3.12 (d, 2"-Heq), 3.17 (s, $CH(OCH_3)_2$), 3.19 (t, 5'-H), 3.46 (br d, 4-H), 3.65 (s, 4-$OCH_3$), 3.92 (br d, 5-H), 4.02 (m, 14-H), 4.41 (dq, 5"-H), 4.50 (d, 4"-H), 4.66 (d, 1'-H), 4.73 (d, 1"-H), 4.83 (m, 9-H), 4.86 (m, 3-H), 4.89 (dd, 2'-H), 6.70 (br d, NH).

(f) In the same manner as in Example 2(c), 13.2 mg of a deacetyled compound (compound represented by the formula (22) mentioned in Preparation Scheme 7 wherein $R_1$ is propionyl group, $R_2$ is hydrogen atom, $R_3$ is methyl group, one of $R_9$ and $R_{10}$ is methyl group, the other is hydrogen atom, $R_{3''}$ is acetyl group, $R_{4''}$ is propionyl group, and X is NH group) was obtained from 16.3 mg of the compound of Example 17(e).

Physicochemical Properties of this Compound (1) Molecular formula: $C_{44}H_{79}N_3O_{16}$ (2) Mass spectrum (FAB): m/z 906 $(M+H)^+$ (3) Specific rotation: $[\alpha]_D^{25}$ −52° (c0.66, $CHCl_3$)

(4) $^1H$ NMR spectrum (300 MHz, $CDCl_3$) δ (ppm): 0.83 (d, 8-$CH_3$), 0.93 (br t, 7-H), 1.01 (d, 6"-H), 1.07 (t, 3-$OCOCH_2CH_3$), 1.09 (d, 14-$CH_3$), 1.12 (t, 4"-$OCOCH_2CH_3$), 1.13 (d, 6'-H), 1.34 (s, 3"-$CH_3$), 1.61 (dd, 2"-Hax), 1.94 (s, 3"-$OCOCH_3$), 2.22 (s, $NCH_3$), 2.47 (s, 3'-$N(CH_3)_2$), 2.75 (dd, 2-H), 3.03 (s, $CH(OCH_3)_2$), 3.12 (t, 4'-H), 3.14 (d, 2"-Heq), 3.18 (s, $CH(OCH_3)_2$), 3.36 (dd, 2'-H), 3.67 (br d, 4-H), 3.72 (s, 4-$OCH_3$), 3.87 (br d, 5-H), 4.06 (m, 14-H), 4.37 (dd, $CH(OCH_3)_2$), 4.42 (d, 1'-H), 4.48 (m, 5"-H), 4.51 (d, 4"-H), 4.77 (d, 1"-H), 4.81 (br d, 3-H), 6.12 (br d, NH).

(g) In the same manner as in Example 2(d), 11.1 mg of the title compound was obtained from 13.2 mg of the compound of Example 17(f).

Physicochemical Properties of this Compound (1) Molecular formula: $C_{42}H_{73}N_3O_{15}$ (2) Mass spectrum (FAB): m/z 860 $(M+H)^+$ (3) Specific rotation: $[\alpha]_D^{26}$ −69° (c0.55, $CHCl_3$)

(4) $^1H$ NMR spectrum (300 MHz, $CDCl_3$) δ (ppm): 0.84 (d, 8-$CH_3$), 0.93 (br t, 7-H), 1.01 (d, 6"-H), 1.06 (d, 6'-H), 1.09 (d, 14-$CH_3$), 1.11 (t, 3-$OCOCH_2CH_3$), 1.12 (t, 4"-$OCOCH_2CH_3$), 1.34 (s, 3"-$CH_3$), 1.42 (br dd, 6-$CH_2$), 1.61 (dd, 2"-Hax), 1.78 (m, 13-H), 1.85 (m, 6-H), 1.93 (s, 3"-$OCOCH_3$), 2.23 (s, $NCH_3$), 2.47 (s, 3'-$N(CH_3)_2$), 2.77 (dd, 2-H), 2.93 (dd, 6-$CH_2$), 3.11 (t, 4'-H), 3.14 (d, 2"-Heq), 3.31 (dd, 2'-H), 3.39 (br d, 9-H), 3.70 (br d, 4-H), 3.71 (s, 4-$OCH_3$), 3.81 (br d, 5-H), 4.06 (m, 14-H), 4.36 (d, 1'-H), 4.45 (dq, 5"-H), 4.51 (d, 4"-H), 4.77 (d, 1"-H), 4.92 (br d, 3-H), 6.25 (br d, NH), 9.58 (s, CHO).

Example 18

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is methyl group, the other is hydrogen atom, $R_{4'}$ is a group represented by the formula (a), $R_{3''}$ is acetyl group, $R_{4''}$ is propionyl group, and X is NH group compounds, provided that the substituents $R_9$ and $R_{10}$ are exchanged compared with the compound of Example 17

(a) In the same manner as in Example 8(d), 31.9 mg of an amine compound (compound represented by the formula (21) mentioned in Preparation Scheme 7 wherein $R_3$ is hydrogen atom, one of $R_9$ and $R_{10}$ is methyl group, the other is hydrogen atom, $R_{3''}$ is acetyl group, $R_{4''}$ is propionyl group, and X is NH group, provided that the substituents $R_9$ and $R_{10}$ are exchanged compared with the compound of Example 17(d)) was obtained from 53.4 mg of the isomer B of Example 17(c).

Physicochemical Properties of this Compound (1) Molecular formula: $C_{47}H_{81}N_3O_{18}$ (2) Mass spectrum (FAB): m/z 976 $(M+H)^+$ (3) Specific rotation: $[\alpha]_D^{27}$ −83° (c0.57, $CHCl_3$)

(4) $^1H$ NMR spectrum (300 MHz, $CDCl_3$) δ (ppm): 0.88 (d, 8-$CH_3$), 1.00 (d, 6"-H), 1.08 (t, 3-$OCOCH_2CH_3$), 1.12 (t, 4"-$OCOCH_2CH_3$), 1.16 (d, 14-$CH_3$), 1.16 (d, 6'-H), 1.34 (s, 3"-$CH_3$), 1.44 (br dd, 6-$CH_2$), 1.61 (dd, 2"-Hax), 1.95 (s, 3"-$OCOCH_3$), 1.97 (s, 9-$OCOCH_3$), 2.03 (s, 2'-$OCOCH_3$), 2.36 (s, 3'-$N(CH_3)_2$), 2.55 (t, 3'-H), 3.11 (s, $CH(OCH_3)_2$), 3.18 (s, $CH(OCH_3)_2$), 3.46 (s, 4-$OCH_3$), 3.82 (br d, 5-H), 4.08 (m, 14-H), 4.41 (dq, 5"-H), 4.50 (d, 4"-H), 4.56 (d, 1'-H), 4.74 (d, 1"-H), 4.90 (dd, 2'-H), 5.10 (br dd, 3-H), 7.01 (br d, NH).

(b) In the same manner as in Example 8(e), 23.7 mg of a methylated compound (compound represented by the formula (21) mentioned in Preparation Scheme 7 wherein $R_3$ is methyl group, one of $R_9$ and $R_{10}$ is methyl group, the other is hydrogen atom, $R_{3''}$ is acetyl group, $R_{4''}$ is propionyl group, and X is NH group, provided that the substituents $R_9$ and $R_{10}$ are exchanged compared with the compound of Example 17(e)) was obtained from 31.9 mg of the compound of Example 18(a).

Physicochemical Properties of this Compound (1) Molecular formula: $C_{48}H_{83}N_3O_{18}$ (2) Mass spectrum (FAB): m/z 990 $(M+H)^+$ (3) Specific rotation: $[\alpha]_D^{24}$ −57° (c1.2, $CHCl_3$)

(4) $^1H$ NMR spectrum (300 MHz, $CDCl_3$) δ (ppm): 0.84 (d, 8-$CH_3$), 1.00 (d, 6"-H), 1.08 (t, 3-$OCOCH_2CH_3$), 1.12 (t, 4"-$OCOCH_2CH_3$), 1.14 (d, 6'-H), 1.15 (d, 14-$CH_3$), 1.34 (s, 3"-$CH_3$), 1.44 (br dd, 6-$CH_2$), 1.61 (dd, 2"-Hax), 1.97 (s, 3"-$OCOCH_3$), 1.97 (s, 9-$OCOCH_3$), 1.97 (s, 2'-$OCOCH_3$), 2.18 (s, $NCH_3$), 2.36 (s, 3'-$N(CH_3)_2$), 2.54 (t, 3'-H), 2.71 (m, 10-H), 3.06 (s, $CH(OCH_3)_2$), 3.12 (d, 2"-Heq), 3.18 (s, $CH(OCH_3)_2$), 3.30 (br d, 4-H), 3.49 (s, 4-$OCH_3$), 3.85 (br d, 5-H), 3.90 (m, 14-H), 4.41 (dq, 5"-H), 4.50 (d, 4"-H), 4.64 (d, 1'-H), 4.74 (d, 1"-H), 4.77 (m, 9-H), 4.90 (dd, 2'-H), 4.95 (m, 3-H).

(c) In the same manner as in Example 2(c), 6.1 mg of a deacetyled compound (compound represented by the formula (22) mentioned in Preparation Scheme 7 wherein $R_1$ is propionyl group, $R_2$ is hydrogen atom, $R_3$ is methyl group, one of $R_9$ and $R_{10}$ is methyl group, the other is hydrogen atom, $R_{3''}$ is acetyl group, $R_{4''}$ is propionyl group, and X is NH group, provided that the substituents $R_9$ and $R_{10}$ are exchanged compared with the compound of Example 17(f)) was obtained from 8.0 mg of the compound of Example 18(b).

Physicochemical Properties of this Compound (1) Molecular formula: $C_{44}H_{79}N_3O_{16}$ (2) Mass spectrum (FAB): m/z 906 $(M+H)^+$ (3) Specific rotation: $[\alpha]_D^{26}$ −44° (c0.52, $CHCl_3$)

(4) $^1H$ NMR spectrum (300 MHz, $CDCl_3$) δ (ppm): 0.85 (d, 8-$CH_3$), 0.98 (br dd, 7-H), 1.02 (d, 6"-H), 1.07 (t, 3-$OCOCH_2CH_3$), 1.13 (t, 4"-$OCOCH_2CH_3$), 1.15 (d, 14-$CH_3$), 1.15 (d, 6'-H), 1.35 (s, 3"-$CH_3$), 1.45 (br dd, 6-$CH_2$), 1.63 (dd, 2"-Hax), 1.76 (m, 13-H), 1.89 (br dd, 6-$CH_2$), 1.94 (s, 3"-$OCOCH_3$), 2.29 (s, $NCH_3$), 2.48 (s, 3'-$N(CH_3)_2$), 3.11 (s, $CH(OCH_3)_2$), 3.15 (d, 2"-Heq), 3.20 (s, $CH(OCH_3)_2$), 3.33 (dd, 2'-H), 3.36 (br d, 4-H), 3.54 (s, 4-$OCH_3$), 3.61 (br d, 9-H), 3.78 (br d, 5-H), 3.90 (m, 14-H), 4.38 (dd, $CH(OCH_3)_2$), 4.41 (d, 1'-H), 4.46 (dq, 5"-H), 4.52 (d, 4"-H), 4.78 (d, 1"-H), 5.11 (br dd, 3-H), 7.40 (br s, NH).

(d) In the same manner as in Example 2(d), 11.7 mg of the title compound was obtained from 16.5 mg of the compound of Example 18(c).

Physicochemical Properties of this Compound (1) Molecular formula: $C_{42}H_{73}N_3O_{15}$ (2) Mass spectrum (FAB): m/z 860 $(M+H)^+$ (3) Specific rotation: $[\alpha]_D^{25}$ −61° (c0.59, $CHCl_3$)

(4) $^1H$ NMR spectrum (300 MHz, $CDCl_3$) δ (ppm): 0.85 (d, 8-$CH_3$), 0.97 (br t, 7-H), 1.02 (d, 6"-H), 1.06 (d, 14-$CH_3$), 1.09 (t, 3-$OCOCH_2CH_3$), 1.12 (t, 4"-$OCOCH_2CH_3$), 1.16 (d, 6'-H), 1.34 (s, 3"-$CH_3$), 1.43 (m, 8-H), 1.62 (dd, 2"-Hax), 1.72 (br dd, 13-H), 1.92 (s, 3"-$OCOCH_3$), 2.13 (dd, 10-H), 2.24 (br dd, 6-$CH_2$), 2.23 (s, $NCH_3$), 2.48 (s, 3'-$N(CH_3)_2$), 2.97 (dd, 6-$CH_2$), 3.14 (m, 4'-H), 3.14 (m, 5'-H), 3.15 (d, 2"-Heq), 3.25 (dd, 2'-H), 3.46 (dd, 4-H), 3.53 (s, 4-$OCH_3$), 3.64 (br d, 9-H), 3.79 (br d, 5-H), 3.82 (m, 14-H), 4.38 (d, 1'-H), 4.42 (dq, 5"-H), 4.51 (d, 4"-H), 4.78 (d, 1"-H), 5.14 (br dd, 3-H), 7.74 (br s, NH), 9.58 (s, CHO).

Example 19

Preparation method of (−)-(3R4S,5S,6R8R9R)-9-acetoxy-5-[2-O-acetyl-4-O-(2,6-dideoxy-3-C-methyl-4-O-propionyl-α-L-ribo-hexopyranosyl)-3,6-dideoxy-3-dimethylamino-β-D-glucopyranosyl]-6-(2,2-dimethoxyethyl)-4-methoxy-8-methyl-10-oxo-3-propionyloxydecanoic acid (compound represented by the formula (4) wherein $R_1$ is propionyl group, $R_2$ is acetyl group, $R_{2'}$ is acetyl group, $R_{3''}$ is hydrogen atom, $R_{4''}$ is propionyl group, Y is formyl group, and Z is dimethoxymethyl group)

(a) In the same manner as in Example 1(a), 21.3 g of 9,2'-di-O-acetylmidecamycin 18-dimethyl acetal (compound represented by the formula (6) mentioned in Preparation Scheme 1 wherein $R_1$ is propionyl group, $R_2$ is acetyl group, $R_{13}$ is methyl group, $R_{3''}$ is hydrogen atom, and $R_{4''}$ is propionyl group) was obtained from 20.4 g of 9-O-acetylmidecamycin 18-dimethyl acetal (WO02/64607). Further, from 4.00 g of this compound, 1.77 g of 9,2'-di-O-acetyl-10,11,12,13-tetrahydro-10,11,12,13-tetrahydroxymidecamycin 18-dimethyl acetal (compound represented by the formula (7) mentioned in Preparation Scheme 1 wherein $R_1$ is propionyl group, $R_2$ is acetyl group, $R_{13}$ is methyl group, $R_{3''}$ is hydrogen atom, and $R_{4''}$ is propionyl group) was obtained in the same manner as in Example 1(a).

Physicochemical Properties of this Compound (1) Molecular formula: $C_{47}H_{81}NO_{21}$ (2) Mass spectrum (FAB): m/z 1012 $(M+H)^+$ (3) Specific rotation: $[\alpha]_D^{21}$ −74° (c1.0, $CHCl_3$)

(4) $^1H$ NMR spectrum (300 MHz, $CDCl_3$) δ (ppm): 0.96 (d, 19-H), 1.12 (s, 3"-$CH_3$), 1.13 (t, 3-$OCOCH_2CH_3$), 1.14 (d, 6"-H), 1.18 (t, 4"-$OCOCH_2CH_3$), 1.27 (d, 16-H), 1.27 (d, 6'-H), 1.43 (br dd, 7-H), 1.53 (br dd, 14-H), 1.63 (m, 6-H), 1.69 (br dd, 14-H), 1.72 (m, 17-H), 1.85 (dd, 2"-Hax), 2.02 (d, 2"-Heq), 2.05 (s, 9-$OCOCH_3$), 2.17 (s, 2'-$OCOCH_3$), 2.35 (m, 8-H), 2.42 (s, 3'-$N(CH_3)_2$), 2.49 (dd, 2-H), 2.73 (dd, 2-H), 2.73 (t, 3'-H), 3.18 (s, 18-OCH3), 3.23 (s, 18-OCH3), 3.34 (t, 4'-H), 3.57 (s, 4-$OCH_3$), 3.62 (br d, 12-H), 3.86 (br d, 5-H), 3.90 (dd, 10-H), 4.10 (m, 13-H), 4.38 (dq, 5"-H), 4.40 (dd, 18-H), 4.63 (d, 4"-H), 4.74 (d, 1'-H), 5.01 (dd, 2'-H), 5.02 (br d, 9-H), 5.07 (m, 15-H), 5.08 (d, 1"-H), 5.35 (br d, 3-H).

(b) In an amount of 10 g of the compound of Example 19(a) was dissolved in 300 ml of benzene, added with 8.38 g of sodium carbonate, and then added with 11 g of lead tetraacetate as three portions with intervals of 5 minutes. The reaction mixture was stirred at room temperature for 30 minutes, and then insoluble matter was removed by filtration through a Cerite layer by using 260 ml of ethyl acetate. The filtrate was concentrated to about 80 ml under reduced pressure, added with 100 ml of acetonitrile, and concentrated to about 80 ml under reduced pressure. The same substitution and concentration procedures were further repeated 2 times to obtain about 80 ml of a solution containing (−)-(1R)-1-methyl-3-oxopropyl (3$R_4$S,5S,6R8R9R)-9-acetoxy-5-[2-O-acetyl-4-O-(2,6-dideoxy-3-C-methyl-4-O-propionyl-α-L-ribo-hexopyranosyl)-3,6-dideoxy-3-dimethylamino-β-D-glucopyranosyl]-6-(2,2-dimethoxyethyl)-4-methoxy-8-methyl-10-oxo-3-propionyloxydecanoate (compound represented by the formula (8) mentioned in Preparation Scheme 1 wherein $R_1$ is propionyl group, $R_2$ is acetyl group, $R_{13}$ is methyl group, $R_{3''}$ is hydrogen atom and $R_{4''}$ is propionyl group). This solution was added with 300 ml of acetonitrile, added with 2.1 ml of 1,8-diazabicyclo[5.4.0]-undecene, and stirred at room temperature for 4.5 hours. The reaction mixture was concentrated under reduced pressure, and the resulting residue was purified by silica gel column chromatography (chloroform/methanol (30:1 to 20:1)) to obtain 6.07 g of the title compound.

Physicochemical Properties of this Compound (1) Molecular formula: $C_{41}H_{69}NO_{19}$ (2) Mass spectrum (FAB): m/z 880 $(M+H)^+$ (3) Specific rotation: $[\alpha]_D^{25}$ −53° (c0.56, $CHCl_3$)

(4) $^1H$ NMR spectrum (300 MHz, $CDCl_3$) δ (ppm): 0.95 (d, 8-$CH_3$), 1.04 (s, 3"-$CH_3$), 1.04 (t, 3-$OCOCH_2CH_3$), 1.05 (d, 6"-H), 1.10 (t, 4"-$OCOCH_2CH_3$), 1.19 (d, 6'-H), 1.43 (m, 6-$CH_2$), 1.56 (m, 7-H), 1.77 (dd, 2"-Hax), 1.94 (d, 2"-Heq), 1.99 (s, 2'-$OCOCH_3$), 2.11 (s, 9-$OCOCH_3$), 2.33 (s, 3'-N$(CH_3)_2$), 2.58 (dd, 2-H), 2.65 (t, 3'-H), 2.72 (dd, 2-H), 3.09 (s, $CH(OCH_3)_2$), 3.18 (s, $CH(OCH_3)_2$), 3.26 (t, 4'-H), 3.26 (t, 5'-H), 3.42 (br d, 4-H), 3.46 (s, 4-$OCH_3$), 3.76 (br d, 5-H), 4.31 (dq, 5"-H), 4.37 (dd, $CH(OCH_3)_2$), 4.54 (d, 4"-H), 4.62 (d, 1'-H), 4.80 (br d, 9-H), 4.91 (dd, 2'-H), 4.99 (d, 1"-H), 5.17 (br dd, 3-H), 9.48 (s, 10-H).

Example 20

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is trans-3-(quinolin-4-yl)-2-propenyl group, the other is hydrogen atom, $R_{4'}$ is a group represented by the formula (a), $R_{3''}$ is hydrogen atom, $R_{4''}$ is propionyl group, and X is NH group (a) In the same manner as in Example 4(a), except that the compound of Reference Example 12 was used instead of the compound of Reference Example 3, 433 mg of an azide compound (compound represented by the formula (20) mentioned in Preparation Scheme 7 wherein $R_3$ is methyl group, one of $R_9$ and $R_{10}$ is allyl group, the other is hydrogen atom, $R_{3''}$ is hydrogen atom, $R_{4''}$ is propionyl group, and X is azido group) was obtained as an about 1:1 mixture (measured according to intensities of specific signals) from 693 mg of the compound of Example 19.

Physicochemical Properties of this Compound (1) Molecular formula: $C_{48}H_{83}N_5O_{18}$ (2) Mass spectrum (FAB): m/z 1018 $(M+H)^+$ (3) Specific rotation: $[\alpha]_D^{24}$ −54° (c0.84, $CHCl_3$)

(4) $^1H$ NMR spectrum (300 MHz, $CDCl_3$) δ (ppm): 0.81 (d, 8-$CH_3$), 1.04 (s, 3"-$CH_3$), 1.05 (d, 6"-H), 1.06 (t, 3-$OCOCH_2CH_3$), 1.10 (t, 4"-$OCOCH_2CH_3$), 1.19 (d, 6'-$CH_3$), 1.26 (m, 7-H), 1.47 (m, 6-$CH_2$), 1.76 (dd, 2"-Hax), 1.94 (d, 2"-Heq), 2.33 (s, 3'-N$(CH_3)_2$), 2.42 (s, $NCH_3$), 2.74 (br t, 12-H), 3.14 (s, $CH(OCH_3)_2$), 3.19 (s, $CH(OCH_3)_2$), 3.26 (m, 4'-H), 3.26 (m, 5'-H), 3.41 (br d, 4-H), 3.46 and 3.48 (each s, 4-$OCH_3$), 3.81 (br d, 5-H), 4.30 (dq, 5"-H), 4.47 (dd, $CH(OCH_3)_2$), 4.54 (d, 4"-H), 4.66 (d, 1'-H), 4.92 (dd, 2'-H), 4.99 (d, 1"-H), 5.06 (m, 3-H), 5.09 (m, $CH_2$═CH), 5.73 (ddt, $CH_2$═CH).

(b) In an amount of 1.06 g of the compound of Example 20(a) was dissolved in 50 ml of acetonitrile and 5 ml of water, added with 6 ml of a 0.52 M solution of trimethylphosphine in toluene, and stirred at 80° C. for 6 hours and 30 minutes. The reaction mixture was concentrated under reduced pressure, and the resulting residue was purified by silica gel column chromatography (chloroform/methanol (10:1 to 5:1)) to obtain 548 mg of an azide-reduced compound (compound represented by the formula (20) mentioned in Preparation Scheme 7 wherein $R_3$ is methyl group, one of $R_9$ and $R_{10}$ is allyl group, the other is hydrogen atom, $R_{3''}$ is hydrogen atom, $R_{4''}$ is propionyl group, and X is amino group) as an about 1:1 mixture (measured according to intensities of specific signals).

Physicochemical Properties of this Compound (1) Molecular formula: $C_{48}H_{85}N_3O_{18}$ (2) Mass spectrum (FAB): m/z 992 $(M+H)^+$ (3) Specific rotation: $[\alpha]_D^{20}$ −49° (c0.86, $CHCl_3$)

(4) $^1H$ NMR spectrum (300 MHz, $CDCl_3$) δ (ppm): 0.84 (d, 8-$CH_3$), 1.02 and 1.03 (each t, 3-$OCOCH_2CH_3$), 1.05 (s, 3"-$CH_3$), 1.06 (d, 6"-H), 1.10 (t, 4"-$OCOCH_2CH_3$), 1.19 (d, 6'-$CH_3$), 1.38 (m, 6-$CH_2$), 1.61 (m, 8-H), 1.77 (dd, 2"-Hax), 1.95 (d, 2"-Heq), 2.19 and 2.23 (each s, $NCH_3$), 2.34 (s, 3'-N$(CH_3)_2$), 3.06 (s, $CH(OCH_3)_2$), 3.18 and 3.18 (each s, $CH(OCH_3)_2$), 3.27 (m, 4'-H), 3.27 (m, 5'-H), 3.43 and 3.59 (each br d, 4-H), 3.53 and 3.56 (each s, 4-$OCH_3$), 3.81 (br d, 5-H), 4.31 (dq, 5"-H), 4.41 (m, $CH(OCH_3)_2$), 4.54 (d, 4"-H), 4.72 and 4.75 (each d, 1'-H), 4.93 (dd, 2'-H), 5.00 (d, 1"-H), 5.03 (m, $CH_2$═CH), 5.58 (m, $CH_2$═CH).

(c) In the same manner as in Example 4(c), 338 mg of an isomer A (compound represented by the formula (21) mentioned in Preparation Scheme 7 wherein $R_3$ is methyl group, one of $R_9$ and $R_{10}$ is allyl group, the other is hydrogen atom, $R_{3''}$ is hydrogen atom, $R_{4''}$ is propionyl group, and X is NH group), and 316 mg of an isomer B (compound represented by the formula (21) mentioned in Preparation Scheme 7 wherein $R_3$ is methyl group, one of $R_9$ and $R_{10}$ is allyl group, the other is hydrogen atom, $R_{3''}$ is hydrogen atom, $R_{4''}$ is propionyl group, and X is NH group, provided that the substituents $R_9$ and $R_{10}$ are exchanged compared with the isomer A) were obtained from 909 mg of the compound of Example 20(b).

Physicochemical Properties of the Isomer A (1) Molecular formula: $C_{48}H_{83}N_3O_{17}$ (2) Mass spectrum (FAB): m/z 974 $(M+H)^+$ (3) Specific rotation: $[\alpha]_D^{21}$ −57° (c0.52, $CHCl_3$)

(4) $^1H$ NMR spectrum (300 MHz, $CDCl_3$) δ (ppm): 0.81 (d, 8-$CH_3$), 1.05 (s, 3"-$CH_3$), 1.05 (d, 6"-H), 1.06 (t, 3-$OCOCH_2CH_3$), 1.10 (t, 4"-$OCOCH_2CH_3$), 1.20 (d, 6'-H), 1.50 (br dd, 6-$CH_2$), 1.57 (m, 8-H), 1.77 (dd, 2"-Hax), 1.95 (d, 2"-Heq), 1.95 (s, 9-$OCOCH_3$), 1.99 (s, 2'-$OCOCH_3$), 2.19 (s, $NCH_3$), 2.34 (s, 3'-N$(CH_3)_2$), 2.65 (t, 3'-H), 2.69 (dd, 2-H), 2.99 (s, $CH(OCH_3)_2$), 3.17 (s, $CH(OCH_3)_2$), 3.26 (t, 5'-H), 3.39 (br d, 4-H), 3.65 (s, 4-$OCH_3$), 3.94 (br d, 5-H), 3.99 (m, 14-H), 4.30 (dq, 5"-H), 4.49 (dd, $CH(OCH_3)_2$), 4.55 (d, 4"-H), 4.69 (d, 1'-H), 4.84 (br dd, 3-H), 4.93 (dd, 2'-H), 4.99 (m, $CH_2$═CH), 5.00 (d, 1"-H), 5.66 (ddt, $CH_2$═CH), 6.45 (br d, NH).

Physicochemical Properties of the Isomer B (1) Molecular formula: $C_{48}H_{83}N_3O_{17}$ (2) Mass spectrum (FAB): m/z 974 $(M+H)^+$ (3) Specific rotation: $[\alpha]_D^{24}$ −53° (c0.40, $CHCl_3$)

(4) $^1H$ NMR spectrum (300 MHz, $CDCl_3$) δ (ppm): 0.85 (d, 8-$CH_3$), 1.05 (s, 3"-$CH_3$), 1.06 (d, 6"-H), 1.07 (t, 3-$OCOCH_2CH_3$), 1.10 (t, 4"-$OCOCH_2CH_3$), 1.20 (d, 6'-H), 1.43 (br dd, 6-$CH_2$), 1.77 (dd, 2"-Hax), 1.95 (d, 2"-Heq), 1.95 (s, 9-$OCOCH_3$), 1.95 (s, 2'-$OCOCH_3$), 2.10 (dd, 10-H), 2.19 (s, $NCH_3$), 2.34 (s, 3'-N$(CH_3)_2$), 2.65 (t, 3'-H), 3.06 (s, $CH(OCH_3)_2$), 3.06 (t, 4'-H), 3.18 (s, $CH(OCH_3)_2$), 3.27 (br d, 4-H), 3.29 (dq, 5'-H), 3.49 (s, 4-$OCH_3$), 3.87 (br d, 5-H), 4.31 (dq, 5"-H), 4.47 (m, $CH(OCH_3)_2$), 4.55 (d, 4"-H), 4.67 (d, 1'-H), 4.76 (m, 9-H), 4.94 (dd, 2'-H), 5.00 (d, 1"-H), 5.68 (ddt, $CH_2$═CH).

(d) In an amount of 338 mg of the isomer A of Example 20(c) was dissolved in 20 ml of acetonitrile under argon atmosphere, added with 8.1 mg of palladium(II) acetate, 22 mg of tri-o-tolylphosphine, 150 mg of 4-bromoquinoline and 98 μl of triethylamine, stirred at 50° C. for 1 hour, then warmed to 80° C., and stirred for 24 hours. The reaction mixture was added with 8.5 mg of palladium(II) acetate, 22.2 mg of tri-o-tolylphosphine, and 15 mg of 4-bromoquinoline, and further stirred at 80° C. for 16 hours, and then the reaction mixture was diluted with 50 ml of ethyl acetate, and washed with 20 ml of 8% aqueous sodium hydrogencarbonate. The aqueous layer was extracted twice with 10 ml of ethyl acetate, and the organic layers were combined, and washed with 25% brine. The organic layer was dried over anhydrous sodium sulfate, and then filtered. The filtrate was concentrated under reduced pressure, and the resulting residue was purified by silica gel column chromatography (chloroform/methanol (50:1)), and further purified by preparative TLC (chloroform/methanol/aqueous ammonia (20:1:0.1)) to obtain 181 mg of a coupling compound A (compound represented by the formula (21) mentioned in Preparation Scheme 7 wherein $R_3$ is methyl group, one of $R_9$ and $R_{10}$ is trans-3-(quinolin-4-yl)-2-propenyl group, the other is hydrogen atom, $R_{3''}$ is hydrogen atom, $R_{4''}$ is propionyl group, and X is NH group), and 27.8 mg of a coupling compound B (compound represented by the formula (21) mentioned in Preparation Scheme 7 wherein $R_3$ is methyl group, one of $R_9$ and $R_{10}$ is trans-3-(quinolin-4-yl)-1-propenyl group, the other is hydrogen atom, $R_{3''}$ is hydrogen atom, $R_{4''}$ is propionyl group, and X is NH group).

Physicochemical Properties of the Coupling Compound A (1) Molecular formula: $C_{57}H_{88}N_4O_{17}$ (2) Mass spectrum (FAB): m/z 1101 $(M+H)^+$ (3) Specific rotation: $[\alpha]_D^{20}$ −49° (c0.78, $CHCl_3$)

(4) $^1H$ NMR spectrum (300 MHz, $CDCl_3$) δ (ppm): 0.81 (d, 8-$CH_3$), 1.03 (s, 3"-$CH_3$), 1.03 (t, 3-$OCOCH_2CH_3$), 1.04 (d, 6"-H), 1.08 (t, 4"-$OCOCH_2CH_3$), 1.18 (d, 6'-H), 1.24 (m, 7-H), 1.48 (br dd, 6-$CH_2$), 1.57 (m, 8-H), 1.75 (dd, 2"-Hax), 1.92 (d, 2"-Heq), 1.94 (s, 9-$OCOCH_3$), 1.97 (s, 2'-$OCOCH_3$), 2.21 (s, $NCH_3$), 2.32 (s, 3'-$N(CH_3)_2$), 2.64 (t, 3'-H), 2.98 (s, $CH(OCH_3)_2$), 3.15 (s, $CH(OCH_3)_2$), 3.24 (m, 4'-H), 3.27 (m, 5'-H), 3.34 (br d, 4-H), 3.62 (s, 4-$OCH_3$), 3.93 (br d, 5-H), 4.14 (m, 14-H), 4.29 (dq, 5"-H), 4.47 (dd, $CH(OCH_3)_2$), 4.57 (d, 4"-H), 4.67 (d, 1'-H), 4.83 (m, 9-H), 4.85 (br dd, 3-H), 4.91 (dd, 2'-H), 4.98 (d, 1"-H), 6.32 (dt, quinoline-CH═CH), 6.80 (br d, NH), 7.05 (d, quinoline-CH), 7.33 (d, quinoline), 7.45 (ddd, quinoline), 7.61 (ddd, quinoline), 8.00 (br d, quinoline), 8.00 (br d, quinoline), 8.74 (d, quinoline).

Physicochemical Properties of the Coupling Compound B (1) Molecular formula: $C_{57}H_{88}N_4O_{17}$ (2) Mass spectrum (FAB): m/z 1101 $(M+H)^+$ (3) $^1H$ NMR spectrum (300 MHz, $CDCl_3$) δ (ppm): 0.79 (d, 8-$CH_3$), 1.04 (s, 3"-$CH_3$), 1.05 (d, 6"-H), 1.05 (t, 3-$OCOCH_2CH_3$), 1.10 (t, 4"-$OCOCH_2CH_3$), 1.19 (d, 6'-H), 1.46 (br dd, 6-$CH_2$), 1.59 (m, 8-H), 1.70 (br dd, 6-$CH_2$), 1.77 (dd, 2"-Hax), 1.93 (s, 9-$OCOCH_3$), 1.97 (s, 2'-$OCOCH_3$), 2.15 (s, $NCH_3$), 2.33 (s, 3'-$N(CH_3)_2$), 2.65 (t, 3'-H), 2.69 (dd, 2-H), 2.99 (s, $CH(OCH_3)_2$), 3.16 (s, $CH(OCH_3)_2$), 3.22 (m, 4'-H), 3.25 (m, 5'-H), 3.32 (br d, 4-H), 3.61 (s, 4-$OCH_3$), 3.75 (d, quinoline-$CH_2$), 3.92 (br d, 5-H), 4.30 (dq, 5"-H), 4.48 (dd, $CH(OCH_3)_2$), 4.54 (d, 4"-H), 4.68 (d, 1'-H), 4.80 (br d, 9-H), 4.85 (br d, 3-H), 4.92 (dd, 2'-H), 5.00 (d, 1"-H), 5.42 (dd, 14-CH), 5.77 (ddd, 14-CH═CH), 6.98 (br d, NH), 7.16 (d, quinoline), 7.48 (ddd, quinoline), 7.63 (ddd, quinoline), 7.91 (dd, quinoline), 8.04 (dd, quinoline), 8.75 (d, quinoline).

(e) In the same manner as in Example 2(c), 144 mg of a deacetyled compound (compound represented by the formula (22) mentioned in Preparation Scheme 7 wherein $R_1$ is propionyl group, $R_2$ is hydrogen atom, $R_3$ is methyl group, one of $R_9$ and $R_{10}$ is trans-3-(quinolin-4-yl)-2-propenyl group, the other is hydrogen atom, $R_{3''}$ is hydrogen atom, $R_{4''}$ is propionyl group, and X is NH group) was obtained from 181 mg of the coupling compound A of Example 20(d).

Physicochemical Properties of this Compound (1) Molecular formula: $C_{53}H_{84}N_4O_{15}$ (2) Mass spectrum (FAB): m/z 1017 $(M+H)^+$ (3) Specific rotation: $[\alpha]_D^{20}$ −28° (c0.50, $CHCl_3$)

(4) $^1H$ NMR spectrum (300 MHz, $CDCl_3$) δ (ppm): 0.87 (d, 8-$CH_3$), 1.04 (t, 3-$OCOCH_2CH_3$), 1.04 (s, 3"-$CH_3$), 1.05 (d, 6"-H), 1.10 (t, 4"-$OCOCH_2CH_3$), 1.20 (d, 6'-H), 1.39 (m, 13-H), 1.56 (br dd, 6-$CH_2$), 1.72 (br dd, 6-$CH_2$), 1.76 (dd, 2"-Hax), 1.93 (d, 2"-Heq), 2.18 (s, $NCH_3$), 2.44 (s, 3'-N$(CH_3)_2$), 2.76 (dd, 2-H), 3.06 (s, $CH(OCH_3)_2$), 3.19 (s, $CH(OCH_3)_2$), 3.22 (m, 4'-H), 3.22 (m, 5'-H), 3.36 (br dd, 9-H), 3.53 (dd, 2'-H), 3.70 (s, 4-$OCH_3$), 3.75 (br d, 4-H), 3.88 (br d, 5-H), 4.28 (m, 14-H), 4.37 (d, 1'-H), 4.40 (dq, 5"-H), 4.55 (d, 4"-H), 4.82 (br d, 3-H), 5.00 (d, 1"-H), 6.15 (br d, NH), 6.34 (dt, CH═CH), 7.07 (d, quinoline-CH), 7.34 (d, quinoline), 7.45 (ddd, quinoline), 7.63 (ddd, quinoline), 7.99 (br d, quinoline), 8.02 (br d, quinoline), 8.76 (d, quinoline).

(f) In the same manner as in Example 2(d), 15.6 mg of the title compound was obtained from 40.7 mg of the compound of Example 20(e).

Physicochemical Properties of this Compound (1) Molecular formula: $C_{51}H_{78}N_4O_{14}$ (2) Mass spectrum (FAB): m/z 971 $(M+H)^+$ (3) Specific rotation: $[\alpha]_D^{20}$ −44° (c0.78, $CHCl_3$)

(4) $^1H$ NMR spectrum (300 MHz, $CDCl_3$) δ (ppm): 0.88 (d, 8-$CH_3$), 1.04 (s, 3"-$CH_3$), 1.06 (d, 6"-H), 1.08 (t, 3-$OCOCH_2CH$ 3), 1.11 (t, 4"-$OCOCH_2CH_3$), 1.13 (d, 6'-H), 1.28 (br t, 8-H), 1.54 (br dd, 7-H), 1.76 (dd, 2"-Hax), 1.93 (d, 2"-Heq), 2.20 (s, $NCH_3$), 2.44 (s, 3'-$N(CH_3)_2$), 2.78 (dd, 2-H), 2.90 (dd, 6-$CH_2$), 3.21 (m, 4'-H), 3.21 (m, 5'-H), 3.38 (br dd, 9-H), 3.48 (dd, 2'-H), 3.68 (s, 4-$OCH_3$), 3.76 (br d, 4-H), 3.82 (br d, 5-H), 4.26 (m, 14-H), 4.34 (d, 1'-H), 4.39 (dq, 5"-H), 4.55 (d, 4"-H), 4.95 (br d, 3-H), 4.99 (d, 1"-H), 6.28 (br d, NH), 6.34 (dt, CH═CH), 7.08 (d, quinoline-CH), 7.35 (d, quinoline), 7.47 (ddd, quinoline), 7.63 (ddd, quinoline), 8.00 (br d, quinoline), 8.03 (br d, quinoline), 8.76 (d, quinoline), 9.59 (s, CHO).

Example 21

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is trans-3-(quinolin-4-yl)-2-propenyl group, the other is hydrogen atom, $R_{4'}$ is hydrogen atom, X is NH group, and the substituent $R_9$ and $R_{10}$ are the same as those of the compound of Example 20

In the same manner as Example 2(d), 11.3 mg of the title compound was obtained from 40.7 mg of the compound of Example 20(e).

Physicochemical Properties of this Compound (1) Molecular formula: $C_{41}H_{62}N_4O_{10}$ (2) Mass spectrum (FAB): m/z 771 $(M+H)^+$ (3) Specific rotation: $[\alpha]_D^{21}$ −8.7° (c0.57, $CHCl_3$)

(4) $^1H$ NMR spectrum (300 MHz, $CDCl_3$) δ (ppm): 0.88 (d, 8-$CH_3$), 1.08 (t, 3-$OCOCH_2CH_3$), 1.17 (d, 6'-H), 1.30 (br t, 8-H), 1.45 (m, 13-H), 1.53 (br dd, 7-H), 1.89 (m, 6-H), 1.92 (m, 13-H), 2.22 (s, $NCH_3$), 2.46 (s, 3'-$N(CH_3)_2$), 2.78 (dd, 2-H), 2.92 (br dd, 6-$CH_2$), 2.97 (t, 4'-H), 3.22 (dq, 5'-H), 3.40 (br dd, 9-H), 3.47 (dd, 2'-H), 3.69 (s, 4-$OCH_3$), 3.76 (br d, 4-H), 3.83 (br d, 5-H), 4.26 (m, 14-H), 4.35 (d, 1'-H), 4.95 (br d, 3-H), 6.34 (dt, CH═CH), 7.18 (d, quinoline-CH), 7.35 (d, quinoline), 7.48 (br dd, quinoline), 7.64 (br dd, quinoline), 8.00 (br d, quinoline), 8.03 (br d, quinoline), 8.76 (d, quinoline), 9.61 (s, CHO).

Example 22

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is trans-3-(quinolin-4-yl)-2-propenyl group, the other is hydrogen atom, $R_{4'}$ is a group represented by the formula (a), $R_{3''}$ is hydrogen atom, $R_{4''}$ is propionyl group, and X is NH group, provided that the substituents $R_9$ and $R_{10}$ are exchanged compared with the compound of Example 20

(a) In the same manner as in Example 20(d), 184 mg of a coupling compound A (compound represented by the formula (21) mentioned in Preparation Scheme 7 wherein $R_3$ is methyl group, one of $R_9$ and $R_{10}$ is trans-3-(quinolin-4-yl)-2-propenyl group, the other is hydrogen atom, $R_{3''}$ is hydrogen atom, $R_{4''}$ is propionyl group, and X is NH group, provided that the substituents $R_9$ and $R_{10}$ are exchanged compared with the coupling compound A of Example 20(d)), and 41 mg of a coupling compound B (compound represented by the formula (21) mentioned in Preparation Scheme 7 wherein $R_3$ is methyl group, one of $R_9$ and $R_{10}$ is trans-3-(quinolin-4-yl)-1-propenyl group, the other is hydrogen atom, $R_{3''}$ is hydrogen atom, $R_{4''}$ is propionyl group, and X is NH group, provided that the substituents $R_9$ and $R_{10}$ are exchanged compared with the coupling compound B of Example 20(d)) were obtained from 316 mg of the isomer B of Example 20(c).

Physicochemical Properties of the Coupling Compound A (1) Molecular formula: $C_{57}H_{88}N_4O_{17}$ (2) Mass spectrum (FAB): m/z 1101 $(M+H)^+$ (3) Specific rotation: $[\alpha]_D^{22}$ −46° (c0.89, $CHCl_3$)

(4) $^1H$ NMR spectrum (300 MHz, $CDCl_3$) δ (ppm): 0.84 (d, 8-$CH_3$), 1.04 (s, 3"-$CH_3$), 1.05 (d, 6"-H), 1.09 (t, 3-$OCOCH_2CH_3$), 1.10 (t, 4"-$OCOCH_2CH_3$), 1.20 (d, 6'-H), 1.43 (br dd, 6-$CH_2$), 1.63 (m, 8-H), 1.76 (dd, 2"-Hax), 1.89 (d, 2"-Heq), 1.95 (s, 9-$OCOCH_3$), 1.95 (s, 2'-$OCOCH_3$), 2.20 (s, $NCH_3$), 2.32 (s, 3'-$N(CH_3)_2$), 2.64 (t, 3'-H), 3.05 (s, $CH(OCH_3)_2$), 3.17 (s, $CH(OCH_3)_2$), 3.49 (s, 4-$OCH_3$), 3.87 (br d, 5-H), 4.30 (dq, 5"-H), 4.45 (m, $CH(OCH_3)_2$), 4.54 (d, 4"-H), 4.65 (d, 1'-H), 4.77 (m, 9-H), 4.93 (dd, 2'-H), 4.99 (d, 1"-H), 5.03 (br dd, 3-H), 6.35 (dt, CH═CH), 7.08 (d, quinoline-CH), 7.34 (d, quinoline), 7.48 (ddd, quinoline), 7.63 (ddd, quinoline), 8.01 (br d, quinoline), 8.01 (br d, quinoline), 8.70 (d, quinoline).

Physicochemical Properties of the Coupling Compound B (1) Molecular formula: $C_{57}H_{88}N_4O_{17}$ (2) Mass spectrum (FAB): m/z 1101 $(M+H)^+$ (3) Specific rotation: $[\alpha]_D^{20}$ −43° (c0.64, $CHCl_3$)

(4) $^1H$ NMR spectrum (300 MHz, $CDCl_3$) δ (ppm): 0.75 (d, 8-$CH_3$), 1.04 (d, 6"-H), 1.04 (s, 3"-$CH_3$), 1.06 (t, 3-$OCOCH_2CH_3$), 1.10 (t, 4"-$OCOCH_2CH_3$), 1.19 (d, 6'-H), 1.38 (br dd, 6-$CH_2$), 1.62 (m, 8-H), 1.76 (dd, 2"-Hax), 1.93 (d, 2"-Heq), 1.93 (s, 9-$OCOCH_3$), 1.93 (s, 2'-$OCOCH_3$), 2.14 (s, $NCH_3$), 2.29 (s, 3'-$N(CH_3)_2$), 2.62 (t, 3'-H), 3.04 (s, $CH(OCH_3)_2$), 3.16 (s, $CH(OCH_3)_2$), 3.23 (m, 4'-H), 3.26 (m, 5'-H), 3.44 (s, 4-$OCH_3$), 3.74 (br d, quinoline-$CH_2$), 3.87 (br d, 5-H), 4.29 (dq, 5"-H), 4.45 (m, $CH(OCH_3)_2$), 4.53 (d, 4"-H), 4.63 (d, 1'-H), 4.74 (m, 9-H), 4.90 (dd, 2'-H), 4.99 (d, 1"-H), 5.54 (br d, 14-CH), 5.75 (br dd, 14-CH═CH), 7.22 (d, quinoline), 7.48 (br dd, quinoline), 7.63 (br dd, quinoline), 7.91 (br d, quinoline), 8.03 (br d, quinoline), 8.12 (br d, NH), 8.74 (d, quinoline).

(b) In the same manner as in Example 2(c), 146 mg of a deacetyled compound (compound represented by the formula (22) mentioned in Preparation Scheme 7 wherein $R_1$ is propionyl group, $R_2$ is hydrogen atom, $R_3$ is methyl group, one of $R_9$ and $R_{10}$ is trans-3-(quinolin-4-yl)-2-propenyl group, the other is hydrogen atom, $R_{3'}$ is hydrogen atom, $R_{4''}$ is propionyl group, and X is NH group, provided that the substituents $R_9$ and $R_{10}$ are exchanged compared with the compound of Example 20(e)) was obtained from 184 mg of the coupling compound A of Example 22(a).

Physicochemical Properties of this Compound (1) Molecular formula: $C_{53}H_{84}N_4O_{15}$ (2) Mass spectrum (FAB): m/z 1017 $(M+H)^+$ (3) Specific rotation: $[\alpha]_D^{17}$ −39° (c0.69, $CHCl_3$)

(4) $^1H$ NMR spectrum (300 MHz, $CDCl_3$) δ (ppm): 0.84 (d, 8-$CH_3$), 0.96 (br dd, 7-H), 1.03 (t, 3-$OCOCH_2CH_3$), 1.04 (s, 3"-$CH_3$), 1.05 (d, 6"-H), 1.11 (t, 4"-$OCOCH_2CH_3$), 1.20 (d, 6'-H), 1.33 (br dd, 7-H), 1.51 (br dd, 6-$CH_2$), 1.54 (m, 8-H), 1.76 (dd, 2"-Hax), 1.94 (d, 2"-Heq), 2.29 (s, $NCH_3$), 2.42 (s, 3'-$N(CH_3)_2$), 2.71 (dd, 2-H), 3.12 (s, $CH(OCH_3)_2$), 3.20 (s, $CH(OCH_3)_2$), 3.21 (m, 4'-H), 3.24 (m, 5'-H), 3.37 (br d, 4-H), 3.48 (dd, 2'-H), 3.53 (s, 4-$OCH_3$), 3.56 (br d, 9-H), 3.81 (br d, 5-H), 3.96 (m, 14-H), 4.34 (d, 1'-H), 4.39 (m, 5"-H), 4.55 (d, 4"-H), 5.00 (d, 1"-H), 5.14 (br dd, 3-H), 6.35 (dt, CH═CH), 7.07 (d, quinoline-CH), 7.33 (d, quinoline), 7.48 (ddd, quinoline), 7.63 (ddd, quinoline), 8.00 (br d, quinoline), 8.02 (br d, quinoline), 8.76 (d, quinoline).

(c) In the same manner as in Example 2(d), 18.3 mg of the title compound was obtained from 39.0 mg of the compound of Example 22(b).

Physicochemical Properties of this Compound (1) Molecular formula: $C_{51}H_{78}N_4O_{14}$ (2) Mass spectrum (FAB): m/z 971 $(M+H)^+$ (3) Specific rotation: $[\alpha]_D^{21}$ −49° (c0.92, $CHCl_3$)

(4) $^1H$ NMR spectrum (300 MHz, $CDCl_3$) δ (ppm): 0.85 (d, 8-$CH_3$), 1.04 (s, 3"-$CH_3$), 1.05 (d, 6"-H), 1.07 (t, 3-$OCOCH_2CH_3$), 1.10 (t, 4"-$OCOCH_2CH_3$), 1.11 (d, 6'-H), 1.40 (br d, 8-H), 1.76 (dd, 2"-Hax), 1.80 (m, 13-H), 1.93 (d, 2"-Heq), 2.36 (s, $NCH_3$), 2.42 (s, 3'-$N(CH_3)_2$), 2.75 (dd, 10-H), 2.93 (dd, 6-$CH_2$), 3.21 (m, 4'-H), 3.21 (m, 5'-H), 3.43 (dd, 2'-H), 3.52 (s, 4-$OCH_3$), 3.62 (br d, 9-H), 3.79 (br d, 5-H), 3.84 (m, 14-H), 4.34 (d, 1'-H), 4.38 (dq, 5"-H), 4.54 (d, 4"-H), 4.99 (d, 1"-H), 5.19 (br dd, 3-H), 6.36 (dt, quinoline —CH═CH), 7.07 (d, quinoline-CH), 7.35 (d, quinoline), 7.48 (ddd, quinoline), 7.63 (ddd, quinoline), 8.00 (br d, quinoline), 8.02 (br d, quinoline), 8.76 (d, quinoline), 9.57 (s, CHO).

Example 23

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is trans-3-(quinolin-4-yl)-2-propenyl group, the other is hydrogen atom, $R_{4'}$ is hydrogen atom, and X is NH group, provided that the substituents $R_9$ and $R_{10}$ are exchanged compared with the compound of Example 21

In the same manner as in Example 2(d), 11.1 mg of the title compound was obtained from 39.0 mg of the compound of Example 22(b).

Physicochemical Properties of this Compound (1) Molecular formula: $C_{41}H_{62}N_4O_{10}$ (2) Mass spectrum (FAB): m/z 771 $(M+H)^+$ (3) Specific rotation: $[\alpha]_D^{21}$ −20° (c0.56, $CHCl_3$)

(4) $^1H$ NMR spectrum (300 MHz, $CDCl_3$) δ (ppm): 0.85 (d, 8-$CH_3$), 0.95 (br dd, 7-H), 1.04 (s, 3"-$CH_3$), 1.07 (t, 3-$OCOCH_2CH_3$), 1.16 (d, 6'-H), 1.38 (br dd, 7-H), 1.42 (m, 8-H), 1.80 (m, 13-H), 2.35 (s, $NCH_3$), 2.41 (s, 3'-$N(CH_3)_2$), 2.76 (dd, 10-H), 2.95 (d, 6-$CH_2$), 3.00 (t, 4'-H), 3.21 (dq, 5'-H), 3.40 (dd, 2'-H), 3.52 (s, 4-$OCH_3$), 3.63 (br d, 9-H), 3.81 (br d, 5-H), 3.85 (m, 14-H), 4.36 (d, 1'-H), 5.19 (br dd, 3-H), 6.36 (dt, CH═CH), 7.08 (d, quinoline-CH), 7.36 (d, quinoline), 7.49 (ddd, quinoline), 7.64 (ddd, quinoline), 7.69 (br s, NH), 8.00 (br d, quinoline), 8.03 (br d, quinoline), 8.76 (d, quinoline), 9.59 (s, CHO).

Example 24

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is 3-(quinolin-4-yl)propyl group, the other is hydrogen atom, $R_{4'}$ is a group represented by the formula (a), $R_{3''}$ is hydrogen atom, $R_{4''}$ is propionyl group, and X is NH group (a) In an amount of 104 mg of the compound of Example 20(e) was dissolved in 10 ml of ethanol, and added with 120 μl of acetic acid and 52.3 mg of 10% Pd—C catalyst. The reaction vessel was purged with hydrogen, and the reaction mixture was stirred for 5 hours. The reaction mixture was filtered through a Celite layer, and washed with methanol, and the filtrate was concentrated under reduced pressure. The resulting residue was purified by silica gel column chromatography (chloroform/methanol (25:1)) to obtain 49.2 mg of a double bond-reduced compound (compound represented by the formula (22) mentioned in Preparation Scheme 7 wherein $R_1$ is propionyl group, $R_2$ is hydrogen atom, $R_3$ is methyl group, one of $R_9$ and $R_{10}$ is 3-(quinolin-4-yl)propyl group, the other is hydrogen atom, $R_{3''}$ is hydrogen atom, $R_{4''}$ is propionyl group, and X is NH group).

Physicochemical Properties of this Compound (1) Molecular formula: $C_{53}H_{86}N_4O_{15}$ (2) Mass spectrum (FAB): m/z 1019 $(M+H)^+$ (3) $^1H$ NMR spectrum (300 MHz, $CDCl_3$) δ (ppm): 0.85 (d, 8-$CH_3$), 1.05 (d, 6"-H), 1.05 (t, 3-$OCOCH_2CH_3$), 1.05 (s, 3"-$CH_3$), 1.10 (t, 4"-$OCOCH_2CH_3$), 1.20 (d, 6'-H), 1.76 (dd, 2"-Hax), 1.94 (d, 2"-Heq), 2.45 (s, 3'-$N(CH_3)_2$), 2.76 (dd, 2-H), 3.00 (m, quinoline-$CH_2$), 3.04 (s, $CH(OCH_3)_2$), 3.18 (s, $CH(OCH_3)_2$), 3.25 (m, 4'-H), 3.25 (m, 5'-H), 3.51 (dd, 2'-H), 3.70 (s, 4-$OCH_3$), 3.89 (br d, 5-H), 4.02 (m, 14-H), 4.40 (d, 1'-H), 4.38 (dq, 5"-H), 4.55 (d, 4"-H), 4.80 (br d, 3-H), 5.01 (d, 1"-H), 7.14 (d, quinoline), 7.47 (br dd, quinoline), 7.62 (br dd, quinoline), 7.93 (br d, quinoline), 8.03 (br d, quinoline), 8.72 (d, quinoline).

(b) In the same manner as in Example 2(d), 10.6 mg of the title compound was obtained from 29.0 mg of the compound of Example 24(a).

Physicochemical Properties of this Compound (1) Molecular formula: $C_{51}H_{80}N_4O_{14}$ (2) Mass spectrum (FAB): m/z 973 $(M+H)^+$ (3) Specific rotation: $[\alpha]_D^{20}$ −51° (c0.53, $CHCl_3$)

(4) $^1H$ NMR spectrum (300 MHz, $CDCl_3$) δ (ppm): 0.87 (d, 8-$CH_3$), 1.05 (s, 3"-$CH_3$), 1.06 (d, 6"-H), 1.07 (t, 3-$OCOCH_2CH_3$), 1.11 (t, 4"-$OCOCH_2CH_3$), 1.13 (d, 6'-H), 1.29 (br dd, 7-H), 1.36 (m, 13-H), 1.76 (dd, 2"-Hax), 1.94 (d, 2"-Heq), 2.21 (s, $NCH_3$), 2.44 (s, 3'-$N(CH_3)_2$), 2.79 (dd, 2-H), 2.89 (dd, 6-$CH_2$), 3.01 (ddd, quinoline-$CH_2$), 3.20 (m, 4'-H), 3.22 (m, 5'-H), 3.39 (br d, 9-H), 3.48 (dd, 2'-H), 3.70 (s, 4-$OCH_3$), 3.76 (br d, 4-H), 3.82 (br d, 5-H), 4.06 (m, 14-H), 4.35 (d, 1'-H), 4.40 (dq, 5"-H), 4.55 (d, 4"-H), 4.91 (br d, 3-H), 5.00 (d, 1"-H), 7.15 (d, quinoline), 7.48 (ddd, quinoline), 7.63 (ddd, quinoline), 7.94 (br d, quinoline), 8.03 (br d, quinoline), 8.73 (d, quinoline), 9.58 (s, CHO).

Example 25

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is 3-(quinolin-4-yl)propyl group, the other is hydrogen atom, $R_{4'}$ is hydrogen atom, and X is NH group In the same manner as in Example 2(d), 8.8 mg of the title compound was obtained from 29.0 mg of the compound of Example 24(a).

Physicochemical Properties of this Compound (1) Molecular formula: $C_{41}H_{64}N_4O_{10}$ (2) Mass spectrum (FAB): m/z 773 $(M+H)^+$ (3) Specific rotation: $[\alpha]_D^{26}$ −21° (c0.44, $CHCl_3$)

(4) $^1H$ NMR spectrum (300 MHz, $CDCl_3$) δ (ppm): 0.87 (d, 8-$CH_3$), 1.10 (t, 3-$OCOCH_2CH_3$), 1.18 (d, 6'-H), 1.29 (br dd, 7-H), 1.35 (m, 13-H), 1.74 (m, quinoline-$CH_2CH_2$), 1.86 (br t, 6-H), 2.20 (s, $NCH_3$), 2.46 (s, 3'-$N(CH_3)_2$), 2.79 (dd, 2-H), 2.94 (dd, 6-$CH_2$), 2.98 (t, 4'-H), 3.02 (ddd, quinoline-$CH_2$), 3.23 (dq, 5'-H), 3.38 (br dd, 9-H), 3.47 (dd, 2'-H), 3.70 (s, 4-$OCH_3$), 3.76 (br d, 4-H), 3.83 (br d, 5-H), 4.07 (m, 14-H), 4.36 (d, 1'-H), 4.92 (br d, 3-H), 6.02 (br d, NH), 7.15 (d, quinoline), 7.48 (ddd, quinoline), 7.63 (ddd, quinoline), 7.94 (br d, quinoline), 8.04 (br d, quinoline), 8.73 (d, quinoline), 9.60 (s, CHO).

Example 26

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is 3-(quinolin-4-yl)propyl group, the other is hydrogen atom, $R_{4'}$ is a group represented by the formula (a), $R_3$ is hydrogen atom, $R_{4''}$ is propionyl group, and X is NH group, provided that the substituents $R_9$ and $R_{10}$ are exchanged compared with the compound of Example 24

(a) In the same manner as in Example 24(a), 75.8 mg of a double bond-reduced compound (compound represented by the formula (22) mentioned in Preparation Scheme 7 wherein $R_1$ is propionyl group, $R_2$ is hydrogen atom, $R_3$ is methyl group, one of $R_9$ and $R_{10}$ is 3-(quinolin-4-yl)propyl group, the other is hydrogen atom, $R_{3''}$ is hydrogen atom, $R_{4''}$ is propionyl group, and X is NH group, provided that the substituents $R_9$ and $R_{10}$ are exchanged compared with the compound of Example 24(a)) was obtained from 107 mg of the compound of Example 22(b).

Physicochemical Properties of this Compound (1) Molecular formula: $C_{53}H_{86}N_4O_{15}$ (2) Mass spectrum (FAB): m/z 1019 $(M+H)^+$ (3) Specific rotation: $[\alpha]_D^{22}$ −36° (c0.43, $CHCl_3$)

(4) $^1H$ NMR spectrum (300 MHz, $CDCl_3$) δ (ppm): 0.84 (d, 8-$CH_3$), 0.92 (br dd, 7-H), 1.04 (s, 3"-$CH_3$), 1.05 (t, 3-$OCOCH_2CH_3$), 1.05 (d, 6"-H), 1.10 (t, 4"-$OCOCH_2CH_3$), 1.20 (d, 6'-H), 1.32 (br dd, 7-H), 1.76 (dd, 2"-Hax), 1.83 (br dd, 6-$CH_2$), 1.93 (d, 2"-Heq), 2.27 (s, $NCH_3$), 2.43 (s, 3'-$N(CH_3)_2$), 2.54 (br t, 13-H), 3.01 (ddd, quinoline-$CH_2$), 3.12 (s, $CH(OCH_3)_2$), 3.19 (s, $CH(OCH_3)_2$), 3.21 (m, 4'-H), 3.24 (m, 5'-H), 3.28 (br d, 4-H), 3.51 (s, 4-$OCH_3$), 3.79 (br d, 5-H), 3.84 (m, 14-H), 4.32 (d, 1'-H), 4.37 (dd, $CH(OCH_3)_2$), 4.39 (dq, 5"-H), 4.54 (d, 4"-H), 5.00 (d, 1"-H), 5.11 (br dd, 3-H), 6.73 (br s, NH), 7.13 (d, quinoline), 7.48 (br dd, quinoline), 7.62 (br dd, quinoline), 7.94 (br d, quinoline), 8.02 (br d, quinoline), 8.71 (d, quinoline).

(b) In the same manner as in Example 2(d), 17.0 mg of the title compound was obtained from 35.0 mg of the compound of Example 26(a).

Physicochemical Properties of this Compound (1) Molecular formula: $C_{51}H_{80}N_4O_{14}$ (2) Mass spectrum (FAB): m/z 973 $(M+H)^+$ (3) Specific rotation: $[\alpha]_D^{23}$ −43° (c0.85, $CHCl_3$)

(4) $^1H$ NMR spectrum (300 MHz, $CDCl_3$) δ (ppm): 0.87 (d, 8-$CH_3$), 0.91 (br dd, 7-H), 1.04 (s, 3"-$CH_3$), 1.06 (d, 6"-H), 1.08 (t, 3-$OCOCH_2CH_3$), 1.10 (t, 4"-$OCOCH_2CH_3$), 1.11 (d, 6'-H), 1.38 (m, 8-H), 1.48 (br dd, 13-H), 1.76 (dd, 2"-Hax), 1.94 (d, 2"-Heq), 2.23 (dd, 6-$CH_2$), 2.33 (s, $NCH_3$), 2.45 (s, 3'-$N(CH_3)_2$), 2.91 (dd, 6-$CH_2$), 3.02 (br dd, quinoline-$CH_2$), 3.20 (m, 4'-H), 3.21 (m, 5'-H), 3.43 (br d, 4-H), 3.49 (s, 4-$OCH_3$), 3.56 (br d, 9-H), 3.71 (m, 14-H), 3.77 (br d, 5-H), 4.34 (d, 1'-H), 4.39 (dq, 5"-H), 4.55 (d, 4"-H), 4.99 (d, 1"-H), 5.15 (br dd, 3-H), 7.14 (d, quinoline), 7.26 (br s, NH), 7.48 (ddd, quinoline), 7.62 (ddd, quinoline), 7.94 (br d, quinoline), 8.02 (br d, quinoline), 8.71 (d, quinoline), 9.56 (s, CHO).

Example 27

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is 3-(quinolin-4-yl)propyl group, the other is hydrogen atom, $R_{4'}$ is hydrogen atom, and X is NH group, provided that the substituents $R_9$ and $R_{10}$ are exchanged compared with the compound of Example 25

In the same manner as in Example 2(d), 10.5 mg of the title compound was obtained from 35.0 mg of the compound of Example 26(a).

Physicochemical Properties of this Compound (1) Molecular formula: $C_{41}H_{64}N_4O_{10}$ (2) Mass spectrum (FAB): m/z 773 $(M+H)^+$ (3) Specific rotation: $[\alpha]_D^{23}$ −14° (c0.53, $CHCl_3$)

(4) $^1H$ NMR spectrum (300 MHz, $CDCl_3$) δ (ppm): 0.86 (d, 8-$CH_3$), 0.93 (br dd, 7-H), 1.08 (t, 3-$OCOCH_2CH_3$), 1.16 (d, 6'-H), 1.96 (br t, 6-H), 2.31 (s, $NCH_3$), 2.43 (s, 3'-N $(CH_3)_2$), 2.96 (dd, 6-$CH_2$), 2.96 (t, 4'-H), 3.21 (dq, 5'-H), 3.42 (br d, 4-H), 3.44 (dd, 2'-H), 3.50 (s, 4-$OCH_3$), 3.57 (br d, 9-H), 3.72 (m, 14-H), 3.79 (br d, 5-H), 4.36 (d, 1'-H), 5.16 (br dd, 3-H), 7.15 (d, quinoline), 7.25 (br s, NH), 7.49 (ddd, quinoline), 7.63 (ddd, quinoline), 7.94 (br d, quinoline), 8.03 (br d, quinoline), 8.72 (d, quinoline), 9.59 (s, CHO).

Example 28

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is trans-3-(quinolin-4-yl)-1-propenyl group, the other is hydrogen atom, $R_{4'}$ is a group represented by the formula (a), $R_{3''}$ is hydrogen atom, $R_{4''}$ is propionyl group, and X is NH group (a) In the same manner as in Example 2(c), 16.7 mg of a deacetyled compound (compound represented by the formula (22) mentioned in Preparation Scheme 7 wherein $R_1$ is propionyl group, $R_2$ is hydrogen atom, $R_3$ is methyl group, one of $R_8$ and $R_{10}$ is trans-3-(quinolin-4-yl)-1-propenyl group, the other is hydrogen atom, $R_{3''}$ is hydrogen atom, $R_{4''}$ is propionyl group, and X is NH group) was obtained from 27.8 mg of the coupling compound B of Example 20(d).

Physicochemical Properties of this Compound (1) Molecular formula: $C_{41}H_{64}N_4O_{10}$ (2) Mass spectrum (FAB): m/z 773 $(M+H)^+$ (3) Specific rotation: $[\alpha]_D^{23}$ −14° (c0.53, $CHCl_3$)

(4) $^1H$ NMR spectrum (300 MHz, $CDCl_3$) δ (ppm): 0.85 (d, 8-$CH_3$), 1.04 (s, 3"-$CH_3$), 1.05 (d, 6"-H), 1.05 (t, 3-$OCOCH_2CH_3$), 1.10 (t, 4"-$OCOCH_2CH_3$), 1.20 (d, 6'-H), 1.34 (m, 13-H), 1.39 (br dd, 6-$CH_2$), 1.50 (br dd, 6-$CH_2$), 1.76 (dd, 2"-Hax), 1.93 (d, 2"-Heq), 2.15 (s, $NCH_3$), 2.43 (s, 3'-$N(CH_3)_2$), 2.76 (dd, 2-H), 3.04 (s, $CH(OCH_3)_2$), 3.18 (s, $CH(OCH_3)_2$), 3.22 (m, 4'-H), 3.24 (m, 5'-H), 3.36 (br dd, 9-H), 3.52 (dd, 2'-H), 3.69 (s, 4-$OCH_3$), 3.87 (br d, 5-H), 4.33 (dd, $CH(OCH_3)_2$), 4.37 (d, 1'-H), 4.40 (dq, 5"-H), 4.55 (d, 4"-H), 4.60 (m, 14-H), 4.79 (br d, 3-H), 5.00 (d, 1"-H), 5.42 (dd, 14-CH), 5.77 (ddd, 14-CH═CH), 6.18 (br d, NH), 7.15 (d, quinoline), 7.48 (ddd, quinoline), 7.64 (ddd, quinoline), 7.91 (br d, quinoline), 8.04 (br d, quinoline), 8.75 (d, quinoline).

(b) In the same manner as in Example 2(d), 6.1 mg of the title compound was obtained from 16.7 mg of the compound of Example 28(a).

Physicochemical Properties of this Compound (1) Molecular formula: $C_{51}H_{78}N_4O_{14}$ (2) Mass spectrum (FAB): m/z 971 $(M+H)^+$ (3) Specific rotation: $[\alpha]_D^{19}$ −34° (c0.31, $CHCl_3$)

(4) $^1H$ NMR spectrum (300 MHz, $CDCl_3$) δ (ppm): 0.87 (d, 8-$CH_3$), 1.05 (s, 3"-$CH_3$), 1.06 (d, 6"-H), 1.10 (t, 3-$OCOCH_2CH_3$), 1.11 (t, 4"-$OCOCH_2CH_3$), 1.13 (d, 6'-H), 1.26 (br dd, 7-H), 1.39 (m, 13-H), 1.52 (br dd, 8-H), 1.77 (dd, 2"-Hax), 1.94 (d, 2"-Heq), 2.18 (s, $NCH_3$), 2.45 (s, 3'-$N(CH_3)_2$), 2.79 (dd, 2-H), 2.90 (dd, 6-$CH_2$), 3.21 (m, 4'-H), 3.21 (m, 5'-H), 3.38 (br dd, 9-H), 3.48 (dd, 2'-H), 3.68 (s, 4-$OCH_3$), 3.74 (br d, 4-H), 3.82 (br d, 5-H), 4.35 (d, 1'-H), 4.40 (dq, 5"-H), 4.55 (d, 4"-H), 4.60 (m, 14-H), 4.93 (br d, 3-H), 5.00 (d, 1"-H), 5.43 (dd, 14-CH), 5.80 (ddd, 14-CH═CH), 6.30 (br d, NH), 7.16 (d, quinoline), 7.50 (ddd, quinoline), 7.65 (ddd, quinoline), 7.92 (br d, quinoline), 8.05 (br d, quinoline), 8.77 (d, quinoline), 9.59 (s, CHO).

Example 29

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is trans-3-(quinolin-4-yl)-1-propenyl group, the other is hydrogen atom, $R_{4'}$ is a group represented by the formula (a), $R_{3''}$ is hydrogen atom, $R_{4''}$ is propionyl group, and X is NH group, provided that the substituents $R_9$ and $R_{10}$ are exchanged compared with the compound of Example 28

(a) In the same manner as in Example 2(c), 20.6 mg of a deacetyled compound (compound represented by the formula (22) mentioned in Preparation Scheme 7 wherein $R_1$ is propionyl group, $R_2$ is hydrogen atom, $R_3$ is methyl group, one of $R_9$ and $R_{10}$ is trans-3-(quinolin-4-yl)-1-propenyl group, the other is hydrogen atom, $R_{3''}$ is hydrogen atom, $R_{4''}$ is propionyl group, and X is NH group, provided that the substituents $R_9$ and $R_{10}$ are exchanged compared with the compound of Example 28 (a)) was obtained from 40.8 mg of the coupling compound B of Example 22(a).

Physicochemical Properties of this Compound (1) Molecular formula: $C_{53}H_{84}N_4O_{15}$ (2) Mass spectrum (FAB): m/z 1017 $(M+H)^+$ (3) Specific rotation: $[\alpha]_D^{16}$ −51° (c1.0, $CHCl_3$)

(4) $^1H$ NMR spectrum (300 MHz, $CDCl_3$) δ (ppm): 0.76 (d, 8-$CH_3$), 0.86 (br dd, 7-H), 1.03 (t, 3-$OCOCH_2CH_3$), 1.04 (s, 3"-$CH_3$), 1.06 (d, 6"-H), 1.10 (t, 4"-$OCOCH_2CH_3$), 1.18 (d, 6'-H), 1.29 (m, 6-H), 1.43 (br dd, 6-$CH_2$), 1.46 (m, 8-H), 1.50 (m, 13-H), 1.76 (dd, 2"-Hax), 1.94 (d, 2"-Heq), 2.27 (s, $NCH_3$), 2.45 (s, 3'-$N(CH_3)_2$), 2.57 (br dd, 12-H), 3.06 (s, $CH(OCH_3)_2$), 3.17 (s, $CH(OCH_3)_2$), 3.22 (m, 4'-H), 3.23 (br d, 4-H), 3.24 (m, 5'-H), 3.41 (s, 4-$OCH_3$), 3.51 (dd, 2'-H), 3.56 (br d, 9-H), 3.73 (br d, quinoline-$CH_2$), 3.77 (br d, 5-H), 4.37 (d, 1'-H), 4.40 (dq, 5"-H), 4.55 (d, 4"-H), 5.00 (d, 1"-H), 5.03 (br dd, 3-H), 5.36 (dd, 14-CH), 5.76 (ddd, 14-CH═CH), 7.17 (d, quinoline), 7.48 (ddd, quinoline), 7.62 (ddd, quinoline), 7.78 (br d, NH), 7.91 (br d, quinoline), 8.02 (br d, quinoline), 8.73 (d, quinoline).

(b) In the same manner as in Example 2(d), 7.8 mg of the title compound was obtained from 20.6 mg of the compound of Example 29(a).

Physicochemical Properties of this Compound (1) Molecular formula: $C_{51}H_{78}N_4O_{14}$ (2) Mass spectrum (FAB): m/z 971 $(M+H)^+$ (3) Specific rotation: $[\alpha]_D^{18}$ −66° (c0.39, $CHCl_3$)

(4) $^1H$ NMR spectrum (300 MHz, $CDCl_3$) δ (ppm): 0.74 (d, 8-$CH_3$), 1.05 (s, 3"-$CH_3$), 1.06 (d, 6"-H), 1.06 (t, 3-$OCOCH_2CH_3$), 1.10 (d, 6'-H), 1.11 (t, 4"-$OCOCH_2CH_3$), 1.30 (br dd, 8-H), 1.61 (m, 13-H), 1.77 (dd, 2"-Hax), 1.95 (d, 2"-Heq), 2.14 (dd, 6-$CH_2$), 2.28 (s, $NCH_3$), 2.50 (s, 3'-N$(CH_3)_2$), 2.97 (dd, 6-$CH_2$), 3.12 (br d, 4-H), 3.21 (m, 4'-H), 3.21 (m, 5'-H), 3.33 (s, 4-$OCH_3$), 3.52 (dd, 2'-H), 3.58 (br dd, 9-H), 4.34 (d, 1'-H), 4.42 (dq, 5"-H), 4.56 (d, 4"-H), 5.01 (m, 3-H), 5.01 (d, 1"-H), 5.29 (dd, 14-CH), 5.76 (ddd, 14-CH═CH), 7.20 (d, quinoline), 7.50 (ddd, quinoline), 7.63 (ddd, quinoline), 7.93 (dd, quinoline), 8.02 (dd, quinoline), 8.22 (br d, NH), 8.73 (d, quinoline), 9.55 (s, CHO).

Example 30

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is trans-3-(quinolin-3-yl)-2-propenyl group, the other is hydrogen atom, $R_{4'}$ is a group represented by the formula (a), $R_{3''}$ is hydrogen atom, $R_{4''}$ is propionyl group, and X is NH group (a) In an amount of 186 mg of the isomer A of Example 20(c) was dissolved in 6 ml of N,N-dimethylformamide under argon atmosphere, added with 4.72 mg of palladium(II) acetate, 26.9 mg of sodium hydrogencarbonate, 57.2 mg of tetrabutylammonium chloride, and 33 μl of 3-bromoquinoline, and stirred at 110° C. for 2 hours. The reaction mixture was diluted with 15 ml of ethyl acetate, washed twice with 8 ml of water, and once with 8 ml of 25% brine, and the organic layer was dried over anhydrous sodium sulfate, and then filtered. The filtrate was concentrated under reduced pressure, and the resulting residue was purified by silica gel column chromatography (chloroform/methanol (50:1 to 20:1)) to obtain 123 mg of a coupling compound (compound represented by the formula (21) mentioned in Preparation Scheme 7 wherein $R_3$ is methyl group, one of $R_9$ and $R_{10}$ is trans-3-(quinolin-3-yl)-2-propenyl group, the other is hydrogen atom, $R_{3''}$ is hydrogen atom, $R_{4''}$ is propionyl group, and X is NH group).

Physicochemical Properties of this Compound (1) Molecular formula: $C_{57}H_{88}N_4O_{17}$ (2) Mass spectrum (FAB): m/z 1101 $(M+H)^+$ (3) Specific rotation: $[\alpha]_D^{18}$ −55° (c0.65, $CHCl_3$)

(4) $^1H$ NMR spectrum (300 MHz, $CDCl_3$) δ (ppm): 0.81 (d, 8-$CH_3$), 1.04 (t, 3-$OCOCH_2CH_3$), 1.04 (s, 3"-$CH_3$), 1.05 (d, 6"-H), 1.10 (t, 4"-$OCOCH_2CH_3$), 1.19 (d, 6'-H), 1.24 (br dd, 7-H), 1.36 (m, 13-H), 1.50 (br dd, 6-$CH_2$), 1.58 (m, 8-H), 1.68 (br dd, 6-$CH_2$), 1.76 (dd, 2"-Hax), 1.94 (d, 2"-Heq), 1.95 (s, 9-$OCOCH_3$), 1.98 (s, 2'-$OCOCH_3$), 2.21 (s, $NCH_3$), 2.33 (s, 3'-$N(CH_3)_2$), 2.65 (t, 3'-H), 2.68 (dd, 2-H), 2.99 (s, $CH(OCH_3)_2$), 3.16 (s, $CH(OCH_3)_2$), 3.25 (m, 4'-H), 3.28 (m, 5'-H), 3.36 (br d, 4-H), 3.63 (s, 4-$OCH_3$), 3.93 (br d, 5-H), 4.14 (m, 14-H), 4.30 (dq, 5"-H), 4.48 (dd, $CH(OCH_3)_2$), 4.54 (d, 4"-H), 4.68 (d, 1'-H), 4.83 (m, 9-H), 4.85 (br d, 3-H), 4.92 (dd, 2'-H), 4.99 (d, 1"-H), 6.30 (dt, CH═CH), 6.50 (d, quinoline-CH), 6.62 (br d, NH), 7.44 (ddd, quinoline), 7.57 (ddd, quinoline), 7.70 (br d, quinoline), 7.93 (d, quinoline), 7.87 (br d, quinoline), 8.86 (d, quinoline).

(b) In the same manner as in Example 2(c), 105 mg of a deacetyled compound (compound represented by the formula (22) mentioned in Preparation Scheme 7 wherein $R_1$ is propionyl group, $R_2$ is hydrogen atom, $R_3$ is methyl group, one of $R_9$ and $R_{10}$ is trans-3-(quinolin-3-yl)-2-propenyl group, the other is hydrogen atom, $R_{3''}$ is hydrogen atom, $R_{4''}$ is propionyl group, and X is NH group) was obtained from 123 mg of the compound of Example 30(a).

Physicochemical Properties of this Compound (1) Molecular formula: $C_{53}H_{84}N_4O_{15}$ (2) Mass spectrum (FAB): m/z 1017 $(M+H)^+$ (3) Specific rotation: $[\alpha]_D^{19}$ −32° (c0.81, $CHCl_3$)

(4) $^1H$ NMR spectrum (300 MHz, $CDCl_3$) δ (ppm): 0.85 (d, 8-$CH_3$), 1.04 (t, 3-$OCOCH_2CH_3$), 1.04 (s, 3"-$CH_3$), 1.05 (d, 6"-H), 1.10 (t, 4"-$OCOCH_2CH_3$), 1.19 (d, 6'-H), 1.52 (m, 6-$CH_2$), 1.57 (m, 8-H), 1.71 (m, 6-$CH_2$), 1.75 (dd, 2"-Hax), 1.93 (d, 2"-Heq), 2.17 (s, $NCH_3$), 2.43 (s, 3'-$N(CH_3)_2$), 2.76 (dd, 2-H), 3.05 (s, $CH(OCH_3)_2$), 3.18 (s, $CH(OCH_3)_2$), 3.23 (m, 4'-H), 3.23 (m, 5'-H), 3.34 (br dd, 9-H), 3.53 (dd, 2'-H), 3.69 (s, 4-$OCH_3$), 3.74 (br d, 4-H), 3.88 (br d, 5-H), 4.22 (m, 14-H), 4.34 (dd, $CH(OCH_3)_2$), 4.37 (d, 1'-H), 4.40 (dq, 5"-H), 4.54 (d, 4"-H), 4.81 (br dd, 3-H), 5.00 (d, 1"-H), 6.07 (br d, NH), 6.31 (dt, CH═CH), 6.51 (d, quinoline-$CH_2$), 7.44 (ddd, quinoline), 7.58 (ddd, quinoline), 7.70 (br d, quinoline), 7.93 (br s, quinoline), 7.98 (br d, quinoline), 8.86 (d, quinoline).

(c) In the same manner as in Example 2(d), 16.6 mg of the title compound was obtained from 40.5 mg of the compound of Example 30(b).

Physicochemical Properties of this Compound (1) Molecular formula: $C_{51}H_{78}N_4O_{14}$ (2) Mass spectrum (FAB): m/z 971 $(M+H)^+$ (3) Specific rotation: $[\alpha]_D^{23}$ −48° (c0.83, $CHCl_3$)

(4) $^1H$ NMR spectrum (300 MHz, $CDCl_3$) δ (ppm): 0.83 (br dd, 7-H), 0.87 (d, 8-$CH_3$), 1.04 (s, 3"-$CH_3$), 1.05 (d, 6"-H), 1.09 (t, 3-$OCOCH_2CH_3$), 1.11 (t, 4"-$OCOCH_2CH_3$), 1.12 (d, 6'-H), 1.29 (m, 8-H), 1.41 (m, 13-H), 1.52 (br dd, 7-H), 1.76 (dd, 2"-Hax), 1.93 (d, 2"-Heq), 2.21 (s, $NCH_3$), 2.44 (s, 3'-$N(CH_3)_2$), 2.78 (dd, 2-H), 2.90 (dd, 6-$CH_2$), 3.20 (m, 4'-H), 3.20 (m, 5'-H), 3.38 (br dd, 9-H), 3.48 (dd, 2'-H), 3.69 (s, 4-$OCH_3$), 3.76 (br d, 4-H), 3.82 (br d, 5-H), 4.22 (m, 14-H), 4.34 (d, 1'-H), 4.40 (dq, 5"-H), 4.55 (d, 4"-H), 4.94 (br d, 3-H), 5.00 (d, 1"-H), 6.21 (br d, NH), 6.31 (dt, CH═CH), 6.52 (d, quinoline-$CH_2$), 7.45 (ddd, quinoline), 7.59 (ddd, quinoline), 7.71 (br d, quinoline), 7.94 (br s, quinoline), 7.98 (br d, quinoline), 8.87 (d, quinoline), 9.59 (s, CHO).

Example 31

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is trans-3-(quinolin-3-yl)-2-propenyl group, the other is hydrogen atom, $R_{4'}$ is hydrogen atom, and X is NH group In the same manner as in Example 2(d), 9.9 mg of the title compound was obtained from 40.5 mg of the compound of Example 30(b).

Physicochemical Properties of this Compound (1) Molecular formula: $C_{41}H_{62}N_4O_{10}$ (2) Mass spectrum (FAB): m/z 771 $(M+H)^+$ (3) Specific rotation: $[\alpha]_D^{23}$ −14° (c0.50, $CHCl_3$)

(4) $^1H$ NMR spectrum (300 MHz, $CDCl_3$) δ (ppm): 0.88 (d, 8-$CH_3$), 1.09 (t, 3-$OCOCH_2CH_3$), 1.18 (d, 6'-H), 1.30 (m, 8-H), 1.43 (m, 13-H), 1.53 (br dd, 7-H), 1.85 (m, 6-H), 1.91 (m, 13-H), 2.22 (s, $NCH_3$), 2.46 (s, 3'-$N(CH_3)_2$), 2.78 (dd, 2-H), 2.95 (dd, 6-$CH_2$), 2.98 (t, 4'-H), 3.23 (dq, 5'-H), 3.39 (br dd, 9-H), 3.47 (dd, 2'-H), 3.69 (s, 4-$OCH_3$), 3.77 (br d, 4-H), 3.83 (br d, 5-H), 4.22 (m, 14-H), 4.36 (d, 1'-H), 4.95 (br d, 3-H), 6.22 (br d, NH), 6.32 (dt, CH═CH), 6.53 (d, quinoline-$CH_2$), 7.45 (ddd, quinoline), 7.59 (ddd, quinoline), 7.72 (br d, quinoline), 7.95 (br s, quinoline), 7.99 (br d, quinoline), 8.87 (d, quinoline), 9.61 (s, CHO).

Example 32

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is trans-3-(quinolin-3-yl)-2-propenyl group, the other is hydrogen atom, $R_{4'}$ is a group represented by the formula (a), $R_{3''}$ is hydrogen atom, $R_{4''}$ is propionyl group, and X is NH group, provided that the substituents $R_9$ and $R_{10}$ are exchanged compared with the compound of Example 30

(a) In the same manner as in Example 20(d), except that 3-bromoquinoline was used instead of 4-bromoquinoline, 82.2 mg of a coupling compound (compound represented by the formula (21) mentioned in Preparation Scheme 7 wherein $R_3$ is methyl group, one of $R_9$ and $R_{10}$ is trans-3-(quinolin-3-yl)-2-propenyl group, the other is hydrogen atom, $R_{3''}$ is hydrogen atom, $R_{4''}$ is propionyl group, and X is NH group, provided that the substituents $R_9$ and $R_{10}$ are exchanged compared with the compound of Example 30(a)) was obtained from 173 mg of the isomer B of Example 20(c).

Physicochemical Properties of this Compound (1) Molecular formula: $C_{57}H_{88}N_4O_{17}$ (2) Mass spectrum (FAB): m/z 1101 $(M+H)^+$ (3) Specific rotation: $[\alpha]_D^{18}$ −37° (c0.70, $CHCl_3$)

(4) $^1H$ NMR spectrum (300 MHz, $CDCl_3$) δ (ppm): 0.83 (d, 8-$CH_3$), 1.04 (d, 6"-H), 1.04 (s, 3"-$CH_3$), 1.05 (t, 3-$OCOCH_2CH_3$), 1.09 (t, 4"-$OCOCH_2CH_3$), 1.20 (d, 6'-H), 1.41 (br dd, 6-$CH_2$), 1.65 (m, 8-H), 1.76 (dd, 2"-Hax), 1.93 (s, 9-$OCOCH_3$), 1.95 (s, 2'-$OCOCH_3$), 2.18 (s, $NCH_3$), 2.32 (s, 3'-$N(CH_3)_2$), 2.65 (t, 3'-H), 3.04 (s, $CH(OCH_3)_2$), 3.17 (s, $CH(OCH_3)_2$), 3.24 (m, 4'-H), 3.27 (m, 5'-H), 3.50 (s, 4-$OCH_3$), 3.87 (br d, 5-H), 4.30 (dq, 5"-H), 4.46 (m, $CH(OCH_3)_2$), 4.54 (d, 4"-H), 4.66 (d, 1'-H), 4.76 (m, 3-H), 4.94 (dd, 2'-H), 4.99 (d, 1"-H), 5.00 (m, 9-H), 6.32 (dt, CH═CH), 6.52 (d, quinoline-CH), 7.44 (ddd, quinoline), 7.58 (ddd, quinoline), 7.71 (br d, quinoline), 7.93 (br s, quinoline), 7.97 (br d, quinoline), 8.86 (d, quinoline).

(b) In the same manner as in Example 2(c), 61.0 mg of a deacetyled compound (compound represented by the formula (22) mentioned in Preparation Scheme 7 wherein $R_1$ is propionyl group, $R_2$ is hydrogen atom, $R_3$ is methyl group, one of $R_9$ and $R_{10}$ is trans-3-(quinolin-3-yl)-2-propenyl group, the other is hydrogen atom, $R_{3''}$ is hydrogen atom, $R_{4''}$ is propionyl group, and X is NH group, provided that the substituents $R_9$ and $R_{10}$ are exchanged compared with the compound of Example 30(b)) was obtained from 82.2 mg of the compound of Example 32(a).

Physicochemical Properties of this Compound (1) Molecular formula: $C_{53}H_{84}N_4O_{15}$ (2) Mass spectrum (FAB): m/z 1017 $(M+H)^+$ (3) Specific rotation: $[\alpha]_D^{22}$ −97° (c0.83, $CHCl_3$)

(4) $^1H$ NMR spectrum (300 MHz, $CDCl_3$) δ (ppm): 0.45 (d, 8-$CH_3$), 1.04 (t, 3-$OCOCH_2CH_3$), 1.07 (s, 3"-$CH_3$), 1.11 (d, 6"-H), 1.12 (t, 4"-$OCOCH_2CH_3$), 1.20 (d, 6'-H), 1.36 (m, 6-$CH_2$), 1.41 (m, 8-H), 1.78 (dd, 2"-Hax), 1.97 (d, 2"-Heq), 2.37 (s, $NCH_3$), 2.58 (s, 3'-$N(CH_3)_2$), 2.78 (dd, 2-H), 3.02 (s, $CH(OCH_3)_2$), 3.17 (s, $CH(OCH_3)_2$), 3.32 (m, 4'-H), 3.36 (m, 5'-H), 3.53 (br d, 4-H), 3.76 (dd, 2'-H), 3.77 (s, 4-$OCH_3$), 3.93 (br d, 5-H), 4.00 (m, 14-H), 4.39 (dd, $CH(OCH_3)_2$), 4.47 (dq, 5"-H), 4.57 (d, 4"-H), 4.58 (d, 1'-H), 5.05 (m, 3-H), 5.11 (d, 1"-H), 6.46 (br dd, CH═CH), 6.53 (d, quinoline-CH), 7.47 (ddd, quinoline), 7.61 (ddd, quinoline), 7.72 (br d, quinoline), 7.87 (d, quinoline), 7.99 (br d, quinoline), 8.54 (br s, NH), 9.08 (d, quinoline).

(c) In the same manner as in Example 2(d), 8.2 mg of the title compound was obtained from 20.8 mg of the compound of Example 32(b).

Physicochemical Properties of this Compound (1) Molecular formula: $C_{51}H_{78}N_4O_{14}$ (2) Mass spectrum (FAB): m/z 971 $(M+H)^+$ (3) Specific rotation: $[\alpha]_D^{18}$ −119° (c0.41, $CHCl_3$)

(4) $^1H$ NMR spectrum (300 MHz, $CDCl_3$) δ (ppm): 0.43 (d, 8-$CH_3$), 1.07 (s, 3"-$CH_3$), 1.09 (t, 3-$OCOCH_2CH_3$), 1.11 (d, 6'-H), 1.11 (d, 6"-H), 1.13 (t, 4"-$OCOCH_2CH_3$), 1.77 (dd, 2"-Hax), 1.97 (d, 2"-Heq), 2.10 (s, $NCH_3$), 2.61 (s, 3'-$N(CH_3)_2$), 2.72 (dd, 2-H), 2.81 (dd, 6-$CH_2$), 3.23 (m, 4'-H), 3.25 (m, 5'-H), 3.59 (br d, 4-H), 3.72 (s, 4-$OCH_3$), 3.91 (br d, 5-H), 3.93 (m, 14-H), 4.47 (dq, 5"-H), 4.51 (d, 1'-H), 4.57

(d, 4"-H), 5.03 (d, 1"-H), 5.05 (m, 3-H), 6.42 (br dd, CH═CH), 6.53 (d, quinoline-CH), 7.49 (ddd, quinoline), 7.62 (ddd, quinoline), 7.72 (br d, quinoline), 7.88 (br s, quinoline), 8.02 (br d, quinoline), 8.77 (br d, NH), 9.04 (br s, quinoline), 9.53 (s, CHO).

Example 33

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is 3-(quinolin-3-yl)propyl group, the other is hydrogen atom, $R_{4'}$ is a group represented by the formula (a), $R_{3''}$ is hydrogen atom, $R_{4''}$ is propionyl group, and X is NH group (a) In the same manner as in Example 24(a), 41.1 mg of a double bond-reduced compound (compound represented by the formula (22) mentioned in Preparation Scheme 7 wherein $R_1$ is propionyl group, $R_2$ is hydrogen atom, $R_3$ is methyl group, one of $R_9$ and $R_{10}$ is 3-(quinolin-3-yl)propyl group, the other is hydrogen atom, $R_{3''}$ is hydrogen atom, $R_{4''}$ is propionyl group, and X is NH group) was obtained from 64.2 mg of the compound of Example 30(b).

Physicochemical Properties of this Compound (1) Molecular formula: $C_{53}H_{86}N_4O_{15}$ (2) Mass spectrum (FAB): m/z 1019 $(M+H)^+$ (3) Specific rotation: $[\alpha]_D^{21}$ −39° (c0.61, $CHCl_3$)

(4) $^1H$ NMR spectrum (300 MHz, $CDCl_3$) δ (ppm): 0.84 (d, 8-$CH_3$), 1.03 (s, 3"-$CH_3$), 1.04 (t, 3-$OCOCH_2CH_3$), 1.04 (d, 6"-H), 1.09 (t, 4"-$OCOCH_2CH_3$), 1.19 (d, 6'-H), 1.74 (dd, 2"-Hax), 1.92 (d, 2"-Heq), 2.14 (s, $NCH_3$), 2.45 (s, 3'-$N(CH_3)_2$), 2.71 (m, quinoline-$CH_2$), 3.03 (s, $CH(OCH_3)_2$), 3.17 (s, $CH(OCH_3)_2$), 3.21 (m, 4'-H), 3.24 (m, 5'-H), 3.29 (br dd, 9-H), 3.52 (dd, 2'-H), 3.69 (s, 4-$OCH_3$), 3.74 (br d, 4-H), 3.87 (br d, 5-H), 4.05 (m, 14-H), 4.34 (dd, $CH(OCH_3)_2$), 4.36 (d, 1'-H), 4.39 (dq, 5"-H), 4.53 (d, 4"-H), 4.77 (br d, 3-H), 4.99 (d, 1"-H), 5.82 (br d, NH), 7.43 (ddd, quinoline), 7.57 (ddd, quinoline), 7.67 (br d, quinoline), 7.82 (d, quinoline), 7.98 (br d, quinoline), 8.66 (d, quinoline).

(b) In the same manner as in Example 2(d), 20.0 mg of the title compound was obtained from 41.1 mg of the compound of Example 33(a).

Physicochemical Properties of this Compound (1) Molecular formula: $C_{51}H_{80}N_4O_{14}$ (2) Mass spectrum (FAB): m/z 973 $(M+H)^+$ (3) Specific rotation: $[\alpha]_D^{22}$ −54° (c1.0, $CHCl_3$)

(4) $^1H$ NMR spectrum (300 MHz, $CDCl_3$) δ (ppm): 0.86 (d, 8-$CH_3$), 1.04 (s, 3"-$CH_3$), 1.06 (d, 6"-H), 1.09 (t, 3-$OCOCH_2CH_3$), 1.10 (t, 4"-$OCOCH_2CH_3$), 1.12 (d, 6'-H), 1.28 (m, 8-H), 1.33 (m, 13-H), 1.69 (m, quinoline-$CH_2CH_2$), 1.69 (m, 6-H), 1.76 (dd, 2"-Hax), 1.93 (d, 2"-Heq), 2.19 (s, $NCH_3$), 2.44 (s, 3'-$N(CH_3)_2$), 2.73 (m, quinoline-$CH_2$), 2.79 (dd, 2-H), 2.89 (dd, 6-$CH_2$), 3.20 (m, 4'-H), 3.21 (m, 5'-H), 3.37 (br dd, 9-H), 3.48 (dd, 2'-H), 3.69 (s, 4-$OCH_3$), 3.76 (br d, 4-H), 3.82 (br d, 5-H), 4.04 (m, 14-H), 4.34 (d, 1'-H), 4.39 (dq, 5"-H), 4.55 (d, 4"-H), 4.91 (br d, 3-H), 4.99 (d, 1"-H), 6.00 (br d, NH), 7.45 (ddd, quinoline), 7.58 (ddd, quinoline), 7.69 (br d, quinoline), 7.83 (d, quinoline), 8.00 (br d, quinoline), 8.68 (d, quinoline), 9.58 (s, CHO).

Example 34

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is 3-(quinolin-3-yl)propyl group, the other is hydrogen atom, $R_{4'}$ is hydrogen atom, and X is NH group In the same manner as in Example 2(d), 9.3 mg of the title compound was obtained from 41.1 mg of the compound of Example 33(a).

Physicochemical Properties of this Compound (1) Molecular formula: $C_{41}H_{64}N_4O_{10}$ (2) Mass spectrum (FAB): m/z 773 $(M+H)^+$ (3) Specific rotation: $[\alpha]_D^{22}$ −21° (c0.47, $CHCl_3$)

(4) $^1H$ NMR spectrum (300 MHz, $CDCl_3$) δ (ppm): 0.87 (d, 8-$CH_3$), 1.10 (t, 3-$OCOCH_2CH_3$), 1.18 (d, 6'-H), 1.29 (m, 8-H), 1.36 (m, 13-H), 1.70 (m, quinoline-$CH_2CH_2$), 1.78 (m, 13-H), 1.86 (br t, 6-H), 2.20 (s, $NCH_3$), 2.47 (s, 3'-$N(CH_3)_2$), 2.75 (m, quinoline-$CH_2$), 2.80 (dd, 2-H), 2.94 (dd, 6-$CH_2$), 2.98 (t, 4'-H), 3.23 (dq, 5'-H), 3.38 (br dd, 9-H), 3.47 (dd, 2'-H), 3.70 (s, 4-$OCH_3$), 3.76 (br d, 4-H), 3.83 (br d, 5-H), 4.05 (m, 14-H), 4.36 (d, 1'-H), 4.91 (br d, 3-H), 5.99 (br d, NH), 7.45 (ddd, quinoline), 7.59 (ddd, quinoline), 7.70 (br d, quinoline), 7.84 (d, quinoline), 8.00 (br d, quinoline), 8.68 (d, quinoline), 9.60 (s, CHO).

Example 35

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is 3-(quinolin-3-yl)propyl group, the other is hydrogen atom, $R_{4'}$ is a group represented by the formula (a), $R_{3''}$ is hydrogen atom, $R_{4''}$ is propionyl group, and X is NH group, provided that the substituents $R_9$ and $R_{10}$ are exchanged compared with the compound of Example 33

(a) In the same manner as in Example 24(a), 34.3 mg of a double bond-reduced compound (compound represented by the formula (22) mentioned in Preparation Scheme 7 wherein $R_1$ is propionyl group, $R_2$ is hydrogen atom, $R_3$ is methyl group, one of $R_9$ and $R_{10}$ is 3-(quinolin-3-yl)propyl group, the other is hydrogen atom, $R_{3''}$ is hydrogen atom, $R_{4''}$ is propionyl group, and X is NH group, provided that the substituents $R_9$ and $R_{10}$ are exchanged compared with the compound of Example 33(a)) was obtained from 40.2 mg of the compound of Example 32(b).

Physicochemical Properties of this Compound (1) Molecular formula: $C_{53}H_{86}N_4O_{15}$ (2) Mass spectrum (FAB): m/z 1019 $(M+H)^+$ (3) Specific rotation: $[\alpha]_D^{18}$ −56° (c0.43, $CHCl_3$)

(4) $^1H$ NMR spectrum (300 MHz, $CDCl_3$) δ (ppm): 0.13 (d, 8-$CH_3$), 0.34 (m, 7-H), 1.02 (t, 3-$OCOCH_2CH_3$), 1.07 (s, 3"-$CH_3$), 1.10 (d, 6"-H), 1.11 (t, 4"-$OCOCH_2CH_3$), 1.21 (d, 6'-H), 1.42 (m, 13-H), 1.78 (dd, 2"-Hax), 1.97 (d, 2"-Heq), 2.26 (s, $NCH_3$), 2.53 (s, 3'-$N(CH_3)_2$), 2.68 (br dd, quinoline-$CH_2$), 2.87 (br dd, quinoline-$CH_2$), 2.99 (s, $CH(OCH_3)_2$), 3.15 (br d, 4-H), 3.18 (s, $CH(OCH_3)_2$), 3.29 (m, 4'-H), 3.31 (m, 5'-H), 3.48 (m, 9-H), 3.68 (s, 4-$OCH_3$), 3.79 (dd, 2'-H), 3.83 (br d, 5-H), 4.03 (m, 14-H), 4.40 (dd, $CH(OCH_3)_2$), 4.47 (dq, 5"-H), 4.57 (d, 4"-H), 4.57 (d, 1'-H), 4.83 (m, 3-H), 5.06 (d, 1"-H), 7.47 (ddd, quinoline), 7.60 (ddd, quinoline), 7.73 (br d, quinoline), 7.86 (d, quinoline), 7.94 (br d, quinoline), 8.03 (br d, NH), 8.64 (d, quinoline).

(b) In the same manner as in Example 2(d), 7.8 mg of the title compound was obtained from 34.3 mg of the compound of Example 35(a).

Physicochemical Properties of this Compound (1) Molecular formula: $C_{51}H_{80}N_4O_{14}$ (2) Mass spectrum (FAB): m/z 973 $(M+H)^+$ (3) Specific rotation: $[\alpha]_D^{6}$-75° (c0.39, $CHCl_3$)

(4) $^1H$ NMR spectrum (300 MHz, $CDCl_3$) δ (ppm): 0.18 (d, 8-$CH_3$), 1.04 (s, 3"-$CH_3$), 1.06 (t, 3-$OCOCH_2CH_3$), 1.08 (d, 6"-H), 1.12 (d, 6'-H), 1.12 (t, 4"-$OCOCH_2CH_3$), 1.78 (dd, 2"-Hax), 1.97 (d, 2"-Heq), 2.89 (br d, 6-$CH_2$), 2.55 (s, 3'-$N(CH_3)_2$), 2.88 (m, quinoline-$CH_2$), 2.93 (dd, 6-$CH_2$), 3.26 (m, 4'-H), 3.26 (m, 5'-H), 3.52 (m, 9-H), 3.69 (s, 4-$OCH_3$), 3.79 (br d, 5-H), 4.02 (m, 14-H), 4.49 (dq, 5"-H), 4.50 (d, 1'-H), 4.57 (d, 4"-H), 4.88 (br d, 3-H), 5.05 (d, 1"-H), 7.48 (ddd, quinoline), 7.63 (ddd, quinoline), 7.74 (br d, quinoline), 7.87 (d, quinoline), 7.96 (br d, quinoline), 8.24 (br s, NH), 8.65 (d, quinoline), 9.54 (s, CHO).

Example 36

Preparation method of the compound represented by the formula (2) wherein $R_1$ is propionyl group, $R_2$ is hydrogen atom, $R_3$ is methyl group, $R_5$, $R_6$, $R_7$ and $R_8$ are hydrogen atoms, one of $R_9$ and $R_{10}$ is 3-(quinolin-3-yl)propyl group, the other is hydrogen atom, $R_{4'}$ is hydrogen atom, and X is NH group, provided that the substituents $R_9$ and $R_{10}$ are exchanged compared with the compound of Example 34

In the same manner as in Example 2(d), 15.3 mg of the title compound was obtained from 34.3 mg of the compound of Example 35(a).

Physicochemical Properties of this Compound (1) Molecular formula: $C_{41}H_{64}N_4O_{10}$ (2) Mass spectrum (FAB): m/z 773 $(M+H)^+$ (3) Specific rotation: $[\alpha]_D^{17}$-54° (c0.77, $CHCl_3$)

(4) $^1H$ NMR spectrum (300 MHz, $CDCl_3$) δ (ppm): 0.14 (d, 8-$CH_3$), 0.31 (m, 7-H), 1.06 (t, 3-$OCOCH_2CH_3$), 1.16 (d, 6'-H), 1.26 (m, 14-$CH_2$), 1.42 (m, 13-H), 1.78 (m, 13-H), 1.93 (m, 10-H), 2.01 (br d, 6-$CH_2$), 2.17 (br d, 10-H), 2.25 (s, $NCH_3$), 2.41 (t, 3'-H), 2.56 (s, 3'-$N(CH_3)_2$), 2.90 (br dd, quinoline-$CH_2$), 2.97 (dd, 6-$CH_2$), 3.00 (t, 4'-H), 3.12 (br d, 4-H), 3.27 (dq, 5'-H), 3.49 (m, 9-H), 3.68 (s, 4-$OCH_3$), 3.78 (dd, 2'-H), 3.81 (br d, 5-H), 4.03 (m, 14-H), 4.53 (d, 1'-H), 4.84 (br dd, 3-H), 7.48 (ddd, quinoline), 7.63 (ddd, quinoline), 7.74 (br d, quinoline), 7.87 (d, quinoline), 7.94 (br d, quinoline), 8.22 (br d, NH), 8.64 (d, quinoline), 9.55 (s, CHO).

Example 37

Preparation method of the compound represented by the formula (2) wherein $R_1$ is propionyl group, $R_2$ is hydrogen atom, $R_3$ is 3-(quinolin-4-yl)propyl group, $R_5$, $R_6$, $R_7$, $R_8$, $R_9$ and $R_{10}$ are hydrogen atoms, $R_{4'}$ is a group represented by the formula (a), $R_{3''}$ is hydrogen atom, $R_{4''}$ is propionyl group, and X is NH group (a) In the same manner as in Example 2(a), except that the compound of Reference Example 13 was used instead of the compound of Reference Example 1, 5.97 g of an azide compound (compound represented by the formula (20) mentioned in Preparation Scheme 7 wherein $R_3$ is 4-methoxybenzyl group, $R_9$, $R_{10}$ and $R_{3''}$ are hydrogen atoms, $R_{4''}$ is propionyl group, and X is azido group) was obtained from 6.16 g of the compound of Example 19.

Physicochemical Properties of this Compound (1) Molecular formula: $C_{52}H_{85}N_5O_{19}$ (2) Mass spectrum (FAB): m/z 1084 $(M+H)^+$ (3) Specific rotation: $[\alpha]_D^{23}$ −56° (c0.30, $CHCl_3$)

(4) $^1H$ NMR spectrum (300 MHz, $CDCl_3$) δ (ppm): 0.84 (d, 8-$CH_3$), 1.11 (s, 3"-$CH_3$), 1.12 (t, 3-$OCOCH_2CH_3$), 1.14 (d, 6"-H), 1.16 (t, 4"-$OCOCH_2CH_3$), 1.25 (d, 6'-H), 1.47 (m, 6-$CH_2$), 1.62 (m, 7-H), 1.83 (dd, 2"-Hax), 1.86 (m,$(CH_2)_3N_3$), 2.01 (d, 2"-Heq), 2.01 (s, 9-$OCOCH_3$), 2.04 (s, 2'-$OCOCH_3$), 2.39 (s, 3'-$N(CH_3)_2$), 2.70 (m, $(CH_2)_3N_3$), 3.19 (s, $CH(OCH_3)_2$), 3.25 (s, $CH(OCH_3)_2$), 3.30 (m, 4'-H), 3.33 (m, 5'-H), 3.47 (br d, 4-H), 3.49 (s, 4-$OCH_3$), 3.78 (s, $C_6H_4$—$OCH_3$), 3.79 (s, $C_6H_4CH_2$), 3.87 (br d, 5-H), 4.37 (dq, 5"-H), 4.52 (dd, $CH(OCH_3)_2$), 4.60 (d, 4"-H), 4.71 (d, 1'-H), 4.97 (dd, 2'-H), 5.05 (d, 1"-H), 5.13 (br d, 9-H), 5.14 (br dd, 3-H), 6.86 (d, $C_6H_4$), 7.29 (d, $C_6H_4$).

(b) In the same manner as in Example 4(b), 4.41 g of an azide-reduced compound (compound represented by the formula (20) mentioned in Preparation Scheme 7 wherein $R_3$ is 4-methoxybenzyl group, $R_9$, $R_{10}$ and $R_{3''}$ are hydrogen atoms, $R_{4''}$ is propionyl group, and X is amino group) was obtained from 5.93 g of the compound of Example 37(a).

Physicochemical Properties of this Compound (1) Molecular formula: $C_{52}H_{87}N_3O_{19}$ (2) Mass spectrum (FAB): m/z 1058 $(M+H)^+$ (3) Specific rotation: $[\alpha]_D^{25}$ −64° (c0.42, $CHCl_3$)

(4) $^1H$ NMR spectrum (300 MHz, $CDCl_3$) δ (ppm): 0.95 (d, 8-$CH_3$), 1.08 (t, 3-$OCOCH_2CH_3$), 1.11 (s, 3"-$CH_3$), 1.12 (d, 6"-H), 1.17 (t, 4"-$OCOCH_2CH_3$), 1.26 (d, 6'-H), 1.48 (m, 6-$CH_2$), 1.72 (m, 7-H), 1.83 (dd, 2"-Hax), 2.02 (d, 2"-Heq), 2.06 (s, 9-$OCOCH_3$), 2.21 (s, 2'-$OCOCH_3$), 2.40 (s, 3'-$N(CH_3)_2$), 2.71 (m, $(CH_2)_3$ $NH_2$), 3.08 (s, $CH(OCH_3)_2$), 3.10 (br d, 4-H), 3.24 (s, $CH(OCH_3)_2$), 3.32 (m, 4'-H), 3.35 (m, 5'-H), 3.64 (s, 4-$OCH_3$), 3.69 (d, $C_6H_4CH_2$), 3.78 (s, $C_6H_4$—$OCH_3$), 3.88 (d, $C_6H_4CH_2$), 4.00 (br d, 5-H), 4.38 (dq, 5"-H), 4.49 (dd, $CH(OCH_3)_2$), 4.61 (d, 4"-H), 4.81 (d, 1'-H), 5.01 (dd, 2'-H), 5.07 (d, 1"-H), 5.27 (br dd, 3-H), 5.44 (br d, 9-H), 6.82 (d, $C_6H_4$), 7.03 (d, $C_6H_4$).

(c) In the same manner as in Example 4(c), 3.13 g of a cyclized compound (compound represented by the formula (21) mentioned in Preparation Scheme 7 wherein $R_3$ is 4-methoxybenzyl group, $R_9$, $R_{10}$ and $R_{3''}$ are hydrogen atoms, $R_{4''}$ is propionyl group, and X is NH group) was obtained from 4.40 g of the compound of Example 37(b).

Physicochemical Properties of this Compound (1) Molecular formula: $C_{52}H_{85}N_3O_{18}$ (2) Mass spectrum (FAB): m/z 1040 $(M+H)^+$ (3) Specific rotation: $[\alpha]^{26}$ −90° (c0.40, $CHCl_3$)

(4) $^1H$ NMR spectrum (300 MHz, $CDCl_3$) δ (ppm): 0.81 (d, 8-$CH_3$), 1.11 (s, 3"-$CH_3$), 1.12 (t, 3-$OCOCH_2CH_3$), 1.13 (d, 6"-H), 1.16 (t, 4"-$OCOCH_2CH_3$), 1.25 (d, 6'-H), 1.50 (m, 6-$CH_2$), 1.83 (dd, 2"-Hax), 1.98 (s, 9-$OCOCH_3$), 2.00 (d, 2"-Heq), 2.03 (s, 2'-$OCOCH_3$), 2.40 (s, 3'-$N(CH_3)_2$), 2.71 (t, 3'-H), 3.03 (s, $CH(OCH_3)_2$), 3.22 (s, $CH(OCH_3)_2$), 3.31 (m, 4'-H), 3.34 (m, 5'-H), 3.35 (br d, 4-H), 3.38 (d, $C_6H_4CH_2$), 3.56 (d, $C_6H_4CH_2$), 3.64 (s, 4-$OCH_3$), 3.78 (s, $C_6H_4$—$OCH_3$), 3.98 (br d, 5-H), 4.36 (dq, 5"-H), 4.50 (dd, $CH(OCH_3)_2$), 4.60 (d, 4"-H), 4.73 (d, 1'-H), 4.86 (br d, 9-H), 4.98 (dd, 2'-H), 5.04 (br dd, 3-H), 5.06 (d, 1"-H), 6.81 (d, $C_6H_4$), 6.96 (br d, NH), 7.18 (d, $C_6H_4$).

(d) In the same manner as in Example 8(d), 241 mg of an amine compound (compound represented by the formula (21) mentioned in Preparation Scheme 7 wherein $R_3$, $R_9$, $R_{10}$ and $R_{3''}$ are hydrogen atoms, $R_{4''}$ is propionyl group, and X is NH group) was obtained from 300 mg of the compound of Example 37(c).

Physicochemical Properties of this Compound (1) Molecular formula: $C_{44}H_{77}N_3O_{17}$ (2) Mass spectrum (FAB): m/z 920 $(M+H)^+$ (3) $^1$H NMR spectrum (300 MHz, $CDCl_3$) δ (ppm): 0.90 (d, 8-$CH_3$), 1.10 (s, 3"-$CH_3$), 1.12 (t, 3-$OCOCH_2CH_3$), 1.13 (d, 6"-H), 1.16 (t, 4"-$OCOCH_2CH_3$), 1.25 (d, 6'-H), 1.50 (m, 6-$CH_2$), 1.83 (dd, 2"-Hax), 2.01 (d, 2"-Heq), 2.04 (s, 9-$OCOCH_3$), 2.08 (s, 2'-$OCOCH_3$), 2.40 (s, 3'-$N(CH_3)_2$), 2.72 (t, 3'-H), 3.12 (s, $CH(OCH_3)_2$), 3.23 (s, $CH(OCH_3)_2$), 3.29 (dd, 4-H), 3.30 (m, 4'-H), 3.30 (m, 5'-H), 3.57 (s, 4-$OCH_3$), 3.92 (br d, 5-H), 4.36 (dq, 5"-H), 4.49 (dd, $CH(OCH_3)_2$), 4.60 (d, 4"-H), 4.69 (d, 1'-H), 4.98 (dd, 2'-H), 5.00 (br dd, 3-H), 5.05 (d, 1"-H), 7.92 (br d, NH).

(e) In the same manner as in Example 8(e), except that 3-(quinolin-4-yl)propionaldehyde was used instead of the 37% formaldehyde aqueous solution, 187 mg of an N-alkyl compound (compound represented by the formula (21) mentioned in Preparation Scheme 7 wherein $R_3$ is 3-(quinolin-4-yl)propyl group, $R_9$, $R_{10}$ and $R_{3''}$ are hydrogen atoms, $R_{4''}$ is propionyl group, and X is NH group) was obtained from 241 mg of the compound of Example 37(d).

Physicochemical Properties of this Compound (1) Molecular formula: $C_{56}H_{88}N_4O_{17}$ (2) Mass spectrum (FAB): m/z 1089 $(M+H)^+$ (3) Specific rotation: $[\alpha]_D^{26}$ −81° (c0.22, $CHCl_3$)

(4) $^1$H NMR spectrum (300 MHz, $CDCl_3$) δ (ppm): 0.90 (d, 8-$CH_3$), 1.11 (t, 3-$OCOCH_2CH_3$), 1.11 (s, 3"-$CH_3$), 1.13 (d, 6"-H), 1.17 (t, 4"-$OCOCH_2CH_3$), 1.26 (d, 6'-H), 1.54 (m, 6-$CH_2$), 1.83 (dd, 2"-Hax), 1.92 (s, 9-$OCOCH_3$), 2.01 (d, 2"-Heq), 2.04 (s, 2'-$OCOCH_3$), 2.40 (s, 3'-$N(CH_3)_2$), 2.72 (t, 3'-H), 3.03 (s, $CH(OCH_3)_2$), 3.23 (s, $CH(OCH_3)_2$), 3.32 (m, 4'-H), 3.35 (m, 5'-H), 3.39 (br d, 4-H), 3.66 (s, 4-$OCH_3$), 3.99 (br d, 5-H), 4.37 (dq, 5"-H), 4.51 (dd, $CH(OCH_3)_2$), 4.61 (d, 4"-H), 4.74 (d, 1'-H), 4.85 (br d, 9-H), 4.99 (dd, 2'-H), 5.02 (br dd, 3-H), 5.06 (d, 1"-H), 6.97 (br d, NH), 7.24 (d, quinoline), 7.55 (ddd, quinoline), 7.69 (ddd, quinoline), 8.04 (dd, quinoline), 8.10 (dd, quinoline), 8.79 (d, quinoline).

(f) In an amount of 90 mg of the compound of Example 37(e) was added with 6.3 ml of methanol, dissolved therein, stirred at 50° C. for 146 hours, and then stirred at room temperature for 70 hours. The reaction mixture was concentrated under reduced pressure, and the resulting residue was purified by preparative TLC (chloroform/methanol/aqueous ammonia (10:1:0.1)) to obtain 69 mg of a 2'-deacetylated compound (compound represented by the formula (22) mentioned in Preparation Scheme 7 wherein $R_1$ is propionyl group, $R_2$ is hydrogen atom, $R_3$ is 3-(quinolin-4-yl)propyl group, $R_9$, $R_{10}$ and $R_{3''}$ are hydrogen atoms, $R_{4''}$ is propionyl group, and X is NH group).

Physicochemical Properties of this Compound (1) Molecular formula: $C_{52}H_{84}N_4O_{15}$ (2) Mass spectrum (FAB): m/z 1005 $(M+H)^+$ (3) Specific rotation: $[\alpha]_D^{21}$ −53° (c0.50, $CHCl_3$)

(4) $^1$H NMR spectrum (300 MHz, $CDCl_3$) δ (ppm): 0.88 (d, 8-$CH_3$), 1.11 (s, 3"-$CH_3$), 1.12 (t, 3-$OCOCH_2CH_3$), 1.12 (d, 6"-H), 1.17 (t, 4"-$OCOCH_2CH_3$), 1.26 (d, 6'-H), 1.64 (m, 6-$CH_{26}$—$CH_2$), 1.83 (dd, 2"-Hax), 2.00 (d, 2"-Heq), 2.50 (s, 3'-$N(CH_3)_2$), 2.78 (dd, 2-H), 3.10 (s, $CH(OCH_3)_2$), 3.25 (s, $CH(OCH_3)_2$), 3.32 (m, 4'-H), 3.32 (m, 5'-H), 3.46 (br d, 9-H), 3.57 (dd, 2'-H), 3.59 (br d, 4-H), 3.75 (s, 4-$OCH_3$), 3.98 (br d, 5-H), 4.45 (dq, 5"-H), 4.48 (dd, $CH(OCH_3)_2$), 4.49 (d, 1'-H), 4.61 (d, 4"-H), 4.90 (br dd, 3-H), 5.07 (d, 1"-H), 6.48 (br d, NH), 7.23 (d, quinoline), 7.55 (ddd, quinoline), 7.70 (ddd, quinoline), 8.02 (dd, quinoline), 8.10 (dd, quinoline), 8.80 (d, quinoline).

(g) In the same manner as in Example 2(d), 28 mg of the title compound was obtained from 66 mg of the compound of Example 37(f).

Physicochemical Properties of this Compound (1) Molecular formula: $C_{50}H_{78}N_4O_{14}$ (2) Mass spectrum (FAB): m/z 959 $(M+H)^+$ (3) Specific rotation: $[\alpha]_D^{21}$ −78° (c0.50, $CHCl_3$)

(4) $^1$H NMR spectrum (300 MHz, $CDCl_3$) δ (ppm): 0.89 (d, 8-$CH_3$), 1.10 (s, 3"-$CH_3$), 1.12 (d, 6"-H), 1.16 (t, 3-$OCOCH_2CH_3$), 1.16 (t, 4"-$OCOCH_2CH_3$), 1.18 (d, 6'-H), 1.49 (br d, 8-H), 1.82 (dd, 2"-Hax), 1.91 (m, quinoline-$(CH_2)_3$), 2.00 (d, 2"-Heq), 2.50 (s, 3'-$N(CH_3)_2$), 2.64 (m, quinoline-$(CH_2)_3$), 2.97 (br dd, 6-$CH_2$), 3.08 (m, quinoline-$(CH_2)_3$), 3.27 (m, 4'-H), 3.28 (m, 5'-H), 3.48 (br d, 9-H), 3.52 (dd, 2'-H), 3.64 (dd, 4-H), 3.73 (s, 4-$OCH_3$), 3.91 (br d, 5-H), 4.44 (d, 1'-H), 4.45 (dq, 5"-H), 4.61 (d, 4"-H), 4.97 (br dd, 3-H), 5.06 (d, 1"-H), 6.63 (br d, NH), 7.23 (d, quinoline), 7.55 (ddd, quinoline), 7.69 (ddd, quinoline), 8.01 (dd, quinoline), 8.10 (dd, quinoline), 8.80 (d, quinoline), 9.64 (s, CHO).

Example 38

Preparation method of the compound represented by the formula (2) wherein $R_1$ is propionyl group, $R_2$ is hydrogen atom, $R_3$ is 3-(quinolin-4-yl)propyl group, $R_5$, $R_6$, $R_7$, $R_8$, $R_9$, $R_{10}$ and $R_{4'}$ are hydrogen atoms, X is NH group In the same manner as in Example 2(d), 12 mg of the title compound was obtained from 66 mg of the compound of Example 37(f).

Physicochemical Properties of this Compound (1) Molecular formula: $C_{40}H_{62}N_4O_{10}$ (2) Mass spectrum (FAB): m/z 759 $(M+H)^+$ (3) Specific rotation: $[\alpha]_D^{22}$ −48° (c0.35, $CHCl_3$)

(4) $^1$H NMR spectrum (300 MHz, $CDCl_3$) δ (ppm): 0.89 (d, 8-$CH_3$), 1.16 (t, 3-$OCOCH_2CH_3$), 1.23 (d, 6'-H), 1.50 (br d, 8-H), 1.92 (m, quinoline-$(CH_2)_3$), 2.51 (s, 3'-$N(CH_3)_2$), 2.63 (m, quinoline-$(CH_2)_3$), 3.02 (br dd, 6-$CH_2$), 3.08 (m, quinoline-$(CH_2)_3$), 3.29 (m, 5'-H), 3.47 (br d, 9-H), 3.51 (dd, 2'-H), 3.63 (dd, 4-H), 3.74 (s, 4-$OCH_3$), 3.92 (br d, 5-H), 4.46 (d, 1'-H), 4.97 (br dd, 3-H), 6.64 (br d, NH), 7.23 (d, quinoline), 7.55 (ddd, quinoline), 7.70 (ddd, quinoline), 8.01 (dd, quinoline), 8.10 (dd, quinoline), 8.79 (d, quinoline), 9.66 (s, CHO).

Example 39

Preparation method of the compound represented by the formula (2) wherein $R_1$ and $R_2$ are hydrogen atoms, $R_3$ is 3-(quinolin-4-yl)propyl group, $R_5$, $R_6$, $R_7$, $R_8$, $R_9$ and $R_{10}$ are hydrogen atoms, $R_{4'}$ is a group represented by the formula (a), $R_{3''}$ is hydrogen atom, $R_{4''}$ is propionyl group, and X is NH group (a) In an amount of 84 mg of the compound of Example 37(e) was added with 5.9 ml of methanol dissolved therein, and stirred at 50° C. for 88 hours, and then at 65° C. for 71 hours. The reaction mixture was concentrated under reduced pressure, and the resulting residue was purified by preparative TLC (chloroform/methanol/aqueous ammonia (5:1:0.1)) to obtain 13 mg of a 3,9,2'-deacylated compound (compound represented by the formula (22) mentioned in Preparation Scheme 7 wherein $R_1$ and $R_2$ are hydrogen atoms, $R_3$ is 3-(quinolin-4-yl)propyl group, $R_9$, $R_{10}$ and $R_{3''}$ are hydrogen atoms, $R_{4''}$ is propionyl group, and X is NH group), and 37 mg of a 3,9,2',4"-deacylated compound (compound represented by the formula (22) mentioned in Preparation Scheme 7 wherein $R_1$ and $R_2$ are hydrogen atoms, $R_3$ is 3-(quinolin-4-yl)propyl group, $R_9$, $R_{10}$, $R_{3''}$ and $R_{4''}$ are hydrogen atoms, and X is NH group).

Physicochemical Properties of the 3,9,2'-deacylated Compound (1) Molecular formula: $C_{49}H_{80}N_4O_{14}$ (2) Mass spectrum (FAB): m/z 949 $(M+H)^+$ (3) Specific rotation: $[\alpha]_D^{16}$ −84° (c0.25, $CHCl_3$)

(4) $^1H$ NMR spectrum (300 MHz, $CDCl_3$) δ (ppm): 0.88 (d, 8-$CH_3$), 1.10 (s, 3"-$CH_3$), 1.11 (d, 6"-H), 1.17 (t, 4"-$OCOCH_2CH_3$), 1.27 (d, 6'-H), 1.65 (m, 6-$CH_2$), 1.82 (dd, 2"-Hax), 1.99 (d, 2"-Heq), 2.49 (s, 3'-$N(CH_3)_2$), 3.09 (m, quinoline-$(CH_2)_3$), 3.26 (br d, 4-H), 3.28 (m, 4'-H), 3.30 (m, 5'-H), 3.30 (s, $CH(OCH_3)_2$), 3.32 (s, $CH(OCH_3)_2$), 3.45 (br d, 9-H), 3.59 (dd, 2'-H), 3.67 (s, 4-$OCH_3$), 3.94 (br d, 5-H), 3.94 (br dd, 3-H), 4.35 (d, 1'-H), 4.46 (dq, 5"-H), 4.51 (dd, $CH(OCH_3)_2$), 4.61 (d, 4"-H), 5.06 (d, 1"-H), 6.24 (br d, NH), 7.22 (d, quinoline), 7.56 (ddd, quinoline), 7.70 (ddd, quinoline), 8.01 (dd, quinoline), 8.10 (dd, quinoline), 8.79 (d, quinoline).

Physicochemical Properties of the 3,9,2',4"-deacylated Compound (1) Molecular formula: $C_{46}H_{76}N_4O_{13}$ (2) Mass spectrum (FAB): m/z 893 $(M+H)^+$ (3) Specific rotation: $[\alpha]_D^{17}$ −79° (c0.50, $CHCl_3$)

(4) $^1H$ NMR spectrum (300 MHz, $CDCl_3$) δ (ppm): 0.88 (d, 8-$CH_3$), 1.22 (s, 3"-$CH_3$), 1.27 (d, 6"-H), 1.28 (d, 6'-H), 1.60 (m, 6-$CH_2$), 1.74 (dd, 2"-Hax), 1.92 (m, quinoline-$(CH_2)_3$), 2.01 (d, 2"-Heq), 2.46 (s, 3'-$N(CH_3)_2$), 2.93 (d, 4"-H), 3.09 (m, quinoline-$(CH_2)_3$), 3.25 (br d, 4-H), 3.27 (m, 4'-H), 3.29 (s, $CH(OCH_3)_2$), 3.30 (m, 5'-H), 3.32 (s, $CH(OCH_3)_2$), 3.43 (br d, 9-H), 3.59 (dd, 2'-H), 3.66 (s, 4-$OCH_3$), 3.94 (br d, 5-H), 3.94 (br dd, 3-H), 4.06 (dq, 5"-H), 4.35 (d, 1'-H), 4.51 (dd, $CH(OCH_3)_2$), 5.07 (d, 1"-H), 6.25 (br d, NH), 7.22 (d, quinoline), 7.55 (ddd, quinoline), 7.70 (ddd, quinoline), 8.01 (dd, quinoline), 8.10 (dd, quinoline), 8.79 (d, quinoline).

(b) In the same manner as in Example 2(d), 6 mg of the title compound was obtained from 12 mg of the 3,9,2'-deacylated compound of Example 39(a).

Physicochemical Properties of this Compound (1) Molecular formula: $C_{47}H_{74}N_4O_{13}$ (2) Mass spectrum (FAB): m/z 903 $(M+H)^+$ (3) Specific rotation: $[\alpha]_D^{18}$ −96° (c0.30, $CHCl_3$)

(4) $^1H$ NMR spectrum (300 MHz, $CDCl_3$) δ (ppm): 0.88 (d, 8-$CH_3$), 1.11 (s, 3"-$CH_3$), 1.12 (d, 6"-H), 1.17 (t, 4"-$OCOCH_2CH_3$), 1.22 (d, 6'-H), 1.58 (m, 8-H), 1.82 (dd, 2"-Hax), 1.94 (m, quinoline-$(CH_2)_3$), 1.99 (d, 2"-Heq), 2.49 (s, 3'-$N(CH_3)_2$), 2.61 (m, quinoline-$(CH_2)_3$), 3.01 (dd, 6-$CH_2$), 3.08 (m, quinoline-$(CH_2)_3$), 3.27 (m, 4'-H), 3.28 (m, 5'-H), 3.42 (dd, 4-H), 3.43 (br d, 9-H), 3.54 (dd, 2'-H), 3.66 (s, 4-$OCH_3$), 3.79 (br d, 5-H), 4.06 (br dd, 3-H), 4.32 (d, 1'-H), 4.46 (dq, 5"-H), 4.61 (d, 4"-H), 5.06 (d, 1"-H), 6.40 (br d, NH), 7.23 (d, quinoline), 7.56 (ddd, quinoline), 7.70 (ddd, quinoline), 8.01 (dd, quinoline), 8.11 (dd, quinoline), 8.80 (d, quinoline), 9.74 (s, CHO).

Example 40

Preparation method of the compound represented by the formula (2) wherein $R_1$ and $R_2$ are hydrogen atoms, $R_3$ is 3-(quinolin-4-yl)propyl group, $R_5$, $R_6$, $R_7$, $R_8$, $R_9$ and $R_{10}$ are hydrogen atoms, $R_{4'}$ is a group represented by the formula (a), $R_{3''}$ and $R_{4''}$ are hydrogen atoms, and X is NH group In the same manner as in Example 2(d), 6 mg of the title compound was obtained from 36 mg of the 3,9,2',4"-deacylated compound of Example 39(a).

Physicochemical Properties of this Compound (1) Molecular formula: $C_{44}H_{70}N_4O_{12}$ (2) Mass spectrum (FAB): m/z 847 $(M+H)^+$ (3) Specific rotation: $[\alpha]_D^{21}$ −74° (c0.35, $CHCl_3$)

(4) $^1H$ NMR spectrum (300 MHz, $CDCl_3$) δ (ppm): 0.89 (d, 8-$CH_3$), 1.22 (s, 3"-$CH_3$), 1.24 (d, 6"-H), 1.28 (d, 6'-H), 1.59 (m, 8-H), 1.74 (dd, 2"-Hax), 1.93 (m, quinoline-$(CH_2)_3$), 2.02 (d, 2"-Heq), 2.47 (s, 3'-$N(CH_3)_2$), 2.65 (m, quinoline-$(CH_2)_3$), 2.93 (d, 4"-H), 2.98 (dd, 6-$CH_2$), 3.07 (m, quinoline-$(CH_2)_3$), 3.26 (m, 4'-H), 3.27 (m, 5'-H), 3.41 (dd, 4-H), 3.42 (br d, 9-H), 3.55 (dd, 2'-H), 3.66 (s, 4-$OCH_3$), 3.78 (br d, 5-H), 4.06 (dq, 5"-H), 4.06 (br dd, 3-H), 4.31 (d, 1'-H), 5.06 (d, 1"-H), 6.36 (br d, NH), 7.22 (d, quinoline), 7.56 (ddd, quinoline), 7.70 (ddd, quinoline), 8.01 (dd, quinoline), 8.11 (dd, quinoline), 8.80 (d, quinoline), 9.74 (s, CHO).

Example 41

Preparation method of the compound represented by the formula (2) wherein $R_1$ and $R_2$ are hydrogen atoms, $R_3$ is 3-(quinolin-4-yl)propyl group, $R_5$, $R_6$, $R_7$, $R_8$, $R_9$, $R_{10}$ and $R_{4'}$, are hydrogen atoms, and X is NH group In the same manner as in Example 2(d), 5 mg of the title compound was obtained from 36 mg of the 3,9,2',4"-deacylated compound of Example 39(a).

Physicochemical Properties of this Compound (1) Molecular formula: $C_{37}H_{58}N_4O_9$ (2) Mass spectrum (FAB): m/z 703 $(M+H)^+$ (3) Specific rotation: $[\alpha]_D^{23}$ −52° (c0.25, $CHCl_3$)

(4) $^1H$ NMR spectrum (300 MHz, $CDCl_3$) δ (ppm): 0.89 (d, 8-$CH_3$), 1.26 (d, 6'-H), 1.58 m, 8-H), 1.92 (m, quinoline-$(CH_2)_3$), 2.50 (s, 3'-$N(CH_3)_2$), 2.66 (m, quinoline-$(CH_2)_3$), 3.02 (t, 4'-H), 3.04 (dd, 6-$CH_2$), 3.06 (m, quinoline-$(CH_2)_3$), 3.28 (dq, 5'-H), 3.40 (dd, 4-H), 3.41 (br d, 9-H), 3.53 (dd, 2'-H), 3.66 (s, 4-$OCH_3$), 3.77 (br d, 5-H), 4.06 (br dd, 3-H), 4.32 (d, 1'-H), 6.34 (br d, NH), 7.23 (d, quinoline), 7.56 (ddd, quinoline), 7.70 (ddd, quinoline), 8.01 (dd, quinoline), 8.11 (dd, quinoline), 8.80 (d, quinoline), 9.75 (s, CHO).

Preparation Scheme 8
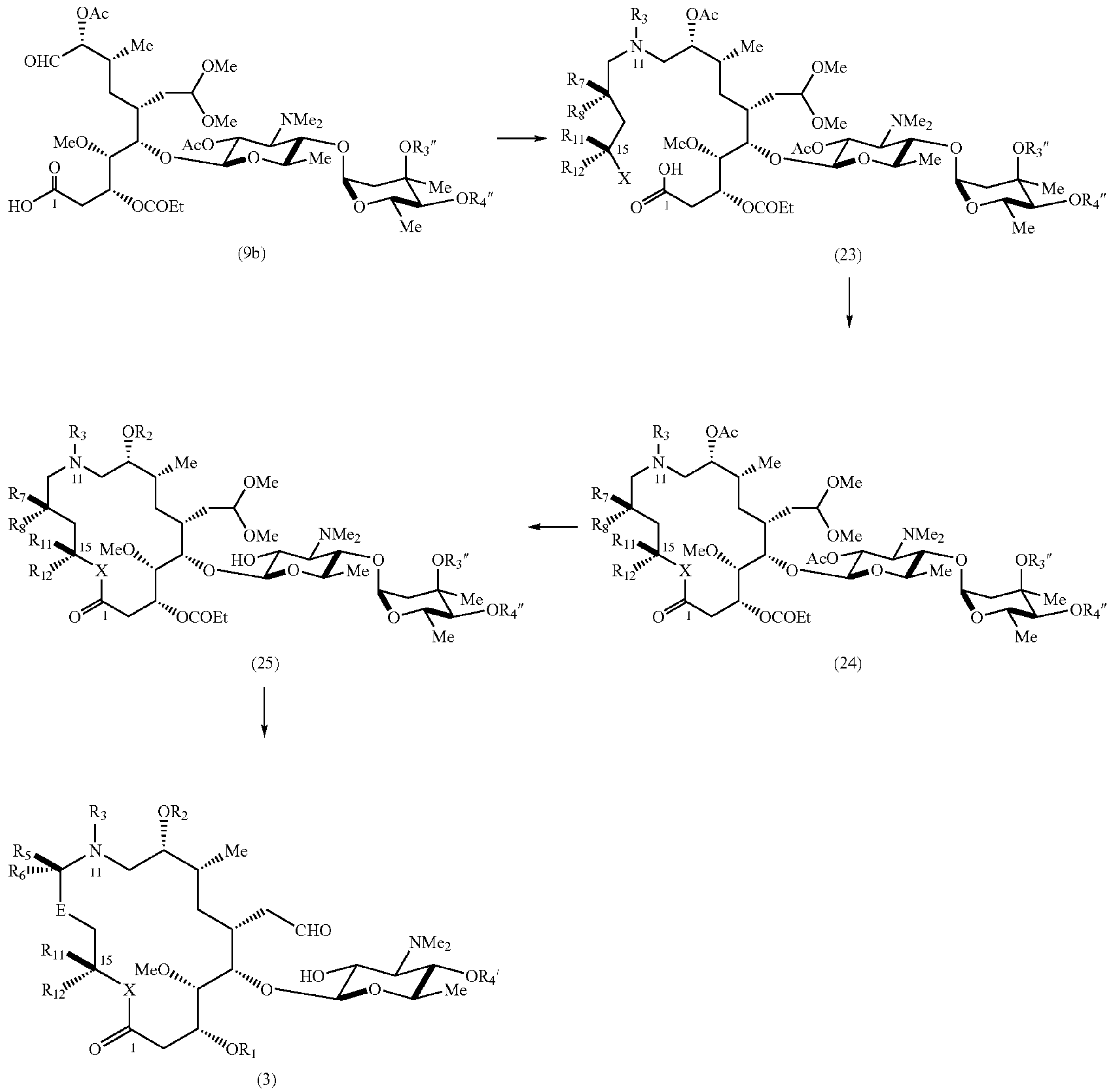
(9b)
(23)
(24)
(25)
(3)
Preparation Scheme 9
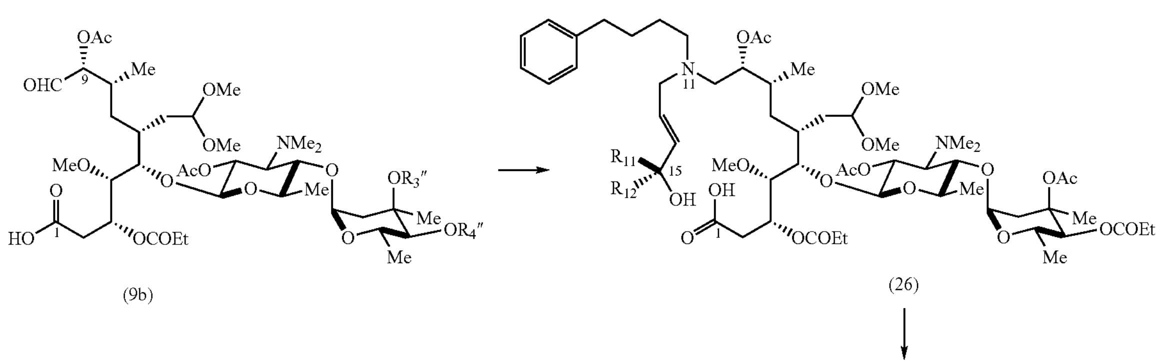
(9b)
(26)

-continued
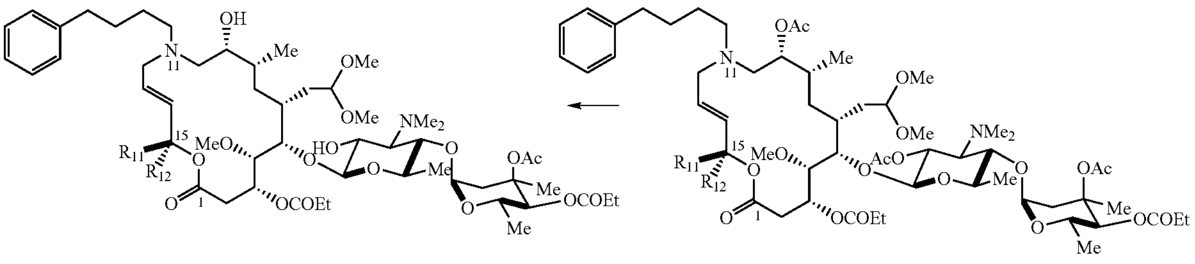
(28) (27)
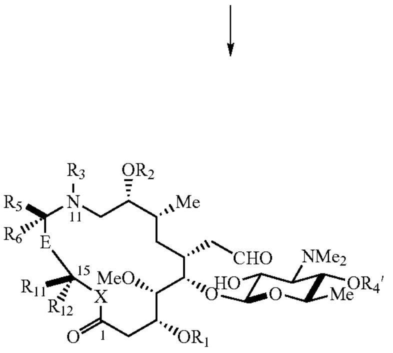
(3)
Preparation Scheme 10
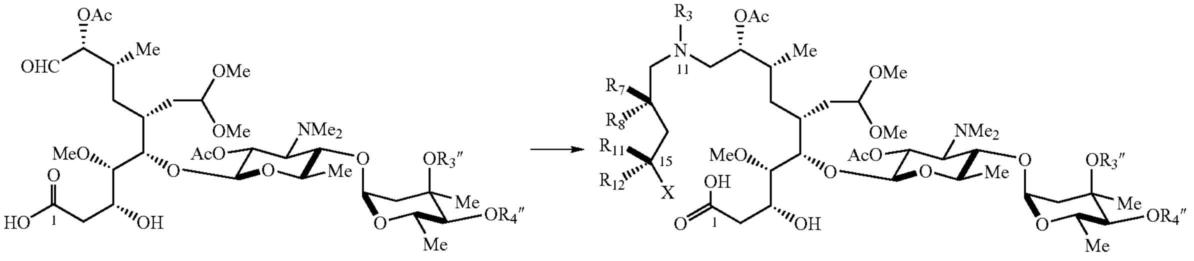
(29) (30)
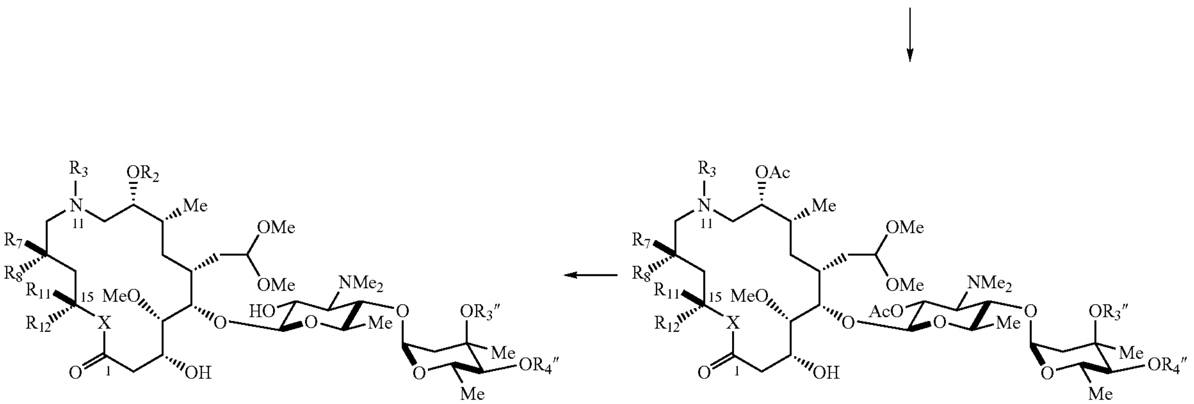
(32) (31)

-continued

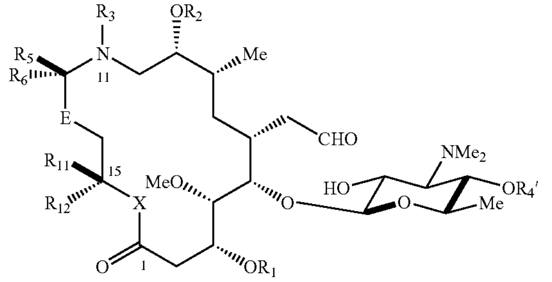

(3)

Example 42

Preparation method of the compound represented by the formula (3) wherein $R_1$ is propionyl group, $R_2$ is acetyl group, $R_3$ is 4-phenylbutyl group, $R_5$ and $R_6$ are hydrogen atoms, E is a group represented by the formula (b), $R_7$, $R_8$, $R_9$, $R_{10}$ and $R_{11}$ are hydrogen atoms, $R_{12}$ is methyl group, $R_{4'}$ is a group represented by the formula (a), $R_{3''}$ is acetyl group, $R_{4''}$ is propionyl group, and X is oxygen atom (a) In the same manner as in Example 2(a), except that the compound of Reference Example 14 was used instead of the compound of Reference Example 1, 534 mg of an amine compound (compound represented by the formula (23) mentioned in Preparation Scheme 8 wherein $R_3$ is 4-phenylbutyl group, $R_7$, $R_8$ and $R_{11}$ are hydrogen atoms, $R_{12}$ is methyl group, $R_{3''}$ is acetyl group, $R_{4''}$ is propionyl group, and X is hydroxyl group) was obtained from 645 mg of the compound of Example 1.

Physicochemical Properties of this Compound (1) Molecular formula: $C_{58}H_{96}N_2O_{20}$ (2) Mass spectrum (FAB): m/z 1141 $(M+H)^+$ (3) Specific rotation: $[\alpha]_D^{25}$ −54° (c0.31, $CHCl_3$)

(4) $^1H$ NMR spectrum (300 MHz, $CDCl_3$) δ (ppm): 0.88 (d, 8-$CH_3$), 1.07 (d, 6"-H), 1.14 (t, 3-$OCOCH_2CH_3$), 1.18 (d, 15-$CH_3$), 1.19 (t, 4"-$OCOCH_2CH_3$), 1.41 (s, 3"-$CH_3$), 1.68 (dd, 2"-Hax), 2.02 (s, 3"-$OCOCH_3$), 2.07 (s, 9-$OCOCH_3$), 2.15 (s, 2'-$OCOCH_3$), 2.43 (s, 3'-$N(CH_3)_2$), 2.62 (t, 3'-H), 2.78 (dd, 2-H), 3.12 (t, 4'-H), 3.17 (s, $CH(OCH_3)_2$), 3.19 (d, 2"-Heq), 3.24 (s, $CH(OCH_3)_2$), 3.59 (s, 4-$OCH_3$), 3.82 (br d, 5-H), 3.84 (m, 15-H), 3.39 (dd, $CH(OCH_3)_2$), 4.49 (dq, 5"-H), 4.57 (d, 4"-H), 4.70 (d, 1'-H), 4.80 (d, 1"-H), 4.94 (dd, 2'-H), 5.09 (m, 9-H), 5.17 (m, 3-H), 7.13-7.28 (m, $C_6H_5$).

(b) In the same manner as in Example 2(b), 21 mg of a cyclized compound (compound represented by the formula (24) mentioned in Preparation Scheme 8 wherein $R_3$ is 4-phenylbutyl group, $R_7$, $R_8$ and $R_{11}$ are hydrogen atoms, $R_{12}$ is methyl group, $R_{3''}$ is acetyl group, $R_{4''}$ is propionyl group, and X is oxygen atom) was obtained from 50 mg of the compound of Example 42(a).

Physicochemical Properties of this Compound (1) Molecular formula: $C_{58}H_{94}N_2O_{19}$ (2) Mass spectrum (FAB): m/z 1123 $(M+H)^+$ (3) Specific rotation: $[\alpha]_D^{21}$ −67° (c0.50, $CHCl_3$)

(4) $^1H$ NMR spectrum (300 MHz, $CDCl_3$) δ (ppm): 0.89 (d, 8-$CH_3$), 1.07 (d, 6"-H), 1.14 (t, 3-$OCOCH_2CH_3$), 1.18 (d, 6'-H), 1.19 (t, 4"-$OCOCH_2CH_3$), 1.23 (d, 15-$CH_3$), 1.36 (br dd, 7-H), 1.41 (s, 3"-$CH_3$), 1.67 (dd, 2"-Hax), 1.87 (br dd, 6-$CH_2$), 2.02 (s, 3"-$OCOCH_3$), 2.03 (s, 9-$OCOCH_3$), 2.05 (s, 2'-$OCOCH_3$), 2.43 (s, 3'-$N(CH_3)_2$), 2.80 (dd, 2-H), 3.13 (t, 4'-H), 3.15 (s, $CH(OCH_3)_2$), 3.19 (d, 2"-Heq), 3.24 (s, $CH(OCH_3)_2$), 3.33 (br d, 4-H), 3.52 (s, 4-$OCH_3$), 3.82 (br d, 5-H), 4.39 (dd, $CH(OCH_3)_2$), 4.48 (dq, 5"-H), 4.57 (d, 4"-H), 4.67 (d, 1'-H), 4.81 (d, 1"-H), 4.90 (m, 9-H), 4.90 (m, 15-H), 4.95 (dd, 2'-H), 5.32 (br t, 3-H), 7.13-7.32 (m, $C_6H_5$).

(c) In the same manner as in Example 2(c), 30 mg of 9-acetoxyazalide (compound represented by the formula (25) mentioned in Preparation Scheme 8 wherein $R_2$ is acetyl group, $R_3$ is 4-phenylbutyl group, $R_7$, $R_8$ and $R_{11}$ are hydrogen atoms, $R_{12}$ is methyl group, $R_3$ is acetyl group, $R_{4''}$ is propionyl group, and X is oxygen atom), and 34 mg of 9-hydroxyazalide (compound represented by the formula (25) mentioned in Preparation Scheme 8 wherein $R_2$ is hydrogen atom, $R_3$ is 4-phenylbutyl group, $R_7$, $R_8$ and $R_{11}$ are hydrogen atoms, $R_{12}$ is methyl group, $R_{3''}$ is acetyl group, $R_{4''}$ is propionyl group, and X is oxygen atom) were obtained from 113 mg of the compound of Example 42(b).

Physicochemical Properties of 9-acetoxyazalide (1) Molecular formula: $C_{56}H_{92}N_2O_{18}$ (2) Mass spectrum (FAB): m/z 1081 $(M+H)^+$ (3) Specific rotation: $[\alpha]_D^{22}$ −44° (c0.72, $CHCl_3$)

(4) $^1H$ NMR spectrum (300 MHz, $CDCl_3$) δ (ppm): 0.90 (d, 8-$CH_3$), 0.94 (m, 7-H), 1.09 (d, 6"-H), 1.14 (t, 3-$OCOCH_2CH_3$), 1.19 (t, 4"-$OCOCH_2CH_3$), 1.20 (d, 6'-H), 1.23 (d, 15-$CH_3$), 1.42 (s, 3"-$CH_3$), 1.69 (dd, 2"-Hax), 1.92 (br dd, 6-$CH_2$), 2.02 (s, 3"-$OCOCH_3$), 2.02 (s, 9-$OCOCH_3$), 2.54 (s, 3'-$N(CH_3)_2$), 2.61 (t, $C_6H_5(CH_2)_3$), 2.86 (dd, 2-H), 3.17 (s, $CH(OCH_3)_2$), 3.21 (d, 2"-Heq), 3.25 (s, $CH(OCH_3)_2$), 3.43 (br d, 4-H), 3.44 (dd, 2'-H), 3.59 (s, 4-$OCH_3$), 3.81 (br d, 5-H), 4.39 (dd, $CH(OCH_3)_2$), 4.42 (d, 1'-H), 4.53 (dq, 5"-H), 4.58 (d, 4"-H), 4.84 (d, 1"-H), 4.91 (m, 9-H), 4.91 (m, 15-H), 5.38 (br t, 3-H), 7.13-7.31 (m, $C_6H_5$).

Physicochemical Properties of 9-hydroxyazalide (1) Molecular formula: $C_{54}H_{90}N_2O_{17}$ (2) Mass spectrum (FAB): m/z 1039 $(M+H)^+$ (3) Specific rotation: $[\alpha]_D^{23}$ −43° (c1.1, $CHCl_3$)

(4) $^1H$ NMR spectrum (300 MHz, $CDCl_3$) δ (ppm): 0.85 (d, 8-$CH_3$), 1.09 (d, 6"-H), 1.11 (t, 3-$OCOCH_2CH_3$), 1.20 (t, 4"-$OCOCH_2CH_3$), 1.20 (d, 6'-H), 1.22 (d, 15-$CH_3$), 1.42 (s, 3"-$CH_3$), 1.69 (dd, 2"-Hax), 1.76 (m, 6-H), 1.91 (br dd, 6-$CH_2$), 2.02 (s, 3"-$OCOCH_3$), 2.28 (br d, 10-H), 2.39 (t, 3'-H), 2.54 (s, 3'-$N(CH_3)_2$), 3.10 (s, $CH(OCH_3)_2$), 3.19 (t, 4'-H), 3.21 (d, 2"-Heq), 3.25 (s, $CH(OCH_3)_2$), 3.46 (dd, 2'-H), 3.53 (br d, 4-H), 3.60 (s, 4-$OCH_3$), 3.77 (br dd, 9-H), 3.85 (br d, 5-H), 4.42 (dd, $CH(OCH_3)_2$), 4.47 (d, 1'-H), 4.54 (m, 5"-H), 4.58 (m, 4"-H), 4.79 (m, 15-H), 4.84 (d, 1"-H), 5.40 (m, 3-H), 7.14-7.32 (m, $C_6H_5$).

(d) In the same manner as in Example 2(d), 23 mg of the title compound was obtained from 29 mg of 9-acetoxyazalide of Example 42(c).

Physicochemical Properties of this Compound (1) Molecular formula: $C_{54}H_6N_2O_{17}$ (2) Mass spectrum (FAB): m/z 1035 $(M+H)^+$ (3) Specific rotation: $[\alpha]_D^{23}$ −43° (c0.54, $CHCl_3$)

(4) $^1H$ NMR spectrum (300 MHz, $CDCl_3$) δ (ppm): 0.89 (d, 8-$CH_3$), 1.04 (br dd, 7-H), 1.09 (d, 6"-H), 1.14 (d, 6'-H), 1.16 (t, 3-$OCOCH_2CH_3$), 1.19 (t, 4"-$OCOCH_2CH_3$), 1.24 (d, 15-$CH_3$), 1.42 (s, 3"-$CH_3$), 1.70 (dd, 2"-Hax), 1.98 (s, 9-$OCOCH_3$), 2.01 (s, 3"-$OCOCH_3$), 2.17 (m, 6-H), 2.26 (br d, 6-$CH_2$), 2.55 (s, 3'-$N(CH_3)_2$), 2.78 (dd, 2-H), 2.94 (dd, 6-$CH_2$), 3.22 (m, 4'-H), 3.22 (m, 5'-H), 3.22 (d, 2"-Heq), 3.34 (dd, 2'-H), 3.50 (dd, 4-H), 3.59 (s, 4-$OCH_3$), 3.85 (br d, 5-H), 4.42 (d, 1'-H), 4.51 (dq, 5"-H), 4.59 (d, 4"-H), 4.84 (m, 15-H), 4.85 (d, 1"-H), 4.95 (m, 9-H), 5.52 (m, 3-H), 7.16-7.27 (m, $C_6H_5$), 9.62 (s, CHO).

Example 43

Preparation method of the compound represented by the formula (3) wherein $R_1$ is propionyl group, $R_2$ is hydrogen atom, $R_3$ is 4-phenylbutyl group, $R_5$ and $R_6$ are hydrogen atoms, E is a group represented by the formula (b), $R_7$, $R_8$, $R_9$, $R_{10}$ and $R_{11}$ are hydrogen atoms, $R_{12}$ is methyl group, $R_{4'}$ is a group represented by the formula (a), $R_{3''}$ is acetyl group, $R_{4''}$ is propionyl group, and X is oxygen atom In the same manner as in Example 2(d), 29 mg of the title compound was obtained from 33 mg of 9-hydroxyazalide of Example 42(c).

Physicochemical Properties of this Compound (1) Molecular formula: $C_{52}H_{84}N_2O_{16}$ (2) Mass spectrum (FAB): m/z 993 $(M+H)^+$ (3) Specific rotation: $[\alpha]_D^{24}$ −48° (c0.64, $CHCl_3$)

(4) $^1H$ NMR spectrum (300 MHz, $CDCl_3$) δ (ppm): 0.85 (d, 8-$CH_3$), 1.04 (br dd, 7-H), 1.09 (d, 6"-H), 1.13 (d, 6'-H), 1.16 (t, 3-$OCOCH_2CH_3$), 1.19 (t, 4"-$OCOCH_2CH_3$), 1.23 (d, 15-$CH_3$), 1.31 (m, 8-H), 1.42 (s, 3"-$CH_3$), 1.69 (dd, 2"-Hax), 1.81 (br dd, 7-H), 2.01 (s, 3"-$OCOCH_3$), 2.15 (m, 6-H), 2.30 (br d, 6-$CH_2$), 2.55 (s, 3'-$N(CH_3)_2$), 2.94 (dd, 6-$CH_2$), 3.21 (m, 4'-H), 3.21 (m, 5'-H), 3.22 (d, 2"-Heq), 3.36 (dd, 2'-H), 3.57 (br d, 4-H), 3.60 (s, 4-$OCH_3$), 3.80 (br dd, 9-H), 3.87 (br d, 5-H), 4.42 (d, 1'-H), 4.52 (dq, 5"-H), 4.59 (d, 4"-H), 4.77 (m, 15-H), 4.85 (d, 1"-H), 5.54 (br dd, 3-H), 7.14-7.32 (m, $C_6H_5$), 9.63 (s, CHO).

Example 44

Preparation method of the compound represented by the formula (3) wherein $R_1$ is propionyl group, $R_2$ is hydrogen atom, $R_3$ is 4-phenylbutyl group, $R_5$ and $R_6$ are hydrogen atoms, E is a group represented by the formula (b), $R_7$, $R_8$, $R_9$, $R_{10}$ and $R_{11}$ are hydrogen atoms, $R_{12}$ is methyl group, $R_{4'}$ is a group represented by the formula (a), $R_{3''}$ is hydrogen atom, $R_{4''}$ is propionyl group, and X is oxygen atom (a) In the same manner as in Example 2(a), except that the compound of Reference Example 14 was used instead of the compound of Reference Example 1, 146 mg of an amine compound (compound represented by the formula (23) mentioned in Preparation Scheme 8 wherein $R_3$ is 4-phenylbutyl group, $R_7$, $R_8$ and $R_{11}$ are hydrogen atoms, $R_{12}$ is methyl group, $R_{3''}$ is hydrogen atom, $R_{4''}$ is propionyl group, and X is hydroxyl group) was obtained from 214 mg of the compound of Example 19.

Physicochemical Properties of this Compound (1) Molecular formula: $C_{56}H_{94}N_2O_{19}$ (2) Mass spectrum (FAB): m/z 1099 $(M+H)^+$ (3) Specific rotation: $[\alpha]_D^{26}$ −51° (c1.0, $CHCl_3$)

(4) $^1H$ NMR spectrum (300 MHz, $CDCl_3$) δ (ppm): 0.82 (d, 8-$CH_3$), 1.04 (s, 3"-$CH_3$), 1.05 (d, 6"-H), 1.07 (t, 3-$OCOCH_2CH_3$), 1.09 (t, 4"-$OCOCH_2CH_3$), 1.10 (d, 15-$CH_3$), 1.18 (d, 6'-H), 1.39 (br dd, 6-$CH_2$), 1.76 (dd, 2"-Hax), 1.94 (d, 2"-Heq), 1.99 (s, 9-$OCOCH_3$), 2.04 (s, 2'-$OCOCH_3$), 2.33 (s, 3'-$N(CH_3)_2$), 3.11 (s, $CH(OCH_3)_2$), 3.17 (s, $CH(OCH_3)_2$), 3.23 (m, 4'-H), 3.26 (m, 5'-H), 3.52 (s, 4-$OCH_3$), 3.68 (dq, 15-H), 3.75 (br d, 5-H), 4.32 (dq, 5"-H), 4.54 (d, 4"-H), 4.66 (d, 1'-H), 4.91 (dd, 2'-H), 4.99 (d, 1"-H), 5.11 (m, 3-H), 7.06-7.16 (m, $C_6H_5$), 7.17-7.25 (m, $C_6H_5$).

(b) In the same manner as in Example 2(b), 100 mg of a cyclized compound (compound represented by the formula (24) mentioned in Preparation Scheme 8 wherein $R_3$ is 4-phenylbutyl group, $R_7$, $R_8$ and $R_{11}$ are hydrogen atoms, $R_{12}$ is methyl group, $R_{3''}$ is hydrogen atom, $R_{4''}$ is propionyl group, and X is oxygen atom) was obtained from 376 mg of the compound of Example 44(a).

Physicochemical Properties of this Compound (1) Molecular formula: $C_{56}H_{92}N_2O_{18}$ (2) Mass spectrum (FAB): m/z 1081 $(M+H)^+$ (3) Specific rotation: $[\alpha]_D^{27}$ −54° (c0.53, $CHCl_3$)

(4) $^1H$ NMR spectrum (300 MHz, $CDCl_3$) δ (ppm): 0.82 (d, 8-$CH_3$), 1.05 (s, 3"-$CH_3$), 1.05 (d, 6"-H), 1.06 (t, 3-$OCOCH_2CH_3$), 1.11 (t, 4"-$OCOCH_2CH_3$), 1.15 (d, 15-$CH_3$), 1.19 (d, 6'-H), 1.77 (dd, 2"-Hax), 1.94 (d, 2"-Heq), 1.97 (s, 9-$OCOCH_3$), 1.97 (s, 2'-$OCOCH_3$), 2.33 (s, 3'-$N(CH_3)_2$), 2.65 (t, 3'-H), 2.72 (dd, 2-H), 3.07 (s, $CH(OCH_3)_2$), 3.17 (s, $CH(OCH_3)_2$), 3.18 (t, 4'-H), 3.44 (s, 4-$OCH_3$), 3.76 (br d, 5-H), 4.32 (dq, 5"-H), 4.55 (d, 4"-H), 4.63 (d, 1'-H), 4.82 (m, 15-H), 4.92 (dd, 2'-H), 5.00 (d, 1"-H), 5.26 (br dd, 3-H), 7.05-7.14 (m, $C_6H_5$), 7.16-7.24 (m, $C_6H_5$).

(c) In the same manner as in Example 2(c), 46 mg of a deacetyled compound (compound represented by the formula (25) mentioned in Preparation Scheme 8 wherein $R_2$ is hydrogen atom, $R_3$ is 4-phenylbutyl group, $R_7$, $R_8$ and $R_{11}$ are hydrogen atoms, $R_{12}$ is methyl group, $R_{3''}$ is hydrogen atom, $R_{4''}$ is propionyl group, and X is oxygen atom) was obtained from 100 mg of the compound of Example 44(b).

Physicochemical Properties of this Compound (1) Molecular formula: $C_{52}H_{88}N_2O_{16}$ (2) Mass spectrum (FAB): m/z 997 $(M+H)^+$ (3) Specific rotation: $[\alpha]_D^{25}$ −28° (c0.38, $CHCl_3$)

(4) $^1H$ NMR spectrum (300 MHz, $CDCl_3$) δ (ppm): 0.79 (d, 8-$CH_3$), 0.98 (br dd, 7-H), 1.04 (t, 3-$OCOCH_2CH_3$), 1.05 (s, 3"-$CH_3$), 1.06 (d, 6"-H), 1.11 (t, 4"-$OCOCH_2CH_3$), 1.15 (d, 15-$CH_3$), 1.21 (d, 6'-H), 1.35 (m, 8-H), 1.77 (dd, 2"-Hax), 1.84 (br dd, 6-$CH_2$), 1.94 (d, 2"-Heq), 2.44 (s, 3'-$N(CH_3)_2$), 3.06 (s, $CH(OCH_3)_2$), 3.19 (s, $CH(OCH_3)_2$), 3.23 (m, 4'-H), 3.23 (m, 5'-H), 3.45 (br d, 4-H), 3.51 (s, 4-$OCH_3$), 3.53 (dd, 2'-H), 3.69 (br d, 9-H), 3.81 (br d, 5-H), 4.33 (dd, $CH(OCH_3)_2$), 4.38 (d, 1'-H), 4.42 (dq, 5"-H), 4.55 (d, 4"-H), 4.73 (m, 15-H), 5.01 (d, 1"-H), 5.32 (br t, 3-H), 7.06-7.16 (m, $C_6H_5$), 7.17-7.28 (m, $C_6H_5$).

(d) In the same manner as in Example 2(d), 17 mg of the title compound was obtained from 46 mg of the compound of Example 44(c).

Physicochemical Properties of this Compound (1) Molecular formula: $C_{50}H_{82}N_2O_{15}$ (2) Mass spectrum (FAB): m/z 951 $(M+H)^+$ (3) Specific rotation: $[\alpha]_D^{26}$ −45° (c0.27, $CHCl_3$)

(4) $^1$H NMR spectrum (300 MHz, $CDCl_3$) δ (ppm): 0.79 (d, 8-$CH_3$), 0.95 (br dd, 7-H), 1.05 (s, 3"-$CH_3$), 1.06 (d, 6"-H), 1.09 (t, 3-$OCOCH_2CH_3$), 1.11 (t, 4"-$OCOCH_2CH_3$), 1.14 (d, 15-$CH_3$), 1.18 (d, 6'-H), 1.25 (m, 8-H), 1.78 (dd, 2"-Hax), 1.94 (d, 2"-Heq), 2.09 (br t, 6-H), 2.25 (br d, 6-$CH_2$), 2.44 (s, 3'-$N(CH_3)_2$), 2.61 (dd, 2-H), 2.84 (dd, 6-$CH_2$), 3.20 (m, 4'-H), 3.20 (m, 5'-H), 3.46 (dd, 2'-H), 3.50 (s, 4-$OCH_3$), 3.76 (br d, 9-H), 3.81 (br d, 5-H), 4.33 (d, 1'-H), 4.39 (dq, 5"-H), 4.55 (d, 4"-H), 4.72 (m, 15-H), 5.00 (d, 1"-H), 5.47 (br d, 3-H), 7.06-7.16 (m, $C_6H_5$), 7.16-7.26 (m, $C_6H_5$), 9.55 (s, CHO).

Example 45

Preparation method of the compound represented by the formula (3) wherein $R_1$ is propionyl group, $R_2$ is hydrogen atom, $R_3$ is 4-phenylbutyl group, $R_5$ and $R_6$ are hydrogen atoms, E is a group represented by the formula (b), $R_7$, $R_8$, $R_9$, $R_{10}$ and $R_{11}$ are hydrogen atoms, $R_{12}$ is methyl group, $R_{4'}$ is hydrogen atom, and X is oxygen atom In the same manner as in Example 2(d), 13 mg of the title compound was obtained from 46 mg of the compound of Example 44(c).

Physicochemical Properties of this Compound (1) Molecular formula: $C_{40}H_{66}N_2O_{11}$ (2) Mass spectrum (FAB): m/z 751 $(M+H)^+$ (3) Specific rotation: $[\alpha]_D^{26}$ −4.6° (c0.63, $CHCl_3$)

(4) $^1$H NMR spectrum (300 MHz, $CDCl_3$) δ (ppm): 0.78 (d, 8-$CH_3$), 0.96 (br dd, 7-H), 1.09 (t, 3-$OCOCH_2CH_3$), 1.16 (d, 15-$CH_3$), 1.17 (d, 6'-H), 1.26 (m, 8-H), 1.73 (br dd, 7-H), 2.17 (m, 6-H), 2.28 (t, 3'-H), 2.43 (s, 3'-$N(CH_3)_2$), 2.89 (dd, 6-$CH_2$), 2.95 (t, 4'-H), 3.22 (dq, 5'-H), 3.45 (dd, 2'-H), 3.49 (br d, 4-H), 3.51 (s, 4-$OCH_3$), 3.75 (br dd, 9-H), 3.83 (br d, 5-H), 4.34 (d, 1'-H), 4.71 (ddq, 15-H), 5.47 (br d, 3-H), 7.06-7.16 (m, $C_6H_5$), 7.17-7.25 (m, $C_6H_5$), 9.57 (s, CHO).

Example 46

Preparation method of the compound represented by the formula (3) wherein $R_1$ is propionyl group, $R_2$ is hydrogen atom, $R_3$ is 4-phenylbutyl group, $R_5$ and $R_6$ are hydrogen atoms, E is a group represented by the formula (c), one of $R_{11}$ and $R_{12}$ is methyl group, the other is hydrogen atom, $R_{4'}$ is a group represented by the formula (a), $R_{3''}$ is acetyl group, $R_{4''}$ is propionyl group, and X is oxygen atom (a) In the same manner as in Example 2(a), except that the compound of Reference Example 15 was used instead of the compound of Reference Example 1, 117 mg of an amine compound (compound represented by the formula (26) mentioned in Preparation Scheme 9 wherein one of $R_{11}$ or $R_{12}$ is methyl group, and the other is hydrogen atom) was obtained as an about 1:1 mixture (measured according to intensities of specific signals) from 360 mg of the compound of Example 1.

Physicochemical Properties of this Compound (1) Molecular formula: $C_{58}H_{94}N_2O_{20}$ (2) Mass spectrum (FAB): m/z 1139 $(M+H)^+$ (3) $^1$H NMR spectrum (300 MHz, $CDCl_3$) δ (ppm): 0.86 and 0.92 (each d, 8-$CH_3$), 1.07 (d, 6"-H), 1.14 and 1.15 (each t, 3-$OCOCH_2CH_3$), 1.19 (d, 6'-H), 1.19 (t, 4"-$OCOCH_2CH_3$), 1.24 (d, 15-$CH_3$), 1.41 (s, 3"-$CH_3$), 1.67 (dd, 2"-Hax), 1.89 (m, 6-$CH_2$), 2.42 and 2.43 (each s, 3'-$N(CH_3)_2$), 3.21 and 3.22 (each s, $CH(OCH_3)_2$), 3.24 and 3.26 (each s, $CH(OCH_3)_2$), 3.55 and 3.58 (each s, 4-$OCH_3$), 3.81 and 3.88 (each br d, 5-H), 4.31 (m, $CH(CH_3)OH$), 4.56 (d, 4"-H), 4.70 (d, 1'-H), 4.80 (d, 1"-H), 4.94 (dd, 2'-H), 5.82 (m, CH═CH), 7.13-7.32 (m, $C_6H_5$).

(b) In the same manner as in Example 2(b), 13.5 mg of an isomer A (compound represented by the formula (27) mentioned in Preparation Scheme 9 wherein one of $R_{11}$ and $R_{12}$ is methyl group, and the other is hydrogen atom), and 15.4 mg of an isomer B (compound represented by the formula (27) mentioned in Preparation Scheme 9 wherein one of $R_{11}$ and $R_{12}$ is methyl group, and the other is hydrogen atom, provided that the substituents $R_{11}$ and $R_{12}$ are exchanged compared with the isomer A) were obtained from 111 mg of the compound of Example 46(a).

Physicochemical Properties of the Isomer A (1) Molecular formula: $C_{58}H_{92}N_2O_{19}$ (2) Mass spectrum (FAB): m/z 1121 $(M+H)^+$ (3) Specific rotation: $[\alpha]_D^{25}$ −64° (c0.31, $CHCl_3$)

(4) $^1$H NMR spectrum (300 MHz, $CDCl_3$) δ (ppm): 0.91 (d, 8-$CH_3$), 1.07 (d, 6"-H), 1.16 (t, 3-$OCOCH_2CH_3$), 1.19 (t, 4"-$OCOCH_2CH_3$), 1.20 (d, 6'-H), 1.33 (d, 15-$CH_3$), 1.42 (s, 3"-$CH_3$), 1.67 (dd, 2"-Hax), 1.87 (br dd, 6-$CH_2$), 2.02 (s, 3"-$OCOCH_3$), 2.02 (s, 9-$OCOCH_3$), 2.05 (s, 2'-$OCOCH_3$), 2.44 (s, 3'-$N(CH_3)_2$), 2.78 (dd, 2-H), 3.14 (s, $CH(OCH_3)_2$), 3.19 (d, 2"-Heq), 3.24 (s, $CH(OCH_3)_2$), 3.55 (s, 4-$OCH_3$), 3.86 (br d, 5-H), 4.45 (dd, $CH(OCH_3)_2$), 4.49 (dq, 5"-H), 4.57 (d, 4"-H), 4.68 (d, 1'-H), 4.81 (d, 1"-H), 4.98 (dd, 2'-H), 5.06 (br d, 9-H), 5.17 (m, 3-H), 5.28 (dq, 15-H), 5.49 (dd, 14-H), 5.87 (m, 13-H, 7.13-7.31 (m, $C_6H_5$).

Physicochemical Properties of the Isomer (B)

(1) Molecular formula: $C_{58}H_{92}N_2O_{19}$ (2) Mass spectrum (FAB): m/z 1121 $(M+H)^+$ (3) Specific rotation: $[\alpha]_D^{25}$ −55° (c0.31, $CHCl_3$)

(4) $^1$H NMR spectrum (300 MHz, $CDCl_3$) δ (ppm): 0.89 (d, 8-$CH_3$), 1.07 (d, 6"-H), 1.14 (t, 3-$OCOCH_2CH_3$), 1.19 (d, 6'-H), 1.19 (t, 4"-$OCOCH_2CH_3$), 1.37 (d, 15-$CH_3$), 1.41 (s, 3"-$CH_3$), 1.67 (dd, 2"-Hax), 1.82 (br dd, 6-$CH_2$), 2.02 (s, 3"-$OCOCH_3$), 2.06 (s, 9-$OCOCH_3$), 2.08 (s, 2'-$OCOCH_3$), 2.43 (s, 3'-$N(CH_3)_2$), 2.86 (dd, 2-H), 2.98 (m, 12-H), 3.13 (s, $CH(OCH_3)_2$), 3.19 (d, 2"-Heq), 3.23 (s, $CH(OCH_3)_2$), 3.32 (br d, 4-H), 3.55 (s, 4-$OCH_3$), 3.88 (br d, 5-H), 4.43 (dd, $CH(OCH_3)_2$), 4.51 (dq, 5"-H), 4.57 (d, 4"-H), 4.67 (d, 1'-H), 4.80 (d, 1"-H), 4.96 (dd, 2'-H), 5.02 (m, 9-H), 5.15 (m, 3-H), 5.33 (dq, 15-H), 5.58 (dd, 14-H), 5.84 (m, 13-H), 7.15-7.29 (m, $C_6H_5$).

(c) In the same manner as in Example 2(c), 12 mg of a deacetyled compound (compound represented by the formula (28) mentioned in Preparation Scheme 9 wherein one of $R_{11}$ and $R_{12}$ is methyl group, and the other is hydrogen atom) was obtained from 113 mg of the isomer A of Example 46(b).

Physicochemical Properties of this Compound (1) Molecular formula: $C_{54}H_{88}N_2O_{17}$ (2) Mass spectrum (FAB): m/z 1037 $(M+H)^+$ (3) $^1$H NMR spectrum (300 MHz, $CDCl_3$) δ (ppm): 0.86 (d, 8-$CH_3$), 1.09 (d, 6"-H), 1.13 (t, 3-$OCOCH_2CH_3$), 1.20 (d, 6'-H), 1.20 (t, 4"-$OCOCH_2CH_3$), 1.32 (d, 15-$CH_3$), 1.42 (s, 3"-$CH_3$), 1.68 (dd, 2"-Hax), 1.91 (m, 6-$CH_2$), 2.02 (s, 3"-$OCOCH_3$), 2.54 (s, 3'-$N(CH_3)_2$), 2.66 (dd, 2-H), 2.83 (dd, 2-H), 3.18 (s, $CH(OCH_3)_2$), 3.25 (s, $CH(OCH_3)_2$), 3.35 (m, 9-H), 3.50 (dd, 2'-H), 3.52 (br d, 4-H), 3.59 (s, 4-$OCH_3$), 3.90 (br d, 5-H), 4.49 (d, 1'-H), 4.57 (d, 4"-H), 4.57 (dq, 5"-H), 4.84 (d, 1"-H), 5.26 (dq, 15-H), 5.30 (m, 3-H), 5.62 (dd, 14-H), 5.80 (m, 13-H), 7.14-7.28 (m, $C_6H_5$).

(d) In the same manner as in Example 2(d), 8.1 mg of the title compound was obtained from 12 mg of the compound of Example 46(c).

Physicochemical Properties of this Compound (1) Molecular formula: $C_{52}H_{82}N_2O_{16}$ (2) Mass spectrum (FAB): m/z 991 $(M+H)^+$ (3) Specific rotation: $[\alpha]_D^{23}$ −60° (c0.35, $CHCl_3$)

(4) $^1$H NMR spectrum (300 MHz, $CDCl_3$) δ (ppm): 0.87 (d, 8-$CH_3$), 1.09 (d, 6"-H), 1.14 (d, 6'-H), 1.16 (t, 3-$OCOCH_2CH_3$), 1.19 (t, 4"-$OCOCH_2CH_3$), 1.34 (d, 15-$CH_3$), 1.42 (s, 3"-$CH_3$), 1.48 (m, 8-H), 1.69 (dd, 2"-Hax), 2.01 (s, 3"-$OCOCH_3$), 2.55 (s, 3'-$N(CH_3)_2$), 2.66 (dd, 2-H), 2.79 (dd, 2-H), 2.96 (dd, 6-$CH_2$), 3.11 (m, 12-H), 3.21 (m, 4'-H), 3.21 (m, 5'-H), 3.22 (d, 2"-Heq), 3.40 (m, 9-H), 3.40 (dd, 2'-H), 3.55 (dd, 4-H), 3.59 (s, 4-$OCH_3$), 3.93 (br d, 5-H), 4.44 (d, 1'-H), 4.54 (dq, 5"-H), 4.59 (d, 4"-H), 4.85 (d, 1"-H), 5.27 (dq, 15-H), 5.39 (br d, 3-H), 5.64 (dd, 14-H), 5.84 (m, 13-H), 7.14-7.31 (m, $C_6H_5$), 9.64 (s, CHO).

Example 47

Preparation method of the compound represented by the formula (3) wherein $R_1$ is propionyl group, $R_2$ is hydrogen atom, $R_3$ is 4-phenylbutyl group, $R_5$ and $R_6$ are hydrogen atoms, E is a group represented by the formula (c), one of $R_{11}$ and $R_{12}$ is methyl group, the other is hydrogen atom, $R_{4'}$ is a group represented by the formula (a), $R_{3''}$ is acetyl group, $R_{4''}$ is propionyl group, and X is oxygen atom, provided that the substituents $R_{11}$ and $R_{12}$ are exchanged compared with the compound of Example (a) In the same manner as in Example 2(c), 14 mg of a deacetyled compound (compound represented by the formula (28) mentioned in Preparation Scheme 9 wherein one of $R_{11}$ and $R_{12}$ is methyl group, the other is hydrogen atom, provided that the substituents $R_{11}$ and $R_{12}$ are exchanged compared with the compound of Example 46 (c)) was obtained from 15 mg of the isomer B of Example 46(b).

Physicochemical Properties of this Compound (1) Molecular formula: $C_{54}H_{88}N_2O_{17}$ (2) Mass spectrum (FAB): m/z 1037 $(M+H)^+$ (3) $^1$H NMR spectrum (300 MHz, $CDCl_3$) δ (ppm): 1.01 (d, 8-$CH_3$), 1.09 (d, 6"-H), 1.14 (t, 3-$OCOCH_2CH_3$), 1.20 (t, 4"-$OCOCH_2CH_3$), 1.21 (d, 6'-H), 1.32 (d, 15-$CH_3$), 1.42 (s, 3"-$CH_3$), 1.69 (dd, 2"-Hax), 1.94 (m, 6-$CH_2$), 2.02 (s, 3"-$OCOCH_3$), 2.55 (s, 3'-$N(CH_3)_2$), 2.77 (dd, 2-H), 2.82 (dd, 12-H), 3.16 (s, $CH(OCH_3)_2$), 3.25 (s, $CH(OCH_3)_2$), 3.43 (dd, 2'-H), 3.59 (s, 4-$OCH_3$), 3.88 (br d, 5-H), 4.46 (d, 1'-H), 4.54 (dq, 5"-H), 4.59 (d, 4"-H), 4.85 (d, 1"-H), 5.24 (dq, 15-H), 5.27 (m, 3-H), 5.45 (dd, 14-H), 5.86 (m, 13-H), 7.14-7.32 (m, $C_6H_5$).

(b) In the same manner as in Example 2(d), 8.6 mg of the title compound was obtained from 14 mg of the compound of Example 47(a).

Physicochemical Properties of this Compound (1) Molecular formula: $C_{52}H_{82}N_2O_{16}$ (2) Mass spectrum (FAB): m/z 991 $(M+H)^+$ (3) Specific rotation: $[\alpha]_D^{23}$ −37° (c0.39, $CHCl_3$)

(4) $^1$H NMR spectrum (300 MHz, $CDCl_3$) δ (ppm): 0.86 (m, 7-H), 0.97 (d, 8-$CH_3$), 1.09 (d, 6"-H), 1.13 (d, 6'-H), 1.18 (t, 3-$OCOCH_2CH_3$), 1.19 (t, 4"-$OCOCH_2CH_3$), 1.33 (d, 15-$CH_3$), 1.42 (s, 3"-$CH_3$), 1.43 (m, 8-H), 1.55 (m, 7-H), 1.70 (dd, 2"-Hax), 2.01 (s, 3"-$OCOCH_3$), 2.05 (m, 6-H), 2.29 (dd, 6-$CH_2$), 2.55 (s, 3'-$N(CH_3)_2$), 2.80 (dd, 2-H), 2.87 (br dd, 12-H), 3.01 (dd, 6-$CH_2$), 3.21 (m, 5'-H), 3.22 (d, 2"-Heq), 3.23 (m, 4'-H), 3.33 (dd, 2'-H), 3.39 (dd, 4-H), 3.59 (s, 4-$OCH_3$), 3.91 (br d, 5-H), 4.40 (d, 1'-H), 4.52 (dq, 5"-H), 4.59 (d, 4"-H), 4.86 (d, 1"-H), 5.25 (dq, 15-H), 5.39 (br dd, 3-H), 5.49 (dd, 14-H), 5.86 (m, 13-H), 7.16-7.31 (m, $C_6H_5$), 9.62 (s, CHO).

Example 48

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(quinolin-4-yl)-2-propenyl group, $R_{4'}$ is a group represented by the formula (a), $R_{3''}$ is hydrogen atom, $R_{4''}$ is propionyl group, and X is oxygen atom (a) In the same manner as in Example 2(a), except that the compound of Reference Example 16 was used instead of the compound of Reference Example 1, 77 mg of an amine compound (compound represented by the formula (23) mentioned in Preparation Scheme 8 wherein $R_3$ is methyl group, $R_7$ and $R_8$ are hydrogen atoms, one of $R_{11}$ and $R_{12}$ is allyl group, the other is hydrogen atom, $R_{3''}$ is hydrogen atom, $R_{4''}$ is propionyl group, and X is hydroxyl group) was obtained as an about 1:1 mixture (measured according to intensities of specific signals) from 102 mg of the compound of Example 19.

Physicochemical Properties of this Compound (1) Molecular formula: $C_{49}H_{86}N_2O_{19}$ (1) Mass spectrum (FAB): m/z 1007 $(M+H)^+$ (b) In an amount of 374 mg of 2-methyl-6-nitrobenzoic anhydride (Tetrahedron Lett., 43, 7535-7539 (2002)) and 266 mg of 4-dimethylaminopyridine were dissolved in 200 ml of methylene chloride, added dropwise with a solution of 730 mg of the compound of Example 48(a) in methylene chloride (200 ml) over 2.5 hours under ice cooling, and then stirred for 2 hours. The reaction mixture was added with saturated aqueous ammonium chloride, and extracted with chloroform, and the organic layer was dried over anhydrous magnesium sulfate, and then filtered. The filtrate was concentrated under reduced pressure, and the resulting residue was purified by silica gel column chromatography (diethyl ether/acetone/aqueous ammonia (100:5:0.1)) to obtain 339 mg of an isomer A (compound represented by the formula (24) mentioned in Preparation Scheme 8 wherein $R_3$ is methyl group, $R_7$, $R_8$ and $R_{12}$ are hydrogen atoms, $R_{11}$ is allyl group, $R_{3''}$ is hydrogen atom, $R_{4''}$ is propionyl group, and X is oxygen atom), and 149 mg of an isomer B (compound represented by the formula (24) mentioned in Preparation Scheme 8 wherein $R_3$ is methyl group, $R_7$, $R_8$ and $R_{11}$ are hydrogen atoms, $R_{12}$ is allyl group, $R_{3''}$ is hydrogen atom, $R_{4''}$ is propionyl group, and X is oxygen atom). Physicochemical properties of the isomer A (1) Molecular formula: $C_{49}H_{84}N_2O_{18}$ (2) Mass spectrum (FAB): m/z 989 $(M+H)^+$ (3) Specific rotation: $[\alpha]_D^{15}$ −47° (c1.98, $CHCl_3$)

(4) $^1$H NMR spectrum (300 MHz, $CDCl_3$) δ (ppm): 0.91 (d, 8-$CH_3$), 1.11 (s, 3"-$CH_3$), 1.12 (d, 6"-H), 1.13 (t, 3-$OCOCH_2CH_3$), 1.17 (t, 4"-$OCOCH_2CH_3$), 1.27 (d, 6'-H), 1.83 (dd, 2"-Hax), 2.01 (d, 2"-Heq), 2.04 (s, 9-$OCOCH_3$), 2.04 (s, 2'-$OCOCH_3$), 2.21 (s, $NCH_3$), 2.25 (m, 15-$CH_2$), 2.37 (m, 10-H), 2.40 (s, 3'-$N(CH_3)_2$), 2.57 (dd, 2-H), 2.72 (t, 3'-H), 2.86 (dd, 2-H), 3.14 (s, $CH(OCH_3)_2$), 3.25 (s, $CH(OCH_3)_2$), 3.29 (m, 4'-H), 3.31 (m, 5'-H), 3.61 (s, 4-$OCH_3$), 3.66 (br d, 4-H), 3.93 (br d, 5-H), 4.28 (s, 3"-OH), 4.38 ((dq, 5"-H), 4.55 (dd, $CH(OCH_3)_2$), 4.61 (d, 4"-H), 4.73 (d, 1'-H), 4.90 (m, 9-H), 4.97 (dd, 2"-H), 4.99 (br dd, 3-H), 4.99 (m, 15-H), 5.01 (d, 1"-H), 5.02 (d, $CH{=}CH_2$), 5.71 (m, $CH{=}CH_2$).

Physicochemical Properties of the Isomer B (1) Molecular formula: $C_{49}H_{84}N_2O_{18}$ (2) Mass spectrum (FAB): m/z 989 $(M+H)^+$ (3) Specific rotation: $[\alpha]_D^{17}$ −58° (c3.31, $CHCl_3$)

(4) $^1$H NMR spectrum (300 MHz, $CDCl_3$) δ (ppm): 0.94 (d, 8-$CH_3$), 1.10 (s, 3"-$CH_3$), 1.11 (d, 6"-H), 1.12 (t, 3-$OCOCH_2CH_3$), 1.16 (t, 4"-$OCOCH_2CH_3$), 1.26 (d, 6'-H), 1.56 (br dd, 6-$CH_2$), 1.65 (m, 14-H), 1.83 (dd, 2"-Hax), 1.99 (d, 2"-Heq), 2.03 (s, 9-$OCOCH_3$), 2.03 (s, 2'-$OCOCH_3$), 2.20 (s, $NCH_3$), 2.29 (m, 15-$CH_2$), 2.39 (s, 3'-$N(CH_3)_2$), 2.50 (m, 10-H), 2.62 (br d, 2-H), 2.71 (t, 3'-H), 2.73 (dd, 2-H), 3.16 (s, $CH(OCH_3)_2$), 3.24 (s, $CH(OCH_3)_2$), 3.34 (m, 4'-H), 3.39 (m, 5'-H), 3.40 (br d, 4-H), 3.52 (s, 4-$OCH_3$), 3.89 (br d, 5-H), 4.25 (s, 3"-OH), 4.36 (dq, 5"-H), 4.49 (dd, $CH(OCH_3)_2$), 4.60 (d, 4"-H), 4.69 (d, 1'-H), 5.05 (dd, 2'-H), 5.05 (m, 9-H), 5.06 (m, 15-H), 5.10 (d, 1"-H), 5.10 (d, $CH{=}CH_2$), 5.23 (br dd, 3-H), 5.71 (m, $CH{=}CH_2$).

(c) In an amount of 485 mg of the isomer A of Example 48(b) and 204 mg of 4-bromoquinoline were dissolved in 4.9 ml of 1,4-dioxane, and added with 67.4 mg of tris(dibenzylideneacetone)dipalladium(0) and 210 µl of dicyclohexylmethylamine. The reaction vessel was purged with argon, and then the reaction mixture was added with 845 µl of a 0.174 M solution of tri-tert-butylphosphine in 1,4-dioxane, stirred at 50° C. for 24 hours, then further added with 67.4 mg of tris(dibenzylideneacetone)dipalladium(0) and 210 µl of a 0.174 M solution of tri-tert-butylphosphine in 1,4-dioxane, and further stirred for 24 hours. The reaction mixture was returned to room temperature, and the catalyst was removed by filtration. Then, the filtrate was concentrated under reduced pressure, and the resulting residue was purified by silica gel column chromatography (ethyl acetate/acetone (2:1) and chloroform/methanol (20:1)) to obtain 231 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(quinolin-4-yl)-2-propenyl group, $R_3$ is hydrogen atom, $R_{4''}$ is propionyl group, and X is oxygen atom).

Physicochemical Properties of this Compound (1) Molecular formula: $C_{58}H_{89}N_3O_{18}$ (2) Mass spectrum (FAB): m/z 1116 $(M+H)^+$ (3) Specific rotation: $[\alpha]_D^{20}$ −21° (c1.08, $CHCl_3$)

(4) $^1$H NMR spectrum (300 MHz, $CDCl_3$) δ (ppm): 0.91 (d, 8-$CH_3$), 1.11 (s, 3"-$CH_3$), 1.11 (t, 3-$OCOCH_2CH_3$), 1.12 (d, 6"-H), 1.16 (t, 4"-$OCOCH_2CH_3$), 1.26 (d, 6'-H), 1.83 (dd, 2"-Hax), 1.99 (d, 2"-Heq), 2.03 (s, 9-$OCOCH_3$), 2.04 (s, 2'-$OCOCH_3$), 2.23 (s, $NCH_3$), 2.40 (s, 3'-$N(CH_3)_2$), 2.45 (m, 10-H), 2.59 (dd, 2-H), 2.61 (m, 15-$CH_2$), 2.71 (t, 3'-H), 2.84 (dd, 2-H), 3.14 (s, $CH(OCH_3)_2$), 3.24 (s, $CH(OCH_3)_2$), 3.32 (m, 4'-H), 3.37 (m, 5'-H), 3.55 (s, 4-$OCH_3$), 3.61 (br d, 4-H), 3.93 (br d, 5-H), 4.26 (br s, 3"-OH), 4.37 (dq, 5"-H), 4.55 (dd, $CH(OCH_3)_2$), 4.60 (d, 4"-H), 4.71 (d, 1'-H), 4.91 (m, 9-H), 5.00 (dd, 2'-H), 5.06 (d, 1"-H), 5.06 (br dd, 3-H), 5.18 (m, 15-H), 6.36 (dt, CH=CH), 7.14 (d, CH=CH), 7.39 (d, quinoline), 7.54 (ddd, quinoline), 7.70 (ddd, quinoline), 8.07 (br d, quinoline), 8.09 (br d, quinoline), 8.82 (d, quinoline).

(d) In the same manner as in Example 2(c), 69.1 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(quinolin-4-yl)-2-propenyl group, $R_{3''}$ is hydrogen atom, $R_{4''}$ is propionyl group, and X is oxygen atom) was obtained from 182 mg of the compound of Example 48(c).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{18}$ −35° (c0.71, $CHCl_3$)

(4) $^1$H NMR spectrum (300 MHz, $CDCl_3$) δ (ppm): 0.87 (d, 8-$CH_3$), 1.08 (t, 3-$OCOCH_2CH_3$), 1.11 (s, 3"-$CH_3$), 1.12 (d, 6"-H), 1.17 (t, 4"-$OCOCH_2CH_3$), 1.26 (d, 6'-H), 1.82 (dd, 2"-Hax), 1.99 (d, 2"-Heq), 2.33 (s, $NCH_3$), 2.49 (s, 3'-$N(CH_3)_2$), 2.61 (dd, 2-H), 2.61 (m, 15-$CH_2$), 2.79 (dd, 2-H), 3.15 (s, $CH(OCH_3)_2$), 3.24 (s, $CH(OCH_3)_2$), 3.35 (m, 9-H), 3.58 (s, 4-$OCH_3$), 3.89 (br d, 5-H), 4.31 (d, 1'-H), 4.45 (dq, 5"-H), 4.46 (dd, $CH(OCH_3)_2$), 4.61 (d, 4"-H), 5.07 (d, 1"-H), 5.17 (m, 15-H), 5.47 (m, 3-H), 6.35 (dt, CH=CH), 7.12 (d, CH=CH), 7.37 (d, quinoline), 7.54 (ddd, quinoline), 7.70 (ddd, quinoline), 8.07 (br d, quinoline), 8.09 (br d, quinoline), 8.81 (d, quinoline).

(e) In the same manner as in Example 2(d), 8.2 mg of the title compound was obtained from 14.1 mg of the compound of Example 48(d).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{18}$ −38° (c0.41, $CHCl_3$)

(4) $^1$H NMR spectrum (300 MHz, $CDCl_3$) δ (ppm): 0.91 (d, 8-$CH_3$), 1.11 (s, 3"-$CH_3$), 1.12 (d, 6"-H), 1.14 (t, 3-$OCOCH_2CH_3$), 1.17 (t, 4"-$OCOCH_2CH_3$), 1.20 (d, 6'-H), 1.82 (dd, 2"-Hax), 1.99 (d, 2"-Heq), 2.33 (s, $NCH_3$), 2.50 (s, 3'-$N(CH_3)_2$), 2.63 (dd, 2-H), 3.24 (m, 4'-H), 3.27 (m, 5'-H), 3.36 (m, 9-H), 3.54 (dd, 2'-H), 3.58 (s, 4-$OCH_3$), 3.85 (br d, 4-H), 3.99 (br d, 5-H), 4.36 (d, 1'-H), 4.47 (dq, 5"-H), 4.61 (d, 4"-H), 5.06 (d, 1"-H), 5.17 (m, 15-H), 5.54 (m, 3-H), 6.35 (dt, CH=CH), 7.13 (d, CH=CH), 7.38 (d, quinoline), 7.55 (ddd, quinoline), 7.71 (ddd, quinoline), 8.06 (br d, quinoline), 8.09 (br d, quinoline), 8.82 (d, quinoline), 9.64 (s, CHO).

Example 49

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{11}$ are hydrogen atoms, $R_{12}$ is trans-3-(quinolin-4-yl)-2-propenyl group, $R_{4'}$ is a group represented by the formula (a), $R_{3''}$ is hydrogen atom, $R_{4''}$ is propionyl group, and X is oxygen atom (a) In the same manner as in Example 48(c), 78.1 mg of a coupling compound (compound represented by the formula (24) mentioned in Preparation Scheme 8 wherein $R_3$ is methyl group, $R_7$, $R_8$ and $R_{11}$ are hydrogen atoms, $R_{12}$ is trans-3-(quinolin-4-yl)-2-propenyl group, $R_{3''}$ is hydrogen atom, $R_{4''}$ is propionyl group, and X is oxygen atom) was obtained from 274 mg of the isomer B of Example 48(b).

Physicochemical Properties of this Compound (1) Molecular formula: $C_{58}H_{89}N_3O_{18}$ (2) Mass spectrum (FAB): m/z 1116 $(M+H)^+$ (3) Specific rotation: $[\alpha]_D^{18}$ −59° (c1.07, $CHCl_3$)

(4) $^1$H NMR spectrum (300 MHz, $CDCl_3$) δ (ppm): 0.94 (d, 8-$CH_3$), 1.10 (s, 3"-$CH_3$), 1.11 (d, 6"-H), 1.12 (t, 3-$OCOCH_2CH_3$), 1.16 (t, 4"-$OCOCH_2CH_3$), 1.26 (d, 6'-H), 1.82 (dd, 2"-Hax), 1.99 (d, 2"-Heq), 2.00 (s, 9-$OCOCH_3$), 2.03 (s, 2'-$OCOCH_3$), 2.23 (s, $NCH_3$), 2.39 (s, 3'-$N(CH_3)_2$), 2.70 (t, 3'-H), 3.16 (s, $CH(OCH_3)_2$), 3.24 (s, $CH(OCH_3)_2$), 3.31 (m, 4'-H), 3.33 (m, 5'-H), 3.39 (br d, 4-H), 3.52 (s, 4-$OCH_3$), 3.88 (br d, 5-H), 4.24 (s, 3"-OH), 4.36 (dq, 5"-H), 4.49 (dd, $CH(OCH_3)_2$), 4.60 (d, 4"-H), 4.69 (d, 1'-H), 4.99 (dd, 2'-H), 5.05 (d, 1"-H), 5.14 (m, 15-H), 5.25 (br dd, 3-H), 6.36 (dt, CH═CH), 7.12 (d, CH═CH), 7.38 (d, quinoline), 7.54 (ddd, quinoline), 7.69 (ddd, quinoline), 8.05 (br d, quinoline), 8.08 (br d, quinoline), 8.83 (d, quinoline).

(b) In the same manner as in Example 2(c), 44 mg of a deacetyled compound (compound represented by the formula (25) mentioned in Preparation Scheme 8 wherein $R_2$ is hydrogen atom, $R_3$ is methyl group, $R_7$, $R_8$ and $R_{11}$ are hydrogen atoms, $R_{12}$ is trans-3-(quinolin-4-yl)-2-propenyl group, $R_{3''}$ is hydrogen atom, $R_{4''}$ is propionyl group, and X is oxygen atom) was obtained from 78.1 mg of the compound of Example 49(a).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{16}$ −53° (c2.2, $CHCl_3$)

(4) $^1H$ NMR spectrum (300 MHz, $CDCl_3$) δ (ppm): 0.99 (d, 8-$CH_3$), 1.10 (s, 3"-$CH_3$), 1.10 (t, 3-$OCOCH_2CH_3$), 1.11 (d, 6"-H), 1.16 (t, 4"-$OCOCH_2CH_3$), 1.24 (d, 6'-H), 1.81 (dd, 2"-Hax), 1.98 (d, 2"-Heq), 2.34 (s, $NCH_3$), 2.46 (s, 3'-$N(CH_3)_2$), 3.15 (s, $CH(OCH_3)_2$), 3.24 (s, $CH(OCH_3)_2$), 3.49 (br d, 4-H), 3.51 (s, 4-$OCH_3$), 3.56 (dd, 2'-H), 3.82 (br d, 5-H), 4.43 (d, 1'-H), 4.46 (dd, $CH(OCH_3)_2$), 4.49 (dq, 5"-H), 4.60 (d, 4"-H), 4.99 (m, 15-H), 5.05 (d, 1"-H), 5.36 (br dd, 3-H), 6.36 (dt, CH═CH), 7.11 (d, CH═CH), 7.42 (d, quinoline), 7.53 (ddd, quinoline), 7.69 (ddd, quinoline), 8.04 (br d, quinoline), 8.08 (br d, quinoline), 8.83 (d, quinoline).

(c) In the same manner as in Example 2(d), 10.6 mg of the title compound was obtained from 21.8 mg of the compound of Example 49(b).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{17}$ −49° (c0.53, $CHCl_3$)

(4) $^1H$ NMR spectrum (300 MHz, $CDCl_3$) δ (ppm): 1.04 (d, 8-$CH_3$), 1.10 (s, 3"-$CH_3$), 1.12 (d, 6"-H), 1.15 (t, 3-$OCOCH_2CH_3$), 1.16 (d, 6'-H), 1.17 (t, 4"-$OCOCH_2CH_3$), 1.81 (dd, 2"-Hax), 1.99 (d, 2"-Heq), 2.35 (s, $NCH_3$), 2.47 (s, 3'-$N(CH_3)_2$), 2.91 (dd, 6-$CH_2$), 3.24 (m, 4'-H), 3.24 (m, 5'-H), 3.47 (dd, 2'-H), 3.48 (s, 4-$OCH_3$), 3.56 (br d, 4-H), 3.84 (br d, 5-H), 4.29 (br s, 3"-OH), 4.35 (d, 1'-H), 4.44 (dq, 5"-H), 4.61 (d, 4"-H), 5.01 (m, 15-H), 5.05 (d, 1"-H), 5.48 (br dd, 3-H), 6.42 (dt, CH═CH), 7.14 (d, CH═CH), 7.48 (d, quinoline), 7.55 (ddd, quinoline), 7.70 (ddd, quinoline), 8.05 (br d, quinoline), 8.09 (br d, quinoline), 8.85 (d, quinoline), 9.63 (s, CHO).

Example 50

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is 3-(quinolin-4-yl)propyl group, $R_{4'}$ is a group represented by the formula (a), $R_{3''}$ is hydrogen atom, $R_{4''}$ is propionyl group, and X is oxygen atom (a) In the same manner as in Example 8(d), except that a mixed solvent of 1,4-dioxane/water (2:1) was used instead of 1,4-dioxane, 15.3 mg of a double bond-reduced compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is 3-(quinolin-4-yl)propyl group, $R_{3''}$ is hydrogen atom, $R_{4''}$ is propionyl group, and X is oxygen atom) was obtained from 25.1 mg of the compound of Example 48(d).

Physicochemical Properties of this Compound (1) Molecular formula: $C_{54}H_{87}N_3O_{16}$ (2) Mass spectrum (FAB): m/z 1034 $(M+H)^+$ (3) Specific rotation: $[\alpha]_D^{16}$ −29° (c0.77, $CHCl_3$)

(4) $^1H$ NMR spectrum (300 MHz, $CDCl_3$) δ (ppm): 0.89 (d, 8-$CH_3$), 1.08 (t, 3-$OCOCH_2CH_3$), 1.11 (s, 3"-$CH_3$), 1.12 (d, 6"-H), 1.17 (t, 4"-$OCOCH_2CH_3$), 1.26 (d, 6'-H), 1.82 (dd, 2"-Hax), 2.00 (d, 2"-Heq), 2.31 (s, 11-$NCH_3$), 2.50 (s, 3'-$N(CH_3)_2$), 2.57 (dd, 2-H), 2.82 (dd, 2-H), 3.07 (t, quinoline-$CH_2$), 3.14 (s, $CH(OCH_3)_2$), 3.25 (s, $CH(OCH_3)_2$), 3.62 (dd, 2'-H), 3.66 (s, 4-$OCH_3$), 3.89 (br d, 4-H), 3.98 (br d, 5-H), 4.45 (d, 1'-H), 4.47 (dq, 5"-H), 4.50 (dd, $CH(OCH_3)_2$), 4.61 (d, 4"-H), 5.04 (m, 15-H), 5.07 (d, 1"-H), 5.40 (br dd, 3-H), 7.20 (d, quinoline), 7.54 (ddd, quinoline), 7.69 (ddd, quinoline), 7.99 (br d, quinoline), 8.10 (br d, quinoline), 8.79 (d, quinoline).

(b) In the same manner as in Example 2(d), 8.8 mg of the title compound was obtained from 15.3 mg of the compound of Example 50(a).

Physicochemical Properties of this Compound (1) Molecular formula: $C_{52}H_{81}N_3O_{15}$ (2) Mass spectrum (FAB): m/z 988 $(M+H)^+$ (3) Specific rotation: $[\alpha]_D^{15}$ −34° (c0.44, $CHCl_3$)

(4) $^1H$ NMR spectrum (300 MHz, $CDCl_3$) δ (ppm): 0.93 (d, 8-$CH_3$), 1.11 (s, 3"-$CH_3$), 1.12 (d, 6"-H), 1.13 (t, 3-$OCOCH_2CH_3$), 1.17 (t, 4"-$OCOCH_2CH_3$), 1.25 (d, 6'-H), 1.82 (dd, 2"-Hax), 2.00 (d, 2"-Heq), 2.33 (s, $NCH_3$), 2.50 (s, 3'-$N(CH_3)_2$), 2.58 (dd, 2-H), 3.07 (t, quinoline-$CH_2$), 3.26 (m, 4'-H), 3.29 (m, 5'-H), 3.56 (dd, 2'-H), 3.65 (s, 4-$OCH_3$), 3.86 (br d, 4-H), 3.99 (br d, 5-H), 4.38 (d, 1'-H), 4.46 (dq, 5"-H), 4.61 (d, 4"-H), 5.06 (d, 1"-H), 5.09 (m, 15-H), 5.45 (m, 3-H), 7.21 (d, quinoline), 7.55 (ddd, quinoline), 7.70 (ddd, quinoline), 8.01 (br d, quinoline), 8.11 (dd, quinoline), 8.79 (d, quinoline), 9.64 (s, CHO).

Example 51

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{11}$ are hydrogen atoms, $R_{12}$ is 3-(quinolin-4-yl)propyl group, $R_{4'}$ is a group represented by the formula (a), $R_{3''}$ is hydrogen atom, $R_{4''}$ is propionyl group, and X is oxygen atom (a) In the same manner as in Example 8(d), except that a mixed solvent of 1,4-dioxane/water (2:1) was used instead of 1,4-dioxane, 20 mg of a double bond-reduced compound (compound represented by the formula (25) mentioned in Preparation Scheme 8 wherein $R_2$ is hydrogen atom, $R_3$ is methyl group, $R_7$, $R_8$ and $R_{11}$ are hydrogen atoms, $R_{12}$ is 3-(quinolin-4-yl)propyl group, $R_{3''}$ is hydrogen atom, $R_4$ is propionyl group, and X is oxygen atom) was obtained from 21 mg of the compound of Example 49(b).

Physicochemical Properties of this Compound (1) Molecular formula: $C_{54}H_{87}N_3O_{16}$ (2) Mass spectrum (FAB): m/z 1034 $(M+H)^+$ (3) Specific rotation: $[\alpha]_D^{17}$ −40° (c1.0, $CHCl_3$)

(4) $^1H$ NMR spectrum (300 MHz, $CDCl_3$) δ (ppm): 0.98 (d, 8-$CH_3$), 1.11 (s, 3"-$CH_3$), 1.12 (d, 6"-H), 1.12 (t, 3-$OCOCH_2CH_3$), 1.17 (t, 4"-$OCOCH_2CH_3$), 1.26 (d, 6'-H), 1.82 (dd, 2"-Hax), 1.99 (d, 2"-Heq), 2.31 (s, $NCH_3$), 2.49 (s, 3'-$N(CH_3)_2$), 2.63 (dd, 2-H), 2.69 (dd, 2-H), 3.06 (br t, quinoline-$CH_2$), 3.17 (s, $CH(OCH_3)_2$), 3.25 (s, $CH(OCH_3)_2$), 3.28 (m, 5'-H), 3.43 (br d, 4-H), 3.53 (s, 4-$OCH_3$), 3.57 (dd, 2'-H), 3.84 (br d, 5-H), 4.40 (d, 1'-H), 4.43 (dd, $CH(OCH_3)_2$), 4.47 (dq, 5"-H), 4.61 (d, 4"-H), 4.89 (m, 15-H), 5.06 (d, 1"-H), 5.30 (br dd, 3-H), 7.20 (d, quinoline), 7.55 (ddd, quinoline), 7.69 (ddd, quinoline), 7.98 (br d, quinoline), 8.10 (br d, quinoline), 8.79 (d, quinoline).

(b) In the same manner as in Example 2(d), 7.9 mg of the title compound was obtained from 20 mg of the compound of Example 51(a).

Physicochemical Properties of this Compound (1) Molecular formula: $C_{52}H_{81}N_3O_{15}$ (2) Mass spectrum (FAB): m/z 988 $(M+H)^+$ (3) Specific rotation: $[\alpha]_D^{15}$ −45° (c0.40, $CHCl_3$)

(4) $^1H$ NMR spectrum (300 MHz, $CDCl_3$) δ (ppm): 1.00 (d, 8-$CH_3$), 1.11 (s, 3"-$CH_3$), 1.12 (d, 6"-H), 1.15 (t, 3-$OCOCH_2CH_3$), 1.17 (t, 4"-$OCOCH_2CH_3$), 1.18 (d, 6'-H), 1.83 (dd, 2"-Hax), 2.00 (d, 2"-Heq), 2.34 (s, $NCH_3$), 2.50 (s, 3'-$N(CH_3)_2$), 2.91 (dd, 6-$CH_2$), 3.07 (br t, quinoline-$CH_2$), 3.26 (m, 4'-H), 3.26 (m, 5'-H), 3.51 (dd, 2'-H), 3.52 (s, 4-$OCH_3$), 3.86 (br d, 5-H), 4.38 (d, 1'-H), 4.46 (dq, 5"-H), 4.61 (d, 4"-H), 4.90 (m, 15-H), 5.06 (d, 1"-H), 5.42 (br dd, 3-H), 7.21 (d, quinoline), 7.56 (ddd, quinoline), 7.70 (ddd, quinoline), 7.99 (br d, quinoline), 8.11 (br d, quinoline), 8.80 (d, quinoline), 9.63 (s, CHO).

Example 52

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is allyl group, $R_{4'}$ is a group represented by the formula (a), $R_{3''}$ is hydrogen atom, $R_{4''}$ is propionyl group, and X is oxygen atom (a) In the same manner as in Example 2(c), 9.7 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is allyl group, $R_{3''}$ is hydrogen atom, $R_{4''}$ is propionyl group, and X is oxygen atom) was obtained from 25 mg of the isomer A of Example 48(b).

Physicochemical Properties of this Compound (1) Molecular formula: $C_{45}H_{80}N_2O_{16}$ (2) Mass spectrum (ES): m/z 905 $(M+H)^+$ (3) Specific rotation: $[\alpha]_D^{21}$ −30° (c0.49, $CHCl_3$)

(4) $^1H$ NMR spectrum (300 MHz, $CDCl_3$) δ (ppm): 0.88 (d, 8-$CH_3$), 1.11 (s, 3"-$CH_3$), 1.11 (t, 3-$OCOCH_2CH_3$), 1.12 (d, 6"-H), 1.17 (t, 4"-$OCOCH_2CH_3$), 1.27 (d, 6'-H), 1.82 (dd, 2"-Hax), 2.00 (d, 2"-Heq), 2.30 (s, $NCH_3$), 2.43 (q, 3-$OCOCH_2CH_3$), 2.44 (q, 4"-$OCOCH_2CH_3$), 2.50 (s, 3'-N $(CH_3)_2$), 2.58 (dd, 2-H), 2.82 (dd, 2-H), 3.15 (s, $CH(OCH_3)_2$), 3.25 (s, $CH(OCH_3)_2$), 3.27 (m, 4'-H), 3.30 (m, 5'-H), 3.60 (dd, 2'-H), 3.67 (s, 4-$OCH_3$), 3.90 (br d, 4-H), 3.98 (br d, 5H), 4.44 (d, 1'-H), 4.47 (dq, 5"-H), 4.47 (dd, $CH(OCH_3)_2$), 4.61 (d, 4"-H), 5.00 (m, 15-H), 5.05 (d, $CH{=}CH_2$), 5.08 (d, 1"-H), 5.43 (br d, 3-H), 5.70 (m, $CH{=}CH_2$).

(b) In the same manner as in Example 2(d), 5.1 mg of the title compound was obtained from 9.7 mg of the compound of Example 52(a).

Physicochemical Properties of this Compound (1) Molecular formula: $C_{43}H_{74}N_2O_{15}$ (2) Mass spectrum (FAB): m/z 859 $(M+H)^+$ (3) Specific rotation: $[\alpha]_D^{19}$ −35° (c0.26, $CHCl_3$)

(4) $^1H$ NMR spectrum (300 MHz, $CDCl_3$) δ (ppm): 0.92 (d, 8-$CH_3$), 1.11 (s, 3"-$CH_3$), 1.12 (d, 6"-H), 1.16 (t, 3-$OCOCH_2CH_3$), 1.17 (t, 4"-$OCOCH_2CH_3$), 1.20 (d, 6'-H), 1.82 (dd, 2"-Hax), 2.00 (d, 2"-Heq), 2.33 (s, $NCH_3$), 2.50 (s, 3'-$N(CH_3)_2$), 2.60 (dd, 2-H), 2.89 (dd, 6-$CH_2$), 3.27 (m, 4'-H), 3.27 (m, 5'-H), 3.38 (m, 9-H), 3.56 (dd, 2'-H), 3.67 (s, 4-$OCH_3$), 3.86 (br d, 4-H), 3.99 (br d, 5-H), 4.38 (d, 1'-H), 4.47 (dq, 5"-H), 4.61 (d, 4"-H), 5.01 (m, 15-H), 5.05 (d, $CH{=}CH_2$), 5.08 (d, 1"-H), 5.47 (m, 3-H), 5.69 (m, $CH{=}CH_2$), 9.64 (s, CHO).

Example 53

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(quinolin-3-yl)-2-propenyl group, $R_{4'}$ is a group represented by the formula (a), $R_{3''}$ is hydrogen atom, $R_{4''}$ is propionyl group, and X is oxygen atom (a) In the same manner as in Example 48(c), except that 3-bromoquinoline was used instead of 4-bromoquinoline, 30 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(quinolin-3-yl)-2-propenyl group, $R_{3''}$ is hydrogen atom, $R_{4''}$ is propionyl group, and X is oxygen atom) was obtained from 106 mg of the isomer A of Example 48(b).

Physicochemical Properties of this Compound (1) Molecular formula: $C_{58}H_{89}N_3O_{18}$ (2) Mass spectrum (FAB): m/z 1116 $(M+H)^+$ (3) Specific rotation: $[\alpha]_D^{21}$ −42° (c1.5, $CHCl_3$)

(4) $^1H$ NMR spectrum (300 MHz, $CDCl_3$) δ (ppm): 0.90 (d, 8-$CH_3$), 1.10 (s, 3"-$CH_3$), 1.11 (d, 6"-H), 1.11 (t, 3-$OCOCH_2CH_3$), 1.16 (t, 4"-$OCOCH_2CH_3$), 1.25 (d, 6'-H), 1.82 (dd, 2"-Hax), 2.00 (d, 2"-Heq), 2.02 (s, 9-$OCOCH_3$), 2.04 (s, 2'-$OCOCH_3$), 2.22 (s, $NCH_3$), 2.39 (s, 3'-$N(CH_3)_2$), 2.54 (m, 15-$CH_2$), 2.71 (t, 3'-H), 2.84 (dd, 2-H), 3.13 (s, $CH(OCH_3)_2$), 3.23 (s, $CH(OCH_3)_2$), 3.31 (m, 4'-H), 3.34 (m, 5'-H), 3.56 (s, 4-$OCH_3$), 3.93 (br d, 5-H), 4.27 (br s, 3"-OH), 4.36 (dq, 5"-H), 4.54 (dd, $CH(OCH_3)_2$), 4.60 (d, 4"-H), 4.71 (d, 1'-H), 4.89 (m, 9-H), 4.99 (dd, 2'-H), 5.05 (d, 1"-H), 5.13 (m, 15-H), 6.34 (dt, $CH{=}CH$), 6.59 (d, $CH{=}CH$), 7.50 (br t, quinoline), 7.64 (ddd, quinoline), 7.76 (br d, quinoline), 7.99 (d, quinoline), 8.03 (d, quinoline), 8.92 (d, quinoline).

(b) In the same manner as in Example 2(c), 16.7 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(quinolin-3-yl)-2-propenyl group, $R_{3''}$ is hydrogen atom, $R_{4''}$ is propionyl group, and X is oxygen atom) was obtained from 29.8 mg of the compound of Example 53(a).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{21}$ −38° (c0.84, $CHCl_3$)

(4) $^1H$ NMR spectrum (300 MHz, $CDCl_3$) δ (ppm): 0.87 (d, 8-$CH_3$), 1.09 (t, 3-$OCOCH_2CH_3$), 1.11 (s, 3"-$CH_3$), 1.12 (d, 6"-H), 1.17 (t, 4"-$OCOCH_2CH_3$), 1.26 (d, 6'-H), 1.40 (m, 8-H), 1.82 (dd, 2"-Hax), 1.99 (d, 2"-Heq), 2.30 (s, $NCH_3$), 2.49 (s, 3'-$N(CH_3)_2$), 2.60 (dd, 2-H), 2.80 (dd, 2-H), 3.15 (s, $CH(OCH_3)_2$), 3.24 (s, $CH(OCH_3)_2$), 3.28 (m, 4'-H), 3.30 (m, 5'-H), 3.56 (dd, 2'-H), 3.62 (s, 4-$OCH_3$), 3.89 (br d, 4-H), 3.98 (br d, 5-H), 4.42 (d, 1'-H), 4.45 (dd, $CH(OCH_3)_2$), 4.47 (dq, 5"-H), 4.61 (d, 4"-H), 5.07 (d, 1"-H), 5.13 (m, 15-H), 5.48 (m, 3-H), 6.33 (dt, CH═CH), 6.57 (d, CH═CH), 7.51 (ddd, quinoline), 7.65 (ddd, quinoline), 7.76 (dd, quinoline), 7.98 (d, quinoline), 8.04 (br d, quinoline), 8.92 (d, quinoline).

(c) In the same manner as in Example 2(d), 7.1 mg of the title compound was obtained from 16.7 mg of the compound of Example 53(b).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{21}$-51° (c0.36, $CHCl_3$)

(4) $^1H$ NMR spectrum (300 MHz, $CDCl_3$) δ (ppm): 0.91 (d, 8-$CH_3$), 1.11 (s, 3"-$CH_3$), 1.12 (d, 6"-H), 1.14 (t, 3-$OCOCH_2CH_3$), 1.17 (t, 4"-$OCOCH_2CH_3$), 1.18 (d, 6'-H), 1.32 (m, 8-H), 1.82 (dd, 2"-Hax), 2.00 (d, 2"-Heq), 2.33 (s, $NCH_3$), 2.49 (s, 3'-$N(CH_3)_2$), 2.62 (dd, 2-H), 2.84 (dd, 2-H), 2.87 (dd, 6-$CH_2$), 3.25 (m, 4'-H), 3.25 (m, 5'-H), 3.38 (m, 9-H), 3.55 (dd, 2'-H), 3.62 (s, 4-$OCH_3$), 3.85 (br d, 4-H), 3.99 (br d, 5-H), 4.37 (d, 1'-H), 4.46 (dq, 5"-H), 4.61 (d, 4"-H), 5.06 (d, 1"-H), 5.13 (m, 15-H), 5.53 (m, 3-H), 6.34 (dt, CH═CH), 6.58 (d, CH═CH), 7.52 (ddd, quinoline), 7.65 (ddd, quinoline), 7.76 (dd, quinoline), 7.98 (d, quinoline), 8.05 (br d, quinoline), 8.92 (d, quinoline), 9.64 (s, CHO).

Example 54

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is trans-3-(quinolin-4-yl)-1-propenyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom (a) In the same manner as in Example 2(a), except that the compound of Reference Example 18 was used instead of the compound of Reference Example 1, 1.84 g of an isomer A (compound represented by the formula (23) mentioned in Preparation Scheme 8 wherein $R_3$ is methyl group, one of $R_7$ and $R_8$ is allyl group, the other is hydrogen atom, $R_{11}$ and $R_{12}$ are hydrogen atoms, $R_{3''}$ is hydrogen atom, $R_{4''}$ is propionyl group, and X is hydroxyl group), and 1.39 g of an isomer B (compound represented by the formula (23) mentioned in Preparation Scheme 8 wherein $R_3$ is methyl group, one of $R_7$ and $R_8$ is allyl group, the other is hydrogen atom, $R_{11}$ and $R_{12}$ are hydrogen atoms, $R_{3''}$ is hydrogen atom, $R_{4''}$ is propionyl group, and X is hydroxyl group, provided that the substituents $R_7$ and $R_9$ are exchanged compared with the isomer A) were obtained from 4.07 g of the compound of Example 19.

Physicochemical Properties of the Isomer A (1) Molecular formula: $C_{49}H_{86}N_2O_{19}$ (2) Mass spectrum (FAB): m/z 1007 $(M+H)^+$ (3) Specific rotation: $[\alpha]_D^{17}$ −56° (c0.80, $CHCl_3$)

(4) $^1H$ NMR spectrum (300 MHz, $CDCl_3$) δ (ppm): 0.90 (d, 8-$CH_3$), 1.11 (s, 3"-$CH_3$), 1.12 (d, 6"-H), 1.14 (t, 3-$OCOCH_2CH_3$), 1.16 (t, 4"-$OCOCH_2CH_3$), 1.17 (d, 6'-H), 1.83 (dd, 2"-Hax), 2.00 (d, 2"-Heq), 2.03 (s, 9-$OCOCH_3$), 2.05 (s, 2'-$OCOCH_3$), 2.39 (s, 3'-$N(CH_3)_2$), 2.48 (s, $NCH_3$), 2.58 (dd, 10-H), 2.71 (t, 3'-H), 3.16 (s, $CH(OCH_3)_2$), 3.24 (s, $CH(OCH_3)_2$), 3.30 (m, 4'-H), 3.33 (m, 5'-H), 3.55 (s, 4-$OCH_3$), 3.76 (m, 15-H), 3.86 (br d, 5-H), 4.37 (dq, 5"-H), 4.50 (dd, $CH(OCH_3)_2$), 4.60 (d, 4"-H), 4.73 (d, 1'-H), 4.98 (dd, 2'-H), 5.03 (m, CH═$CH_2$), 5.06 (dd, 1"-H), 5.15 (m, 9-H), 5.16 (m, 3-H), 5.70 (ddt, CH═$CH_2$).

Physicochemical Properties of the Isomer B (1) Molecular formula: $C_{49}H_{86}N_2O_{19}$ (2) Mass spectrum (FAB): m/z 1007 $(M+H)^+$ (3) Specific rotation: $[\alpha]_D^{17}$ −42° (c1.5, $CHCl_3$)

(4) $^1H$ NMR spectrum (300 MHz, $CDCl_3$) δ (ppm): 0.91 (d, 8-$CH_3$), 1.11 (s, 3"-$CH_3$), 1.12 (d, 6"-H), 1.13 (t, 3-$OCOCH_2CH_3$), 1.15 (t, 4"-$OCOCH_2CH_3$), 1.25 (d, 6'-H), 1.83 (dd, 2"-Hax), 1.94 (m, 13-H), 1.99 (d, 2"-Heq), 2.00 (d, 2"-Heq), 2.03 (s, 9-$OCOCH_3$), 2.06 (s, 2'-$OCOCH_3$), 2.40 (s, 3'-$N(CH_3)_2$), 2.51 (s, $NCH_3$), 2.71 (t, 3'-H), 3.19 (s, $CH(OCH_3)_2$), 3.25 (s, $CH(OCH_3)_2$), 3.30 (m, 4'-H), 3.33 (m, 5'-H), 3.54 (s, 4-$OCH_3$), 3.56 (br d, 4-H), 3.77 (m, 15-H), 3.86 (br d, 5-H), 4.37 (dq, 5"-H), 4.61 (d, 4"-H), 4.72 (d, 1'-H), 4.80 (dd, $CH(OCH_3)_2$), 4.98 (dd, 2'-H), 5.03 (m, CH═$CH_2$), 5.07 (d, 1"-H), 5.19 (m, 9-H), 5.21 (m, 3-H), 5.71 (ddt, CH═$CH_2$).

(b) In the same manner as in Example 48(b), 866 mg of a cyclized compound (compound represented by the formula (24) mentioned in Preparation Scheme 8 wherein $R_3$ is methyl group, one of $R_7$ and $R_8$ is allyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 1.39 g of the isomer A of Example 54(a).

Physicochemical Properties of this Compound (1) Molecular formula: $C_{49}H_{84}N_2O_{18}$ (2) Mass spectrum (FAB): m/z 989 $(M+H)^+$ (3) Specific rotation: $[\alpha]_D^{19}$ −70° (c0.3, $CHCl_3$)

(4) $^1H$ NMR spectrum (300 MHz, $CDCl_3$) δ (ppm): 0.94 (d, 8-$CH_3$), 1.11 (s, 3"-$CH_3$), 1.12 (d, 6"-H), 1.13 (t, 3-$OCOCH_2CH_3$), 1.17 (t, 4"-$OCOCH_2CH_3$), 1.26 (d, 6'-H), 1.58 (m, 14-H), 1.84 (dd, 2"-Hax), 2.00 (d, 2"-Heq), 2.03 (s, 9-$OCOCH_3$), 2.04 (s, 2'-$OCOCH_3$), 2.40 (s, $NCH_3$), 2.40 (s, 3'-$N(CH_3)_2$), 2.61 (dd, 10-H), 2.71 (t, 3'-H), 3.16 (s, $CH(OCH_3)_2$), 3.24 (s, $CH(OCH_3)_2$), 3.26 (br d, 4-H), 3.28 (t, 4'-H), 3.33 (dq, 5'-H), 3.53 (s, 4-$OCH_3$), 3.90 (brd, 5-H), 4.20 (m, 15-H), 4.38 (dq, 5"-H), 4.50 (dd, $CH(OCH_3)_2$), 4.61 (d, 4"-H), 4.70 (d, 1'-H), 5.07 (d, 1"-H),), 5.19 (br dd, 3-H), 5.75 (ddt, CH═$CH_2$).

(c) In the same manner as in Example 48(c), 185 mg of a trans-isomer of a coupling compound (compound represented by the formula (24) mentioned in Preparation Scheme 8 wherein $R_3$ is methyl group, one of $R_7$ and $R_8$ is trans-3-(quinolin-4-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom), and 18 mg of a cis-isomer of a coupling compound (compound represented by the formula (24) mentioned in Preparation Scheme 8 wherein $R_3$ is methyl group, one of $R_7$ and $R_8$ is cis-3-(quinolin-4-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom) were obtained from 367 mg of the compound of Example 54(b).

Physicochemical Properties of the Trans-isomer (1) Molecular formula: $C_{58}H_{89}N_3O_{18}$ (2) Mass spectrum (FAB): m/z 1116 $(M+H)^+$ (3) Specific rotation: $[c]_D^{20}$ −64° (c1.0, $CHCl_3$)

(4) $^1H$ NMR spectrum (300 MHz, $CDCl_3$) δ (ppm): 0.94 (d, 8-$CH_3$), 1.02 (t, 3-$OCOCH_2CH_3$), 1.12 (d, 6"-H), 1.16 (t, 4"-$OCOCH_2CH_3$), 1.19 (s, 3"-$CH_3$), 1.24 (d, 6'-H), 1.83 (dd, 2"-Hax), 2.00 (d, 2"-Heq), 2.02 (s, 9-$OCOCH_3$), 2.03 (s, 2'-$OCOCH_3$), 2.25 (s, $NCH_3$), 2.39 (s, 3'-$N(CH_3)_2$), 3.08 (s, $CH(OCH_3)_2$), 3.21 (s, $CH(OCH_3)_2$), 3.32 (m, 4'-H), 3.32 (m, 5'-H), 3.52 (s, 4-$OCH_3$), 3.78 (d, quinoline-$CH_2$), 3.87 (br d, 5-H), 4.12 (m, 15-H), 4.26 (br s, 3"-OH), 4.36 (dq, 5"-H), 4.44 (dd, $CH(OCH_3)_2$), 4.60 (d, 4"-H), 4.69 (d, 1'-H), 4.99 (dd, 2'-H), 5.05 (d, 1"-H), 5.22 (m, 3-H), 5.25 (dd, 13-CH), 5.88 (dt, CH═CH), 7.23 (d, quinoline), 7.53 (ddd, quinoline), 7.69 (ddd, quinoline), 8.00 (br d, quinoline), 8.09 (br d, quinoline), 8.80 (d, quinoline).

Physicochemical Properties of the Cis-isomer (1) Molecular formula: $C_{58}H_{89}N_3O_{18}$ (2) Mass spectrum (FAB): m/z 1116 $(M+H)^+$ (3) Specific rotation: $[\alpha]_D^{20}$ −65° (c0.9, $CHCl_3$)

(4) $^1H$ NMR spectrum (300 MHz, $CDCl_3$) δ (ppm): 0.93 (t, 3-$OCOCH_2CH_3$), 0.95 (d, 8-$CH_3$), 1.10 (s, 3"-$CH_3$), 1.11 (d, 6"-H), 1.16 (t, 4"-$OCOCH_2CH_3$), 1.24 (d, 6'-H), 1.83 (dd, 2"-Hax), 2.00 (d, 2"-Heq), 2.03 (s, 9-$OCOCH_3$), 2.05 (s, 2'-$OCOCH_3$), 2.31 (s, $NCH_3$), 2.39 (s, 3'-$N(CH_3)_2$), 3.05 (s, $CH(OCH_3)_2$), 3.20 (s, $CH(OCH_3)_2$), 3.33 (m, 4'-H), 3.33 (m, 5'-H), 3.35 (br d, 4-H), 3.54 (s, 4-$OCH_3$), 3.87 (br d, 5-H), 3.93 (br d, quinoline-$CH_2$), 4.07 (dd, 15-H), 4.26 (br s, 3"-OH), 4.36 (dd, 15-H), 4.37 (m, 5"-H), 4.49 (dd, $CH(OCH_3)_2$), 4.60 (d, 4"-H), 4.69 (d, 1'-H), 4.99 (dd, 2'-H), 5.05 (d, 1"-H), 5.21 (m, 3-H), 5.33 (dd, 13-CH), 5.69 (dt, CH═CH), 7.27 (d, quinoline), 7.53 (ddd, quinoline), 7.69 (ddd, quinoline), 8.06 (br d, quinoline), 8.10 (br d, quinoline), 8.80 (d, quinoline).

(d) In an amount of 24 mg of the trans-isomer of Example 54(c) was dissolved in 2 ml of methanol, and stirred at 50° C. for 72 hours. The reaction mixture was concentrated under reduced pressure, and the resulting residue was purified by preparative TLC (chloroform/methanol/28% aqueous ammonia (10:1:0.05)) to obtain 24 mg of a deacetyled compound (compound represented by the formula (25) mentioned in Preparation Scheme 8 wherein $R_2$ is hydrogen atom, $R_3$ is methyl group, one of $R_7$ and $R_8$ is trans-3-(quinolin-4-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{18}$ −45° (c0.7, $CHCl_3$)

(4) $^1H$ NMR spectrum (300 MHz, $CDCl_3$) δ (ppm): 0.86 (d, 8-$CH_3$), 0.94 (t, 3'-$OCOCH_2CH_3$), 1.12 (d, 6"-H), 1.17 (t, 4"-$OCOCH_2CH_3$), 1.19 (s, 3"-$CH_3$), 1.24 (d, 6'-H), 1.82 (dd, 2"-Hax), 1.99 (d, 2"-Heq), 2.07 (m, 14-H), 2.29 (s, $NCH_3$), 2.49 (s, 3'-$N(CH_3)_2$), 3.20 (s, $CH(OCH_3)_2$), 3.21 (t, 4'-H), 3.28 (m, 5'-H), 3.58 (s, 4-$OCH_3$), 3.79 (br d, quinoline-$CH_2$), 4.00 (m, 15-H), 4.36 (d, 1'-H), 4.37 (m, 9-H), 4.48 (dq, 5"-H), 4.61 (d, 4"-H), 5.06 (d, 1"-H), 5.21 (dd, 13-CH), 5.76 (br dd, 3-H), 6.00 (dt, CH═CH), 7.24 (d, quinoline), 7.53 (ddd, quinoline), 7.69 (ddd, quinoline), 8.00 (br d, quinoline), 8.10 (br d, quinoline), 8.80 (d, quinoline).

(e) In the same manner as in Example 2(d), 18 mg of the title compound was obtained from 33 mg of the compound of Example 54(d).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{20}$ −48° (c0.9, $CHCl_3$)

(4) $^1H$ NMR spectrum (300 MHz, $CDCl_3$) δ (ppm): 0.88 (d, 8-$CH_3$), 0.93 (m, 7-H), 1.01 (t, 3-$OCOCH_2CH_3$), 1.11 (s, 3"-$CH_3$), 1.12 (d, 6"-H), 1.17 (t, 4"-$OCOCH_2CH_3$), 1.19 (d, 6'-H), 1.38 (m, 14-H), 1.82 (dd, 2"-Hax), 1.99 (d, 2"-Heq), 2.06 (m, 14-H), 2.28 (s, $NCH_3$), 2.49 (s, 3'-$N(CH_3)_2$), 2.84 (dd, 6-$CH_2$), 3.25 (m, 4'-H), 3.25 (m, 5'-H), 3.53 (dd, 2'-H), 3.60 (br d, 4-H), 3.57 (s, 4-$OCH_3$), 3.78 (br d, quinoline-$CH_2$), 3.81 (br d, 5-H), 4.33 (d, 1'-H), 4.46 (dq, 5"-H), 4.60 (d, 4"-H), 5.05 (d, 1"-H), 5.18 (dd, 13-CH), 5.82 (br dd, 3-H), 5.97 (dt, CH═CH), 7.24 (d, quinoline), 7.54 (ddd, quinoline), 7.69 (ddd, quinoline), 8.00 (dd, quinoline), 8.10 (dd, quinoline), 8.81 (d, quinoline), 9.61 (s, CHO).

Example 55

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is trans-3-(quinolin-4-yl)-1-propenyl group, the other is hydrogen atom, $R_9$, $R_{10}$, $R_{11}$ and $R_{12}$ are hydrogen atoms, $R_{4'}$ is hydrogen atom, and X is oxygen atom In the same manner as in Example 2(d), 4.8 mg of the title compound was obtained from 33 mg of the compound of Example 54(d).

Physicochemical Properties of this Compound (1) Molecular formula: $C_{42}H_{63}N_3O_{11}$ (2) Mass spectrum (FAB): m/z 786 $(M+H)^+$ (3) Specific rotation: $[\alpha]_D^{21}$ −27° (c0.2, $CHCl_3$)

(4) $^1H$ NMR spectrum (300 MHz, $CDCl_3$) δ (ppm): 0.89 (d, 8-$CH_3$), 0.94 (m, 7-H), 1.01 (t, 3-$OCOCH_2CH_3$), 1.24 (d, 6'-H), 1.29 (m, 8-H), 1.39 (m, 14-H), 1.85 (m, 6-H), 2.07 (m, 14-H), 2.28 (s, $NCH_3$), 2.49 (s, 3'-$N(CH_3)_2$), 2.56 (m, 13-H), 2.64 (m, 2-H), 2.89 (dd, 6-$CH_2$), 3.00 (t, 4'-H), 3.24 (dq, 5'-H), 3.52 (dd, 2'-H), 3.58 (s, 4-$OCH_3$), 3.60 (dd, 4-H), 3.78 (br d, quinoline-$CH_2$), 3.83 (br d, 5-H), 4.00 (m, 15-H), 4.33 (d, 1'-H), 5.18 (dd, 13-CH), 5.83 (br dd, 3-H), 5.98 (dt, CH═CH), 7.24 (d, quinoline), 7.54 (ddd, quinoline), 7.69 (ddd, quinoline), 8.00 (br d, quinoline), 8.10 (br d, quinoline), 8.81 (d, quinoline), 9.64 (s, CHO).

Example 56

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is cis-3-(quinolin-4-yl)-1-propenyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom (a) In the same manner as in Example 54(b), 8.7 mg of a deacetyled compound (compound represented by the formula (25) mentioned in Preparation Scheme 8 wherein $R_2$ is hydrogen atom, $R_3$ is methyl group, one of $R_7$ and $R_8$ is cis-3-(quinolin-4-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 18 mg of the cis-isomer of Example 54(c).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{18}$ −47° (c0.4, $CHCl_3$)

(4) $^1H$ NMR spectrum (300 MHz, $CDCl_3$) δ (ppm): 0.83 (t, 3-$OCOCH_2CH_3$), 0.88 (d, 8-$CH_3$), 1.10 (s, 3"-$CH_3$), 1.12 (d, 6"-H), 1.17 (t, 4"-$OCOCH_2CH_3$), 1.23 (d, 6'-H), 1.81 (dd, 2"-Hax), 1.98 (d, 2"-Heq), 2.17 (q, 3-$OCOCH_2CH_3$), 2.35 (s, 11-$NCH_3$), 2.48 (s, 3'-$N(CH_3)_2$), 2.54 (dd, 2-H), 2.65 (dd, 2-H), 3.06 (m, 13-H), 3.10 (s, $CH(OCH_3)_2$), 3.26 (m, 4'-H), 3.26 (m, 5'-H), 3.55 (dd, 2'-H), 3.60 (s, 4-$OCH_3$), 3.67 (br d, 4-H), 3.82 (br d, 5-H), 3.99 (br d, quinoline-$CH_2$), 4.03 (m, 15-H), 4.21 (m, 15-H), 4.34 (d, 1'-H), 4.37 (dd, $CH(OCH_3)_2$), 4.47 (dq, 5"-H), 4.60 (d, 4"-H), 5.05 (d, 1"-H), 5.24 (dd, 13-CH), 5.66 (dt, CH═CH), 5.79 (m, 3-H), 7.29 (d, quinoline), 7.53 (ddd, quinoline), 7.69 (ddd, quinoline), 8.05 (dd, quinoline), 8.10 (dd, quinoline), 8.80 (d, quinoline).

(b) In the same manner as in Example 2(d), 4.6 mg of the title compound was obtained from 8.7 mg of the compound of Example 56(a).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{20}$ −37° (c0.2, $CHCl_3$)

(4) $^1H$ NMR spectrum (300 MHz, $CDCl_3$) δ (ppm): 0.92 (d, 8-$CH_3$), 0.93 (t, 3-$OCOCH_2CH_3$), 1.13 (d, 6"-H), 1.17 (t, 4"-$OCOCH_2CH_3$), 1.24 (d, 6'-H), 1.82 (dd, 2"-Hax), 2.00 (d, 2"-Heq), 2.50 (s, 3'-$N(CH_3)_2$), 3.27 (m, 4'-H), 3.27 (m, 5'-H), 3.57 (s, 4-$OCH_3$), 4.33 (d, 1'-H), 4.46 (m, 5"-H), 4.60 (d, 4"-H), 5.05 (d, 1"-H), 7.24 (d, quinoline), 7.54 (ddd, quinoline), 7.69 (ddd, quinoline), 8.00 (br d, quinoline), 8.10 (br d, quinoline), 8.81 (d, quinoline), 9.61 (s, CHO).

Example 57

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is 3-(quinolin-4-yl)propyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom (a) In the same manner as in Example 24(a), 16 mg of a double bond-reduced compound (compound represented by the formula (25) mentioned in Preparation Scheme 8 wherein $R_2$ is hydrogen atom, $R_3$ is methyl group, one of $R_7$ and $R_8$ is 3-(quinolin-4-yl)propyl group, the other is hydrogen atom, $R_{11}$ and $R_{12}$ are hydrogen atoms, $R_{3''}$ is hydrogen atom, $R_{4''}$ is propionyl group, and X is oxygen atom), and 11 mg of a quinoline-reduced compound (compound represented by the formula (25) mentioned in Preparation Scheme 8 wherein $R_2$ is hydrogen atom, $R_3$ is methyl group, one of $R_7$ and $R_8$ is 3-(1,2,3,4-tetrahydroquinolin-4-yl)propyl group, the other is hydrogen atom, $R_{11}$ and $R_{12}$ are hydrogen atoms, $R_{3''}$ is hydrogen atom, $R_{4''}$ is propionyl group, and X is oxygen atom) were obtained from 66 mg of the compound of Example 54(d).

Physicochemical Properties of the Double Bond-reduced Compound (1) Molecular formula: $C_{54}H_{87}N_3O_{16}$ (2) Mass spectrum (FAB): m/z 1034 $(M+H)^+$ (3) Specific rotation: $[\alpha]_D^{21}$ −47° (c0.8, $CHCl_3$)

(4) $^1H$ NMR spectrum (300 MHz, $CDCl_3$) δ (ppm): 0.84 (d, 8-$CH_3$), 0.89 (m, 7-H), 1.02 (t, 3-$OCOCH_2CH_3$), 1.10 (d, 6"-H), 1.11 (s, 3"-$CH_3$), 1.17 (t, 4"-$OCOCH_2CH_3$), 1.24 (d, 6'-H), 1.82 (dd, 2"-Hax), 1.99 (d, 2"-Heq), 2.49 (s, $NCH_3$), 2.49 (s, 3'-$N(CH_3)_2$), 2.62 (m, 2-H), 2.67 (m, 13-H), 3.17 (s, $CH(OCH_3)_2$), 3.25 (m, 4'-H), 3.26 (m, 5'-H), 3.52 (s, 4-$OCH_3$), 3.58 (dd, 2'-H), 3.82 (br d, 5-H), 4.37 (d, 1'-H), 4.46 (dq, 5"-H), 4.60 (d, 4"-H), 5.06 (d, 1"-H), 5.76 (br dd, 3-H), 7.22 (d, quinoline), 7.54 (ddd, quinoline), 7.69 (ddd, quinoline), 8.01 (br d, quinoline), 8.10 (br d, quinoline), 8.78 (d, quinoline).

Physicochemical Properties of the Quinoline-reduced Compound (1) Molecular formula: $C_{54}H_{91}N_3O_{16}$ (2) Mass spectrum (FAB): m/z 1038 $(M+H)^+$ (3) Specific rotation: $[\alpha]_D^{22}$ −47° (c0.5, $CHCl_3$)

(4) $^1H$ NMR spectrum (300 MHz, $CDCl_3$) δ (ppm): 0.85 (d, 8-$CH_3$), 1.08 (t, 3-$OCOCH_2CH_3$), 1.11 (s, 3"-$CH_3$), 1.12 (d, 6"-H), 1.17 (t, 4]-$OCOCH_2CH_3$), 1.26 (d, 6'-H), 1.82 (dd, 2"-Hax), 2.00 (d, 2"-Heq), 2.30 (s, $NCH_3$), 2.50 (s, 3'-$N(CH_3)_2$), 2.64 (m, 2-H), 3.16 (s, $CH(OCH_3)_2$), 3.24 (s, $CH(OCH_3)_2$), 3.28 (m, 4'-H), 3.28 (m, 5'-H), 3.60 (dd, 2'-H), 3.63 (s, 4-$OCH_3$), 3.86 (br d, 5-H), 4.04 (m, 9-H), 4.40 (d, 1'-H), 4.48 (dq, 5"-H), 4.61 (d, 4"-H), 5.07 (d, 1"-H), 5.73 (m, 3-H), 6.46 (d, quinoline), 6.59 (t, quinoline), 6.95 (t, quinoline), 6.94 (d, quinoline).

(b) In the same manner as in Example 2(d), 6.8 mg of the title compound was obtained from 16 mg of the double bond-reduced compound of Example 57(a).

Physicochemical Properties of this Compound (1) Molecular formula: $C_{52}H_{81}N_3O_{15}$ (2) Mass spectrum (FAB): m/z 988 $(M+H)^+$ (3) Specific rotation: $[\alpha]_D^{19}$ −47° (c0.3, $CHCl_3$)

(4) $^1H$ NMR spectrum (300 MHz, $CDCl_3$) δ (ppm): 0.88 (d, 8-$CH_3$), 1.07 (t, 3-$OCOCH_2CH_3$), 1.11 (s, 3"-$CH_3$), 1.11 (d, 6"-H), 1.17 (t, 4"-$OCOCH_2CH_3$), 1.25 (d, 6'-H), 1.82 (dd, 2"-Hax), 2.00 (d, 2"-Heq), 2.50 (s, 3'-$N(CH_3)_2$), 2.65 (m, 2-H), 3.26 (m, 4'-H), 3.26 (m, 5'-H), 3.56 (dd, 2'-H), 3.61 (s, 4-$OCH_3$), 3.80 (br d, 5-H), 4.34 (d, 1'-H), 4.46 (m, 5"-H), 4.61 (d, 4"-H), 5.07 (d, 1"-H), 5.82 (m, 3-H), 7.23 (d, quinoline), 7.55 (ddd, quinoline), 7.70 (ddd, quinoline), 8.02 (br d, quinoline), 8.11 (br d, quinoline), 8.79 (d, quinoline), 9.60 (s, CHO).

Example 58

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is 3-(quinolin-4-yl)propyl group, the other is hydrogen atom, $R_9$, $R_{10}$, $R_{11}$ and $R_{12}$ are hydrogen atoms, $R_{4'}$ is hydrogen atom, and X is oxygen atom In the same manner as in Example 2(d), 3.5 mg of the title compound was obtained from 16 mg of the double bond-reduced compound of Example 57(a).

Physicochemical Properties of this Compound (1) Molecular formula: $C_{42}H_{65}N_3O_{11}$ (2) Mass spectrum (FAB): m/z 788 $(M+H)^+$ (3) Specific rotation: $[\alpha]_D^{20}$ +62° (c0.2, $CHCl_3$)

(4) $^1$H NMR spectrum (300 MHz, $CDCl_3$) δ (ppm): 0.87 (d, 8-$CH_3$), 1.08 (t, 3-$OCOCH_2CH_3$), 1.23 (dd, 13-$CH_2CH_2$), 1.28 (d, 6'-H), 2.49 (s, 3'-$N(CH_3)_2$), 2.66 (m, 2-H), 3.33 (m, 5'-H), 3.56 (dd, 2'-H), 3.62 (s, 4-$OCH_3$), 3.81 (br d, 5-H), 4.34 (d, 1'-H), 5.81 (br dd, 3-H), 7.23 (d, quinoline), 7.55 (ddd, quinoline), 7.70 (ddd, quinoline), 8.02 (br d, quinoline), 8.11 (br d, quinoline), 8.79 (d, quinoline), 9.61 (s, CHO).

Example 59

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is 3-(1,2,3,4-tetrahydroquinolin-4-yl)propyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom (a) In the same manner as in Example 8(e), except that methanol was used instead of ethanol, 7.6 mg of a methylated compound (compound represented by the formula (25) mentioned in Preparation Scheme 8 wherein $R_2$ is hydrogen atom, $R_3$ is methyl group, one of $R_7$ and $R_8$ is 3-(1-methyl-1,2,3,4-tetrahydroquinolin-4-yl)propyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 11 mg of the quinoline-reduced compound Example 57(a).

Physicochemical Properties of this Compound (1) Molecular formula: $C_{55}H_{93}N_3O_{16}$ (2) Mass spectrum (FAB): m/z 1052 $(M+H)^+$ (3) Specific rotation: $[\alpha]_D^{19}$ −45° (c0.4, $CHCl_3$)

(4) $^1$H NMR spectrum (300 MHz, $CDCl_3$) δ (ppm): 0.85 (d, 8-$CH_3$), 1.08 (t, 3-$OCOCH_2CH_3$), 1.11 (s, 3"-$CH_3$), 1.12 (d, 6"-H), 1.17 (t, 4"-$OCOCH_2CH_3$), 1.26 (d, 6'-H), 1.82 (dd, 2"-Hax), 2.00 (d, 2"-Heq), 2.29 (s, 11-$NCH_3$), 2.50 (s, 3'-$N(CH_3)_2$), 2.64 (m, 2-H), 2.88 (s, $NCH_3$), 3.16 (s, $CH(OCH_3)_2$), 3.24 (s, $CH(OCH_3)_2$), 3.27 (m, 4'-H), 3.30 (m, 5'-H), 3.60 (dd, 2'-H), 3.63 (s, 4-$OCH_3$), 3.71 (m, quinoline-$CH_2$), 3.85 (br d, 5-H), 4.41 (d, 1'-H), 4.48 (dq, 5"-H), 4.61 (d, 4"-H), 5.07 (d, 1"-H), 5.73 (m, 3-H), 6.58 (d, quinoline), 6.60 (t, quinoline), 6.96 (d, quinoline), 7.07 (t, quinoline).

(b) In the same manner as in Example 2(d), 3.6 mg of the title compound was obtained from 7.6 mg of the compound of Example 59(a).

Physicochemical Properties of this Compound (1) Molecular formula: $C_{53}H_{87}N_3O_{15}$ (2) Mass spectrum (FAB): m/z 1006 $(M+H)^+$ (3) Specific rotation: $[\alpha]_D^{21}$ −6.1° (c0.2, $CHCl_3$)

(4) $^1$H NMR spectrum (300 MHz, $CDCl_3$) δ (ppm): 1.03 (d, 8-$CH_3$), 1.11 (t, 3-$OCOCH_2CH_3$), 1.11 (s, 3"-$CH_3$), 1.12 (d, 6"-H), 1.17 (t, 4"-$OCOCH_2CH_3$), 1.22 (d, 6'-H), 1.83 (dd, 2"-Hax), 2.00 (d, 2"-Heq), 2.50 (s, 11-$NCH_3$), 2.50 (s, 3'-$N(CH_3)_2$), 2.69 (m, 2-H), 2.88 (s, $NCH_3$), 3.27 (m, 4'-H), 3.27 (m, 5'-H), 3.60 (s, 4-$OCH_3$), 3.80 (br d, 5-H), 4.34 (d, 1'-H), 4.46 (dq, 5"-H), 4.61 (d, 4"-H), 5.07 (d, 1"-H), 5.78 (m, 3-H), 6.58 (d, quinoline), 6.59 (t, quinoline), 6.96 (d, quinoline), 7.07 (t, quinoline), 9.63 (s, CHO).

Example 60

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is trans-3-(quinolin-4-yl)-1-propenyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom, provided that the substituents $R_7$ and $R_8$ are exchanged compared with the compound of Example 54

(a) In the same manner as in Example 48(b), 454 mg of a cyclized compound (compound represented by the formula (24) mentioned in Preparation Scheme 8 wherein $R_3$ is methyl group, one of $R_7$ and $R_8$ is allyl group, the other is hydrogen atom, $R_{11}$ and $R_{12}$ are hydrogen atoms, $R_3$ is hydrogen atom, $R_4$ is propionyl group, and X is oxygen atom, provided that the substituents $R_7$ and $R_8$ are exchanged compared with the compound of Example 54(b)) was obtained from 862 mg of the isomer B of Example 54(a).

Physicochemical Properties of this Compound (1) Molecular formula: $C_{49}H_{84}N_2O_{18}$ (2) Mass spectrum (FAB): m/z 989 $(M+H)^+$ (3) Specific rotation: $[\alpha]_D^{19}$ −68° (c0.3, $CHCl_3$)

(4) $^1$H NMR spectrum (300 MHz, $CDCl_3$) δ (ppm): 0.94 (d, 8-$CH_3$), 1.11 (s, 3"-$CH_3$), 1.12 (d, 6"-H), 1.12 (t, 3-$OCOCH_2CH_3$), 1.17 (t, 4"-$OCOCH_2CH_3$), 1.26 (d, 6'-H), 1.84 (dd, 2"-Hax), 1.95 (br dd, 13-H), 2.01 (d, 2"-Heq), 2.03 (s, 9-$OCOCH_3$), 2.05 (s, 2'-$OCOCH_3$), 2.25 (s, $NCH_3$), 2.41 (s, 3'-$N(CH_3)_2$), 2.53 (dd, 10-H), 2.69 (m, 2-H), 2.72 (t, 3'-H), 3.13 (s, $CH(OCH_3)_2$), 3.24 (s, $CH(OCH_3)_2$), 3.33 (m, 4'-H), 3.34 (br d, 4-H), 3.35 (m, 5'-H), 3.54 (s, 4-$OCH_3$), 3.89 (br d, 5-H), 4.16 (m, 15-H), 4.38 (dq, 5"-H), 4.49 (dd, $CH(OCH_3)_2$), 4.61 (d, 4"-H), 4.72 (d, 1'-H), 5.07 (d, 1"-H),), 5.23 (br dd, 3-H), 5.72 (ddd, $CH{=}CH_2$).

(b) In the same manner as in Example 48(c), 102 mg of a trans-isomer of a coupling compound (compound represented by the formula (24) mentioned in Preparation Scheme 8 wherein $R_3$ is methyl group, one of $R_7$ and $R_8$ is trans-3-(quinolin-4-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom, provided that the substituents $R_7$ and $R_8$ are exchanged compared with the trans-isomer of the coupling compound of Example 54(c)), and 13 mg of a cis-isomer of a coupling compound (compound represented by the formula (24) mentioned in Preparation Scheme 8 wherein $R_3$ is methyl group, one of $R_7$ and $R_8$ is cis-3-(quinolin-4-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom, provided that the substituents $R_7$ and $R_8$ are exchanged compared with the cis-isomer of the coupling compound of Example 54(c)) were obtained from 232 mg of the compound of Example 60(a).

Physicochemical Properties of the Trans-isomer (1) Molecular formula: $C_{58}H_{89}N_3O_{18}$ (2) Mass spectrum (FAB): m/z 1116 $(M+H)^+$ (3) Specific rotation: $[\alpha]_D^{17}$-29° (c1.3, $CHCl_3$)

(4) $^1$H NMR spectrum (300 MHz, $CDCl_3$) δ (ppm): 0.93 (d, 8-$CH_3$), 1.11 (s, 3"-$CH_3$), 1.11 (t, 3-$OCOCH_2CH_3$), 1.12 (d, 6"-H), 1.17 (t, 4"-$OCOCH_2CH_3$), 1.26 (d, 6'-H), 1.83 (dd, 2"-Hax), 1.92 (s, 9-$OCOCH_3$), 1.99 (s, 2'-$OCOCH_3$), 2.01 (d, 2"-Heq), 2.25 (s, $NCH_3$), 2.39 (s, 3'-$N(CH_3)_2$), 2.66

(m, 2-H), 2.70 (t, 3'-H), 3.11 (s, $CH(OCH_3)_2$), 3.23 (s, $CH(OCH_3)_2$), 3.32 (m, 4'-H), 3.34 (m, 5'-H), 3.51 (s, 4-$OCH_3$), 3.80 (br d, quinoline-$CH_2$), 3.90 (br d, 5-H), 4.10 (m, 15-H), 4.17 (m, 15-H), 4.26 (br s, 3"-OH), 4.37 (dq, 5"-H), 4.49 (dd, $CH(OCH_3)_2$), 4.61 (d, 4"-H), 4.70 (d, 1'-H), 4.96 (m, 9-H), 4.99 (dd, 2'-H), 5.06 (d, 1"-H), 5.24 (br dd, 3-H), 5.50 (dd, 13-CH), 5.65 (dt, CH═CH), 7.24 (d, quinoline), 7.55 (ddd, quinoline), 7.70 (ddd, quinoline), 8.02 (br d, quinoline), 8.09 (br d, quinoline), 8.81 (d, quinoline).

Physicochemical Properties of the Cis-isomer (1) Molecular formula: $C_{58}H_{89}N_3O_{18}$ (2) Mass spectrum (FAB): m/z 1116 $(M+H)^+$ (3) Specific rotation: $[\alpha]_D^{18}$ −32° (c0.3, $CHCl_3$)

(4) $^1H$ NMR spectrum (300 MHz, $CDCl_3$) δ (ppm): 0.95 (d, 8-$CH_3$), 1.11 (s, 3"-$CH_3$), 1.11 (t, 3-$OCOCH_2CH_3$), 1.12 (d, 6"-H), 1.17 (t, 4"-$OCOCH_2CH_3$), 1.26 (d, 6'-H), 1.83 (dd, 2"-Hax), 1.93 (s, 9-$OCOCH_3$), 1.96 (d, 2"-Heq), 2:00 (s, 2'-$OCOCH_3$), 2.23 (s, $NCH_3$), 2.38 (s, 3'-$N(CH_3)_2$), 2.52 (dd, 10-H), 2.59 (dd, 2-H), 2.70 (t, 3'-H), 2.82 (m, 13-H), 3.13 (s, $CH(OCH_3)_2$), 3.23 (s, $CH(OCH_3)_2$), 3.25 (br d, 4-H), 3.31 (m, 4'-H), 3.33 (m, 5'-H), 3.87 (m, quinoline-$CH_2$), 4.11 (m, 15-H), 4.24 (m, 15-H), 4.36 (dq, 5"-H), 4.50 (dd, $CH(OCH_3)_2$), 4.61 (d, 4"-H), 4.69 (d, 1'-H), 4.98 (dd, 2'-H), 5.06 (d, 1"-H), 5.25 (br dd, 3-H), 5.53 (dd, 13-CH), 5.70 (dt, CH═CH), 7.27 (d, quinoline), 7.56 (ddd, quinoline), 7.71 (ddd, quinoline), 8.04 (br d, quinoline), 8.11 (br d, quinoline), 8.81 (d, quinoline).

(c) In the same manner as in Example 54(b), 43 mg of a deacetyled compound (compound represented by the formula (25) mentioned in Preparation Scheme 8 wherein $R_2$ is hydrogen atom, $R_3$ is methyl group, one of $R_7$ and $R_8$ is trans-3-(quinolin-4-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom, provided that the substituents $R_7$ and $R_8$ are exchanged compared with the compound of Example 54(d)) was obtained from 151 mg of the trans-isomer of the coupling compound of Example 60(b).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{20}$ −37° (c0.9, $CHCl_3$)

(4) $^1H$ NMR spectrum (300 MHz, $CDCl_3$) δ (ppm): 0.97 (d, 8-$CH_3$), 1.08 (d, 6"-H), 1.11 (s, 3"-$CH_3$), 1.11 (t, 3-$OCOCH_2CH_3$), 1.17 (t, 4"-$OCOCH_2CH_3$), 1.24 (d, 6'-H), 1.83 (dd, 2"-Hax), 2.00 (d, 2"-Heq), 2.27 (s, $NCH_3$), 2.50 (s, 3'-$N(CH_3)_2$), 2.63 (m, 2-H), 3.12 (s, $CH(OCH_3)_2$), 3.24 (s, $CH(OCH_3)_2$), 3.28 (m, 4'-H), 3.31 (m, 5'-H), 3.48 (br d, 4-H), 3.55 (s, 4-$OCH_3$), 3.83 (br d, quinoline-$CH_2$), 3.89 (br d, 5-H), 3.97 (m, 15-H), 4.25 (m, 15-H), 4.46 (dq, 5"-H), 4.47 (d, 1'-H), 4.61 (d, 4"-H), 5.07 (d, 1"-H), 5.35 (br dd, 3-H), 5.49 (dd, 13-CH), 5.65 (dt, CH═CH), 7.26 (d, quinoline), 7.53 (ddd, quinoline), 7.69 (ddd, quinoline), 8.04 (br d, quinoline), 8.10 (br d, quinoline), 8.81 (d, quinoline).

(d) In the same manner as in Example 2(d), 6.8 mg of the title compound was obtained from 26 mg of the compound of Example 60(c).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{19}$ −46° (c0.3, $CHCl_3$)

(4) $^1H$ NMR spectrum (300 MHz, $CDCl_3$) δ (ppm): 1.02 (d, 8-$CH_3$), 1.08 (d, 6"-H), 1.11 (s, 3"-$CH_3$), 1.14 (t, 3-$OCOCH_2CH_3$), 1.17 (t, 4"-$OCOCH_2CH_3$), 1.24 (d, 6'-H), 1.83 (dd, 2"-Hax), 2.00 (d, 2"-Heq), 2.51 (s, 3'-$N(CH_3)_2$), 3.28 (m, 4'-H), 3.28 (m, 5'-H), 3.55 (s, 4-$OCH_3$), 4.43 (d, 1'-H), 4.45 (dq, 5"-H), 4.61 (d, 4"-H), 5.06 (d, 1"-H), 5.41 (m, 3-H), 5.51 (dd, 13-CH), 5.79 (dt, CH═CH), 7.25 (d, quinoline), 7.54 (ddd, quinoline), 7.69 (ddd, quinoline), 8.04 (br d, quinoline), 8.04 (br d, quinoline), 8.10 (d, quinoline), 9.63 (s, CHO).

Example 61

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is trans-3-(quinolin-4-yl)-1-propenyl group, the other is hydrogen atom, $R_9$, $R_{10}$, $R_{11}$ and $R_{12}$ are hydrogen atoms, $R_4$ is hydrogen atom, and X is oxygen atom, provided that the substituents $R_7$ and $R_8$ are exchanged compared with the compound of Example 55

In the same manner as in Example 2(d), 4.0 mg of the title compound was obtained from 26 mg of the compound of Example 60(c).

Physicochemical Properties of this Compound (1) Molecular formula: $C_{42}H_{63}N_3O_{11}$ (2) Mass spectrum (FAB): m/z 786 $(M+H)^+$ (3) Specific rotation: $[\alpha]_9^{D1}$ +20° (c0.2, $CHCl_3$)

(4) $^1H$ NMR spectrum (300 MHz, $CDCl_3$) δ (ppm): 1.01 (d, 8-$CH_3$), 1.14 (t, 3-$OCOCH_2CH_3$), 1.23 (d, 6'-H), 1.41 (m, 8-H), 1.54 (m, 7-H), 2.63 (s, 3'-$N(CH_3)_2$), 2.96 (dd, 6-$CH_2$), 3.15 (t, 4'-H), 3.30 (dq, 5'-H), 3.54 (s, 4-$OCH_3$), 3.88 (m, quinoline-$CH_2$), 3.95 (m, 15-H), 4.26 (m, 15-H), 4.45 (d, 1'-H), 5.39 (m, 3-H), 5.40 (dd, 13-CH), 5.86 (dt, CH═CH), 7.30 (d, quinoline), 7.54 (ddd, quinoline), 7.69 (ddd, quinoline), 8.07 (dd, quinoline), 8.10 (dd, quinoline), 8.81 (d, quinoline), 9.65 (s, CHO).

Example 62

Preparation method of the compound represented by the formula (3) wherein $R_1$ is propionyl group, $R_2$ is acetyl group, $R_3$ is methyl group, $R_5$ and $R_6$ are hydrogen atoms, E is a group represented by the formula (b), one of $R_7$ and $R_8$ is cis-3-(quinolin-4-yl)-1-propenyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom, provided that the substituents $R_7$ and $R_8$ are exchanged compared with the compound of Example 56

(a) In the same manner as in Example 54(b), 5.5 mg of a deacetyled compound (compound represented by the formula (25) mentioned in Preparation Scheme 8 wherein $R_2$ is acetyl group, $R_3$ is methyl group, one of $R_7$ and $R_8$ is cis-3-(quinolin-4-yl)-1-propenyl group, the other is hydrogen atom, $R_{11}$ and $R_{12}$ are hydrogen atoms, $R_3$ is hydrogen atom, $R_{4''}$ is propionyl group, and X is oxygen atom, provided that the substituents $R_7$ and $R_8$ are exchanged compared with the compound of Example 56 (a)) was obtained from 18 mg of the cis-isomer of the coupling compound of Example 60(b).

Physicochemical Properties of this Compound (1) Molecular formula: $C_{56}H_{87}N_3O_{17}$ (2) Mass spectrum (FAB): m/z 1074 $(M+H)^+$ (3) $^1H$ NMR spectrum (300 MHz, $CDCl_3$) δ (ppm): 0.97 (d, 8-$CH_3$), 1.06 (d, 6"-H), 1.11 (s, 3"-$CH_3$), 1.17 (t, 3-$OCOCH_2CH_3$), 1.23 (t, 4"-$OCOCH_2CH_3$), 1.24 (d, 6'-H), 1.83 (dd, 2"-Hax), 1.96 (d, 2"-Heq), 2.05 (s, 9-$OCOCH_3$), 2.50 (s, 3'-$N(CH_3)_2$), 2.70 (m, 2-H), 3.25 (s, $CH(OCH_3)_2$), 3.27 (s, $CH(OCH_3)_2$), 3.29 (m, 5'-H), 3.42 (br d, 4-H), 3.57 (s, 4-$OCH_3$), 3.92 (br d, 5-H), 4.17 (m, 15-H), 4.33 (m, 15-H), 4.45 (d, 1'-H), 4.47 (dq, 5"-H), 4.61 (d, 4"-H), 5.07 (d, 1"-H), 5.27 (m, 3-H), 5.37 (dd, 13-CH), 5.83 (dt, CH═CH), 7.40 (d, quinoline), 7.55 (ddd, quinoline), 7.71 (ddd, quinoline), 8.09 (br d, quinoline), 8.09 (br d, quinoline), 8.82 (d, quinoline).

(b) In the same manner as in Example 2(d), 2.1 mg of the title compound was obtained from 5.5 mg of the compound of Example 62(a).

Physicochemical Properties of this Compound (1) Molecular formula: $C_{54}H_{51}N_3O_{16}$ (2) Mass spectrum (FAB): m/z 1028 $(M+H)^+$ (3) Specific rotation: $[\alpha]_D^{19}$ −23° (c0.1, $CHCl_3$)

(4) $^1H$ NMR spectrum (300 MHz, $CDCl_3$) δ (ppm): 0.98 (d, 8-$CH_3$), 1.12 (s, 3"-$CH_3$), 1.13 (d, 6"-H), 1.17 (t, 3-$OCOCH_2CH_3$), 1.23 (t, 4"-$OCOCH_2CH_3$), 1.24 (d, 6'-H), 1.84 (dd, 2"-Hax), 1.96 (d, 2"-Heq), 2.03 (s, 9-$OCOCH_3$), 2.75 (m, 2-H), 3.60 (s, 4-$OCH_3$), 3.93 (m, 15-H), 4.20 (m, 15-H), 4.41 (dq, 5"-H), 4.62 (d, 4"-H), 5.07 (d, 1"-H), 5.43 (m, 3-H), 5.61 (dd, 13-CH), 5.99 (dt, CH═CH), 7.18 (d, quinoline), 7.52 (ddd, quinoline), 7.69 (ddd, quinoline), 8.10 (br d, quinoline), 8.10 (br d, quinoline), 8.82 (d, quinoline), 9.62 (s, CHO).

Example 63

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is 3-(quinolin-4-yl)propyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_4$ is propionyl group, and X is oxygen atom, provided that the substituents $R_7$ and $R_8$ are exchanged compared with the compound of Example 57

(a) In the same manner as in Example 24(a), 10 mg of a double bond-reduced compound (compound represented by the formula (25) mentioned in Preparation Scheme 8 wherein $R_2$ is hydrogen atom, $R_3$ is methyl group, one of $R_7$ and $R_8$ is 3-(quinolin-4-yl)propyl group, the other is hydrogen atom, $R_{11}$ and $R_{12}$ are hydrogen atoms, $R_{3''}$ is hydrogen atom, $R_4$ is propionyl group, and X is oxygen atom, provided that the substituents $R_7$ and $R_8$ are exchanged compared with the compound of Example 57(a)) was obtained from 16 mg of the compound of Example 60(c).

Physicochemical Properties of this Compound (1) Molecular formula: $C_{54}H_{87}N_3O_{16}$ (2) Mass spectrum (FAB): m/z 1034 $(M+H)^+$ (3) Specific rotation: $[\alpha]_D^{20}$ −40° (c0.5, $CHCl_3$)

(4) $^1H$ NMR spectrum (300 MHz, $CDCl_3$) δ (ppm): 0.98 (m, 7-H), 1.08 (d, 8-$CH_3$), 1.10 (d, 6"-H), 1.11 (s, 3"-$CH_3$), 1.17 (t, 3-$OCOCH_2CH_3$), 1.23 (t, 4"-$OCOCH_2CH_3$), 1.24 (d, 6'-H), 1.83 (dd, 2"-Hax), 2.00 (d, 2"-Heq), 2.50 (s, 3'-$N(CH_3)_2$), 2.63 (dd, 2-H), 3.12 (s, $CH(OCH_3)_2$), 3.24 (s, $CH(OCH_3)_2$), 3.28 (m, 4'-H), 3.31 (m, 5'-H), 3.52 (s, 4-$OCH_3$), 3.85 (br d, 5-H), 4.01 (m, 15-H), 4.25 (m, 15-H), 4.45 (d, 1'-H), 4.48 (dq, 5"-H), 4.61 (d, 4"-H), 5.07 (d, 1"-H), 5.31 (m, 3-H), 7.26 (d, quinoline), 7.56 (ddd, quinoline), 7.69 (ddd, quinoline), 8.10 (br d, quinoline), 8.10 (br d, quinoline), 8.79 (d, quinoline).

(b) In the same manner as in Example 2(d), 3.2 mg of the title compound was obtained from 10 mg of the compound of Example 63(a).

Physicochemical Properties of this Compound (1) Molecular formula: $C_{52}H_{81}N_3O_{15}$ (2) Mass spectrum (FAB): m/z 988 $(M+H)^+$ (3) Specific rotation: $[\alpha]_D^{21}$ −48° (c0.2, $CHCl_3$)

(4) $^1H$ NMR spectrum (300 MHz, $CDCl_3$) δ (ppm): 1.12 (s, 3"-H), 1.14 (d, 6"-H), 1.16 (d, 8-$CH_3$), 1.17 (d, 6'-H), 1.17 (t, 3-$OCOCH_2CH_3$), 1.24 (t, 4"-$OCOCH_2CH_3$), 1.83 (dd, 2"-Hax), 2.01 (d, 2"-Heq), 2.52 (s, 3'-$N(CH_3)_2$), 2.64 (dd, 2-H), 3.27 (m, 4'-H), 3.27 (m, 5'-H), 3.50 (dd, 2'-H), 3.52 (s, 4-$OCH_3$), 3.82 (br d, 5-H), 4.03 (m, 15-H), 4.22 (m, 15-H), 4.43 (d, 1'-H), 4.44 (dq, 5"-H), 4.62 (d, 4"-H), 5.06 (d, 1"-H), 5.27 (m, 3-H), 7.32 (d, quinoline), 7.57 (ddd, quinoline), 7.69 (ddd, quinoline), 8.10 (br d, quinoline), 8.10 (br d, quinoline), 8.80 (d, quinoline), 9.63 (s, CHO).

Example 64

Preparation method of the compound represented by the formula (3) wherein $R_1$ is propionyl group, $R_2$ is hydrogen atom, $R_3$ is 4-phenylbutyl group, $R_5$, $R_6$, $R_{11}$ and $R_{12}$ is hydrogen atom, E is a group represented by the formula (b), $R_7$, $R_8$, $R_9$ and $R_{10}$ is hydrogen atom, $R_{4'}$ is a group represented by the formula (a), $R_{3''}$ is acetyl group, $R_{4''}$ is propionyl group, and X is NH group (a) In the same manner as in Example 4(a), except that 324 mg of the compound of Reference Example 19 was used instead of the compound of Reference Example 3, 426 mg of an azide compound (compound represented by the formula (23) mentioned in Preparation Scheme 8 wherein $R_3$ is 4-phenylbutyl group, $R_7$, $R_8$, $R_{11}$ and $R_{12}$ are hydrogen atoms, $R_{3''}$ is acetyl group, $R_{4''}$ is propionyl group, and X is azido group) was obtained from 658 mg of the compound of Example 1.

Physicochemical Properties of this Compound (1) Molecular formula: $C_{57}H_{93}N_5O_{19}$ (2) Mass spectrum (FAB): m/z 1152 $(M+H)^+$ (3) Specific rotation: $[\alpha]_D^{24}$ −66° (c0.51, $CHCl_3$)

(4) $^1H$ NMR spectrum (300 MHz, $CDCl_3$) δ (ppm): 0.79 (d, 8-$CH_3$), 1.00 (d, 6"-H), 1.09 (t, 3-$OCOCH_2CH_3$), 1.12 (t, 4"-$OCOCH_2CH_3$), 1.12 (d, 6'-H), 1.18 (m, 7-H), 1.34 (s, 3"-$CH_3$), 1.60 (dd, 2"-Hax), 1.92 (s, 3"-$OCOCH_3$), 1.96 (s, 9-$OCOCH_3$), 1.96 (s, 2'-$OCOCH_3$), 2.36 (s, 3'-$N(CH_3)_2$), 3.05 (t, 4'-H), 3.11 (d, 2"-Heq), 3.17 (s, $CH(OCH_3)_2$), 3.19 (s, $CH(OCH_3)_2$), 3.24 (t, 15-H), 3.41 (br d, 4-H), 3.48 (s, 4-$OCH_3$), 3.82 (br d, 5-H), 4.41 (dq, 5"-H), 4.49 (d, 4"-H), 4.63 (d, 1'-H), 4.73 (d, 1"-H), 4.88 (dd, 2'-H), 5.04 (br dd, 3-H), 5.10 (br d, 9-H), 7.08-7.15 (m, $C_6H_5$), 7.19-7.24 (m, $C_6H_5$).

(b) In the same manner as in Example 7(b), 131 mg of an azide-reduced compound (compound represented by the formula (23) mentioned in Preparation Scheme 8 wherein $R_3$ is 4-phenylbutyl group, $R_7$, $R_8$, $R_{11}$ and $R_{12}$ are hydrogen atoms, $R_{3''}$ is acetyl group, $R_{4''}$ is propionyl group, and X is amino group) was obtained from 353 mg of the compound of Example 64(a).

Physicochemical Properties of this Compound (1) Molecular formula: $C_{57}H_{95}N_3O_{19}$ (2) Mass spectrum (FAB): m/z 1126 $(M+H)^+$ (3) Specific rotation: $[\alpha]_D^{23}$ −55° (c0.80, $CHCl_3$)

(4) $^1H$ NMR spectrum (300 MHz, $CDCl_3$) δ (ppm): 0.81 (d, 8-$CH_3$), 0.99 (d, 6"-H), 1.02 (t, 3-$OCOCH_2CH_3$), 1.11 (d, 6'-H), 1.11 (t, 4"-$OCOCH_2CH_3$), 1.33 (s, 3"-$CH_3$), 1.58 (dd, 2"-Hax), 1.77 (m, 6-$CH_2$), 1.90 (s, 3"-$OCOCH_3$), 1.93 (s, 9-$OCOCH_3$), 1.94 (s, 2'-$OCOCH_3$), 2.35 (s, 3'-$N(CH_3)_2$), 3.04 (t, 4'-H), 3.06 (s, $CH(OCH_3)_2$), 3.11 (d, 2"-Heq), 3.17 (s, $CH(OCH_3)_2$), 3.49 (s, 4-$OCH_3$), 3.56 (br d, 4-H), 3.84 (br d, 5-H), 4.40 (m, 5"-H), 4.49 (d, 4"-H), 4.68 (d, 1'-H), 4.72 (d, 1"-H), 4.87 (dd, 2'-H), 5.07 (m, 3-H), 5.09 (m, 9-H), 7.07-7.12 (m, $C_6H_5$), 7.17-7.22 (m, $C_6H_5$).

(c) In the same manner as in Example 4 (c), 54.8 mg of a cyclized compound (compound represented by the formula (24) mentioned in Preparation Scheme 8 wherein $R_3$ is 4-phenylbutyl group, $R_7$, $R_8$, $R_{11}$ and $R_{12}$ are hydrogen atoms, $R_{3''}$ is acetyl group, $R_{4''}$ is propionyl group, and X is NH group) was obtained from 131 mg of the compound of Example 64(b).

Physicochemical Properties of this Compound (1) Molecular formula: $C_{57}H_{93}N_3O_{18}$ (2) Mass spectrum (FAB): m/z 1108 $(M+H)^+$ (3) Specific rotation: $[\alpha]_D^{24}$ −73° (c0.46, $CHCl_3$)

(4) $^1H$ NMR spectrum (300 MHz, $CDCl_3$) δ (ppm): 0.84 (d, 8-$CH_3$), 0.99 (d, 6"-H), 1.06 (t, 3-$OCOCH_2CH_3$), 1.11 (t, 4"-$OCOCH_2CH_3$), 1.12 (d, 6'-H), 1.33 (s, 3"-$CH_3$), 1.59 (dd, 2"-Hax), 1.93 (s, 3"-$OCOCH_3$), 1.94 (s, 9-$OCOCH_3$), 1.95 (s, 2'-$OCOCH_3$), 2.35 (s, 3'-$N(CH_3)_2$), 2.67 (dd, 2-H), 2.87 (br dd, 15-H), 3.03 (s, $CH(OCH_3)_2$), 3.05 (t, 4'-H), 3.11 (d, 2"-Heq), 3.17 (s, $CH(OCH_3)_2$), 3.41 (br d, 4-H), 3.58 (s, 4-$OCH_3$), 3.85 (br d, 5-H), 4.40 (dq, 5"-H), 4.48 (d, 4"-H), 4.62 (d, 1'-H), 4.72 (d, 1"-H), 4.80 (m, 3-H), 4.85 (m, 9-H), 4.89 (dd, 2'-H), 6.40 (br d, NH), 7.05-7.09 (m, $C_6H_5$), 7.16-7.20 (m, $C_6H_5$).

(d) In the same manner as in Example 2(c), 46.5 mg of a deacetyled compound (compound represented by the formula (25) mentioned in Preparation Scheme 8 wherein $R_2$ is hydrogen atom, $R_3$ is 4-phenylbutyl group, $R_7$, $R_8$, $R_{11}$ and $R_{12}$ are hydrogen atoms, $R_{3''}$ is acetyl group, $R_{4''}$ is propionyl group, and X is NH group) was obtained from 54.8 mg of the compound of Example 64(c).

Physicochemical Properties of this Compound (1) Molecular formula: $C_{53}H_{89}N_3O_{16}$ (2) Mass spectrum (FAB): m/z 1024 $(M+H)^+$ (3) Specific rotation: $[\alpha]_D^{25}$ −55° (c0.64, $CHCl_3$)

(4) $^1H$ NMR spectrum (300 MHz, $CDCl_3$) δ (ppm): 0.79 (d, 8-$CH_3$), 1.01 (d, 6"-H), 1.06 (t, 3-$OCOCH_2CH_3$), 1.12 (t, 4"-$OCOCH_2CH_3$), 1.13 (d, 6'-H), 1.34 (s, 3"-$CH_3$), 1.61 (dd, 2"-Hax), 1.75 (m, 6-$CH_2$), 1.94 (s, 3"-$OCOCH_3$), 2.30 (t, 3'-H), 2.46 (s, 3'-$N(CH_3)_2$), 2.55 (t, $C_6H_5(CH_2)_4$), 2.68 (dd, 2-H), 3.07 (s, $CH(OCH_3)_2$), 3.10 (t, 4'-H), 3.15 (d, 2"-Heq), 3.19 (s, $CH(OCH_3)_2$), 3.39 (dd, 2'-H), 3.70 (s, 4-$OCH_3$), 3.82 (br d, 5-H), 4.48 (m, 5"-H), 4.49 (m, 4"-H), 4.76 (d, 1"-H), 5.25 (br dd, 3-H), 7.08-7.13 (m, $C_6H_5$), 7.18-7.24 (m, $C_6H_5$).

(e) In the same manner as in Example 2(d), 44.3 mg of the title compound was obtained from 46.5 mg of the compound of Example 64(d).

Physicochemical Properties of this Compound (1) Molecular formula: $C_{51}H_{83}N_3O_{15}$ (2) Mass spectrum (FAB): m/z 978 $(M+H)^+$ (3) Specific rotation: $[\alpha]_D^{24}$ −66° (c0.45, $CHCl_3$)

(4) $^1H$ NMR spectrum (300 MHz, $CDCl_3$) δ (ppm): 0.78 (d, 8-$CH_3$), 1.01 (d, 6"-H), 1.07 (d, 6'-H), 1.11 (t, 3-$OCOCH_2CH_3$), 1.12 (t, 4"-$OCOCH_2CH_3$), 1.27 (m, 8-H), 1.34 (s, 3"-$CH_3$), 1.61 (dd, 2"-Hax), 1.94 (s, 3"-$OCOCH_3$), 2.47 (s, 3'-$N(CH_3)_2$), 2.55 (t, $C_6H_5(CH_2)_4$), 2.72 (dd, 2-H), 2.83 (dd, 6-$CH_2$), 3.10 (m, 4'-H), 3.13 (m, 5'-H), 3.14 (d, 2"-Heq), 3.33 (dd, 2'-H), 3.64 (s, 4-$OCH_3$), 3.71 (br d, 4-H), 3.81 (br d, 5-H), 4.33 (d, 1'-H), 4.45 (dq, 5"-H), 4.51 (d, 4"-H), 4.77 (d, 1"-H), 5.35 (br dd, 3-H), 6.35 (br d, NH), 7.08-7.12 (m, $C_6H_5$), 7.18-7.23 (m, $C_6H_5$), 9.59 (s, CHO).

Example 65

Preparation method of the compound represented by the formula (3) wherein $R_1$ is propionyl group, $R_2$ is hydrogen atom, $R_3$ is methyl group, $R_5$ and $R_6$ are hydrogen atoms, one of $R_{11}$ and $R_{12}$ is methyl group, the other is hydrogen atom, E is a group represented by the formula (b), $R_7$, $R_8$, $R_9$ and $R_{10}$ are hydrogen atoms, $R_{4'}$ is a group represented by the formula (a), $R_{3''}$ is hydrogen atom, $R_{4''}$ is propionyl group, and X is NH group (a) In the same manner as in Example 4(a), except that 24.8 mg of the compound of Reference Example 20 was used instead of the compound of Reference Example 3, 23.4 mg of an azide compound (compound represented by the formula (23) mentioned in Preparation Scheme 8 wherein $R_3$ is methyl group, $R_7$ and $R_8$ are hydrogen atoms, one of $R_{11}$ and $R_{12}$ is methyl group, the other is hydrogen atom, $R_{3''}$ is hydrogen atom, $R_{4''}$ is propionyl group, and X is azido group) was obtained as an about 1:1 mixture (measured according to intensities of specific signals) from 50.4 mg of the compound of Example 19.

Physicochemical Properties of this Compound (1) Molecular formula: $C_{47}H_{83}N_5O_{18}$ (2) Mass spectrum (FAB): m/z 1006 $(M+H)^+$ (3) Specific rotation: $[\alpha]_D^{23}$ −56° (c0.66, $CHCl_3$)

(4) $^1H$ NMR spectrum (300 MHz, $CDCl_3$) δ (ppm): 0.80 (d, 8-$CH_3$), 1.04 (s, 3"-$CH_3$), 1.04 (d, 6"-H), 1.07 (t, 3-$OCOCH_2CH_3$), 1.10 (t, 4"-$OCOCH_2CH_3$), 1.19 (d, 6'-H), 1.20 (d, 15-$CH_3$), 1.38 (m, 14-H), 1.42 (m, 6-$CH_2$), 1.76 (dd, 2"-Hax), 1.93 (d, 2"-Heq), 1.97 (s, 9-$OCOCH_3$), 1.97 (s, 2'-$OCOCH_3$), 2.32 (s, 3'-$N(CH_3)_2$), 2.50 (dd, 2-H), 2.84 (d, 10-H), 3.16 (s, $CH(OCH_3)_2$), 3.19 (s, $CH(OCH_3)_2$), 3.24 (dq, 5'-H), 3.38 (br d, 4-H), 3.47 (s, 4-$OCH_3$), 3.83 (br d, 5-H), 4.30 (dq, 5"-H), 4.51 (dd, $CH(OCH_3)_2$), 4.53 (d, 4"-H), 4.66 (d, 1'-H), 4.91 (dd, 2'-H), 4.99 (d, 1"-H), 5.03 (m, 3-H), 5.07 (m, 9-H).

(b) In the same manner as in Example 7(b), 164 mg of an azide-reduced compound (compound represented by the formula (23) mentioned in Preparation Scheme 8 wherein $R_3$ is methyl group, $R_7$ and $R_8$ are hydrogen atoms, one of $R_{11}$ and $R_{12}$ is methyl group, the other is hydrogen atom, $R_{3''}$ is hydrogen atom, $R_{4''}$ is propionyl group, and X is amino group) was obtained as an about 1:1 mixture (measured according to intensities of specific signals) from 291 mg of the compound of Example 65(a).

Physicochemical Properties of this Compound (1) Molecular formula: $C_{47}H_{85}N_3O_{18}$ (2) Mass spectrum (FAB): m/z 980 $(M+H)^+$ (3) Specific rotation: $[\alpha]_D^{23}$ −49° (c0.82, $CHCl_3$)

(4) $^1H$ NMR spectrum (300 MHz, $CDCl_3$) δ (ppm): 0.81 (d, 8-$CH_3$), 1.01 (t, 3-$OCOCH_2CH_3$), 1.03 (s, 3"-$CH_3$), 1.04 (d, 6"-H), 1.09 (t, 4"-$OCOCH_2CH_3$), 1.17 (d, 15-$CH_3$), 1.17 (d, 6'-H), 1.75 (dd, 2"-Hax), 1.93 (d, 2"-Heq), 2.32 (s, 3'-$N(CH_3)_2$), 3.05 and 3.06 (each s, $CH(OCH_3)_2$), 3.16 (s, $CH(OCH_3)_2$), 3.23 (m, 4'-H), 3.26 (m, 5'-H), 3.49 (s, 4-$OCH_3$), 3.85 and 3.87 (each br d, 5-H), 4.29 (m, 5"-H), 4.53 (d, 4"-H), 4.70 and 4.71 (each d, 1'-H), 4.90 (dd, 2'-H), 4.98 (d, 1"-H), 5.09 (m, 3-H), 5.12 (m, 9-H).

(c) In the same manner as in Example 4(c), 54.5 mg of an isomer A of a cyclized compound (compound represented by the formula (24) mentioned in Preparation Scheme 8 wherein $R_3$ is methyl group, $R_7$ and $R_8$ are hydrogen atoms, one of $R_{11}$ and $R_{12}$ is methyl group, the other is hydrogen atom, $R_{3''}$ is hydrogen atom, $R_{4''}$ is propionyl group, and X is NH group), and 43.4 mg of an isomer B of a cyclized compound (compound represented by the formula (24) mentioned in Preparation Scheme 8 wherein $R_3$ is methyl group, $R_7$ and $R_8$ are hydrogen atoms, one of $R_{11}$ and $R_{12}$ is methyl group, the other is hydrogen atom, $R_{3''}$ is hydrogen atom, $R_{4''}$ is propionyl group, and X is NH group, provided that the substituents $R_{11}$ and $R_{12}$ are exchanged compared with the isomer A) were obtained from 164 mg of the compound of Example 65(b).

Physicochemical Properties of the Isomer A (1) Molecular formula: $C_{47}H_{83}N_3O_{17}$ (2) Mass spectrum (FAB): m/z 962 $(M+H)^+$ (3) Specific rotation: $[\alpha]_D^{21}$ −50° (c0.59, $CHCl_3$)

(4) $^1H$ NMR spectrum (300 MHz, $CDCl_3$) δ (ppm): 0.84 (d, 8-$CH_3$), 1.04 (s, 3"-$CH_3$), 1.05 (d, 6"-H), 1.05 (d, 15-$CH_3$), 1.06 (t, 3-$OCOCH_2CH_3$), 1.10 (t, 4"-$OCOCH_2CH_3$), 1.25 (d, 6'-H), 1.27 (br dd, 7-H), 1.43 (m, 13-H), 1.76 (dd, 2"-Hax), 1.89 (d, 2"-Heq), 1.97 (s, 9-$OCOCH_3$), 1.99 (s, 2'-$OCOCH_3$), 2.15 (s, $NCH_3$), 2.33 (s, 3'-$N(CH_3)_2$), 2.47 (dd, 12-H), 2.65 (t, 3'-H), 2.75 (dd, 2-H), 3.03 (s, $CH(OCH_3)_2$), 3.17 (s, $CH(OCH_3)_2$), 3.27 (t, 5'-H), 3.61 (s, 4-$OCH_3$), 3.62 (br d, 4-H), 3.91 (br d, 5-H), 3.98 (ddq, 15-H), 4.30 (dq, 5"-H), 4.51 (ddq, 15-H), 4.54 (d, 4"-H), 4.69 (d, 1'-H), 4.77 (m, 3-H), 4.81 (m, 9-H), 4.93 (dd, 2'-H), 5.00 (d, 1"-H), 5.83 (br d, NH).

Physicochemical Properties of the Isomer B (1) Molecular formula: $C_{47}H_{83}N_3O_{17}$ (2) Mass spectrum (FAB): m/z 962 $(M+H)^+$ (3) $^1H$ NMR spectrum (300 MHz, $CDCl_3$) δ (ppm): 0.88 (d, 8-$CH_3$), 1.04 (s, 3"-$CH_3$), 1.07 (t, 3-$OCOCH_2CH_3$), 1.08 (t, 4"-$OCOCH_2CH_3$), 1.25 (d, 6'-H), 1.82 (dd, 2"-Hax), 1.92 (d, 2"-Heq), 1.99 (s, 9-$OCOCH_3$), 1.99 (s, 2'-$OCOCH_3$), 2.36 (s, 3'-$N(CH_3)_2$), 2.42 (dd, 2-H), 2.56 (dd, 2-H), 2.81 (t, 3'-H), 3.16 (s, $CH(OCH_3)_2$), 3.21 (s, $CH(OCH_3)_2$), 3.83 (br d, 5-H), 3.98 (ddq, 15-H), 4.33 (dq, 5"-H), 4.50 (d, 4"-H), 4.70 (d, 1'-H), 4.91 (dd, 2'-H), 5.02 (d, 1"-H).

(d) In the same manner as in Example 2(c), 40.2 mg of a deacetyled compound (compound represented by the formula (25) mentioned in Preparation Scheme 8 wherein $R_2$ is hydrogen atom, $R_3$ is methyl group, $R_7$ and $R_8$ are hydrogen atoms, one of $R_{11}$ and $R_{12}$ is methyl group, the other is hydrogen atom, $R_{3''}$ is hydrogen atom, $R_{4''}$ is propionyl group, and X is NH group) was obtained from 54.5 mg of the isomer A of Example 65(c).

Physicochemical Properties of this Compound (1) Molecular formula: $C_{43}H_{79}N_3O_{15}$ (2) Mass spectrum (FAB): m/z 878 $(M+H)^+$ (3) Specific rotation: $[\alpha]_D^{21}$ −41° (c0.47, $CHCl_3$)

(4) $^1H$ NMR spectrum (300 MHz, $CDCl_3$) δ (ppm): 0.75 (d, 8-$CH_3$), 1.05 (t, 3-$OCOCH_2CH_3$), 1.05 (s, 3"-$CH_3$), 1.06 (d, 6"-H), 1.07 (d, 15-$CH_3$), 1.11 (t, 4"-$OCOCH_2CH_3$), 1.25 (d, 6'-H), 1.30 (br dd, 8-H), 1.53 (m, 7-H), 1.70 (m, 7-H), 1.76 (dd, 2"-Hax), 1.94 (d, 2"-Heq), 2.23 (s, $NCH_3$), 2.44 (s, 3'-$N(CH_3)_2$), 2.57 (dd, 12-H), 2.74 (dd, 2-H), 3.06 (s, $CH(OCH_3)_2$), 3.19 (s, $CH(OCH_3)_2$), 3.54 (dd, 2'-H), 3.69 (s, 4-$OCH_3$), 3.90 (m, 15-H), 4.41 (dq, 5"-H), 4.55 (d, 4"-H), 5.01 (d, 1"-H), 5.25 (m, 3-H), 5.71 (br d, NH).

(e) In the same manner as in Example 2(d), 19.6 mg of the title compound was obtained from 40.2 mg of the compound of Example 65(d).

Physicochemical Properties of this Compound (1) Molecular formula: $C_{41}H_{73}N_3O_{14}$ (2) Mass spectrum (FAB): m/z 832 $(M+H)^+$ (3) Specific rotation: $[\alpha]_D^{20}$ −52° (c0.45, $CHCl_3$)

(4) $^1H$ NMR spectrum (300 MHz, $CDCl_3$) δ (ppm): 0.79 (d, 8-$CH_3$), 1.05 (s, 3"-$CH_3$), 1.06 (d, 6"-H), 1.07 (d, 15-$CH_3$), 1.07 (t, 3-$OCOCH_2CH_3$), 1.11 (t, 4"-$OCOCH_2CH_3$), 1.14 (d, 6'-H), 1.78 (dd, 2"-Hax), 1.93 (d, 2"-Heq), 2.25 (s, $NCH_3$), 2.44 (s, 3'-$N(CH_3)_2$), 2.76 (dd, 6-$CH_2$), 2.81 (dd, 2-H), 3.49 (dd, 2'-H), 3.67 (s, 4-$OCH_3$), 3.83 (br d, 5-H), 3.93 (m, 15-H), 3.96 (br d, 4-H), 4.32 (d, 1'-H), 4.40 (dq, 5"-H), 4.54 (d, 4"-H), 5.00 (d, 1"-H), 5.31 (m, 3-H), 5.73 (br d, NH), 9.59 (s, CHO).

Example 66

Preparation method of the compound represented by the formula (3) wherein $R_1$ is propionyl group, $R_2$ is hydrogen atom, $R_3$ is methyl group, $R_5$ and $R_6$ are hydrogen atoms, one of $R_{11}$ and $R_{12}$ is methyl group, the other is hydrogen atom, E is a group represented by the formula (b), $R_7$, $R_8$, $R_9$ and $R_{10}$ are hydrogen atoms, $R_{4'}$ is hydrogen atom, and X is NH group In the same manner as in Example 2(d), 9.9 mg of the title compound was obtained from 40.2 mg of the compound of Example 65(d).

Physicochemical Properties of this Compound (1) Molecular formula: $C_{31}H_{57}N_3O_{10}$ (2) Mass spectrum (FAB): m/z 632 $(M+H)^+$ (3) Specific rotation: $[\alpha]_D^{22}$ −13° (c0.50, $CHCl_3$)

(4) $^1H$ NMR spectrum (300 MHz, $CDCl_3$) δ (ppm): 0.79 (d, 8-$CH_3$), 1.06 (d, 15-$CH_3$), 1.10 (t, 3-$OCOCH_2CH_3$), 1.19 (d, 6'-H), 1.23 (m, 8-H), 1.51 (br dd, 7-H), 2.24 (s, $NCH_3$), 2.44 (s, 3'-$N(CH_3)_2$), 2.77 (dd, 2-H), 2.85 (dd, 6-$CH_2$), 2.94 (t, 4'-H), 3.48 (dd, 2'-H), 3.68 (s, 4-$OCH_3$), 3.85 (br d, 5-H), 3.93 (m, 15-H), 3.94 (br d, 4-H), 4.33 (d, 1'-H), 5.31 (br d, 3-H), 5.76 (br d, NH), 9.61 (s, CHO).

Example 67

Preparation method of the compound represented by the formula (3) wherein $R_1$ is propionyl group, $R_2$ is hydrogen atom, $R_3$ is methyl group, $R_5$ and $R_6$ are hydrogen atoms, one of $R_{11}$ and $R_{12}$ is methyl group, the other is hydrogen atom, E is a group represented by the formula (b), $R_7$, $R_8$, $R_9$ and $R_{10}$ are hydrogen atoms, $R_{4'}$ is a group represented by the formula (a), $R_{3''}$ is hydrogen atom, $R_{4''}$ is propionyl group, and X is NH group, provided that the substituents $R_{11}$ and $R_{12}$ are exchanged compared with the compound of Example 65

(a) In the same manner as in Example 2(c), 27.8 mg of a deacetyled compound (compound represented by the formula (25) mentioned in Preparation Scheme 8 wherein $R_2$ is hydrogen atom, $R_3$ is methyl group, $R_7$ and $R_8$ are hydrogen atoms, one of $R_{11}$ and $R_{12}$ is methyl group, the other is hydrogen atom, $R_{3''}$ is hydrogen atom, $R_{4''}$ is propionyl group, and X is NH group, provided that the substituents $R_{11}$ and $R_{12}$ are exchanged compared with the compound of Example 65(d)) was obtained from 43.4 mg of the isomer B of Example 65(c).

Physicochemical Properties of this Compound (1) Molecular formula: $C_{43}H_{79}N_3O_{15}$ (2) Mass spectrum (FAB): m/z 878 $(M+H)^+$ (3) Specific rotation: $[\alpha]_D^{22}$ −64° (c0.36, $CHCl_3$)

(4) $^1H$ NMR spectrum (300 MHz, $CDCl_3$) δ (ppm): 0.89 (d, 8-$CH_3$), 1.03 (s, 3"-$CH_3$), 1.04 (d, 15-$CH_3$), 1.04 (d, 6"-H), 1.07 (t, 3-$OCOCH_2CH_3$), 1.10 (t, 4"-$OCOCH_2CH_3$), 1.18 (d, 6'-H), 1.75 (dd, 2"-Hax), 1.84 (m, 6-$CH_2$), 1.92 (d, 2"-Heq), 2.18 (dd, 10-H), 2.25 (s, $NCH_3$), 2.41 (s, 3'-$N(CH_3)_2$), 2.49 (dd, 10-H), 2.58 (dd, 2-H), 2.71 (m, 12-H), 3.19 (s, $CH(OCH_3)_2$), 3.27 (br d, 4-H), 3.35 (m, 9-H), 3.47 (s, 4-$OCH_3$), 3.51 (dd, 2'-H), 3.72 (br d, 5-H), 3.82 (m, 15-H), 4.22 (d, 1'-H), 4.35 (dd, $CH(OCH_3)_2$), 4.40 (dq, 5"-H), 4.53 (d, 4"-H), 4.99 (d, 1"-H), 5.21 (br dd, 3-H), 5.51 (br d, NH).

(b) In the same manner as in Example 2(d), 14.5 mg of the title compound was obtained from 27.8 mg of the compound of Example 67(a).

Physicochemical Properties of this Compound (1) Molecular formula: $C_{41}H_{73}N_3O_4$ (2) Mass spectrum (FAB): m/z 832 $(M+H)^+$ (3) Specific rotation: $[\alpha]_D^{18}$ −57° (c0.73, $CHCl_3$)

(4) $^1H$ NMR spectrum (300 MHz, $CDCl_3$) δ (ppm): 0.86 (br dd, 7-H), 0.90 (d, 8-$CH_3$), 1.04 (s, 3"-$CH_3$), 1.05 (d, 6"-H), 1.07 (d, 15-$CH_3$), 1.09 (t, 3-$OCOCH_2CH_3$), 1.10 (t, 4"-$OCOCH_2CH_3$), 1.14 (d, 6'-H), 1.75 (dd, 2"-Hax), 1.84 (br dd, 7-H), 1.93 (d, 2"-Heq), 2.27 (s, $NCH_3$), 2.42 (s, 3'-N$(CH_3)_2$), 2.54 (dd, 10-H), 2.59 (dd, 2-H), 2.70 (m, 12-H), 2.80 (dd, 6-$CH_2$), 3.18 (m, 4'-H), 3.18 (m, 5'-H), 3.33 (ddd, 9-H), 3.41 (br d, 4-H), 3.48 (s, 4-$OCH_3$), 3.77 (dd, 5-H), 3.80 (m, 15-H), 4.24 (d, 1'-H), 4.39 (dq, 5"-H), 4.54 (d, 4"-H), 4.99 (d, 1"-H), 5.38 (br dd, 3-H), 5.61 (br d, NH), 9.60 (s, CHO).

Example 68

Preparation method of the compound represented by the formula (24) mentioned in Preparation Scheme 8 wherein $R_3$ is methyl group, $R_7$, $R_8$ and $R_{11}$ are hydrogen atoms, $R_{12}$ is allyl group, $R_{3''}$ is hydrogen atom, $R_{4''}$ is propionyl group, and X is oxygen atom (a) In the same manner as in Example 2(a), except that the compound of Reference Example 17 was used instead of the compound of Reference Example 1, 520 mg of an amine compound (compound represented by the formula (23) mentioned in Preparation Scheme 8 wherein $R_3$ is methyl group, $R_7$, $R_8$ and $R_{11}$ are hydrogen atoms, $R_{12}$ is allyl group, $R_{3''}$ is hydrogen atom, $R_{4''}$ is propionyl group, and X is hydroxyl group) was obtained from 619 mg of the compound of Example 19.

Physicochemical Properties of this Compound (1) Molecular formula: $C_{49}H_{86}N_2O_{19}$ (2) Mass spectrum (FAB): m/z 1007 $(M+H)^+$ (3) Specific rotation: $[\alpha]_D^{20}$ −54.4° (c1.12, $CHCl_3$)

(4) $^1H$ NMR spectrum (300 MHz, $CDCl_3$) δ (ppm): 0.86 (d, 8-$CH_3$), 1.10 (s, 3"-$CH_3$), 1.11 (d, 6"-H), 1.13 (t, 3-$OCOCH_2CH_3$), 1.16 (t, 4"-$OCOCH_2CH_3$), 1.25 (d, 6'-H), 1.82 (dd, 2"-Hax), 2.00 (d, 2"-Heq), 2.03 (s, 9-$OCOCH_3$), 2.03 (s, 2'-$OCOCH_3$), 2.21 (m, 15-$CH_2$), 2.39 (s, 3'-$N(CH_3)_2$), 2.51 (s, $NCH_3$), 2.71 (t, 3'-H), 2.75 (dd, 2-H), 2.98 (dd, 10-H), 3.20 (s, $CH(OCH_3)_2$), 3.24 (s, $CH(OCH_3)_2$), 3.29 (m, 4'-H), 3.32 (m, 5'-H), 3.47 (br d, 4-H), 3.53 (s, 4-$OCH_3$), 3.68 (m, 15-H), 3.88 (br d, 5-H), 4.37 (dq, 5"-H), 4.54 (dd, $CH(OCH_3)_2$), 4.60 (d, 4"-H), 4.73 (d, 1'-H), 4.97 (dd, 2'-H), 5.04 (d, $CH{=}CH_2$), 5.05 (d, 1"-H), 5.13 (m, 9-H), 5.18 (br t, 3-H), 5.79 (m, 15-$CH_2CH$).

(b) In the same manner as in Example 48(b), 367 mg of the title compound was obtained from 520 mg of the compound of Example 68(a).

The mass spectrum (FAB) and $^1H$ NMR spectrum (300 MHz, $CDCl_3$) of this compound were corresponded to those of the isomer B of Example 48 (b).

Example 69

Preparation method of ($3R_4S$,5S,$6R_8R_9R$)-9-acetoxy-5-[2-O-acetyl-4-O-(4-O-n-butyryl-2,6-dideoxy-3-C-methyl-3-O-propionyl-α-L-ribo-hexopyranosyl)-3,6-dideoxy-3-dimethylamino-β-D-glucopyranosyl]-6-(2,2-dimethoxyethyl)-3-hydroxy-4-methoxy-8-methyl-10-oxo-3-propionyloxydecanoic acid (compound represented by the formula (4) wherein $R_1$ is hydrogen atom, $R_2$ is acetyl group, $R_{2'}$ is acetyl group, $R_{3''}$ is propionyl group, $R_{4''}$ is n-butyryl group, Y is formyl group, and Z is dimethoxymethyl group)

(a) In an amount of 1.79 g of 9-O-acetyl-rokitamycin (J. Antibiot., 34, 1011, 1981) was added with 27 ml of methanol and 23 ml of methyl orthoformate, dissolved therein, added with 672 mg of pyridinium paratoluenesulfonate, and stirred at 50° C. for 3 days. The reaction mixture was concentrated under reduced pressure, then added with 55 ml of ethyl acetate, successively washed three times with 30 ml of water, with 30 ml of saturated aqueous sodium hydrogen-carbonate, and with 30 ml of saturated brine. The organic layer was dried over anhydrous sodium sulfate, and filtered, and then the filtrate was concentrated under reduced pressure. The resulting residue was purified by flush silica gel column chromatography (chloroform/methanol (80:1 to 70:1)) to obtain 1.12 g of 9-O-acetyl-rokitamycin 18-dimethyl acetal.

Physicochemical Properties of this Compound (1) Molecular formula: $C_{46}H_{77}NO_{17}$ (2) Mass spectrum (FAB): m/z 916 $(M+H)^+$ (3) Specific rotation: $[\alpha]_D^{20}$ −53° (c1.0, $CHCl_3$)

(4) $^1H$ NMR spectrum (300 MHz, $CDCl_3$) δ (ppm): 0.91 (br dd, 7-H), 0.98 (t, 4"-$OCOCH_2CH_2CH_3$), 0.99 (d, 19-H), 1.09 (d, 6"-H), 1.12 (t, 3"-$OCOCH_2CH_3$), 1.22 (d, 6'-H), 1.30 (d, 16-H), 1.42 (s, 3"-$CH_3$), 1.56 (br dd, 7-H), 1.70 (m, 4"-$OCOCH_2CH_2CH_3$), 1.82 (br dd, 17-H), 2.00 (s, 9-$OCOCH_3$), 2.11 (br dd, 14-H), 2.22 (br d, 2-H), 2.38 (t, 4"-$OCOCH_2CH_2CH_3$), 2.49 (br d, 14-H), 2.53 (s, 3'-$N(CH_3)_2$), 2.68 (dd, 2-H), 3.06 (br d, 4-H), 3.19 (m, 4'-H), 3.21 (m, 5'-H), 3.23 (d, 2"-Heq), 3.33 (s, $CH(OCH_3)_2$), 3.41 (dd, 2'-H), 3.42 (s, $CH(OCH_3)_2$), 3.53 (s, 4-$OCH_3$), 3.75 (br d, 3-H), 4.12 (br d, 5-H), 4.53 (d, 1'-H), 4.54 (dq, 5"-H), 4.59 (d, 4"-H), 4.84 (d, 1"-H), 5.28 (m, 15-H), 5.35 (dd, 9-H), 5.59 (dd, 10-H), 5.65 (br dd, 13-H), 6.01 (dd, 12-H), 6.36 (dd, 11-H).

(b) Acetylation was performed in the same manner as in Example 1(a) to obtain 959 mg of 9,2'-di-O-acetyl-rokitamycin 18-dimethyl acetal (compound represented by the formula (6) mentioned in Preparation Scheme 1 wherein $R_1$ is hydrogen atom, $R_2$ is acetyl group, $R_{13}$ is methyl group, $R_{3''}$ is propionyl group, and $R_{4''}$ is n-butyryl group) from 1.05 g of the compound of Example 69(a).

Physicochemical Properties of this Compound (1) Molecular formula: $C_{48}H_{79}NO_{18}$ (2) Mass spectrum (FAB): m/z 958 $(M+H)^+$ (3) Specific rotation: $[\alpha]_D^{21}$ −84° (c1.0, $CHCl_3$)

(4) $^1$H NMR spectrum (300 MHz, $CDCl_3$) δ (ppm): 0.80 (br dd, 7-H), 0.98 (t, 4"-$OCOCH_2CH_2CH_3$), 0.99 (d, 19-H), 1.07 (d, 6"-H), 1.13 (t, 3"-$OCOCH_2CH_3$), 1.20 (d, 6'-H), 1.30 (d, 16-H), 1.42 (s, 3"-$CH_3$), 1.49 (br dd, 7-H), 1.67 (dd, 2"-Hax), 1.69 (m, 4"-$OCOCH_2CH_2CH_3$), 1.99 (s, 9-$OCOCH_3$), 2.03 (s, 2'-$OCOCH_3$), 2.06 (br dd, 14-H), 2.19 (br d, 2-H), 2.38 (t, 4"-$OCOCH_2CH_2CH_3$), 2.42 (s, 3'-N$(CH_3)_2$), 2.57 (t, 3'-H), 2.66 (dd, 2-H), 2.96 (br d, 4-H), 3.11 (t, 4'-H), 3.19 (d, 2"-Heq), 3.20 (dq, 5'-H), 3.31 (s, $CH(OCH_3)_2$), 3.41 (s, $CH(OCH_3)_2$), 3.47 (s, 4-$OCH_3$), 3.74 (br d, 3-H), 4.07 (br d, 5-H), 4.47 (dq, 5"-H), 4.57 (d, 4"-H), 4.71 (d, 1'-H), 4.80 (d, 1"-H), 4.95 (dd, 2'-H), 5.28 (m, 15-H), 5.36 (dd, 9-H), 5.58 (dd, 10-H), 5.64 (br dd, 13-H), 5.97 (dd, 12-H), 6.37 (dd, 11-H).

(c) A tetraol was prepared in the same manner as in Example 1(a) to obtain 1.26 g of 9,2'-di-O-acetyl-10,11,12,13-tetrahydro-10,11,12,13-tetrahydroxyrokitamycin 18-dimethyl acetal (compound represented by the formula (7) mentioned in Preparation Scheme 1 wherein $R_1$ is hydrogen atom, $R_2$ is acetyl group, $R_{13}$ is methyl group, $R_{3''}$ is propionyl group, and $R_{4''}$ is n-butyryl group) was obtained from 1.99 g of the compound of Example 69(b).

Physicochemical Properties of this Compound (1) Molecular formula: $C_{48}H_{83}NO_{22}$ (2) Mass spectrum (FAB): m/z 1026 $(M+H)^+$ (3) Specific rotation: $[\alpha]_D^{21}$ −93° (c1.0, $CHCl_3$)

(4) $^1$H NMR spectrum (300 MHz, $CDCl_3$) δ (ppm): 0.98 (t, 4"-$OCOCH_2CH_2CH_3$), 1.08 (d, 6"-H), 1.16 (t, 3"-$OCOCH_2CH_3$), 1.23 (d, 6'-H), 1.30 (d, 16-H), 1.42 (s, 3"-$CH_3$), 1.70 (m, 4"-$OCOCH_2CH_2CH_3$), 2.05 (s, 9-$OCOCH_3$), 2.14 (s, 2'-$OCOCH_3$), 2.29 (q, 3"-$OCOCH_2CH_3$), 2.37 (t, 4"-$OCOCH_2CH_2CH_3$), 2.43 (s, 3'-N$(CH_3)_2$), 2.48 (br d, 2-H), 2.59 (t, 3'-H), 2.69 (dd, 2-H), 3.15 (t, 4'-H), 3.21 (d, 2"-Heq), 3.23 (dq, 5'-H), 3.30 (s, $CH(OCH_3)_2$), 3.40 (s, $CH(OCH_3)_2$), 3.51 (s, 4-$OCH_3$), 3.89 (br d, 5-H), 4.25 (br dd, 3-H), 4.49 (dq, 5"-H), 4.58 (d, 4"-H), 4.83 (d, 1"-H), 4.95 (dd, 2'-H), 5.03 (br d, 9-H).

(d) In the same manner as in Example 1(b), (−)-(1R)-1-methyl-3-oxopropyl (3R4S,5S,6R8R9R)-9-acetoxy-5-[2-O-acetyl-4-O-(4-O-n-butyryl-2,6-dideoxy-3-C-methyl-3-O-propionyl-α-L-ribo-hexopyranosyl)-3,6-dideoxy-3-dimethylamino-β-D-glucopyranosyl]-6-(2,2-dimethoxyethyl)-3-hydroxy-4-methoxy-8-methyl-10-oxodecanoate (compound represented by the formula (8) mentioned in Preparation Scheme 1 wherein $R_1$ is hydrogen atom, $R_2$ is acetyl group, $R_{13}$ is methyl group, $R_{3''}$ is propionyl group, and $R_{4''}$ is n-butyryl group) was obtained from 1 g of the compound of Example 69(c). This compound was treated in the same manner as in Example 1(c) to obtain 327 mg of the title compound.

Physicochemical Properties of this Compound (1) Molecular formula: $C_{47}H_{71}NO_{19}$ (2) Mass spectrum (FAB): m/z 894 $(M+H)^+$ (3) $^1$H NMR spectrum (300 MHz, $CDCl_3$) δ (ppm): 0.97 (t, 4"-$OCOCH_2CH_2CH_3$), 1.02 (d, 8-$CH_3$), 1.07 (d, 6"-H), 1.15 (t, 3"-$OCOCH_2CH_3$), 1.21 (d, 6'-H), 1.42 (s, 3"-$CH_3$), 1.70 (m, 4"-$OCOCH_2CH_2CH_3$), 2.05 (s, 9-$OCOCH_3$), 2.18 (s, 2'-$OCOCH_3$), 2.29 (q, 3"-$OCOCH_2CH_3$), 2.37 (t, 4"-$OCOCH_2CH_2CH_3$), 2.43 (s, 3'-N$(CH_3)_2$), 2.60 (t, $C_6H_5(CH_2)_3$), 2.67 (dd, 2-H), 3.13 (t, 4'-H), 3.20 (d, 2"-Heq), 3.31 (s, $CH(OCH_3)_2$), 3.50 (s, 4-$OCH_3$), 3.90 (br d, 5-H), 4.14 (m, 3-H), 4.49 (dq, 5"-H), 4.57 (d, 4"-H), 4.60 (d, 1'-H), 4.81 (d, 1"-H), 4.92 (m, 9-H), 4.94 (dd, 2'-H), 9.55 (s, CHO).

Example 70

Preparation method of the compound represented by the formula (3) wherein $R_1$ and $R_2$ are hydrogen atoms, $R_3$ is 3-(quinolin-4-yl)propyl group, $R_5$ and $R_6$ are hydrogen atoms, E is a group represented by the formula (b), $R_7$, $R_8$, $R_9$, $R_{10}$ and $R_{11}$ are hydrogen atoms, $R_{12}$ is methyl group, $R_4$ is a group represented by the formula (a), $R_{3''}$ is propionyl group, $R_{4''}$ is n-butyryl group, and X is oxygen atom (a) In the same manner as in Example 2(a), except that sodium cyanoborohydride was used instead of sodium borohydride, and the compound of Reference Example 21 was used instead of the compound of Reference Example 1, 40 mg of an amine compound (compound represented by the formula (30) mentioned in Preparation Scheme 10 wherein $R_3$ is 3-(quinolin-4-yl)propyl group, $R_7$, $R_8$ and $R_{11}$ are hydrogen atoms, $R_{12}$ is methyl group, $R_{3''}$ is propionyl group, $R_{4''}$ is n-butyryl group, and X is hydroxyl group) was obtained from 50 mg of the compound of Example 69.

Physicochemical Properties of this Compound (1) Molecular formula: $C_{59}H_{95}N_3O_{19}$ (2) Mass spectrum (FAB): m/z 1150 $(M+H)^+$ (3) Specific rotation: $[\alpha]_D^{25}$ −80° (c1.0, $CHCl_3$)

(4) $^1$H NMR spectrum (300 MHz, $CDCl_3$) δ (ppm): 0.86 (d, 8-$CH_3$), 0.98 (t, 4"-$OCOCH_2CH_2CH_3$), 1.07 (d, 6"-H), 1.13 (d, $CH_3CHOH$), 1.16 (t, 3"-$OCOCH_2CH_3$), 1.21 (d, 6'-H), 1.41 (s, 3"-$CH_3$), 1.70 (m, 4"-$OCOCH_2CH_2CH_3$), 1.99 (s, 9-$OCOCH_3$), 2.03 (s, 2'-$OCOCH_3$), 2.38 (t, 4"-$OCOCH_2CH_2CH_3$), 2.41 (s, 3'-N$(CH_3)_2$), 2.59 (m, 3'-H), 2.68 (dd, 2-H), 3.32 (s, $CH(OCH_3)_2$), 3.32 (s, $CH(OCH_3)_2$), 3.47 (s, 4-$OCH_3$), 3.76 (m, $CH_3CHOH$), 3.91 (br d, 5-H), 4.02 (br dd, 3-H), 4.47 (dq, 5"-H), 4.57 (d, 4"-H), 4.59 (d, 1'-H), 4.80 (d, 1"-H), 4.93 (dd, 2'-H), 5.14 (m, 9-H), 7.25 (br d, quinoline), 7.58 (ddd, quinoline), 7.71 (ddd, quinoline), 8.02 (br d, quinoline), 8.11 (br d, quinoline), 8.80 (d, quinoline).

(b) In the same manner as in Example 2(b), 69 mg of a cyclized compound (compound represented by the formula (31) mentioned in Preparation Scheme 10 wherein $R_3$ is 3-(quinolin-4-yl)propyl group, $R_7$, $R_8$ and $R_{11}$ are hydrogen atoms, $R_{12}$ is methyl group, $R_{3''}$ is propionyl group, $R_{4''}$ is n-butyryl group, and X is oxygen atom) was obtained from 168 mg of the compound of Example 70(a).

Physicochemical Properties of this Compound (1) Molecular formula: $C_{59}H_{93}N_3O_{18}$ (2) Mass spectrum (FAB): m/z 1132 $(M+H)^+$ (3) Specific rotation: $[\alpha]_D^{25}$ −83° (c0.70, $CHCl_3$)

(4) $^1$H NMR spectrum (300 MHz, $CDCl_3$) δ (ppm): 0.97 (d, 8-$CH_3$), 0.98 (t, 4"-$OCOCH_2CH_2CH_3$), 1.07 (d, 6"-H), 1.15 (t, 3"-$OCOCH_2CH_3$), 1.20 (d, 6'-H), 1.24 (d, 15-$CH_3$), 1.42 (s, 3"-$CH_3$), 2.04 (s, 9-$OCOCH_3$), 2.05 (s, 2'-$OCOCH_3$), 2.38 (t, 4"-$OCOCH_2CH_2CH_3$), 2.43 (s, 3'-N$(CH_3)_2$), 2.59 (t, 3'-H), 2.68 (dd, 2-H), 3.13 (t, 4'-H), 3.21 (d, 2"-Heq), 3.32 (s, $CH(OCH_3)_2$), 3.36 (s, $CH(OCH_3)_2$), 3.50 (s, 4-$OCH_3$), 3.98 (br d, 5-H), 4.26 (m, 3-H), 4.49 (dq, 5"-H), 4.57 (d, 4"-H), 4.64 (d, 1'-H), 4.81 (d, 1"-H), 4.96 (dd, 2'-H), 4.99 (m, 15-H), 5.12 (m, 9-H), 7.27 (d, quinoline), 7.58 (ddd, quinoline), 7.71 (ddd, quinoline), 8.07 (br d, quinoline), 8.11 (br d, quinoline), 8.81 (d, quinoline).

(c) In the same manner as in Example 2(c), 15 mg of a deacetyled compound (compound represented by the formula (32) mentioned in Preparation Scheme 10 wherein $R_2$ is hydrogen atom, $R_3$ is 3-(quinolin-4-yl)propyl group, $R_7$, $R_8$ and $R_{11}$ are hydrogen atoms, $R_{12}$ is methyl group, $R_{3''}$ is propionyl group, $R_{4''}$ is n-butyryl group, and X is oxygen atom) was obtained from 25 mg of the compound of Example 70 (b).

Physicochemical Properties of this Compound (1) Molecular formula: $C_{53}H_{83}N_3O_{15}$ (2) Mass spectrum (FAB): m/z 1048 $(M+H)^+$ (3) Specific rotation: $[\alpha]_D^{20}$ −77° (c0.90, $CHCl_3$)

(4) $^1H$ NMR spectrum (300 MHz, $CDCl_3$) δ (ppm): 0.97 (d, 8-$CH_3$), 0.98 (t, 4"-$OCOCH_2CH_2CH_3$), 1.09 (d, 6"-H), 1.13 (t, 3"-$OCOCH_2CH_3$), 1.22 (d, 6'-H), 1.24 (d, 15-$CH_3$), 1.42 (s, 3"-$CH_3$), 2.38 (t, 4"-$OCOCH_2CH_2CH_3$), 2.53 (s, 3'-$N(CH_3)_2$), 3.15 (t, 4'-H), 3.20 (dq, 5'-H), 3.22 (d, 2"-Heq), 3.30 (s, $CH(OCH_3)_2$), 3.33 (s, $CH(OCH_3)_2$), 3.44 (m, 9-H), 3.48 (dd, 2'-H), 3.57 (s, 4-$OCH_3$), 3.95 (br d, 5-H), 4.26 (br dd, 3-H), 4.38 (d, 1'-H), 4.51 (dd, $CH(OCH_3)_2$), 4.55 (m, 5"-H), 4.57 (m, 4"-H), 4.83 (d, 1"-H), 4.91 (m, 15-H), 7.25 (d, quinoline), 7.58 (ddd, quinoline), 7.72 (ddd, quinoline), 8.03 (br d, quinoline), 8.13 (br d, quinoline), 8.82 (d, quinoline).

(d) In the same manner as in Example 2(d), 13 mg of the title compound was obtained from 15 mg of the compound of Example 70(c).

Physicochemical Properties of this Compound (1) Molecular formula: $C_{54}H_{86}N_2O_{17}$ (2) Mass spectrum (FAB): m/z 1002 $(M+H)^+$ (3) Specific rotation: $[\alpha]_D^{25}$ −75° (c0.50, $CHCl_3$)

(4) $^1H$ NMR spectrum (300 MHz, $CDCl_3$) δ (ppm): 0.94 (d, 8-$CH_3$), 0.98 (t, 4"-$OCOCH_2CH_2CH_3$), 1.08 (d, 6"-H), 1.13 (t, 3"-$OCOCH_2CH_3$), 1.18 (d, 6'-H), 1.24 (d, 15-$CH_3$), 1.42 (s, 3"-$CH_3$), 1.69 (m, 4"-$OCOCH_2CH_2CH_3$), 1.93 (m, 11-$CH_2CH_2$), 2.43 (s, 3'-$N(CH_3)_2$), 2.96 (dd, 6-$CH_2$), 3.18 (t, 4'-H), 3.21 (m, 5'-H), 3.22 (d, 2"-Heq), 3.42 (dd, 2'-H), 3.57 (s, 4-$OCH_3$), 3.90 (dd, 5-H), 4.29 (br dd, 3-H), 4.35 (d, 1'-H), 4.54 (dq, 5"-H), 4.58 (d, 4"-H), 4.83 (d, 1"-H), 4.89 (m, 15-H), 5.12 (m, 9-H), 7.24 (d, quinoline), 7.57 (ddd, quinoline), 7.72 (ddd, quinoline), 8.01 (br d, quinoline), 8.13 (br d, quinoline), 8.81 (d, quinoline), 9.73 (s, CHO).

Example 71

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is trans-3-(quinolin-3-yl)-1-propenyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom (a) In the same manner as in Example 48(c), except that 3-bromoquinoline was used instead of 4-bromoquinoline, 32.3 mg of a trans-isomer of a coupling compound (compound represented by the formula (24) mentioned in Preparation Scheme 8 wherein $R_3$ is methyl group, one of $R_7$ and $R_8$ is trans-3-(quinolin-3-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom), and 15.4 mg of a cis-isomer of a coupling compound (compound represented by the formula (24) mentioned in Preparation Scheme 8 wherein $R_3$ is methyl group, one of $R_7$ and $R_8$ is cis-3-(quinolin-3-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom) were obtained from 994 mg of the compound of Example 54(b).

Physicochemical Properties of the Trans-isomer (1) Molecular formula: $C_{58}H_{89}N_3O_{18}$ (2) Mass spectrum (FAB): m/z 1116 $(M+H)^+$ (3) Specific rotation: $[\alpha]_D^{25}$ −64° (c0.35, $CHCl_3$)

(4) $^1H$ NMR spectrum (300 MHz, $CDCl_3$) δ (ppm): 0.95 (d, 8-$CH_3$), 1.02 (t, 3-$OCOCH_2CH_3$), 1.11 (s, 3"-$CH_3$), 1.12 (d, 6"-H), 1.17 (t, 4"-$OCOCH_2CH_3$), 1.26 (d, 6'-H), 1.39 (m, 14-H), 1.83 (dd, 2"-Hax), 2.00 (d, 2"-Heq), 2.03 (s, 9-$OCOCH_3$), 2.05 (s, 2'-$OCOCH_3$), 2.12 (m, 14-H), 2.28 (s, $NCH_3$), 2.40 (s, 3'-$N(CH_3)_2$), 3.12 (s, $CH(OCH_3)_2$), 3.22 (s, $CH(OCH_3)_2$), 3.52 (d, quinoline-$CH_2$), 3.53 (s, 4-$OCH_3$), 3.88 (d, 5-H), 4.16 (m, 15-H), 4.37 (dq, 5"-H), 4.45 (dd, $CH(OCH_3)_2$), 4.61 (d, 4"-H), 4.70 (d, 1'-H), 5.00 (dd, 2'-H), 5.06 (d, 1"-H), 5.23 (m, 3-H), 5.29 (dd, 13-CH), 5.84 (dt, CH═CH), 7.51 (ddd, quinoline), 7.65 (ddd, quinoline), 7.77 (br d, quinoline), 7.96 (d, quinoline), 8.06 (br d, quinoline), 8.74 (d, quinoline).

Physicochemical Properties of the Cis-isomer (1) Molecular formula: $C_{58}H_{89}N_3O_{18}$ (2) Mass spectrum (FAB): m/z 1116 $(M+H)^+$ (3) Specific rotation: $[\alpha]_D^{24}$ −61° (c0.77, $CHCl_3$)

(4) $^1H$ NMR spectrum (300 MHz, $CDCl_3$) δ (ppm): 0.96 (d, 8-$CH_3$), 1.01 (t, 3-$OCOCH_2CH_3$), 1.11 (s, 3"-$CH_3$), 1.12 (d, 6"-H), 1.17 (t, 4"-$OCOCH_2CH_3$), 1.26 (d, 6'-H), 1.84 (dd, 2"-Hax), 2.00 (d, 2"-Heq), 2.04 (s, 9-$OCOCH_3$), 2.06 (s, 2'-$OCOCH_3$), 2.31 (s, $NCH_3$), 2.40 (s, 3'-$N(CH_3)_2$), 2.49 (dd, 2-H), 3.08 (s, $CH(OCH_3)_2$), 3.21 (s, $CH(OCH_3)_2$), 3.55 (s, 4-$OCH_3$), 3.69 (d, quinoline-$CH_2$), 3.89 (d, 5-H), 4.07 (m, 15-H), 4.37 (dq, 5"-H), 4.50 (m, $CH(OCH_3)_2$), 4.61 (d, 4"-H), 4.71 (d, 1'-H), 5.06 (d, 1"-H), 5.23 (m, 3-H), 5.31 (m, 13-CH), 5.70 (dt, CH═CH), 7.51 (ddd, quinoline), 7.65 (ddd, quinoline), 7.77 (br d, quinoline), 7.94 (d, quinoline), 8.05 (br d, quinoline), 8.80 (d, quinoline).

(b) In the same manner as in Example 2(c), 32.3 mg of the trans-isomer of Example 71(a) was reacted at room temperature for 6 days, and further reacted at 50° C. for 64 hours to obtain 9.8 mg of a deacetyled compound (compound represented by the formula (25) mentioned in Preparation Scheme 8 wherein $R_2$ is hydrogen atom, $R_3$ is methyl group, one of $R_7$ and $R_8$ is trans-3-(quinolin-3-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{24}$ −56° (c0.49, $CHCl_3$)

(4) $^1H$ NMR spectrum (300 MHz, $CDCl_3$) δ (ppm): 0.88 (d, 8-$CH_3$), 0.93 (t, 3-$OCOCH_2CH_3$), 1.11 (s, 3"-$CH_3$), 1.12 (d, 6"-H), 1.18 (t, 4"-$OCOCH_2CH_3$), 1.25 (d, 6'-H), 1.82 (dd, 2"-Hax), 2.00 (d, 2"-Heq), 2.26 (q, 3-$OCOCH_2CH_3$), 2.32 (s, $NCH_3$), 2.49 (s, 3'-$N(CH_3)_2$), 2.63 (m, 2-H), 3.08 (s, $CH(OCH_3)_2$), 3.20 (s, $CH(OCH_3)_2$), 3.26 (t, 4'-H), 3.52 (d, quinoline-$CH_2$), 3.59 (s, 4-$OCH_3$), 3.81 (d, 5-H), 4.04 (m, 15-H), 4.47 (dq, 5"-H), 4.61 (d, 4"-H), 5.07 (d, 1"-H), 5.24 (dd, 13-CH), 5.76 (t, 3-H), 5.97 (dt, CH═CH), 7.52 (ddd, quinoline), 7.66 (ddd, quinoline), 7.77 (br d, quinoline), 7.90 (d, quinoline), 8.07 (br d, quinoline), 8.74 (d, quinoline).

(c) In the same manner as in Example 2(d), 4.8 mg of the title compound was obtained from 9.8 mg of the compound of Example 71(b).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{25}$ −61° (c0.24, $CHCl_3$)

(4) $^1H$ NMR spectrum (300 MHz, $CDCl_3$) δ (ppm): 0.90 (d, 8-$CH_3$), 1.00 (t, 3-$OCOCH_2CH_3$), 1.12 (s, 3"-$CH_3$), 1.13 (d, 6"-H), 1.18 (t, 4"-$OCOCH_2CH_3$), 1.20 (d, 6'-H), 1.44 (m, 14-H), 1.83 (dd, 2"-Hax), 2.00 (d, 2"-Heq), 2.11 (m, 14-H), 2.32 (s, $NCH_3$), 2.50 (s, 3'-$N(CH_3)_2$), 2.60 (m, 2-H), 2.85 (dd, 6-$CH_2$), 3.25 (t, 4'-H), 3.53 (d, quinoline-$CH_2$), 3.59 (s, 4-$OCH_3$), 3.62 (d, 4-H), 3.82 (d, 5-H), 4.07 (m, 15-H), 4.33 (d, 1'-H), 4.46 (dq, 5"-H), 4.61 (d, 4"-H), 5.06 (d, 1"-H), 5.24 (dd, 13-CH), 5.85 (t, 3-H), 5.95 (dt, CH═CH), 7.53 (ddd, quinoline), 7.66 (ddd, quinoline), 7.78 (dd, quinoline), 7.91 (d, quinoline), 8.07 (br d, quinoline), 8.75 (d, quinoline), 9.62 (s, CHO).

Example 72

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is cis-3-(quinolin-3-yl)-1-propenyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom (a) In the same manner as in Example 71(b), 4.3 mg of a deacetyled compound (compound represented by the formula (25) mentioned in Preparation Scheme 8 wherein $R_2$ is hydrogen atom, $R_3$ is methyl group, one of $R_7$ and $R_8$ is cis-3-(quinolin-3-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 15.4 mg of the cis-isomer of Example 71(a).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{25}$ −40° (c0.22, $CHCl_3$)

(4) $^1H$ NMR spectrum (300 MHz, $CDCl_3$) δ (ppm): 0.89 (d, 8-$CH_3$), 0.93 (t, 3-$OCOCH_2CH_3$), 1.11 (s, 3"-$CH_3$), 1.12 (d, 6"-H), 1.18 (t, 4"-$OCOCH_2CH_3$), 1.25 (d, 6'-H), 1.82 (dd, 2"-Hax), 1.99 (d, 2"-Heq), 2.24 (q, 3-$OCOCH_2CH_3$), 2.35 (s, $NCH_3$), 2.49 (s, 3'-$N(CH_3)_2$), 2.62 (dd, 2-H), 2.95 (s, $CH(OCH_3)_2$), 3.15 (s, $CH(OCH_3)_2$), 3.61 (s, 4-$OCH_3$), 3.68 (d, 4-H), 3.75 (m, quinoline-$CH_2$), 3.81 (d, 5-H), 4.00 (m, 15-H), 4.19 (m, 15-H), 4.39 (d, 1'-H), 4.47 (dq, 5"-H), 4.61 (d, 4"-H), 5.07 (d, 1"-H), 5.25 (t, 13-CH), 5.70 (dt, CH═CH), 5.79 (m, 3-H), 7.52 (t, quinoline), 7.66 (t, quinoline), 7.76 (d, quinoline), 7.95 (s, quinoline), 8.06 (d, quinoline), 8.80 (d, quinoline).

(b) In the same manner as in Example 2(d), 2.4 mg of the title compound was obtained from 4.3 mg of the compound of Example 72(a).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{26}$ −32° (c0.12, $CHCl_3$)

(4) $^1H$ NMR spectrum (300 MHz, $CDCl_3$) δ (ppm): 0.83 (d, 8-$CH_3$), 1.04 (t, 3-$OCOCH_2CH_3$), 1.11 (s, 3"-$CH_3$), 1.13 (d, 6"-H), 1.18 (t, 4"-$OCOCH_2CH_3$), 1.19 (d, 6'-H), 1.83 (dd, 2"-Hax), 2.00 (d, 2"-Heq), 2.30 (s, $NCH_3$), 2.50 (s, 3'-$N(CH_3)_2$), 2.69 (dd, 2-H), 2.88 (dd, 6-$CH_2$), 2.94 (m, 13-H), 3.55 (dd, 2'-H), 3.59 (s, 4-$OCH_3$), 3.83 (m, quinoline-$CH_2$), 4.01 (m, 15-H), 4.27 (m, 15-H), 4.35 (d, 1'-H), 4.46 (dq, 5"-H), 4.61 (d, 4"-H), 5.06 (d, 1"-H), 5.31 (t, 13-CH), 5.74 (m, 3-H), 5.79 (dt, CH═CH), 7.51 (ddd, quinoline), 7.65 (ddd, quinoline), 7.75 (dd, quinoline), 7.93 (d, quinoline), 8.05 (br d, quinoline), 8.78 (d, quinoline), 9.63 (s, CHO).

Example 73

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is trans-3-(quinolin-3-yl)-1-propenyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom, provided that the substituents $R_7$ and $R_8$ are exchanged compared with the compound of Example 71

(a) In the same manner as in Example 48(c), except that 3-bromoquinoline was used instead of 4-bromoquinoline, 62 mg of a coupling compound (compound represented by the formula (24) mentioned in Preparation Scheme 8 wherein $R_3$ is methyl group, one of $R_7$ and $R_8$ is trans-3-(quinolin-3-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom, provided that the substituents $R_7$ and $R_8$ are exchanged compared with the trans-isomer of a coupling compound of Example 71(a)) was obtained from 194.4 mg of the compound of Example 60(a).

Physicochemical Properties of this Compound (1) Molecular formula: $C_{58}H_{89}N_3O_{18}$ (2) Mass spectrum (FAB): m/z 1116 $(M+H)^+$ (3) Specific rotation: $[\alpha]_D^{25}$ −34° (c0.66, $CHCl_3$)

(4) $^1H$ NMR spectrum (300 MHz, $CDCl_3$) δ (ppm): 0.93 (d, 8-$CH_3$), 1.08 (t, 3-$OCOCH_2CH_3$), 1.10 (s, 3"-$CH_3$), 1.11 (d, 6"-H), 1.16 (t, 4"-$OCOCH_2CH_3$), 1.26 (d, 6'-H), 1.83 (dd, 2"-Hax), 1.95 (s, 9-$OCOCH_3$), 1.97 (s, 2'-$OCOCH_3$), 2.27 (s, $NCH_3$), 2.38 (s, 3'-$N(CH_3)_2$), 2.70 (t, 3'-H), 3.11 (s, $CH(OCH_3)_2$), 3.23 (s, $CH(OCH_3)_2$), 3.31 (t, 4'-H), 3.51 (s, 4-$OCH_3$), 3.51 (d, quinoline-$CH_2$), 3.89 (d, 5-H), 4.22 (m, 15-H), 4.36 (dq, 5"-H), 4.49 (dd, $CH(OCH_3)_2$), 4.60 (d, 4"-H), 4.70 (d, 1'-H), 4.98 (dd, 2'-H), 5.05 (d, 1"-H), 5.24 (t, 3-H), 5.48 (dd, 13-CH), 5.62 (dt, CH═CH), 7.51 (t, quinoline), 7.65 (m, quinoline), 7.76 (d, quinoline), 7.90 (d, quinoline), 8.05 (d, quinoline), 8.73 (d, quinoline).

(b) In the same manner as in Example 2(c), 62 mg of the coupling compound of Example 73(a) was reacted at 40° C. for 34.5 hours to obtain 12.2 mg of a deacetyled compound (compound represented by the formula (25) mentioned in Preparation Scheme 8 wherein $R_2$ is hydrogen atom, $R_3$ is methyl group, one of $R_7$ and $R_8$ is trans-3-(quinolin-3-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom, provided that the substituents $R_7$ and $R_8$ are exchanged compared with the compound of Example 71(b)).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{24}$ −36° (c0.61, $CHCl_3$)

(4) $^1H$ NMR spectrum (300 MHz, $CDCl_3$) δ (ppm): 0.95 (d, 8-$CH_3$), 1.10 (t, 3-$OCOCH_2CH_3$), 1.12 (s, 3"-$CH_3$), 1.13 (d, 6"-H), 1.18 (t, 4"-$OCOCH_2CH_3$), 1.27 (d, 6'-H), 1.83 (dd, 2"-Hax), 2.01 (d, 2"-Heq), 2.34 (s, $NCH_3$), 2.51 (s, 3'-$N(CH_3)_2$), 2.66 (d, 2-H), 3.12 (s, $CH(OCH_3)_2$), 3.25 (s, $CH(OCH_3)_2$), 3.50 (d, 4-H), 3.57 (d, quinoline-$CH_2$), 3.58 (s, 4-$OCH_3$), 3.91 (d, 5-H), 4.05 (m, 15-H), 4.29 (m, 15-H), 4.49 (d, 1'-H), 4.62 (d, 4"-H), 5.08 (d, 1"-H), 5.35 (t, 3-H), 5.48 (dd, 13-CH), 5.74 (dt, CH=CH), 7.52 (t, quinoline), 7.66 (t, quinoline), 7.77 (d, quinoline), 7.93 (s, quinoline), 8.08 (d, quinoline), 8.76 (d, quinoline).

(d) In the same manner as in Example 2(d), 5.3 mg of the title compound was obtained from 12.2 mg of the compound of Example 73(b).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{26}$ −50° (c0.25, $CHCl_3$)

(4) $^1H$ NMR spectrum (300 MHz, $CDCl_3$) δ (ppm): 0.94 (d, 8-$CH_3$), 1.13 (d, 6"-H), 1.16 (s, 3"-$CH_3$), 1.18 (t, 4"-$OCOCH_2CH_3$), 1.19 (d, 6'-H), 1.84 (dd, 2"-Hax), 2.01 (d, 2"-Heq), 2.36 (s, $NCH_3$), 2.53 (s, 3'-$N(CH_3)_2$), 2.91 (dd, 6-$CH_2$), 3.59 (s, 4-$OCH_3$), 3.90 (d, 5-H), 4.09 (m, 15-H), 4.26 (m, 15-H), 4.44 (d, 1'-H), 4.62 (d, 4"-H), 5.07 (d, 1"-H), 5.44 (m, 3-H), 5.47 (dd, 13-CH), 5.75 (dt, CH=CH), 7.52 (t, quinoline), 7.66 (t, quinoline), 7.78 (d, quinoline), 7.94 (s, quinoline), 8.08 (d, quinoline), 8.77 (d, quinoline), 9.64 (s, CHO).

Example 74

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is trans-3-(quinolin-6-yl)-1-propenyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom (a) In the same manner as in Example 48(c), except that 6-bromoquinoline was used instead of 4-bromoquinoline, 32.5 mg of a coupling compound (compound represented by the formula (24) mentioned in Preparation Scheme 8 wherein $R_3$ is methyl group, one of $R_7$ and $R_8$ is trans-3-(quinolin-6-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 117.1 mg of the compound of Example 54 (b).

Physicochemical Properties of this Compound (1) Molecular formula: $C_{58}H_{89}N_3O_{18}$ (2) Mass spectrum (FAB): m/z 1116 $(M+H)^+$ (3) Specific rotation: $[\alpha]_D^{26}$ −60° (c0.73, $CHCl_3$)

(4) $^1H$ NMR spectrum (300 MHz, $CDCl_3$) δ (ppm): 0.95 (d, 8-$CH_3$), 1.02 (t, 3-$OCOCH_2CH_3$), 1.11 (s, 3"-$CH_3$), 1.12 (d, 6"-H), 1.17 (t, 4"-$OCOCH_2CH_3$), 1.25 (d, 6'-H), 1.83 (dd, 2"-Hax), 2.01 (d, 2"-Heq), 2.02 (s, 9-$OCOCH_3$), 2.05 (s, 2'-$OCOCH_3$), 2.28 (s, $NCH_3$), 2.40 (s, 3'-$N(CH_3)_2$), 3.11 (s, $CH(OCH_3)_2$), 3.21 (s, $CH(OCH_3)_2$), 3.52 (d, quinoline-$CH_2$), 3.53 (s, 4-$OCH_3$), 3.87 (d, 5-H), 4.37 (dq, 5"-H), 4.45 (dd, $CH(OCH_3)_2$), 4.61 (d, 4"-H), 4.69 (d, 1'-H), 4.99 (dd, 2'-H), 5.06 (d, 1"-H), 5.24 (m, 3-H), 5.28 (dd, 13-CH), 5.84 (dt, CH=CH), 7.36 (dd, quinoline), 7.54 (d, quinoline), 7.56 (s, quinoline), 8.00 (d, quinoline), 8.10 (d, quinoline), 8.85 (d, quinoline).

(b) In the same manner as in Example 71(b), 14.6 mg of a deacetyled compound (compound represented by the formula (25) mentioned in Preparation Scheme 8 wherein $R_2$ is hydrogen atom, $R_3$ is methyl group, one of $R_7$ and $R_8$ is trans-3-(quinolin-6-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 32.5 mg of the compound of Example 74(a).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{25}$ −50° (c0.73, $CHCl_3$)

(4) $^1H$ NMR spectrum (300 MHz, $CDCl_3$) δ (ppm): 0.88 (d, 8-$CH_3$), 0.92 (t, 3-$OCOCH_2CH_3$), 1.11 (s, 3"-$CH_3$), 1.12 (d, 6"-H), 1.18 (t, 4"-$OCOCH_2CH_3$), 1.25 (d, 6'-H), 1.82 (dd, 2"-Hax), 2.00 (d, 2"-Heq), 2.25 (q, 3-$OCOCH_2CH_3$), 2.33 (s, $NCH_3$), 2.49 (s, 3'-$N(CH_3)_2$), 2.62 (d, 2-H), 3.09 (s, $CH(OCH_3)_2$), 3.20 (s, $CH(OCH_3)_2$), 3.52 (d, quinoline-$CH_2$), 3.59 (s, 4-$OCH_3$), 3.81 (d, 5-H), 4.07 (m, 15-H), 4.47 (dq, 5"-H), 4.61 (d, 4"-H), 5.07 (d, 1"-H), 5.24 (dd, 13-CH), 5.75 (t, 3-H), 5.97 (dt, CH=CH), 7.37 (dd, quinoline), 7.54 (d, quinoline), 7.57 (s, quinoline), 8.01 (d, quinoline), 8.10 (d, quinoline), 8.85 (d, quinoline).

(c) In the same manner as in Example 2(d), 7.8 mg of the title compound was obtained from 14.6 mg of the compound of Example 74(b).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{24}$ −51° (c0.39, $CHCl_3$)

(4) $^1H$ NMR spectrum (300 MHz, $CDCl_3$) δ (ppm): 0.90 (d, 8-$CH_3$), 0.99 (t, 3-$OCOCH_2CH_3$), 1.12 (s, 3"-$CH_3$), 1.13 (d, 6"-H), 1.18 (t, 4"-$OCOCH_2CH_3$), 1.20 (d, 6'-H), 1.45 (m, 14-H), 1.83 (dd, 2"-Hax), 2.00 (d, 2"-Heq), 2.32 (s, $NCH_3$), 2.50 (s, 3'-$N(CH_3)_2$), 2.66 (d, 2-H), 2.85 (dd, 6-$CH_2$), 3.53 (d, quinoline-$CH_2$), 3.59 (s, 4-$OCH_3$), 3.62 (d, 4-H), 3.82 (d, 5-H), 4.08 (m, 15-H), 4.33 (d, 1'-H), 4.46 (dq, 5"-H), 4.61 (d, 4"-H), 5.06 (d, 1"-H), 5.23 (dd, 13-CH), 5.84 (t, 3-H), 5.94 (dt, CH=CH), 7.38 (dd, quinoline), 7.54 (dd, quinoline), 7.57 (s, quinoline), 8.02 (d, quinoline), 8.12 (d, quinoline), 8.86 (d, quinoline), 9.62 (s, CHO).

Example 75

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is trans-3-(quinolin-8-yl)-1-propenyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom (a) In the same manner as in Example 48(c), except that 8-bromoquinoline was used instead of 4-bromoquinoline, 20.3 mg of a coupling compound (compound represented by the formula (24) mentioned in Preparation Scheme 8 wherein $R_3$ is methyl group, one of $R_7$ and $R_8$ is trans-3-(quinolin-8-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 119.6 mg of the compound of Example 54(b).

Physicochemical Properties of this Compound (1) Molecular formula: $C_{58}H_{89}N_3O_{18}$ (2) Mass spectrum (FAB): m/z 1116 $(M+H)^+$ (3) Specific rotation: $[\alpha]_D^{26}$ −59° (c1.0, $CHCl_3$)

(4) $^1H$ NMR spectrum (300 MHz, $CDCl_3$) δ (ppm): 0.95 (d, 8-$CH_3$), 1.04 (t, 3-$OCOCH_2CH_3$), 1.11 (s, 3"-$CH_3$), 1.12 (d, 6"-H), 1.17 (t, 4"-$OCOCH_2CH_3$), 1.26 (d, 6'-H), 1.84 (dd, 2"-Hax), 2.00 (d, 2"-Heq), 2.03 (s, 9-$OCOCH_3$), 2.04 (s, 2'-$OCOCH_3$), 2.10 (m, 14-H), 2.26 (s, $NCH_3$), 2.32 (dq, 3-$OCOCH_2CH_3$), 2.40 (s, 3'-$N(CH_3)_2$), 2.43 (dq, $OCOCH_2CH_3$), 2.72 (t, 3'-H), 3.13 (s, $CH(OCH_3)_2$), 3.23 (s, $CH(OCH_3)_2$), 3.32 (t, 4'-H), 3.53 (s, 4-$OCH_3$), 3.87 (d, 5-H), 4.01 (d, quinoline-$CH_2$), 4.10 (dt, 15-H), 4.19 (dt, 15-H), 4.37 (dq, 5"-H), 4.46 (dd, $CH(OCH_3)_2$), 4.61 (d, 4"-H), 4.70 (d, 1'-H), 4.94 (dd, 9-H), 5.00 (dd, 2'-H), 5.06 (d, 1"-H), 5.23 (m, 3-H), 5.31 (dd, 13-CH), 5.92 (dt, CH═CH), 7.39 (dd, quinoline), 7.46 (t, quinoline), 7.54 (d, quinoline), 7.67 (d, quinoline), 8.13 (dd, quinoline), 8.92 (dd, quinoline).

(b) In the same manner as in Example 71(b), 10.3 mg of a deacetyled compound (compound represented by the formula (25) mentioned in Preparation Scheme 8 wherein $R_2$ is hydrogen atom, $R_3$ is methyl group, one of $R_7$ and $R_8$ is trans-3-(quinolin-8-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 20.3 mg of the compound of Example 75(a).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{26}$ −57° (c0.52, $CHCl_3$)

(4) $^1H$ NMR spectrum (300 MHz, $CDCl_3$) δ (ppm): 0.87 (d, 8-$CH_3$), 0.92 (t, 3-$OCOCH_2CH_3$), 1.11 (s, 3"-$CH_3$), 1.12 (d, 6"-H), 1.18 (t, 4"-$OCOCH_2CH_3$), 1.25 (d, 6'-H), 1.38 (m, 8-H), 1.82 (dd, 2"-Hax), 2.00 (d, 2"-Heq), 2.07 (m, 14-H), 2.24 (q, 3-$OCOCH_2CH_3$), 2.31 (s, $NCH_3$), 2.44 (q, 4"-$OCOCH_2CH_3$), 2.49 (s, 3'-$N(CH_3)_2$), 2.62 (m, 2-H), 3.12 (s, $CH(OCH_3)_2$), 3.22 (s, $CH(OCH_3)_2$), 3.58 (s, 4-$OCH_3$), 3.81 (d, 5-H), 3.98 (m, 15-H), 4.01 (d, quinoline-$CH_2$), 4.08 (m, 15-H), 4.48 (dq, 5"-H), 4.61 (d, 4"-H), 5.07 (d, 1"-H), 5.28 (dd, 13-CH), 5.73 (t, 3-H), 6.02 (dt, CH═CH), 7.40 (dd, quinoline), 7.47 (t, quinoline), 7.55 (d, quinoline), 7.68 (d, quinoline), 8.14 (dd, quinoline), 8.92 (dd, quinoline).

(c) In the same manner as in Example 2(d), 5.5 mg of the title compound was obtained from 10.3 mg of the compound of Example 75(b).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{25}$ −61° (c0.23, $CHCl_3$)

(4) $^1H$ NMR spectrum (300 MHz, $CDCl_3$) δ (ppm): 0.89 (d, 8-$CH_3$), 0.99 (t, 3-$OCOCH_2CH_3$), 1.12 (s, 3"-$CH_3$), 1.13 (d, 6"-H), 1.18 (t, 4"-$OCOCH_2CH_3$), 1.20 (d, 6'-H), 1.30 (m, 8-H), 1.46 (m, 14-H), 1.83 (dd, 2"-Hax), 2.00 (d, 2"-Heq), 2.07 (m, 14-H), 2.26 (dd, 6-$CH_2$), 2.30 (s, $NCH_3$), 2.50 (s, 3'-$N(CH_3)_2$), 2.65 (d, 2-H), 2.85 (dd, 6-$CH_2$), 3.25 (t, 4'-H), 3.55 (dd, 2'-H), 3.59 (s, 4-$OCH_3$), 3.63 (d, 4-H), 3.81 (d, 5-H), 4.02 (d, quinoline-$CH_2$), 4.10 (m, 15-H), 4.32 (d, 1'-H), 4.47 (dq, 5"-H), 4.62 (d, 4"-H), 5.06 (d, 1"-H), 5.27 (dd, 13-CH), 5.79 (t, 3-H), 6.00 (dt, CH═CH), 7.40 (dd, quinoline), 7.48 (t, quinoline), 7.55 (d, quinoline), 7.68 (dd, quinoline), 8.14 (dd, quinoline), 8.93 (dd, quinoline), 9.63 (s, CHO).

Example 76

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is trans-3-(isoquinolin-4-yl)-1-propenyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom (a) In the same manner as in Example 48(c), except that 4-bromoisoquinoline was used instead of 4-bromoquinoline, 24.2 mg of a coupling compound (compound represented by the formula (24) mentioned in Preparation Scheme 8 wherein $R_3$ is methyl group, one of $R_7$ and $R_8$ is trans-3-(isoquinolin-4-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 116.2 mg of the compound of Example 54(b).

Physicochemical Properties of this Compound (1) Molecular formula: $C_{58}H_{89}N_3O_{18}$ (2) Mass spectrum (FAB): m/z 1116 $(M+H)^+$ (3) Specific rotation: $[\alpha]_D^{25}$ −49° (c1.0, $CHCl_3$)

(4) $^1H$ NMR spectrum (300 MHz, $CDCl_3$) δ (ppm): 0.92 (d, 8-$CH_3$), 1.06 (d, 6"-H), 1.13 (t, 3-$OCOCH_2CH_3$), 1.10 (s, 3"-$CH_3$), 1.18 (t, 4"-$OCOCH_2CH_3$), 1.25 (d, 6'-H), 1.55 (m, 6-$CH_2$), 1.76 (m, 8-H), 1.83 (dd, 2"-Hax), 2.00 (s, 9-$OCOCH_3$), 2.01 (s, 2"-$OCOCH_3$), 2.24 (s, $NCH_3$), 2.30 (m, 10-H), 2.39 (s, 3'-$N(CH_3)_2$), 2.68 (m, 3'-H), 3.08 (s, $CH(OCH_3)_2$), 3.20 (s, $CH(OCH_3)_2$), 3.32 (m, 4'-H), 3.32 (m, 5'-H), 3.52 (dd, 4-$OCH_3$), 3.72 (d, iso quinoline-$CH_2$), 3.86 (m, 5-H), 4.36 (d, 5"-H), 4.42 (dd, $CH(OCH_3)_2$), 4.60 (d, 4"-H), 4.68 (d, 1'-H), 4.96 (m, 9-H), 4.98 (dd, 2'-H), 5.06 (d, 1"-H), 5.21 (dd, CH═CH), 5.85 (dt, CH═CH), 7.58 (t, isoquinoline), 7.69 (t, isoquinoline), 7.96 (d, isoquinoline), 8.00 (m, isoquinoline), 8.34 (s, isoquinoline), 9.11 (d, isoquinoline).

(b) In the same manner as in Example 2(c), 19.0 mg of a deacetyled compound (compound represented by the formula (25) mentioned in Preparation Scheme 8 wherein $R_2$ is hydrogen atom, $R_3$ is methyl group, one of $R_7$ and $R_8$ is trans-3-(isoquinolin-4-yl)-1-propenyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 38.9 mg of the compound of Example 76(a).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{26}$ −44° (c0.9, $CHCl_3$)

(4) $^1H$ NMR spectrum (300 MHz, $CDCl_3$) δ (ppm): 0.86 (d, 8-$CH_3$), 0.94 (t, 3-$OCOCH_2CH_3$), 1.10 (s, 3"-$CH_3$), 1.11 (d, 6"-H), 1.16 (t, 4"-$OCOCH_2CH_3$), 1.24 (d, 6'-H), 1.32 (m, 8-H), 1.80 (dd, 2"-Hax), 1.99 (d, 2"-Heq), 2.28 (s, $NCH_3$), 2.38 (m, 10-H), 2.48 (s, 3'-$N(CH_3)_2$), 2.52 (m, 2-H), 3.20 (s, $CH(OCH_3)_2$), 3.26 (m, 4'-H), 3.26 (m, 5'-H), 3.56 (m, 2'-H), 3.57 (s, 4-$OCH_3$), 3.72 (d, isoquinoline-$CH_2$), 3.80 (m, 5-H), 4.36 (m, 1'-H), 4.36 (m, $CH(OCH_3)_2$), 4.46 (m, 5"-H), 4.68 (d, 4"-H), 5.06 (d, 1"-H), 5.16 (dd, CH═CH), 5.71 (dd, 3-H), 5.96 (m, CH═CH), 7.58 (t, isoquinoline), 7.69 (t, isoquinoline), 7.96 (m, isoquinoline), 8.33 (s, isoquinoline), 9.12 (d, isoquinoline).

(c) In the same manner as in Example 2(d), 7.4 mg of the title compound was obtained from 16.8 mg of the compound of Example 76(b).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{26}$ −44° (c0.9, $CHCl_3$)

(4) $^1H$ NMR spectrum (300 MHz, $CDCl_3$) δ (ppm): 0.89 (d, 8-$CH_3$), 1.00 (t, 3-$OCOCH_2CH_3$), 1.11 (s, 3"-$CH_3$), 1.14

(d, 6"-H), 1.17 (t, 4"-$OCOCH_2CH_3$), 1.18 (d, 6'-H), 1.29 (m, 8-H), 1.82 (dd, 2"-Hax), 1.99 (d, 2"-Heq), 2.24 (m, 6-$CH_2$), 2.30 (s, $NCH_3$), 2.50 (s, 3'-$N(CH_3)_2$), 2.64 (m, 2-H), 3.25 (m, 4'-H), 3.25 (m, 5'-H), 3.54 (dd, 2'-H), 3.58 (s, 4-$OCH_3$), 3.60 (m, 4-H), 3.72 (d, isoquinoline-$CH_2$), 3.80 (br d, 5-H), 4.32 (d, 1'-H), 4.45 (m, 5"-H), 4.60 (d, 4"-H), 5.06 (d, 1"-H), 5.16 (m, CH═CH), 5.79 (m, 3-H), 5.96 (m, CH═CH), 7.58 (t, isoquinoline), 7.69 (t, isoquinoline), 7.98 (m, isoquinoline), 8.36 (s, isoquinoline), 9.15 (s, isoquinoline), 9.64 (s, CHO).

Example 77

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is trans-3-(naphthalen-2-yl)-2-propenyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom (a) In the same manner as in Example 30(a), except that 2-bromonaphthalene was used instead of 3-bromoquinoline, 13.6 mg of a coupling compound (compound represented by the formula (24) mentioned in Preparation Scheme 8 wherein $R_3$ is methyl group, one of $R_7$ and $R_8$ is trans-3-(naphthalen-2-yl)-2-propenyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 25.6 mg of the compound of Example 54(b).

Physicochemical Properties of this Compound (1) Molecular formula: $C_{59}H_{90}N_2O_{18}$ (2) Mass spectrum (FAB): m/z 1115 $(M+H)^+$ (3) Specific rotation: $[\alpha]_D^{25}$ −54° (c1.0, $CHCl_3$)

(4) $^1$H NMR spectrum (300 MHz, $CDCl_3$) δ (ppm): 0.95 (d, 8-$CH_3$), 1.11 (s, 3"-$CH_3$), 1.12 (d, 6"-H), 1.13 (t, 3-$OCOCH_2CH_3$), 1.16 (t, 4"-$OCOCH_2CH_3$), 1.26 (d, 6'-H), 1.86 (dd, 2"-Hax), 2.00 (d, 2"-Heq), 2.02 (s, 9-$OCOCH_3$), 2.04 (s, 2'-$OCOCH_3$), 2.26 (m, 13-$CH_2$), 2.30 (s, $NCH_3$), 2.40 (s, 3'-$N(CH_3)_2$), 2.64 (m, 10-H), 2.72 (dd, 3'-H), 2.80 (m, 2-H), 3.16 (s, $CH(OCH_3)_2$), 3.24 (s, $CH(OCH_3)_2$), 3.32 (m, 4'-H), 3.34 (m, 5'-H), 3.36 (m, 4-H), 3.54 (s, 4-$OCH_3$), 3.91 (br d, 5-H), 4.26 (m, 15-H), 4.38 (dq, 5"-H), 4.50 (dd, $CH(OCH_3)_2$), 4.61 (d, 4"-H), 4.71 (d, 1'-H), 4.94 (m, 9-H), 5.00 (dd, 2'-H), 5.06 (d, 1"-H), 5.23 (br dd, 3-H), 6.34 (dt, CH═CH), 6.55 (d, CH═CH), 7.40 (m, naphthalene), 7.56 (d, naphthalene), 7.66 (s, naphthalene), 7.75 (dd, naphthalene).

(b) In the same manner as in Example 2(c), 8.0 mg of a deacetyled compound (compound represented by the formula (25) mentioned in Preparation Scheme 8 wherein $R_2$ is hydrogen atom, $R_3$ is methyl group, one of $R_7$ and $R_8$ is trans-3-(naphthalen-2-yl)-2-propenyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 33.5 mg of the compound of Example 77(a).

Physicochemical Properties of this Compound (1) Molecular formula: $C_{55}H_{86}N_2O_{16}$ (2) Mass spectrum (FAB): m/z 1031 $(M+H)^+$ (3) Specific rotation: $[\alpha]_D^{24}$ −46° (c1.0, $CHCl_3$)

(4) $^1$H NMR spectrum (300 MHz, $CDCl_3$) δ (ppm): 0.86 (d, 8-$CH_3$), 1.11 (s, 3"-$CH_3$), 1.12 (d, 6"-H), 1.13 (t, 3-$OCOCH_2CH_3$), 1.17 (t, 4"-$OCOCH_2CH_3$), 1.24 (d, 6'-H), 1.30 (m, 6-$CH_2$), 1.84 (dd, 2"-Hax), 2.00 (d, 2"-Heq), 2.34 (m, 13-$CH_2$), 2.36 (s, $NCH_3$), 2.50 (s, 3'-$N(CH_3)_2$), 2.65 (dd, 2-H), 3.14 (s, $CH(OCH_3)_2$), 3.24 (s, $CH(OCH_3)_2$), 3.28 (m, 4'-H), 3.30 (m, 5'-H), 3.59 (dd, 2'-H), 3.62 (s, 4-$OCH_3$), 3.86 (br d, 5-H), 4.10 (m, 15-H), 4.41 (d, 1'-H), 4.48 (dq, 5"-H), 4.62 (d, 4"-H), 5.06 (d, 1"-H), 5.78 (br dd, 3-H), 6.34 (dt, CH═CH), 6.55 (d, CH═CH), 7.43 (m, naphthalene), 7.56 (d, naphthalene), 7.65 (s, naphthalene), 7.76 (dd, naphthalene).

(c) In the same manner as in Example 2(d), 3.7 mg of the title compound was obtained from 12.4 mg of the compound of Example 77(b).

Physicochemical Properties of this Compound (1) Molecular formula: $C_{53}H_{80}N_2O_{15}$ (2) Mass spectrum (FAB): m/z 985 $(M+H)^+$ (3) Specific rotation: $[\alpha]_D^{23}$ −47° (c1.0, $CHCl_3$)

(4) $^1$H NMR spectrum (300 MHz, $CDCl_3$) δ (ppm): 0.87 (d, 8-$CH_3$), 1.10 (s, 3"-$CH_3$), 1.12 (d, 6"-H), 1.18 (t, 3-$OCOCH_2CH_3$), 1.20 (t, 4"-$OCOCH_2CH_3$), 1.22 (d, 6'-H), 1.82 (dd, 2"-Hax), 2.00 (d, 2"-Heq), 2.34 (s, $NCH_3$), 2.50 (s, 3'-$N(CH_3)_2$), 2.67 (dd, 2-H), 2.85 (dd, 6-$CH_2$), 3.28 (m, 4'-H), 3.28 (m, 5'-H), 3.55 (dd, 2'-H), 3.62 (s, 4-$OCH_3$), 3.66 (br d, 4-H), 3.83 (br d, 5-H), 4.12 (m, 15-H), 4.35 (d, 1'-H), 4.46 (dq, 5"-H), 4.61 (d, 4"-H), 5.07 (d, 1"-H), 5.85 (br dd, 3-H), 6.37 (dt, CH═CH), 6.55 (d, CH═CH), 7.42 (m, naphthalene), 7.58 (d, naphthalene), 7.67 (s, naphthalene), 7.76 (dd, naphthalene), 9.65 (s, CHO).

Example 78

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is 3-(quinolin-3-yl)propyl group, $R_{4'}$ is a group represented by the formula (a), $R_{3''}$ is hydrogen atom, $R_{4''}$ is propionyl group, and X is oxygen atom (a) In the same manner as in Example 2(a), except that acetic acid was not used, and the compound of Reference Example 22 was used instead of the compound of Reference Example 1, 1.58 g of an amine compound (compound represented by the formula (23) mentioned in Preparation Scheme 8 wherein $R_3$ is methyl group, $R_7$, $R_8$ and $R_{12}$ are hydrogen atoms, $R_{11}$ is allyl group, $R_{3''}$ is hydrogen atom, $R_{4''}$ is propionyl group, and X is hydroxyl group) was obtained from 1.85 g of the compound of Example 19.

Physicochemical Properties of this Compound (1) Molecular formula: $C_{49}H_{86}N_2O_{19}$ (2) Mass spectrum (FAB): m/z 1007 $(M+H)^+$ (3) Specific rotation: $[\alpha]_D^{22}$ −57° (c1.12, $CHCl_3$)

(4) $^1$H NMR spectrum (300 MHz, $CDCl_3$) δ (ppm): 0.88 (d, 8-$CH_3$), 1.11 (s, 3"-$CH_3$), 1.12 (d, 6"-H), 1.14 (t, 3-$OCOCH_2CH_3$), 1.16 (t, 4"-$OCOCH_2CH_3$), 1.26 (d, 6'-H), 1.83 (dd, 2"-Hax), 2.00 (d, 2"-Heq), 2.04 (s, 9-$OCOCH_3$), 2.04 (s, 2'-$OCOCH_3$), 2.23 (m, 15-$CH_2$), 2.40 (s, 3'-$N(CH_3)_2$), 2.48 (s, $NCH_3$), 2.72 (dd, 3'-H), 2.74 (dd, 2-H), 2.87 (dd, 2-H), 3.21 (s, $CH(OCH_3)_2$), 3.25 (s, $CH(OCH_3)_2$), 3.31 (dd, 4'-H), 3.32 (m, 5'-H), 3.46 (d, 4-H), 3.55 (s, 4-$OCH_3$), 3.65 (m, 15-H), 3.88 (d, 5-H), 4.25 (br s, 3"-OH), 4.37 (dq, 5"-H), 4.54 (dd, $CH(OCH_3)_2$), 4.61 (d, 4"-H), 4.73 (d, 1'-H), 4.98 (dd, 2'-H), 5.04 (d, 1"-H), 5.07 (m, 15-$CH_2$—CH═CH), 5.14 (br t, 3-H), 5.14 (m, 9-H), 5.81 (m, 15-$CH_2$—CH═CH).

(b) In the same manner as in Example 48(b), 825 mg of a cyclized compound (compound represented by the formula (24) mentioned in Preparation Scheme 8 wherein $R_3$ is methyl group, $R_7$, $R_8$ and $R_{12}$ are hydrogen atoms, $R_{11}$ is allyl group, $R_{3''}$ is hydrogen atom, $R_{4''}$ is propionyl group, and X is oxygen atom) was obtained from 1.58 g of the compound of Example 78(a).

The mass spectrum (FAB) and $^1$H NMR spectrum (300 MHz, $CDCl_3$) of this compound were corresponded to those of the isomer A of Example 48 (b).

(c) In the same manner as in Example 48 (c), except that 3-bromoquinoline was used instead of 4-bromoquinoline, 83.4 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(quinolin-3-yl)-2-propenyl group, $R_{3''}$ is hydrogen atom, $R_{4''}$ is propionyl group, and X is oxygen atom) was obtained from 201 mg of the compound of Example 78(b).

The mass spectrum (FAB) and $^1$H NMR spectrum (300 MHz, $CDCl_3$) of this compound were corresponded to those of the compound of Example 53(a).

(d) In the same manner as in Example 2(c), 24.4 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(quinolin-3-yl)-2-propenyl group, $R_{3''}$ is hydrogen atom, $R_{4''}$ is propionyl group, and X is oxygen atom) was obtained from 39.2 mg of the compound of Example 78(c).

The mass spectrum (FAB) and $^1$H NMR spectrum (300 MHz, $CDCl_3$) of this compound were corresponded to those of the compound of Example 53(b).

(e) In the same manner as in Example 50(a), 15.3 mg of a double bond-reduced compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is 3-(quinolin-3-yl)propyl group, $R_{3''}$ is hydrogen atom, $R_{4''}$ is propionyl group, and X is oxygen atom) was obtained from 24.4 mg of the compound of Example 78(d).

Physicochemical Properties of this Compound (1) Molecular formula: $C_{54}H_{87}N_3O_{16}$ (2) Mass spectrum (FAB): m/z 1034 $(M+H)^+$ (3) Specific rotation: $[\alpha]_D^{25}$ −30° (c1.00, $CHCl_3$)

(4) $^1$H NMR spectrum (300 MHz, $CDCl_3$) δ (ppm): 0.89 (d, 8-$CH_3$), 1.08 (t, 3-$OCOCH_2CH_3$), 1.11 (s, 3"-$CH_3$), 1.12 (d, 6"-H), 1.17 (t, 4"-$OCOCH_2CH_3$), 1.27 (d, 6'-H), 1.82 (dd, 2"-Hax), 2.00 (d, 2"-Heq), 2.28 (s, $NCH_3$), 2.43 (q, 3-$OCOCH_2CH_3$), 2.44 (q, 4"-$OCOCH_2CH_3$), 2.50 (s, 3'-N$(CH_3)_2$), 2.58 (dd, 2-H), 2.79 (dd, quinoline-$CH_2$), 2.83 (dd, 2-H), 3.15 (s, $CH(OCH_3)_2$), 3.24 (s, $CH(OCH_3)_2$), 3.29 (dd, 4'-H), 3.31 (m, 5'-H), 3.60 (dd, 2'-H), 3.66 (s, 4-$OCH_3$), 3.89 (d, 4-H), 3.98 (d, 5-H), 4.43 (d, 1'-H), 4.45 (dd, $CH(OCH_3)_2$), 4.47 (dq, 5"-H), 4.61 (d, 4"-H), 5.03 (m, 15-H), 5.07 (d, 1"-H), 5.41 (m, 3-H), 7.51 (ddd, quinoline), 7.65 (ddd, quinoline), 7.75 (dd, quinoline), 7.89 (d, quinoline), 8.06 (br d, quinoline), 8.74 (d, quinoline).

(f) In the same manner as in Example 2(d), 5.2 mg of the title compound was obtained from 15.3 mg of the compound of Example 78(e).

Physicochemical Properties of this Compound (1) Molecular formula: $C_{52}H_{51}N_3O_{15}$ (2) Mass spectrum (FAB): m/z 988 $(M+H)^+$ (3) Specific rotation: $[\alpha]_D^{24}$ −57° (c0.43, $CHCl_3$)

(4) $^1$H NMR spectrum (300 MHz, $CDCl_3$) δ (ppm): 0.91 (d, 8-$CH_3$), 1.11 (s, 3"-$CH_3$), 1.12 (d, 6"-H), 1.13 (t, 3-$OCOCH_2CH_3$), 1.17 (t, 4"-$OCOCH_2CH_3$), 1.21 (d, 6'-H), 1.81 (dd, 2"-Hax), 2.00 (d, 2"-Heq), 2.29 (s, $NCH_3$), 2.29 (d, 10-H), 2.43 (q, 3-$OCOCH_2CH_3$), 2.44 (q, 4"-$OCOCH_2CH_3$), 2.50 (s, 3'-N$(CH_3)_2$), 2.60 (dd, 2-H), 2.84 (dd, 2-H), 3.27 (m, 4'-H), 3.27 (m, 5'-H), 3.36 (m, 9-H), 3.56 (dd, 2'-H), 3.66 (s, 4-$OCH_3$), 3.85 (d, 4-H), 4.00 (d, 5-H), 4.37 (d, 1'-H), 4.46 (dq, 5"-H), 4.62 (d, 4"-H), 5.04 (m, 15-H), 5.06 (d, 1"-H), 5.47 (m, 3-H), 7.52 (ddd, quinoline), 7.65 (ddd, quinoline), 7.75 (dd, quinoline), 7.89 (d, quinoline), 8.06 (br d, quinoline), 8.74 (d, quinoline), 9.64 (s, CHO).

Example 79

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is 3-(quinolin-3-yl)propyl group, $R_{4'}$ is hydrogen atom, and X is oxygen atom In the same manner as in Example 2(d), 3.3 mg of the title compound was obtained from 15.3 mg of the compound of Example 78(e).

Physicochemical Properties of this Compound (1) Molecular formula: $C_{42}H_{65}N_3O_{11}$ (2) Mass spectrum (FAB): m/z 788 $(M+H)^+$ (3) Specific rotation: $[\alpha]_D^{24}$ −18° (c0.28, $CHCl_3$)

(4) $^1$H NMR spectrum (300 MHz, $CDCl_3$) δ (ppm): 0.93 (d, 8-$CH_3$), 1.13 (t, 3-$OCOCH_2CH_3$), 1.24 (d, 6'-H), 2.32 (s, $NCH_3$), 2.36 (d, 10-H), 2.39 (q, 3-$OCOCH_2CH_3$), 2.51 (s, 3'-N$(CH_3)_2$), 2.60 (dd, 2-H), 2.86 (dd, 2-H), 3.02 (t, 4'-H), 3.29 (m, 5'-H), 3.38 (m, 9-H), 3.55 (dd, 2'-H), 3.66 (s, 4-$OCH_3$), 3.87 (d, 4-H), 3.99 (d, 5-H), 4.39 (d, 1'-H), 5.04 (m, 15-H), 5.46 (m, 3-H), 7.52 (ddd, quinoline), 7.66 (ddd, quinoline), 7.75 (dd, quinoline), 7.89 (d, quinoline), 8.07 (br d, quinoline), 8.74 (d, quinoline), 9.66 (s, CHO).

Example 80

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(quinolin-6-yl)-2-propenyl group, $R_{4'}$ is a group represented by the formula (a), $R_{3''}$ is hydrogen atom, $R_{4''}$ is propionyl group, and X is oxygen atom (a) In the same manner as in Example 48(c), except that 6-bromoquinoline was used instead of 4-bromoquinoline, 98.9 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(quinolin-6-yl)-2-propenyl group, $R_3$ is hydrogen atom, $R_{4''}$ is propionyl group, and X is oxygen atom) was obtained from 205 mg of the compound of Example 78(b).

Physicochemical Properties of this Compound (1) Molecular formula: $C_{58}H_{89}N_3O_{18}$ (2) Mass spectrum (FAB): m/z 1116 $(M+H)^+$ (3) Specific rotation: $[\alpha]_D^{27}$ −45° (c1.00, $CHCl_3$)

(4) $^1$H NMR spectrum (300 MHz, $CDCl_3$) δ (ppm): 0.90 (d, 8-$CH_3$), 1.10 (s, 3"-$CH_3$), 1.10 (t, 3-$OCOCH_2CH_3$), 1.11

(d, 6"-H), 1.15 (t, 4"-$OCOCH_2CH_3$), 1.25 (d, 6'-H), 1.82 (dd, 2"-Hax), 2.00 (d, 2"-Heq), 2.02 (s, 9-$OCOCH_3$), 2.03 (s, 2'-$OCOCH_3$), 2.21 (s, $NCH_3$), 2.39 (s, 3'-$N(CH_3)_2$), 2.52 (m, 15-$CH_2$), 2.58 (dd, 2-H), 2.70 (t, 3'-H), 2.83 (dd, 2-H), 3.13 (s, $CH(OCH_3)_2$), 3.23 (s, $CH(OCH_3)_2$), 3.32 (dd, 4'-H), 3.32 (m, 5'-H), 3.55 (s, 4-$OCH_3$), 3.61 (d, 4-H), 3.92 (d, 5-H), 4.26 (br s, 3"-OH), 4.36 (dq, 5"-H), 4.53 (dd, $CH(OCH_3)_2$), 4.59 (d, 4"-H), 4.70 (d, 1'-H), 4.89 (m, 9-H), 4.99 (dd, 2'-H), 5.05 (d, 1"-H), 5.05 (br t, 3-H), 5.12 (m, 15-H), 6.27 (dt, 15-$CH_2$—CH═CH), 6.58 (d, 15-$CH_2$—CH═CH), 7.35 (dd, quinoline), 7.63 (d, quinoline), 7.77 (dd, quinoline), 7.99 (d, quinoline), 8.08 (dd, quinoline), 8.82 (dd, quinoline).

(b) In the same manner as in Example 2(c), 31.7 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(quinolin-6-yl)-2-propenyl group, $R_{3''}$ is hydrogen atom, $R_{4''}$ is propionyl group, and X is oxygen atom) was obtained from 51.9 mg of the compound of Example 80(a).

Physicochemical Properties of this Compound (1) Molecular formula: $C_{54}H_{85}N_3O_{16}$ (2) Mass spectrum (FAB): m/z 1032 $(M+H)^+$ (3) Specific rotation: $[\alpha]_D^{25}$ −41° (c1.00, $CHCl_3$)

(4) $^1H$ NMR spectrum (300 MHz, $CDCl_3$) δ (ppm): 0.85 (d, 8-$CH_3$), 1.09 (t, 3-$OCOCH_2CH_3$), 1.10 (s, 3"-$CH_3$), 1.11 (d, 6"-H), 1.16 (t, 4"-$OCOCH_2CH_3$), 1.26 (d, 6'-H), 1.81 (dd, 2"-Hax), 1.99 (d, 2"-Heq), 2.29 (s, $NCH_3$), 2.42 (q, 3-$OCOCH_2CH_3$), 2.43 (q, 4"-$OCOCH_2CH_3$), 2.48 (s, 3'-$N(CH_3)_2$), 2.60 (dd, 2-H), 2.79 (dd, 2-H), 3.15 (s, $CH(OCH_3)_2$), 3.24 (s, $CH(OCH_3)_2$), 3.27 (t, 4'-H), 3.30 (m, 5'-H), 3.32 (m, 9-H), 3.59 (dd, 2'-H), 3.59 (s, 4-$OCH_3$), 3.88 (d, 4-H), 3.99 (d, 5-H), 4.41 (d, 1'-H), 4.46 (dd, $CH(OCH_3)_2$), 4.49 (dq, 5"-H), 4.60 (d, 4"-H), 5.06 (d, 1"-H), 5.12 (m, 15-H), 5.47 (m, 3-H), 6.26 (dt, 15-$CH_2$—CH═CH), 6.57 (d, 15-$CH_2$—CH═CH), 7.36 (dt, quinoline), 7.61 (d, quinoline), 7.76 (dd, quinoline), 8.00 (d, quinoline), 8.07 (d, quinoline), 8.83 (dd, quinoline).

(c) In the same manner as in Example 2(d), 19.6 mg of the title compound was obtained from 31.7 mg of the compound of Example 80(b).

Physicochemical Properties of this Compound (1) Molecular formula: $C_{52}H_{79}N_3O_{15}$ (2) Mass spectrum (FAB): m/z 986 $(M+H)^+$ (3) Specific rotation: $[\alpha]_D^{24}$ −34° (c1.00, $CHCl_3$)

(4) $^1H$ NMR spectrum (300 MHz, $CDCl_3$) δ (ppm): 0.90 (d, 8-$CH_3$), 1.10 (s, 3"-$CH_3$), 1.12 (d, 6"-H), 1.14 (t, 3-$OCOCH_2CH_3$), 1.17 (t, 4"-$OCOCH_2CH_3$), 1.20 (d, 6'-H), 1.82 (dd, 2"-Hax), 1.99 (d, 2"-Heq), 2.30 (d, 10-H), 2.30 (s, $NCH_3$), 2.42 (q, 3-$OCOCH_2CH_3$), 2.44 (q, 4"-$OCOCH_2CH_3$), 2.49 (s, 3'-$N(CH_3)_2$), 2.61 (dd, 2-H), 2.86 (dd, 2-H), 3.26 (t, 4'-H), 3.27 (m, 5'-H), 3.38 (m, 9-H), 3.54 (dd, 2'-H), 3.60 (s, 4-$OCH_3$), 3.86 (d, 4-H), 4.00 (d, 5-H), 4.35 (d, 1'-H), 4.46 (dq, 5"-H), 4.60 (d, 4"-H), 5.05 (d, 1"-H), 5.13 (m, 15-H), 5.54 (m, 3-H), 6.26 (dt, 15-$CH_2$—CH═CH), 6.58 (d, 15-$CH_2$—CH═CH), 7.37 (dd, quinoline), 7.62 (d, quinoline), 7.76 (dd, quinoline), 8.01 (d, quinoline), 8.09 (dd, quinoline), 8.83 (dd, quinoline), 9.64 (s, CHO).

Example 81

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(quinolin-6-yl)-2-propenyl group, $R_{4'}$ is hydrogen atom, and X is oxygen atom In the same manner as in Example 2(d), 9.1 mg of the title compound was obtained from 31.7 mg of the compound of Example 80(b).

Physicochemical Properties of this Compound (1) Molecular formula: $C_{42}H_{63}N_3O_{11}$ (2) Mass spectrum (FAB): m/z 786 $(M+H)^+$ (3) Specific rotation: $[\alpha]_D^{24}$ −12° (c0.76, $CHCl_3$)

(4) $^1H$ NMR spectrum (300 MHz, $CDCl_3$) δ (ppm): 0.91 (d, 8-$CH_3$), 1.14 (t, 3-$OCOCH_2CH_3$), 1.24 (d, 6'-H), 2.32 (s, $NCH_3$), 2.33 (d, 10-H), 2.35 (s, 3'-$N(CH_3)_2$), 2.39 (q, 3-$OCOCH_2CH_3$), 2.62 (dd, 2-H), 2.83 (dd, 2-H), 3.03 (t, 4'-H), 3.24 (m, 5'-H), 3.37 (m, 9-H), 3.53 (dd, 2'-H), 3.60 (s, 4-$OCH_3$), 3.86 (d, 4-H), 3.99 (d, 5-H), 4.37 (d, 1'-H), 5.13 (m, 15-H), 5.53 (m, 3-H), 6.26 (dt, 15-$CH_2$—CH═CH), 6.59 (d, 15-$CH_2$—CH═CH), 7.37 (dd, quinoline), 7.63 (d, quinoline), 7.77 (dd, quinoline), 8.01 (d, quinoline), 8.09 (dd, quinoline), 8.84 (dd, quinoline), 9.66 (s, CHO).

Example 82

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(pyridin-3-yl)-2-propenyl group, $R_{4'}$ is a group represented by the formula (a), $R_{3''}$ is hydrogen atom, $R_{4''}$ is propionyl group, and X is oxygen atom (a) In the same manner as in Example 48(c), except that 3-bromopyridine was used instead of 4-bromoquinoline, 42.9 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(pyridin-3-yl)-2-propenyl group, $R_3$ is hydrogen atom, $R_{4''}$ is propionyl group, and X is oxygen atom) was obtained from 194 mg of the compound of Example 78(b).

Physicochemical Properties of this Compound (1) Molecular formula: $C_{54}H_{87}N_3O_{18}$ (2) Mass spectrum (FAB): m/z 1066 $(M+H)^+$ (3) Specific rotation: $[\alpha]_D^{27}$ −43° (c1.00, $CHCl_3$)

(4) $^1H$ NMR spectrum (300 MHz, $CDCl_3$) δ (ppm): 0.89 (d, 8-$CH_3$), 1.09 (s, 3"-$CH_3$), 1.10 (d, 6"-H), 1.11 (t, 3-$OCOCH_2CH_3$), 1.15 (t, 4"-$OCOCH_2CH_3$), 1.25 (d, 6'-H), 1.82 (dd, 2"-Hax), 1.99 (d, 2"-Heq), 2.02 (s, 9-$OCOCH_3$), 2.02 (s, 2'-$OCOCH_3$), 2.20 (s, $NCH_3$), 2.39 (s, 3'-$N(CH_3)_2$), 2.47 (m, 15-$CH_2$), 2.56 (dd, 2-H), 2.71 (t, 3'-H), 2.83 (dd, 2-H), 3.13 (s, $CH(OCH_3)_2$), 3.23 (s, $CH(OCH_3)_2$), 3.32 (m, 4'-H), 3.32 (m, 5'-H), 3.56 (s, 4-$OCH_3$), 3.59 (d, 4-H), 3.92 (d, 5-H), 4.25 (br s, 3"-OH), 4.36 (dq, 5"-H), 4.53 (dd, $CH(OCH_3)_2$), 4.59 (d, 4"-H), 4.70 (d, 1'-H), 4.88 (m, 9-H), 4.99 (dd, 2'-H), 5.05 (d, 1"-H), 6.17 (dt, 15-$CH_2$—CH═CH), 6.40 (d, 15-$CH_2$—CH═CH), 7.19 (dd, pyridine), 7.63 (dt, pyridine), 8.41 (dd, pyridine), 8.52 (d, pyridine).

(b) In the same manner as in Example 2(c), 20.8 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(pyridin-3-yl)-2-propenyl group, $R_{3''}$ is hydrogen atom, $R_{4''}$ is propionyl group, and X is oxygen atom) was obtained from 42.9 mg of the compound of Example 82(a).

Physicochemical Properties of this Compound (1) Molecular formula: $C_{50}H_{83}N_3O_{16}$ (2) Mass spectrum (FAB): m/z 982 $(M+H)^+$ (3) Specific rotation: $[\alpha]_D^{26}$ −43° (c1.00, $CHCl_3$)

(4) $^1$H NMR spectrum (300 MHz, $CDCl_3$) δ (ppm): 0.86 (d, 8-$CH_3$), 1.10 (t, 3-$OCOCH_2CH_3$), 1.10 (s, 3"-$CH_3$), 1.12 (d, 6"-H), 1.17 (t, 4"-$OCOCH_2CH_3$), 1.26 (d, 6'-H), 1.82 (dd, 2"-Hax), 1.99 (d, 2"-Heq), 2.29 (s, $NCH_3$), 2.42 (q, 3-$OCOCH_2CH_3$), 2.43 (q, 4"-$OCOCH_2CH_3$), 2.49 (s, 3'-N$(CH_3)_2$), 2.58 (dd, 2-H), 2.78 (dd, 2-H), 3.15 (s, $CH(OCH_3)_2$), 3.24 (s, $CH(OCH_3)_2$), 3.28 (m, 4'-H), 3.30 (m, 5'-H), 3.35 (m, 9-H), 3.59 (dd, 2'-H), 3.62 (s, 4-$OCH_3$), 3.89 (d, 4-H), 3.98 (d, 5-H), 4.42 (d, 1'-H), 4.45 (dd, $CH(OCH_3)_2$), 4.47 (dq, 5"-H), 4.61 (d, 4"-H), 5.07 (d, 1"-H), 5.08 (m, 15-H), 5.46 (m, 3-H), 6.17 (dt, 15-$CH_2$—CH═CH), 6.39 (d, 15-$CH_2$—CH═CH), 7.20 (dd, pyridine), 7.62 (dt, pyridine), 8.43 (dd, pyridine), 8.52 (t, pyridine).

(c) In the same manner as in Example 2(d), 10.8 mg of the title compound was obtained from 20.8 mg of the compound of Example 82(b).

Physicochemical Properties of this Compound (1) Molecular formula: $C_{48}H_{77}N_3O_{15}$ (2) Mass spectrum (FAB): m/z 986 $(M+H)^+$ (3) Specific rotation: $[\alpha]_D^{26}$ −52° (c0.90, $CHCl_3$)

(4) $^1$H NMR spectrum (300 MHz, $CDCl_3$) δ (ppm): 0.90 (d, 8-$CH_3$), 1.10 (s, 3"-$CH_3$), 1.12 (d, 6"-H), 1.14 (t, 3-$OCOCH_2CH_3$), 1.17 (t, 4"-$OCOCH_2CH_3$), 1.18 (d, 6'-H), 1.82 (dd, 2"-Hax), 1.99 (d, 2"-Heq), 2.30 (d, 10-H), 2.30 (s, $NCH_3$), 2.43 (q, 3-$OCOCH_2CH_3$), 2.44 (q, 4"-$OCOCH_2CH_3$), 2.49 (s, 3'-N$(CH_3)_2$), 2.60 (dd, 2-H), 2.86 (dd, 2-H), 3.27 (m, 4'-H), 3.27 (m, 5'-H), 3.32 (m, 9-H), 3.55 (dd, 2'-H), 3.62 (s, 4-$OCH_3$), 3.85 (d, 4-H), 3.99 (d, 5-H), 4.36 (d, 1'-H), 4.47 (dq, 5"-H), 4.61 (d, 4"-H), 5.06 (d, 1"-H), 5.08 (m, 15-H), 5.53 (m, 3-H), 6.17 (dt, 15-$CH_2$—CH═CH), 6.40 (d, 15-$CH_2$—CH═CH), 7.20 (dd, pyridine), 7.62 (dt, pyridine), 8.43 (dd, pyridine), 8.52 (d, pyridine), 9.64 (s, CHO).

Example 83

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(pyridin-3-yl)-2-propenyl group, $R_{4'}$ is hydrogen atom, and X is oxygen atom In the same manner as in Example 2(d), 3.5 mg of the title compound was obtained from 20.8 mg of the compound of Example 82(b).

Physicochemical Properties of this Compound (1) Molecular formula: $C_{38}H_{61}N_3O_{11}$ (2) Mass spectrum (FAB): m/z 736 $(M+H)^+$ (3) Specific rotation: $[\alpha]_D^{23}$ −19° (c0.29, $CHCl_3$)

(4) $^1$H NMR spectrum (300 MHz, $CDCl_3$) δ (ppm): 0.90 (d, 8-$CH_3$), 1.15 (t, 3-$OCOCH_2CH_3$), 1.24 (d, 6'-H), 2.30 (d, 10-H), 2.30 (s, $NCH_3$), 2.40 (q, 3-$OCOCH_2CH_3$), 2.49 (s, 3'-N$(CH_3)_2$), 2.61 (dd, 2-H), 2.81 (dd, 2-H), 3.00 (t, 4'-H), 3.29 (m, 5'-H), 3.31 (m, 9-H), 3.53 (dd, 2'-H), 3.63 (s, 4-$OCH_3$), 3.86 (d, 4-H), 3.99 (d, 5-H), 4.38 (d, 1'-H), 5.09 (m, 15-H), 5.54 (m, 3-H), 6.17 (dt, 15-$CH_2$—CH═CH), 6.40 (d, 15-$CH_2$—CH═CH), 7.21 (dd, pyridine), 7.63 (dt, pyridine), 8.43 (dd, pyridine), 8.53 (d, pyridine), 9.66 (s, CHO).

Example 84

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(naphthalen-2-yl)-2-propenyl group, $R_{4'}$ is a group represented by the formula (a), $R_{3''}$ is hydrogen atom, $R_{4''}$ is propionyl group, and X is oxygen atom (a) In the same manner as in Example 48(c), except that 2-bromonaphthalene was used instead of 4-bromoquinoline, 81.2 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(naphthalen-2-yl)-2-propenyl group, $R_{3''}$ is hydrogen atom, $R_{4''}$ is propionyl group, and X is oxygen atom) was obtained from 161 mg of the compound of Example 78(b).

Physicochemical Properties of this Compound (1) Molecular formula: $C_{59}H_{90}N_2O_{18}$ (2) Mass spectrum (FAB): m/z 1115 $(M+H)^+$ (3) Specific rotation: $[\alpha]_D^{27}$ −48° (c1.00, $CHCl_3$)

(4) $^1$H NMR spectrum (300 MHz, $CDCl_3$) δ (ppm): 0.90 (d, 8-$CH_3$), 1.10 (s, 3"-$CH_3$), 1.11 (d, 6"-H), 1.11 (t, 3-$OCOCH_2CH_3$), 1.16 (t, 4"-$OCOCH_2CH_3$), 1.26 (d, 6'-H), 1.82 (dd, 2"-Hax), 2.00 (d, 2"-Heq), 2.03 (s, 9-$OCOCH_3$), 2.04 (s, 2'-$OCOCH_3$), 2.22 (s, $NCH_3$), 2.39 (s, 3'-N$(CH_3)_2$), 2.51 (m, 15-$CH_2$), 2.59 (dd, 2-H), 2.71 (t, 3'-H), 2.84 (dd, 2-H), 3.14 (s, $CH(OCH_3)_2$), 3.24 (s, $CH(OCH_3)_2$), 3.32 (m, 4'-H), 3.32 (m, 5'-H), 3.56 (s, 4-$OCH_3$), 3.64 (d, 4-H), 3.92 (d, 5-H), 4.26 (br s, 3"-OH), 4.37 (dq, 5"-H), 4.54 (dd, $CH(OCH_3)_2$), 4.60 (d, 4"-H), 4.71 (d, 1'-H), 4.90 (m, 9-H), 5.00 (dd, 2'-H), 5.05 (d, 1"-H), 5.05 (br t, 3-H), 5.12 (m, 15-H), 6.22 (dt, 15-$CH_2$—CH═CH), 6.58 (d, 15-$CH_2$—CH═CH), 7.41 (m, naphthalene), 7.53 (dd, naphthalene), 7.65 (s, naphthalene), 7.75 (m, naphthalene).

(b) In the same manner as in Example 2(c), 43.5 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(naphthalen-2-yl)-2-propenyl group, $R_{3''}$ is hydrogen atom, $R_{4''}$ is propionyl group, and X is oxygen atom) was obtained from 81.2 mg of the compound of Example 84(a).

Physicochemical Properties of this Compound (1) Molecular formula: $C_{55}H_{86}N_2O_{16}$ (2) Mass spectrum (FAB): m/z 1031 $(M+H)^+$ (3) Specific rotation: $[\alpha]_D^{26}$ −47° (c1.00, $CHCl_3$)

(4) $^1$H NMR spectrum (300 MHz, $CDCl_3$) δ (ppm): 0.87 (d, 8-$CH_3$), 1.09 (t, 3-$OCOCH_2CH_3$), 1.11 (s, 3"-$CH_3$), 1.12 (d, 6"-H), 1.17 (t, 4"-$OCOCH_2CH_3$), 1.26 (d, 6'-H), 1.82 (dd, 2"-Hax), 1.99 (d, 2"-Heq), 2.29 (s, $NCH_3$), 2.43 (q, 3-$OCOCH_2CH_3$), 2.44 (q, 4"-$OCOCH_2CH_3$), 2.49 (s, 3'-N$(CH_3)_2$), 2.60 (dd, 2-H), 2.79 (dd, 2-H), 3.16 (s, $CH(OCH_3)_2$), 3.25 (s, $CH(OCH_3)_2$), 3.28 (m, 4'-H), 3.30 (m, 5'-H), 3.33 (m, 9-H), 3.60 (dd, 2'-H), 3.60 (s, 4-$OCH_3$), 3.89 (d, 4-H), 4.00 (d, 5-H), 4.41 (d, 1'-H), 4.45 (dd, $CH(OCH_3)_2$), 4.47 (dq, 5"-H), 4.61 (d, 4"-H), 5.07 (d, 1"-H), 5.12 (m, 15-H), 5.47 (m, 3-H), 6.32 (dt, 15-$CH_2$—CH═CH), 6.57 (d, 15-$CH_2$—CH═CH), 7.42 (m, naphthalene), 7.52 (dd, naphthalene), 7.64 (s, naphthalene), 7.75 (m, naphthalene).

(c) In the same manner as in Example 2(d), 12.8 mg of the title compound was obtained from 21.9 mg of the compound of Example 84(b).

Physicochemical Properties of this Compound (1) Molecular formula: $C_{53}H_{80}N_2O_{15}$ (2) Mass spectrum (FAB): m/z 985 $(M+H)^+$ (3) Specific rotation: $[\alpha]_D^{26}$ −41° (c1.07, $CHCl_3$)

(4) $^1H$ NMR spectrum (300 MHz, $CDCl_3$) δ (ppm): 0.91 (d, 8-$CH_3$), 1.11 (s, 3"-$CH_3$), 1.12 (d, 6"-H), 1.14 (t, 3-$OCOCH_2CH_3$), 1.17 (t, 4"-$OCOCH_2CH_3$), 1.18 (d, 6'-H), 1.82 (dd, 2"-Hax), 2.00 (d, 2"-Heq), 2.30 (d, 10-H), 2.31 (s, $NCH_3$), 2.43 (q, 3-$OCOCH_2CH_3$), 2.44 (q, 4"-$OCOCH_2CH_3$), 2.49 (s, 3'-$N(CH_3)_2$), 2.62 (dd, 2-H), 2.84 (dd, 2-H), 3.27 (m, 4'-H), 3.27 (m, 5'-H), 3.35 (m, 9-H), 3.55 (dd, 2'-H), 3.60 (s, 4-$OCH_3$), 3.85 (d, 4-H), 4.01 (d, 5-H), 4.36 (d, 1'-H), 4.47 (dq, 5"-H), 4.61 (d, 4"-H), 5.06 (d, 1"-H), 5.13 (m, 15-H), 5.53 (m, 3-H), 6.21 (dt, 15-$CH_2$—CH═CH), 6.58 (d, 15-$CH_2$—CH═CH), 7.43 (m, naphthalene), 7.53 (dd, naphthalene), 7.65 (s, naphthalene), 7.76 (dt, naphthalene), 9.64 (s, CHO).

Example 85

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(naphthalen-2-yl)-2-propenyl group, $R_{4'}$ is hydrogen atom, and X is oxygen atom In the same manner as in Example 2(d), 4.9 mg of the title compound was obtained from 21.9 mg of the compound of Example 84(b).

Physicochemical Properties of this Compound (1) Molecular formula: $C_{43}H_{64}N_2O_{11}$ (2) Mass spectrum (FAB): m/z 785 $(M+H)^+$ (3) Specific rotation: $[\alpha]_D^{23}$ −13° (c0.41, $CHCl_3$)

(4) $^1H$ NMR spectrum (300 MHz, $CDCl_3$) δ (ppm): 0.91 (d, 8-$CH_3$), 1.14 (t, 3-$OCOCH_2CH_3$), 1.24 (d, 6'-H), 2.31 (d, 10-H), 2.31 (s, $NCH_3$), 2.39 (q, 3-$OCOCH_2CH_3$), 2.49 (s, 3'-$N(CH_3)_2$), 2.62 (dd, 2-H), 2.82 (dd, 2-H), 3.00 (t, 4'-H), 3.27 (m, 5'-H), 3.35 (m, 9-H), 3.53 (dd, 2'-H), 3.61 (s, 4-$OCH_3$), 3.86 (d, 4-H), 4.00 (d, 5-H), 4.37 (d, 1'-H), 5.13 (m, 15-H), 5.54 (m, 3-H), 6.23 (dt, 15-$CH_2$—CH═CH), 6.58 (d, 15-$CH_2$—CH═CH), 7.43 (dt, naphthalene), 7.53 (dt, naphthalene), 7.65 (dd, naphthalene), 7.76 (d, naphthalene), 9.66 (s, CHO).

Example 86

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-phenyl-2-propenyl group, $R_{4'}$ is a group represented by the formula (a), $R_{3''}$ is hydrogen atom, $R_{4''}$ is propionyl group, and X is oxygen atom (a) In the same manner as in Example 48(c), except that bromobenzene was used instead of 4-bromoquinoline, 69.0 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-phenyl-2-propenyl group, $R_{3''}$ is hydrogen atom, $R_{4''}$ is propionyl group, and X is oxygen atom) was obtained from 78.7 mg of the isomer A of Example 78(b).

Physicochemical Properties of this Compound (1) Molecular formula: $C_{55}H_{88}N_2O_{18}$ (2) Mass spectrum (FAB): m/z 1065 $(M+H)^+$ (3) $^1H$ NMR spectrum (300 MHz, $CDCl_3$) δ (ppm): 0.90 (d, 8-$CH_3$), 1.10 (s, 3"-$CH_3$), 1.11 (t, 3-$OCOCH_2CH_3$), 1.12 (d, 6"-H), 1.16 (t, 4"-$OCOCH_2CH_3$), 1.25 (d, 6'-H), 1.72 (m, 8-H), 1.83 (dd, 2"-Hax), 2.00 (d, 2"-Heq), 2.04 (s, 9-$OCOCH_3$), 2.04 (s, 2'-$OCOCH_3$), 2.20 (s, $NCH_3$), 2.40 (s, 3'-$N(CH_3)_2$), 2.42 (m, 10-H), 2.44 (dd, 15-$CH_2$), 2.57 (m, 2-H), 2.71 (t, 3'-H), 2.84 (dd, 2'-H), 3.13 (s, $CH(OCH_3)_2$), 3.23 (s, $CH(OCH_3)_2$), 3.34 (m, 4'-H), 3.34 (m, 5'-H), 3.58 (s, 4-$OCH_3$), 3.65 (br d, 4-H), 3.92 (br d, 5-H), 4.37 (dq, 5"-H), 4.55 (dd, $CH(OCH_3)_2$), 4.60 (d, 4"-H), 4.72 (d, 1'-H), 4.88 (m, 9-H), 5.00 (dd, 2'-H), 5.06 (d, 1"-H), 6.09 (dt, CH═CH), 6.42 (d, CH═CH), 7.30 (m, $C_6H_5$).

(b) In the same manner as in Example 2(c), 37.3 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-phenyl-2-propenyl group, $R_{3''}$ is hydrogen atom, $R_{4''}$ is propionyl group, and X is oxygen atom) was obtained from 69.0 mg of the compound of Example 86(a).

Physicochemical Properties of this Compound (1) Molecular formula: $C_{51}H_{84}N_3O_{16}$ (2) Mass spectrum (FAB): m/z 981 $(M+H)^+$ (3) $^1H$ NMR spectrum (300 MHz, $CDCl_3$) δ (ppm): 0.86 (d, 8-$CH_3$), 1.10 (t, 3-$OCOCH_2CH_3$), 1.11 (s, 3"-$CH_3$), 1.12 (d, 6"-H), 1.17 (t, 4"-$OCOCH_2CH_3$), 1.26 (d, 6'-H), 1.38 (m, 8-H), 1.82 (dd, 2"-Hax), 1.99 (d, 2"-Heq), 2.30 (s, $NCH_3$), 2.44 (m, 3'-H), 2.45 (dd, 15-$CH_2$), 2.50 (s, 3'-$N(CH_3)_2$), 2.58 (dd, 2-H), 2.78 (dd, 2-H), 3.14 (s, $CH(OCH_3)_2$), 3.24 (s, $CH(OCH_3)_2$), 3.30 (m, 4'-H), 3.30 (m, 5'-H), 3.59 (dd, 2'-H), 3.65 (s, 4-$OCH_3$), 3.89 (br d, 4-H), 4.00 (br d, 5-H), 4.44 (m, $CH(OCH_3)_2$), 4.46 (dq, 5"-H), 4.61 (d, 4"-H), 5.07 (dd, 1"-H), 5.09 (m, 15-H), 5.47 (m, 3-H), 7.30 (m, $C_6H_5$).

(c) In the same manner as in Example 2(d), 19.0 mg of the title compound was obtained from 37.3 mg of the compound of Example 86(b).

Physicochemical Properties of this Compound (1) Molecular formula: $C_{49}H_{78}N_2O_{15}$ (2) Mass spectrum (FAB): m/z 935 $(M+H)^+$ (3) Specific rotation: $[\alpha]_D^{16}$ −55° (c1.0, $CHCl_3$)

(4) $^1H$ NMR spectrum (300 MHz, $CDCl_3$) δ (ppm): 0.90 (d, 8-$CH_3$), 1.11 (s, 3"-$CH_3$), 1.12 (d, 6"-H), 1.14 (t, 3-$OCOCH_2CH_3$), 1.16 (t, 4"-$OCOCH_2CH_3$), 1.19 (d, 6'-H), 1.30 (m, 8-H), 1.82 (dd, 2"-Hax), 2.00 (d, 2"-Heq), 2.30 (s, $NCH_3$), 2.45 (m, 3'-H), 2.49 (s, 3'-$N(CH_3)_2$), 2.61 (dd, 2-H), 2.82 (dd, 2-H), 2.88 (dd, 6-$CH_2$), 3.28 (m, 4'-H), 3.28 (m, 5'-H), 3.36 (m, 9-H), 3.55 (dd, 2'-H), 3.60 (s, 4-$OCH_3$), 3.84 (br d, 4-H), 4.00 (br d, 5-H), 4.36 (d, 1'-H), 4.46 (dq, 5"-H), 4.61 (d, 4"-H), 5.06 (d, 1"-H), 5.09 (m, 15-H), 5.52 (m, 3-H), 7.30 (m, $C_6H_5$), 9.64 (s, CHO).

Example 87

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(naphthalen-1-yl)-2-propenyl group, $R_{4'}$ is a group represented by the formula (a), $R_{3''}$ is hydrogen atom, $R_{4''}$ is propionyl group, and X is oxygen atom (a) In the same manner as in Example 48(c), except that 1-bromonaphthalene was used instead of 4-bromoquinoline, 115 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(naphthalen-1-yl)-2-propenyl group, $R_{3''}$ is hydrogen atom, $R_{4''}$ is propionyl group, and X is oxygen atom) was obtained from 176 mg of the compound of Example 78(b).

Physicochemical Properties of this Compound (1) Molecular formula: $C_{59}H_{90}N_2O_{18}$ (2) Mass spectrum (FAB): m/z 1115 $(M+H)^+$ (3) Specific rotation: $[\alpha]_D^{22}$ −43° (c1.00, $CHCl_3$)

(4) $^1H$ NMR spectrum (300 MHz, $CDCl_3$) δ (ppm): 0.91 (d, 8-$CH_3$), 1.11 (s, 3"-$CH_3$), 1.11 (t, 3-$OCOCH_2CH_3$), 1.12 (d, 6"-H), 1.17 (t, 4"-$OCOCH_2CH_3$), 1.26 (d, 6'-H), 1.83 (dd, 2"-Hax), 2.00 (d, 2"-Heq), 2.03 (s, 9-$OCOCH_3$), 2.05 (s, 2'-$OCOCH_3$), 2.23 (s, $NCH_3$), 2.40 (s, 3'-$N(CH_3)_2$), 2.55 (m, 15-$CH_2$), 2.60 (dd, 2-H), 2.71 (t, 3'-H), 2.85 (dd, 2-H), 3.14 (s, $CH(OCH_3)_2$), 3.24 (s, $CH(OCH_3)_2$), 3.32 (m, 4'-H), 3.32 (m, 5'-H), 3.56 (s, 4-$OCH_3$), 3.68 (d, 4-H), 3.93 (d, 5-H), 4.28 (br s, 3"-OH), 4.38 (dq, 5"-H), 4.56 (dd, $CH(OCH_3)_2$), 4.61 (d, 4"-H), 4.72 (d, 1'-H), 4.91 (m, 9-H), 5.00 (dd, 2'-H), 5.06 (d, 1"-H), 5.17 (m, 15-H), 6.11 (dt, 15-$CH_2$—CH═CH), 7.15 (d, 15-$CH_2$—CH═CH), 7.40 (t, naphthalene), 7.48 (m, naphthalene), 7.74 (d, naphthalene), 7.83 (m, naphthalene), 7.86 (m, naphthalene).

(b) In the same manner as in Example 2(c), 91.4 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(naphthalen-1-yl)-2-propenyl group, $R_{3''}$ is hydrogen atom, $R_{4''}$ is propionyl group, and X is oxygen atom) was obtained from 115 mg of the compound of Example 87(a).

Physicochemical Properties of this Compound (1) Molecular formula: $C_{55}H_{86}N_2O_{16}$ (2) Mass spectrum (FAB): m/z 1031 $(M+H)^+$ (3) Specific rotation: $[\alpha]_D^{22}$ −34° (c1.00, $CHCl_3$)

(4) $^1H$ NMR spectrum (300 MHz, $CDCl_3$) δ (ppm): 0.87 (d, 8-$CH_3$), 1.07 (t, 3-$OCOCH_2CH_3$), 1.11 (s, 3"-$CH_3$), 1.12 (d, 6"-H), 1.17 (t, 4"-$OCOCH_2CH_3$), 1.26 (d, 6'-H), 1.81 (dd, 2"-Hax), 1.99 (d, 2"-Heq), 2.30 (s, $NCH_3$), 2.42 (q, 3-$OCOCH_2CH_3$), 2.43 (q, 4"-$OCOCH_2CH_3$), 2.49 (s, 3'-$N(CH_3)_2$), 2.60 (dd, 2-H), 2.80 (dd, 2-H), 3.15 (s, $CH(OCH_3)_2$), 3.24 (s, $CH(OCH_3)_2$), 3.28 (m, 4'-H), 3.30 (m, 5'-H), 3.32 (m, 9-H), 3.56 (dd, 2'-H), 3.58 (s, 4-$OCH_3$), 3.89 (d, 4-H), 4.01 (d, 5-H), 4.42 (d, 1'-H), 4.45 (dd, $CH(OCH_3)_2$), 4.47 (dq, 5"-H), 4.60 (d, 4"-H), 5.06 (d, 1"-H), 5.10 (m, 15-H), 5.47 (m, 3-H), 6.07 (dt, 15-$CH_2$—CH═CH), 7.13 (d, 15-$CH_2$—CH═CH), 7.38 (t, naphthalene), 7.47 (m, naphthalene), 7.73 (d, naphthalene), 7.82 (dd, naphthalene), 8.04 (d, naphthalene).

(c) In the same manner as in Example 2(d), 47.4 mg of the title compound was obtained from 91.4 mg of the compound of Example 87(b).

Physicochemical Properties of this Compound (1) Molecular formula: $C_{53}H_{80}N_2O_{15}$ (2) Mass spectrum (FAB): m/z 985 $(M+H)^+$ (3) Specific rotation: $[\alpha]_D^{22}$ −44° (c1.00, $CHCl_3$)

(4) $^1H$ NMR spectrum (300 MHz, $CDCl_3$) δ (ppm): 0.90 (d, 8-$CH_3$), 1.10 (s, 3"-$CH_3$), 1.12 (d, 6"-H), 1.13 (t, 3-$OCOCH_2CH_3$), 1.16 (t, 4"-$OCOCH_2CH_3$), 1.18 (d, 6'-H), 1.82 (dd, 2"-Hax), 1.99 (d, 2"-Heq), 2.31 (d, 10-H), 2.31 (s, $NCH_3$), 2.41 (q, 3-$OCOCH_2CH_3$), 2.43 (q, 4"-$OCOCH_2CH_3$), 2.49 (s, 3'-$N(CH_3)_2$), 2.58 (dd, 2-H), 2.82 (dd, 2-H), 3.27 (m, 4'-H), 3.27 (m, 5'-H), 3.34 (m, 9-H), 3.54 (dd, 2'-H), 3.57 (s, 4-$OCH_3$), 3.84 (d, 4-H), 4.02 (d, 5-H), 4.36 (d, 1'-H), 4.47 (dq, 5"-H), 4.60 (d, 4"-H), 5.05 (d, 1"-H), 5.16 (m, 15-H), 5.53 (m, 3-H), 6.10 (dt, 15-$CH_2$—CH═CH), 7.14 (d, 15-$CH_2$—CH═CH), 7.39 (dt, naphthalene), 7.47 (dt, naphthalene), 7.73 (dd, naphthalene), 7.82 (d, naphthalene), 8.04 (d, naphthalene), 9.63 (s, CHO).

Example 88

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(2-fluoro-4-((R)-5-(hydroxymethyl)oxazolidin-2-on-3-yl)phenyl)-2-propenyl group, $R_{4'}$ is a group represented by the formula (a), $R_{3''}$ is hydrogen atom, $R_{4''}$ is propionyl group, and X is oxygen atom (a) In the same manner as in Example 48(c), except that (R)-3-(3-fluoro-4-iodophenyl)-5-(hydroxymethyl)oxazolidin-2-one was used instead of 4-bromoquinoline, 72.9 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(2-fluoro-4-((R)-5-(hydroxymethyl)oxazolidin-2-on-3-yl)phenyl)-2-propenyl group, $R_{3''}$ is hydrogen atom, $R_{4''}$ is propionyl group, and X is oxygen atom) was obtained from 191 mg the compound of Example 78(b).

Physicochemical Properties of this Compound (1) Molecular formula: $C_{58}H_{92}FN_3O_{21}$ (2) Mass spectrum (FAB): m/z 1198 $(M+H)^+$ (3) Specific rotation: [α]D$^{25}$ −53° (c1.00, $CHCl_3$)

(4) $^1H$ NMR spectrum (300 MHz, $CDCl_3$) δ (ppm): 0.91 (d, 8-$CH_3$), 1.10 (s, 3"-$CH_3$), 1.12 (d, 6"-H), 1.11 (t, 3-$OCOCH_2CH_3$), 1.16 (t, 4"-$OCOCH_2CH_3$), 1.27 (d, 6'-H), 1.83 (dd, 2"-Hax), 2.00 (d, 2"-Heq), 2.04 (s, 9-$OCOCH_3$), 2.04 (s, 2'-$OCOCH_3$), 2.22 (s, $NCH_3$), 2.40 (s, 3'-$N(CH_3)_2$), 2.58 (dd, 2-H), 2.72 (t, 3'-H), 2.85 (dd, 2-H), 3.14 (s, $CH(OCH_3)_2$), 3.24 (s, $CH(OCH_3)_2$), 3.34 (m, 4'-H), 3.34 (m, 5'-H), 3.58 (s, 4-$OCH_3$), 3.66 (d, 4-H), 3.75 (dd, oxazolidinone), 3.98 (m, oxazolidinone), 3.93 (d, 5-H), 4.28 (br s, 3"-OH), 4.38 (dq, 5"-H), 4.55 (dd, $CH(OCH_3)_2$), 4.61 (d, 4"-H), 4.72 (d, 1'-H), 4.74 (m, oxazolidinone), 4.90 (m, 9-H), 5.00 (dd, 2'-H), 5.07 (d, 1"-H), 6.13 (dt, 15-$CH_2$—CH═CH), 6.50 (d, 15-$CH_2$—CH═CH), 7.19 (t, $C_6H_3$), 7.35 (dt, $C_6H_3$), 7.38 (d, $C_6H_3$).

(b) In the same manner as in Example 2(c), 19.6 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(2-fluoro-4-((R)-5-(hydroxymethyl)oxazolidin-2-on-3-yl)phenyl)-2-propenyl group, $R_{3''}$ is hydrogen atom, $R_{4''}$ is propionyl group, and X is oxygen atom) was obtained from 37.1 mg of the compound of Example 88(a).

Physicochemical Properties of this Compound (1) Molecular formula: $C_{55}H_{88}FN_3O_{19}$ (2) Mass spectrum (FAB): m/z 1114 $(M+H)^+$ (3) Specific rotation: $[\alpha]_D^{25}$ −51° (c1.00, $CHCl_3$)

(4) $^1H$ NMR spectrum (300 MHz, $CDCl_3$) δ (ppm): 0.86 (d, 8-$CH_3$), 1.10 (t, 3-$OCOCH_2CH_3$), 1.10 (s, 3"-$CH_3$), 1.12 (d, 6"-H), 1.17 (t, 4"-$OCOCH_2CH_3$), 1.26 (d, 6'-H), 1.82 (dd, 2"-Hax), 1.99 (d, 2"-Heq), 2.29 (s, $NCH_3$), 2.42 (q, 3-$OCOCH_2CH_3$), 2.43 (q, 4"-$OCOCH_2CH_3$), 2.49 (s, 3'-$N(CH_3)_2$), 2.59 (dd, 2-H), 2.79 (dd, 2-H), 3.15 (s, $CH(OCH_3)_2$), 3.24 (s, $CH(OCH_3)_2$), 3.28 (m, 4'-H), 3.30 (m, 5'-H), 3.33 (m, 9-H), 3.60 (dd, 2'-H), 3.62 (s, 4-$OCH_3$), 3.75 (dd, oxazolidinone), 3.89 (d, 4-H), 3.98 (m, oxazolidinone), 4.43 (d, 1'-H), 4.45 (dd, $CH(OCH_3)_2$), 4.47 (dq, 5"-H), 4.61 (d, 4"-H), 4.74 (m, oxazolidinone), 5.06 (d, 1"-H), 5.08 (m, 15-H), 5.46 (m, 3-H), 6.11 (dt, 15-$CH_2$—CH═CH), 6.48 (d, 15-$CH_2$—CH═CH), 7.17 (dt, $C_6H_3$), 7.33 (dt, $C_6H_3$), 7.38 (dd, $C_6H_3$).

(c) In the same manner as in Example 2(d), 8.6 mg of the title compound was obtained from 19.6 mg of the compound of Example 88(b).

Physicochemical Properties of this Compound (1) Molecular formula: $C_{53}H_{82}FN_3O_{18}$ (2) Mass spectrum (FAB): m/z 1068 $(M+H)^+$ (3) Specific rotation: $[\alpha]_D^{24}$ −66° (c0.72, $CHCl_3$)

(4) $^1H$ NMR spectrum (300 MHz, $CDCl_3$) δ (ppm): 0.90 (d, 8-$CH_3$), 1.11 (s, 3"-$CH_3$), 1.12 (d, 6"-H), 1.15 (t, 3-$OCOCH_2CH_3$), 1.17 (t, 4"-$OCOCH_2CH_3$), 1.20 (d, 6'-H), 1.82 (dd, 2"-Hax), 2.00 (d, 2"-Heq), 2.30 (d, 10-H), 2.31 (s, $NCH_3$), 2.43 (q, 3-$OCOCH_2CH_3$), 2.44 (q, 4"-$OCOCH_2CH_3$), 2.50 (s, 3'-$N(CH_3)_2$), 2.62 (dd, 2-H), 2.86 (dd, 2-H), 3.27 (m, 4'-H), 3.27 (m, 5'-H), 3.34 (m, 9-H), 3.55 (dd, 2'-H), 3.62 (s, 4-$OCH_3$), 3.75 (dd, oxazolidinone), 3.85 (d, 4-H), 3.99 (m, oxazolidinone), 4.32 (br s, 3"-OH), 4.37 (d, 1'-H), 4.46 (dq, 5"-H), 4.61 (d, 4"-H), 4.75 (m, oxazolidinone), 5.06 (d, 1"-H), 5.09 (m, 15-H), 5.52 (m, 3-H), 6.11 (dt, 15-$CH_2$—CH═CH), 6.48 (d, 15-$CH_2$—CH═CH), 7.18 (dd, $C_6H_3$), 7.36 (dd, $C_6H_3$), 7.40 (d, $C_6H_3$), 9.64 (s, CHO).

Example 89

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(2-fluoro-4-((R)-5-(hydroxymethyl)oxazolidin-2-on-3-yl)phenyl)-2-propenyl group, $R_{4'}$ is hydrogen atom, and X is oxygen atom In the same manner as in Example 2(d), 3.5 mg of the title compound was obtained from 19.6 mg of the compound of Example 88(b).

Physicochemical Properties of this Compound (1) Molecular formula: $C_{43}H_{66}FN_3O_{14}$ (2) Mass spectrum (FAB): m/z 868 $(M+H)^+$ (3) Specific rotation: $[\alpha]_D^{25}$ −33° (c0.29, $CHCl_3$)

(4) $^1H$ NMR spectrum (300 MHz, $CDCl_3$) δ (ppm): 0.91 (d, 8-$CH_3$), 1.15 (t, 3-$OCOCH_2CH_3$), 1.25 (d, 6'-H), 2.33 (s, $NCH_3$), 2.36 (d, 10-H), 2.43 (q, 3-$OCOCH_2CH_3$), 2.51 (s, 3'-$N(CH_3)_2$), 2.62 (dd, 2-H), 2.84 (dd, 2-H), 3.05 (t, 4'-H), 3.30 (m, 5'-H), 3.35 (m, 9-H), 3.54 (dd, 2'-H), 3.63 (s, 4-$OCH_3$), 3.76 (dd, oxazolidinone), 3.86 (d, 4-H), 3.99 (m, oxazolidinone), 4.38 (d, 1'-H), 5.09 (m, 15-H), 5.52 (m, 3-H), 6.12 (dt, 15-$CH_2$—CH═CH), 6.49 (d, 15-$CH_2$—CH═CH), 7.19 (dd, $C_6H_3$), 7.36 (dd, $C_6H_3$), 7.40 (d, $C_6H_3$), 9.66 (s, CHO).

Example 90

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(quinolin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 2(a), except that acetic acid was not added, and the compound of Reference Example 22 was used instead of the compound of Reference Example 1, 2.94 g of an amine compound (compound represented by the formula (23) mentioned in Preparation Scheme 8 wherein $R_3$ is methyl group, $R_7$, $R_8$ and $R_{12}$ are hydrogen atoms, $R_{11}$ is allyl group, $R_{3''}$ is acetyl group, $R_{4''}$ is propionyl group, and X is hydroxyl group) was obtained from 4.58 g of the compound of Example 1.

Physicochemical Properties of this Compound (1) Molecular formula: $C_{51}H_{88}N_2O_{20}$ (2) Mass spectrum (FAB): m/z 1049 $(M+H)^+$ (3) Specific rotation: $[\alpha]_D^{26}$ −640 (c1.0, $CHCl_3$)

(4) $^1H$ NMR spectrum (300 MHz, $CDCl_3$) δ (ppm): 0.86 (d, 8-$CH_3$), 1.05 (d, 6"-H) 1.14 (t, 3-$OCOCH_2CH_3$), 1.16 (t, 4"-$OCOCH_2CH_3$), 1.17 (d, 6'-H), 1.27 (m, 6-H), 1.30 (m, 7-H), 1.39 (s, 3"-$CH_3$), 1.44 (m, 14-H), 1.66 (dd, 2"-Hax), 1.86 (m, 6-$CH_2$), 2.01 (s, 3"-$OCOCH_3$), 2.02 (s, 9-$OCOCH_3$), 2.04 (s, 2'-$OCOCH_3$), 2.21 (m, $CH_2CH$═$CH_2$), 2.22 (s, $NCH_3$), 2.36 (q, 3-$OCOCH_2CH_3$), 2.42 (q, 4"-$OCOCH_2CH_3$), 2.41 (s, 3'-$N(CH_3)_2$), 2.60 (dd, 2-H), 2.64 (m, 3'-H), 3.10 (m, 4'-H), 3.20 (s, $CH(OCH_3)_2$), 3.21 (d, 2"-Heq), 3.24 (s, $CH(OCH_3)_2$), 3.46 (br d, 4-H), 3.58 (s, 4-$OCH_3$), 3.63 (m, 15-H), 3.86 (br d, 5-H), 4.48 (m, 5"-H), 4.50 (dd, $CH(OCH_3)_2$), 4.54 (d, 4"-H), 4.68 (d, 1'-H), 4.78 (d, 1"-H), 4.90 (m, 9-H), 4.93 (dd, 2'-H), 5.04 (m, CH═$CH_2$), 5.12 (m, 15-H), 5.16 (m, 3-H), 5.82 (ddt, CH═$CH_2$).

(b) In the same manner as in Example 48(b), 1.40 g of a cyclized compound (compound represented by the formula (24) mentioned in Preparation Scheme 8 wherein $R_3$ is methyl group, $R_7$, $R_8$ and $R_{12}$ are hydrogen atoms, $R_{11}$ is allyl group, $R_{3''}$ is acetyl group, $R_{4''}$ is propionyl group, and X is oxygen atom) was obtained from 2.94 g of the compound of Example 90(a).

Physicochemical Properties of this Compound (1) Molecular formula: $C_{51}H_{86}N_2O_{19}$ (2) Mass spectrum (FAB): m/z 1031 $(M+H)^+$ (3) Specific rotation: $[\alpha]_D^{25}$ −54° (c0.8, $CHCl_3$)

(4) $^1H$ NMR spectrum (300 MHz, $CDCl_3$) δ (ppm): 0.90 (d, 8-$CH_3$), 1.05 (d, 6"-H), 1.14 (t, 3-$OCOCH_2CH_3$), 1.18 (t, 4"-$OCOCH_2CH_3$), 1.19 (d, 6'-H), 1.22 (m, 7-H), 1.39 (s, 3"-$CH_3$), 1.44 (m, 6-$CH_2$), 1.66 (dd, 2"-Hax), 1.74 (m, 8-H), 2.00 (s, 3"-$OCOCH_3$), 2.03 (s, 9-$OCOCH_3$), 2.04 (s, 2'-$OCOCH_3$), 2.22 (s, $NCH_3$), 2.38 (q, 3-$OCOCH_2CH_3$), 2.41 (q, 4"-$OCOCH_2CH_3$), 2.42 (s, 3'-$N(CH_3)_2$), 2.56 (dd, 2-H), 2.60 (t, 3'-H), 2.86 (dd, 2-H), 3.12 (t, 4'-H), 3.13 (m, 2"-Heq), 3.14 (s, $CH(OCH_3)_2$), 3.24 (s, $CH(OCH_3)_2$), 3.25 (m, 5'-H), 3.60 (m, 4-H), 3.61 (s, 4-$OCH_3$), 3.90 (br d, 5-H), 4.48 (dq, 5"-H), 4.54 (dd, $CH(OCH_3)_2$), 4.55 (d, 4"-H), 4.68

(d, 1'-H), 4.79 (d, 1"-H), 4.90 (m, 9-H), 4.95 (dd, 2'-H), 5.02 (m, 3-H), 5.04 (m, 15-H), 5.06 (m, CH═$CH_2$), 5.70 (ddt, CH═$CH_2$).

(c) In the same manner as in Example 48(c), except that 3-bromoquinoline was used instead of 4-bromoquinoline, 59.6 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(quinolin-3-yl)-2-propenyl group, $R_{3''}$ is acetyl group, $R_{4''}$ is propionyl group, and X is oxygen atom) was obtained from 169.5 mg of the compound of Example 90(b).

Physicochemical Properties of this Compound (1) Molecular formula: $C_{60}H_{91}N_3O_{19}$ (2) Mass spectrum (FAB): m/z 1158 $(M+H)^+$ (3) Specific rotation: $[\alpha]_D^{24}$ −63° (c0.8, $CHCl_3$)

(4) $^1H$ NMR spectrum (300 MHz, $CDCl_3$) δ (ppm): 0.90 (d, 8-$CH_3$), 1.06 (d, 6"-H), 1.14 (d, 6'-H), 1.17 (t, 3-$OCOCH_2CH_3$), 1.18 (t, 4"-$OCOCH_2CH_3$), 1.39 (s, 3"-$CH_3$), 1.64 (m, 6-$CH_2$), 1.65 (dd, 2"-Hax), 1.74 (m, 8-H), 2.00 (s, 3"-$OCOCH_3$), 2.02 (s, 9-$OCOCH_3$), 2.04 (s, 2'-$OCOCH_3$), 2.22 (s, $NCH_3$), 2.40 (m, 10-H), 2.42 (s 3'-$N(CH_3)_2$), 2.56 (dd, 2-H), 2.60 (t, 3'-H), 2.85 (dd, 2-H), 3.12 (m, 4'-H), 3.14 (s, $CH(OCH_3)_2$), 3.22 (m, 2"-Heq), 3.23 (s, $CH(OCH_3)_2$), 3.25 (m, 5'-H), 3.58 (s, 4-$OCH_3$), 3.59 (m, 4-H), 3.90 (br d, 5-H), 4.48 (m, 5"-H), 4.54 (dd, $CH(OCH_3)_2$), 4.56 (d, 4"-H), 4.68 (d, 1'-H), 4.79 (d, 1"-H), 4.90 (m, 9-H), 4.96 (dd, 2'-H), 5.02 (m, 3-H), 5.04 (m, 15-H), 6.35 (dt, CH═CH), 6.58 (ddt, CH═CH), 7.50 (m, quinoline), 7.65 (m, quinoline), 7.76 (br d, quinoline), 8.00 (br s, quinoline), 8.04 (br d, quinoline), 8.93 (d, quinoline).

(d) In the same manner as in Example 2(c), 16.1 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(quinolin-3-yl)-2-propenyl group, $R_{3''}$ is acetyl group, $R_{4''}$ is propionyl group, and X is oxygen atom) was obtained from 59.6 mg of the compound of Example 90(c).

Physicochemical Properties of this Compound (1) Molecular formula: $C_{56}H_{87}N_3O_{17}$ (2) Mass spectrum (FAB): m/z 1074 $(M+H)^+$ (3) Specific rotation: $[\alpha]_D^{24}$ −46° (c0.8, $CHCl_3$)

(4) $^1H$ NMR spectrum (300 MHz, $CDCl_3$) δ (ppm): 0.88 (d, 8-$CH_3$), 1.08 (d, 6"-H), 1.17 (t, 3-$OCOCH_2CH_3$), 1.17 (t, 4"-$OCOCH_2CH_3$), 1.18 (d, 6'-H), 1.40 (s, 3"-$CH_3$), 1.54 (m, 8-H), 1.58 (m, 6-$CH_2$), 1.66 (dd, 2"-Hax), 2.00 (s, 3"-$OCOCH_3$), 2.35 (s, $NCH_3$), 2.52 (s 3'-$N(CH_3)_2$), 2.56 (dd, 2-H), 2.72 (m, 3'-H), 2.80 (dd, 2-H), 3.14 (s, $CH(OCH_3)_2$), 3.16 (m, 4'-H), 3.18 (m, 2"-Heq), 3.20 (m, 5'-H), 3.23 (s, $CH(OCH_3)_2$), 3.46 (dd, 2'-H), 3.63 (s, 4-$OCH_3$), 3.86 (m, 4-H), 3.94 (br d, 5-H), 4.45 (m, 1'-H), 4.46 (d, 4"-H), 4.56 (dd, $CH(OCH_3)_2$), 4.56 (m, 5"-H), 4.82 (d, 1"-H), 5.12 (m, 15-H), 5.44 (m, 3-H), 6.33 (dt, CH═CH), 6.55 (ddt, CH═CH), 7.50 (m, quinoline), 7.65 (m, quinoline), 7.76 (br d, quinoline), 8.00 (d, quinoline), 8.04 (br d, quinoline), 8.92 (d, quinoline).

(e) In the same manner as in Example 2(d), 6.0 mg of the title compound was obtained from 16.1 mg of the compound of Example 90(d).

Physicochemical Properties of this Compound (1) Molecular formula: $C_{54}H_{81}N_3O_{16}$ (2) Mass spectrum (FAB): m/z 1028 $(M+H)^+$ (3) Specific rotation: $[\alpha]_D^{24}$ −68° (c0.3, $CHCl_3$)

(4) $^1H$ NMR spectrum (300 MHz, $CDCl_3$) δ (ppm): 0.88 (d, 8-$CH_3$), 1.08 (d, 6"-H), 1.14 (d, 6'-H), 1.16 (t, 3-$OCOCH_2CH_3$), 1.18 (t, 4"-$OCOCH_2CH_3$), 1.40 (s, 3"-$CH_3$), 1.42 (m, 8-H), 1.68 (dd, 2"-Hax), 2.00 (s, 3"-$OCOCH_3$), 2.33 (s, $NCH_3$), 2.53 (s 3'-$N(CH_3)_2$), 2.60 (dd, 2-H), 2.64 (dd, 2-H), 2.84 (dd, 6-$CH_2$), 3.18 (m, 4'-H), 3.20 (d, 2"-Heq), 3.36 (m, 9-H), 3.39 (dd, 2'-H), 3.65 (s, 4-$OCH_3$), 3.86 (br d, 4-H), 3.96 (br d, 5-H), 4.38 (m, 1"-H), 4.52 (m, 5"-H), 4.57 (d, 4"-H), 4.83 (d, 1"-H), 5.12 (m, 15-H), 5.55 (m, 3-H), 6.34 (dt, CH═CH), 6.58 (ddt, CH═CH), 7.52 (m, quinoline), 7.65 (m, quinoline), 7.76 (m, quinoline), 8.00 (d, quinoline), 8.04 (br d, quinoline), 8.92 (d, quinoline), 9.65 (s, CHO).

Example 91

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is 3-(quinolin-3-yl)propyl group, $R_{4'}$ is a group represented by the formula (a), $R_{3''}$ is acetyl group, $R_{4''}$ is propionyl group, and X is oxygen atom (a) In the same manner as in Example 8(d), except that a mixed solvent of 1,4-dioxane/water (2:1) was used instead of 1,4-dioxane, 14.8 mg of a double bond-reduced compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is 3-(quinolin-3-yl)propyl group, $R_{3''}$ is acetyl group, $R_{4''}$ is propionyl group, and X is oxygen atom) was obtained from 16.0 mg of the compound of Example 90(d).

Physicochemical Properties of this Compound (1) Molecular formula: $C_{56}H_{89}N_3O_{17}$ (2) Mass spectrum (FAB): m/z 1076 $(M+H)^+$ (3) Specific rotation: $[\alpha]_D^{24}$ −39° (c0.7, $CHCl_3$)

(4) $^1H$ NMR spectrum (300 MHz, $CDCl_3$) δ (ppm): 0.89 (d, 8-$CH_3$), 1.08 (d, 6"-H), 1.17 (t, 3-$OCOCH_2CH_3$), 1.17 (t, 4"-$OCOCH_2CH_3$), 1.16 (d, 6'-H), 1.40 (s, 3"-$CH_3$), 1.57 (m, 8-H), 1.58 (m, 6-$CH_2$), 1.66 (dd, 2"-Hax), 2.00 (s, 3"-$OCOCH_3$), 2.35 (s, $NCH_3$), 2.52 (s, 3'-$N(CH_3)_2$), 2.56 (t, 3'-H), 2.58 (dd, 2-H), 2.78 (dd, 2-H), 3.12 (s, $CH(OCH_3)_2$), 3.16 (m, 4'-H), 3.19 (d, 2"-Heq), 3.21 (m, 5'-H), 3.24 (s, $CH(OCH_3)_2$), 3.46 (dd, 2'-H), 3.63 (s, 4-$OCH_3$), 3.86 (m, 4-H), 3.92 (br d, 5-H), 4.45 (m, 1'-H), 4.46 (d, 4"-H), 4.56 (dd, $CH(OCH_3)_2$), 4.56 (d, 5"-H), 4.82 (d, 1"-H), 5.02 (m, 15-H), 5.40 (m, 3-H), 7.50 (m, quinoline), 7.65 (m, quinoline), 7.76 (br d, quinoline), 7.92 (d, quinoline), 8.04 (br d, quinoline), 8.73 (d, quinoline).

(b) In the same manner as in Example 2(d), 6.2 mg of the title compound was obtained from 14.8 mg of the compound of Example 91(a).

Physicochemical Properties of this Compound (1) Molecular formula: $C_{54}H_{83}N_3O_{16}$ (2) Mass spectrum (FAB): m/z 1031 $(M+H)^+$ (3) Specific rotation: $[\alpha]_D^{25}$ −55° (c0.4, $CHCl_3$)

(4) $^1H$ NMR spectrum (300 MHz, $CDCl_3$) δ (ppm): 0.90 (d, 8-$CH_3$), 1.08 (d, 6"-H), 1.12 (d, 6'-H), 1.13 (t, 3-$OCOCH_2CH_3$), 1.19 (t, 4"-$OCOCH_2CH_3$), 1.40 (s, 3"-$CH_3$), 1.58 (m, 8-H), 1.68 (dd, 2"-Hax), 2.00 (s, 3"-$OCOCH_3$), 2.34 (s, $NCH_3$), 2.53 (s 3'-$N(CH_3)_2$), 2.60 (dd, 2-H), 2.81 (dd, 2-H), 2.88 (m, 6-$CH_2$), 3.19 (d, 2"-Heq), 3.20 (m, 4'-H), 3.20 (m, 5'-H), 3.69 (s, 4-$OCH_3$), 3.86 (br d, 4-H), 3.96 (br d, 5-H), 4.40 (d, 1'-H), 4.54 (m, 5"-H), 4.82 (d, 1"-H), 5.02 (m, 15-H), 5.47 (m, 3-H), 7.52 (m, quinoline), 7.65 (m, quinoline), 7.76 (br d, quinoline), 7.90 (d, quinoline), 8.04 (d, quinoline), 8.75 (d, quinoline), 9.64 (s, CHO).

Example 92

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(6-nitroquinolin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 3-bromo-6-nitroquinoline (Justus Liebigs Ann. Chem. 1966, 699, 98-106) was used instead of 4-bromoquinoline, 48.8 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(6-nitroquinolin-3-yl)-2-propenyl group, $R_{3''}$ is acetyl group, $R_{4''}$ is propionyl group, and X is oxygen atom) was obtained from 67.6 mg of the compound of Example 90(b).

Physicochemical Properties of this Compound (1) Molecular formula: $C_{60}H_{90}N_4O_{21}$ (2) Mass spectrum (FAB): m/z 1203 $(M+H)^+$ (3) $^1H$ NMR spectrum (300 MHz, $CDCl_3$) δ (ppm): 0.92 (d, 8-$CH_3$), 1.07 (d, 6"-H), 1.15 (t, 3-$OCOCH_2CH_3$), 1.19 (t, 4"-$OCOCH_2CH_3$), 1.21 (d, 6'-H), 1.41 (s, 3"-$CH_3$), 1.68 (dd, 2"-Hax), 1.79 (m, 8-H), 1.94 (m, 6-$CH_2$), 2.02 (s, 3"-$OCOCH_3$), 2.04 (s, 9-$OCOCH_3$), 2.06 (s, 2'-$OCOCH_3$), 2.25 (s, $NCH_3$), 2.36 (q, 3-$OCOCH_2CH_3$), 2.43 (q, 4"-$OCOCH_2CH_3$), 2.87 (dd, 2-H), 3.14 (s, $CH(OCH_3)_2$), 3.17 (t, 4'-H), 3.20 (d, 2"-Heq), 3.25 (s, $CH(OCH_3)_2$), 3.55 (d, 4-H), 3.60 (s, 4-$OCH_3$), 3.95 (d, 5-H), 4.48 (dq, 5"-H), 4.57 (d, 4"-H), 4.69 (d, 1'-H), 4.81 (d, 1"-H), 4.92 (m, 9-H), 4.98 (dd, 2'-H), 5.09 (m, 3-H), 5.17 (m, 15-H), 6.49 (dt, CH═CH), 6.65 (d, CH═CH), 8.19 (d, quinoline), 8.21 (d, quinoline), 8.41 (dd, quinoline), 8.76 (d, quinoline), 9.11 (d, quinoline).

(b) In the same manner as in Example 73(b), 26.6 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(6-nitroquinolin-3-yl)-2-propenyl group, $R_{3''}$ is acetyl group, $R_{4''}$ is propionyl group, and X is oxygen atom) was obtained from 48.8 mg of the compound of Example 92(a).

Physicochemical Properties of this Compound (1) Molecular formula: $C_{56}H_{86}N_4O_{19}$ (2) Mass spectrum (FAB): m/z 1119 $(M+H)^+$ (3) $^1H$ NMR spectrum (300 MHz, $CDCl_3$) δ (ppm): 0.88 (d, 8-$CH_3$), 1.09 (d, 6"-H), 1.12 (t, 3-$OCOCH_2CH_3$), 1.20 (t, 4"-$OCOCH_2CH_3$), 1.21 (d, 6'-H), 1.42 (s, 3"-$CH_3$), 1.45 (m, 8-H), 1.68 (dd, 2"-Hax), 1.80 (m, 14-H), 1.85 (m, 6-$CH_2$), 2.01 (s, 3"-$OCOCH_3$), 2.35 (s, $NCH_3$), 2.38 (q, 3-$OCOCH_2CH_3$), 2.43 (q, 4"-$OCOCH_2CH_3$), 2.54 (s, 3'-N$(CH_3)_2$), 2.83 (dd, 2-H), 3.15 (s, $CH(OCH_3)_2$), 3.18 (t, 4'-H), 3.21 (d, 2"-Heq), 3.25 (s, $CH(OCH_3)_2$), 3.37 (m, 9-H), 3.47 (dd, 2'-H), 3.66 (s, 4-$OCH_3$), 3.89 (d, 4-H), 3.94 (d, 5-H), 4.46 (d, 1'-H), 4.54 (dq, 5"-H), 4.58 (d, 4"-H), 4.84 (d, 1"-H), 5.14 (m, 15-H), 5.47 (dd, 3-H), 6.46 (dt, CH═CH), 6.62 (d, CH═CH), 8.17 (d, quinoline), 8.19 (d, quinoline), 8.42 (dd, quinoline), 8.75 (d, quinoline), 9.10 (d, quinoline).

(c) In the same manner as in Example 2(d), 20.2 mg of the title compound was obtained from 26.6 mg of the compound of Example 92(b).

Physicochemical Properties of this Compound (1) Molecular formula: $C_{54}H_{80}N_4O_{18}$ (2) Mass spectrum (FAB): m/z 1073 $(M+H)^+$ (3) Specific rotation: $[\alpha]_D^{24}$ −58° (c0.61, $CHCl_3$)

(4) $^1H$ NMR spectrum (300 MHz, $CDCl_3$) δ (ppm): 0.89 (d, 8-$CH_3$), 1.09 (d, 6"-H), 1.14 (d, 6'-H), 1.17 (t, 3-$OCOCH_2CH_3$), 1.19 (t, 4"-$OCOCH_2CH_3$), 1.36 (m, 8-H), 1.42 (s, 3"-$CH_3$), 1.69 (dd, 2"-Hax), 1.80 (dd, 14-H), 2.01 (s, 3"-$OCOCH_3$), 2.32 (s, $NCH_3$), 2.43 (q, 4"-$OCOCH_2CH_3$), 2.54 (s, 3'-N$(CH_3)_2$), 2.84 (dd, 2-H), 2.90 (dd, 6-$CH_2$), 3.18 (t, 4'-H), 3.21 (d, 2"-Heq), 3.39 (dd, 2'-H), 3.67 (s, 4-$OCH_3$), 3.87 (d, 4-H), 3.95 (d, 5-H), 4.40 (d, 1'-H), 4.52 (dq, 5"-H), 4.58 (d, 4"-H), 4.84 (d, 1"-H), 5.14 (m, 15-H), 5.58 (dd, 3-H), 6.46 (dt, CH═CH), 6.62 (d, CH═CH), 8.16 (d, quinoline), 8.19 (d, quinoline), 8.41 (dd, quinoline), 8.75 (d, quinoline), 9.10 (d, quinoline), 9.66 (s, CHO).

Example 93

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(6-cyanoquinolin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that the compound of Reference Example 24 was used instead of 4-bromoquinoline, 46.4 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(6-cyanoquinolin-3-yl)-2-propenyl group, $R_{3''}$ is acetyl group, $R_{4''}$ is propionyl group, and X is oxygen atom) was obtained from 77.4 mg of the compound of Example 90(b).

Physicochemical Properties of this Compound (1) Molecular formula: $C_{61}H_{90}N_4O_{19}$ (2) Mass spectrum (FAB): m/z 1183 $(M+H)^+$ (3) $^1H$ NMR spectrum (300 MHz, $CDCl_3$) δ (ppm): 0.92 (d, 8-$CH_3$), 1.07 (d, 6"-H), 1.14 (t, 3-$OCOCH_2CH_3$), 1.19 (t, 4"-$OCOCH_2CH_3$), 1.21 (d, 6'-H), 1.41 (s, 3"-$CH_3$), 1.55 (m, 13-H), 1.68 (dd, 2"-Hax), 2.02 (s, 3"-$OCOCH_3$), 2.04 (s, 9-$OCOCH_3$), 2.05 (s, 2'-$OCOCH_3$), 2.25 (s, $NCH_3$), 2.36 (q, 3-$OCOCH_2CH_3$), 2.43 (q, 4"-$OCOCH_2CH_3$), 2.43 (s, 3'-N$(CH_3)_2$), 2.87 (dd, 2-H), 3.15 (t, 4'-H), 3.15 (s, $CH(OCH_3)_2$), 3.19 (d, 2"-Heq), 3.25 (s, $CH(OCH_3)_2$), 3.56 (d, 4-H), 3.60 (s, 4-$OCH_3$), 3.94 (d, 5-H), 4.48 (dq, 5"-H), 4.57 (d, 4"-H), 4.69 (d, 1'-H), 4.81 (d, 1"-H), 4.92 (m, 9-H), 4.98 (dd, 2'-H), 5.08 (m, 3-H), 5.16 (m, 15-H), 6.46 (dt, CH═CH), 6.63 (d, CH═CH), 7.79 (dd, quinoline), 8.07 (d, quinoline), 8.14 (d, quinoline), 8.20 (d, quinoline), 9.07 (d, quinoline).

(b) In the same manner as in Example 73(b), 25.8 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(6-cyanoquinolin-3-yl)-2-propenyl group, $R_{3''}$ is acetyl group, $R_{4''}$ is propionyl group, and X is oxygen atom) was obtained from 46.4 mg of the compound of Example 93(a).

Physicochemical Properties of this Compound (1) Molecular formula: $C_{57}H_{86}N_4O_{17}$ (2) Mass spectrum (FAB): m/z 1099 $(M+H)^+$ (3) $^1$H NMR spectrum (300 MHz, $CDCl_3$) δ (ppm): 0.88 (d, 8-$CH_3$), 1.09 (d, 6"-H), 1.12 (t, 3-$OCOCH_2CH_3$), 1.20 (t, 4"-$OCOCH_2CH_3$), 1.21 (d, 6'-H), 1.42 (s, 3"-$CH_3$), 1.46 (m, 8-H), 1.68 (dd, 2"-Hax), 1.79 (m, 14-H), 1.84 (m, 6-$CH_2$), 2.02 (s, 3"-$OCOCH_3$), 2.34 (s, $NCH_3$), 2.43 (q, 4'-$OCOCH_2CH_3$), 2.54 (s, 3'-$N(CH_3)_2$), 2.82 (dd, 2-H), 3.15 (s, $CH(OCH_3)_2$), 3.18 (t, 4'-H), 3.21 (d, 2"-Heq), 3.26 (s, $CH(OCH_3)_2$), 3.36 (m, 9-H), 3.47 (dd, 2'-H), 3.66 (s, 4-$OCH_3$), 3.89 (d, 4-H), 3.95 (d, 5-H), 4.47 (d, 1'-H), 4.50 (dd, $CH(OCH_3)_2$), 4.59 (d, 4"-H), 4.84 (d, 1"-H), 5.14 (m, 15-H), 5.48 (dd, 3-H), 6.43 (dt, CH═CH), 6.60 (d, CH═CH), 7.80 (dd, quinoline), 8.03 (d, quinoline), 8.15 (d, quinoline), 8.19 (d, quinoline), 9.06 (d, quinoline).

(c) In the same manner as in Example 2(d), 20.8 mg of the title compound was obtained from 25.8 mg of the compound of Example 93(b).

Physicochemical Properties of this Compound (1) Molecular formula: $C_{55}H_{80}N_4O_{16}$ (2) Mass spectrum (FAB): m/z 1053 $(M+H)^+$ (3) Specific rotation: $[\alpha]_D^{22}$ −54° (c1.0, $CHCl_3$)

(4) $^1$H NMR spectrum (300 MHz, $CDCl_3$) δ (ppm): 0.89 (d, 8-$CH_3$), 1.09 (d, 6"-H), 1.14 (d, 6'-H), 1.17 (t, 3-$OCOCH_2CH_3$), 1.19 (t, 4"-$OCOCH_2CH_3$), 1.37 (m, 8-H), 1.42 (s, 3"-$CH_3$), 1.69 (dd, 2"-Hax), 1.78 (m, 14-H), 2.01 (s, 3"-$OCOCH_3$), 2.32 (s, $NCH_3$), 2.43 (q, 4"-$OCOCH_2CH_3$), 2.54 (s, 3'-$N(CH_3)_2$), 2.60 (q, 3-$OCOCH_2CH_3$), 2.84 (dd, 2-H), 2.91 (dd, 6-$CH_2$), 3.21 (d, 2"-Heq), 3.39 (dd, 2'-H), 3.66 (s, 4-$OCH_3$), 3.87 (d, 4-H), 3.95 (d, 5-H), 4.40 (d, 1'-H), 4.52 (dq, 5"-H), 4.58 (d, 4"-H), 4.84 (d, 1"-H), 5.13 (m, 15-H), 5.57 (dd, 3-H), 6.43 (dt, CH═CH), 6.60 (d, CH═CH), 7.80 (dd, quinoline), 8.03 (d, quinoline), 8.15 (d, quinoline), 8.19 (d, quinoline), 9.06 (d, quinoline), 9.65 (s, CHO).

Example 94

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(1,8-naphthyridin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 3-bromo-1,8-naphthyridine (YAKUGAKU ZASSHI, 1974, 94, 1328-1334) was used instead of 4-bromoquinoline, 11.5 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(1,8-naphthyridin-3-yl)-2-propenyl group, $R_{3''}$ is acetyl group, $R_{4''}$ is propionyl group, and X is oxygen atom) was obtained from 79.6 mg of the compound of Example 90(b).

Physicochemical Properties of this Compound (1) Molecular formula: $C_{59}H_{90}N_4O_{19}$ (2) Mass spectrum (FAB): m/z 1159 $(M+H)^+$ (3) Specific rotation: $[\alpha]_D^{15}$ −42° (c0.58, $CHCl_3$)

(4) $^1$H NMR spectrum (300 MHz, $CDCl_3$) δ (ppm): 0.92 (d, 8-$CH_3$), 1.07 (d, 6"-H), 1.14 (t, 3-$OCOCH_2CH_3$), 1.19 (t, 4"-$OCOCH_2CH_3$), 1.21 (d, 6'-H), 1.41 (s, 3"-$CH_3$), 1.53 (m, 13-H), 1.67 (dd, 2"-Hax), 1.77 (m, 14-H), 1.84 (m, 8-H), 2.02 (s, 3"-$OCOCH_3$), 2.04 (s, 9-$OCOCH_3$), 2.05 (s, 2'-$OCOCH_3$), 2.24 (s, $NCH_3$), 2.35 (q, 3-$OCOCH_2CH_3$), 2.43 (q, 4"-$OCOCH_2CH_3$), 2.43 (s, 3'-$N(CH_3)_2$), 2.62 (t, 3'-H), 2.62 (dd, 2-H), 2.87 (dd, 2-H), 3.15 (s, $CH(OCH_3)_2$), 3.19 (d, 2"-Heq), 3.25 (s, $CH(OCH_3)_2$), 3.59 (s, 4-$OCH_3$), 3.94 (d, 5-H), 4.48 (dq, 5"-H), 4.57 (d, 4"-H), 4.70 (d, 1'-H), 4.81 (d, 1"-H), 4.92 (m, 9-H), 4.97 (dd, 2'-H), 5.07 (m, 3-H), 5.16 (m, 15-H), 6.43 (dt, CH═CH), 6.63 (d, CH═CH), 7.48 (dd, naphthyridine), 8.04 (d, naphthyridine), 8.17 (d, naphthyridine), 9.07 (d, naphthyridine), 9.18 (d, naphthyridine).

(b) In the same manner as in Example 73(b), 3.3 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(1,8-naphthyridin-3-yl)-2-propenyl group, $R_{3''}$ is acetyl group, $R_{4''}$ is propionyl group, and X is oxygen atom) was obtained from 11.5 mg of the compound of Example 94(a).

Physicochemical Properties of this Compound (1) Molecular formula: $C_{55}H_{86}N_4O_{17}$ (2) Mass spectrum (FAB): m/z 1075 $(M+H)^+$ (3) $^1$H NMR spectrum (300 MHz, $CDCl_3$) δ (ppm): 0.89 (d, 8-$CH_3$), 1.09 (d, 6"-H), 1.11 (t, 3-$OCOCH_2CH_3$), 1.20 (t, 4"-$OCOCH_2CH_3$), 1.21 (d, 6'-H), 1.42 (s, 3"-$CH_3$), 1.45 (m, 8-H), 1.68 (dd, 2"-Hax), 1.84 (m, 14-H), 1.89 (m, 6-$CH_2$), 2.01 (s, 3"-$OCOCH_3$), 2.35 (s, $NCH_3$), 2.43 (q, 4"-$OCOCH_2CH_3$), 2.53 (s, 3'-$N(CH_3)_2$), 2.62 (dd, 2-H), 2.71 (m, 12-H), 2.83 (dd, 2-H), 3.15 (s, $CH(OCH_3)_2$), 3.20 (d, 2"-Heq), 3.25 (s, $CH(OCH_3)_2$), 3.39 (m, 9-H), 3.47 (dd, 2'-H), 3.66 (s, 4-$OCH_3$), 3.88 (d, 4-H), 3.95 (d, 5-H), 4.46 (d, 1'-H), 4.55 (dq, 5"-H), 4.58 (d, 4"-H), 4.84 (d, 1"-H), 5.13 (m, 15-H), 5.46 (m, 3-H), 6.41 (dt, CH═CH), 6.61 (d, CH═CH), 7.49 (dd, naphthyridine), 8.03 (d, naphthyridine), 8.16 (d, naphthyridine), 9.07 (dd, naphthyridine), 9.16 (d, naphthyridine).

(c) In the same manner as in Example 2(d), 3.25 mg of the title compound was obtained from 3.3 mg of the compound of Example 94(b).

Physicochemical Properties of this Compound (1) Molecular formula: $C_{53}H_{80}N_4O_{16}$ (2) Mass spectrum (FAB): m/z 1029 $(M+H)^+$ (3) Specific rotation: $[\alpha]_D^{20}$ −40° (c0.16, $CHCl_3$)

(4) $^1$H NMR spectrum (300 MHz, $CDCl_3$) δ (ppm): 0.94 (d, 8-$CH_3$), 1.09 (d, 6"-H), 1.14 (d, 6'-H), 1.14 (t, 3-$OCOCH_2CH_3$), 1.19 (t, 4"-$OCOCH_2CH_3$), 1.38 (m, 8-H), 1.42 (s, 3"-$CH_3$), 1.60 (m, 7-H), 1.69 (dd, 2"-Hax), 2.00 (s, 3"-$OCOCH_3$), 2.40 (q, 4"-$OCOCH_2CH_3$), 2.55 (s, 3'-$N(CH_3)_2$), 2.59 (q, 3-$OCOCH_2CH_3$), 2.87 (dd, 2-H), 2.93 (dd, 6-$CH_2$), 3.22 (d, 2"-Heq), 3.38 (dd, 2'-H), 3.53 (m, 9-H), 3.66 (s, 4-$OCH_3$), 3.86 (d, 4-H), 3.93 (d, 5-H), 4.41 (d, 1'-H), 4.51 (dq, 5"-H), 4.58 (d, 4"-H), 4.84 (d, 1"-H), 5.12 (m, 15-H), 5.47 (m, 3-H), 6.40 (dt, CH═CH), 6.62 (d, CH═CH), 7.49 (dd, naphthyridine), 8.03 (d, naphthyridine), 8.17 (dd, naphthyridine), 9.07 (dd, naphthyridine), 9.16 (d, naphthyridine), 9.65 (s, CHO).

Example 95

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(naphthalen-2- yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 2-bromonaphthalene was used instead of 4-bromoquinoline, 62 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(naphthalen-2-yl)-2-propenyl group, $R_{3''}$ is acetyl group, $R_{4''}$ is propionyl group, and X is oxygen atom) was obtained from 108 mg of the compound of Example 90(b).

Physicochemical Properties of this Compound (1) Molecular formula: $C_{61}H_{92}N_2O_{19}$ (2) Mass spectrum (FAB): m/z 1157 $(M+H)^+$ (3) Specific rotation: $[\alpha]_D^{22}$ −610 (c1.0, $CHCl_3$)

(4) $^1H$ NMR spectrum (300 MHz, $CDCl_3$) δ (ppm): 0.92 (d, 8-$CH_3$), 1.07 (d, 6"-H), 1.13 (t, 3-$OCOCH_2CH_3$), 1.19 (t, 4"-$OCOCH_2CH_3$), 1.20 (d, 6'-H), 1.41 (s, 3"-$CH_3$), 1.67 (dd, 2"-H), 2.01 (s, 3"-$OCOCH_3$), 2.04 (s, 9-$OCOCH_3$), 2.06 (s, 2'-$OCOCH_3$), 2.23 (s, $NCH_3$), 2.43 (s, 3'-$N(CH_3)_2$), 2.62 (dd, 2-H), 2.62 (t, 3'-H), 2.86 (dd, 2-H), 3.15 (t, 4'-H), 3.16 (s, $CH(OCH_3)_2$), 3.19 (d, 2"-Heq), 3.25 (s, $CH(OCH_3)_2$), 3.26 (m, 5'-H), 3.59 (s, 4-$OCH_3$), 3.64 (br d, 4-H), 3.93 (br d, 5-H), 4.49 (dq, 5"-H), 4.55 (s, $CH(OCH_3)_2$), 4.57 (d, 4"-H), 4.70 (d, 1'-H), 4.81 (d, 1"-H), 4.91 (m, 9-H), 4.97 (dd, 2'-H), 5.07 (br dd, 3-H), 5.14 (m, 15-H), 6.25 (dt, CH═CH), 6.60 (d, CH═CH), 7.38-7.48 (m, naphthalene), 7.55 (dd, naphthalene), 7.68 (br s, naphthalene), 7.76 (d, naphthalene), 7.78 (d, naphthalene), 7.78 (d, naphthalene).

(b) In the same manner as in Example 2(c), 41 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(naphthalen-2-yl)-2-propenyl group, $R_{3''}$ is acetyl group, $R_{4''}$ is propionyl group, and X is oxygen atom) was obtained from 59 mg of the compound of Example 95(a).

Physicochemical Properties of this Compound (1) Molecular formula: $C_{57}H_{88}N_2O_{17}$ (2) Mass spectrum (FAB): m/z 1073 $(M+H)^+$ (3) Specific rotation: $[\alpha]_D^{24}$ −54° (c1.0, $CHCl_3$)

(4) $^1H$ NMR spectrum (300 MHz, $CDCl_3$) δ (ppm): 0.89 (d, 8-$CH_3$), 1.11 (d, 6"-H), 1.13 (t, 3-$OCOCH_2CH_3$), 1.21 (t, 4"-$OCOCH_2CH_3$), 1.23 (d, 6'-H), 1.44 (s, 3"-$CH_3$), 1.70 (dd, 2"-H), 1.87 (dd, 6-$CH_2$), 2.03 (s, 3"-$OCOCH_3$), 2.33 (s, $NCH_3$), 2.55 (s, 3'-$N(CH_3)_2$), 2.64 (dd, 2-H), 2.69 (dd, 12-H), 2.83 (dd, 2-H), 3.18 (s, $CH(OCH_3)_2$), 3.22 (d, 2"-Heq), 3.27 (s, $CH(OCH_3)_2$), 3.33 (m, 9-H), 3.51 (dd, 2'-H), 3.65 (s, 4-$OCH_3$), 3.90 (br d, 5-H), 4.02 (br d, 4-H), 4.47 (d, 1'-H), 4.52 (dd, $CH(OCH_3)_2$), 4.59 (m, 4"-H), 4.59 (m, 5"-H), 4.85 (d, 1"-H), 5.15 (m, 15-H), 5.51 (m, 3-H), 6.25 (dt, CH═$CH_2$), 6.50 (d, CH═$CH_2$), 7.41-7.51 (m, naphthalene), 7.56 (dd, naphthalene), 7.68 (br s, naphthalene), 7.78 (d, naphthalene), 7.77-7.86 (m, naphthalene).

(c) In the same manner as in Example 2(d), 34 mg of the title compound was obtained from 41 mg of the compound of Example 95(b).

Physicochemical Properties of this Compound (1) Molecular formula: $C_{55}H_{82}N_2O_{16}$ (2) Mass spectrum (FAB): m/z 1027 $(M+H)^+$ (3) Specific rotation: $[\alpha]_D^{22}$ −58° (c0.73, $CHCl_3$)

(4) $^1H$ NMR spectrum (300 MHz, $CDCl_3$) δ (ppm): 0.82 (d, 8-$CH_3$), 1.01 (d, 6"-H), 1.07 (d, 6'-H), 1.09 (t, 3-$OCOCH_2CH_3$), 1.12 (t, 4"-$OCOCH_2CH_3$), 1.28 (m, 8-H), 1.34 (s, 3"-$CH_3$), 1.61 (dd, 2"-H), 1.93 (s, 3"-$OCOCH_3$), 2.20 (br dd, 12-H), 2.24 (s, $NCH_3$), 2.47 (s, 3'-$N(CH_3)_2$), 2.76 (dd, 2-H), 2.82 (dd, 6-$CH_2$), 3.09 (m, 4'-H), 3.11 (m, 5'-H), 3.14 (d, 2"-Heq), 3.29 (m, 9-H), 3.34 (dd, 2'-H), 3.57 (s, 4-$OCH_3$), 3.79 (br d, 5-H), 3.93 (br d, 4-H), 4.32 (d, 1'-H), 4.46 (dq, 5"-H), 4.51 (d, 4"-H), 4.76 (d, 1"-H), 5.05 (m, 15-H), 5.51 (m, 3-H), 6.16 (dt, CH═$CH_2$), 6.51 (d, CH═$CH_2$), 7.32-7.42 (m, naphthalene), 7.47 (dd, naphthalene), 7.60 (br s, naphthalene), 7.69 (d, naphthalene), 7.71 (d, 7.68 (br s, naphthalene), 7.76 (d, naphthalene), 7.71 (d, naphthalene), 9.58 (s, CHO).

Example 96

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(phenanthren-9-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 9-bromophenanthrene was used instead of 4-bromoquinoline, 54 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(phenanthren-9-yl)-2-propenyl group, $R_{3''}$ is acetyl group, $R_{4''}$ is propionyl group, and X is oxygen atom) was obtained from 70 mg of the compound of Example 90(b).

Physicochemical Properties of this Compound (1) Molecular formula: $C_{65}H_{94}N_2O_{19}$ (2) Mass spectrum (FAB): m/z 1207 $(M+H)^+$ (3) Specific rotation: $[\alpha]_D^{22}$ −57° (c1.0, $CHCl_3$)

(4) $^1H$ NMR spectrum (300 MHz, $CDCl_3$) δ (ppm): 0.93 (d, 8-$CH_3$), 1.07 (d, 6"-H), 1.12 (t, 3-$OCOCH_2CH_3$), 1.19 (t, 4"-$OCOCH_2CH_3$), 1.20 (d, 6'-H), 1.41 (s, 3"-$CH_3$), 1.70 (m, 7-H), 1.67 (dd, 2"-H), 2.01 (s, 3"-$OCOCH_3$), 2.03 (s, 9-$OCOCH_3$), 2.06 (s, 2'-$OCOCH_3$), 2.24 (s, $NCH_3$), 2.43 (s, 3'-$N(CH_3)_2$), 2.66 (dd, 2-H), 2.88 (dd, 2-H), 3.11 (t, 4'-H), 3.16 (s, $CH(OCH_3)_2$), 3.19 (d, 2"-Heq), 3.25 (s, $CH(OCH_3)_2$), 3.26 (m, 5'-H), 3.58 (s, 4-$OCH_3$), 3.68 (br d, 4-H), 3.93 (br d, 5-H), 4.50 (dq, 5"-H), 4.57 (d, 4"-H), 4.70 (d, 1'-H), 4.81 (d, 1"-H), 4.92 (m, 9-H), 4.97 (dd, 2'-H), 5.08 (br d, 3-H), 5.21 (m, 15-H), 6.20 (dt, CH═CH), 7.17 (d, CH═CH), 7.54-7.72 (m, phenanthrene), 7.74 (s, phenanthrene), 7.86 (br dd, phenanthrene), 8.12 (dd, phenanthrene), 8.65 (dd, phenanthrene), 8.72 (dd, phenanthrene).

(b) In the same manner as in Example 2(c), 33 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(phenanthren-9-yl)-2-propenyl group, $R_{3''}$ is acetyl group, $R_{4''}$ is propionyl group, and X is oxygen atom) was obtained from 54 mg of the compound of Example 96(a).

Physicochemical Properties of this Compound (1) Molecular formula: $C_{61}H_{90}N_2O_{17}$ (2) Mass spectrum (FAB): m/z 1123 $(M+H)^+$ (3) Specific rotation: $[\alpha]_D^{22}$ −55° (c1.0, $CHCl_3$)

(4) $^1H$ NMR spectrum (300 MHz, $CDCl_3$) δ (ppm): 0.89 (d, 8-$CH_3$), 1.09 (d, 6"-H), 1.10 (t, 3-$OCOCH_2CH_3$), 1.19 (t, 4"-$OCOCH_2CH_3$), 1.21 (d, 6'-H), 1.42 (s, 3"-$CH_3$), 1.44 (m, 8-H), 1.68 (dd, 2"-H), 1.84 (m, 6-$CH_2$), 1.98 (m, 6-H), 2.01 (s, 3"-$OCOCH_3$), 2.36 (s, $NCH_3$), 2.53 (s, 3'-$N(CH_3)_2$), 2.61 (m, 15-$CH_2$), 2.65 (dd, 2-H), 2.75 (dd, 12-H), 2.85 (dd, 2-H), 3.16 (s, $CH(OCH_3)_2$), 3.21 (d, 2"-Heq), 3.26 (s, $CH(OCH_3)_2$), 3.38 (m, 9-H), 3.48 (dd, 2'-H), 3.62 (s, 4-$OCH_3$), 3.89 (br d, 5-H), 4.02 (br d, 4-H), 4.46 (d, 1'-H), 4.50 (dd, $CH(OCH_3)_2$), 4.57 (m, 4"-H), 4.57 (m, 5"-H), 4.83 (d, 1"-H), 5.20 (m, 15-H), 5.48 (m, 3-H), 6.20 (dt, CH═$CH_2$), 7.15 (d, CH═$CH_2$), 7.54-7.72 (m, phenanthrene), 7.74 (s, phenanthrene), 7.85 (br dd, phenanthrene), 8.11 (dd, phenanthrene), 8.65 (dd, phenanthrene), 8.72 (dd, phenanthrene).

(c) In the same manner as in Example 2(d), 26 mg of the title compound was obtained from 32 mg of the compound of Example 96(b).

Physicochemical Properties of this Compound (1) Molecular formula: $C_{59}H_{84}N_2O_{16}$ (2) Mass spectrum (FAB): m/z 1077 $(M+H)^+$ (3) Specific rotation: $[\alpha]_D^{22}$ −57° (c1.0, $CHCl_3$)

(4) $^1H$ NMR spectrum (300 MHz, $CDCl_3$) δ (ppm): 0.84 (d, 8-$CH_3$), 1.01 (d, 6"-H), 1.07 (d, 6'-H), 1.08 (t, 3-$OCOCH_2CH_3$), 1.12 (t, 4"-$OCOCH_2CH_3$), 1.30 (m, 8-H), 1.34 (s, 3"-$CH_3$), 1.61 (dd, 2"-H), 1.93 (s, 3"-$OCOCH_3$), 2.29 (s, $NCH_3$), 2.47 (s, 3'-$N(CH_3)_2$), 2.70 (dd, 12-H), 2.80 (dd, 2-H), 2.83 (dd, 6-$CH_2$), 3.09 (t, 4'-H), 3.12 (m, 5'-H), 3.14 (d, 2"-Heq), 3.38 (m, 9-H), 3.33 (dd, 2'-H), 3.55 (s, 4-$OCH_3$), 3.80 (br d, 5-H), 3.94 (br d, 4-H), 4.32 (d, 1'-H), 4.46 (m, 5"-H), 4.51 (m, 4"-H), 4.76 (d, 1"-H), 5.12 (m, 15-H), 5.49 (m, 3-H), 6.12 (dt, CH═$CH_2$), 7.08 (d, CH═$CH_2$), 7.43-7.64 (m, phenanthrene), 7.67 (s, phenanthrene), 7.78 (br dd, phenanthrene), 8.03 (dd, phenanthrene), 8.57 (br d, phenanthrene), 8.64 (dd, phenanthrene), 9.58 (s, CHO).

Example 97

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(benzo[b]thiophen-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 3-bromobenzo[b]thiophene was used instead of 4-bromoquinoline, 43 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(benzo[b]thiophen-3-yl)-2-propenyl group, $R_{3''}$ is acetyl group, $R_{4''}$ is propionyl group, and X is oxygen atom) was obtained from 50 mg of the compound of Example 90(b).

Physicochemical Properties of this Compound (1) Molecular formula: $C_{59}H_{90}N_2O_{19}S$ (2) Mass spectrum (FAB): m/z 1163 $(M+H)^+$ (3) $^1H$ NMR spectrum (300 MHz, $CDCl_3$) δ (ppm): 0.92 (d, 8-$CH_3$), 1.07 (d, 6"-H), 1.13 (t, 3-$OCOCH_2CH_3$), 1.19 (t, 4"-$OCOCH_2CH_3$), 1.21 (d, 6'-H), 1.41 (s, 3"-$CH_3$), 1.67 (dd, 2"-H), 2.02 (s, 3"-$OCOCH_3$), 2.04 (s, 9-$OCOCH_3$), 2.06 (s, 2'-$OCOCH_3$), 2.31 (s, $NCH_3$), 2.43 (s, 3'-$N(CH_3)_2$), 2.62 (t, 3'-H), 2.62 (dd, 2-H), 2.86 (dd, 2-H), 3.16 (s, $CH(OCH_3)_2$), 3.19 (d, 2"-Heq), 3.25 (s, $CH(OCH_3)_2$), 3.59 (s, 4-$OCH_3$), 3.64 (br d, 4-H), 3.93 (br d, 5-H), 4.49 (dq, 5"-H), 4.57 (d, 4"-H), 4.70 (d, 1'-H), 4.81 (d, 1"-H), 4.92 (m, 9-H), 4.97 (dd, 2'-H), 5.07 (br d, 3-H), 5.15 (m, 15-H), 6.19 (dt, CH═CH), 6.70 (d, CH═CH), 7.30-7.43 (m, benzo[b]thiophene), 7.37 (s, benzo[b]thiophene), 7.86 (each t, benzo[b]thiophene).

(b) In the same manner as in Example 2(c), 21 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(benzo[b]thiophen-3-yl)-2-propenyl group, $R_{3''}$ is acetyl group, $R_{4''}$ is propionyl group, and X is oxygen atom) was obtained from 43 mg of the compound of Example 97(a).

Physicochemical Properties of this Compound (1) Molecular formula: $C_{55}H_{86}N_2O_{17}S$ (2) Mass spectrum (FAB): m/z 1079 $(M+H)^+$ (3) Specific rotation: $[\alpha]_D^{20}$ −50° (c0.44, $CHCl_3$)

(4) $^1H$ NMR spectrum (300 MHz, $CDCl_3$) δ (ppm): 0.88 (d, 8-$CH_3$), 1.09 (d, 6"-H), 1.11 (t, 3-$OCOCH_2CH_3$), 1.20 (t, 4"-$OCOCH_2CH_3$), 1.21 (d, 6'-H), 1.42 (s, 3"-$CH_3$), 1.68 (dd, 2"-H), 1.85 (m, 6-$CH_2$), 1.99 (m, 6-H), 2.02 (s, 3"-$OCOCH_3$), 2.33 (s, $NCH_3$), 2.54 (s, 3'-$N(CH_3)_2$), 2.61 (dd, 2-H), 2.67 (dd, 12-H), 2.81 (dd, 2-H), 3.15 (s, $CH(OCH_3)_2$), 3.21 (d, 2"-Heq), 3.26 (s, $CH(OCH_3)_2$), 3.33 (m, 9-H), 3.49 (dd, 2'-H), 3.63 (s, 4-$OCH_3$), 3.88 (br d, 5-H), 3.99 (br d, 4-H), 4.46 (d, 1'-H), 4.50 (dd, $CH(OCH_3)_2$), 4.57 (m, 4"-H), 4.57 (m, 5"-H), 4.83 (d, 1"-H), 5.14 (m, 15-H), 5.48 (br d, 3-H), 6.18 (dt, CH═$CH_2$), 6.69 (d, CH═$CH_2$), 7.32-7.45 (m, benzo[b]thiophene), 7.35 (s, benzo[b]thiophene), 7.85 (m, benzo[b]thiophene).

(c) In the same manner as in Example 2(d), 17 mg of the title compound was obtained from 20 mg of the compound of Example 97(b).

Physicochemical Properties of this Compound (1) Molecular formula: $C_{53}H_{80}N_2O_{16}S$ (2) Mass spectrum (FAB): m/z 1033 $(M+H)^+$ (3) Specific rotation: $[\alpha]_D^{21}$ −57° (c0.84, $CHCl_3$)

(4) $^1H$ NMR spectrum (300 MHz, $CDCl_3$) δ (ppm): 0.89 (d, 8-$CH_3$), 1.09 (d, 6"-H), 1.14 (d, 6'-H), 1.16 (t, 3-$OCOCH_2CH_3$), 1.19 (t, 4"-$OCOCH_2CH_3$), 1.34 (m, 8-H), 1.41 (s, 3"-$CH_3$), 1.68 (dd, 2"-H), 2.01 (s, 3"-$OCOCH_3$), 2.31 (s, $NCH_3$), 2.54 (s, 3'-$N(CH_3)_2$), 2.83 (dd, 2-H), 2.89 (dd, 6-$CH_2$), 3.19 (m, 4'-H), 3.19 (m, 5'-H), 3.21 (d, 2"-Heq), 3.36 (m, 9-H), 3.41 (dd, 2'-H), 3.64 (s, 4-$OCH_3$), 3.86 (br d, 5-H), 4.00 (br d, 4-H), 4.39 (d, 1'-H), 4.54 (dq, 5"-H), 4.58 (d, 4"-H), 4.84 (d, 1"-H), 5.13 (m, 15-H), 5.57 (br d, 3-H), 6.17 (dt, CH═$CH_2$), 6.69 (d, CH═$CH_2$), 7.32-7.43 (m, benzo[b]thiophene), 7.35 (s, benzo[b]thiophene), 7.85 (m, benzo[b]thiophene), 9.65 (s, CHO).

Example 98

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(benzo[c][1,2,5]oxadiazol-5-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 5-bromobenzo[c][1,2,5]oxadiazole was used instead of 4-bromoquinoline, 56.3 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(benzo[c][1,2,5]oxadiazol-5-yl)-2-propenyl group, $R_{3''}$ is acetyl group, $R_{4''}$ is propionyl group, and X is oxygen atom) was obtained from 74.5 mg of the compound of Example 90(b).

Physicochemical Properties of this Compound (1) Molecular formula: $C_{57}H_{88}N_4O_{20}$ (2) Mass spectrum (FAB): m/z 1149 $(M+H)^+$ (3) $^1H$ NMR spectrum (300 MHz, $CDCl_3$) δ (ppm): 0.89 (d, 8-$CH_3$), 1.04 (d, 6"-H), 1.12 (t, 3-$OCOCH_2CH_3$), 1.16 (t, 4"-$OCOCH_2CH_3$), 1.18 (d, 6'-H), 1.39 (s, 3"-$CH_3$), 1.65 (dd, 2"-Hax), 1.99 (s, 9-$OCOCH_3$), 2.01 (s, 3"-$OCOCH_3$), 2.03 (s, 2'-$OCOCH_3$), 2.21 (s, $NCH_3$), 2.41 (s, 3'-$N(CH_3)_2$), 2.60 (t, 3'-H), 2.61 (dd, 2-H), 2.83 (dd, 2-H), 3.12 (s, $CH(OCH_3)_2$), 3.14 (t, 4'-H), 3.16 (d, 2"-Heq), 3.21 (m, 5'-H), 3.22 (s, $CH(OCH_3)_2$), 3.52 (d, 4-H), 3.56 (s, 4-$OCH_3$), 3.91 (d, 5-H), 4.48 (dq, 5"-H), 4.53 (dd, $CH(OCH_3)_2$), 4.54 (d, 4"-H), 4.67 (d, 1'-H), 4.78 (d, 1"-H), 4.89 (m, 9-H), 4.95 (dd, 2'-H), 5.07 (br t, 3-H), 5.10 (m, 15-H), 6.34 (dt, 15-$CH_2$—CH═CH), 6.53 (d, 15-$CH_2$—CH═CH), 7.55 (m, benzooxadiazole), 7.74 (d, benzooxadiazole).

(b) In the same manner as in Example 2(c), 34.1 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(benzo[c][1,2,5]oxadiazol-5-yl)-2-propenyl group, $R_{3''}$ is acetyl group, $R_{4''}$ is propionyl group, and X is oxygen atom) was obtained from 56.3 mg of the compound of Example 98(a).

Physicochemical Properties of this Compound (1) Molecular formula: $C_{53}H_{84}N_4O_{18}$ (2) Mass spectrum (FAB): m/z 1065 $(M+H)^+$ (3) $^1H$ NMR spectrum (300 MHz, $CDCl_3$) δ (ppm): 0.85 (d, 8-$CH_3$), 1.07 (d, 6"-H), 1.10 (t, 3-$OCOCH_2CH_3$), 1.18 (t, 4"-$OCOCH_2CH_3$), 1.19 (d, 6'-H), 1.40 (s, 3"-$CH_3$), 1.67 (dd, 2"-Hax), 2.00 (s, 3"-$OCOCH_3$), 2.30 (s, $NCH_3$), 2.39 (q, 3-$OCOCH_2CH_3$), 2.42 (q, 4"-$OCOCH_2CH_3$), 2.52 (s, 3'-N$(CH_3)_2$), 2.60 (dd, 2-H), 2.79 (dd, 2-H), 3.13 (s, $CH(OCH_3)_2$), 3.17 (t, 4'-H), 3.19 (d, 2"-Heq), 3.22 (m, 5'-H), 3.24 (s, $CH(OCH_3)_2$), 3.45 (dd, 2'-H), 3.64 (s, 4-$OCH_3$), 3.87 (d, 4-H), 3.95 (d, 5-H), 4.45 (d, 1'-H), 4.48 (dd, $CH(OCH_3)_2$), 4.54 (dq, 5"-H), 4.57 (d, 4"-H), 4.82 (d, 1"-H), 5.12 (m, 15-H), 5.48 (m, 3-H), 6.32 (dt, 15-$CH_2$—CH═CH), 6.52 (d, 15-$CH_2$—CH═CH), 7.54 (m, benzooxadiazole), 7.75 (d, benzooxadiazole).

(c) In the same manner as in Example 2(d), 27.6 mg of the title compound was obtained from 34.1 mg of the compound of Example 98(b).

Physicochemical Properties of this Compound (1) Molecular formula: $C_{51}H_{78}N_4O_{17}$ (2) Mass spectrum (FAB): m/z 1019 $(M+H)^+$ (3) Specific rotation: $[\alpha]_D^{17}$ −50° (c1.00, $CHCl_3$)

(4) $^1H$ NMR spectrum (300 MHz, $CDCl_3$) δ (ppm): 0.87 (d, 8-$CH_3$), 1.07 (d, 6"-H), 1.12 (d, 6'-H), 1.15 (t, 3-$OCOCH_2CH_3$), 1.18 (t, 4"-$OCOCH_2CH_3$), 1.40 (s, 3"-$CH_3$), 1.67 (dd, 2"-Hax), 1.99 (s, 3"-$OCOCH_3$), 2.30 (s, $NCH_3$), 2.41 (q, 3-$OCOCH_2CH_3$), 2.41 (q, 4"-$OCOCH_2CH_3$), 2.53 (s, 3'-$N(CH_3)_2$), 2.60 (dd, 2-H), 2.81 (dd, 2-H), 3.17 (m, 4'-H), 3.17 (m, 5'-H), 3.21 (d, 2"-Heq), 3.34 (m, 9-H), 3.37 (dd, 2'-H), 3.64 (s, 4-$OCH_3$), 3.85 (d, 4-H), 3.95 (d, 5-H), 4.38 (d, 1'-H), 4.51 (dq, 5"-H), 4.57 (d, 4"-H), 4.82 (d, 1"-H), 5.10 (m, 15-H), 5.57 (m, 3-H), 6.32 (dt, 15-$CH_2$—CH═CH), 6.52 (d, 15-$CH_2$—CH═CH), 7.54 (dt, benzooxadiazole), 7.75 (dt, benzooxadiazole), 9.63 (s, CHO).

Example 99

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(4-(1H-pyrazol-1-yl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 3-bromo(4-(1H-pyrazol-1-yl)benzene was used instead of 4-bromoquinoline, 63 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(4-(1H-pyrazol-1-yl)phenyl)-2-propenyl group, $R_{3''}$ is acetyl group, $R_{41}$ is propionyl group, and X is oxygen atom) was obtained from 70 mg of the compound of Example 90(b).

Physicochemical Properties of this Compound (1) Molecular formula: $C_{60}H_{92}N_4O_{19}$ (2) Mass spectrum (FAB): m/z 1173 $(M+H)^+$ (3) Specific rotation: $[\alpha]_D^{20}$-48° (c1.0, $CHCl_3$)

(4) $^1H$ NMR spectrum (300 MHz, $CDCl_3$) δ (ppm): 0.92 (d, 8-$CH_3$), 1.07 (d, 6"-H), 1.14 (t, 3-$OCOCH_2CH_3$), 1.19 (t, 4"-$OCOCH_2CH_3$), 1.21 (d, 6'-H), 1.41 (s, 3"-$CH_3$), 1.67 (dd, 2"-H), 2.02 (s, 3"-$OCOCH_3$), 2.04 (s, 9-$OCOCH_3$), 2.05 (s, 2'-$OCOCH_3$), 2.23 (s, $NCH_3$), 2.43 (s, 3'-$N(CH_3)_2$), 2.64 (t, 3'-H), 2.86 (dd, 2-H), 3.16 (s, $CH(OCH_3)_2$), 3.19 (d, 2"-Heq), 3.26 (s, $CH(OCH_3)_2$), 3.60 (s, 4-$OCH_3$), 3.63 (br d, 4-H), 3.93 (br d, 5-H), 4.49 (dq, 5"-H), 4.57 (d, 4"-H), 4.70 (d, 1'-H), 4.81 (d, 1"-H), 4.91 (m, 9-H), 4.98 (dd, 2'-H), 5.07 (m, 3-H), 5.10 (m, 15-H), 6.14 (dt, CH═CH), 6.45 (d, CH═CH), 6.47 (dd, pyrazole), 7.42 (d, $C_6H_4$), 7.63 (d, $C_6H_4$), 7.72 (d, pyrazole), 7.92 (d, pyrazole).

(b) In the same manner as in Example 2(c), 26 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(4-(1H-pyrazol-1-yl)phenyl)-2-propenyl group, $R_{3''}$ is acetyl group, $R_{4''}$ is propionyl group, and X is oxygen atom) was obtained from 62 mg of the compound of Example 99(a).

Physicochemical Properties of this Compound (1) Molecular formula: $C_{56}H_{88}N_4O_{17}$ (2) Mass spectrum (FAB): m/z 1089 $(M+H)^+$ (3) Specific rotation: $[\alpha]_D^{20}$ −53° (c0.81, $CHCl_3$)

(4) $^1H$ NMR spectrum (300 MHz, $CDCl_3$) δ (ppm): 0.88 (d, 8-$CH_3$), 1.09 (d, 6"-H), 1.12 (t, 3-$OCOCH_2CH_3$), 1.20 (t, 4"-$OCOCH_2CH_3$), 1.21 (d, 6'-H), 1.42 (s, 3"-$CH_3$), 1.45 (m, 8-H), 1.68 (dd, 2"-H), 1.85 (m, 6-$CH_2$), 2.02 (s, 3"-$OCOCH_3$), 2.34 (s, $NCH_3$), 2.54 (s, 3'-$N(CH_3)_2$), 2.62 (dd, 2-H), 2.70 (dd, 12-H), 2.82 (dd, 2-H), 3.16 (s, $CH(OCH_3)_2$), 3.21 (d, 2"-Heq), 3.26 (s, $CH(OCH_3)_2$), 3.36 (m, 9-H), 3.48 (dd, 2'-H), 3.66 (s, 4-$OCH_3$), 3.88 (br d, 5-H), 3.99 (br d, 4-H), 4.46 (d, 1'-H), 4.50 (dd, $CH(OCH_3)_2$), 4.57 (m, 4"-H), 4.57 (m, 5"-H), 4.83 (d, 1"-H), 5.10 (m, 15-H), 5.47 (m, 3-H), 6.12 (dt, CH═$CH_2$), 6.44 (d, CH═$CH_2$), 6.47 (dd, pyrazole), 7.40 (d, $C_6H_4$), 7.63 (d, $C_6H_4$), 7.72 (d, pyrazole), 7.92 (d, pyrazole).

(c) In the same manner as in Example 2(d), 22 mg of the title compound was obtained from 25 mg of the compound of Example 99(b).

Physicochemical Properties of this Compound (1) Molecular formula: $C_{54}H_{82}N_4O_{16}$ (2) Mass spectrum (FAB): m/z 1043 $(M+H)^+$ (3) Specific rotation: $[\alpha]_D^{21}$ −62° (c0.84, $CHCl_3$)

(4) $^1H$ NMR spectrum (300 MHz, $CDCl_3$) δ (ppm): 0.89 (d, 8-$CH_3$), 1.09 (d, 6"-H), 1.14 (d, 6'-H), 1.17 (t, 3-$OCOCH_2CH_3$), 1.19 (t, 4"-$OCOCH_2CH_3$), 1.35 (m, 8-H), 1.41 (s, 3"-$CH_3$), 1.69 (dd, 2"-H), 2.01 (s, 3"-$OCOCH_3$), 2.31 (s, $NCH_3$), 2.54 (s, 3'-$N(CH_3)_2$), 2.83 (dd, 2-H), 2.89 (dd, 6-$CH_2$), 3.17 (m, 4'-H), 3.20 (m, 5'-H), 3.21 (d, 2"-Heq), 3.36 (m, 9-H), 3.41 (dd, 2'-H), 3.64 (s, 4-$OCH_3$), 3.87 (br d, 5-H), 4.00 (br d, 4-H), 4.40 (d, 1'-H), 4.54 (dq, 5"-H), 4.58 (d, 4"-H), 4.84 (d, 1"-H), 5.10 (m, 15-H), 5.58 (br dd, 3-H), 6.12 (dt, $CH{=}CH_2$), 6.44 (d, $CH{=}CH_2$), 6.47 (dd, pyrazole), 7.40 (d, $C_6H_4$), 7.63 (d, $C_6H_4$), 7.72 (d, pyrazole), 7.92 (d, pyrazole), 9.66 (s, CHO).

Example 100

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(2-fluoro-4-(1H-tetrazol-1-yl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 1-(4-bromo-3-fluorophenyl)-1H-tetrazole was used instead of 4-bromoquinoline, 58.1 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(2-fluoro-4-(1H-tetrazol-1-yl)phenyl)-2-propenyl group, $R_{3''}$ is acetyl group, $R_{4''}$ is propionyl group, and X is oxygen atom) was obtained from 76.1 mg of the compound of Example 90(b).

Physicochemical Properties of this Compound (1) Molecular formula: $C_{58}H_{89}FN_6O_{19}$ (2) Mass spectrum (FAB): m/z 1193 $(M+H)^+$ (3) $^1H$ NMR spectrum (300 MHz, $CDCl_3$) δ (ppm): 0.89 (d, 8-$CH_3$), 1.04 (d, 6"-H), 1.11 (t, 3-$OCOCH_2CH_3$), 1.16 (t, 4"-$OCOCH_2CH_3$), 1.17 (d, 6'-H), 1.38 (s, 3"-$CH_3$), 1.64 (dd, 2"-Hax), 1.99 (s, 9-$OCOCH_3$), 2.01 (s, 3"-$OCOCH_3$), 2.02 (s, 2'-$OCOCH_3$), 2.20 (s, $NCH_3$), 2.40 (s, 3'-$N(CH_3)_2$), 2.59 (dd, 2-H), 2.59 (t, 3'-H), 2.84 (dd, 2-H), 3.12 (s, $CH(OCH_3)_2$), 3.18 (t, 4'-H), 3.18 (d, 2"-Heq), 3.21 (m, 5'-H), 3.22 (s, $CH(OCH_3)_2$), 3.56 (d, 4-H), 3.58 (s, 4-$OCH_3$), 3.91 (d, 5-H), 4.46 (dq, 5"-H), 4.52 (dd, $CH(OCH_3)_2$), 4.54 (d, 4"-H), 4.67 (d, 1'-H), 4.78 (d, 1"-H), 4.89 (m, 9-H), 4.94 (dd, 2'-H), 5.06 (br t, 3-H), 5.09 (m, 15-H), 6.32 (dt, 15-$CH_2$—$CH{=}CH$), 6.57 (d, 15-$CH_2$—$CH{=}CH$), 7.45 (m, $C_6H_3$), 7.61 (t, $C_6H_3$), 9.01 (s, tetrazole).

(b) In the same manner as in Example 2(c), 31.6 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(2-fluoro-4-(1H-tetrazol-1-yl)phenyl)-2-propenyl group, $R_{3''}$ is acetyl group, $R_{4''}$ is propionyl group, and X is oxygen atom) was obtained from 58.1 mg of the compound of Example 100(a).

Physicochemical Properties of this Compound (1) Molecular formula: $C_{54}H_{85}FN_6O_{17}$ (2) Mass spectrum (FAB): m/z 1109 $(M+H)^+$ (3) $^1H$ NMR spectrum (300 MHz, $CDCl_3$) δ (ppm): 0.85 (d, 8-$CH_3$), 1.07 (d, 6"-H), 1.11 (t, 3-$OCOCH_2CH_3$), 1.18 (t, 4"-$OCOCH_2CH_3$), 1.19 (d, 6'-H), 1.40 (s, 3"-$CH_3$), 1.67 (dd, 2"-Hax), 2.00 (s, 3"-$OCOCH_3$), 2.31 (s, $NCH_3$), 2.39 (q, 3-$OCOCH_2CH_3$), 2.42 (q, 4"-$OCOCH_2CH_3$), 2.52 (s, 3'-$N(CH_3)_2$), 2.60 (dd, 2-H), 2.80 (dd, 2-H), 3.13 (s, $CH(OCH_3)_2$), 3.17 (t, 4'-H), 3.19 (d, 2"-Heq), 3.22 (m, 5'-H), 3.24 (s, $CH(OCH_3)_2$), 3.46 (dd, 2'-H), 3.65 (s, 4-$OCH_3$), 3.88 (d, 4-H), 3.97 (d, 5-H), 4.45 (d, 1'-H), 4.48 (dd, $CH(OCH_3)_2$), 4.54 (dq, 5"-H), 4.57 (d, 4"-H), 4.82 (d, 1"-H), 5.12 (m, 15-H), 5.49 (m, 3-H), 6.31 (dt, 15-$CH_2$—$CH{=}CH$), 6.57 (d, 15-$CH_2$—$CH{=}CH$), 7.45 (m, $C_6H_3$), 7.60 (t, $C_6H_3$), 8.97 (s, tetrazole).

(c) In the same manner as in Example 2(d), 25.5 mg of the title compound was obtained from 34.1 mg of the compound of Example 100(b).

Physicochemical Properties of this Compound (1) Molecular formula: $C_{52}H_{79}FN_6O_{16}$ (2) Mass spectrum (FAB): m/z 1063 $(M+H)^+$ (3) Specific rotation: $[\alpha]_D^{16}$ −49° (c1.00, $CHCl_3$)

(4) $^1H$ NMR spectrum (300 MHz, $CDCl_3$) δ (ppm): 0.87 (d, 8-$CH_3$), 1.07 (d, 6"-H), 1.13 (d, 6'-H), 1.16 (t, 3-$OCOCH_2CH_3$), 1.19 (t, 4"-$OCOCH_2CH_3$), 1.40 (s, 3"-$CH_3$), 1.68 (dd, 2"-Hax), 1.99 (s, 3"-$OCOCH_3$), 2.30 (s, $NCH_3$), 2.42 (q, 3-$OCOCH_2CH_3$), 2.42 (q, 4"-$OCOCH_2CH_3$), 2.53 (s, 3'-$N(CH_3)_2$), 2.60 (dd, 2-H), 2.82 (dd, 2-H), 3.17 (m, 4'-H), 3.17 (m, 5'-H), 3.21 (d, 2"-Heq), 3.35 (m, 9-H), 3.38 (dd, 2'-H), 3.66 (s, 4-$OCH_3$), 3.86 (d, 4-H), 3.97 (d, 5-H), 4.39 (d, 1'-H), 4.51 (dq, 5"-H), 4.57 (d, 4"-H), 4.83 (d, 1"-H), 5.11 (m, 15-H), 5.57 (m, 3-H), 6.31 (dt, 15-$CH_2$—$CH{=}CH$), 6.35 (d, 15-$CH_2$—$CH{=}CH$), 7.45 (m, $C_6H_3$), 7.60 (t, $C_6H_3$), 8.98 (s, tetrazole), 9.64 (s, CHO).

Example 101

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(4-(isoxazol-5-yl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 5-(4-bromophenyl)isoxazole was used instead of 4-bromoquinoline, 65.8 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(4-(isoxazol-5-yl)phenyl)-2-propenyl group, $R_{3''}$ is acetyl group, $R_{4''}$ is propionyl group, and X is oxygen atom) was obtained from 76.3 mg of the compound of Example 90(b).

Physicochemical Properties of this Compound (1) Molecular formula: $C_{60}H_{91}N_3O_{20}$ (2) Mass spectrum (FAB): m/z 1173 $(M+H)^+$ (3) $^1H$ NMR spectrum (300 MHz, $CDCl_3$) δ (ppm): 0.89 (d, 8-$CH_3$), 1.04 (d, 6"-H), 1.12 (t, 3-$OCOCH_2CH_3$), 1.16 (t, 4"-$OCOCH_2CH_3$), 1.18 (d, 6'-H), 1.39 (s, 3"-$CH_3$), 1.65 (dd, 2"-Hax), 1.99 (s, 9-$OCOCH_3$), 2.01 (s, 3"-$OCOCH_3$), 2.03 (s, 2'-$OCOCH_3$), 2.21 (s, $NCH_3$), 2.41 (s, 3'-$N(CH_3)_2$), 2.58 (dd, 2-H), 2.59 (t, 3'-H), 2.83 (dd, 2-H), 3.13 (s, $CH(OCH_3)_2$), 3.14 (t, 4'-H), 3.16 (d, 2"-Heq), 3.21 (m, 5'-H), 3.23 (s, $CH(OCH_3)_2$), 3.57 (s, 4-$OCH_3$), 3.59 (d, 4-H), 3.90 (d, 5-H), 4.46 (dq, 5"-H), 4.52 (dd, $CH(OCH_3)_2$), 4.54 (d, 4"-H), 4.67 (d, 1'-H), 4.78 (d, 1"-H), 4.89 (m, 9-H), 4.95 (dd, 2'-H), 5.05 (br t, 3-H), 5.06 (m, 15-H), 6.20 (dt, 15-$CH_2$—

CH=CH), 6.44 (d, 15-$CH_2$—CH=CH), 6.47 (d, isoxazole), 7.40 (d, $C_6H_4$), 7.70 (d, $C_6H_4$), 8.28 (d, isoxazole).

(b) In the same manner as in Example 2(c), 34.1 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(4-(isoxazol-5-yl)phenyl)-2-propenyl group, $R_{3''}$ is acetyl group, $R_{4''}$ is propionyl group, and X is oxygen atom) was obtained from 65.8 mg of the compound of Example 101(a).

Physicochemical Properties of this Compound (1) Molecular formula: $C_{56}H_{87}N_3O_{18}$ (2) Mass spectrum (FAB): m/z 1090 $(M+H)^+$ (3) $^1H$ NMR spectrum (300 MHz, $CDCl_3$) δ (ppm): 0.85 (d, 8-$CH_3$), 1.07 (d, 6"-H), 1.10 (t, 3-$OCOCH_2CH_3$), 1.18 (t, 4"-$OCOCH_2CH_3$), 1.19 (d, 6'-H), 1.40 (s, 3"-$CH_3$), 1.67 (dd, 2"-Hax), 2.00 (s, 3"-$OCOCH_3$) 2.30 (s, $NCH_3$), 2.39 (q, 3-$OCOCH_2CH_3$), 2.42 (q, 4"-$OCOCH_2CH_3$), 2.52 (s, 3'-N$(CH_3)_2$), 2.59 (dd, 2-H), 2.79 (dd, 2-H), 3.13 (s, $CH(OCH_3)_2$), 3.16 (t, 4'-H), 3.19 (d, 2"-Heq), 3.22 (m, 5'-H), 3.24 (s, $CH(OCH_3)_2$), 3.47 (dd, 2'-H), 3.64 (s, 4-$OCH_3$), 3.87 (d, 4-H), 3.98 (d, 5-H), 4.45 (d, 1'-H), 4.49 (dd, $CH(OCH_3)_2$), 4.54 (dq, 5"-H), 4.57 (d, 4"-H), 4.82 (d, 1"-H), 5.09 (m, 15-H), 5.47 (m, 3-H), 6.19 (dt, 15-$CH_2$—CH=CH), 6.83 (d, 15-$CH_2$—CH=CH), 6.49 (d, isoxazole), 7.40 (d, $C_6H_4$), 7.71 (d, $C_6H_4$), 7.27 (d, isoxazole).

(c) In the same manner as in Example 2(d), 28.2 mg of the title compound was obtained from 34.1 mg of the compound of Example 101(b).

Physicochemical Properties of this Compound (1) Molecular formula: $C_{54}H_{81}N_3O_{17}$ (2) Mass spectrum (FAB): m/z 1044 $(M+H)^+$ (3) Specific rotation: $[\alpha]_D^{19}$ −52° (c1.00, $CHCl_3$)

(4) $^1H$ NMR spectrum (300 MHz, $CDCl_3$) δ (ppm): 0.87 (d, 8-$CH_3$), 1.07 (d, 6"-H), 1.13 (d, 6'-H), 1.15 (t, 3-$OCOCH_2CH_3$), 1.18 (t, 4"-$OCOCH_2CH_3$), 1.40 (s, 3"-$CH_3$), 1.67 (dd, 2"-Hax), 1.99 (s, 3"-$OCOCH_3$), 2.30 (s, $NCH_3$), 2.42 (q, 3-$OCOCH_2CH_3$), 2.42 (q, 4"-$OCOCH_2CH_3$), 2.53 (s, 3'-N$(CH_3)_2$), 2.60 (dd, 2-H), 2.81 (dd, 2-H), 3.17 (t, 4'-H), 3.17 (m, 5'-H), 3.20 (d, 2"-Heq), 3.35 (m, 9-H), 3.39 (dd, 2'-H), 3.64 (s, 4-$OCH_3$), 3.85 (d, 4-H), 3.97 (d, 5-H), 4.38 (d, 1'-H), 4.52 (dq, 5"-H), 4.57 (d, 4"-H), 4.82 (d, 1"-H), 5.09 (m, 15-H), 5.56 (m, 3-H), 6.19 (dt, 15-$CH_2$—CH=CH), 6.43 (d, 15-$CH_2$—CH=CH), 6.49 (d, isoxazole), 7.40 (d, $C_6H_4$), 7.71 (d, $C_6H_4$), 7.27 (d, isoxazole), 9.64 (s, CHO).

Example 102

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(4-(pyridin-3-yl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 3-(4-bromophenyl)pyridine (J. Med. Chem. 1999, 42, 3572-3587) was used instead of 4-bromoquinoline, 75.7 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(4-(pyridin-3-yl)phenyl)-2-propenyl group, $R_{3''}$ is acetyl group, $R_{4''}$ is propionyl group, and X is oxygen atom) was obtained from 79.7 mg of the compound of Example 90(b).

Physicochemical Properties of this Compound (1) Molecular formula: $C_{62}H_{93}N_3O_{19}$ (2) Mass spectrum (FAB): m/z 1184 $(M+H)^+$ (3) Specific rotation: $[\alpha]_D^{18}$ −51° (c0.66, $CHCl_3$)

(4) $^1H$ NMR spectrum (300 MHz, $CDCl_3$) δ (ppm): 0.92 (d, 8-$CH_3$), 1.07 (d, 6"-H), 1.14 (t, 3-$OCOCH_2CH_3$), 1.19 (t, 4"-$OCOCH_2CH_3$), 1.20 (d, 6'-H), 1.41 (s, 3"-$CH_3$), 1.52 (m, 13-H), 1.67 (dd, 2"-Hax), 1.76 (m, 8-H), 2.02 (s, 3"-$OCOCH_3$), 2.04 (s, 9-$OCOCH_3$), 2.06 (s, 2'-$OCOCH_3$), 2.23 (s, $NCH_3$), 2.35 (q, 3-$OCOCH_2CH_3$), 2.43 (q, 4"-$OCOCH_2CH_3$), 2.43 (s, 3'-N$(CH_3)_2$), 2.62 (t, 3'-H), 2.86 (dd, 2-H), 3.14 (t, 4'-H), 3.16 (s, $CH(OCH_3)_2$), 3.19 (d, 2"-Heq), 3.25 (s, $CH(OCH_3)_2$), 3.61 (s, 4-$OCH_3$), 3.93 (d, 5-H), 4.48 (dq, 5"-H), 4.57 (d, 4"-H), 4.70 (d, 1'-H), 4.81 (d, 1"-H), 4.92 (m, 9-H), 4.98 (dd, 2'-H), 5.07 (m, 3-H), 5.13 (m, 15-H), 6.19 (dt, CH=CH), 6.49 (d, CH=CH), 7.36 (dd, pyridine), 7.45 (d, $C_6H_4$), 7.53 (d, $C_6H_4$), 7.87 (m, pyridine), 8.58 (dd, pyridine), 8.84 (d, pyridine).

(b) In the same manner as in Example 73(b), 39.5 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(4-(pyridin-3-yl)phenyl)-2-propenyl group, $R_{3''}$ is acetyl group, $R_{4''}$ is propionyl group, and X is oxygen atom) was obtained from 75.7 mg of the compound of Example 102(a).

Physicochemical Properties of this Compound (1) Molecular formula: $C_{58}H_{89}N_3O_{17}$ (2) Mass spectrum (FAB): m/z 1100 $(M+H)^+$ (3) $^1H$ NMR spectrum (300 MHz, $CDCl_3$) δ (ppm): 0.89 (d, 8-$CH_3$), 1.09 (d, 6"-H), 1.12 (t, 3-$OCOCH_2CH_3$), 1.20 (t, 4"-$OCOCH_2CH_3$), 1.21 (d, 6'-H), 1.42 (s, 3"-$CH_3$), 1.46 (m, 8-H), 1.68 (dd, 2"-Hax), 1.85 (m, 6-$CH_2$), 2.01 (s, 3"-$OCOCH_3$), 2.35 (q, 3-$OCOCH_2CH_3$), 2.36 (s, $NCH_3$), 2.43 (q, 4"-$OCOCH_2CH_3$), 2.54 (s, 3'-N$(CH_3)_2$), 2.62 (dd, 2-H), 2.82 (dd, 2-H), 3.16 (s, $CH(OCH_3)_2$), 3.21 (d, 2"-Heq), 3.26 (s, $CH(OCH_3)_2$), 3.41 (m, 9-H), 3.48 (dd, 2'-H), 3.66 (s, 4-$OCH_3$), 3.88 (d, 4-H), 3.98 (d, 5-H), 4.47 (d, 1'-H), 4.58 (d, 4"-H), 4.83 (d, 1"-H), 5.10 (m, 15-H), 5.46 (m, 3-H), 6.17 (dt, CH=CH), 6.47 (d, CH=CH), 7.36 (dd, pyridine), 7.43 (d, $C_6H_4$), 7.53 (d, $C_6H_4$), 7.87 (m, pyridine), 8.58 (dd, pyridine), 8.84 (d, pyridine).

(c) In the same manner as in Example 2(d), 34.1 mg of the title compound was obtained from 39.5 mg of the compound of Example 102(b).

Physicochemical Properties of this Compound (1) Molecular formula: $C_{56}H_{83}N_3O_{16}$ (2) Mass spectrum (FAB): m/z 1054 $(M+H)^+$ (3) Specific rotation: $[\alpha]_D^{15}$ −53° (c0.55, $CHCl_3$)

(4) $^1H$ NMR spectrum (300 MHz, $CDCl_3$) δ (ppm): 0.90 (d, 8-$CH_3$), 1.09 (d, 6"-H), 1.14 (d, 6'-H), 1.17 (t, 3-$OCOCH_2CH_3$), 1.19 (t, 4"-$OCOCH_2CH_3$), 1.37 (m, 8-H), 1.42 (s, 3"-$CH_3$), 1.59 (m, 13-H), 1.59 (m, 7-H), 1.69 (dd, 2"-Hax), 2.01 (s, 3"-$OCOCH_3$), 2.34 (s, $NCH_3$), 2.43 (q, 4"-$OCOCH_2CH_3$), 2.54 (s, 3'-N$(CH_3)_2$), 2.84 (dd, 2-H), 2.90 (dd, 6-$CH_2$), 3.17 (t, 4'-H), 3.21 (d, 2"-Heq), 3.40 (dd, 2'-H), 3.66 (s, 4-$OCH_3$), 3.87 (d, 4-H), 3.99 (d, 5-H), 4.40 (d, 1'-H), 4.53 (dq, 5"-H), 4.58 (d, 4"-H), 4.84 (d, 1"-H), 5.10 (m, 15-H), 5.56 (m, 3-H), 6.17 (dt, CH=CH), 6.47 (d, CH═CH), 7.36 (dd, pyridine), 7.43 (d, $C_6H_4$), 7.53 (d, $C_6H_4$), 7.87 (m, pyridine), 8.58 (dd, pyridine), 8.84 (d, pyridine), 9.65 (s, CHO).

Example 103

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(4-(pyridin-4-yl)phenyl)-2-propenyl group, $R_{4'}$ is a group represented by the formula (a), $R_{3'}$ is acetyl group, $R_{4''}$ is propionyl group, and X is oxygen atom (a) In the same manner as in Example 48(c), except that 4-(4-bromophenyl)pyridine (J. Med. Chem. 1999, 42, 3572-3587) was used instead of 4-bromoquinoline, 44.0 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(4-(pyridin-4-yl)phenyl)-2-propenyl group, $R_{3''}$ is acetyl group, $R_{4''}$ is propionyl group, and X is oxygen atom) was obtained from 71.9 mg of the compound of Example 90(b).

Physicochemical Properties of this Compound (1) Molecular formula: $C_{62}H_{93}N_3O_{19}$ (2) Mass spectrum (FAB): m/z 1184 $(M+H)^+$ (3) $^1$H NMR spectrum (300 MHz, $CDCl_3$) δ (ppm): 0.92 (d, 8-$CH_3$), 1.07 (d, 6"-H), 1.14 (t, 3-$OCOCH_2CH_3$), 1.19 (t, 4"-$OCOCH_2CH_3$), 1.21 (d, 6'-H), 1.41 (s, 3"-$CH_3$), 1.52 (m, 13-H), 1.67 (dd, 2"-Hax), 1.75 (m, 8-H), 2.02 (s, 3"-$OCOCH_3$), 2.04 (s, 9-$OCOCH_3$), 2.06 (s, 2'-$OCOCH_3$), 2.23 (s, $NCH_3$), 2.35 (q, 3-$OCOCH_2CH_3$), 2.43 (q, 4"-$OCOCH_2CH_3$), 2.43 (s, 3'-$N(CH_3)_2$), 2.62 (t, 3'-H), 2.62 (dd, 2-H), 2.86 (dd, 2-H), 3.14 (t, 4'-H), 3.16 (s, $CH(OCH_3)_2$), 3.19 (d, 2"-Heq), 3.26 (s, $CH(OCH_3)_2$), 3.60 (s, 4-$OCH_3$), 3.94 (d, 5-H), 4.48 (dq, 5"-H), 4.57 (d, 4"-H), 4.70 (d, 1'-H), 4.81 (d, 1"-H), 4.92 (m, 9-H), 4.98 (dd, 2'-H), 5.07 (m, 3-H), 5.12 (m, 15-H), 6.22 (dt, CH═CH), 6.49 (d, CH═CH), 7.45 (d, $C_6H_4$), 7.50 (d, pyridine), 7.59 (d, $C_6H_4$), 8.65 (d, pyridine).

(b) In the same manner as in Example 73(b), 22.7 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(4-(pyridin-4-yl)phenyl)-2-propenyl group, $R_{3''}$ is acetyl group, $R_{4''}$ is propionyl group, and X is oxygen atom) was obtained from 44.0 mg of the compound of Example 103(a).

Physicochemical Properties of this Compound (1) Molecular formula: $C_{58}H_{89}N_3O_{17}$ (2) Mass spectrum (FAB): m/z 1100 $(M+H)^+$ (3) $^1$H NMR spectrum (300 MHz, $CDCl_3$) δ (ppm): 0.88 (d, 8-$CH_3$), 1.09 (d, 6"-H), 1.12 (t, 3-$OCOCH_2CH_3$), 1.20 (t, 4"-$OCOCH_2CH_3$), 1.21 (d, 6'-H), 1.42 (s, 3"-$CH_3$), 1.45 (m, 8-H), 1.68 (dd, 2"-Hax), 1.75 (m, 14-H), 1.85 (m, 6-$CH_2$), 2.01 (s, 3"-$OCOCH_3$), 2.33 (q, 3-$OCOCH_2CH_3$), 2.35 (s, $NCH_3$), 2.43 (q, 4"-$OCOCH_2CH_3$), 2.54 (s, 3'-$N(CH_3)_2$), 2.62 (dd, 2-H), 2.81 (dd, 2-H), 3.15 (s, $CH(OCH_3)_2$), 3.17 (t, 4'-H), 3.21 (d, 2"-Heq), 3.26 (s, $CH(OCH_3)_2$), 3.37 (m, 9-H), 3.48 (dd, 2'-H), 3.65 (s, 4-$OCH_3$), 3.88 (d, 4-H), 3.98 (d, 5-H), 4.46 (d, 1'-H), 4.50 (dd, $CH(OCH_3)_2$), 4.59 (d, 4"-H), 4.83 (d, 1"-H), 5.10 (m, 15-H), 5.47 (m, 3-H), 6.19 (dt, CH═CH), 6.47 (d, CH═CH), 7.44 (d, $C_6H_4$), 7.50 (dd, pyridine), 7.59 (d, $C_6H_4$), 8.65 (d, pyridine).

(c) In the same manner as in Example 2(d), 20.0 mg of the title compound was obtained from 22.7 mg of the compound of Example 103(b).

Physicochemical Properties of this Compound (1) Molecular formula: $C_{56}H_{83}N_3O_{16}$ (2) Mass spectrum (FAB): m/z 1054 $(M+H)^+$ (3) Specific rotation: $[\alpha]_D^{18}$ −58° (c1.0, $CHCl_3$)

(4) $^1$H NMR spectrum (300 MHz, $CDCl_3$) δ (ppm): 0.90 (d, 8-$CH_3$), 1.09 (d, 6"-H), 1.14 (d, 6'-H), 1.17 (t, 3-$OCOCH_2CH_3$), 1.19 (t, 4"-$OCOCH_2CH_3$), 1.42 (s, 3"-$CH_3$), 1.69 (dd, 2"-Hax), 2.01 (s, 3"-$OCOCH_3$), 2.34 (s, $NCH_3$), 2.43 (q, 4"-$OCOCH_2CH_3$), 2.54 (s, 3'-$N(CH_3)_2$), 2.83 (dd, 2-H), 2.90 (dd, 6-$CH_2$), 3.17 (t, 4'-H), 3.21 (d, 2"-Heq), 3.40 (dd, 2'-H), 3.66 (s, 4-$OCH_3$), 3.87 (d, 4-H), 3.99 (d, 5-H), 4.40 (d, 1'-H), 4.52 (dq, 5"-H), 4.58 (d, 4"-H), 4.84 (d, 1"-H), 5.10 (m, 15-H), 5.56 (m, 3-H), 6.19 (dt, CH═CH), 6.47 (d, CH═CH), 7.44 (d, $C_6H_4$), 7.50 (dd, pyridine), 7.59 (d, $C_6H_4$), 8.65 (d, pyridine), 9.65 (s, CHO).

Example 104

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(4-(pyridin-2-yl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 2-(4-bromophenyl)pyridine (J. Med. Chem. 1999, 42, 3572-3587) was used instead of 4-bromoquinoline, 72.0 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(4-(pyridin-2-yl)phenyl)-2-propenyl group, $R_{3''}$ is acetyl group, $R_{4''}$ is propionyl group, and X is oxygen atom) was obtained from 86.5 mg of the compound of Example 90(b).

Physicochemical Properties of this Compound (1) Molecular formula: $C_{62}H_{93}N_3O_{19}$ (2) Mass spectrum (FAB): m/z 1184 $(M+H)^+$ (3) $^1$H NMR spectrum (300 MHz, $CDCl_3$) δ (ppm): 0.92 (d, 8-$CH_3$), 1.07 (d, 6"-H), 1.14 (t, 3-$OCOCH_2CH_3$), 1.19 (t, 4"-$OCOCH_2CH_3$), 1.20 (d, 6'-H), 1.41 (s, 3"-$CH_3$), 1.68 (dd, 2"-Hax), 2.02 (s, 3"-$OCOCH_3$), 2.04 (s, 9-$OCOCH_3$), 2.06 (s, 2'-$OCOCH_3$), 2.24 (s, $NCH_3$), 2.43 (q, 4"-$OCOCH_2CH_3$), 2.43 (s, 3'-$N(CH_3)_2$), 2.61 (dd, 2-H), 2.62 (t, 3'-H), 2.87 (dd, 2-H), 3.14 (t, 4'-H), 3.16 (s, $CH(OCH_3)_2$), 3.25 (s, $CH(OCH_3)_2$), 3.61 (s, 4-$OCH_3$), 3.65 (d, 4-H), 3.93 (d, 5-H), 4.48 (dq, 5"-H), 4.57 (d, 4"-H), 4.70 (d, 1'-H), 4.81 (d, 1"-H), 4.92 (m, 9-H), 4.97 (dd, 2'-H), 5.06 (m, 3-H), 5.11 (m, 15-H), 6.20 (dt, CH═CH), 6.49 (d, CH═CH), 7.22 (ddd, pyridine), 7.44 (d, $C_6H_4$), 7.43 (m, pyridine), 7.94 (d, $C_6H_4$), 8.68 (m, pyridine).

(b) In the same manner as in Example 73(b), 37.3 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(4-(pyridin-2-yl)phenyl)-2-propenyl group, $R_{3''}$ is acetyl group, $R_{4''}$ is propionyl group, and X is oxygen atom) was obtained from 72.0 mg of the compound of Example 104(a).

Physicochemical Properties of this Compound (1) Molecular formula: $C_{58}H_{89}N_3O_{17}$ (2) Mass spectrum (FAB): m/z 1100 $(M+H)^+$ (3) $^1$H NMR spectrum (300 MHz, $CDCl_3$) δ (ppm): 0.88 (d, 8-$CH_3$), 1.09 (d, 6"-H), 1.12 (t, 3-$OCOCH_2CH_3$), 1.20 (t, 4"-$OCOCH_2CH_3$), 1.21 (d, 6'-H), 1.42 (s, 3"-$CH_3$), 1.44 (m, 8-H), 1.68 (dd, 2"-Hax), 2.02 (s, 3"-$OCOCH_3$), 2.33 (q, 3-$OCOCH_2CH_3$), 2.34 (s, $NCH_3$), 2.43 (q, 4"-$OCOCH_2CH_3$), 2.54 (s, 3'-$N(CH_3)_2$), 2.62 (dd, 2-H), 2.70 (m, 12-H), 2.83 (dd, 2-H), 3.16 (s, $CH(OCH_3)_2$), 3.21 (d, 2"-Heq), 3.26 (s, $CH(OCH_3)_2$), 3.37 (m, 9-H), 3.49 (dd, 2'-H), 3.66 (s, 4-$OCH_3$), 3.89 (d, 4-H), 4.00 (d, 5-H), 4.47 (d, 1'-H), 4.50 (dd, $CH(OCH_3)_2$), 4.59 (d, 4"-H), 4.83 (d, 1"-H), 5.11 (m, 15-H), 5.48 (dd, 3-H), 6.19 (dt, CH═CH), 6.47 (d, CH═CH), 7.22 (m, pyridine), 7.43 (d, $C_6H_4$), 7.73 (m, pyridine), 7.94 (d, $C_6H_4$), 8.69 (m, pyridine).

(c) In the same manner as in Example 2(d), 31.3 mg of the title compound was obtained from 37.3 mg of the compound of Example 104(b).

Physicochemical Properties of this Compound (1) Molecular formula: $C_{56}H_{83}N_3O_{16}$ (2) Mass spectrum (FAB): m/z 1054 $(M+H)^+$ (3) Specific rotation: $[\alpha]_D^{18}$ −55° (c0.54, $CHCl_3$)

(4) $^1$H NMR spectrum (300 MHz, $CDCl_3$) δ (ppm): 0.90 (d, 8-$CH_3$), 1.09 (d, 6"-H), 1.14 (d, 6'-H), 1.17 (t, 3-$OCOCH_2CH_3$), 1.19 (t, 4"-$OCOCH_2CH_3$), 1.36 (m, 8-H), 1.42 (s, 3"-$CH_3$), 1.68 (dd, 2"-Hax), 2.01 (s, 3"-$OCOCH_3$), 2.33 (s, $NCH_3$), 2.42 (q, 3-$OCOCH_2CH_3$), 2.43 (q, 4"-$OCOCH_2CH_3$), 2.54 (s, 3'-$N(CH_3)_2$), 2.59 (q, 3-$OCOCH_2CH_3$), 2.65 (dd, 2-H), 2.72 (m, 12-H), 2.84 (dd, 2-H), 2.89 (dd, 6-$CH_2$), 3.17 (t, 4'-H), 3.21 (d, 2"-Heq), 3.41 (dd, 2'-H), 3.67 (s, 4-$OCH_3$), 3.87 (d, 4-H), 4.00 (d, 5-H), 4.40 (d, 1'-H), 4.53 (dq, 5"-H), 4.58 (d, 4"-H), 4.84 (d, 1"-H), 5.10 (m, 15-H), 5.56 (m, 3-H), 6.18 (dt, CH═CH), 6.47 (d, CH═CH), 7.22 (m, pyridine), 7.43 (d, $C_6H_4$), 7.73 (m, pyridine), 7.94 (d, $C_6H_4$), 8.68 (m, pyridine), 9.65 (s, CHO).

Example 105

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(4-fluoro-3-(1H-pyrazol-1-yl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 3-bromo(4-fluoro-3-(1H-pyrazol-1-yl)benzene was used instead of 4-bromoquinoline, 44 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(4-fluoro-3-(1H-pyrazol-1-yl)phenyl)-2-propenyl group, $R_{3''}$ is acetyl group, $R_4$ is propionyl group, and X is oxygen atom) was obtained from 65 mg of the compound of Example 90(b).

Physicochemical Properties of this Compound (1) Molecular formula: $C_{60}H_{91}N_4FO_{19}$ (2) Mass spectrum (FAB): m/z 1191 $(M+H)^+$ (3) $^1$H NMR spectrum (300 MHz, $CDCl_3$) δ (ppm): 0.92 (d, 8-$CH_3$), 1.07 (d, 6"-H), 1.14 (t, 3-$OCOCH_2CH_3$), 1.19 (t, 4"-$OCOCH_2CH_3$), 1.21 (d, 6'-H), 1.41 (s, 3"-$CH_3$), 1.67 (dd, 2"-H), 2.02 (s, 3"-$OCOCH_3$), 2.04 (s, 9-$OCOCH_3$), 2.05 (s, 2'-$OCOCH_3$), 2.23 (s, $NCH_3$), 2.43 (s, 3'-$N(CH_3)_2$), 2.54 (dd, 12-H), 2.64 (t, 3'-H), 2.86 (dd, 2-H), 3.15 (s, $CH(OCH_3)_2$), 3.19 (d, 2"-Heq), 3.25 (s, $CH(OCH_3)_2$), 3.60 (s, 4-$OCH_3$), 3.93 (br d, 5-H), 4.49 (dq, 5"-H), 4.57 (d, 4"-H), 4.70 (d, 1'-H), 4.81 (d, 1"-H), 4.90 (m, 9-H), 4.97 (dd, 2'-H), 5.05 (m, 3-H), 5.07 (m, 15-H), 6.14 (dt, CH═CH), 6.43 (d, CH═CH), 6.49 (dd, pyrazole), 7.21-7.30 (m, $C_6H_3F$), 7.74 (d, pyrazole), 7.87 (dd, $C_6H_3F$), 8.01 (d, pyrazole).

(b) In the same manner as in Example 2(c), 17 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(4-fluoro-3-(1H-pyrazol-1-yl)phenyl)-2-propenyl group, $R_{3''}$ is acetyl group, $R_{4''}$ is propionyl group, and X is oxygen atom) was obtained from 43 mg of the compound of Example 105(a).

Physicochemical Properties of this Compound (1) Molecular formula: $C_{56}H_{87}N_4FO_{17}$ (2) Mass spectrum (FAB): m/z 1107 $(M+H)^+$ (3) $^1$H NMR spectrum (300 MHz, $CDCl_3$) δ (ppm): 0.88 (d, 8-$CH_3$), 1.09 (d, 6"-H), 1.11 (t, 3-$OCOCH_2CH_3$), 1.20 (t, 4"-$OCOCH_2CH_3$), 1.21 (d, 6'-H), 1.42 (s, 3"-$CH_3$), 1.71 (dd, 2"-H), 1.92 (m, 6-$CH_2$), 2.02 (s, 3"-$OCOCH_3$), 2.35 (s, $NCH_3$), 2.54 (s, 3'-$N(CH_3)_2$), 2.60 (dd, 2-H), 2.69 (m, 12-H), 2.81 (dd, 2-H), 3.15 (s, $CH(OCH_3)_2$), 3.21 (d, 2"-Heq), 3.26 (s, $CH(OCH_3)_2$), 3.38 (m, 9-H), 3.48 (dd, 2'-H), 3.65 (s, 4-$OCH_3$), 3.88 (br d, 4-H), 3.98 (br d, 5-H), 4.47 (d, 1'-H), 4.48 (dd, $CH(OCH_3)_2$), 4.57 (m, 4"-H), 4.57 (m, 5"-H), 4.84 (d, 1"-H), 5.08 (m, 15-H), 5.46 (m, 3-H), 6.13 (dt, CH═$CH_2$), 6.42 (d, CH═$CH_2$), 6.49 (dd, pyrazole), 7.11-7.25 (m, $C_6H_3F$), 7.75 (d, pyrazole), 7.87 (dd, $C_6H_3F$), 8.01 (d, pyrazole).

(c) In the same manner as in Example 2(d), 15 mg of the title compound was obtained from 17 mg of the compound of Example 105(b).

Physicochemical Properties of this Compound (1) Molecular formula: $C_{54}H_{81}N_4FO_{16}$ (2) Mass spectrum (FAB): m/z 1061 $(M+H)^+$ (3) Specific rotation: $[\alpha]_D^{21}$ −55° (c0.48, $CHCl_3$)

(4) $^1$H NMR spectrum (300 MHz, $CDCl_3$) δ (ppm): 0.89 (d, 8-$CH_3$), 1.09 (d, 6"-H), 1.14 (d, 6'-H), 1.17 (t, 3-$OCOCH_2CH_3$), 1.19 (t, 4"-$OCOCH_2CH_3$), 1.34 (m, 8-H), 1.42 (s, 3"-$CH_3$), 1.69 (dd, 2"-H), 2.01 (s, 3"-$OCOCH_3$), 2.30 (s, $NCH_3$), 2.54 (s, 3'-$N(CH_3)_2$), 2.83 (dd, 2-H), 2.90 (dd, 6-$CH_2$), 3.18 (m, 4'-H), 3.18 (m, 5'-H), 3.21 (d, 2"-Heq), 3.35 (m, 9-H), 3.41 (dd, 2'-H), 3.66 (s, 4-$OCH_3$), 3.87 (br d, 5-H), 3.99 (br d, 4-H), 4.40 (d, 1'-H), 4.54 (dq, 5"-H), 4.59 (d, 4"-H), 4.84 (d, 1"-H), 5.07 (m, 15-H), 5.57 (m, 3-H), 6.13 (dt, CH═$CH_2$), 6.42 (d, CH═$CH_2$), 6.49 (dd, pyrazole), 7.11-7.25 (m, $C_6H_3F$), 7.75 (d, pyrazole), 7.87 (dd, $C_6H_3F$), 8.01 (d, pyrazole), 9.65 (s, CHO).

Example 106

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(3-(2-methylthiazol-4-yl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 4-(3-bromophenyl)-2-methylthiazole was used instead of 4-bromoquinoline, 65.8 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(3-(2-methylthiazol-4-yl)phenyl)-2-propenyl group, $R_{3''}$ is acetyl group, $R_{4''}$ is propionyl group, and X is oxygen atom) was obtained from 75.6 mg of the compound of Example 90(b).

Physicochemical Properties of this Compound (1) Molecular formula: $C_{61}H_{93}N_3O_{19}S$ (2) Mass spectrum (FAB): m/z 1204 $(M+H)^+$ (3) $^1H$ NMR spectrum (300 MHz, $CDCl_3$) δ (ppm): 0.90 (d, 8-$CH_3$), 1.05 (d, 6"-H), 1.12 (t, 3-$OCOCH_2CH_3$), 1.18 (t, 4"-$OCOCH_2CH_3$), 1.19 (d, 6'-H), 1.40 (s, 3"-$CH_3$), 1.65 (dd, 2"-Hax), 2.00 (s, 9-$OCOCH_3$), 2.02 (s, 3"-$OCOCH_3$), 2.04 (s, 2'-$OCOCH_3$), 2.21 (s, $NCH_3$), 2.41 (s, 3'-$N(CH_3)_2$), 2.60 (dd, 2-H), 2.60 (dd, 3'-H), 2.76 (s, thiazole-$CH_3$), 2.85 (dd, 2-H), 3.13 (s, $CH(OCH_3)_2$), 3.20 (m, 4'-H), 3.20 (d, 2"-Heq), 3.22 (m, 5'-H), 3.25 (s, $CH(OCH_3)_2$), 3.58 (s, 4-$OCH_3$), 3.63 (d, 4-H), 3.91 (d, 5-H), 4.47 (dq, 5"-H), 4.53 (dd, $CH(OCH_3)_2$), 4.55 (d, 4"-H), 4.68 (d, 1'-H), 4.79 (d, 1"-H), 4.90 (m, 9-H), 4.96 (dd, 2'-H), 5.06 (br t, 3-H), 5.06 (m, 15-H), 6.18 (dt, 15-$CH_2$—CH═CH), 6.47 (d, 15-$CH_2$—CH═CH), 7.31 (m, $C_6H_4$), 7.69 (dt, $C_6H_4$), 7.83 (s, thiazole).

(b) In the same manner as in Example 2(c), 34.8 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(3-(2-methylthiazol-4-yl)phenyl)-2-propenyl group, $R_3$ is acetyl group, $R_4$ is propionyl group, and X is oxygen atom) was obtained from 60.6 mg of the compound of Example 106(a).

Physicochemical Properties of this Compound (1) Molecular formula: $C_{57}H_{89}N_3O_{17}S$ (2) Mass spectrum (FAB): m/z 1020 $(M+H)^+$ (3) $^1H$ NMR spectrum (300 MHz, $CDCl_3$) δ (ppm): 0.86 (d, 8-$CH_3$), 1.07 (d, 6"-H), 1.10 (t, 3-$OCOCH_2CH_3$), 1.18 (t, 4"-$OCOCH_2CH_3$), 1.20 (d, 6'-H), 1.41 (s, 3"-$CH_3$), 1.20 (d, 6'-H), 1.67 (dd, 2"-Hax), 2.00 (s, 3"-$OCOCH_3$), 2.30 (s, $NCH_3$), 2.42 (q, 3-$OCOCH_2CH_3$), 2.45 (q, 4"-$OCOCH_2CH_3$), 2.52 (s, 3'-$N(CH_3)_2$), 2.59 (dd, 2-H), 2.77 (s, thiazole-$CH_3$), 2.79 (dd, 2-H), 3.14 (s, $CH(OCH_3)_2$), 3.17 (t, 4'-H), 3.19 (d, 2"-Heq), 3.22 (m, 5'-H), 3.24 (s, $CH(OCH_3)_2$), 3.48 (dd, 2'-H), 3.62 (s, 4-$OCH_3$), 3.87 (d, 4-H), 3.99 (d, 5-H), 4.44 (d, 1'-H), 4.48 (dd, $CH(OCH_3)_2$), 4.49 (dq, 5"-H), 4.56 (d, 4"-H), 4.82 (d, 1"-H), 5.09 (m, 15-H), 5.47 (m, 3-H), 6.17 (dt, 15-$CH_2$—CH═CH), 6.46 (d, 15-$CH_2$—CH═CH), 7.30 (m, $C_6H_4$), 7.69 (dt, $C_6H_4$), 7.82 (s, thiazole).

(c) In the same manner as in Example 2(d), 29.5 mg of the title compound was obtained from 34.8 mg of the compound of Example 106(b).

Physicochemical Properties of this Compound (1) Molecular formula: $C_{55}H_{83}N_3O_{16}S$ (2) Mass spectrum (FAB): m/z 1074 $(M+H)^+$ (3) Specific rotation: $[\alpha]_D^{15}$ −50° (c1.00, $CHCl_3$)

(4) $^1H$ NMR spectrum (300 MHz, $CDCl_3$) δ (ppm): 0.88 (d, 8-$CH_3$), 1.07 (d, 6"-H), 1.13 (d, 6'-H), 1.15 (t, 3-$OCOCH_2CH_3$), 1.18 (t, 4"-$OCOCH_2CH_3$), 1.40 (s, 3"-$CH_3$), 1.67 (dd, 2"-Hax), 1.99 (s, 3"-$OCOCH_3$), 2.30 (s, $NCH_3$), 2.42 (q, 3-$OCOCH_2CH_3$), 2.42 (q, 4"-$OCOCH_2CH_3$), 2.53 (s, 3'-$N(CH_3)_2$), 2.62 (dd, 2-H), 2.77 (s, thiazole-$CH_3$), 2.87 (dd, 2-H), 3.17 (m, 4'-H), 3.17 (m, 5'-H), 3.21 (d, 2"-Heq), 3.35 (m, 9-H), 3.40 (dd, 2'-H), 3.63 (s, 4-$OCH_3$), 3.85 (d, 4-H), 3.99 (d, 5-H), 4.38 (d, 1'-H), 4.52 (dq, 5"-H), 4.57 (d, 4"-H), 4.82 (d, 1"-H), 5.09 (m, 15-H), 5.56 (m, 3-H), 6.17 (dt, 15-$CH_2$—CH═CH), 6.46 (d, 15-$CH_2$—CH═CH), 7.30 (m, $C_6H_4$), 7.69 (dt, $C_6H_4$), 7.83 (s, thiazole), 9.63 (s, CHO).

Example 107

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(3-biphenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 3-bromobiphenyl was used instead of 4-bromoquinoline, 49.4 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(3-biphenyl)-2-propenyl group, $R_{3''}$ is acetyl group, $R_{4''}$ is propionyl group, and X is oxygen atom) was obtained from 51.7 mg of the compound of Example 90(b).

Physicochemical Properties of this Compound (1) Molecular formula: $C_{63}H_{94}N_2O_{19}$ (2) Mass spectrum (FAB): m/z 1183 $(M+H)^+$ (3) $^1H$ NMR spectrum (300 MHz, $CDCl_3$) δ (ppm): 0.91 (d, 8-$CH_3$), 1.06 (d, 6"-H), 1.12 (t, 3-$OCOCH_2CH_3$), 1.18 (t, 4"-$OCOCH_2CH_3$), 1.19 (d, 6'-H), 1.40 (s, 3"-$CH_3$), 1.60 (m, 6-$CH_2$), 1.66 (dd, 2"-Hax), 1.74 (m, 8-H), 2.00 (s, 3"-$OCOCH_3$), 2.02 (s, 9-$OCOCH_3$), 2.04 (s, 2'-$OCOCH_3$), 2.22 (s, $NCH_3$), 2.42 (s, 3'-$N(CH_3)_2$), 2.60 (t, 3'-H), 2.84 (dd, 2-H), 3.13 (s, $CH(OCH_3)_2$), 3.14 (m, 5'-H), 3.14 (m, 4'-H), 3.24 (s, $CH(OCH_3)_2$), 3.26 (d, 2"-Heq), 3.58 (s, 4-$OCH_3$), 3.60 (br d, 4-H), 3.91 (br d, 5-H), 4.54 (m, $CH(OCH_3)_2$), 4.55 (d, 4"-H), 4.46 (dq, 5"-H), 4.69 (d, 1'-H), 4.79 (d, 1"-H), 4.90 (m, 9-H), 4.96 (dd, 2'-H), 5.06 (m, 3-H), 6.17 (dt, CH═CH), 6.49 (dd, CH═CH), 7.34 (m, biphenyl), 7.42 (m, biphenyl), 7.52 (br s, biphenyl), 7.56 (d, biphenyl).

(b) In the same manner as in Example 2(c), 30.6 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(3-biphenyl)-2-propenyl group, $R_{3''}$ is acetyl group, $R_{4''}$ is propionyl group, and X is oxygen atom) was obtained from 49.4 mg of the compound of Example 107(a).

Physicochemical Properties of this Compound (1) Molecular formula: $C_{59}H_{50}N_2O_{17}$ (2) Mass spectrum (FAB): m/z 1099 $(M+H)^+$ (3) $^1H$ NMR spectrum (300 MHz, $CDCl_3$) δ (ppm): 0.86 (d, 8-$CH_3$), 1.07 (d, 6"-H), 1.10 (t, 3-$OCOCH_2CH_3$), 1.18 (t, 4"-$OCOCH_2CH_3$), 1.19 (d, 6'-H), 1.40 (s, 3"-$CH_3$), 1.40 (m, 8-H), 1.56 (m, 6-$CH_2$), 1.67 (dd, 2"-Hax), 2.00 (s, 3"-$OCOCH_3$), 2.33 (s, $NCH_3$), 2.34 (q, 3-$OCOCH_2CH_3$), 2.43 (q, 4"-$OCOCH_2CH_3$), 2.52 (s, 3'-$N(CH_3)_2$), 2.60 (dd, 2-H), 2.82 (dd, 2-H), 3.14 (s, $CH(OCH_3)_2$), 3.18 (m, 5'-H), 3.24 (m, 4'-H), 3.24 (s, $CH(OCH_3)_2$), 3.44 (d, 2"-Heq), 3.61 (s, 4-$OCH_3$), 3.87 (br d, 4-H), 3.98 (br d, 5-H), 4.46 (m, 1'-H), 4.46 (m, $CH(OCH_3)_2$), 4.56 (dq, 5"-H), 4.81 (d, 1"-H), 5.08 (m, 15-H), 5.46 (m, 9-H), 6.16 (dt, CH═CH), 6.46 (dd, CH═CH), 7.35 (m, biphenyl), 7.42 (m, biphenyl), 7.51 (br s, biphenyl), 7.57 (d, biphenyl).

(c) In the same manner as in Example 2(d), 19.2 mg of the title compound was obtained from 30.6 mg of the compound of Example 107(b).

Physicochemical Properties of this Compound (1) Molecular formula: $C_{57}H_{84}N_2O_{16}$ (2) Mass spectrum (FAB): m/z 1053 $(M+H)^+$ (3) Specific rotation: $[\alpha]_D^{17}$ −42° (c1.0, $CHCl_3$)

(4) $^1H$ NMR spectrum (300 MHz, $CDCl_3$) δ (ppm): 0.89 (d, 8-$CH_3$), 1.08 (d, 6"-H), 1.12 (d, 6'-H), 1.14 (t, 3-$OCOCH_2CH_3$), 1.18 (t, 4"-$OCOCH_2CH_3$), 1.34 (m, 6-H), 1.40 (s, 3"-$CH_3$), 1.67 (dd, 2"-Hax), 2.00 (s, 3"-$OCOCH_3$), 2.34 (s, $NCH_3$), 2.48 (dd, 15-$CH_2$), 2.54 (s, 3'-$N(CH_3)_2$), 2.62 (dd, 2-H), 2.82 (dd, 2-H), 2.89 (dd, 6-$CH_2$), 3.18 (m, 4'-H), 3.18 (m, 5'-H), 3.20 (d, 2"-Heq), 3.39 (dd, 2'-H), 3.61 (s, 4-$OCH_3$), 3.84 (br d, 4-H), 3.98 (br d, 5-H), 4.38 (m, 1'-H), 4.52 (m, 5"-H), 4.58 (d, 4"-H), 4.82 (d, 1"-H), 5.08 (m, 15-H), 5.54 (m, 9-H), 6.16 (dt, CH═CH), 6.47 (dd, CH═CH), 7.34 (m, biphenyl), 7.43 (m, biphenyl), 7.51 (br s, biphenyl), 7.57 (d, biphenyl), 9.64 (s, CHO).

Example 108

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(3-(pyridin-3-yl)phenyl)-2-propenyl group, $R_{4'}$ is a group represented by the formula (a), $R_{3''}$ is acetyl group, $R_{4''}$ is propionyl group; and X is oxygen atom (a) In the same manner as in Example 48(c), except that 3-(3-bromophenyl)pyridine (WO2001038326) was used instead of 4-bromoquinoline, 56.5 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(3-(pyridin-3-yl)phenyl)-2-propenyl group, $R_{3''}$ is acetyl group, $R_{4''}$ is propionyl group, and X is oxygen atom) was obtained from 75.7 mg of the compound of Example 90(b).

Physicochemical Properties of this Compound (1) Molecular formula: $C_{62}H_{93}N_3O_{19}$ (2) Mass spectrum (FAB): m/z 1184 $(M+H)^+$ (3) $^1H$ NMR spectrum (300 MHz, $CDCl_3$) δ (ppm): 0.92 (d, 8-$CH_3$), 1.07 (d, 6"-H), 1.13 (t, 3-$OCOCH_2CH_3$), 1.19 (t, 4"-$OCOCH_2CH_3$), 1.21 (d, 6'-H), 1.52 (m, 13-H), 1.67 (dd, 2"-Hax), 1.75 (m, 8-H), 2.02 (s, 3"-$OCOCH_3$), 2.04 (s, 9-$OCOCH_3$), 2.06 (s, 2'-$OCOCH_3$), 2.23 (s, $NCH_3$), 2.43 (q, 4"-$OCOCH_2CH_3$), 2.43 (s, 3'-$N(CH_3)_2$), 2.62 (dd, 2-H), 2.62 (t, 3'-H), 2.86 (dd, 2-H), 3.14 (t, 4'-H), 3.15 (s, $CH(OCH_3)_2$), 3.19 (d, 2"-Heq), 3.25 (s, $CH(OCH_3)_2$), 3.60 (s, 4-$OCH_3$), 3.93 (d, 5-H), 4.48 (dq, 5"-H), 4.57 (d, 4"-H), 4.70 (d, 1'-H), 4.81 (d, 1"-H), 4.91 (m, 9-H), 4.97 (dd, 2'-H), 5.06 (m, 3-H), 5.11 (m, 15-H), 6.21 (dt, CH═CH), 6.51 (d, CH═CH), 7.35-7.43 (m, pyridine and $C_6H_4$), 7.55 (s, $C_6H_4$), 7.88 (d, pyridine), 8.60 (d, pyridine), 8.84 (s, pyridine).

(b) In the same manner as in Example 73(b), 24.8 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(3-(pyridin-3-yl)phenyl)-2-propenyl group, $R_{3''}$ is acetyl group, $R_{4''}$ is propionyl group, and X is oxygen atom) was obtained from 56.5 mg of the compound of Example 108(a).

Physicochemical Properties of this Compound (1) Molecular formula: $C_{58}H_{89}N_3O_{17}$ (2) Mass spectrum (FAB): m/z 1100 $(M+H)^+$ (3) $^1H$ NMR spectrum (300 MHz, $CDCl_3$) δ (ppm): 0.88 (d, 8-$CH_3$), 1.09 (d, 6"-H), 1.11 (t, 3-$OCOCH_2CH_3$), 1.20 (t, 4"-$OCOCH_2CH_3$), 1.21 (d, 6'-H), 1.42 (s, 3"-$CH_3$), 1.45 (m, 8-H), 1.68 (dd, 2"-Hax), 1.75 (m, 14-H), 1.85 (m, 6-$CH_2$), 2.02 (s, 3"-$OCOCH_3$), 2.32 (q, 3-$OCOCH_2CH_3$), 2.43 (q, 4"-$OCOCH_2CH_3$), 2.54 (s, 3'-$N(CH_3)_2$), 2.61 (dd, 2-H), 2.70 (m, 12-H), 2.82 (dd, 2-H), 3.15 (s, $CH(OCH_3)_2$), 3.17 (t, 4'-H), 3.21 (d, 2"-Heq), 3.25 (s, $CH(OCH_3)_2$), 3.38 (m, 9-H), 3.48 (dd, 2'-H), 3.64 (s, 4-$OCH_3$), 3.88 (d, 4-H), 3.97 (d, 5-H), 4.46 (d, 1'-H), 4.49 (dd, $CH(OCH_3)_2$), 4.59 (d, 4"-H), 4.83 (d, 1"-H), 5.10 (m, 15-H), 5.46 (dd, 3-H), 6.19 (dt, CH═CH), 6.50 (d, CH═CH), 7.35-7.46 (m, pyridine and $C_6H_4$), 7.51 (d, $C_6H_4$), 7.87 (m, pyridine), 8.60 (dd, ptridine), 8.84 (d, pyridine).

(c) In the same manner as in Example 2(d), 20.5 mg of the title compound was obtained from 24.8 mg of the compound of Example 108(b).

Physicochemical Properties of this Compound (1) Molecular formula: $C_{56}H_{83}N_3O_{16}$ (2) Mass spectrum (FAB): m/z 1054 $(M+H)^+$ (3) Specific rotation: $[\alpha]_D^{17}$ −52° (c1.0, $CHCl_3$)

(4) $^1H$ NMR spectrum (300 MHz, $CDCl_3$) δ (ppm): 0.89 (d, 8-$CH_3$), 1.09 (d, 6"-H), 1.14 (d, 6'-H), 1.16 (t, 3-$OCOCH_2CH_3$), 1.19 (t, 4"-$OCOCH_2CH_3$), 1.36 (m, 8-H), 1.42 (s, 3"-$CH_3$), 1.69 (dd, 2"-Hax), 2.01 (s, 3"-$OCOCH_3$), 2.32 (s, $NCH_3$), 2.43 (q, 4"-$OCOCH_2CH_3$), 2.54 (s, 3'-$N(CH_3)_2$), 2.63 (dd, 2-H), 2.69 (m, 12-H), 2.83 (dd, 2-H), 2.90 (dd, 6-$CH_2$), 3.17 (t, 4'-H), 3.21 (d, 2"-Heq), 3.36 (m, 9-H), 3.40 (dd, 2'-H), 3.65 (s, 4-$OCH_3$), 3.86 (d, 4-H), 3.99 (d, 5-H), 4.39 (d, 1'-H), 4.53 (dq, 5"-H), 4.59 (d, 4"-H), 4.84 (d, 1"-H), 5.10 (m, 15-H), 5.57 (dd, 3-H), 6.19 (dt, CH═CH), 6.50 (d, CH═CH), 7.35-7.47 (m, pyridine and $C_6H_4$), 7.51 (s, $C_6H_4$), 7.87 (m, pyridine), 8.60 (dd, pyridine), 8.84 (d, pyridine), 9.65 (s, CHO).

Example 109

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(3-(pyridin-4-yl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that the compound of Reference Example 25 was used instead of 4-bromoquinoline, 76.5 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(3-(pyridin-4-yl)phenyl)-2-propenyl group, $R_{3''}$ is acetyl group, $R_{4''}$ is propionyl group, and X is oxygen atom) was obtained from 75.5 mg of the compound of Example 90(b).

Physicochemical Properties of this Compound (1) Molecular formula: $C_{62}H_{93}N_3O_{19}$ (2) Mass spectrum (FAB): m/z 1184 $(M+H)^+$ (3) $^1H$ NMR spectrum (300 MHz, $CDCl_3$) δ (ppm): 0.92 (d, 8-$CH_3$), 1.07 (d, 6"-H), 1.13 (t, 3-$OCOCH_2CH_3$), 1.20 (t, 4"-$OCOCH_2CH_3$), 1.21 (d, 6'-H), 1.41 (s, 3"-$CH_3$), 1.51 (m, 13-H), 1.67 (dd, 2"-Hax), 2.02 (s, 3"-$OCOCH_3$), 2.04 (s, 9-$OCOCH_3$), 2.06 (s, 2'-$OCOCH_3$), 2.23 (s, $NCH_3$), 2.34 (q, 3-$OCOCH_2CH_3$), 2.43 (q, 4"-$OCOCH_2CH_3$), 2.44 (s, 3'-N $(CH_3)_2$), 2.62 (t, 3'-H), 2.62 (dd, 2-H), 2.86 (dd, 2-H), 3.14 (t, 4'-H), 3.15 (s, $CH(OCH_3)_2$), 3.19 (d, 2"-Heq), 3.25 (s, $CH(OCH_3)_2$), 3.60 (s, 4-$OCH_3$), 3.61 (d, 4-H), 3.93 (d, 5-H), 4.48 (dq, 5"-H), 4.57 (d, 4"-H), 4.70 (d, 1'-H), 4.81 (d, 1"-H), 4.91 (m, 9-H), 4.98 (dd, 2'-H), 5.07 (m, 3-H), 5.11 (m, 15-H), 6.22 (dt, CH═CH), 6.52 (d, CH═CH), 7.41-7.52 (m, pyridine and $C_6H_4$), 7.58 (s, $C_6H_4$), 8.66 (d, pyridine).

(b) In the same manner as in Example 73(b), 26.4 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(3-(pyridin-4-yl)phenyl)-2-propenyl group, $R_{3''}$ is acetyl group, $R_{4''}$ is propionyl group, and X is oxygen atom) was obtained from 76.5 mg of the compound of Example 109(a).

Physicochemical Properties of this Compound (1) Molecular formula: $C_{58}H_{89}N_3O_{17}$ (2) Mass spectrum (FAB): m/z 1100 $(M+H)^+$ (3) $^1H$ NMR spectrum (300 MHz, $CDCl_3$) δ (ppm): 0.88 (d, 8-$CH_3$), 1.09 (d, 6"-H), 1.10 (t, 3-$OCOCH_2CH_3$), 1.20 (t, 4"-$OCOCH_2CH_3$), 1.21 (d, 6'-H), 1.42 (s, 3"-$CH_3$), 1.45 (m, 8-H), 1.68 (dd, 2"-Hax), 2.02 (s, 3"-$OCOCH_3$), 2.34 (s, $NCH_3$), 2.43 (q, 4"-$OCOCH_2CH_3$), 2.54 (s, 3'-$N(CH_3)_2$), 2.62 (dd, 2-H), 2.81 (dd, 2-H), 3.15 (s, $CH(OCH_3)_2$), 3.17 (t, 4'-H), 3.21 (d, 2"-Heq), 3.25 (s, $CH(OCH_3)_2$), 3.48 (dd, 2'-H), 3.64 (s, 4-$OCH_3$), 3.88 (d, 4-H), 3.97 (d, 5-H), 4.46 (d, 1'-H), 4.49 (dd, $CH(OCH_3)_2$), 4.52 (d, 4"-H), 4.84 (d, 1"-H), 5.10 (m, 15-H), 5.47 (m, 3-H), 6.20 (dt, CH═CH), 6.49 (d, CH═CH), 7.40-7.51 (m, pyridine and $C_6H_4$), 7.56 (s, $C_6H_4$), 8.66 (m, pyridine).

(c) In the same manner as in Example 2(d), 17.1 mg of the title compound was obtained from 26.4 mg of the compound of Example 109(b).

Physicochemical Properties of this Compound (1) Molecular formula: $C_{56}H_{83}N_3O_{16}$ (2) Mass spectrum (FAB): m/z 1054 $(M+H)^+$ (3) Specific rotation: $[\alpha]_D^{18}$ −52° (c0.86, $CHCl_3$)

(4) $^1H$ NMR spectrum (300 MHz, $CDCl_3$) δ (ppm): 0.89 (d, 8-$CH_3$), 1.09 (d, 6"-H), 1.14 (d, 6'-H), 1.16 (t, 3-$OCOCH_2CH_3$), 1.19 (t, 4"-$OCOCH_2CH_3$), 1.36 (m, 8-H), 1.42 (s, 3"-$CH_3$), 1.69 (dd, 2"-Hax), 2.01 (s, 3"-$OCOCH_3$), 2.32 (s, $NCH_3$), 2.43 (q, 4"-$OCOCH_2CH_3$), 2.54 (s, 3'-N $(CH_3)_2$), 2.64 (dd, 2-H), 2.83 (dd, 2-H), 2.90 (dd, 6-$CH_2$), 3.17 (t, 4'-H), 3.21 (d, 2"-Heq), 3.40 (dd, 2'-H), 3.65 (s, 4-$OCH_3$), 3.86 (d, 4-H), 3.98 (d, 5-H), 4.39 (d, 1'-H), 4.52 (dq, 5"-H), 4.58 (d, 4"-H), 4.84 (d, 1"-H), 5.10 (m, 15-H), 5.57 (m, 3-H), 6.20 (dt, CH═CH), 6.50 (d, CH═CH), 7.39-7.51 (m, pyridine and $C_6H_4$), 7.57 (s, $C_6H_4$), 8.66 (m, pyridine), 9.65 (s, CHO).

Example 110

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(3-(1H-imidazol-1-yl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that the compound of Reference Example 26 was used instead of 4-bromoquinoline, 17.0 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(3-(1H-imidazol-1-yl) phenyl)-2-propenyl group, $R_{3''}$ is acetyl group, $R_{4''}$ is propionyl group, and X is oxygen atom) was obtained from 75.1 mg of the compound of Example 90 (b).

Physicochemical Properties of this Compound (1) Molecular formula: $C_{60}H_{92}N_4O_{19}$ (2) Mass spectrum (FAB): m/z 1173 $(M+H)^+$ (3) $^1H$ NMR spectrum (300 MHz, $CDCl_3$) δ (ppm): 0.92 (d, 8-$CH_3$), 1.07 (d, 6"-H), 1.13 (t, 3-$OCOCH_2CH_3$), 1.19 (t, 4"-$OCOCH_2CH_3$), 1.21 (d, 6'-H), 1.42 (s, 3"-$CH_3$), 1.67 (dd, 2"-Hax), 2.02 (s, 3"-$OCOCH_3$), 2.04 (s, 9-$OCOCH_3$), 2.05 (s, 2'-$OCOCH_3$), 2.23 (s, $NCH_3$), 2.43 (q, 4"-$OCOCH_2CH_3$), 2.43 (s, 3'-$N(CH_3)_2$), 2.62 (dd, 2-H), 2.62 (t, 3'-H), 2.86 (dd, 2-H), 3.14 (s, $CH(OCH_3)_2$), 3.14 (t, 4'-H), 3.19 (d, 2"-Heq), 3.25 (s, $CH(OCH_3)_2$), 3.59 (d, 4-H), 3.60 (s, 4-$OCH_3$), 3.94 (d, 5-H), 4.48 (dq, 5"-H), 4.57 (d, 4"-H), 4.70 (d, 1'-H), 4.81 (d, 1"-H), 4.91 (m, 9-H), 4.97 (dd, 2'-H), 5.07 (m, 3-H), 5.10 (m, 15-H), 6.22 (dt, CH═CH), 6.48 (d, CH═CH), 7.19-7.45 (m, imidazole and $C_6H_4$), 7.88 (s, imidazole).

(b) In the same manner as in Example 73(b), 6.2 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(3-(1H-imidazol-1-yl)phenyl)-2-propenyl group, $R_{3''}$ is acetyl group, $R_{4''}$ is propionyl group, and X is oxygen atom) was obtained from 17.0 mg of the compound of Example 110(a).

Physicochemical Properties of this Compound (1) Molecular formula: $C_{56}H_{88}N_4O_{17}$ (2) Mass spectrum (FAB): m/z 1089 $(M+H)^+$ (3) $^1H$ NMR spectrum (300 MHz, $CDCl_3$) δ (ppm): 0.89 (d, 8-$CH_3$), 1.09 (d, 6"-H), 1.11 (t, 3-$OCOCH_2CH_3$), 1.20 (t, 4"-$OCOCH_2CH_3$), 1.21 (d, 6'-H), 1.42 (s, 3"-$CH_3$), 1.69 (dd, 2"-Hax), 1.87 (m, 6-$CH_2$), 2.02 (s, 3"-$OCOCH_3$), 2.35 (q, 3-$OCOCH_2CH_3$), 2.37 (s, $NCH_3$), 2.43 (q, 4"-$OCOCH_2CH_3$), 2.54 (s, 3'-$N(CH_3)_2$), 2.61 (dd, 2-H), 2.82 (dd, 2-H), 3.15 (s, $CH(OCH_3)_2$), 3.21 (d, 2"-Heq), 3.25 (s, $CH(OCH_3)_2$), 3.42 (m, 9-H), 3.47 (dd, 2'-H), 3.65 (s, 4-$OCH_3$), 3.88 (d, 4-H), 3.96 (d, 5-H), 4.47 (d, 1'-H), 4.59 (d, 4"-H), 4.84 (d, 1"-H), 5.09 (m, 15-H), 5.45 (m, 3-H), 6.20 (dt, CH═CH), 6.46 (d, CH═CH), 7.21-7.43 (m, imidazole and $C_6H_4$), 7.87 (s, imidazole).

(c) In the same manner as in Example 2(d), 5.37 mg of the title compound was obtained from 6.2 mg of the compound of Example 110(b).

Physicochemical Properties of this Compound (1) Molecular formula: $C_{54}H_{82}N_4O_{16}$ (2) Mass spectrum (FAB): m/z 1043 $(M+H)^+$ (3) Specific rotation: $[\alpha]_D^{17}$ −51° (c0.27, $CHCl_3$)

(4) $^1H$ NMR spectrum (300 MHz, $CDCl_3$) δ (ppm): 0.90 (d, 8-$CH_3$), 1.09 (d, 6"-H), 1.16 (d, 6'-H), 1.16 (t, 3-$OCOCH_2CH_3$), 1.19 (t, 4"-$OCOCH_2CH_3$), 1.42 (s, 3"-$CH_3$), 1.69 (dd, 2"-Hax), 2.01 (s, 3"-$OCOCH_3$), 2.35 (s, $NCH_3$), 2.43 (q, 4"-$OCOCH_2CH_3$), 2.54 (s, 3'-$N(CH_3)_2$), 2.64 (dd, 2-H), 2.83 (dd, 2-H), 2.90 (dd, 6-$CH_2$), 3.18 (t, 4'-H), 3.21 (d, 2"-Heq), 3.39 (dd, 2'-H), 3.65 (s, 4-$OCH_3$), 3.86 (d, 4-H), 3.96 (d, 5-H), 4.40 (d, 1'-H), 4.52 (dq, 5"-H), 4.58 (d, 4"-H), 4.84 (d, 1"-H), 5.09 (m, 15-H), 5.50 (m, 3-H), 6.20 (dt, CH═CH), 6.46 (d, CH═CH), 7.21-7.45 (m, imidazole and $C_6H_4$), 7.86 (s, imidazole), 9.65 (s, CHO).

Example 111

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(3-(pyrimidin-5-yl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that the compound of Reference Example 27 was used instead of 4-bromoquinoline, 69.9 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(3-(pyrimidin-5-yl)phenyl)-2-propenyl group, $R_{3''}$ is acetyl group, $R_{4''}$ is propionyl group, and X is oxygen atom) was obtained from 74.8 mg of the compound of Example 90 (b).

Physicochemical Properties of this Compound (1) Molecular formula: $C_{61}H_{92}N_4O_{19}$ (2) Mass spectrum (FAB): m/z 1185 $(M+H)^+$ (3) $^1H$ NMR spectrum (300 MHz, $CDCl_3$) δ (ppm): 0.92 (d, 8-$CH_3$), 1.07 (d, 6"-H), 1.13 (t, 3-$OCOCH_2CH_3$), 1.20 (t, 4"-$OCOCH_2CH_3$), 1.21 (d, 6'-H), 1.42 (s, 3"-$CH_3$), 1.52 (m, 13-H), 1.68 (dd, 2"-Hax), 1.76 (m, 8-H), 2.02 (s, 3"-$OCOCH_3$), 2.04 (s, 9-$OCOCH_3$), 2.06 (s, 2'-$OCOCH_3$), 2.24 (s, $NCH_3$), 2.43 (q, 4"-$OCOCH_2CH_3$), 2.44 (s, 3'-N$(CH_3)_2$), 2.62 (dd, 2-H), 2.62 (t, 3'-H), 2.86 (dd, 2-H), 3.15 (s, $CH(OCH_3)_2$), 3.15 (t, 4'-H), 3.19 (d, 2"-Heq), 3.25 (s, $CH(OCH_3)_2$), 3.60 (s, 4-$OCH_3$), 3.61 (d, 4-H), 3.94 (d, 5-H), 4.49 (dq, 5"-H), 4.57 (d, 4"-H), 4.70 (d, 1'-H), 4.81 (d, 1"-H), 4.92 (m, 9-H), 4.98 (dd, 2'-H), 5.07 (m, 3-H), 5.12 (m, 15-H), 6.24 (dt, CH═CH), 6.52 (d, CH═CH), 7.45 (m, $C_6H_4$), 7.53 (s, $C_6H_4$), 8.96 (s, pyrimidine), 9.21 (s, pyrimidine).

(b) In the same manner as in Example 73(b), 43.7 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(3-(pyrimidin-5-yl)phenyl)-2-propenyl group, $R_{3''}$ is acetyl group, $R_{4''}$ is propionyl group, and X is oxygen atom) was obtained from 69.9 mg of the compound of Example 111(a).

Physicochemical Properties of this Compound (1) Molecular formula: $C_{57}H_{88}N_4O_{17}$ (2) Mass spectrum (FAB): m/z 1101 $(M+H)^+$ (3) $^1H$ NMR spectrum (300 MHz, $CDCl_3$) δ (ppm): 0.88 (d, 8-$CH_3$), 1.09 (d, 6"-H), 1.11 (t, 3-$OCOCH_2CH_3$), 1.20 (t, 4"-$OCOCH_2CH_3$), 1.21 (d, 6'-H), 1.42 (s, 3"-$CH_3$), 1.69 (dd, 2"-Hax), 2.02 (s, 3"-$OCOCH_3$), 2.35 (q, 3-$OCOCH_2CH_3$), 2.36 (s, $NCH_3$), 2.43 (q, 4"-$OCOCH_2CH_3$), 2.54 (s, 3'-N$(CH_3)_2$), 2.62 (dd, 2-H), 2.70 (m, 12-H), 2.82 (dd, 2-H), 3.15 (s, $CH(OCH_3)_2$), 3.21 (d, 2"-Heq), 3.25 (s, $CH(OCH_3)_2$), 3.38 (m, 9-H), 3.48 (dd, 2'-H), 3.64 (s, 4-$OCH_3$), 3.88 (d, 4-H), 3.96 (d, 5-H), 4.46 (d, 1'-H), 4.49 (dd, $CH(OCH_3)_2$), 4.59 (d, 4"-H), 4.84 (d, 1"-H), 5.10 (m, 15-H), 5.46 (m, 3-H), 6.21 (dt, CH═CH), 6.50 (d, CH═CH), 7.44 (m, $C_6H_4$), 7.50 (s, $C_6H_4$), 8.95 (s, pyrimidine), 9.22 (s, pyrimidine).

(c) In the same manner as in Example 2(d), 33.7 mg of the title compound was obtained from 43.7 mg of the compound of Example 111(b).

Physicochemical Properties of this Compound (1) Molecular formula: $C_{55}H_{82}N_4O_{16}$ (2) Mass spectrum (FAB): m/z 1055 $(M+H)^+$ (3) Specific rotation: $[\alpha]_D^{18}$ −52° (c0.51, $CHCl_3$)

(4) $^1H$ NMR spectrum (300 MHz, $CDCl_3$) δ (ppm): 0.90 (d, 8-$CH_3$), 1.09 (d, 6"-H), 1.14 (d, 6'-H), 1.16 (t, 3-$OCOCH_2CH_3$), 1.20 (t, 4"-$OCOCH_2CH_3$), 1.37 (m, 8-H), 1.42 (s, 3"-$CH_3$), 1.69 (dd, 2"-Hax), 2.01 (s, 3"-$OCOCH_3$), 2.35 (s, $NCH_3$), 2.43 (q, 4"-$OCOCH_2CH_3$), 2.55 (s, 3'-N$(CH_3)_2$), 2.64 (dd, 2-H), 2.83 (dd, 2-H), 2.90 (dd, 6-$CH_2$), 3.18 (t, 4'-H), 3.21 (d, 2"-Heq), 3.40 (dd, 2'-H), 3.65 (s, 4-$OCH_3$), 3.86 (d, 4-H), 3.97 (d, 5-H), 4.40 (d, 1'-H), 4.52 (dq, 5"-H), 4.59 (d, 4"-H), 4.84 (d, 1"-H), 5.11 (m, 15-H), 5.56 (m, 3-H), 6.21 (dt, CH═CH), 6.50 (d, CH═CH), 7.44 (m, $C_6H_4$), 7.50 (s, $C_6H_4$), 8.95 (s, pyrimidine), 9.22 (s, pyrimidine), 9.65 (s, CHO).

Example 112

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(5-phenylpyridin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 3-bromo-5-phenylpyridine (Bioorg. & Med. Chem. Lett. 2003, 13, 2825-2828) was used instead of 4-bromoquinoline, 55.7 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(5-phenylpyridin-3-yl)-2-propenyl group, $R_{3''}$ is acetyl group, $R_{4''}$ is propionyl group, and X is oxygen atom) was obtained from 70.2 mg of the compound of Example 90(b).

Physicochemical Properties of this Compound (1) Molecular formula: $C_{62}H_{93}N_3O_{19}$ (2) Mass spectrum (FAB): m/z 1184 $(M+H)^+$ (3) $^1H$ NMR spectrum (300 MHz, $CDCl_3$) δ (ppm): 0.92 (d, 8-$CH_3$), 1.07 (d, 6"-H), 1.13 (t, 3-$OCOCH_2CH_3$), 1.19 (t, 4"-$OCOCH_2CH_3$), 1.21 (d, 6'-H), 1.41 (s, 3"-$CH_3$), 1.52 (m, 13-H), 1.67 (dd, 2"-Hax), 2.02 (s, 3"-$OCOCH_3$), 2.03 (s, 9-$OCOCH_3$), 2.05 (s, 2'-$OCOCH_3$), 2.23 (s, $NCH_3$), 2.34 (q, 3-$OCOCH_2CH_3$), 2.43 (q, 4"-$OCOCH_2CH_3$), 2.43 (s, 3'-N$(CH_3)_2$), 2.62 (dd, 2-H), 2.62 (t, 3'-H), 2.86 (dd, 2-H), 3.14 (s, $CH(OCH_3)_2$), 3.19 (d, 2"-Heq), 3.25 (s, $CH(OCH_3)_2$), 3.60 (s, 4-$OCH_3$), 3.61 (d, 4-H), 3.93 (d, 5-H), 4.48 (dq, 5"-H), 4.57 (d, 4"-H), 4.70 (d, 1'-H), 4.81 (d, 1"-H), 4.91 (m, 9-H), 4.97 (dd, 2'-H), 5.06 (m, 3-H), 5.12 (m, 15-H), 6.29 (dt, CH═CH), 6.51 (d, CH═CH), 7.39-7.51 (m, $C_6H_5$), 7.58-7.61 (m, $C_6H_5$), 7.83 (t, pyridine), 8.53 (d, pyridine), 8.67 (d, pyridine).

(b) In the same manner as in Example 73(b), 18.4 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(5-phenylpyridin-3-yl)-2-propenyl group, $R_{3''}$ is acetyl group, $R_{4''}$ is propionyl group, and X is oxygen atom) was obtained from 55.7 mg of the compound of Example 112(a).

Physicochemical Properties of this Compound (1) Molecular formula: $C_{58}H_{89}N_3O_{17}$ (2) Mass spectrum (FAB): m/z 1100 $(M+H)^+$ (3) $^1H$ NMR spectrum (300 MHz, $CDCl_3$) δ (ppm): 0.88 (d, 8-$CH_3$), 1.09 (d, 6"-H), 1.11 (t, 3-$OCOCH_2CH_3$), 1.20 (t, 4"-$OCOCH_2CH_3$), 1.21 (d, 6'-H), 1.42 (s, 3"-$CH_3$), 1.68 (dd, 2"-Hax), 2.02 (s, 3"-$OCOCH_3$), 2.35 (s, $NCH_3$), 2.43 (q, 4"-$OCOCH_2CH_3$), 2.54 (s, 3'-$N(CH_3)_2$), 2.61 (dd, 2-H), 2.70 (m, 12-H), 2.82 (dd, 2-H), 3.15 (s, $CH(OCH_3)_2$), 3.17 (t, 4'-H), 3.21 (d, 2"-Heq), 3.25 (s, $CH(OCH_3)_2$), 3.34 (m, 9-H), 3.48 (dd, 2'-H), 3.64 (s, 4-$OCH_3$), 3.88 (d, 4-H), 3.97 (d, 5-H), 4.46 (d, 1'-H), 4.49 (dd, $CH(OCH_3)_2$), 4.59 (d, 4"-H), 4.83 (d, 1"-H), 5.11 (m, 15-H), 5.47 (m, 3-H), 6.27 (dt, CH═CH), 6.49 (d, CH═CH), 7.39-7.51 (m, $C_6H_5$), 7.56-7.60 (m, $C_6H_5$), 7.81 (t, pyridine), 8.52 (d, pyridine), 8.68 (d, pyridine).

(c) In the same manner as in Example 2(d), 15.3 mg of the title compound was obtained from 18.4 mg of the compound of Example 112(b).

Physicochemical Properties of this Compound (1) Molecular formula: $C_{56}H_{83}N_3O_{17}$ (2) Mass spectrum (FAB): m/z 1054 $(M+H)^+$ (3) Specific rotation: $[\alpha]_D^{18}$ −51° (c0.77, $CHCl_3$)

(4) $^1H$ NMR spectrum (300 MHz, $CDCl_3$) δ (ppm): 0.90 (d, 8-$CH_3$), 1.09 (d, 6"-H), 1.14 (d, 6'-H), 1.16 (t, 3-$OCOCH_2CH_3$), 1.19 (t, 4"-$OCOCH_2CH_3$), 1.35 (m, 8-H), 1.42 (s, 3"-$CH_3$), 1.69 (dd, 2"-Hax), 2.01 (s, 3"-$OCOCH_3$), 2.34 (s, $NCH_3$), 2.43 (q, 4"-$OCOCH_2CH_3$), 2.54 (s, 3'-$N(CH_3)_2$), 2.64 (dd, 2-H), 2.84 (dd, 2-H), 2.90 (dd, 6-$CH_2$), 3.17 (t, 4'-H), 3.21 (d, 2"-Heq), 3.40 (dd, 2'-H), 3.66 (s, 4-$OCH_3$), 3.86 (d, 4-H), 3.97 (d, 5-H), 4.40 (d, 1'-H), 4.53 (dq, 5"-H), 4.58 (d, 4"-H), 4.84 (d, 1"-H), 5.10 (m, 15-H), 5.55 (m, 3-H), 6.27 (dt, CH═CH), 6.49 (d, CH═CH), 7.39-7.51 (m, $C_6H_5$), 7.56-7.60 (m, $C_6H_5$), 7.81 (t, pyridine), 8.52 (d, pyridine), 8.68 (d, pyridine), 9.65 (s, CHO).

Example 113

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(3-(1H-1,2,4-triazol-1-yl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 1-(3-bromophenyl)-1H-1,2,4-triazole (WO2002038568) was used instead of 4-bromoquinoline, 47.1 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(3-(1H-1,2,4-triazol-1-yl)phenyl)-2-propenyl group, $R_{3''}$ is acetyl group, $R_{4''}$ is propionyl group, and X is oxygen atom) was obtained from 75.2 mg of the compound of Example 90(b).

Physicochemical Properties of this Compound (1) Molecular formula: $C_{59}H_{91}N_5O_{19}$ (2) Mass spectrum (FAB): m/z 1174 $(M+H)^+$ (3) $^1H$ NMR spectrum (300 MHz, $CDCl_3$) δ (ppm): 0.92 (d, 8-$CH_3$), 1.07 (d, 6"-H), 1.14 (t, 3-$OCOCH_2CH_3$), 1.20 (t, 4"-$OCOCH_2CH_3$), 1.21 (d, 6'-H), 1.42 (s, 3"-$CH_3$), 1.68 (dd, 2"-Hax), 2.02 (s, 3"-$OCOCH_3$), 2.04 (s, 9-$OCOCH_3$), 2.05 (s, 2'-$OCOCH_3$), 2.24 (s, $NCH_3$), 2.36 (q, 3-$OCOCH_2CH_3$), 2.43 (q, 4"-$OCOCH_2CH_3$), 2.44 (s, 3'-$N(CH_3)_2$), 2.62 (dd, 2-H), 2.62 (t, 3'-H), 2.87 (dd, 2-H), 3.14 (s, $CH(OCH_3)_2$), 3.15 (t, 4'-H), 3.19 (d, 2"-Heq), 3.25 (s, $CH(OCH_3)_2$), 3.59 (d, 4-H), 3.60 (s, 4-$OCH_3$), 3.94 (d, 5-H), 4.47 (dq, 5"-H), 4.57 (d, 4"-H), 4.70 (d, 1'-H), 4.81 (d, 1"-H), 4.91 (m, 9-H), 4.98 (dd, 2'-H), 5.08 (m, 3-H), 5.11 (m, 15-H), 6.26 (dt, CH═CH), 6.50 (d, CH═CH), 7.36 (d, $C_6H_4$), 7.43 (t, $C_6H_4$), 7.52 (d, $C_6H_4$), 7.68 (s, $C_6H_4$), 8.11 (s, triazole), 8.61 (s, triazole).

(b) In the same manner as in Example 73(b), 15.0 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(3-(1H-1,2,4-triazol-1-yl)phenyl)-2-propenyl group, $R_{3''}$ is acetyl group, $R_{4''}$ is propionyl group, and X is oxygen atom) was obtained from 47.1 mg of the compound of Example 113(a).

Physicochemical Properties of this Compound (1) Molecular formula: $C_{55}H_{87}N_5O_{17}$ (2) Mass spectrum (FAB): m/z 1090 $(M+H)^+$ (3) $^1H$ NMR spectrum (300 MHz, $CDCl_3$) δ (ppm): 0.88 (d, 8-$CH_3$), 1.09 (d, 6"-H), 1.11 (t, 3-$OCOCH_2CH_3$), 1.20 (t, 4"-$OCOCH_2CH_3$), 1.21 (d, 6'-H), 1.42 (s, 3"-$CH_3$), 1.68 (dd, 2"-Hax), 2.02 (s, 3"-$OCOCH_3$), 2.34 (s, $NCH_3$), 2.43 (q, 4"-$OCOCH_2CH_3$), 2.54 (s, 3'-$N(CH_3)_2$), 2.61 (dd, 2-H), 2.68 (m, 12-H), 2.82 (dd, 2-H), 3.15 (s, $CH(OCH_3)_2$), 3.17 (t, 4'-H), 3.20 (d, 2"-Heq), 3.25 (s, $CH(OCH_3)_2$), 3.35 (m, 9-H), 3.48 (dd, 2'-H), 3.65 (s, 4-$OCH_3$), 3.88 (d, 4-H), 3.97 (d, 5-H), 4.46 (d, 1'-H), 4.50 (dd, $CH(OCH_3)_2$), 4.59 (d, 4"-H), 4.84 (d, 1"-H), 5.10 (m, 15-H), 5.47 (dd, 3-H), 6.25 (dt, CH═CH), 6.48 (d, CH═CH), 7.35 (m, $C_6H_4$), 7.43 (t, $C_6H_4$), 7.51 (m, $C_6H_4$), 7.65 (s, $C_6H_4$), 8.11 (s, triazole), 8.57 (s, triazole).

(c) In the same manner as in Example 2(d), 8.7 mg of the title compound was obtained from 15.0 mg of the compound of Example 113(b).

Physicochemical Properties of this Compound (1) Molecular formula: $C_{53}H_{81}N_5O_{16}$ (2) Mass spectrum (FAB): m/z 1044 $(M+H)^+$ (3) Specific rotation: $[\alpha]_D^{19}$ −60° (c0.44, $CHCl_3$)

(4) $^1H$ NMR spectrum (300 MHz, $CDCl_3$) δ (ppm): 0.90 (d, 8-$CH_3$), 1.09 (d, 6"-H), 1.14 (d, 6'-H), 1.16 (t, 3-$OCOCH_2CH_3$), 1.19 (t, 4"-$OCOCH_2CH_3$), 1.37 (m, 8-H), 1.42 (s, 3"-$CH_3$), 1.69 (dd, 2"-Hax), 2.01 (s, 3"-$OCOCH_3$), 2.35 (s, $NCH_3$), 2.43 (q, 4"-$OCOCH_2CH_3$), 2.54 (s, 3'-$N(CH_3)_2$), 2.84 (dd, 2-H), 2.90 (dd, 6-$CH_2$), 3.18 (t, 4'-H), 3.21 (d, 2"-Heq), 3.40 (dd, 2'-H), 3.65 (s, 4-$OCH_3$), 3.86 (d, 4-H), 3.96 (d, 5-H), 4.40 (d, 1'-H), 4.52 (dq, 5"-H), 4.58 (d, 4"-H), 4.84 (d, 1"-H), 5.09 (m, 15-H), 5.55 (m, 3-H), 6.23 (dt, CH═CH), 6.48 (d, CH═CH), 7.35 (m, $C_6H_4$), 7.43 (t, $C_6H_4$), 7.51 (d, $C_6H_4$), 7.66 (s, $C_6H_4$), 8.11 (s, triazole), 8.57 (s, triazole), 9.65 (s, CHO).

Example 114

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(3-(pyridin-2-yl)phenyl)-2-propenyl group, $R_{4'}$ is a group represented by the formula (a), $R_{3''}$ is acetyl group, $R_{4'}$ is propionyl group, and X is oxygen atom (a) In the same manner as in Example 48(c), except that the compound of Reference Example 28 was used instead of 4-bromoquinoline, 45.1 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(3-(pyridin-2-yl)phenyl)-2-propenyl group, $R_{3''}$ is acetyl group, $R_{4''}$ is propionyl group, and X is oxygen atom) was obtained from 75.2 mg of the compound of Example 90(b).

Physicochemical Properties of this Compound (1) Molecular formula: $C_{62}H_{93}N_3O_{19}$ (2) Mass spectrum (FAB): m/z 1184 $(M+H)^+$ (3) $^1H$ NMR spectrum (300 MHz, $CDCl_3$) δ (ppm): 0.92 (d, 8-$CH_3$), 1.07 (d, 6"-H), 1.13 (t, 3-$OCOCH_2CH_3$), 1.19 (t, 4"-$OCOCH_2CH_3$), 1.20 (d, 6'-H), 1.41 (s, 3"-$CH_3$), 1.67 (dd, 2"-Hax), 1.76 (m, 8-H), 2.02 (s, 3"-$OCOCH_3$), 2.03 (s, 9-$OCOCH_3$), 2.06 (s, 2'-$OCOCH_3$), 2.23 (s, $NCH_3$), 2.34 (q, 3-$OCOCH_2CH_3$), 2.43 (q, 4"-$OCOCH_2CH_3$), 2.43 (s, 3'-N$(CH_3)_2$), 2.62 (t, 3'-H), 2.86 (dd, 2-H), 3.14 (t, 4'-H), 3.15 (s, $CH(OCH_3)_2$), 3.19 (d, 2"-Heq), 3.25 (s, $CH(OCH_3)_2$), 3.60 (s, 4-$OCH_3$), 3.65 (d, 4-H), 3.92 (d, 5-H), 4.48 (dq, 5"-H), 4.57 (d, 4"-H), 4.70 (d, 1'-H), 4.81 (d, 1"-H), 4.91 (m, 9-H), 4.97 (dd, 2'-H), 5.06 (m, 3-H), 5.10 (m, 15-H), 6.22 (dt, CH═CH), 6.53 (d, CH═CH), 7.24 (ddd, pyridine), 7.40 (m, $C_6H_4$), 7.74 (m, pyridine), 7.81 (m, $C_6H_4$), 7.96 (s, $C_6H_4$), 8.70 (m, pyridine).

(b) In the same manner as in Example 73(b), 18.5 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(3-(pyridin-2-yl)phenyl)-2-propenyl group, $R_{3''}$ is acetyl group, $R_{4''}$ is propionyl group, and X is oxygen atom) was obtained from 45.1 mg of the compound of Example 114(a).

Physicochemical Properties of this Compound (1) Molecular formula: $C_{58}H_{89}N_3O_{17}$ (2) Mass spectrum (FAB): m/z 1100 $(M+H)^+$ (3) $^1H$ NMR spectrum (300 MHz, $CDCl_3$) δ (ppm): 0.89 (d, 8-$CH_3$), 1.08 (d, 6"-H), 1.11 (t, 3-$OCOCH_2CH_3$), 1.20 (t, 4"-$OCOCH_2CH_3$), 1.21 (d, 6'-H), 1.42 (s, 3"-$CH_3$), 1.44 (m, 8-H), 1.68 (dd, 2"-Hax), 1.74 (m, 14-H), 1.90 (m, 6-$CH_2$), 2.01 (s, 3"-$OCOCH_3$), 2.30 (dq, 3-$OCOCH_2CH_3$), 2.36 (s, $NCH_3$), 2.43 (q, 4"-$OCOCH_2CH_3$), 2.53 (s, 3'-N$(CH_3)_2$), 2.61 (dd, 2-H), 2.73 (m, 12-H), 2.82 (dd, 2-H), 3.16 (s, $CH(OCH_3)_2$), 3.21 (d, 2"-Heq), 3.25 (s, $CH(OCH_3)_2$), 3.40 (m, 9-H), 3.48 (dd, 2'-H), 3.63 (s, 4-$OCH_3$), 3.87 (d, 4-H), 3.99 (d, 5-H), 4.46 (d, 1'-H), 4.49 (dd, $CH(OCH_3)_2$), 4.59 (d, 4"-H), 4.83 (d, 1"-H), 5.11 (m, 15-H), 5.45 (d, 3-H), 6.21 (dt, CH═CH), 6.51 (d, CH═CH), 7.24 (ddd, pyridine), 7.39 (m, $C_6H_4$), 7.74 (m, pyridine), 7.81 (m, $C_6H_4$), 7.96 (s, $C_6H_4$), 8.70 (m, pyridine).

(c) In the same manner as in Example 2(d), 15.0 mg of the title compound was obtained from 18.5 mg of the compound of Example 114(b).

Physicochemical Properties of this Compound (1) Molecular formula: $C_{56}H_{83}N_3O_{16}$ (2) Mass spectrum (FAB): m/z 1054 $(M+H)^+$ (3) Specific rotation: $[\alpha]_D^{19}$ −52° (c0.75, $CHCl_3$)

(4) $^1H$ NMR spectrum (300 MHz, $CDCl_3$) δ (ppm): 0.90 (d, 8-$CH_3$), 1.09 (d, 6"-H), 1.14 (d, 6'-H), 1.16 (t, 3-$OCOCH_2CH_3$), 1.19 (t, 4"-$OCOCH_2CH_3$), 1.35 (m, 8-H), 1.42 (s, 3"-$CH_3$), 1.68 (dd, 2"-Hax), 2.01 (s, 3"-$OCOCH_3$), 2.33 (s, $NCH_3$), 2.43 (q, 4"-$OCOCH_2CH_3$), 2.54 (s, 3'-N$(CH_3)_2$), 2.62 (dq, 3-$OCOCH_2CH_3$), 2.63 (dd, 2-H), 2.84 (dd, 2-H), 2.89 (dd, 6-$CH_2$), 3.16 (t, 4'-H), 3.21 (d, 2"-Heq), 3.41 (dd, 2'-H), 3.65 (s, 4-$OCH_3$), 3.86 (d, 4-H), 3.99 (d, 5-H), 4.39 (d, 1'-H), 4.53 (dq, 5"-H), 4.58 (d, 4"-H), 4.84 (d, 1"-H), 5.10 (m, 15-H), 5.56 (dd, 3-H), 6.21 (dt, CH═CH), 6.51 (d, CH═CH), 7.24 (ddd, pyridine), 7.39 (m, $C_6H_4$), 7.74 (m, pyridine), 7.81 (m, $C_6H_4$), 7.96 (s, $C_6H_4$), 8.70 (ddd, pyridine), 9.65 (s, CHO).

Example 115

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(5-(pyridin-3-yl)pyridin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 3-(5-bromopyridin-3-yl)pyridine (WO2004002963) was used instead of 4-bromoquinoline, 40.9 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(5-(pyridin-3-yl)pyridin-3-yl)-2-propenyl group, $R_3$ is acetyl group, $R_{4''}$ is propionyl group, and X is oxygen atom) was obtained from 75.7 mg of the compound of Example 90(b).

Physicochemical Properties of this Compound (1) Molecular formula: $C_{61}H_{92}N_4O_{19}$ (2) Mass spectrum (FAB): m/z 1185 $(M+H)^+$ (3) $^1H$ NMR spectrum (300 MHz, $CDCl_3$) δ (ppm): 0.92 (d, 8-$CH_3$), 1.07 (d, 6"-H), 1.12 (t, 3-$OCOCH_2CH_3$), 1.19 (t, 4"-$OCOCH_2CH_3$), 1.21 (d, 6'-H), 1.41 (s, 3"-$CH_3$), 1.67 (dd, 2"-Hax), 2.02 (s, 3"-$OCOCH_3$), 2.04 (s, 9-$OCOCH_3$), 2.05 (s, 2'-$OCOCH_3$), 2.24 (s, $NCH_3$), 2.34 (q, 3-$OCOCH_2CH_3$), 2.43 (q, 4"-$OCOCH_2CH_3$), 2.43 (s, 3'-N$(CH_3)_2$), 2.62 (dd, 2-H), 2.62 (t, 3'-H), 2.87 (dd, 2-H), 3.14 (t, 4'-H), 3.14 (s, $CH(OCH_3)_2$), 3.19 (d, 2"-Heq), 3.25 (s, $CH(OCH_3)_2$), 3.60 (s, 4-$OCH_3$), 3.94 (d, 5-H), 4.48 (dq, 5"-H), 4.57 (d, 4"-H), 4.70 (d, 1'-H), 4.81 (d, 1"-H), 4.92 (m, 9-H), 4.97 (dd, 2'-H), 5.06 (m, 3-H), 5.13 (m, 15-H), 6.32 (dt, CH═CH), 6.52 (d, CH═CH), 7.42 (dd, pyridine), 7.84 (s, pyridine), 7.90 (m, pyridine), 8.60 (d, pyridine), 8.67 (m, pyridine), 8.85 (d, pyridine).

(b) In the same manner as in Example 73(b), 9.4 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(5-(pyridin-3-yl)pyridin-3-yl)-2-propenyl group, $R_{3''}$ is acetyl group, $R_{4''}$ is propionyl group, and X is oxygen atom) was obtained from 40.9 mg of the compound of Example 115(a).

Physicochemical Properties of this Compound (1) Molecular formula: $C_{57}H_{88}N_4O_{17}$ (2) Mass spectrum (FAB): m/z 1101 $(M+H)^+$ (3) $^1H$ NMR spectrum (300 MHz, $CDCl_3$) δ (ppm): 0.88 (d, 8-$CH_3$), 1.09 (d, 6"-H), 1.11 (t, 3-$OCOCH_2CH_3$), 1.20 (t, 4"-$OCOCH_2CH_3$), 1.21 (d, 6'-H), 1.42 (s, 3"-$CH_3$), 1.68 (dd, 2"-Hax), 1.84 (m, 6-$CH_2$), 2.02 (s, 3"-$OCOCH_3$), 2.33 (q, 3-$OCOCH_2CH_3$), 2.35 (s, $NCH_3$), 2.43 (q, 4"-$OCOCH_2CH_3$), 2.54 (s, 3'-N$(CH_3)_2$), 2.61 (dd, 2-H), 2.82 (dd, 2-H), 3.14 (s, $CH(OCH_3)_2$), 3.25 (s, $CH(OCH_3)_2$), 3.36 (m, 9-H), 3.47 (dd, 2'-H), 3.65 (s, 4-$OCH_3$), 3.88 (d, 4-H), 3.95 (d, 5-H), 4.46 (d, 1'-H), 4.49 (dd, $CH(OCH_3)_2$), 4.59 (d, 4"-H), 4.84 (d, 1"-H), 5.11 (m, 15-H), 5.46 (m, 3-H), 6.30 (dt, CH═CH), 6.50 (d, CH═CH), 7.43 (dd, pyridine), 7.82 (t, pyridine), 7.89 (m, pyridine), 8.59 (d, pyridine), 8.67 (m, pyridine), 8.85 (d, pyridine).

(c) In the same manner as in Example 2(d), 6.4 mg of the title compound was obtained from 9.4 mg of the compound of Example 115(b).

Physicochemical Properties of this Compound (1) Molecular formula: $C_{55}H_{82}N_4O_{16}$ (2) Mass spectrum (FAB): m/z 1055 $(M+H)^+$ (3) Specific rotation: $[\alpha]_D^{21}$ −48° (c0.32, $CHCl_3$)

(4) $^1$H NMR spectrum (300 MHz, $CDCl_3$) δ (ppm): 0.90 (d, 8-$CH_3$), 1.09 (d, 6"-H), 1.14 (d, 6'-H), 1.16 (t, 3-$OCOCH_2CH_3$), 1.19 (t, 4"-$OCOCH_2CH_3$), 1.37 (m, 8-H), 1.42 (s, 3"-$CH_3$), 1.69 (dd, 2"-Hax), 2.01 (s, 3"-$OCOCH_3$), 2.36 (s, $NCH_3$), 2.43 (q, 4"-$OCOCH_2CH_3$), 2.55 (s, 3'-N$(CH_3)_2$), 2.84 (dd, 2-H), 2.91 (dd, 6-$CH_2$), 3.18 (t, 4'-H), 3.21 (d, 2"-Heq), 3.39 (dd, 2'-H), 3.66 (s, 4-$OCH_3$), 3.86 (d, 4-H), 3.95 (d, 5-H), 4.40 (d, 1'-H), 4.52 (dq, 5"-H), 4.58 (d, 4"-H), 4.84 (d, 1"-H), 5.10 (m, 15-H), 5.55 (m, 3-H), 6.30 (dt, CH═CH), 6.50 (d, CH═CH), 7.42 (m, pyridine), 7.82 (t, pyridine), 7.89 (m, pyridine), 8.59 (d, pyridine), 8.67 (m, pyridine), 8.85 (d, pyridine), 9.65 (s, CHO).

Example 116

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(2-(pyridin-3-yl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 3-(2-bromophenyl)pyridine (Org. Lett. 2002, 4, 3115-3118) was used instead of 4-bromoquinoline, 34.6 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(2-(pyridin-3-yl)phenyl)-2-propenyl group, $R_{3''}$ is acetyl group, $R_{4''}$ is propionyl group, and X is oxygen atom) was obtained from 74.8 mg of the compound of Example 90(b).

Physicochemical Properties of this Compound (1) Molecular formula: $C_{62}H_{93}N_3O_{19}$ (2) Mass spectrum (FAB): m/z 1184 $(M+H)^+$ (3) $^1$H NMR spectrum (300 MHz, $CDCl_3$) δ (ppm): 0.92 (d, 8-$CH_3$), 1.07 (d, 6"-H), 1.13 (t, 3-$OCOCH_2CH_3$), 1.19 (t, 4"-$OCOCH_2CH_3$), 1.21 (d, 6'-H), 1.42 (s, 3"-$CH_3$), 1.67 (dd, 2"-Hax), 2.02 (s, 3"-$OCOCH_3$), 2.05 (s, 9-$OCOCH_3$ and 2'-$OCOCH_3$), 2.22 (s, $NCH_3$), 2.43 (q, 4"-$OCOCH_2CH_3$), 2.43 (s, 3'-N$(CH_3)_2$), 2.59 (dd, 2-H), 2.62 (t, 3'-H), 2.86 (dd, 2-H), 3.14 (s, CH$(OCH_3)_2$), 3.19 (d, 2"-Heq), 3.25 (s, CH$(OCH_3)_2$), 3.62 (s, 4-$OCH_3$), 3.64 (d, 4-H), 3.93 (d, 5-H), 4.48 (dq, 5"-H), 4.57 (d, 4"-H), 4.71 (d, 1'-H), 4.81 (d, 1"-H), 4.90 (m, 9-H), 4.98 (dd, 2'-H), 5.03 (m, 3-H), 6.07 (dt, CH═CH), 6.34 (d, CH═CH), 7.24-7.39 (m, pyridine and $C_6H_4$), 7.56 (m, $C_6H_4$), 7.65 (m, pyridine), 8.60 (m, pyridine).

(b) In the same manner as in Example 73(b), 19.2 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(2-(pyridin-3-yl)phenyl)-2-propenyl group, $R_{3''}$ is acetyl group, $R_{4''}$ is propionyl group, and X is oxygen atom) was obtained from 34.6 mg of the compound of Example 116(a).

Physicochemical Properties of this Compound (1) Molecular formula: $C_{58}H_{89}N_3O_{17}$ (2) Mass spectrum (FAB): m/z 1100 $(M+H)^+$ (3) $^1$H NMR spectrum (300 MHz, $CDCl_3$) δ (ppm): 0.88 (d, 8-$CH_3$), 1.09 (d, 6"-H), 1.10 (t, 3-$OCOCH_2CH_3$), 1.20 (t, 4"-$OCOCH_2CH_3$), 1.21 (d, 6'-H), 1.42 (s, 3"-$CH_3$), 1.68 (dd, 2"-Hax), 1.84 (m, 6-$CH_2$), 2.02 (s, 3"-$OCOCH_3$), 2.33 (s, $NCH_3$), 2.43 (q, 4"-$OCOCH_2CH_3$), 2.54 (s, 3'-N$(CH_3)_2$), 2.57 (dd, 2-H), 2.66 (m, 12-H), 2.80 (dd, 2-H), 3.14 (s, CH$(OCH_3)_2$), 3.16 (t, 4'-H), 3.21 (d, 2"-Heq), 3.25 (s, CH$(OCH_3)_2$), 3.49 (dd, 2'-H), 3.68 (s, 4-$OCH_3$), 3.88 (d, 4-H), 3.99 (d, 5-H), 4.46 (d, 1'-H), 4.50 (dd, CH$(OCH_3)_2$), 4.59 (d, 4"-H), 4.83 (d, 1"-H), 5.05 (m, 15-H), 5.46 (m, 3-H), 6.06 (dt, CH═CH), 6.32 (d, CH═CH), 7.23-7.37 (m, pyridine and $C_6H_4$), 7.55 (m, $C_6H_4$), 7.65 (m, pyridine), 8.60 (m, pyridine).

(c) In the same manner as in Example 2(d), 15.0 mg of the title compound was obtained from 19.2 mg of the compound of Example 116(b).

Physicochemical Properties of this Compound (1) Molecular formula: $C_{56}H_{83}N_3O_{16}$ (2) Mass spectrum (FAB): m/z 1054 $(M+H)^+$ (3) Specific rotation: $[\alpha]_D^{22}$ −48° (c0.75, $CHCl_3$)

(4) $^1$H NMR spectrum (300 MHz, $CDCl_3$) δ (ppm): 0.90 (d, 8-$CH_3$), 1.09 (d, 6"-H), 1.14 (d, 6'-H), 1.15 (t, 3-$OCOCH_2CH_3$), 1.19 (t, 4"-$OCOCH_2CH_3$), 1.36 (m, 8-H), 1.42 (s, 3"-$CH_3$), 1.69 (dd, 2"-Hax), 2.01 (s, 3"-$OCOCH_3$), 2.35 (s, $NCH_3$), 2.43 (q, 4"-$OCOCH_2CH_3$), 2.55 (s, 3'-N$(CH_3)_2$), 2.82 (dd, 2-H), 2.90 (dd, 6-$CH_2$), 3.17 (t, 4'-H), 3.21 (d, 2"-Heq), 3.41 (dd, 2'-H), 3.68 (s, 4-$OCH_3$), 3.86 (d, 4-H), 3.98 (d, 5-H), 4.40 (d, 1'-H), 4.53 (dq, 5"-H), 4.58 (d, 4"-H), 4.84 (d, 1"-H), 5.04 (m, 15-H), 5.53 (m, 3-H), 6.05 (dt, CH═CH), 6.33 (d, CH═CH), 7.23-7.38 (m, pyridine and $C_6H_4$), 7.55 (m, $C_6H_4$), 7.65 (m, pyridine), 8.60 (m, pyridine), 9.65 (s, CHO).

Example 117

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(4-(4-morpholinesulfonyl)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 1-bromo-4-(4-morpholinesulfonyl) benzene was used instead of 4-bromoquinoline, 73.5 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(4-(4-morpholinesulfonyl)phenyl)-2-propenyl group, $R_{3''}$ is acetyl group, $R_{4''}$ is propionyl group, and X is oxygen atom) was obtained from 77.5 mg of the compound of Example 90(b).

Physicochemical Properties of this Compound (1) Molecular formula: $C_{61}H_{97}N_3O_{22}S$ (2) Mass spectrum (FAB): m/z 1256 $(M+H)^+$ (3) $^1$H NMR spectrum (300 MHz, $CDCl_3$) δ (ppm): 0.88 (d, 8-$CH_3$), 1.03 (d, 6"-H), 1.11 (t, 3-$OCOCH_2CH_3$), 1.16 (t, 4"-$OCOCH_2CH_3$), 1.17 (d, 6'-H), 1.38 (s, 3"-$CH_3$), 1.64 (dd, 2"-Hax), 1.98 (s, 9-$OCOCH_3$), 2.01 (s, 3"-$OCOCH_3$), 2.02 (s, 2'-$OCOCH_3$), 2.19 (s, $NCH_3$), 2.40 (s, 3'-N$(CH_3)_2$), 2.57 (dd, 2-H), 2.59 (t, 3'-H), 2.82 (dd, 2-H), 2.96 (t, morpholine), 3.11 (s, CH$(OCH_3)_2$), 3.13 (t, 4'-H), 3.16 (d, 2"-Heq), 3.20

(m, 5'-H), 3.22 (s, $CH(OCH_3)_2$), 3.54 (d, 4-H), 3.56 (s, 4-$OCH_3$), 3.71 (t, morpholine), 3.90 (d, 5-H), 4.45 (dq, 5"-H), 4.52 (dd, $CH(OCH_3)_2$), 4.53 (d, 4"-H), 4.66 (d, 1'-H), 4.77 (d, 1"-H), 4.88 (m, 9-H), 4.94 (dd, 2'-H), 5.05 (br t, 3-H), 5.06 (m, 15-H), 6.27 (dt, 15-$CH_2$—CH═CH), 6.46 (d, 15-$CH_2$—CH═CH), 7.45 (d, $C_6H_4$), 7.63 (d, $C_6H_4$).

(b) In the same manner as in Example 2(c), 47.3 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(4-(4-morpholinesulfonyl) phenyl)-2-propenyl group, $R_{3''}$ is acetyl group, $R_{4''}$ is propionyl group, and X is oxygen atom) was obtained from 73.5 mg of the compound of Example 117(a).

Physicochemical Properties of this Compound (1) Molecular formula: $C_{57}H_{93}N_3O_{20}S$ (2) Mass spectrum (FAB): m/z 1172 $(M+H)^+$ (3) $^1H$ NMR spectrum (300 MHz, $CDCl_3$) δ (ppm): 0.85 (d, 8-$CH_3$), 1.07 (d, 6"-H), 1.10 (t, 3-$OCOCH_2CH_3$), 1.18 (t, 4"-$OCOCH_2CH_3$), 1.19 (d, 6'-H), 1.40 (s, 3"-$CH_3$), 1.67 (dd, 2"-Hax), 2.00 (s, 3"-$OCOCH_3$), 2.29 (s, $NCH_3$), 2.39 (q, 3-$OCOCH_2CH_3$), 2.42 (q, 4"-$OCOCH_2CH_3$), 2.52 (s, 3'-$N(CH_3)_2$), 2.59 (dd, 2-H), 2.79 (dd, 2-H), 2.97 (t, morpholine), 3.13 (s, $CH(OCH_3)_2$), 3.16 (t, 4'-H), 3.19 (d, 2"-Heq), 3.22 (m, 5'-H), 3.24 (s, $CH(OCH_3)_2$), 3.45 (dd, 2'-H), 3.64 (s, 4-$OCH_3$), 3.72 (t, morpholine), 3.87 (d, 4-H), 3.96 (d, 5-H), 4.45 (d, 1'-H), 4.48 (dd, $CH(OCH_3)_2$), 4.54 (dq, 5"-H), 4.57 (d, 4"-H), 4.82 (d, 1"-H), 5.09 (m, 15-H), 5.48 (m, 3-H), 6.27 (dt, 15-$CH_2$—CH═CH), 6.45 (d, 15-$CH_2$—CH═CH), 7.45 (d, $C_6H_4$), 7.65 (d, $C_6H_4$).

(c) In the same manner as in Example 2(d), 39.8 mg of the title compound was obtained from 47.3 mg of the compound of Example 117(b).

Physicochemical Properties of this Compound (1) Molecular formula: $C_{55}H_{87}N_3O_{19}S$ (2) Mass spectrum (FAB): m/z 1126 $(M+H)^+$ (3) Specific rotation: $[\alpha]_D^{17}$ −51° (c1.00, $CHCl_3$)

(4) $^1H$ NMR spectrum (300 MHz, $CDCl_3$) δ (ppm): 0.87 (d, 8-$CH_3$), 1.07 (d, 6"-H), 1.12 (d, 6'-H), 1.15 (t, 3-$OCOCH_2CH_3$), 1.17 (t, 4"-$OCOCH_2CH_3$), 1.40 (s, 3"-$CH_3$), 1.67 (dd, 2"-Hax), 1.99 (s, 3"-$OCOCH_3$), 2.29 (s, $NCH_3$), 2.41 (q, 3-$OCOCH_2CH_3$), 2.41 (q, 4"-$OCOCH_2CH_3$), 2.53 (s, 3'-$N(CH_3)_2$), 2.60 (dd, 2-H), 2.80 (dd, 2-H), 2.97 (t, morpholine), 3.17 (m, 4'-H), 3.17 (m, 5'-H), 3.20 (d, 2"-Heq), 3.32 (m, 9-H), 3.37 (dd, 2'-H), 3.64 (s, 4-$OCH_3$), 3.72 (t, morpholine), 3.85 (d, 4-H), 3.95 (d, 5-H), 4.38 (d, 1'-H), 4.51 (dq, 5"-H), 4.56 (d, 4"-H), 4.82 (d, 1"-H), 5.09 (m, 15-H), 5.57 (m, 3-H), 6.26 (dt, 15-$CH_2$—CH═CH), 6.45 (d, 15-$CH_2$—CH═CH), 7.45 (d, $C_6H_4$), 7.65 (d, $C_6H_4$), 9.63 (s, CHO).

Example 118

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(4-(6-methylpyridazin-3-yloxy)phenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 3-(4-bromophenoxy)-6-methylpyridazine was used instead of 4-bromoquinoline, 55.7 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(4-(6-methylpyridazin-3-yloxy)phenyl)-2-propenyl group, $R_{3''}$ is acetyl group, $R_{4''}$ is propionyl group, and X is oxygen atom) was obtained from 77.6 mg of the compound of Example 90(b).

Physicochemical Properties of this Compound (1) Molecular formula: $C_{62}H_{94}N_4O_{20}$ (2) Mass spectrum (FAB): m/z 1215 $(M+H)^+$ (3) $^1H$ NMR spectrum (300 MHz, $CDCl_3$) δ (ppm): 0.89 (d, 8-$CH_3$), 1.04 (d, 6"-H), 1.11 (t, 3-$OCOCH_2CH_3$), 1.16 (t, 4"-$OCOCH_2CH_3$), 1.19 (d, 6'-H), 1.39 (s, 3"-$CH_3$), 1.64 (dd, 2"-Hax), 1.99 (s, 9-$OCOCH_3$), 2.02 (s, 3"-$OCOCH_3$), 2.03 (s, 2'-$OCOCH_3$), 2.20 (s, $NCH_3$), 2.41 (s, 3'-$N(CH_3)_2$), 2.62 (s, pyridazine-$CH_3$), 2.84 (dd, 2-H), 3.13 (s, $CH(OCH_3)_2$), 3.14 (t, 4'-H), 3.16 (d, 2"-Heq), 3.21 (m, 5'-H), 3.23 (s, $CH(OCH_3)_2$), 3.59 (s, 4-$OCH_3$), 3.91 (d, 5-H), 4.46 (dq, 5"-H), 4.53 (dd, $CH(OCH_3)_2$), 4.54 (d, 4"-H), 4.68 (d, 1'-H), 4.78 (d, 1"-H), 4.88 (m, 9-H), 4.95 (dd, 2'-H), 5.05 (br t, 3-H), 5.05 (m, 15-H), 6.04 (dt, 15-$CH_2$—CH═CH), 6.41 (d, 15-$CH_2$—CH═CH), 7.02 (d, pyridazine), 7.09 (d, $C_6H_4$), 7.30 (d, pyridazine), 7.33 (d, $C_6H_4$).

(b) In the same manner as in Example 2(c), 32.8 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(4-(6-methylpyridazin-3-yloxy)phenyl)-2-propenyl group, $R_{3''}$ is acetyl group, $R_{4''}$ is propionyl group, and X is oxygen atom) was obtained from 55.7 mg of the compound of Example 118(a).

Physicochemical Properties of this Compound (1) Molecular formula: $C_{58}H_{90}N_4O_{18}$ (2) Mass spectrum (FAB): m/z 1131 $(M+H)^+$ (3) $^1H$ NMR spectrum (300 MHz, $CDCl_3$) δ (ppm): 0.85 (d, 8-$CH_3$), 1.07 (d, 6"-H), 1.10 (t, 3-$OCOCH_2CH_3$), 1.18 (t, 4"-$OCOCH_2CH_3$), 1.19 (d, 6'-H), 1.40 (s, 3"-$CH_3$), 1.66 (dd, 2"-Hax), 2.00 (s, 3"-$OCOCH_3$), 2.30 (s, $NCH_3$), 2.39 (q, 3-$OCOCH_2CH_3$), 2.42 (q, 4"-$OCOCH_2CH_3$), 2.52 (s, 3'-$N(CH_3)_2$), 2.59 (dd, 2-H), 2.63 (s, pyridazine-$CH_3$), 2.80 (dd, 2-H), 3.13 (s, $CH(OCH_3)_2$), 3.17 (t, 4'-H), 3.19 (d, 2"-Heq), 3.22 (m, 5'-H), 3.24 (s, $CH(OCH_3)_2$), 3.48 (dd, 2'-H), 3.65 (s, 4-$OCH_3$), 3.87 (d, 4-H), 3.98 (d, 5-H), 4.45 (d, 1'-H), 4.48 (dd, $CH(OCH_3)_2$), 4.54 (dq, 5"-H), 4.57 (d, 4"-H), 4.82 (d, 1"-H), 5.06 (m, 15-H), 5.47 (m, 3-H), 6.06 (dt, 15-$CH_2$—CH═CH), 6.40 (d, 15-$CH_2$—CH═CH), 7.03 (d, pyridazine), 7.09 (d, $C_6H_4$), 7.30 (d, pyridazine), 7.33 (d, $C_6H_4$).

(c) In the same manner as in Example 2(d), 28.8 mg of the title compound was obtained from 32.8 mg of the compound of Example 118(b).

Physicochemical Properties of this Compound (1) Molecular formula: $C_{56}H_{84}N_4O_{17}$ (2) Mass spectrum (FAB): m/z 1085 $(M+H)^+$ (3) Specific rotation: $[\alpha]_D^{17}$ −44° (c1.00, $CHCl_3$)

(4) $^1H$ NMR spectrum (300 MHz, $CDCl_3$) δ (ppm): 0.88 (d, 8-$CH_3$), 1.07 (d, 6"-H), 1.13 (d, 6'-H), 1.16 (t, 3-$OCOCH_2CH_3$), 1.18 (t, 4"-$OCOCH_2CH_3$), 1.40 (s, 3"-$CH_3$), 1.67 (dd, 2"-Hax), 2.00 (s, 3"-$OCOCH_3$), 2.30 (s, $NCH_3$), 2.42 (q, 3-$OCOCH_2CH_3$), 2.42 (q, 4"-$OCOCH_2CH_3$), 2.53 (s, 3'-$N(CH_3)_2$), 2.59 (dd, 2-H), 2.63 (s, pyridazine-$CH_3$), 2.82 (dd, 2-H), 3.17 (m, 4'-H), 3.17 (m, 5'-H), 3.20 (d, 2"-Heq), 3.34 (m, 9-H), 3.40 (dd, 2'-H), 3.66 (s, 4-$OCH_3$), 3.85 (d, 4-H), 3.98 (d, 5-H), 4.38 (d, 1'-H), 4.52 (dq, 5"-H), 4.57 (d, 4"-H), 4.82 (d, 1"-H), 5.07 (m, 15-H), 5.55 (m, 3-H), 6.04 (dt, 15-$CH_2$—CH═CH), 6.40 (d, 15-$CH_2$—CH═CH), 7.03 (dt, pyridazine), 7.10 (dt, $C_6H_4$), 7.31 (dd, pyridazine), 7.33 (d, $C_6H_4$), 9.64 (s, CHO).

Example 119

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(5-benzoylpyridin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that the compound of Reference Example 35 was used instead of 4-bromoquinoline, 31.5 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(5-benzoylpyridin-3-yl)-2-propenyl group, $R_{3''}$ is acetyl group, $R_{4''}$ is propionyl group, and X is oxygen atom) was obtained from 43.5 mg of the compound of Example 90(b).

Physicochemical Properties of this Compound (1) Molecular formula: $C_{58}H_{89}N_3O_{18}$ (2) Mass spectrum (FAB): m/z 1116 $(M+H)^+$ (3) Specific rotation: $[\alpha]_D^{21}$ −42° (c1.49, $CHCl_3$)

(4) $^1H$ NMR spectrum (300 MHz, $CDCl_3$) δ (ppm): 0.90 (d, 8-$CH_3$), 1.05 (d, 6"-H), 1.11 (t, 3-$OCOCH_2CH_3$), 1.17 (t, 4"-$OCOCH_2CH_3$), 1.19 (d, 6'-H), 1.39 (s, 3"-$CH_3$), 1.65 (dd, 2"-Hax), 2.00 (s, 9-$OCOCH_3$), 2.02 (s, 3"-$OCOCH_3$), 2.03 (s, 2'-$OCOCH_3$), 2.21 (s, $NCH_3$), 2.41 (s, 3'-$N(CH_3)_2$), 2.60 (dd, 2-H), 2.60 (t, 3'-H), 2.85 (dd, 2-H), 3.12 (s, $CH(OCH_3)_2$), 3.15 (t, 4'-H), 3.18 (d, 2"-Heq), 3.21 (m, 5'-H), 3.23 (s, $CH(OCH_3)_2$), 3.59 (d, 4-H), 3.59 (s, 4-$OCH_3$), 3.92 (d, 5-H), 4.47 (dq, 5"-H), 4.52 (dd, $CH(OCH_3)_2$), 4.55 (d, 4"-H), 4.68 (d, 1'-H), 4.78 (d, 1"-H), 4.89 (m, 9-H), 4.95 (dd, 2'-H), 5.03 (br t, 3-H), 5.10 (m, 15-H), 6.29 (dt, 15-$CH_2$—CH═CH), 6.49 (d, 15-$CH_2$—CH═CH), 7.51 (t, $C_6H_5$), 7.63 (dt, $C_6H_5$), 7.80 (ddd, $C_6H_5$), 8.05 (t, pyridine), 8.72 (d, pyridine), 8.76 (d, pyridine).

(b) In the same manner as in Example 2(c), 29.3 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(5-benzoylpyridin-3-yl)-2-propenyl group, $R_{3''}$ is acetyl group, $R_{4''}$ is propionyl group, and X is oxygen atom) was obtained from 31.5 mg of the compound of Example 119(a).

Physicochemical Properties of this Compound (1) Molecular formula: $C_{59}H_{89}N_3O_{18}$ (2) Mass spectrum (FAB): m/z 1128 $(M+H)^+$ (3) $^1H$ NMR spectrum (300 MHz, $CDCl_3$) δ (ppm): 0.86 (d, 8-$CH_3$), 1.07 (d, 6"-H), 1.10 (t, 3-$OCOCH_2CH_3$), 1.18 (t, 4"-$OCOCH_2CH_3$), 1.40 (s, 3"-$CH_3$), 1.19 (d, 6'-H), 1.67 (dd, 2"-Hax), 2.00 (s, 3"-$OCOCH_3$), 2.31 (s, $NCH_3$), 2.39 (q, 3-$OCOCH_2CH_3$), 2.42 (q, 4"-$OCOCH_2CH_3$), 2.52 (s, 3'-$N(CH_3)_2$), 2.59 (dd, 2-H), 2.80 (dd, 2-H), 3.13 (s, $CH(OCH_3)_2$), 3.16 (dd, 4'-H), 3.19 (d, 2"-Heq), 3.22 (m, 5'-H), 3.24 (s, $CH(OCH_3)_2$), 3.46 (dd, 2'-H), 3.65 (s, 4-$OCH_3$), 3.87 (d, 4-H), 3.95 (d, 5-H), 4.45 (d, 1'-H), 4.49 (dd, $CH(OCH_3)_2$), 4.54 (dq, 5"-H), 4.57 (d, 4"-H), 4.82 (d, 1"-H), 5.08 (m, 15-H), 5.45 (m, 3-H), 6.29 (dt, 15-$CH_2$—CH═CH), 6.48 (d, 15-$CH_2$—CH═CH), 7.51 (dt, $C_6H_5$), 7.64 (dt, $C_6H_5$), 7.80 (dd, $C_6H_5$), 8.04 (d, pyridine), 8.72 (d, pyridine), 8.77 (d, pyridine).

(c) In the same manner as in Example 2(d), 13.3 mg of the title compound was obtained from 14.7 mg of the compound of Example 119(b).

Physicochemical Properties of this Compound (1) Molecular formula: $C_{57}H_{83}N_3O_{17}$ (2) Mass spectrum (FAB): m/z 1082 $(M+H)^+$ (3) Specific rotation: $[\alpha]_D^{21}$ −51° (c1.00, $CHCl_3$)

(4) $^1H$ NMR spectrum (300 MHz, $CDCl_3$) δ (ppm): 0.88 (d, 8-$CH_3$), 1.07 (d, 6"-H), 1.13 (d, 6'-H), 1.15 (t, 3-$OCOCH_2CH_3$), 1.18 (t, 4"-$OCOCH_2CH_3$), 1.40 (s, 3"-$CH_3$), 1.67 (dd, 2"-Hax), 2.00 (s, 3"-$OCOCH_3$), 2.30 (s, $NCH_3$), 2.42 (q, 3-$OCOCH_2CH_3$), 2.42 (q, 4"-$OCOCH_2CH_3$), 2.53 (s, 3'-$N(CH_3)_2$), 2.59 (dd, 2-H), 2.83 (dd, 2-H), 3.16 (m, 4'-H), 3.16 (m, 5'-H), 3.20 (d, 2"-Heq), 3.35 (m, 9-H), 3.39 (dd, 2'-H), 3.66 (s, 4-$OCH_3$), 3.85 (d, 4-H), 3.95 (d, 5-H), 4.38 (d, 1'-H), 4.52 (dq, 5"-H), 4.57 (d, 4"-H), 4.83 (d, 1"-H), 5.07 (m, 15-H), 5.55 (m, 3-H), 6.28 (dt, 15-$CH_2$—CH═CH), 6.47 (d, 15-$CH_2$—CH═CH), 7.51 (t, $C_6H_5$), 7.63 (dt, $C_6H_5$), 7.80 (ddd, $C_6H_5$), 8.07 (t, pyridine), 8.72 (d, pyridine), 8.77 (d, pyridine), 9.64 (s, CHO).

Example 120

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(5-phenoxypyridin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that the compound of Reference Example 30 was used instead of 4-bromoquinoline, 30.9 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(5-phenoxypyridin-3-yl)-2-propenyl group, $R_{3''}$ is acetyl group, $R_{4''}$ is propionyl group, and X is oxygen atom) was obtained from 43.5 mg of the compound of Example 90 (b).

Physicochemical Properties of this Compound (1) Molecular formula: $C_{62}H_{93}N_3O_{20}$ (2) Mass spectrum (FAB): m/z 1200 $(M+H)^+$ (3) $^1H$ NMR spectrum (300 MHz, $CDCl_3$) δ (ppm): 0.90 (d, 8-$CH_3$), 1.05 (d, 6"-H), 1.11 (t, 3-$OCOCH_2CH_3$), 1.17 (t, 4"-$OCOCH_2CH_3$), 1.19 (d, 6'-H), 1.39 (s, 3"-$CH_3$), 1.65 (dd, 2"-Hax), 2.00 (s, 9-$OCOCH_3$), 2.02 (s, 3"-$OCOCH_3$), 2.03 (s, 2'-$OCOCH_3$), 2.20 (s, $NCH_3$), 2.41 (s, 3'-$N(CH_3)_2$), 2.59 (dd, 2-H), 2.59 (t, 3'-H), 2.83 (dd, 2-H), 3.12 (s, $CH(OCH_3)_2$), 3.15 (t, 4'-H), 3.18 (d, 2"-Heq), 3.21 (m, 5'-H), 3.23 (s, $CH(OCH_3)_2$), 3.58 (s, 4-$OCH_3$), 3.59 (d, 4-H), 3.91 (d, 5-H), 4.47 (dq, 5"-H), 4.53 (dd, $CH(OCH_3)_2$), 4.55 (d, 4"-H), 4.68 (d, 1'-H), 4.79 (d, 1"-H), 4.89 (m, 9-H), 4.95 (dd, 2'-H), 5.03 (br t, 3-H), 5.05 (m, 15-H), 6.15 (dt, 15-$CH_2$—CH═CH), 6.38 (d, 15-$CH_2$—CH═CH), 7.00 (t, $C_6H_5$), 7.14 (dt, $C_6H_5$), 7.24 (d, $C_6H_5$), 7.35 (d, pyridine), 8.20 (d, pyridine), 8.29 (d, pyridine).

(b) In the same manner as in Example 2(c), 28.7 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(5-phenoxypyridin-3-yl)-2-propenyl group, $R_{3''}$ is acetyl group, $R_{4''}$ is propionyl group, and X is oxygen atom) was obtained from 30.9 mg of the compound of Example 120(a).

Physicochemical Properties of this Compound (1) Molecular formula: $C_{58}H_{89}N_3O_{18}$ (2) Mass spectrum (FAB): m/z 1116 $(M+H)^+$ (3) $^1H$ NMR spectrum (300 MHz, $CDCl_3$) δ (ppm): 0.85 (d, 8-$CH_3$), 1.07 (d, 6"-H), 1.10 (t, 3-$OCOCH_2CH_3$), 1.18 (t, 4"-$OCOCH_2CH_3$), 1.19 (d, 6'-H), 1.40 (s, 3"-$CH_3$), 1.67 (dd, 2"-Hax), 2.00 (s, 3"-$OCOCH_3$), 2.31 (s, $NCH_3$), 2.39 (q, 3-$OCOCH_2CH_3$), 2.42 (q, 4"-$OCOCH_2CH_3$), 2.53 (s, 3'-N$(CH_3)_2$), 2.58 (dd, 2-H), 2.78 (dd, 2-H), 3.13 (s, $CH(OCH_3)_2$), 3.16 (t, 4'-H), 3.19 (d, 2"-Heq), 3.22 (m, 5'-H), 3.24 (s, $CH(OCH_3)_2$), 3.47 (dd, 2'-H), 3.64 (s, 4-$OCH_3$), 3.87 (d, 4-H), 3.95 (d, 5-H), 4.45 (d, 1'-H), 4.49 (dd, $CH(OCH_3)_2$), 4.54 (dq, 5"-H), 4.57 (d, 4"-H), 4.82 (d, 1"-H), 5.05 (m, 15-H), 5.45 (m, 3-H), 6.13 (dt, 15-$CH_2$—CH═CH), 6.37 (d, 15-$CH_2$—CH═CH), 7.01 (dt, $C_6H_5$), 7.15 (dt, $C_6H_5$), 7.23 (dd, pyridine), 7.36 (d, $C_6H_5$), 8.21 (d, pyridine), 8.28 (d, pyridine).

(c) In the same manner as in Example 2(d), 13.3 mg of the title compound was obtained from 14.2 mg of the compound of Example 120(b).

Physicochemical Properties of this Compound (1) Molecular formula: $C_{56}H_{83}N_3O_{17}$ (2) Mass spectrum (FAB): m/z 1070 $(M+H)^+$ (3) Specific rotation: $[\alpha]_D^{21}$ −55° (c1.00, $CHCl_3$)

(4) $^1H$ NMR spectrum (300 MHz, $CDCl_3$) δ (ppm): 0.88 (d, 8-$CH_3$), 1.07 (d, 6"-H), 1.13 (d, 6'-H), 1.15 (t, 3-$OCOCH_2CH_3$), 1.18 (t, 4"-$OCOCH_2CH_3$), 1.40 (s, 3"-$CH_3$), 1.67 (dd, 2"-Hax), 2.00 (s, 3"-$OCOCH_3$), 2.30 (s, $NCH_3$), 2.42 (q, 3-$OCOCH_2CH_3$), 2.42 (q, 4"-$OCOCH_2CH_3$), 2.53 (s, 3'-N$(CH_3)_2$), 2.62 (dd, 2-H), 2.80 (dd, 2-H), 3.16 (m, 4'-H), 3.16 (m, 5'-H), 3.20 (d, 2"-Heq), 3.35 (m, 9-H), 3.39 (dd, 2'-H), 3.65 (s, 4-$OCH_3$), 3.85 (d, 4-H), 3.95 (d, 5-H), 4.38 (d, 1'-H), 4.52 (dq, 5"-H), 4.57 (d, 4"-H), 4.83 (d, 1"-H), 5.04 (m, 15-H), 5.54 (m, 3-H), 6.12 (dt, 15-$CH_2$—CH═CH), 6.37 (d, 15-$CH_2$—CH═CH), 7.01 (dt, $C_6H_5$), 7.15 (dt, $C_6H_5$), 7.23 (dd, pyridine), 7.36 (d, $C_6H_5$), 8.21 (d, pyridine), 8.28 (d, pyridine), 9.63 (s, CHO).

Example 121

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(5-phenylthiopyridin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that the compound of Reference Example 29 was used instead of 4-bromoquinoline, 32.0 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(5-phenylthiopyridin-3-yl)-2-propenyl group, $R_{3''}$ is acetyl group, $R_{4''}$ is propionyl group, and X is oxygen atom) was obtained from 43.5 mg of the compound of Example 90(b).

Physicochemical Properties of this Compound (1) Molecular formula: $C_{62}H_{93}N_3O_{19}S$ (2) Mass spectrum (FAB): m/z 1215 $(M+H)^+$ (3) $^1H$ NMR spectrum (300 MHz, $CDCl_3$) δ (ppm): 0.90 (d, 8-$CH_3$), 1.05 (d, 6"-H), 1.12 (t, 3-$OCOCH_2CH_3$), 1.17 (t, 4"-$OCOCH_2CH_3$), 1.19 (d, 6'-H), 1.39 (s, 3"-$CH_3$), 1.66 (dd, 2"-Hax), 2.00 (s, 9-$OCOCH_3$), 2.02 (s, 3"-$OCOCH_3$), 2.03 (s, 2'-$OCOCH_3$), 2.20 (s, $NCH_3$), 2.41 (s, 3'-N$(CH_3)_2$), 2.60 (dd, 2-H), 2.60 (t, 3'-H), 2.83 (dd, 2-H), 3.12 (s, $CH(OCH_3)_2$), 3.15 (t, 4'-H), 3.17 (d, 2"-Heq), 3.21 (m, 5'-H), 3.23 (s, $CH(OCH_3)_2$), 3.59 (d, 4-H), 3.59 (s, 4-$OCH_3$), 3.92 (d, 5-H), 4.47 (dq, 5"-H), 4.53 (dd, $CH(OCH_3)_2$), 4.45 (d, 4"-H), 4.68 (d, 1'-H), 4.79 (d, 1"-H), 4.88 (m, 9-H), 4.95 (dd, 2'-H), 5.03 (br t, 3-H), 5.04 (m, 15-H), 6.15 (dt, 15-$CH_2$—CH═CH), 6.34 (d, 15-$CH_2$—CH═CH), 7.32 (m, $C_6H_5$), 7.56 (t, pyriine), 8.33 (d, pyriine), 8.38 (d, pyriine).

(b) In the same manner as in Example 2(c), 11.9 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(5-phenylthiopyridin-3-yl)-2-propenyl group, $R_{3''}$ is acetyl group, $R_{4''}$ is propionyl group, and X is oxygen atom) was obtained from 32.0 mg of the compound of Example 121(a).

Physicochemical Properties of this Compound (1) Molecular formula: $C_{58}H_{89}N_3O_{17}S$ (2) Mass spectrum (FAB): m/z 1132 $(M+H)^+$ (3) $^1H$ NMR spectrum (300 MHz, $CDCl_3$) δ (ppm): 0.86 (d, 8-$CH_3$), 1.07 (d, 6"-H), 1.10 (t, 3-$OCOCH_2CH_3$), 1.18 (t, 4"-$OCOCH_2CH_3$), 1.20 (d, 6'-H), 1.41 (s, 3"-$CH_3$), 1.67 (dd, 2"-Hax), 2.01 (s, 3"-$OCOCH_3$), 2.32 (s, $NCH_3$), 2.39 (q, 3-$OCOCH_2CH_3$), 2.42 (q, 4"-$OCOCH_2CH_3$), 2.53 (s, 3'-N$(CH_3)_2$), 2.58 (dd, 2-H), 2.79 (dd, 2-H), 3.13 (s, $CH(OCH_3)_2$), 3.17 (t, 4'-H), 3.19 (d, 2"-Heq), 3.22 (m, 5'-H), 3.24 (s, $CH(OCH_3)_2$), 3.47 (dd, 2'-H), 3.65 (s, 4-$OCH_3$), 3.87 (d, 4-H), 3.95 (d, 5-H), 4.45 (d, 1'-H), 4.49 (dd, $CH(OCH_3)_2$), 4.54 (dq, 5"-H), 4.57 (d, 4"-H), 4.82 (d, 1"-H), 5.04 (m, 15-H), 5.45 (m, 3-H), 6.13 (dt, 15-$CH_2$—CH═CH), 6.33 (d, 15-$CH_2$—CH═CH), 7.35 (m, $C_6H_5$), 7.55 (t, pyridine), 8.34 (d, pyridine), 8.37 (d, pyridine).

(c) In the same manner as in Example 2(d), 11.0 mg of the title compound was obtained from 11.9 mg of the compound of Example 121(b).

Physicochemical Properties of this Compound (1) Molecular formula: $C_{56}H_{83}N_3O_{16}S$ (2) Mass spectrum (FAB): m/z 1086 $(M+H)^+$ (3) Specific rotation: $[\alpha]_D^{22}$ −54° (c0.92, $CHCl_3$)

(4) $^1H$ NMR spectrum (300 MHz, $CDCl_3$) δ (ppm): 0.88 (d, 8-$CH_3$), 1.08 (d, 6"-H), 1.13 (d, 6'-H), 1.15 (t, 3-$OCOCH_2CH_3$), 1.18 (t, 4"-$OCOCH_2CH_3$), 1.40 (s, 3"-$CH_3$), 1.67 (dd, 2"-Hax), 2.00 (s, 3"-$OCOCH_3$), 2.31 (s, $NCH_3$), 2.42 (q, 3-$OCOCH_2CH_3$), 2.42 (q, 4"-$OCOCH_2CH_3$), 2.53 (s, 3'-N$(CH_3)_2$), 2.62 (dd, 2-H), 2.81 (dd, 2-H), 3.16 (m, 4'-H), 3.16 (m, 5'-H), 3.20 (d, 2"-Heq), 3.35 (m, 9-H), 3.39 (dd, 2'-H), 3.66 (s, 4-$OCH_3$), 3.85 (d, 4-H), 3.95 (d, 5-H), 4.39 (d, 1'-H), 4.52 (dq, 5"-H), 4.57 (d, 4"-H), 4.83 (d, 1"-H), 5.04 (m, 15-H), 5.54 (m, 3-H), 6.13 (dt, 15-$CH_2$—CH═CH), 6.33 (d, 15-$CH_2$—CH═CH), 7.35 (dt, $C_6H_5$), 7.54 (dt, pyridine), 8.34 (dd, pyridine), 8.38 (d, pyridine), 9.64 (s, CHO).

Example 122

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(5-phenylaminopyridin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that the compound of Reference Example 31 was used instead of 4-bromoquinoline, 35.9 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(5-phenylaminopyridin-3-yl)-2-propenyl group, $R_3$ is acetyl group, $R_4$ is propionyl group, and X is oxygen atom) was obtained from 43.5 mg of the compound of Example 90(b).

Physicochemical Properties of this Compound (1) Molecular formula: $C_{62}H_{94}N_4O_{19}$ (2) Mass spectrum (FAB): m/z 1199 $(M+H)^+$ (3) $^1H$ NMR spectrum (300 MHz, $CDCl_3$) δ (ppm): 0.89 (d, 8-$CH_3$), 1.05 (d, 6"-H), 1.11 (t, 3-$OCOCH_2CH_3$), 1.17 (t, 4"-$OCOCH_2CH_3$), 1.18 (d, 6'-H), 1.39 (s, 3"-$CH_3$), 1.65 (dd, 2"-Hax), 2.00 (s, 9-$OCOCH_3$), 2.02 (s, 3"-$OCOCH_3$), 2.03 (s, 2'-$OCOCH_3$), 2.20 (s, $NCH_3$), 2.41 (s, 3'-$N(CH_3)_2$), 2.60 (dd, 2-H), 2.60 (t, 3'-H), 2.84 (dd, 2-H), 3.12 (s, $CH(OCH_3)_2$), 3.15 (t, 4'-H), 3.17 (d, 2"-Heq), 3.22 (m, 5'-H), 3.23 (s, $CH(OCH_3)_2$), 3.58 (d, 4-H), 3.58 (s, 4-$OCH_3$), 3.91 (d, 5-H), 4.47 (dq, 5"-H), 4.54 (dd, $CH(OCH_3)_2$), 4.55 (d, 4"-H), 4.68 (d, 1'-H), 4.79 (d, 1"-H), 4.88 (m, 9-H), 4.95 (dd, 2'-H), 5.04 (br t, 3-H), 5.06 (m, 15-H), 6.13 (dt, 15-$CH_2$—CH═CH), 6.36 (d, 15-$CH_2$—CH═CH), 6.97 (t, $C_6H_5$), 7.02 (dt, $C_6H_5$), 7.29 (d, $C_6H_5$), 7.35 (d, pyridine), 8.04 (d, pyridine), 8.22 (d, pyridine).

(b) In the same manner as in Example 2(c), 13.9 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(5-phenylaminopyridin-3-yl)-2-propenyl group, $R_{3''}$ is acetyl group, $R_{4''}$ is propionyl group, and X is oxygen atom) was obtained from 35.9 mg of the compound of Example 122(a).

Physicochemical Properties of this Compound (1) Molecular formula: $C_{58}H_{90}N_4O_{17}$ (2) Mass spectrum (FAB): m/z 1115 $(M+H)^+$ (3) $^1H$ NMR spectrum (300 MHz, $CDCl_3$) δ (ppm): 0.86 (d, 8-$CH_3$), 1.07 (d, 6"-H), 1.10 (t, 3-$OCOCH_2CH_3$), 1.18 (t, 4"-$OCOCH_2CH_3$), 1.19 (d, 6'-H), 1.40 (s, 3"-$CH_3$), 1.67 (dd, 2"-Hax), 2.00 (s, 3"-$OCOCH_3$), 2.32 (s, $NCH_3$), 2.39 (q, 3-$OCOCH_2CH_3$), 2.42 (q, 4"-$OCOCH_2CH_3$), 2.52 (s, 3'-$N(CH_3)_2$), 2.59 (dd, 2-H), 2.79 (dd, 2-H), 3.13 (s, $CH(OCH_3)_2$), 3.16 (t, 4'-H), 3.19 (d, 2"-Heq), 3.22 (m, 5'-H), 3.24 (s, $CH(OCH_3)_2$), 3.47 (dd, 2'-H), 3.64 (s, 4-$OCH_3$), 3.87 (d, 4-H), 3.94 (d, 5-H), 4.45 (d, 1'-H), 4.48 (dd, $CH(OCH_3)_2$), 4.54 (dq, 5"-H), 4.57 (d, 4"-H), 4.82 (d, 1"-H), 5.05 (m, 15-H), 5.44 (m, 3-H), 6.12 (dt, 15-$CH_2$—CH═CH), 6.35 (d, 15-$CH_2$—CH═CH), 6.99 (tt, $C_6H_5$), 7.07 (dd, $C_6H_5$), 7.29 (dd, $C_6H_5$), 7.34 (t, pyridine), 8.08 (d, pyridine), 8.22 (d, pyridine).

(c) In the same manner as in Example 2(d), 12.3 mg of the title compound was obtained from 13.9 mg of the compound of Example 122(b).

Physicochemical Properties of this Compound (1) Molecular formula: $C_{56}H_{84}N_4O_{16}$ (2) Mass spectrum (FAB): m/z 1069 $(M+H)^+$ (3) Specific rotation: $[\alpha]_D^{22}$ −53° (c1.00, $CHCl_3$)

(4) $^1H$ NMR spectrum (300 MHz, $CDCl_3$) δ (ppm): 0.88 (d, 8-$CH_3$), 1.08 (d, 6"-H), 1.13 (d, 6'-H), 1.15 (t, 3-$OCOCH_2CH_3$), 1.18 (t, 4"-$OCOCH_2CH_3$), 1.40 (s, 3"-$CH_3$), 1.67 (dd, 2"-Hax), 2.00 (s, 3"-$OCOCH_3$), 2.31 (s, $NCH_3$), 2.42 (q, 3-$OCOCH_2CH_3$), 2.42 (q, 4"-$OCOCH_2CH_3$), 2.53 (s, 3'-$N(CH_3)_2$), 2.61 (dd, 2-H), 2.81 (dd, 2-H), 3.18 (m, 4'-H), 3.18 (m, 5'-H), 3.20 (d, 2"-Heq), 3.36 (m, 9-H), 3.39 (dd, 2'-H), 3.65 (s, 4-$OCH_3$), 3.85 (d, 4-H), 3.95 (d, 5-H), 4.38 (d, 1'-H), 4.52 (dq, 5"-H), 4.57 (d, 4"-H), 4.83 (d, 1"-H), 5.06 (m, 15-H), 5.54 (m, 3-H), 5.73 (s, NH), 6.12 (dt, 15-$CH_2$—CH═CH), 6.35 (d, 15-$CH_2$—CH═CH), 6.99 (tt, $C_6H_5$), 7.07 (dt, $C_6H_5$), 7.30 (dt, $C_6H_5$), 7.34 (dt, pyridine), 8.09 (d, pyridine), 8.22 (d, pyridine), 9.64 (s, CHO).

Example 123

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(3-cyano-4-fluorophenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 5-bromo-2-fluorobenzonitrile was used instead of 4-bromoquinoline, 59.7 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(3-cyano-4-fluorophenyl)-2-propenyl group, $R_{3''}$ is acetyl group, $R_{4''}$ is propionyl group, and X is oxygen atom) was obtained from 76.6 mg of the compound of Example 90 (b).

Physicochemical Properties of this Compound (1) Molecular formula: $C_{58}H_{88}FN_3O_{19}$ (2) Mass spectrum (FAB): m/z 1150 $(M+H)^+$ (3) $^1H$ NMR spectrum (300 MHz, $CDCl_3$) δ (ppm): 0.91 (d, 8-$CH_3$), 1.06 (d, 6"-H), 1.13 (t, 3-$OCOCH_2CH_3$), 1.18 (t, 4"-$OCOCH_2CH_3$), 1.19 (d, 6'-H), 1.40 (s, 3"-$CH_3$), 1.66 (dd, 2"-Hax), 2.00 (s, 9-$OCOCH_3$), 2.03 (s, 3"-$OCOCH_3$), 2.04 (s, 2'-$OCOCH_3$), 2.22 (s, $NCH_3$), 2.42 (s, 3'-$N(CH_3)_2$), 2.61 (dd, 2-H), 2.61 (t, 3'-H), 2.84 (dd, 2-H), 3.13 (s, $CH(OCH_3)_2$), 3.15 (t, 4'-H), 3.18 (d, 2"-Heq), 3.22 (m, 5'-H), 3.24 (s, $CH(OCH_3)_2$), 3.54 (d, 4-H), 3.58 (s, 4-$OCH_3$), 3.93 (d, 5-H), 4.48 (dq, 5"-H), 4.52 (dd, $CH(OCH_3)_2$), 4.55 (d, 4"-H), 4.68 (d, 1'-H), 4.79 (d, 1"-H), 4.90 (m, 9-H), 4.96 (dd, 2'-H), 5.06 (br t, 3-H), 5.06 (m, 15-H), 6.13 (dt, 15-$CH_2$—CH═CH), 6.37 (d, 15-$CH_2$—CH═CH), 7.12 (t, $C_6H_3$), 7.54 (m, $C_6H_3$).

(b) In the same manner as in Example 2(c), 38.1 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(3-cyano-4-fluorophenyl)-2-propenyl group, $R_{3''}$ is acetyl group, $R_{4''}$ is propionyl group, and X is oxygen atom) was obtained from 59.7 mg of the compound of Example 123(a).

Physicochemical Properties of this Compound (1) Molecular formula: $C_{54}H_{84}FN_3O_{17}$ (2) Mass spectrum (FAB): m/z 1066 $(M+H)^+$ (3) $^1H$ NMR spectrum (300 MHz, $CDCl_3$) δ (ppm): 0.85 (d, 8-$CH_3$), 1.07 (d, 6"-H), 1.11 (t, 3-$OCOCH_2CH_3$), 1.18 (t, 4"-$OCOCH_2CH_3$), 1.40 (s, 3"-$CH_3$), 1.19 (d, 6'-H), 1.67 (dd, 2"-Hax), 2.01 (s, 3"-$OCOCH_3$), 2.30 (s, $NCH_3$), 2.39 (q, 3-$OCOCH_2CH_3$), 2.42 (q, 4"-$OCOCH_2CH_3$), 2.53 (s, 3'-N$(CH_3)_2$), 2.58 (dd, 2-H), 2.78 (dd, 2-H), 3.13 (s, $CH(OCH_3)_2$), 3.17 (t, 4'-H), 3.19 (d, 2"-Heq), 3.22 (m, 5'-H), 3.24 (s, $CH(OCH_3)_2$), 3.46 (dd, 2'-H), 3.65 (s, 4-$OCH_3$), 3.88 (d, 4-H), 3.94 (d, 5-H), 4.45 (d, 1'-H), 4.48 (dd, $CH(OCH_3)_2$), 4.54 (dq, 5"-H), 4.57 (d, 4"-H), 4.82 (d, 1"-H), 5.06 (m, 15-H), 5.47 (m, 3-H), 6.10 (dt, 15-$CH_2$—CH═CH), 6.35 (d, 15-$CH_2$—CH═CH), 7.13 (t, $C_6H_3$), 7.52 (m, $C_6H_3$).

(c) In the same manner as in Example 2(d), 28.6 mg of the title compound was obtained from 38.1 mg of the compound of Example 123(b).

Physicochemical Properties of this Compound (1) Molecular formula: $C_{52}H_{78}FN_3O_{16}$ (2) Mass spectrum (FAB): m/z 1020 $(M+H)^+$ (3) Specific rotation: $[\alpha]_D^{19}$ −48° (c1.00, $CHCl_3$)

(4) $^1H$ NMR spectrum (300 MHz, $CDCl_3$) δ (ppm): 0.87 (d, 8-$CH_3$), 1.08 (d, 6"-H), 1.13 (d, 6'-H), 1.16 (t, 3-$OCOCH_2CH_3$), 1.18 (t, 4"-$OCOCH_2CH_3$), 1.40 (s, 3"-$CH_3$), 1.68 (dd, 2"-Hax), 2.00 (s, 3"-$OCOCH_3$), 2.30 (s, $NCH_3$), 2.42 (q, 3-$OCOCH_2CH_3$), 2.42 (q, 4"-$OCOCH_2CH_3$), 2.53 (s, 3'-N$(CH_3)_2$), 2.62 (dd, 2-H), 2.80 (dd, 2-H), 3.18 (m, 4'-H), 3.18 (m, 5'-H), 3.21 (d, 2"-Heq), 3.35 (m, 9-H), 3.38 (dd, 2'-H), 3.66 (s, 4-$OCH_3$), 3.86 (d, 4-H), 3.94 (d, 5-H), 4.39 (d, 1'-H), 4.54 (dq, 5"-H), 4.57 (d, 4"-H), 4.83 (d, 1"-H), 5.06 (m, 15-H), 5.56 (m, 3-H), 6.10 (dt, 15-$CH_2$—CH═CH), 6.35 (d, 15-$CH_2$—CH═CH), 7.13 (t, $C_6H_3$), 7.52 (m, $C_6H_3$), 9.64 (s, CHO).

Example 124

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(4-hydroxyphenyl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that 4-iodophenol was used instead of 4-bromoquinoline, 31.9 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(4-hydroxyphenyl)-2-propenyl group, $R_{3''}$ is acetyl group, $R_{4''}$ is propionyl group, and X is oxygen atom) was obtained from 75.3 mg of the compound of Example 90(b).

Physicochemical Properties of this Compound (1) Molecular formula: $C_{57}H_{90}N_2O_{20}$ (2) Mass spectrum (FAB): m/z 1123 $(M+H)^+$ (3) $^1H$ NMR spectrum (300 MHz, $CDCl_3$) δ (ppm): 0.90 (d, 8-$CH_3$), 1.05 (d, 6"-H), 1.12 (t, 3-$OCOCH_2CH_3$), 1.18 (t, 4"-$OCOCH_2CH_3$), 1.19 (d, 6'-H), 1.40 (s, 3"-$CH_3$), 1.66 (dd, 2"-Hax), 2.01 (s, 9-$OCOCH_3$), 2.02 (s, 3"-$OCOCH_3$), 2.03 (s, 2'-$OCOCH_3$), 2.24 (s, $NCH_3$), 2.42 (s, 3'-N$(CH_3)_2$), 2.60 (dd, 2-H), 2.60 (t, 3'-H), 2.84 (dd, 2-H), 3.14 (s, $CH(OCH_3)_2$), 3.15 (t, 4'-H), 3.18 (d, 2"-Heq), 3.22 (m, 5'-H), 3.24 (s, $CH(OCH_3)_2$), 3.59 (s, 4-$OCH_3$), 3.62 (d, 4-H), 3.91 (d, 5-H), 4.47 (dq, 5"-H), 4.54 (dd, $CH(OCH_3)_2$), 4.55 (d, 4"-H), 4.68 (d, 1'-H), 4.79 (d, 1"-H), 4.92 (m, 9-H), 4.95 (dd, 2'-H), 5.03 (br t, 3-H), 5.03 (m, 15-H), 5.90 (dt, 15-$CH_2$—CH═CH), 6.32 (d, 15-$CH_2$—CH═CH), 6.73 (d, $C_6H_4$), 7.17 (d, $C_6H_4$).

(b) In the same manner as in Example 2(c), 17.6 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(4-hydroxyphenyl)-2-propenyl group, $R_{3''}$ is acetyl group, $R_{4''}$ is propionyl group, and X is oxygen atom) was obtained from 31.9 mg of the compound of Example 124(a).

Physicochemical Properties of this Compound (1) Molecular formula: $C_{53}H_{86}N_2O_{18}$ (2) Mass spectrum (FAB): m/z 1039 $(M+H)^+$ (3) $^1H$ NMR spectrum (300 MHz, $CDCl_3$) δ (ppm): 0.87 (d, 8-$CH_3$), 1.08 (d, 6"-H), 1.11 (t, 3-$OCOCH_2CH_3$), 1.20 (t, 4"-$OCOCH_2CH_3$), 1.21 (d, 6'-H), 1.42 (s, 3"-$CH_3$), 1.68 (dd, 2"-Hax), 2.02 (s, 3"-$OCOCH_3$), 2.31 (s, $NCH_3$), 2.41 (q, 3-$OCOCH_2CH_3$), 2.43 (q, 4"-$OCOCH_2CH_3$), 2.54 (s, 3'-N$(CH_3)_2$), 2.60 (dd, 2-H), 2.80 (dd, 2-H), 3.15 (s, $CH(OCH_3)_2$), 3.19 (t, 4'-H), 3.21 (d, 2"-Heq), 3.24 (m, 5'-H), 3.25 (s, $CH(OCH_3)_2$), 3.49 (dd, 2'-H), 3.64 (s, 4-$OCH_3$), 3.88 (d, 4-H), 3.99 (d, 5-H), 4.46 (d, 1'-H), 4.49 (dd, $CH(OCH_3)_2$), 4.56 (dq, 5"-H), 4.59 (d, 4"-H), 4.83 (d, 1"-H), 5.06 (m, 15-H), 5.47 (m, 3-H), 5.93 (dt, 15-$CH_2$—CH═CH), 6.34 (d, 15-$CH_2$—CH═CH), 6.76 (d, $C_6H_4$), 7.20 (d, $C_6H_4$).

(c) In the same manner as in Example 2(d), 12.3 mg of the title compound was obtained from 17.6 mg of the compound of Example 124(b).

Physicochemical Properties of this Compound (1) Molecular formula: $C_{51}H_{80}N_2O_{17}$ (2) Mass spectrum (FAB): m/z 993 $(M+H)^+$ (3) Specific rotation: $[\alpha]_D^{19}$ −54° (c1.00, $CHCl_3$)

(4) $^1H$ NMR spectrum (300 MHz, $CDCl_3$) δ (ppm): 0.88 (d, 8-$CH_3$), 1.08 (d, 6"-H), 1.13 (d, 6'-H), 1.15 (t, 3-$OCOCH_2CH_3$), 1.18 (t, 4"-$OCOCH_2CH_3$), 1.40 (s, 3"-$CH_3$), 1.67 (dd, 2"-Hax), 2.00 (s, 3"-$OCOCH_3$), 2.30 (s, $NCH_3$), 2.42 (q, 3-$OCOCH_2CH_3$), 2.42 (q, 4"-$OCOCH_2CH_3$), 2.53 (s, 3'-N$(CH_3)_2$), 2.59 (dd, 2-H), 2.81 (dd, 2-H), 3.17 (m, 4'-H), 3.18 (m, 5'-H), 3.21 (d, 2"-Heq), 3.36 (m, 9-H), 3.39 (dd, 2'-H), 3.64 (s, 4-$OCH_3$), 3.85 (d, 4-H), 3.98 (d, 5-H), 4.38 (d, 1'-H), 4.52 (dq, 5"-H), 4.57 (d, 4"-H), 4.82 (d, 1"-H), 5.05 (m, 15-H), 5.54 (m, 3-H), 5.92 (dt, 15-$CH_2$—CH═CH), 6.32 (d, 15-$CH_2$—CH═CH), 6.75 (d, $C_6H_4$), 7.19 (d, $C_6H_4$), 9.63 (s, CHO).

Example 125

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(5-aminocarbonylpyridin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that the compound of Reference Example 32 was used instead of 4-bromoquinoline, 24.2 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(5-aminocarbonylpyridin-3-yl)-2-propenyl group, $R_{3''}$ is acetyl group, $R_{4''}$ is propionyl group, and X is oxygen atom) was obtained from 43.5 mg of the compound of Example 90(b).

Physicochemical Properties of this Compound (1) Molecular formula: $C_{57}H_{90}N_4O_{20}$ (2) Mass spectrum (FAB): m/z 1151 $(M+H)^+$ (3) $^1$H NMR spectrum (300 MHz, $CDCl_3$) δ (ppm): 0.89 (d, 8-$CH_3$), 1.05 (d, 6"-H), 1.10 (t, 3-$OCOCH_2CH_3$), 1.17 (t, 4"-$OCOCH_2CH_3$), 1.19 (d, 6'-H), 1.39 (s, 3"-$CH_3$), 1.66 (dd, 2"-Hax), 2.00 (s, 9-$OCOCH_3$), 2.01 (s, 3"-$OCOCH_3$), 2.02 (s, 2'-$OCOCH_3$), 2.23 (s, $NCH_3$), 2.41 (s, 3'-$N(CH_3)_2$), 2.59 (t, 3'-H), 2.62 (dd, 2-H), 2.86 (dd, 2-H), 3.10 (s, $CH(OCH_3)_2$), 3.13 (t, 4'-H), 3.17 (d, 2"-Heq), 3.22 (m, 5'-H), 3.22 (s, $CH(OCH_3)_2$), 3.49 (d, 4-H), 3.57 (s, 4-$OCH_3$), 3.91 (d, 5-H), 4.47 (dq, 5"-H), 4.51 (dd, $CH(OCH_3)_2$), 4.55 (d, 4"-H), 4.67 (d, 1'-H), 4.79 (d, 1"-H), 4.88 (m, 9-H), 4.95 (dd, 2'-H), 5.10 (br t, 3-H), 5.10 (m, 15-H), 5.82 (br s, $NH_2$), 6.34 (dt, 15-$CH_2$—CH═CH), 6.46 (d, 15-$CH_2$—CH═CH), 6.65 (br s, $NH_2$), 8.19 (t, pyridine), 8.63 (d, pyridine), 8.86 (d, pyridine).

(b) In the same manner as in Example 2(c), 12.2 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(5-aminocarbonylpyridin-3-yl)-2-propenyl group, $R_{3''}$ is acetyl group, $R_4$ is propionyl group, and X is oxygen atom) was obtained from 24.2 mg of the compound of Example 125(a).

Physicochemical Properties of this Compound (1) Molecular formula: $C_{53}H_{86}N_4O_{18}$ (2) Mass spectrum (FAB): m/z 1067 $(M+H)^+$ (3) $^1$H NMR spectrum (300 MHz, $CDCl_3$) δ (ppm): 0.86 (d, 8-$CH_3$), 1.07 (d, 6"-H), 1.09 (t, 3-$OCOCH_2CH_3$), 1.18 (t, 4"-$OCOCH_2CH_3$), 1.19 (d, 6'-H), 1.40 (s, 3"-$CH_3$), 1.67 (dd, 2"-Hax), 2.00 (s, 3"-$OCOCH_3$), 2.31 (s, $NCH_3$), 2.39 (q, 3-$OCOCH_2CH_3$), 2.42 (q, 4"-$OCOCH_2CH_3$), 2.52 (s, 3'-$N(CH_3)_2$), 2.60 (dd, 2-H), 2.81 (dd, 2-H), 3.11 (s, $CH(OCH_3)_2$), 3.17 (t, 4'-H), 3.19 (d, 2"-Heq), 3.21 (m, 5'-H), 3.23 (s, $CH(OCH_3)_2$), 3.45 (dd, 2'-H), 3.66 (s, 4-$OCH_3$), 3.86 (s, 4-H), 3.86 (s, 5-H), 4.45 (d, 1'-H), 4.48 (dd, $CH(OCH_3)_2$), 4.53 (dq, 5"-H), 4.57 (d, 4"-H), 4.83 (d, 1"-H), 5.08 (m, 15-H), 5.45 (m, 3-H), 6.33 (dt, 15-$CH_2$—CH═CH), 6.46 (d, 15-$CH_2$—CH═CH), 8.17 (t, pyridine), 8.63 (d, pyridine), 8.85 (d, pyridine).

(c) In the same manner as in Example 2(d), 9.2 mg of the title compound was obtained from 12.2 mg of the compound of Example 125(b).

Physicochemical Properties of this Compound (1) Molecular formula: $C_{51}H_{80}N_4O_{17}$ (2) Mass spectrum (FAB): m/z 1021 $(M+H)^+$ (3) Specific rotation: $[\alpha]_D^{21}$ −59° (c0.77, $CHCl_3$)

(4) $^1$H NMR spectrum (300 MHz, $CDCl_3$) δ (ppm): 0.87 (d, 8-$CH_3$), 1.07 (d, 6"-H), 1.13 (d, 6'-H), 1.14 (t, 3-$OCOCH_2CH_3$), 1.18 (t, 4"-$OCOCH_2CH_3$), 1.40 (s, 3"-$CH_3$), 1.68 (dd, 2"-Hax), 1.99 (s, 3"-$OCOCH_3$), 2.31 (s, $NCH_3$), 2.42 (q, 3-$OCOCH_2CH_3$), 2.42 (q, 4"-$OCOCH_2CH_3$), 2.53 (s, 3'-$N(CH_3)_2$), 2.60 (dd, 2-H), 2.83 (dd, 2-H), 3.17 (m, 4'-H), 3.17 (m, 5'-H), 3.20 (d, 2"-Heq), 3.35 (m, 9-H), 3.37 (dd, 2'-H), 3.65 (s, 4-$OCH_3$), 3.85 (s, 4-H), 3.85 (s, 5-H), 4.38 (d, 1'-H), 4.51 (dq, 5"-H), 4.57 (d, 4"-H), 4.83 (d, 1"-H), 5.08 (m, 15-H), 5.54 (m, 3-H), 6.32 (dt, 15-$CH_2$—CH═CH), 6.46 (d, 15-$CH_2$—CH═CH), 8.17 (t, pyridine), 8.62 (d, pyridine), 8.85 (d, pyridine), 9.62 (s, CHO).

Example 126

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_5$, $R_{10}$ and $R_{12}$ are hydrogen atoms, $R_{11}$ is trans-3-(5-diethylaminocarbonylpyridin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that the compound of Reference Example 33 was used instead of 4-bromoquinoline, 28.5 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(5-diethylaminocarbonylpyridin-3-yl)-2-propenyl group, $R_{3'}$ is acetyl group, $R_{4''}$ is propionyl group, and X is oxygen atom) was obtained from 43.5 mg of the compound of Example 90(b).

Physicochemical Properties of this Compound (1) Molecular formula: $C_{61}H_{98}N_4O_{20}$ (2) Mass spectrum (FAB): m/z 1207 $(M+H)^+$ (3) $^1$H NMR spectrum (300 MHz, $CDCl_3$) δ (ppm): 0.90 (d, 8-$CH_3$), 1.05 (d, 6"-H), 1.12 (t, 3-$OCOCH_2CH_3$), 1.17 (t, 4"-$OCOCH_2CH_3$), 1.18 (d, 6'-H), 1.38 (s, 3"-$CH_3$), 1.65 (dd, 2"-Hax), 2.00 (s, 9-$OCOCH_3$), 2.02 (s, 3"-$OCOCH_3$), 2.03 (s, 2'-$OCOCH_3$), 2.20 (s, $NCH_3$), 2.41 (s, 3'-$N(CH_3)_2$), 2.59 (dd, 2-H), 2.59 (t, 3'-H), 2.84 (dd, 2-H), 3.12 (s, $CH(OCH_3)_2$), 3.14 (t, 4'-H), 3.17 (d, 2"-Heq), 3.22 (m, 5'-H), 3.23 (s, $CH(OCH_3)_2$), 3.54 (d, 4-H), 3.59 (s, 4-$OCH_3$), 3.91 (d, 5-H), 4.46 (dq, 5"-H), 4.53 (dd, $CH(OCH_3)_2$), 4.54 (d, 4"-H), 4.68 (d, 1'-H), 4.78 (d, 1"-H), 4.88 (m, 9-H), 4.95 (dd, 2'-H), 5.04 (br t, 3-H), 5.08 (m, 15-H), 6.22 (dt, 15-$CH_2$—CH═CH), 6.42 (d, 15-$CH_2$—CH═CH), 7.66 (t, pyridine), 8.43 (d, pyridine), 8.54 (d, pyridine).

(b) In the same manner as in Example 2(c), 11.7 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(5-diethylaminocarbonylpyridin-3-yl)-2-propenyl group, $R_{3''}$ is acetyl group, $R_{4''}$ is propionyl group, and X is oxygen atom) was obtained from 28.5 mg of the compound of Example 126(a).

Physicochemical Properties of this Compound (1) Molecular formula: $C_{57}H_{94}N_4O_{18}$ (2) Mass spectrum (FAB): m/z 1123 $(M+H)^+$ (3) $^1$H NMR spectrum (300 MHz, $CDCl_3$) δ (ppm): 0.86 (d, 8-$CH_3$), 1.07 (d, 6"-H), 1.11 (t, 3-$OCOCH_2CH_3$), 1.18 (t, 4"-$OCOCH_2CH_3$), 1.19 (d, 6'-H), 1.40 (s, 3"-$CH_3$), 1.67 (dd, 2"-Hax), 2.00 (s, 3"-$OCOCH_3$), 2.30 (s, $NCH_3$), 2.39 (q, 3-$OCOCH_2CH_3$), 2.42 (q, 4"-$OCOCH_2CH_3$), 2.52 (s, 3'-$N(CH_3)_2$), 2.59 (dd, 2-H), 2.81 (dd, 2-H), 3.13 (s, $CH(OCH_3)_2$), 3.16 (t, 4'-H), 3.19 (d, 2"-Heq), 3.22 (m, 5'-H), 3.24 (s, $CH(OCH_3)_2$), 3.47 (dd, 2'-H), 3.67 (s, 4-$OCH_3$), 3.87 (d, 4-H), 3.94 (d, 5-H), 4.45 (d, 1'-H), 4.47 (dd, $CH(OCH_3)_2$), 4.54 (dq, 5"-H), 4.57 (d, 4"-H), 4.82 (d, 1"-H), 5.06 (m, 15-H), 5.45 (m, 3-H), 6.23 (dt, 15-$CH_2$—CH═CH), 6.41 (d, 15-$CH_2$—CH═CH), 7.66 (t, pyridine), 8.44 (d, pyridine), 8.54 (d, pyridine).

(c) In the same manner as in Example 2(d), 10.3 mg of the title compound was obtained from 11.7 mg of the compound of Example 126(b).

Physicochemical Properties of this Compound (1) Molecular formula: $C_{55}H_{88}N_4O_{17}$ (2) Mass spectrum (FAB): m/z 1077 $(M+H)^+$ (3) Specific rotation: $[\alpha]_D^{22}$ −56° (c0.86, $CHCl_3$)

(4) $^1$H NMR spectrum (300 MHz, $CDCl_3$) δ (ppm): 0.88 (d, 8-$CH_3$), 1.07 (d, 6"-H), 1.13 (d, 6'-H), 1.16 (t, 3-$OCOCH_2CH_3$), 1.18 (t, 4"-$OCOCH_2CH_3$), 1.40 (s, 3"-$CH_3$), 1.67 (dd, 2"-Hax), 2.00 (s, 3"-$OCOCH_3$), 2.32 (s, $NCH_3$), 2.42 (q, 3-$OCOCH_2CH_3$), 2.42 (q, 4"-$OCOCH_2CH_3$), 2.53 (s, 3'-$N(CH_3)_2$), 2.60 (dd, 2-H), 2.83 (dd, 2-H), 3.16 (m, 4'-H), 3.16 (m, 5'-H), 3.20 (d, 2"-Heq), 3.35 (m, 9-H), 3.39 (dd, 2'-H), 3.55 (m, $N(CH_2CH_3)_2$), 3.67 (s, 4-$OCH_3$), 3.86 (d, 4-H), 3.94 (d, 5-H), 4.39 (d, 1'-H), 4.52 (dq, 5"-H), 4.57 (d, 4"-H), 4.83 (d, 1"-H), 5.06 (m, 15-H), 5.55 (m, 3-H), 6.22 (dt, 15-$CH_2$—CH═CH), 6.42 (d, 15-$CH_2$—CH═CH), 7.66 (t, pyridine), 8.44 (d, pyridine), 8.54 (d, pyridine), 9.64 (s, CHO).

Example 127

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(5-(N,O-dimethylhydroxyaminocarbonyl)pyridin-3-yl)-2-propenyl group, $R_{4'}$ is a group represented by the formula (a), $R_{3''}$ is acetyl group, $R_{4''}$ is propionyl group, and X is oxygen atom (a) In the same manner as in Example 48(c), except that the compound of Reference Example 34 was used instead of 4-bromoquinoline, 33.7 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-3-(5-(N,O-dimethylhydroxyaminocarbonyl)pyridin-3-yl)-2-prop enyl group, $R_{3''}$ is acetyl group, $R_{4''}$ is propionyl group, and X is oxygen atom) was obtained from 43.5 mg of the compound of Example 90(b).

Physicochemical Properties of this Compound (1) Molecular formula: $C_{59}H_{94}N_4O_{21}$ (2) Mass spectrum (FAB): m/z 1195 $(M+H)^+$ (3) $^1$H NMR spectrum (300 MHz, $CDCl_3$) δ (ppm): 0.90 (d, 8-$CH_3$), 1.05 (d, 6"-H), 1.12 (t, 3-$OCOCH_2CH_3$), 1.17 (t, 4"-$OCOCH_2CH_3$), 1.18 (d, 6'-H), 1.38 (s, 3"-$CH_3$), 1.65 (dd, 2"-Hax), 2.00 (s, 9-$OCOCH_3$), 2.02 (s, 3"-$OCOCH_3$), 2.03 (s, 2'-$OCOCH_3$), 2.20 (s, $NCH_3$), 2.41 (s, 3'-$N(CH_3)_2$), 2.59 (dd, 2-H), 2.59 (t, 3'-H), 2.84 (dd, 2-H), 3.12 (s, $CH(OCH_3)_2$), 3.14 (t, 4'-H), 3.17 (d, 2"-Heq), 3.21 (m, 5'-H), 3.23 (s, $CH(OCH_3)_2$), 3.37 (s, $N(CH_3)OCH_3$), 3.55 (s, $N(CH_3)OCH_3$), 3.59 (s, 4-$OCH_3$), 3.91 (d, 5-H), 4.47 (dq, 5"-H), 4.53 (dd, $CH(OCH_3)_2$), 4.54 (d, 4"-H), 4.68 (d, 1'-H), 4.78 (d, 1"-H), 4.89 (m, 9-H), 4.95 (dd, 2'-H), 5.03 (br t, 3-H), 5.07 (m, 15-H), 6.24 (dt, 15-$CH_2$—CH═CH), 6.44 (d, 15-$CH_2$—CH═CH), 7.95 (t, pyridine), 8.59 (d, pyridine), 8.74 (d, pyridine).

(b) In the same manner as in Example 2(c), 15.4 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(5-(N,O-dimethylhydroxyaminocarbonyl)pyridin-3-yl)-2-propenyl group, $R_{3''}$ is acetyl group, $R_{4''}$ is propionyl group, and X is oxygen atom) was obtained from 33.7 mg of the compound of Example 127(a).

Physicochemical Properties of this Compound (1) Molecular formula: $C_{55}H_{90}N_4O_{19}$ (2) Mass spectrum (FAB): m/z 1111 $(M+H)^+$ (3) $^1$H NMR spectrum (300 MHz, $CDCl_3$) δ (ppm): 0.86 (d, 8-$CH_3$), 1.07 (d, 6"-H), 1.10 (t, 3-$OCOCH_2CH_3$), 1.18 (t, 4"-$OCOCH_2CH_3$), 1.19 (d, 6'-H), 1.40 (s, 3"-$CH_3$), 1.67 (dd, 2"-Hax), 2.00 (s, 3"-$OCOCH_3$), 2.31 (s, $NCH_3$), 2.39 (q, 3-$OCOCH_2CH_3$), 2.41 (q, 4"-$OCOCH_2CH_3$), 2.52 (s, 3'-$N(CH_3)_2$), 2.59 (dd, 2-H), 2.80 (dd, 2-H), 3.13 (s, $CH(OCH_3)_2$), 3.16 (t, 4'-H), 3.19 (d, 2"-Heq), 3.22 (m, 5'-H), 3.24 (s, $CH(OCH_3)_2$), 3.38 (s, $N(CH_3)$ $OCH_3$), 3.47 (dd, 2'-H), 3.55 (s, $N(CH_3)$ $OCH_3$), 3.66 (s, 4-$OCH_3$), 3.87 (d, 4-H), 3.95 (d, 5-H), 4.45 (d, 1'-H), 4.48 (dd, $CH(OCH_3)_2$), 4.54 (dq, 5"-H), 4.57 (d, 4"-H), 4.82 (d, 1"-H), 5.07 (m, 15-H), 5.45 (m, 3-H), 6.24 (dt, 15-$CH_2$—CH═CH), 6.43 (d, 15-$CH_2$—CH═CH), 7.95 (t, pyridine), 8.58 (d, pyridine), 8.75 (d, pyridine).

(c) In the same manner as in Example 2(d), 11.8 mg of the title compound was obtained from 15.4 mg of the compound of Example 127(b).

Physicochemical Properties of this Compound (1) Molecular formula: $C_{53}H_{84}N_4O_{18}$ (2) Mass spectrum (FAB): m/z 1065 $(M+H)^+$ (3) Specific rotation: $[\alpha]_D^{22}$ −59° (c0.98, $CHCl_3$)

(4) $^1$H NMR spectrum (300 MHz, $CDCl_3$) δ (ppm): 0.88 (d, 8-$CH_3$), 1.07 (d, 6"-H), 1.13 (d, 6'-H), 1.15 (t, 3-$OCOCH_2CH_3$), 1.18 (t, 4"-$OCOCH_2CH_3$), 1.40 (s, 3"-$CH_3$), 1.67 (dd, 2"-Hax), 2.00 (s, 3"-$OCOCH_3$), 2.31 (s, $NCH_3$), 2.42 (q, 3-$OCOCH_2CH_3$), 2.42 (q, 4"-$OCOCH_2CH_3$), 2.53 (s, 3'-$N(CH_3)_2$), 2.62 (dd, 2-H), 2.83 (dd, 2-H), 3.16 (m, 4'-H), 3.16 (m, 5'-H), 3.20 (d, 2"-Heq), 3.38 (s, $N(CH_3)OCH_3$), 3.55 (s, $N(CH_3)OCH_3$), 3.66 (s, 4-$OCH_3$), 3.85 (d, 4-H), 3.95 (d, 5-H), 4.39 (d, 1'-H), 4.51 (dq, 5"-H), 4.57 (d, 4"-H), 4.83 (d, 1"-H), 5.07 (m, 15-H), 5.54 (m, 3-H), 6.24 (dt, 15-$CH_2$—CH═CH), 6.43 (d, 15-$CH_2$—CH═CH), 7.95 (t, pyridine), 8.59 (d, pyridine), 8.76 (d, pyridine), 9.64 (s, CHO).

Example 128

Preparation method of the compound represented by the formula (3) wherein $R_1$ and $R_2$ are hydrogen atoms, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_1$ is trans-3-(quinolin-3-yl)-2-propenyl group, $R_{4'}$ is a group represented by the formula (a), $R_{3''}$ is propionyl group, $R_{4''}$ is n-butyryl group, and X is oxygen atom (a) In the same manner as in Example 2(a), except that the compound of Reference Example 22 was used instead of the compound of Reference Example 1, 335 mg of an amine compound (compound represented by the formula (30) mentioned in Preparation Scheme 10 wherein $R_3$ is methyl group, $R_7$, $R_8$ and $R_{12}$ are hydrogen atoms, $R_{11}$ is allyl group, $R_{3''}$ is propionyl group, $R_{4''}$ is n-butyryl group, and X is hydroxyl group) was obtained from 445 mg of the compound of Example 69.

Physicochemical Properties of this Compound (1) Molecular formula: $C_{55}H_{88}N_2O_{19}$ (2) Mass spectrum (FAB): m/z 1021 $(M+H)^+$ (3) Specific rotation: $[\alpha]_D^{19}$ −86° (c1.0, $CHCl_3$)

(4) $^1$H NMR spectrum (300 MHz, $CDCl_3$) δ (ppm): 0.87 (d, 8-$CH_3$), 0.98 (t, 4"-$OCOCH_2CH_2CH_3$), 1.07 (d, 6"-H), 1.16 (t, 3"-$OCOCH_2CH_3$), 1.22 (d, 6'-H), 1.42 (s, 3"-$CH_3$), 1.70 (m, 4"-$OCOCH_2CH_2CH_3$), 2.05 (s, 9-$OCOCH_3$), 2.05 (s, 2'-$OCOCH_3$), 2.38 (t, 4"-$OCOCH_2CH_2CH_3$), 2.42 (s, 3'-N($CH_3$)$_2$), 2.47 (s, $NCH_3$), 2.60 (m, 3'-H), 2.99 (br d, 10-H), 3.13 (t, 4'-H), 3.33 (s, CH($OCH_3$)$_2$), 3.34 (s, CH($OCH_3$)$_2$), 3.54 (s, 4-$OCH_3$), 3.66 (m, 15-H), 3.89 (br d, 5-H), 3.99 (br dd, 3-H), 4.48 (dq, 5"-H), 4.57 (d, 4"-H), 4.61 (d, 1'-H), 4.65 (dd, CH($OCH_3$)$_2$), 4.81 (d, 1"-H), 4.95 (dd, 2'-H), 5.09 (m, CH═$CH_2$), 5.14 (m, 9-H), 5.82 (ddt, CH═$CH_2$).

(b) In the same manner as in Example 48(b), 220 mg of a cyclized compound (compound represented by the formula (31) mentioned in Preparation Scheme 10 wherein $R_3$ is methyl group, $R_7$, $R_8$ and $R_{12}$ are hydrogen atoms, $R_{11}$ is allyl group, $R_3$ is propionyl group, $R_{4''}$ is n-butyryl group, and X is oxygen atom) was obtained from 330 mg of the compound of Example 128(a).

Physicochemical Properties of this Compound (1) Molecular formula: $C_{50}H_{86}N_2O_{18}$ (2) Mass spectrum (FAB): m/z 1003 $(M+H)^+$ (3) Specific rotation: $[\alpha]_D^{19}$ −57° (c1.0, $CHCl_3$)

(4) $^1$H NMR spectrum (300 MHz, $CDCl_3$) δ (ppm): 0.95 (d, 8-$CH_3$), 0.98 (t, 4"-$OCOCH_2CH_2CH_3$), 1.07 (d, 6"-H), 1.15 (t, 3"-$OCOCH_2CH_3$), 1.17 (d, 6'-H), 1.42 (s, 3"-$CH_3$), 1.70 (t, 4"-$OCOCH_2CH_2CH_3$), 2.03 (s, 9-$OCOCH_3$), 2.03 (s, 2'-$OCOCH_3$), 2.42 (s, 3'-N($CH_3$)$_2$), 2.57 (t, 3'-H), 2.72 (dd, 2-H), 3.11 (t, 4'-H), 3.20 (d, 2"-Heq), 3.32 (s, CH($OCH_3$)$_2$), 3.38 (s, CH($OCH_3$)$_2$), 3.49 (s, 4-$OCH_3$), 4.03 (br d, 5-H), 4.13 (m, 3-H), 4.48 (dq, 5"-H), 4.57 (d, 4"-H), 4.67 (d, 1'-H), 4.80 (d, 1"-H), 4.94 (dd, 2'-H), 5.09 (m, CH═$CH_2$), 5.75 (ddt, CH═$CH_2$).

(c) In the same manner as in Example 48(c), except that 3-bromoquinoline was used instead of 4-bromoquinoline, 45 mg of a coupling compound (compound represented by the formula (31) mentioned in Preparation Scheme 10 wherein $R_3$ is methyl group, $R_7$, $R_8$ and $R_{12}$ are hydrogen atoms, $R_{11}$ is trans-3-(quinolin-3-yl)-2-propenyl group, $R_{3''}$ is propionyl group, $R_{4''}$ is n-butyryl group, and X is oxygen atom) was obtained from 70 mg of the compound of Example 128(b).

Physicochemical Properties of this Compound (1) Molecular formula: $C_{53}H_{81}N_3O_{15}$ (2) Mass spectrum (FAB): m/z 1000 $(M+H)^+$ (3) Specific rotation: $[\alpha]_D^{21}$ −55° (c0.48, $CHCl_3$)

(4) $^1$H NMR spectrum (300 MHz, $CDCl_3$) δ (ppm): 0.95 (d, 8-$CH_3$), 0.98 (t, 4"-$OCOCH_2CH_2CH_3$), 1.07 (d, 6"-H), 1.15 (t, 3"-$OCOCH_2CH_3$), 1.17 (d, 6'-H), 1.42 (s, 3"-$CH_3$), 1.70 (t, 4"-$OCOCH_2CH_2CH_3$), 2.02 (s, 9-$OCOCH_3$), 2.03 (s, 2'-$OCOCH_3$), 2.15 (s, $NCH_3$), 2.38 (t, 4"-$OCOCH_2CH_2CH_3$), 2.41 (s, 3'-N($CH_3$)$_2$), 2.60 (t, 3'-H), 2.76 (dd, 2-H), 3.11 (t, 4'-H), 3.25 (d, 2"-Heq), 3.28 (s, CH($OCH_3$)$_2$), 3.35 (s, CH($OCH_3$)$_2$), 3.49 (s, 4-$OCH_3$), 4.04 (br d, 5-H), 4.14 (m, 3-H), 4.48 (dq, 5"-H), 4.57 (d, 4"-H), 4.66 (d, 1'-H), 4.80 (d, 1"-H), 4.94 (dd, 2'-H), 5.07 (m, 15-H), 5.24 (m, 9-H), 6.39 (dt, CH═CH), 6.61 (d, CH═CH), 7.53 (ddd, quinoline), 7.66 (ddd, quinoline), 7.79 (br d, quinoline), 8.02 (d, quinoline), 8.06 (br d, quinoline), 8.95 (d, quinoline).

(d) In the same manner as in Example 2(c), 28 mg of a deacetyled compound (compound represented by the formula (32) mentioned in Preparation Scheme 10 wherein $R_2$ is hydrogen atom, $R_3$ is methyl group, $R_7$, $R_8$ and $R_{12}$ are hydrogen atoms, $R_{11}$ is trans-3-(quinolin-3-yl)-2-propenyl group, $R_{3'}$ is propionyl group, $R_{4''}$ is n-butyryl group, and X is oxygen atom) was obtained from 44 mg of the compound of Example 128(c).

Physicochemical Properties of this Compound (1) Molecular formula: $C_{55}H_{87}N_3O_{16}$ (2) Mass spectrum (FAB): m/z 1046 $(M+H)^+$ (3) $^1$H NMR spectrum (300 MHz, $CDCl_3$) δ (ppm): 0.89 (d, 8-$CH_3$), 0.98 (t, 4"-$OCOCH_2CH_2CH_3$), 1.09 (d, 6"-H), 1.13 (t, 3"-$OCOCH_2CH_3$), 1.22 (d, 6'-H), 1.42 (s, 3"-$CH_3$), 1.70 (t, 4"-$OCOCH_2CH_2CH_3$), 1.93 (br dd, 6-$CH_2$), 2.30 (s, $NCH_3$), 2.39 (t, 3'-H), 2.53 (s, 3'-N($CH_3$)$_2$), 3.15 (t, 4'-H), 3.21 (dq, 5'-H), 3.22 (d, 2"-Heq), 3.29 (each s, CH($OCH_3$)$_2$), 3.38 (m, 9-H), 3.50 (dd, 2'-H), 3.61 (s, 4-$OCH_3$), 3.64 (br d, 4-H), 3.98 (br d, 5-H), 4.31 (m, 3-H), 4.40 (d, 1'-H), 4.55 (m, 5"-H), 4.59 (m, 4"-H), 4.83 (d, 1"-H), 5.13 (m, 15-H), 6.38 (dt, CH═CH), 6.60 (d, CH═CH), 7.53 (ddd, quinoline), 7.67 (ddd, quinoline), 7.79 (br d, quinoline), 8.01 (d, quinoline), 8.06 (br d, quinoline), 8.94 (d, quinoline).

(e) In the same manner as in Example 2(d), 23 mg of the title compound was obtained from 28 mg of the compound of Example 128(d).

Physicochemical Properties of this Compound (1) Molecular formula: $C_{53}H_{81}N_3O_{15}$ (2) Mass spectrum (FAB): m/z 1000 $(M+H)^+$ (3) Specific rotation: $[\alpha]_D^{21}$ −55° (c0.48, $CHCl_3$)

(4) $^1$H NMR spectrum (300 MHz, $CDCl_3$) δ (ppm): 0.89 (d, 8-$CH_3$), 0.98 (t, 4"-$OCOCH_2CH_2CH_3$), 1.09 (d, 6"-H), 1.12 (t, 3"-$OCOCH_2CH_3$), 1.17 (d, 6'-H), 1.42 (s, 3"-$CH_3$), 1.70 (m, 4"-$OCOCH_2CH_2CH_3$), 2.31 (s, $NCH_3$), 2.53 (s, 3'-N($CH_3$)$_2$), 2.94 (br dd, 6-$CH_2$), 3.15 (t, 4'-H), 3.12 (d, 2"-Heq), 3.35 (m, 9-H), 3.41 (dd, 2'-H), 3.61 (s, 4-$OCH_3$), 3.65 (br d, 4-H), 3.89 (br d, 5-H), 4.35 (d, 1'-H), 4.37 (m, 3-H), 4.53 (dq, 5"-H), 4.59 (d, 4"-H), 4.84 (d, 1"-H), 5.12 (m, 15-H), 6.39 (dt, CH═CH), 6.61 (d, CH═CH), 7.53 (ddd, quinoline), 7.66 (ddd, quinoline), 7.79 (br d, quinoline), 8.02 (d, quinoline), 8.06 (br d, quinoline), 8.95 (d, quinoline), 9.73 (s, CHO).

Example 129

Preparation method of the compound represented by the formula (3) wherein $R_1$ and $R_2$ are hydrogen atoms, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(isoquinolin-4-yl)-2-propenyl group, $R_{4'}$ is a group represented by the formula (a), $R_{3''}$ is propionyl group, $R_{4''}$ is n-butyryl group, and X is oxygen atom (a) In the same manner as in Example 48(c), except that 4-bromoisoquinoline was used instead of 4-bromoquinoline, 21.1 mg of a coupling compound (compound represented by the formula (31) mentioned in Preparation Scheme 10 wherein $R_3$ is methyl group, $R_7$, $R_8$ and $R_{12}$ are hydrogen atoms, $R_{11}$ is trans-3-(isoquinolin-4-yl)-2-propenyl group, $R_{3''}$ is propionyl group, $R_{4''}$ is n-butyryl group, and X is oxygen atom) was obtained from 60.5 mg of the compound of Example 128(b).

Physicochemical Properties of this Compound (1) Molecular formula: $C_{59}H_{91}N_3O_{18}$ (2) Mass spectrum (FAB): m/z 1130 $(M+H)^+$ (3) $^1$H NMR spectrum (300 MHz, $CDCl_3$) δ (ppm): 0.95 (d, 8-$CH_3$), 0.98 (t, 4"-$OCOCH_2CH_2CH_3$), 1.07 (d, 6"-H), 1.15 (t, 3"-$OCOCH_2CH_3$), 1.18 (d, 6'-H), 1.42 (s, 3"-$CH_3$), 1.69 (m, 4"-$OCOCH_2CH_2CH_3$), 2.02 (s, 9-$OCOCH_3$), 2.03

(s, 2'-OCOCH$_3$), 2.38 (t, 4"-OCOCH$_2$CH$_2$CH$_3$), 2.41 (s, 3'-N(CH$_3$)$_2$), 2.44 (s, NCH$_3$), 3.11 (t, 4'-H), 3.20 (d, 2"-Heq), 3.30 (s, CH(OCH$_3$)$_2$), 3.36 (s, CH(OCH$_3$)$_2$), 3.50 (s, 4-OCH$_3$), 4.03 (d, 5-H), 4.14 (m, 3-H), 4.46 (dq, 5"-H), 4.57 (d, 4"-H), 4.66 (d, 1'-H), 4.80 (d, 1"-H), 4.94 (dd, 2'-H), 5.06 (m, 9-H), 5.27 (m, 15-H), 6.23 (dt, CH═CH), 7.04 (d, CH═CH), 7.61 (m, isoquinoline), 7.73 (m, isoquinoline), 7.97 (d, isoquinoline), 8.04 (d, isoquinoline), 8.54 (s, isoquinoline), 9.14 (s, isoquinoline).

(b) In the same manner as in Example 73(b), 9.0 mg of a deacetyled compound (compound represented by the formula (32) mentioned in Preparation Scheme 10 wherein $R_2$ is hydrogen atom, $R_3$ is methyl group, $R_7$, $R_8$ and $R_{12}$ are hydrogen atoms, $R_{11}$ is trans-3-(isoquinolin-4-yl)-2-propenyl group, $R_{3''}$ is propionyl group, $R_{4''}$ is n-butyryl group, and X is oxygen atom) was obtained from 21.1 mg of the compound of Example 129(a).

Physicochemical Properties of this Compound (1) Molecular formula: $C_{55}H_{87}N_3O_{16}$ (2) Mass spectrum (FAB): m/z 1046 $(M+H)^+$ (3) $^1$H NMR spectrum (300 MHz, CDCl$_3$) δ (ppm): 0.89 (d, 8-CH$_3$), 0.98 (t, 4"-OCOCH$_2$CH$_2$CH$_3$), 1.08 (d, 6"-H), 1.12 (t, 3"-OCOCH$_2$CH$_3$), 1.21 (d, 6'-H), 1.42 (s, 3"-CH$_3$), 1.70 (m, 4"-OCOCH$_2$CH$_2$CH$_3$), 2.33 (s, NCH$_3$), 2.38 (t, 4"-OCOCH$_2$CH$_2$CH$_3$), 2.52 (s, 3'-N(CH$_3$)$_2$), 3.14 (t, 4'-H), 3.21 (d, 2"-Heq), 3.29 (s, CH(OCH$_3$)$_2$), 3.30 (s, CH(OCH$_3$)$_2$), 3.41 (m, 9-H), 3.50 (dd, 2'-H), 3.60 (s, 4-OCH$_3$), 3.67 (d, 4-H), 3.96 (d, 5-H), 4.31 (m, 3-H), 4.40 (d, 1'-H), 4.58 (d, 4"-H), 4.82 (d, 1"-H), 5.16 (m, 15-H), 6.22 (dt, CH═CH), 7.03 (d, CH═CH), 7.62 (m, isoquinoline), 7.73 (m, isoquinoline), 7.97 (d, isoquinoline), 8.04 (d, isoquinoline), 8.54 (s, isoquinoline), 9.14 (s, isoquinoline).

(c) In the same manner as in Example 2(d), 6.29 mg of the title compound was obtained from 9.0 mg of the compound of Example 129(b).

Physicochemical Properties of this Compound (1) Molecular formula: $C_{53}H_{81}N_3O_{15}$ (2) Mass spectrum (FAB): m/z 1000 $(M+H)^+$ (3) Specific rotation: $[\alpha]_D^{25}$ −61° (c0.31, CHCl$_3$)

(3) $^1$H NMR spectrum (300 MHz, CDCl$_3$) δ (ppm): 0.89 (d, 8-CH$_3$), 0.98 (t, 4"-OCOCH$_2$CH$_2$CH$_3$), 1.09 (d, 6"-H), 1.12 (t, 3"-OCOCH$_2$CH$_3$), 1.17 (d, 6'-H), 1.42 (s, 3"-CH$_3$), 1.70 (m, 4"-OCOCH$_2$CH$_2$CH$_3$), 2.32 (q, 3"-OCOCH$_2$CH$_3$), 2.32 (s, NCH$_3$), 2.38 (t, 4"-OCOCH$_2$CH$_2$CH$_3$), 2.53 (s, 3'-N(CH$_3$)$_2$), 2.93 (dd, 6-CH$_2$), 3.15 (t, 4'-H), 3.22 (d, 2"-Heq), 3.36 (m, 9-H), 3.42 (dd, 2'-H), 3.60 (s, 4-OCH$_3$), 3.68 (d, 4-H), 3.88 (d, 5-H), 4.34 (d, 1'-H), 4.52 (dq, 5"-H), 4.58 (d, 4"-H), 4.83 (d, 1"-H), 5.16 (m, 15-H), 6.23 (dt, CH═CH), 7.04 (d, CH═CH), 7.61 (m, isoquinoline), 7.73 (m, isoquinoline), 7.97 (d, isoquinoline), 8.05 (d, isoquinoline), 8.54 (s, isoquinoline), 9.14 (s, isoquinoline), 9.74 (s, CHO).

Example 130

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is 3-(naphthalen-2-yl)-2-propynyl group, $R_{4'}$ is a group represented by the formula (a), $R_{3''}$ is hydrogen atom, $R_{4''}$ is propionyl group, and X is oxygen atom (a) In the same manner as in Example 2(a), except that acetic acid was not used, and the compound of Reference Example 23 was used instead of the compound of Reference Example 1, 57.5 mg of an amine compound (compound represented by the formula (23) mentioned in Preparation Scheme 8 wherein $R_3$ is methyl group, $R_7$, $R_8$ and $R_{12}$ are hydrogen atoms, $R_{11}$ is 2-propynyl group, $R_{3''}$ is hydrogen atom, $R_{4''}$ is propionyl group, and X is hydroxyl group) was obtained from 53.1 mg of the compound of Example 19.

Physicochemical Properties of this Compound (1) Molecular formula: $C_{49}H_{84}N_2O_{19}$ (2) Mass spectrum (FAB): m/z 1005 $(M+H)^+$ (3) Specific rotation: $[\alpha]_D^{25}$ −46° (c1.00, CHCl$_3$)

(4) $^1$H NMR spectrum (300 MHz, CDCl$_3$) δ (ppm): 0.87 (d, 8-CH$_3$), 1.09 (s, 3"-CH$_3$), 1.10 (d, 6"-H), 1.12 (t, 3-OCOCH$_2$CH$_3$), 1.15 (t, 4"-OCOCH$_2$CH$_3$), 1.24 (d, 6'-H), 1.82 (dd, 2"-Hax), 2.00 (d, 2"-Heq), 2.03 (s, 9-OCOCH$_3$), 2.04 (s, 2'-OCOCH$_3$), 2.38 (s, 3'-N(CH$_3$)$_2$), 2.53 (s, NCH$_3$), 2.62 (d, 10-H), 2.71 (t, 3'-H), 2.81 (dd, 2-H), 2.94 (dd, 2-H), 3.19 (s, CH(OCH$_3$)$_2$), 3.24 (s, CH(OCH$_3$)$_2$), 3.28 (m, 4'-H), 3.32 (m, 5'-H), 3.47 (d, 4-H), 3.53 (s, 4-OCH$_3$), 3.76 (m, 15-H), 3.88 (d, 5-H), 4.36 (br s, 3"-OH), 4.36 (dq, 5"-H), 4.53 (dd, CH(OCH$_3$)$_2$), 4.59 (d, 4"-H), 4.72 (d, 1'-H), 4.97 (dd, 2'-H), 5.05 (d, 1"-H), 5.13 (t, 9-H), 5.15 (br t, 3-H).

(b) In the same manner as in Example 48(b), 9.9 mg of a cyclized compound (compound represented by the formula (24) mentioned in Preparation Scheme 8 wherein $R_3$ is methyl group, $R_7$, $R_8$ and $R_{12}$ are hydrogen atoms, $R_{11}$ is 2-propynyl group, $R_{3''}$ is hydrogen atom, $R_{4''}$ is propionyl group, and X is oxygen atom) was obtained from 57.5 mg of the compound of Example 130(a).

Physicochemical Properties of this Compound (1) Molecular formula: $C_{49}H_{82}N_2O_{18}$ (2) Mass spectrum (FAB): m/z 987 $(M+H)^+$ (3) Specific rotation: $[\alpha]_D^{27}$ −50° (c0.83, CHCl$_3$)

(4) $^1$H NMR spectrum (300 MHz, CDCl$_3$) δ (ppm): 0.91 (d, 8-CH$_3$), 1.11 (s, 3"-CH$_3$), 1.12 (d, 6"-H), 1.13 (t, 3-OCOCH$_2$CH$_3$), 1.17 (t, 4"-OCOCH$_2$CH$_3$), 1.27 (d, 6'-H), 1.84 (dd, 2"-Hax), 2.01 (d, 2"-Heq), 2.04 (s, 9-OCOCH$_3$), 2.04 (s, 2'-OCOCH$_3$), 2.23 (s, NCH$_3$), 2.40 (s, 3'-N(CH$_3$)$_2$), 2.61 (dd, 2-H), 2.72 (t, 3'-H), 2.88 (dd, 2-H), 3.15 (s, CH(OCH$_3$)$_2$), 3.24 (s, CH(OCH$_3$)$_2$), 3.32 (m, 4'-H), 3.35 (m, 5'-H), 3.61 (s, 4-OCH$_3$), 3.64 (d, 4-H), 3.93 (d, 5-H), 4.27 (br s, 3"-OH), 4.38 (dq, 5"-H), 4.55 (dd, CH(OCH$_3$)$_2$), 4.61 (d, 4"-H), 4.73 (d, 1'-H), 4.90 (m, 9-H), 5.01 (dd, 2'-H), 5.05 (br t, 3-H), 5.06 (d, 1"-H), 5.07 (m, 15-H).

(c) In an amount of 30.7 mg of the compound of Example 130(b), and 64.4 mg of 2-bromonaphthalene were dissolved in 614 µl of dioxane, and further successively added with 1.19 mg of bisbenzonitriledichloropalladium, 0.42 mg of copper iodide, and 21.8 µl of diisopropylamine. The inside of the reaction vessel was purged with argon, and the reaction mixture was added with 19.2 µl of a 0.32 N solution of tri-tert-butylphosphine in dioxane, and stirred at room temperature for 4 days. During the stirring, the reaction mixture was added with each of bisbenzonitriledichloropalladium, copper iodide, and 0.32 N solution of tri-tert-butylphosphine in dioxane twice in the same amounts or volumes. The reaction system was added with saturated aqueous ammonium chloride, and extracted with ethyl acetate, and the organic layer was dried over anhydrous magnesium sulfate, and filtered. Then, the filtrate was concentrated under reduced pressure, and the resulting residue was purified by preparative TLC (chloroform/methanol (10:1)) to obtain 13.5 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is 3-(naphthalen-2-yl)-2-propynyl group, $R_{3''}$ is hydrogen atom, $R_{4''}$ is propionyl group, and X is oxygen atom).

Physicochemical Properties of this Compound (1) Molecular formula: $C_{59}H_{88}N_2O_{18}$ (2) Mass spectrum (FAB): m/z 1113 $(M+H)^+$ (3) Specific rotation: $[\alpha]_D^{22}$ −45° (c1.00, $CHCl_3$)

(4) $^1H$ NMR spectrum (300 MHz, $CDCl_3$) δ (ppm): 0.92 (d, 8-$CH_3$), 1.11 (s, 3"-$CH_3$), 1.12 (d, 6"-H), 1.12 (t, 3-$OCOCH_2CH_3$), 1.17 (t, 4"-$OCOCH_2CH_3$), 1.27 (d, 6'-H), 1.84 (dd, 2"-Hax), 2.01 (d, 2"-Heq), 2.04 (s, 9-$OCOCH_3$), 2.06 (s, 2'-$OCOCH_3$), 2.24 (s, $NCH_3$), 2.40 (s, 3'-$N(CH_3)_2$), 2.66 (dd, 2-H), 2.72 (m, 15-$CH_2$), 2.72 (t, 3'-H), 2.90 (dd, 2-H), 3.15 (s, $CH(OCH_3)_2$), 3.25 (s, $CH(OCH_3)_2$), 3.34 (m, 4'-H), 3.34 (m, 5'-H), 3.60 (s, 4-$OCH_3$), 3.68 (d, 4-H), 3.93 (d, 5-H), 4.27 (br s, 3"-OH), 4.38 (dq, 5"-H), 4.56 (dd, $CH(OCH_3)_2$), 4.61 (d, 4"-H), 4.73 (d, 1'-H), 4.91 (m, 9-H), 5.01 (dd, 2'-H), 5.07 (d, 1"-H), 5.09 (br t, 3-H), 5.20 (m, 15-H), 7.41 (dd, naphthalene), 7.46 (m, naphthalene), 7.75 (m, naphthalene), 7.89 (s, naphthalene).

(d) In the same manner as in Example 2(c), 5.8 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is 3-(naphthalen-2-yl)-2-propynyl group, $R_{3''}$ is hydrogen atom, $R_{4''}$ is propionyl group, and X is oxygen atom) was obtained from 13.5 mg of the compound of Example 130(c).

Physicochemical Properties of this Compound (1) Molecular formula: $C_{55}H_{84}N_2O_{16}$ (2) Mass spectrum (FAB): m/z 1029 $(M+H)^+$ (3) Specific rotation: $[\alpha]_D^{23}$ −37° (c0.48, $CHCl_3$)

(4) $^1H$ NMR spectrum (300 MHz, $CDCl_3$) δ (ppm): 0.89 (d, 8-$CH_3$), 1.11 (t, 3-$OCOCH_2CH_3$), 1.11 (s, 3"-$CH_3$), 1.12 (d, 6"-H), 1.17 (t, 4"-$OCOCH_2CH_3$), 1.27 (d, 6'-H), 1.82 (dd, 2"-Hax), 2.00 (d, 2"-Heq), 2.36 (s, $NCH_3$), 2.43 (q, 3-$OCOCH_2CH_3$), 2.44 (q, 4"-$OCOCH_2CH_3$), 2.50 (s, 3'-$N(CH_3)_2$), 2.66 (dd, 2-H), 2.72 (dd, 15-$CH_2$), 2.87 (dd, 2-H), 3.17 (s, $CH(OCH_3)_2$), 3.25 (s, $CH(OCH_3)_2$), 3.29 (m, 4'-H), 3.31 (m, 5'-H), 3.34 (m, 9-H), 3.61 (dd, 2'-H), 3.65 (s, 4-$OCH_3$), 3.90 (d, 4-H), 3.99 (d, 5-H), 4.44 (d, 1'-H), 4.47 (dd, $CH(OCH_3)_2$), 4.49 (dq, 5"-H), 4.61 (d, 4"-H), 5.07 (d, 1"-H), 5.14 (m, 15-H), 5.50 (m, 3-H), 7.40 (dd, naphthalene), 7.47 (m, naphthalene), 7.75 (m, naphthalene), 7.88 (s, naphthalene).

(e) In the same manner as in Example 2(d), 3.9 mg of the title compound was obtained from 5.8 mg of the compound of Example 130(d).

Physicochemical Properties of this Compound (1) Molecular formula: $C_{53}H_{78}N_2O_{15}$ (2) Mass spectrum (FAB): m/z 983 $(M+H)^+$ (3) Specific rotation: $[\alpha]_D^{20}$ −38° (c1.00, $CHCl_3$)

(4) $^1H$ NMR spectrum (300 MHz, $CDCl_3$) δ (ppm): 0.92 (d, 8-$CH_3$), 1.11 (s, 3"-$CH_3$), 1.13 (d, 6"-H), 1.15 (t, 3-$OCOCH_2CH_3$), 1.17 (t, 4"-$OCOCH_2CH_3$), 1.20 (d, 6'-H), 1.83 (dd, 2"-Hax), 2.00 (d, 2"-Heq), 2.38 (s, $NCH_3$), 2.43 (q, 3-$OCOCH_2CH_3$), 2.44 (q, 4"-$OCOCH_2CH_3$), 2.50 (s, 3'-$N(CH_3)_2$), 2.71 (dd, 2-H), 2.87 (dd, 2-H), 3.28 (m, 4'-H), 3.28 (m, 5'-H), 3.41 (m, 9-H), 3.55 (dd, 2'-H), 3.65 (s, 4-$OCH_3$), 3.86 (d, 4-H), 4.00 (d, 5-H), 4.38 (d, 1'-H), 4.47 (dq, 5"-H), 4.61 (d, 4"-H), 5.06 (d, 1"-H), 5.18 (m, 15-H), 5.56 (m, 3-H), 7.40 (dd, naphthalene), 7.47 (m, naphthalene), 7.75 (m, naphthalene), 7.88 (s, naphthalene), 9.64 (s, CHO).

Example 131

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is 3-(quinolin-3-yl)-2-propynyl group, $R_{4'}$ is a group represented by the formula (a), $R_{3''}$ is acetyl group, $R_{4''}$ is propionyl group, and X is oxygen atom (a) In the same manner as in Example 2(a), except that acetic acid was not used, and the compound of Reference Example 23 was used instead of the compound of Reference Example 1, 26.7 mg of an amine compound (compound represented by the formula (23) mentioned in Preparation Scheme 8 wherein $R_3$ is methyl group, $R_7$, $R_8$ and $R_{12}$ are hydrogen atoms, $R_{11}$ is 2-propynyl group, $R_{3''}$ is acetyl group, $R_{4''}$ is propionyl group, and X is hydroxyl group) was obtained from 32.6 mg of the compound of Example 1.

Physicochemical Properties of this Compound (1) Molecular formula: $C_{51}H_{86}N_2O_{20}$ (2) Mass spectrum (FAB): m/z 1047 $(M+H)^+$ (3) $^1H$ NMR spectrum (300 MHz, $CDCl_3$) δ (ppm): 0.87 (d, 8-$CH_3$), 1.05 (d, 6"-H), 1.13 (t, 3-$OCOCH_2CH_3$), 1.17 (t, 4"-$OCOCH_2CH_3$), 1.17 (d, 6'-H), 1.39 (s, 3"-$CH_3$), 1.65 (dd, 2"-Hax), 2.00 (s, 9-$OCOCH_3$), 2.02 (s, 3"-$OCOCH_3$), 2.05 (s, 2'-$OCOCH_3$), 2.41 (s, 3'-$N(CH_3)_2$), 2.53 (s, $NCH_3$), 2.62 (t, 3'-H), 2.81 (dd, 2-H), 2.95 (dd, 2-H), 3.10 (t, 4'-H), 3.14 (d, 2"-Heq), 3.19 (s, $CH(OCH_3)_2$), 3.22 (m, 5'-H), 3.24 (s, $CH(OCH_3)_2$), 3.46 (d, 4-H), 3.54 (s, 4-$OCH_3$), 3.77 (m, 15-H), 3.86 (d, 5-H), 4.47 (dq, 5"-H), 4.53 (dd, $CH(OCH_3)_2$), 4.54 (d, 4"-H), 4.69 (d, 1'-H), 4.78 (d, 1"-H), 4.93 (dd, 2'-H), 5.12 (m, 9-H), 5.18 (br t, 3-H).

(b) In the same manner as in Example 48(b), 187 mg of a cyclized compound (compound represented by the formula (24) mentioned in Preparation Scheme 8 wherein $R_3$ is methyl group, $R_7$, $R_8$ and $R_{12}$ are hydrogen atoms, $R_{11}$ is 2-propynyl group, $R_{3''}$ is acetyl group, $R_{4''}$ is propionyl group, and X is oxygen atom) was obtained from 579 mg of the compound of Example 131(a).

Physicochemical Properties of this Compound (1) Molecular formula: $C_{51}H_{84}N_2O_{19}$ (2) Mass spectrum (FAB): m/z 1029 $(M+H)^+$ (3) $^1H$ NMR spectrum (300 MHz, $CDCl_3$) δ (ppm): 0.91 (d, 8-$CH_3$), 1.06 (d, 6"-H), 1.13 (t, 3-$OCOCH_2CH_3$), 1.18 (t, 4"-$OCOCH_2CH_3$), 1.19 (d, 6'-H), 1.40 (s, 3"-$CH_3$), 1.66 (dd, 2"-Hax), 2.01 (s, 9-$OCOCH_3$), 2.04 (s, 3"-$OCOCH_3$), 2.04 (s, 2'-$OCOCH_3$), 2.22 (s, $NCH_3$), 2.42 (s, 3'-$N(CH_3)_2$), 2.61 (t, 3'-H), 2.63 (dd, 2-H), 2.88 (dd, 2-H), 3.14 (s, $CH(OCH_3)_2$), 3.15 (t, 4'-H), 3.18 (d, 2"-Heq), 3.22 (m, 5'-H), 3.24 (s, $CH(OCH_3)_2$), 3.61 (d, 4-H), 3.62 (s, 4-$OCH_3$), 3.92 (d, 5-H), 4.48 (dq, 5"-H), 4.52 (dd, $CH(OCH_3)_2$), 4.56 (d, 4"-H), 4.69 (d, 1'-H), 4.80 (d, 1"-H), 4.89 (m, 9-H), 4.97 (dd, 2'-H), 5.04 (br t, 3-H), 5.06 (m, 15-H).

(c) In an amount of 176.7 mg of the compound of Example 131(b) was dissolved in 3.5 ml of acetonitrile, added with 117 μl of 3-bromoquinoline, and 38.5 mg of 1,4-diazabicyclo[2.2.2]-octane. The inside of the reaction vessel was purged with argon, and the reaction mixture was added with 3.24 mg of allylpalladium chloride dimer, successively added with 82.2 μl of a 0.42 N solution of tri-tert-butylphosphine in dioxane, and stirred at room temperature for 4 days. During the stirring, the reaction mixture was added with each of allylpalladium chloride dimer, and the solution of tri-tert-butylphosphine in dioxane 4 times in the same amounts or volumes. The reaction system was added with saturated aqueous ammonium chloride, and extracted with ethyl acetate, and the organic layer was dried over anhydrous magnesium sulfate, and filtered. Then, the filtrate was concentrated under reduced pressure, and the resulting residue was purified by silica gel column chromatography (ethyl acetate/chloroform/hexane/28% aqueous ammonia (2:2:2:0.02) and ethyl acetate/chloroform/28% aqueous ammonia (2:1:0.015)) to obtain 152 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is 3-(quinolin-3-yl)-2-propynyl group, $R_{3''}$ is acetyl group, $R_{4''}$ is propionyl group, and X is oxygen atom).

Physicochemical Properties of this Compound (1) Molecular formula: $C_{60}H_{89}N_3O_{19}$ (2) Mass spectrum (FAB): m/z 1156 $(M+H)^+$ (3) $^1H$ NMR spectrum (300 MHz, $CDCl_3$) δ (ppm): 0.91 (d, 8-$CH_3$), 1.05 (d, 6"-H), 1.13 (t, 3-$OCOCH_2CH_3$), 1.18 (t, 4"-$OCOCH_2CH_3$), 1.19 (d, 6'-H), 1.40 (s, 3"-$CH_3$), 1.66 (dd, 2"-Hax), 2.01 (s, 9-$OCOCH_3$), 2.03 (s, 3"-$OCOCH_3$), 2.05 (s, 2'-$OCOCH_3$), 2.23 (s, $NCH_3$), 2.42 (s, 3'-$N(CH_3)_2$), 2.60 (t, 3'-H), 2.69 (dd, 2-H), 2.76 (t, 15-$CH_2$), 2.90 (dd, 2-H), 3.13 (s, $CH(OCH_3)_2$), 3.15 (t, 4'-H), 3.18 (d, 2"-Heq), 3.22 (m, 5'-H), 3.24 (s, $CH(OCH_3)_2$), 3.60 (d, 4-H), 3.61 (s, 4-$OCH_3$), 3.93 (d, 5-H), 4.48 (dq, 5"-H), 4.53 (dd, $CH(OCH_3)_2$), 4.55 (d, 4"-H), 4.69 (d, 1'-H), 4.79 (d, 1"-H), 4.91 (m, 9-H), 4.96 (dd, 2'-H), 5.07 (br t, 3-H), 5.20 (m, 15-H), 7.54 (ddd, quinoline), 7.69 (ddd, quinoline), 7.76 (br d, quinoline), 8.06 (d, quinoline), 8.17 (br d, quinoline), 8.84 (d, quinoline).

(d) In the same manner as in Example 2(c), 6.7 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is 3-(quinolin-3-yl)-2-propynyl group, $R_{3''}$ is acetyl group, $R_{4''}$ is propionyl group, and X is oxygen atom) was obtained from 19.5 mg of the compound of Example 131(c).

Physicochemical Properties of this Compound (1) Molecular formula: $C_{56}H_{85}N_3O_{17}$ (2) Mass spectrum (FAB): m/z 1072 $(M+H)^+$ (3) $^1H$ NMR spectrum (300 MHz, $CDCl_3$) δ (ppm): 0.86 (d, 8-$CH_3$), 1.07 (d, 6"-H), 1.11 (t, 3-$OCOCH_2CH_3$), 1.18 (t, 4"-$OCOCH_2CH_3$), 1.20 (d, 6'-H), 1.41 (s, 3"-$CH_3$), 1.67 (dd, 2"-Hax), 2.01 (s, 3"-$OCOCH_3$), 2.33 (s, $NCH_3$), 2.39 (q, 3-$OCOCH_2CH_3$), 2.42 (q, 4"-$OCOCH_2CH_3$), 2.53 (s, 3'-$N(CH_3)_2$), 2.66 (dd, 2-H), 2.77 (t, 15-$CH_2$), 2.85 (dd, 2-H), 3.14 (s, $CH(OCH_3)_2$), 3.17 (t, 4'-H), 3.19 (d, 2"-Heq), 3.23 (m, 5'-H), 3.24 (s, $CH(OCH_3)_2$), 3.47 (dd, 2'-H), 3.69 (s, 4-$OCH_3$), 3.88 (d, 4-H), 3.96 (d, 5-H), 4.45 (d, 1'-H), 4.49 (dd, $CH(OCH_3)_2$), 4.54 (dq, 5"-H), 4.57 (d, 4"-H), 4.82 (d, 1"-H), 5.15 (m, 15-H), 5.52 (m, 3-H), 7.54 (ddd, quinoline), 7.70 (ddd, quinoline), 7.75 (dd, quinoline), 8.00 (d, quinoline), 8.16 (br d, quinoline), 8.83 (d, quinoline).

(e) In the same manner as in Example 2(d), 5.2 mg of the title compound was obtained from 6.7 mg of the compound of Example 131(d).

Physicochemical Properties of this Compound (1) Molecular formula: $C_{54}H_{79}N_3O_{16}$ (2) Mass spectrum (FAB): m/z 1026 $(M+H)^+$ (3) Specific rotation: $[\alpha]_D^{17}$ −44° (c0.43, $CHCl_3$)

(4) $^1H$ NMR spectrum (300 MHz, $CDCl_3$) δ (ppm): 0.89 (d, 8-$CH_3$), 1.08 (d, 6"-H), 1.13 (d, 6'-H), 1.16 (t, 3-$OCOCH_2CH_3$), 1.18 (t, 4"-$OCOCH_2CH_3$), 1.40 (s, 3"-$CH_3$), 1.68 (dd, 2"-Hax), 2.00 (s, 3"-$OCOCH_3$), 2.35 (s, $NCH_3$), 2.42 (q, 3-$OCOCH_2CH_3$), 2.42 (q, 4"-$OCOCH_2CH_3$), 2.54 (s, 3'-$N(CH_3)_2$), 2.68 (dd, 2-H), 2.77 (dd, 15-$CH_2$), 2.88 (dd, 2-H), 3.18 (m, 4'-H), 3.18 (m, 5'-H), 3.20 (d, 2"-Heq), 3.39 (dd, 2'-H), 3.69 (s, 4-$OCH_3$), 3.86 (d, 4-H), 3.96 (d, 5-H), 4.40 (d, 1'-H), 4.54 (dq, 5"-H), 4.57 (d, 4"-H), 4.83 (d, 1"-H), 5.15 (m, 15-H), 5.62 (m, 3-H), 7.55 (ddd, quinoline), 7.70 (ddd, quinoline), 7.76 (dd, quinoline), 8.06 (d, quinoline), 8.16 (br d, quinoline), 8.84 (d, quinoline), 9.64 (s, CHO).

Example 132

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is cis-3-(quinolin-3-yl)-2-propenyl group, $R_{4'}$ is a group represented by the formula (a), $R_{3''}$ is acetyl group, $R_{4''}$ is propionyl group, and X is oxygen atom (a) In an amount of 38 mg of the compound of Example 131(c) was dissolved in 760 μl of dioxane, the inside of the reaction vessel was purged with argon, and the reaction mixture was added with 22.8 mg of Lindler catalyst. The inside of the reaction vessel was purged again with argon, and then purged with hydrogen, and the reaction mixture was stirred at room temperature for 42 hours. The catalyst was removed by filtration, and then the filtrate was concentrated under reduced pressure. The resulting residue was purified by preparative TLC (chloroform/methanol (10:1)) to obtain 18.7 mg of a cis-double bond compound (compound represented by the formula (24) mentioned in Preparation Scheme 8 wherein $R_3$ is methyl group, $R_7$, $R_8$ and $R_{12}$ are hydrogen atoms, $R_{11}$ is cis-3-(quinolin-3-yl)-2-propenyl group, $R_{3''}$ is acetyl group, $R_{4''}$ is propionyl group, and X is oxygen atom).

Physicochemical Properties of this Compound (1) Molecular formula: $C_{60}H_{91}N_3O_{19}$ (2) Mass spectrum (FAB): m/z 1158 $(M+H)^+$ (3) $^1H$ NMR spectrum (300 MHz, $CDCl_3$) δ (ppm): 0.90 (d, 8-$CH_3$), 1.05 (d, 6"-H), 1.10 (t, 3-$OCOCH_2CH_3$), 1.17 (t, 4"-$OCOCH_2CH_3$), 1.19 (d, 6'-H), 1.40 (s, 3"-$CH_3$), 1.66 (dd, 2"-Hax), 2.01 (s, 9-$OCOCH_3$), 2.03 (s, 3"-$OCOCH_3$), 2.03 (s, 2'-$OCOCH_3$), 2.20 (s, $NCH_3$), 2.42 (s, 3'-$N(CH_3)_2$), 2.59 (dd, 2-H), 2.60 (t, 3'-H), 2.87 (dd, 2-H), 3.12 (s, $CH(OCH_3)_2$), 3.15 (t, 4'-H), 3.18 (d, 2"-Heq), 3.21 (m, 5'-H), 3.23 (s, $CH(OCH_3)_2$), 3.62 (s, 4-$OCH_3$), 3.65 (d, 4-H), 3.92 (d, 5-H), 4.47 (dq, 5"-H), 4.53 (dd, $CH(OCH_3)_2$), 4.55 (d, 4"-H), 4.69 (d, 1'-H), 4.79 (d, 1"-H), 4.88 (m, 9-H), 4.96 (dd, 2'-H), 5.03 (br t, 3-H), 5.13 (m, 15-H), 5.84 (dt, CH═CH), 6.65 (d, CH═CH), 7.53 (ddd, quinoline), 7.68 (ddd, quinoline), 7.83 (br d, quinoline), 8.05 (br s, quinoline), 8.06 (br d, quinoline), 8.80 (d, quinoline).

(b) In the same manner as in Example 2(c), 9.1 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is cis-3-(quinolin-3-yl)-2-propenyl group, $R_{3''}$ is acetyl group, $R_{4''}$ is propionyl group, and X is oxygen atom) was obtained from 18.7 mg of the compound of Example 132(a).

Physicochemical Properties of this Compound (1) Molecular formula: $C_{56}H_{87}N_3O_{17}$ (2) Mass spectrum (FAB): m/z 1074 $(M+H)^+$ (3) $^1$H NMR spectrum (300 MHz, $CDCl_3$) δ (ppm): 0.86 (d, 8-$CH_3$), 1.07 (d, 6"-H), 1.07 (t, 3-$OCOCH_2CH_3$), 1.18 (t, 4"-$OCOCH_2CH_3$), 1.19 (d, 6'-H), 1.41 (s, 3"-$CH_3$), 1.67 (dd, 2"-Hax), 2.00 (s, 3"-$OCOCH_3$), 2.29 (s, $NCH_3$), 2.42 (q, 3-$OCOCH_2CH_3$), 2.42 (q, 4"-$OCOCH_2CH_3$), 2.53 (s, 3'-N$(CH_3)_2$), 2.59 (dd, 2-H), 2.83 (dd, 2-H), 3.12 (s, $CH(OCH_3)_2$), 3.17 (t, 4'-H), 3.19 (d, 2"-Heq), 3.22 (m, 5'-H), 3.24 (s, $CH(OCH_3)_2$), 3.48 (dd, 2'-H), 3.70 (s, 4-$OCH_3$), 3.87 (d, 4-H), 3.98 (d, 5-H), 4.46 (d, 1'-H), 4.48 (dd, $CH(OCH_3)_2$), 4.54 (dq, 5"-H), 4.57 (d, 4"-H), 4.82 (d, 1"-H), 5.11 (m, 15-H), 5.45 (m, 3-H), 5.83 (dt, CH═CH), 6.66 (d, CH═CH), 7.54 (ddd, quinoline), 7.69 (ddd, quinoline), 7.82 (dd, quinoline), 8.05 (d, quinoline), 8.07 (br d, quinoline), 8.80 (d, quinoline).

(c) In the same manner as in Example 2(d), 4.5 mg of the title compound was obtained from 9.1 mg of the compound of Example 132(b).

Physicochemical Properties of this Compound (1) Molecular formula: $C_{54}H_{81}N_3O_{16}$ (2) Mass spectrum (FAB): m/z 1028 $(M+H)^+$ (3) Specific rotation: $[\alpha]D^{17}$ −24° (c0.38, $CHCl_3$)

(4) $^1$H NMR spectrum (300 MHz, $CDCl_3$) δ (ppm): 0.89 (d, 8-$CH_3$), 1.08 (d, 6"-H), 1.12 (t, 3-$OCOCH_2CH_3$), 1.13 (d, 6'-H), 1.18 (t, 4"-$OCOCH_2CH_3$), 1.40 (s, 3"-$CH_3$), 1.68 (dd, 2"-Hax), 2.00 (s, 3"-$OCOCH_3$), 2.31 (s, $NCH_3$), 2.42 (q, 3-$OCOCH_2CH_3$), 2.42 (q, 4"-$OCOCH_2CH_3$), 2.54 (s, 3'-N$(CH_3)_2$), 2.61 (dd, 2-H), 2.86 (dd, 2-H), 3.18 (m, 4'-H), 3.18 (m, 5'-H), 3.20 (d, 2"-Heq), 3.36 (m, 9-H), 3.40 (dd, 2'-H), 3.70 (s, 4-$OCH_3$), 3.86 (d, 4-H), 3.98 (d, 5-H), 4.40 (d, 1'-H), 4.54 (dq, 5"-H), 4.57 (d, 4"-H), 4.83 (d, 1"-H), 5.11 (m, 15-H), 5.53 (m, 3-H), 5.83 (dt, CH═CH), 6.66 (d, CH═CH), 7.53 (ddd, quinoline), 7.69 (ddd, quinoline), 7.83 (dd, quinoline), 8.07 (br d, quinoline), 8.80 (d, quinoline), 9.64 (s, CHO).

Example 133

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is 2-(quinolin-3-yl)ethyl group, $R_{4'}$ is a group represented by the formula (a), $R_{3''}$ is acetyl group, $R_{4''}$ is propionyl group, and X is oxygen atom (a) In the same manner as in Example 2(a), except that acetic acid was not added, and the compound of Reference Example 36 was used instead of the compound of Reference Example 1, 165 mg of an amine compound (compound represented by the formula (23) mentioned in Preparation Scheme 8 wherein $R_3$ is methyl group, $R_7$, $R_8$ and $R_{12}$ are hydrogen atoms, $R_{11}$ is 2-(quinolin-3-yl)ethyl group, $R_{3''}$ is acetyl group, $R_{4''}$ is propionyl group, and X is hydroxyl group) was obtained from 246 mg of the compound of Example 1.

Physicochemical Properties of this Compound (1) Molecular formula: $C_{59}H_{93}N_3O_{20}$ (2) Mass spectrum (FAB): m/z 1164 $(M+H)^+$ (3) $^1$H NMR spectrum (300 MHz, $CDCl_3$) δ (ppm): 0.89 (d, 8-$CH_3$), 1.06 (d, 6"-H), 1.14 (t, 3-$OCOCH_2CH_3$), 1.18 (t, 4"-$OCOCH_2CH_3$), 1.18 (d, 6'-H), 1.40 (s, 3"-$CH_3$), 1.66 (dd, 2"-Hax), 2.02 (s, 9-$OCOCH_3$), 2.02 (s, 3"-$OCOCH_3$), 2.07 (s, 2'-$OCOCH_3$), 2.42 (s, 3'-N$(CH_3)_2$), 2.47 (s, $NCH_3$), 2.61 (t, 3'-H), 2.68 (dd, 2-H), 2.85 (dd, 2-H), 3.20 (s, $CH(OCH_3)_2$), 3.15 (t, 4'-H), 3.18 (d, 2"-Heq), 3.22 (m, 5'-H), 3.25 (s, $CH(OCH_3)_2$), 3.47 (d, 4-H), 3.54 (s, 4-$OCH_3$), 3.87 (d, 5-H), 4.48 (dq, 5"-H), 4.53 (dd, $CH(OCH_3)_2$), 4.55 (d, 4"-H), 4.69 (d, 1'-H), 4.79 (d, 1"-H), 4.94 (dd, 2'-H), 5.16 (m, 9-H), 5.18 (br t, 3-H), 7.50 (ddd, quinoline), 7.63 (ddd, quinoline), 7.76 (br d, quinoline), 7.97 (d, quinoline), 8.05 (br d, quinoline), 8.80 (d, quinoline).

(b) In the same manner as in Example 48(b), 77.3 mg of a cyclized compound (compound represented by the formula (24) mentioned in Preparation Scheme 8 wherein $R_3$ is methyl group, $R_7$, $R_8$ and $R_{12}$ are hydrogen atoms, $R_{11}$ is 2-(quinolin-3-yl)ethyl group, $R_{3''}$ is acetyl group, $R_{4''}$ is propionyl group, and X is oxygen atom) was obtained from 165 mg of the compound of Example 133(a).

Physicochemical Properties of this Compound (1) Molecular formula: $C_{59}H_{91}N_3O_{19}$ (2) Mass spectrum (FAB): m/z 1146 $(M+H)^+$ (3) $^1$H NMR spectrum (300 MHz, $CDCl_3$) δ (ppm): 0.90 (d, 8-$CH_3$), 1.07 (d, 6"-H), 1.13 (t, 3-$OCOCH_2CH_3$), 1.18 (t, 4"-$OCOCH_2CH_3$), 1.19 (d, 6'-H), 1.40 (s, 3"-$CH_3$), 1.66 (dd, 2"-Hax), 2.01 (s, 9-$OCOCH_3$), 2.02 (s, 3"-$OCOCH_3$), 2.04 (s, 2'-$OCOCH_3$), 2.20 (s, $NCH_3$), 2.42 (s, 3'-N$(CH_3)_2$), 2.56 (dd, 2-H), 2.58 (t, 3'-H), 2.83 (dd, 2-H), 3.13 (s, $CH(OCH_3)_2$), 3.15 (t, 4'-H), 3.18 (d, 2"-Heq), 3.22 (m, 5'-H), 3.23 (s, $CH(OCH_3)_2$), 3.61 (s, 4-$OCH_3$), 3.64 (d, 4-H), 3.93 (d, 5-H), 4.48 (dq, 5"-H), 4.53 (dd, $CH(OCH_3)_2$), 4.55 (d, 4"-H), 4.70 (d, 1'-H), 4.79 (d, 1"-H), 4.89 (m, 9-H), 4.96 (dd, 2'-H), 5.03 (br t, 3-H), 5.07 (m, 15-H), 7.50 (ddd, quinoline), 7.65 (ddd, quinoline), 7.75 (dd, quinoline), 7.92 (d, quinoline), 8.05 (br d, quinoline), 8.75 (d, quinoline).

(c) In the same manner as in Example 2(c), 65.8 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is 2-(quinolin-3-yl)ethyl group, $R_{3''}$ is acetyl group, $R_{4''}$ is propionyl group, and X is oxygen atom) was obtained from 77.3 mg of the compound of Example 133(b).

Physicochemical Properties of this Compound (1) Molecular formula: $C_{55}H_{87}N_3O_{17}$ (2) Mass spectrum (FAB): m/z 1062 $(M+H)^+$ (3) $^1$H NMR spectrum (300 MHz, $CDCl_3$) δ (ppm): 0.86 (d, 8-$CH_3$), 1.06 (d, 6"-H), 1.09 (t, 3-$OCOCH_2CH_3$), 1.16 (t, 4"-$OCOCH_2CH_3$), 1.18 (d, 6'-H), 1.39 (s, 3"-$CH_3$), 1.65 (dd, 2"-Hax), 1.99 (s, 3"-$OCOCH_3$), 2.29 (s, $NCH_3$), 2.40 (q, 3-$OCOCH_2CH_3$), 2.40 (q, 4"-$OCOCH_2CH_3$), 2.51 (s, 3'-N$(CH_3)_2$), 2.58 (dd, 2-H), 2.80 (dd, 2-H), 3.12 (s, $CH(OCH_3)_2$), 3.16 (t, 4'-H), 3.19 (d, 2"-Heq), 3.21 (m, 5'-H), 3.23 (s, $CH(OCH_3)_2$), 3.46 (dd, 2'-H), 3.68 (s, 4-$OCH_3$), 3.87 (d, 4-H), 3.97 (d, 5-H), 4.45 (d, 1'-H), 4.49 (dd, $CH(OCH_3)_2$), 4.53 (dq, 5"-H), 4.56 (d, 4"-H), 4.81 (d, 1"-H), 5.07 (m, 15-H), 5.40 (m, 3-H), 7.49 (ddd, quinoline), 7.64 (ddd, quinoline), 7.73 (dd, quinoline), 7.89 (d, quinoline), 8.04 (br d, quinoline), 8.73 (d, quinoline).

(d) In the same manner as in Example 2(d), 56.4 mg of the title compound was obtained from 65.8 mg of the compound of Example 133(c).

Physicochemical Properties of this Compound (1) Molecular formula: $C_{53}H_{81}N_3O_{16}$ (2) Mass spectrum (FAB): m/z 1016 $(M+H)^+$ (3) Specific rotation: $[\alpha]_D^{18}$ −43° (c1.00, $CHCl_3$)

(4) $^1H$ NMR spectrum (300 MHz, $CDCl_3$) δ (ppm): 0.89 (d, 8-$CH_3$), 1.07 (d, 6"-H), 1.12 (d, 6'-H), 1.15 (t, 3-$OCOCH_2CH_3$), 1.17 (t, 4"-$OCOCH_2CH_3$), 1.40 (s, 3"-$CH_3$), 1.67 (dd, 2"-Hax), 1.99 (s, 3"-$OCOCH_3$), 2.30 (s, $NCH_3$), 2.41 (q, 3-$OCOCH_2CH_3$), 2.41 (q, 4"-$OCOCH_2CH_3$), 2.53 (s, 3'-$N(CH_3)_2$), 2.61 (dd, 2-H), 2.83 (dd, 2-H), 3.17 (m, 4'-H), 3.17 (m, 5'-H), 3.20 (d, 2"-Heq), 3.35 (m, 9-H), 3.39 (dd, 2'-H), 3.69 (s, 4-$OCH_3$), 3.86 (d, 4-H), 3.99 (d, 5-H), 4.39 (d, 1'-H), 4.51 (dq, 5"-H), 4.56 (d, 4"-H), 4.82 (d, 1"-H), 5.08 (m, 15-H), 5.49 (m, 3-H), 7.51 (ddd, quinoline), 7.65 (ddd, quinoline), 7.74 (dd, quinoline), 7.90 (d, quinoline), 8.05 (br d, quinoline), 8.74 (d, quinoline), 9.63 (s, CHO).

Example 134

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is 4-(quinolin-3-yl)butyl group, $R_{4'}$ is a group represented by the formula (a), $R_{3''}$ is hydrogen atom, $R_{4''}$ is propionyl group, and X is oxygen atom (a) In an amount of 150 mg of the isomer A of Example 48(b) was dissolved in 2 ml of dichloromethane, added with 51.3 mg of the compound of Reference Example 37, and 25.7 mg of the second generation Grubbs catalyst, and stirred at 40° C. for 2 hours. Then, the reaction mixture was further added with 25.7 mg of the second generation Grubbs catalyst, and stirred at 40° C. for 1.5 hours. The reaction mixture was returned to room temperature, the catalyst was removed by filtration, and then the filtrate was concentrated under reduced pressure. The resulting residue was purified by using LH-20 (hexane/acetone (10:1 to 6:1)) to obtain 27.3 mg of a coupling compound (compound represented by the formula (24) mentioned in Preparation Scheme 8 wherein $R_3$ is methyl group, $R_7$, $R_8$ and $R_{12}$ are hydrogen atoms, $R_{11}$ is trans-4-(quinolin-3-yl)-2-butenyl group, $R_{3''}$ is hydrogen atom, $R_{4''}$ is propionyl group, and X is oxygen atom).

Physicochemical Properties of this Compound (1) Molecular formula: $C_{59}H_{91}N_3O_{18}$ (2) Mass spectrum (FAB): m/z 1130 $(M+H)^+$ (3) $^1H$ NMR spectrum (300 MHz, $CDCl_3$) δ (ppm): 0.90 (d, 8-$CH_3$), 1.10 (s, 3"-$CH_3$), 1.11 (d, 6"-H), 1.12 (t, 3-$OCOCH_2CH_3$), 1.17 (t, 4"-$OCOCH_2CH_3$), 1.26 (d, 6'-H), 1.70 (m, 8-H), 1.84 (dd, 2"-Hax), 2.00 (d, 2"-Heq), 2.03 (s, 9-$OCOCH_3$), 2.03 (s, 2'-$OCOCH_3$), 2.15 (s, $NCH_3$), 2.40 (s, 3'-$N(CH_3)_2$), 2.54 (m, 2-H), 2.71 (t, 3'-H), 2.83 (dd, 2-H), 3.13 (s, $CH(OCH_3)_2$), 3.23 (s, $CH(OCH_3)_2$), 3.33 (m, 4'-H), 3.33 (m, 5'-H), 3.50 (br d, 4-H), 3.57 (d, quinoline-$CH_2$), 3.58 (s, 4-$OCH_3$), 3.92 (br d, 5-H), 4.36 (dq, 5"-H), 4.55 (dd, $CH(OCH_3)_2$), 4.60 (d, 4"-H), 4.72 (d, 1'-H), 4.88 (m, 9-H), 5.00 (dd, 2'-H), 5.06 (d, 1"-H), 5.50 (dt, CH═CH), 5.70 (dt, CH═CH), 7.50 (ddd, quinoline), 7.64 (ddd, quinoline), 7.75 (br d, quinoline), 7.88 (br s, quinoline), 8.05 (br d, quinoline), 8.72 (d, quinoline).

(b) In the same manner as in Example 8(d), 10.0 mg of a double bond-reduced compound (compound represented by the formula (24) mentioned in Preparation Scheme 8 wherein $R_3$ is methyl group, $R_7$, $R_8$ and $R_{12}$ are hydrogen atoms, $R_{11}$ is 4-(quinolin-3-yl)butyl group, $R_{3''}$ is hydrogen atom, $R_{4''}$ is propionyl group, and X is oxygen atom) was obtained from 39.6 mg of the compound of Example 134(a).

Physicochemical Properties of this Compound (1) Molecular formula: $C_{59}H_{93}N_3O_{18}$ (2) Mass spectrum (FAB): m/z 1132 $(M+H)^+$ (3) $^1H$ NMR spectrum (300 MHz, $CDCl_3$) δ (ppm): 0.91 (d, 8-$CH_3$), 1.11 (s, 3"-$CH_3$), 1.12 (d, 6"-H), 1.12 (t, 3-$OCOCH_2CH_3$), 1.17 (t, 4"-$OCOCH_2CH_3$), 1.27 (d, 6'-H), 1.70 (m, 8-H), 1.84 (dd, 2"-Hax), 2.00 (d, 2"-Heq), 2.04 (s, 9-$OCOCH_3$), 2.04 (s, 2'-$OCOCH_3$), 2.20 (s, $NCH_3$), 2.40 (s, 3'-$N(CH_3)_2$), 2.54 (m, 2-H), 2.72 (t, quinoline-$CH_2$), 2.78 (t, 3'-H), 2.86 (dd, 2'-H), 3.13 (s, $CH(OCH_3)_2$), 3.24 (s, $CH(OCH_3)_2$), 3.34 (m, 4'-H), 3.34 (m, 5'-H), 3.60 (s, 4-$OCH_3$), 3.66 (br d, 4-H), 3.94 (br d, 5-H), 4.38 (dq, 5"-H), 4.56 (dd, $CH(OCH_3)_2$), 4.62 (d, 4"-H), 4.73 (d, 1'-H), 4.90 (m, 9-H), 5.00 (dd, 2'-H), 5.07 (d, 1"-H), 7.52 (ddd, quinoline), 7.65 (ddd, quinoline), 7.75 (br d, quinoline), 7.89 (br s, quinoline), 8.06 (br d, quinoline), 8.76 (d, quinoline).

(c) In the same manner as in Example 2(c), 5.0 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is 4-(quinolin-3-yl)butyl group, $R_{3''}$ is hydrogen atom, $R_{4''}$ is propionyl group, and X is oxygen atom) was obtained from 10.0 mg of the compound of Example 134(b).

Physicochemical Properties of this Compound (1) Molecular formula: $C_{55}H_{89}N_3O_{16}$ (2) Mass spectrum (FAB): m/z 1048 $(M+H)^+$ (3) $^1H$ NMR spectrum (300 MHz, $CDCl_3$) δ (ppm): 0.90 (d, 8-$CH_3$), 1.12 (t, 3-$OCOCH_2CH_3$), 1.13 (s, 3"-$CH_3$), 1.16 (t, 4"-$OCOCH_2CH_3$), 1.28 (d, 6'-H), 1.40 (m, 8-H), 1.83 (dd, 2"-Hax), 2.00 (d, 2"-Heq), 2.34 (s, $NCH_3$), 2.44 (m, 3'-H), 2.50 (s, 3'-$N(CH_3)_2$), 2.56 (dd, 2-H), 2.78 (t, quinoline-$CH_2$), 2.84 (dd, 2-H), 3.16 (s, $CH(OCH_3)_2$), 3.24 (s, $CH(OCH_3)_2$), 3.30 (m, 4'-H), 3.30 (m, 5'-H), 3.34 (m, 9-H), 3.60 (dd, 2'-H), 3.65 (s, 4-$OCH_3$), 3.90 (br d, 4-H), 3.97 (br d, 5-H), 4.45 (m, $CH(OCH_3)_2$), 4.47 (dq, 5"-H), 4.62 (d, 4"-H), 4.98 (m, 15-H), 5.08 (dd, 1"-H), 5.40 (m, 3-H), 7.52 (ddd, quinoline), 7.65 (ddd, quinoline), 7.76 (br d, quinoline), 7.88 (br s, quinoline), 8.06 (br d, quinoline), 8.75 (d, quinoline).

(d) In the same manner as in Example 2(d), 3.0 mg of the title compound was obtained from 5.0 mg of the compound of Example 134(c).

Physicochemical Properties of this Compound (1) Molecular formula: $C_{53}H_{83}N_3O_{15}$ (2) Mass spectrum (FAB): m/z 1002 $(M+H)^+$ (3) Specific rotation: $[\alpha]_D^{18}$ −63° (c0.30, $CHCl_3$)

(4) $^1H$ NMR spectrum (300 MHz, $CDCl_3$) δ (ppm): 0.93 (d, 8-$CH_3$), 1.12 (d, 6"-H), 1.13 (s, 3"-$CH_3$), 1.15 (t, 3-$OCOCH_2CH_3$), 1.18 (t, 4"-$OCOCH_2CH_3$), 1.21 (d, 6'-H), 1.34 (m, 8-H), 1.83 (dd, 2"-Hax), 2.00 (d, 2"-Heq), 2.33 (s, $NCH_3$), 2.42 (m, 3'-H), 2.50 (s, 3'-$N(CH_3)_2$), 2.58 (dd, 2-H), 2.60 (t, 6-$CH_2$), 2.78 (t, quinoline-$CH_2$), 2.88 (dd, 2-H), 3.28 (m, 4'-H), 3.28 (m, 5'-H), 3.40 (m, 9-H), 3.56 (dd, 2'-H), 3.65 (s, 4-$OCH_3$), 3.86 (br d, 4-H), 3.99 (br d, 5-H), 4.38 (d, 1'-H), 4.47 (dq, 5"-H), 4.62 (d, 4"-H), 4.98 (m, 15-H), 5.06 (dd, 1"-H), 5.47 (m, 3-H), 7.52 (ddd, quinoline), 7.66 (ddd, quinoline), 7.76 (dd, quinoline), 7.89 (br s, quinoline), 8.06 (br d, quinoline), 8.75 (d, quinoline), 9.64 (s, CHO).

Example 135

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is 4-(naphthalen-2-yl)butyl group, $R_{4'}$ is a group represented by the formula (a), $R_{3''}$ is hydrogen atom, $R_{4''}$ is propionyl group, and X is oxygen atom (a) In the same manner as in Example 134(a), except that the compound of Reference Example 38 was used instead of the compound of Reference Example 37, 26.0 mg of a coupling compound (compound represented by the formula (24) mentioned in Preparation Scheme 8 wherein $R_3$ is methyl group, $R_7$, $R_8$, $R_{12}$ are hydrogen atoms, $R_{11}$ is trans-4-(naphthalen-2-yl)-2-butenyl group, $R_{3''}$ is hydrogen atom, $R_{4''}$ is propionyl group, and X is oxygen atom) was obtained from 100 mg of the isomer A of Example 48(b).

Physicochemical Properties of this Compound (1) Molecular formula: $C_{60}H_{92}N_2O_{18}$ (2) Mass spectrum (FAB): m/z 1129 $(M+H)^+$ (3) $^1H$ NMR spectrum (300 MHz, $CDCl_3$) δ (ppm): 0.92 (d, 8-$CH_3$), 1.07 (s, 3"-$CH_3$), 1.10 (d, 6"-H), 1.13 (t, 3-$OCOCH_2CH_3$), 1.15 (t, 4"-$OCOCH_2CH_3$), 1.25 (d, 6'-H), 1.47 (m, 6-$CH_2$), 1.73 (m, 8-H), 1.84 (dd, 2"-Hax), 2.00 (d, 2"-Heq), 2.04 (s, 9-$OCOCH_3$), 2.04 (s, 2'-$OCOCH_3$), 2.22 (s, $NCH_3$), 2.24 (m, 10-H), 2.40 (s, 3'-$N(CH_3)_2$), 2.58 (m, 2-H), 2.70 (t, 3'-H), 2.82 (dd, 2-H), 3.15 (s, $CH(OCH_3)_2$), 3.24 (s, $CH(OCH_3)_2$), 3.28 (m, 4'-H), 3.28 (m, 5'-H), 3.42 (br d, 4-H), 3.59 (d, naphthalene-$CH_2$), 3.62 (s, 4-$OCH_3$), 3.93 (br d, 5-H), 4.40 (dq, 5"-H), 4.56 (dd, $CH(OCH_3)_2$), 4.60 (d, 4"-H), 4.76 (d, 1'-H), 4.90 (m, 9-H), 5.02 (br dd, 3-H), 5.08 (d, 1"-H), 5.49 (dt, CH═CH), 5.71 (dt, CH═CH), 7.28 (m, naphthalene), 7.42 (m, naphthalene), 7.58 (s, naphthalene), 7.78 (dd, naphthalene).

(b) In the same manner as in Example 8(d), 20.6 mg of a double bond-reduced compound (compound represented by the formula (24) mentioned in Preparation Scheme 8 wherein $R_3$ is methyl group, $R_7$, $R_8$ and $R_{12}$ are hydrogen atoms, $R_{11}$ is 4-(naphthalen-2-yl)butyl group, $R_{3''}$ is hydrogen atom, $R_{4''}$ is propionyl group, and X is oxygen atom) was obtained from 26.0 mg of the compound of Example 135(a).

Physicochemical Properties of this Compound (1) Molecular formula: $C_{60}H_{94}N_2O_{18}$ (2) Mass spectrum (FAB): m/z 1131 $(M+H)^+$ (3) Specific rotation: $[\alpha]_D^{22}$ −48° (1.0, $CHCl_3$)

(4) $^1H$ NMR spectrum (300 MHz, $CDCl_3$) δ (ppm): 0.91 (d, 8-$CH_3$), 1.10 (s, 3"-$CH_3$), 1.12 (d, 6"-H), 1.13 (t, 3-$OCOCH_2CH_3$), 1.18 (t, 4"-$OCOCH_2CH_3$), 1.27 (d, 6'-H), 1.68 (m, 8-H), 1.84 (dd, 2"-Hax), 2.00 (d, 2"-Heq), 2.04 (s, 9-$OCOCH_3$), 2.04 (s, 2'-$OCOCH_3$), 2.22 (s, $NCH_3$), 2.38 (m, 10-H), 2.42 (s, 3'-$N(CH_3)_2$), 2.74 (t, 3'-H), 2.85 (dd, 2-H), 3.14 (s, $CH(OCH_3)_2$), 3.24 (s, $CH(OCH_3)_2$), 3.34 (m, 4'-H), 3.34 (m, 5'-H), 3.60 (s, 4-$OCH_3$), 3.69 (br d, 4-H), 3.94 (br d, 5-H), 4.37 (dq, 5"-H), 4.56 (dd, $CH(OCH_3)_2$), 4.61 (d, 4"-H), 4.74 (d, 1'-H), 4.90 (m, 9-H), 4.98 (m, 2'-H), 5.01 (br dd, 3-H), 5.07 (d, 1"-H), 7.29 (m, naphthalene), 7.41 (m, naphthalene), 7.57 (s, naphthalene), 7.76 (dd, naphthalene).

(c) In the same manner as in Example 2(c), 14.3 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is 4-(naphthalen-2-yl)butyl group, $R_{3''}$ is hydrogen atom, $R_{4''}$ is propionyl group, and X is oxygen atom) was obtained from 20.6 mg of the compound of Example 135(b).

Physicochemical Properties of this Compound (1) Molecular formula: $C_{56}H_{90}N_2O_{16}$ (2) Mass spectrum (FAB): m/z 1047 $(M+H)^+$ (3) Specific rotation: $[\alpha]_D^{21}$ −43° (c0.72, $CHCl_3$)

(4) $^1H$ NMR spectrum (300 MHz, $CDCl_3$) δ (ppm): 0.89 (d, 8-$CH_3$), 1.09 (d, 6"-H), 1.11 (s, 3"-$CH_3$), 1.11 (t, 3-$OCOCH_2CH_3$), 1.17 (t, 4"-$OCOCH_2CH_3$), 1.26 (d, 6'-H), 1.42 (m, 8-H), 1.83 (dd, 2"-Hax), 2.00 (d, 2"-Heq), 2.30 (s, $NCH_3$), 2.43 (m, 3'-H), 2.50 (s, 3'-$N(CH_3)_2$), 2.74 (dd, 2-H), 3.15 (s, $CH(OCH_3)_2$), 3.24 (s, $CH(OCH_3)_2$), 3.30 (m, 4'-H), 3.30 (m, 5'-H), 3.60 (dd, 2'-H), 3.65 (s, 4-$OCH_3$), 3.89 (br d, 4-H), 3.98 (br d, 5-H), 4.42 (m, 1'-H), 4.48 (dq, 5"-H), 4.61 (d, 4"-H), 4.98 (m, 15-H), 5.07 (d, 1"-H), 5.40 (m, 3-H), 7.28 (dd, naphthalene), 7.42 (m, naphthalene), 7.57 (s, naphthalene), 7.77 (dd, naphthalene).

(d) In the same manner as in Example 2(d), 8.3 mg of the title compound was obtained from 14.3 mg of the compound of Example 135(c).

Physicochemical Properties of this Compound (1) Molecular formula: $C_{54}H_{84}N_2O_5$ (2) Mass spectrum (FAB): m/z 1001 $(M+H)^+$ (3) Specific rotation: $[\alpha]_D^{20}$ −46° (c0.42, $CHCl_3$)

(4) $^1H$ NMR spectrum (300 MHz, $CDCl_3$) δ (ppm): 0.94 (d, 8-$CH_3$), 1.11 (s, 3"-$CH_3$), 1.13 (d, 6"-H), 1.15 (t, 3-$OCOCH_2CH_3$), 1.18 (t, 4"-$OCOCH_2CH_3$), 1.20 (d, 6'-H), 1.33 (m, 8-H), 1.82 (dd, 2"-Hax), 2.00 (d, 2"-Heq), 2.32 (s, $NCH_3$), 2.36 (m, 10-H), 2.44 (m, 3'-H), 2.50 (s, 3'-$N(CH_3)_2$), 2.57 (dd, 2-H), 2.75 (dd, 6-$CH_2$), 2.88 (dd, 2-H), 3.27 (m, 4'-H), 3.27 (m, 5'-H), 3.38 (m, 9-H), 3.56 (dd, 2'-H), 3.65 (s, 4-$OCH_3$), 3.95 (br d, 4-H), 4.00 (br d, 5-H), 4.38 (d, 1'-H), 4.47 (dq, 5"-H), 4.62 (d, 4"-H), 4.97 (m, 15-H), 5.07 (d, 1"-H), 5.45 (m, 3-H), 7.29 (dd, naphthalene), 7.42 (m, naphthalene), 7.57 (s, naphthalene), 7.77 (dd, naphthalene), 9.64 (s, CHO).

Example 136

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is 5-(quinolin-3-yl)pentyl group, $R_{4'}$ is a group represented by the formula (a), $R_{3''}$ is hydrogen atom, $R_{4''}$ is propionyl group, and X is oxygen atom (a) In the same manner as in Example 134(a), except that the compound of Reference Example 39 was used instead of the compound of Reference Example 37, 20.5 mg of a coupling compound (compound represented by the formula (24) mentioned in Preparation Scheme 8 wherein $R_3$ is methyl group, $R_7$, $R_8$, $R_{12}$ are hydrogen atoms, $R_{11}$ is trans-5-(quinolin-3-yl)-2-pentenyl group, $R_{3'}$ is hydrogen atom, $R_{4''}$ is propionyl group, and X is oxygen atom) was obtained from 50 mg of the isomer A of Example 48(b).

Physicochemical Properties of this Compound (1) Molecular formula: $C_{60}H_{93}N_3O_{18}$ (2) Mass spectrum (FAB): m/z 1144 $(M+H)^+$ (3) $^1H$ NMR spectrum (300 MHz, $CDCl_3$) δ (ppm): 0.90 (d, 8-$CH_3$), 1.10 (s, 3"-$CH_3$), 1.12 (s, 6"-H), 1.16 (t, 3-$OCOCH_2CH_3$), 1.16 (t, 4"-$OCOCH_2CH_3$), 1.25 (d, 6'-H), 1.70 (m, 8-H), 1.84 (dd, 2"-Hax), 2.00 (d, 2"-Heq), 2.03 (s, 9-$OCOCH_3$), 2.03 (s, 2'-$OCOCH_3$), 2.19 (s, $NCH_3$), 2.40 (s, 3'-$N(CH_3)_2$), 2.54 (m, 2-H), 2.70 (t, quinoline-$CH_2$), 2.83 (dd, 2'-H), 3.13 (s, $CH(OCH_3)_2$), 3.24 (s, $CH(OCH_3)_2$), 3.32 (m, 4'-H), 3.32 (m, 5'-H), 3.50 (br d, 4-H), 3.60 (s, 4-$OCH_3$), 3.93 (br d, 5-H), 4.38 (dq, 5"-H), 4.56 (dd, $CH(OCH_3)_2$), 4.60 (d, 4"-H), 4.72 (d, 1'-H), 4.88 (m, 9-H), 5.02 (dd, 2'-H), 5.05 (d, 1"-H), 5.35 (dt, CH═CH), 5.53 (dt, CH═CH), 7.50 (dd, quinoline), 7.65 (dd, quinoline), 7.75 (d, quinoline), 7.88 (br s, quinoline), 8.05 (d, quinoline), 8.74 (d, quinoline).

(b) In the same manner as in Example 8(d), 10.0 mg of a double bond-reduced compound (compound represented by the formula (24) mentioned in Preparation Scheme 8 wherein $R_3$ is methyl group, $R_7$, $R_8$ and $R_{12}$ are hydrogen atoms, $R_{11}$ is 5-(quinolin-3-yl)pentyl group, $R_{3''}$ is hydrogen atom, $R_{4''}$ is propionyl group, and X is oxygen atom) was obtained from 34.3 mg of the compound of Example 136(a).

Physicochemical Properties of this Compound (1) Molecular formula: $C_{60}H_{95}N_3O_{18}$ (2) Mass spectrum (FAB): m/z 1146 $(M+H)^+$ (3) $^1H$ NMR spectrum (300 MHz, $CDCl_3$) δ (ppm): 0.91 (d, 8-$CH_3$), 1.11 (s, 3"-$CH_3$), 1.12 (s, 6"-H), 1.13 (t, 3-$OCOCH_2CH_3$), 1.17 (t, 4"-$OCOCH_2CH_3$), 1.30 (d, 6'-H), 1.70 (m, 8-H), 1.84 (dd, 2"-Hax), 2.00 (d, 2"-Heq), 2.04 (s, 9-$OCOCH_3$), 2.04 (s, 2'-$OCOCH_3$), 2.22 (s, $NCH_3$), 2.40 (s, 3'-$N(CH_3)_2$), 2.42 (m, 10-H), 2.57 (m, 2-H), 2.76 (t, quinoline-$CH_2$), 2.87 (dd, 2-H), 3.13 (s, $CH(OCH_3)_2$), 3.24 (s, $CH(OCH_3)_2$), 3.34 (m, 4'-H), 3.34 (m, 5'-H), 3.60 (s, 4-$OCH_3$), 3.67 (br d, 4-H), 3.93 (br d, 5-H), 4.37 (dq, 5"-H), 4.56 (dd, $CH(OCH_3)_2$), 4.61 (d, 4"-H), 4.73 (d, 1'-H), 4.90 (m, 9-H), 5.01 (dd, 2'-H), 5.06 (d, 1"-H), 7.52 (ddd, quinoline), 7.65 (ddd, quinoline), 7.75 (br d, quinoline), 7.89 (br s, quinoline), 8.05 (br d, quinoline), 8.75 (d, quinoline).

(c) In the same manner as in Example 2(c), 10.0 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is 5-(quinolin-3-yl)pentyl group, $R_{3''}$ is hydrogen atom, $R_{4''}$ is propionyl group, and X is oxygen atom) was obtained from 12.8 mg of the compound of Example 136(b).

Physicochemical Properties of this Compound (1) Molecular formula: $C_{56}H_{91}N_3O_{16}$ (2) Mass spectrum (FAB): m/z 1062 $(M+H)^+$ (3) $^1H$ NMR spectrum (300 MHz, $CDCl_3$) δ (ppm): 0.89 (d, 8-$CH_3$), 1.10 (t, 3-$OCOCH_2CH_3$), 1.11 (s, 3"-$CH_3$), 1.12 (d, 6"-H), 1.18 (t, 4"-$OCOCH_2CH_3$), 1.26 (d, 6'-H), 1.43 (m, 8-H), 1.82 (dd, 2"-Hax), 2.00 (d, 2"-Heq), 2.40 (m, 3'-H), 2.50 (s, $NCH_3$), 2.40 (s, 3'-$N(CH_3)_2$), 2.58 (dd, 2-H), 2.78 (t, quinoline-$CH_2$), 2.85 (dd, 2-H), 3.15 (s, $CH(OCH_3)_2$), 3.25 (s, $CH(OCH_3)_2$), 3.30 (m, 4'-H), 3.30 (m, 5'-H), 3.60 (dd, 2'-H), 3.66 (s, 4-$OCH_3$), 3.90 (br d, 4-H), 3.97 (br d, 5-H), 4.44 (m, $CH(OCH_3)_2$), 4.47 (d, 1'-H), 4.48 (dq, 5"-H), 4.62 (d, 4"-H), 4.96 (m, 15-H), 5.07 (dd, 1"-H), 5.38 (m, 3-H), 7.52 (ddd, quinoline), 7.65 (ddd, quinoline), 7.76 (br d, quinoline), 7.89 (br s, quinoline), 8.05 (br d, quinoline), 8.75 (d, quinoline).

(d) In the same manner as in Example 2(d), 5.2 mg of the title compound was obtained from 10.0 mg of the compound of Example 136(c).

Physicochemical Properties of this Compound (1) Molecular formula: $C_{54}H_{85}N_3O_{15}$ (2) Mass spectrum (FAB): m/z 1016 $(M+H)^+$ (3) Specific rotation: $[\alpha]_D^{18}$ −62° (c0.26, $CHCl_3$)

(4) $^1H$ NMR spectrum (300 MHz, $CDCl_3$) δ (ppm): 0.92 (d, 8-$CH_3$), 1.12 (s, 3"-$CH_3$), 1.13 (d, 6"-H), 1.15 (t, 3-$OCOCH_2CH_3$), 1.18 (t, 4"-$OCOCH_2CH_3$), 1.24 (d, 6'-H), 1.32 (m, 8-H), 1.84 (dd, 2"-Hax), 2.00 (d, 2"-Heq), 2.36 (s, $NCH_3$), 2.42 (m, 3'-H), 2.50 (s, 3'-$N(CH_3)_2$), 2.58 (dd, 2-H), 2.60 (t, 6-$CH_2$), 2.78 (t, quinoline-$CH_2$), 2.85 (dd, 2-H), 3.28 (m, 4'-H), 3.28 (m, 5'-H), 3.56 (dd, 2'-H), 3.66 (s, 4-$OCH_3$), 3.86 (br d, 4-H), 4.00 (br d, 5-H), 4.38 (d, 1'-H), 4.47 (dq, 5"-H), 4.61 (d, 4"-H), 4.96 (m, 15-H), 5.06 (dd, 1"-H), 5.45 (m, 3-H), 7.51 (ddd, quinoline), 7.65 (ddd, quinoline), 7.76 (br d, quinoline), 7.89 (br s, quinoline), 8.06 (br d, quinoline), 8.74 (d, quinoline), 9.64 (s, CHO).

Example 137

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is 5-(naphthalen-2-yl) pentyl group, $R_{4'}$ is a group represented by the formula (a), $R_{3''}$ is hydrogen atom, $R_{4''}$ is propionyl group, and X is oxygen atom (a) In the same manner as in Example 134(a), except that the compound of Reference Example 40 was used instead of the compound of Reference Example 37, 38.2 mg of a coupling compound (compound represented by the formula (24) mentioned in Preparation Scheme 8 wherein $R_3$ is methyl group, $R_7$, $R_8$, $R_{12}$ are hydrogen atoms, $R_{11}$ is trans-5-(naphthalen-2-yl)-2-pentenyl group, $R_{3''}$ is hydrogen atom, $R_{4''}$ is propionyl group, and X is oxygen atom) was obtained from 50 mg of the isomer A of Example 48(b).

Physicochemical Properties of this Compound (1) Molecular formula: $C_{61}H_{94}N_2O_{18}$ (2) Mass spectrum (FAB): m/z 1143 $(M+H)^+$ (3) $^1H$ NMR spectrum (300 MHz, $CDCl_3$) δ (ppm): 0.92 (d, 8-$CH_3$), 1.08 (s, 3"-$CH_3$), 1.10 (d, 6"-H), 1.12 (t, 3-$OCOCH_2CH_3$), 1.16 (t, 4"-$OCOCH_2CH_3$), 1.26 (d, 6'-H), 1.48 (m, 6-$CH_2$), 1.72 (m, 8-H), 1.84 (dd, 2"-Hax), 2.00 (d, 2"-Heq), 2.04 (s, 9-$OCOCH_3$), 2.04 (s, 2'-$OCOCH_3$), 2.22 (s, $NCH_3$), 2.40 (s, 3'-$N(CH_3)_2$), 2.58 (m, 2-H), 2.72 (t, 3'-H), 2.80 (dd, 2-H), 3.13 (s, $CH(OCH_3)_2$), 3.24 (s, $CH(OCH_3)_2$), 3.28 (m, 4'-H), 3.32 (m, 5'-H), 3.60 (m, 4-H), 3.62 (s, 4-$OCH_3$), 3.93 (br d, 5-H), 4.38 (dq, 5"-H), 4.56 (dd, $CH(OCH_3)_2$), 4.60 (d, 4"-H), 4.73 (d, 1'-H), 4.90 (m, 9-H), 5.02 (br dd, 3-H), 5.07 (d, 1"-H), 5.35 (dt, CH═CH), 5.52 (d, CH═CH), 7.28 (m, naphthalene), 7.42 (m, naphthalene), 7.57 (s, naphthalene), 7.76 (dd, naphthalene).

(b) In the same manner as in Example 2(c), 48.1 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-5-(naphthalen-2-yl)-2-pentenyl group, $R_{3''}$ is hydrogen atom, $R_{4''}$ is propionyl group, and X is oxygen atom) was obtained from 71.2 mg of the compound of Example 137(a).

Physicochemical Properties of this Compound (1) Molecular formula: $C_{57}H_{90}N_2O_{16}$ (2) Mass spectrum (FAB): m/z 1059 $(M+H)^+$ (3) $^1$H NMR spectrum (300 MHz, $CDCl_3$) δ (ppm): 0.92 (d, 8-$CH_3$), 1.09 (s, 3"-$CH_3$), 1.11 (d, 6"-H), 1.12 (t, 3-$OCOCH_2CH_3$), 1.18 (t, 4"-$OCOCH_2CH_3$), 1.24 (d, 6'-H), 1.48 (m, 6-$CH_2$), 1.84 (dd, 2"-Hax), 2.00 (d, 2"-Heq), 2.25 (s, $NCH_3$), 2.40 (m, 2-H), 2.44 (s, 3'-$N(CH_3)_2$), 2.80 (dd, 2-H), 3.16 (s, $CH(OCH_3)_2$), 3.25 (s, $CH(OCH_3)_2$), 3.22 (m, 4'-H), 3.22 (m, 5'-H), 3.60 (dd, 2'-H), 3.66 (s, 4-$OCH_3$), 3.75 (br d, 4-H), 3.95 (br d, 5-H), 4.40 (d, 1'-H), 4.42 (dq, 5"-H), 4.60 (d, 4"-H), 5.07 (d, 1"-H), 5.35 (dt, CH═CH), 5.40 (m, 3-H), 5.50 (d, CH═CH), 7.29 (m, naphthalene), 7.41 (m, naphthalene), 7.58 (s, naphthalene), 7.76 (dd, naphthalene).

(c) In the same manner as in Example 8(d), 15.7 mg of a double bond-reduced compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is 5-(naphthalen-2-yl)pentyl group, $R_{3''}$ is hydrogen atom, $R_{4''}$ is propionyl group, and X is oxygen atom) was obtained from 22.5 mg of the compound of Example 137(b).

Physicochemical Properties of this Compound (1) Molecular formula: $C_{57}H_{92}N_2O_{16}$ (2) Mass spectrum (FAB): m/z 1061 $(M+H)^+$ (3) Specific rotation: $[\alpha]_D^{23}$ −49° (c1.0, $CHCl_3$)

(4) $^1$H NMR spectrum (300 MHz, $CDCl_3$) δ (ppm): 0.89 (d, 8-$CH_3$), 1.10 (s, 3"-$CH_3$), 1.12 (d, 6"-H), 1.13 (t, 3-$OCOCH_2CH_3$), 1.17 (t, 4"-$OCOCH_2CH_3$), 1.27 (d, 6'-H), 1.48 (m, 8-H), 1.82 (dd, 2"-Hax), 2.00 (d, 2"-Heq), 2.30 (s, $NCH_3$), 2.43 (m, 3'-H), 2.49 (s, 3'-$N(CH_3)_2$), 2.74 (dd, 2-H), 3.15 (s, $CH(OCH_3)_2$), 3.24 (s, $CH(OCH_3)_2$), 3.30 (dd, 9-H), 3.34 (m, 4'-H), 3.34 (m, 5'-H), 3.60 (dd, 2'-H), 3.65 (s, 4-$OCH_3$), 3.90 (br d, 4-H), 3.98 (br d, 5-H), 4.44 (dq, 5"-H), 4.48 (d, 1'-H), 4.61 (d, 4"-H), 4.96 (m, 15-H), 5.07 (d, 1"-H), 5.39 (m, 3-H), 7.28 (m, naphthalene), 7.41 (m, naphthalene), 7.57 (s, naphthalene), 7.76 (dd, naphthalene).

(d) In the same manner as in Example 2(d), 11.1 mg of the title compound was obtained from 15.7 mg of the compound of Example 137(c).

Physicochemical Properties of this Compound (1) Molecular formula: $C_{55}H_6N_2O_{15}$ (2) Mass spectrum (FAB): m/z 1015 $(M+H)^+$ (3) Specific rotation: $[\alpha]_D^{22}$ −41° (c0.6, $CHCl_3$)

(4) $^1$H NMR spectrum (300 MHz, $CDCl_3$) δ (ppm): 0.93 (d, 8-$CH_3$), 1.10 (s, 3"-$CH_3$), 1.12 (d, 6"-H), 1.14 (t, 3-$OCOCH_2CH_3$), 1.17 (t, 4"-$OCOCH_2CH_3$), 1.20 (d, 6'-H), 1.32 (m, 8-H), 1.82 (dd, 2"-Hax), 2.00 (d, 2"-Heq), 2.33 (s, $NCH_3$), 2.34 (m, 10-H), 2.43 (m, 3'-H), 2.50 (s, 3'-$N(CH_3)_2$), 2.74 (dd, 2-H), 2.86 (dd, 6-$CH_2$), 3.26 (m, 4'-H), 3.30 (m, 5'-H), 3.40 (m, 9-H), 3.56 (dd, 2'-H), 3.66 (s, 4-$OCH_3$), 3.85 (br d, 4-H), 4.00 (br d, 5-H), 4.38 (d, 1'-H), 4.47 (dq, 5"-H), 4.60 (d, 4"-H), 4.96 (m, 15-H), 5.07 (d, 1"-H), 5.43 (m, 3-H), 7.28 (m, naphthalene), 7.41 (m, naphthalene), 7.60 (s, naphthalene), 7.78 (dd, naphthalene), 9.64 (s, CHO).

Example 138

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), one of $R_7$ and $R_8$ is 5-(quinolin-3-yl)pentyl group, the other is hydrogen atom, $R_9$, $R_{10}$, $R_{11}$ and $R_{12}$ are hydrogen atoms, $R_{4'}$ is a group represented by the formula (a), $R_{3''}$ is hydrogen atom, $R_{4''}$ is propionyl group, and X is oxygen atom (a) In the same manner as in Example 134(a), except that the compound of Reference Example 39 was used instead of the compound of Reference Example 37, 34.2 mg of a coupling compound (compound represented by the formula (24) mentioned in Preparation Scheme 8 wherein $R_3$ is methyl group, one of $R_7$ and $R_8$ is trans-5-(quinolin-3-yl)-2-pentenyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 79.9 mg of the isomer A of Example 54(b).

Physicochemical Properties of this Compound (1) Molecular formula: $C_{60}H_{93}N_3O_{18}$ (2) Mass spectrum (FAB): m/z 1144 $(M+H)^+$ (3) $^1$H NMR spectrum (300 MHz, $CDCl_3$) δ (ppm): 0.94 (d, 8-$CH_3$), 1.12 (t, 3-$OCOCH_2CH_3$), 1.12 (s, 3"-$CH_3$), 1.13 (d, 6"-H), 1.18 (t, 4"-$OCOCH_2CH_3$), 1.27 (d, 6'-H), 1.84 (dd, 2"-Hax), 2.01 (d, 2"-Heq), 2.03 (s, 9-$OCOCH_3$), 2.04 (s, 2'-$OCOCH_3$), 2.13 (d, 12-H), 2.20 (s, $NCH_3$), 2.40 (s, 3'-$N(CH_3)_2$), 2.54 (m, 10-H), 2.67 (dd, 2-H), 2.72 (t, 3'-H), 2.74 (dd, 2-H), 2.86 (t, quinoline-$CH_2$), 3.16 (s, $CH(OCH_3)_2$), 3.25 (s, $CH(OCH_3)_2$), 3.32 (t, 4'-H), 3.53 (s, 4-$OCH_3$), 3.90 (d, 5-H), 4.38 (dq, 5"-H), 4.51 (dd, $CH(OCH_3)_2$), 4.62 (d, 4"-H), 4.71 (d, 1'-H), 4.89 (m, 9-H), 5.00 (dd, 2'-H), 5.07 (d, 1"-H), 5.17 (br dd, 3-H), 5.42 (dt, CH═CH), 5.49 (dt, CH═CH), 7.52 (ddd, quinoline), 7.65 (ddd, quinoline), 7.77 (br d, quinoine), 7.92 (d, quinoline), 8.06 (br d, quinoline), 8.77 (d, quinoline).

(b) In the same manner as in Example 8(d), 8.2 mg of a double bond-reduced compound (compound represented by the formula (24) mentioned in Preparation Scheme 8 wherein $R_3$ is methyl group, one of $R_7$ and $R_8$ is 5-(quinolin-3-yl)pentyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 34.2 mg of the compound of Example 138(a).

Physicochemical Properties of this Compound (1) Molecular formula: $C_{60}H_{95}N_3O_{18}$ (2) Mass spectrum (FAB): m/z 1146 $(M+H)^+$ (3) $^1$H NMR spectrum (300 MHz, $CDCl_3$) δ (ppm): 0.95 (d, 8-$CH_3$), 1.12 (t, 3-$OCOCH_2CH_3$), 1.12 (s, 3"-$CH_3$), 1.13 (d, 6"-H), 1.18 (t, 4"-$OCOCH_2CH_3$), 1.27 (d, 6'-H), 1.37 (m, 13-$CH_2CH_2CH_2$), 1.85 (dd, 2"-Hax), 2.02 (d, 2"-Heq), 2.03 (s, 9-$OCOCH_3$), 2.04 (s, 2'-$OCOCH_3$), 2.21 (d, 12-H), 2.25 (s, $NCH_3$), 2.41 (s, 3'-$N(CH_3)_2$), 2.59 (dd, 10-H), 2.72 (t, 3'-H), 2.80 (t, quinoline-$CH_2$), 3.16 (s, $CH(OCH_3)_2$), 3.25 (s, $CH(OCH_3)_2$), 3.54 (s, 4-$OCH_3$), 3.91 (d, 5-H), 4.20 (m, 15-H), 4.38 (dq, 5"-H), 4.51 (dd, $CH(OCH_3)_2$), 4.62 (d, 4"-H), 4.72 (d, 1'-H), 4.87 (m, 9-H), 5.01 (dd, 2'-H), 5.07 (d, 1"-H), 5.19 (br dd, 3-H), 7.52 (ddd, quinoline), 7.65 (ddd, quinoline), 7.77 (br d, quinoline), 7.92 (br s, quinoline), 8.07 (br d, quinoline), 8.77 (d, quinoline).

(c) In the same manner as in Example 2(c), 1.59 mg of a deacetyled compound (compound represented by the formula (25) mentioned in Preparation Scheme 8 wherein $R_2$ is hydrogen atom, $R_3$ is methyl group, one of $R_7$ and $R_8$ is 5-(quinolin-3-yl)pentyl group, the other is hydrogen atom, $R_{11}$ and $R_{12}$ are hydrogen atoms, $R_{3''}$ is hydrogen atom, $R_{4''}$ is propionyl group, and X is oxygen atom) was obtained from 10.8 mg of the compound of Example 138(b).

Physicochemical Properties of this Compound (1) Molecular formula: $C_{56}H_{91}N_3O_{16}$ (2) Mass spectrum (FAB): m/z 1062 $(M+H)^+$ (3) $^1$H NMR spectrum (300 MHz, $CDCl_3$) δ (ppm): 0.85 (d, 8-$CH_3$), 1.08 (t, 3-$OCOCH_2CH_3$), 1.12 (s, 3"-$CH_3$), 1.13 (d, 6"-H), 1.18 (t, 4"-$OCOCH_2CH_3$), 1.27 (d, 6'-H), 1.38 (m, 13-$CH_2CH_2\underline{CH_2}$), 1.84 (dd, 2"-Hax), 2.01 (d, 2"-Heq), 2.29 (s, $NCH_3$), 2.51 (s, 3'-$N(CH_3)_2$), 2.64 (d, 2-H), 2.80 (t, quinoline-$CH_2$), 3.16 (s, $CH(OCH_3)_2$), 3.25 (s, $CH(OCH_3)_2$), 3.64 (s, 4-$OCH_3$), 3.87 (d, 5-H), 4.03 (m, 15-H), 4.42 (d, 1'-H), 4.63 (d, 4"-H), 5.08 (d, 1"-H), 5.74 (m, 3-H), 7.53 (ddd, quinoline), 7.66 (ddd, quinoline), 7.77 (br d, quinoline), 7.91 (br s, quinoline), 8.07 (br d, quinoline), 8.77 (d, quinoline).

(d) In the same manner as in Example 2(d), 1.21 mg of the title compound was obtained from 1.59 mg of the compound of Example 138(c).

Physicochemical Properties of this Compound (1) Molecular formula: $C_{54}H_{85}N_3O_{15}$ (2) Mass spectrum (FAB): m/z 1016 $(M+H)^+$ (3) $^1$H NMR spectrum (300 MHz, $CDCl_3$) δ (ppm): 0.86 (d, 8-$CH_3$), 1.12 (s, 3"-$CH_3$), 1.13 (d, 6"-H), 1.14 (t, 3-$OCOCH_2CH_3$), 1.18 (t, 4"-$OCOCH_2CH_3$), 1.38 (m, 13-$CH_2CH_2\underline{CH_2}$), 1.83 (dd, 2"-Hax), 2.01 (d, 2"-Heq), 2.30 (br s, $NCH_3$), 2.51 (s, 3'-$N(CH_3)_2$), 2.66 (m, 2-H), 2.80 (t, quinoline-$CH_2$), 3.56 (dd, 2'-H), 3.64 (s, 4-$OCH_3$), 3.67 (d, 4-H), 3.82 (d, 5-H), 4.04 (m, 15-H), 4.34 (d, 1'-H) 4.62 (d, 4"-H), 5.07 (d, 1"-H), 5.79 (m, 3-H), 7.52 (ddd, quinoline), 7.66 (ddd, quinoline), 7.77 (br d, quinoline), 7.91 (d, quinoline), 8.07 (br d, quinoline), 8.77 (d, quinoline), 9.64 (s, CHO).

Preparation Scheme 11

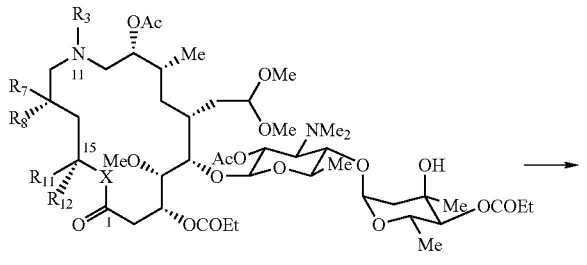

(33)

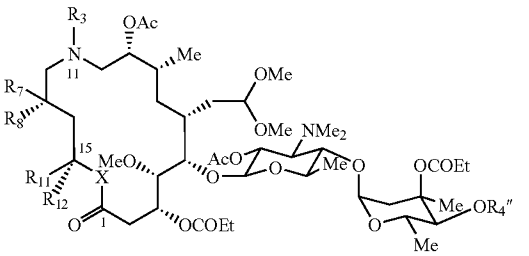

(34)

Example 139

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(quinolin-3-yl)-2-propenyl group, $R_{4'}$ is a group represented by the formula (a), $R_{3''}$ is propionyl group, $R_{4''}$ is isovaleryl group, and X is oxygen atom (a) In an amount of 50 mg of the compound of Example 53(a) was added with 350 μl of pyridine, dissolved therein, added with 270 μl of isovaleric anhydride, and stirred at 100° C. for 68 hours. The reaction mixture was returned to room temperature, then added with 20 ml of ethyl acetate, and successively washed twice with 10 ml of water, three times with 10 ml of 5% aqueous ammonia, and 10 ml of saturated brine. The organic layer was dried over anhydrous sodium sulfate, and filtered, and then the filtrate was concentrated under reduced pressure. The resulting residue was purified by silica gel column chromatography (hexane/acetone/aqueous ammonia (20:10:0.1)) to obtain 39 mg of an acyl compound (compound represented by the formula (34) mentioned in Preparation Scheme 11 wherein $R_3$ is methyl group, $R_7$, $R_8$ and $R_{12}$ are hydrogen atoms, $R_1$ is trans-3-(quinolin-3-yl)-2-propenyl group, $R_{3''}$ is propionyl group, $R_{4''}$ is isovaleryl group, and X is oxygen atom).

Physicochemical Properties of this Compound (1) Molecular formula: $C_{63}H_{97}N_3O_{19}$ (2) Mass spectrum (FAB): m/z 1200 $(M+H)^+$ (3) Specific rotation: $[\alpha]_D^{24}$ −59° (c0.62, $CHCl_3$)

(4) $^1$H NMR spectrum (300 MHz, $CDCl_3$) δ (ppm): 0.92 (d, 8-$CH_3$), 0.99 (d, 4"-$OCOCH_2CH(CH_3)_2$), 1.08 (d, 6"-H), 1.14 (t, 3-$OCOCH_2CH_3$), 1.14 (t, 3"-$OCOCH_2CH_3$), 1.20 (d, 6'-H), 1.42 (s, 3"-$CH_3$), 1.54 (m, 13-H), 1.68 (dd, 2"-H), 2.04 (s, 9-$OCOCH_3$), 2.06 (s, 2'-$OCOCH_3$), 2.24 (s, $NCH_3$), 2.43 (s, 3'-$N(CH_3)_2$), 2.87 (dd, 2-H), 3.13 (t, 4'-H), 3.15 (s, $CH(OCH_3)_2$), 3.20 (d, 2"-Heq), 3.25 (s, $CH(OCH_3)_2$), 3.60 (s, 4-$OCH_3$), 3.93 (br d, 5-H), 4.48 (dq, 5"-H), 4.58 (d, 4"-H), 4.68 (d, 1'-H), 4.80 (d, 1"-H), 4.92 (m, 9-H), 4.97 (dd, 2'-H), 5.08 (br d, 3-H), 5.16 (m, 15-H), 6.37 (dt, CH=CH), 6.61 (d, CH=CH), 7.53 (ddd, quinoline), 7.67 (ddd, quinoline), 7.79 (br d, quinoline), 8.02 (d, quinoline), 8.06 (br d, quinoline), 8.95 (d, quinoline).

(b) In the same manner as in Example 2(c), 19 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(quinolin-3-yl)-2-propenyl group, $R_{3''}$ is propionyl group, $R_{4''}$ is isovaleryl group, and X is oxygen atom) was obtained from 37 mg of the compound of Example 139(a).

Physicochemical Properties of this Compound (1) Molecular formula: $C_{59}H_{83}N_3O_{17}$ (2) Mass spectrum (FAB): m/z 1116 $(M+H)^+$ (3) Specific rotation: $[\alpha]_D^{20}$ −49° (c0.90, $CHCl_3$)

(4) $^1$H NMR spectrum (300 MHz, $CDCl_3$) δ (ppm): 0.89 (d, 8-$CH_3$), 0.99 (d, 4"-$OCOCH_2CH(CH_3)_2$), 1.09 (d, 6"-H), 1.11 (t, 3-$OCOCH_2CH_3$), 1.12 (t, 3"-$OCOCH_2CH_3$), 1.20 (d, 6'-H), 1.43 (s, 3"-$CH_3$), 1.69 (dd, 2"-H), 2.28 (s, $NCH_3$), 2.53 (s, 3'-$N(CH_3)_2$), 2.62 (dd, 2-H), 2.72 (m, 12-H), 2.83 (dd, 2-H), 3.15 (s, $CH(OCH_3)_2$), 3.17 (d, 2"-Heq), 3.25 (s, $CH(OCH_3)_2$), 3.38 (m, 9-H), 3.48 (dd, 2'-H), 3.66 (s, 4-$OCH_3$), 3.89 (br d, 4-H), 3.97 (br d, 5-H), 4.46 (d, 1'-H), 4.48 (dd, $CH(OCH_3)_2$), 4.55 (m, 5"-H), 4.59 (m, 4"-H), 4.82 (d, 1"-H), 5.13 (m, 15-H), 5.45 (br dd, 3-H), 6.36 (dt, $CH{=}CH_2$), 6.59 (d, $CH{=}CH_2$), 7.53 (ddd, quinoline), 7.67 (ddd, quinoline), 7.78 (br d, quinoline), 8.00 (d, quinoline), 8.06 (br d, quinoline), 8.94 (d, quinoline).

(c) In the same manner as in Example 2(d), 14 mg of the title compound was obtained from 18 mg of the compound of Example 139(b).

Physicochemical Properties of this Compound (1) Molecular formula: $C_{57}H_{87}N_3O_{16}$ (2) Mass spectrum (FAB): m/z 1070 $(M+H)^+$ (3) Specific rotation: $[\alpha]_D^{23}$ −58° (c0.70, $CHCl_3$)

(4) $^1H$ NMR spectrum (300 MHz, $CDCl_3$) δ (ppm): 0.90 (d, 8-$CH_3$), 0.99 (d, 4"-$OCOCH_2CH(CH_3)_2$), 1.09 (d, 6"-H), 1.12 (t, 3-$OCOCH_2CH_3$), 1.13 (d, 6'-H), 1.16 (t, 3"-$OCOCH_2CH_3$), 1.35 (m, 8-H), 1.42 (s, 3"-$CH_3$), 1.70 (dd, 2"-H), 2.27 (s, $NCH_3$), 2.53 (s, 3'-$N(CH_3)_2$), 2.84 (dd, 2-H), 2.90 (dd, 6-$CH_2$), 3.16 (m, 4'-H), 3.18 (m, 5'-H), 3.22 (d, 2"-Heq), 3.37 (m, 9-H), 3.40 (dd, 2'-H), 3.66 (s, 4-$OCH_3$), 3.87 (br d, 5-H), 3.98 (br d, 4-H), 4.39 (d, 1'-H), 4.52 (dq, 5"-H), 4.59 (d, 4"-H), 4.83 (d, 1"-H), 5.13 (m, 15-H), 5.57 (br dd, 3-H), 6.35 (dt, $CH{=}CH_2$), 6.59 (d, $CH{=}CH_2$), 7.53 (ddd, quinoline), 7.67 (ddd, quinoline), 7.78 (br d, quinoline), 8.01 (d, quinoline), 8.06 (br d, quinoline), 8.94 (d, quinoline), 9.65 (s, CHO).

Example 140

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_8$, $R_9$, $R_{10}$ and $R_{12}$ are hydrogen atoms, $R_{11}$ is trans-3-(quinolin-3-yl)-2-propenyl group, $R_{4'}$ is a group represented by the formula (a), $R_{3''}$ is propionyl group, $R_{4''}$ is isobutyryl group, and X is oxygen atom (a) In the same manner as in Example 139(a), except that isobutyric anhydride was used instead of isovaleric anhydride, 14 mg of an acyl compound (compound represented by the formula (34) mentioned in Preparation Scheme 11 wherein $R_3$ is methyl group, $R_7$, $R_8$ and $R_{12}$ are hydrogen atoms, $R_{11}$ is trans-3-(quinolin-3-yl)-2-propenyl group, $R_{3''}$ is propionyl group, $R_{4''}$ is isobutyryl group, and X is oxygen atom) was obtained from 60 mg of the compound of Example 53(a).

Physicochemical Properties of this Compound (1) Molecular formula: $C_{62}H_{95}N_3O_{19}$ (2) Mass spectrum (FAB): m/z 1186 $(M+H)^+$ (3) Specific rotation: $[\alpha]_D^{24}$ −57° (c0.69, $CHCl_3$)

(4) $^1H$ NMR spectrum (300 MHz, $CDCl_3$) δ (ppm): 0.92 (d, 8-$CH_3$), 1.06 (d, 6"-H), 1.19 (d, 6'-H), 1.20 (d, 4"-$OCOCH(CH_3)_2$), 1.41 (s, 3"-$CH_3$), 1.68 (dd, 2"-H), 2.04 (s, 9-$OCOCH_3$), 2.06 (s, 2'-$OCOCH_3$), 2.24 (s, $NCH_3$), 2.42 (s, 3'-$N(CH_3)_2$), 2.65 (t, 3'-H), 2.89 (dd, 2-H), 3.15 (s, $CH(OCH_3)_2$), 3.19 (d, 2"-Heq), 3.25 (s, $CH(OCH_3)_2$), 3.59 (s, 4-$OCH_3$), 3.61 (br d, 4-H), 3.93 (br d, 5-H), 4.49 (dq, 5"-H), 4.55 (d, 4"-H), 4.68 (d, 1'-H), 4.80 (d, 1"-H), 4.92 (m, 9-H), 4.97 (dd, 2'-H), 5.07 (br dd, 3-H), 5.14 (m, 15-H), 6.37 (dt, $CH{=}CH$), 6.61 (d, $CH{=}CH$), 7.52 (ddd, quinoline), 7.66 (ddd, quinoline), 7.78 (br d, quinoline), 8.02 (d, quinoline), 8.06 (br d, quinoline), 8.95 (d, quinoline).

(b) In the same manner as in Example 2(c), 16 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(quinolin-3-yl)-2-propenyl group, $R_{3''}$ is propionyl group, $R_{4''}$ is isobutyryl group, and X is oxygen atom) was obtained from 33 mg of the compound of Example 140(a).

Physicochemical Properties of this Compound (1) Molecular formula: $C_{58}H_{91}N_3O_{17}$ (2) Mass spectrum (FAB): m/z 1102 $(M+H)^+$ (3) Specific rotation: $[\alpha]_D^{24}$ −47° (c0.78, $CHCl_3$)

(4) $^1H$ NMR spectrum (300 MHz, $CDCl_3$) δ (ppm): 0.88 (d, 8-$CH_3$), 1.07 (d, 6"-H), 1.11 (t, 3-$OCOCH_2CH_3$), 1.13 (t, 3"-$OCOCH_2CH_3$), 1.20 (d, 6'-H), 1.23 (d, 4"-$OCOCH(CH_3)_2$), 1.41 (s, 3"-$CH_3$), 1.70 (dd, 2"-H), 1.94 (m, 6-H), 2.34 (s, $NCH_3$), 2.53 (s, 3'-$N(CH_3)_2$), 2.82 (dd, 2-H), 3.15 (s, $CH(OCH_3)_2$), 3.18 (d, 2"-Heq), 3.25 (s, $CH(OCH_3)_2$), 3.36 (m, 9-H), 3.48 (dd, 2'-H), 3.65 (s, 4-$OCH_3$), 3.89 (br d, 5-H), 3.97 (br d, 4-H), 4.45 (d, 1'-H), 4.49 (dd, $CH(OCH_3)_2$), 4.56 (m, 4"-H), 4.56 (m, 5"-H), 4.83 (d, 1"-H), 5.13 (m, 15-H), 5.47 (br dd, 3-H), 6.36 (dt, $CH{=}CH_2$), 6.59 (d, $CH{=}CH_2$), 7.56 (ddd, quinoline), 7.66 (ddd, quinoline), 7.78 (br d, quinoline), 8.00 (d, quinoline), 8.06 (br d, quinoline), 8.94 (d, quinoline).

(c) In the same manner as in Example 2(d), 12 mg of the title compound was obtained from 15 mg of the compound of Example 140(b).

Physicochemical Properties of this Compound (1) Molecular formula: $C_{56}H_{85}N_3O_{16}$ (2) Mass spectrum (FAB): m/z 1056 $(M+H)^+$ (3) Specific rotation: $[\alpha]_D^{25}$ −55 (c0.52, $CHCl_3$)

(4) $^1H$ NMR spectrum (300 MHz, $CDCl_3$) δ (ppm): 0.90 (d, 8-$CH_3$), 1.08 (d, 6"-H), 1.13 (t, 3-$OCOCH_2CH_3$), 1.14 (d, 6'-H), 1.16 (t, 3"-$OCOCH_2CH_3$), 1.20 (d, 4"-$OCOCH(CH_3)_2$), 1.22 (d, 4"-$OCOCH(CH_3)_2$), 1.34 (m, 8-H), 1.41 (s, 3"-$CH_3$), 1.70 (dd, 2"-H), 2.32 (s, $NCH_3$), 2.53 (s, 3'-$N(CH_3)_2$), 2.84 (dd, 2-H), 2.89 (dd, 6-$CH_2$), 3.16 (m, 4'-H), 3.18 (m, 5'-H), 3.21 (d, 2"-Heq), 3.36 (m, 9-H), 3.40 (dd, 2'-H), 3.66 (s, 4-$OCH_3$), 3.87 (br d, 5-H), 3.98 (br d, 4-H), 4.38 (d, 1'-H), 4.53 (dq, 5"-H), 4.56 (d, 4"-H), 4.83 (d, 1"-H), 5.13 (m, 15-H), 5.57 (br dd, 3-H), 6.35 (dt, $CH{=}CH_2$), 6.59 (d, $CH{=}CH_2$), 7.52 (ddd, quinoline), 7.66 (ddd, quinoline), 7.78 (br d, quinoline), 8.00 (d, quinoline), 8.06 (br d, quinoline), 8.94 (d, quinoline), 9.65 (s, CHO).

Example 141

Preparation method of the compound represented by the formula (3) wherein $R_1$ is propionyl group, $R_2$ is hydrogen atom, $R_3$ is methyl group, $R_5$ and $R_6$ are hydrogen atoms, E is a group represented by the formula (b), $R_7$, $R_9$, $R_9$, $R_{10}$ and $R_{12}$ are hydrogen atoms, $R_{11}$ is trans-3-(quinolin-3-yl)-2-propenyl group, $R_{4'}$ is a group represented by the formula (a), $R_{3''}$ is propionyl group, $R_{4''}$ is n-butyryl group, and X is oxygen atom (a) In the same manner as in Example 139(a), except that butyric anhydride was used instead of isovaleric anhydride, 49 mg of an acyl compound (compound represented by the formula (34) mentioned in Preparation Scheme 11 wherein $R_3$ is methyl group, $R_7$, $R_8$ and $R_{12}$ are hydrogen atoms, $R_{11}$ is trans-3-(quinolin-3-yl)-2-propenyl group, $R_{3''}$ is propionyl group, $R_{4''}$ is n-butyryl group, and X is oxygen atom) was obtained from 60 mg of the compound of Example 53(a).

Physicochemical Properties of this Compound (1) Molecular formula: $C_{62}H_{95}N_3O_{19}$ (2) Mass spectrum (FAB): m/z 1186 $(M+H)^+$ (3) Specific rotation: $[\alpha]_D^{24}$ −580 (c1.0, $CHCl_3$)

(4) $^1H$ NMR spectrum (300 MHz, $CDCl_3$) δ (ppm): 0.92 (d, 8-$CH_3$), 0.98 (d, 4"-OCO$(CH_2)_2CH_3$), 1.07 (d, 6"-H), 1.14 (t, 3-$OCOCH_2CH_3$), 1.15 (t, 3"-$OCOCH_2CH_3$), 1.20 (d, 6'-H), 1.42 (s, 3"-$CH_3$), 1.70 (m, 4"-OCO$(CH_2)_2CH_3$), 2.04 (s, 9-$OCOCH_3$), 2.05 (s, 2'-$OCOCH_3$), 2.24 (s, $NCH_3$), 2.43 (s, 3'-$N(CH_3)_2$), 2.62 (dd, 2-H), 2.86 (dd, 2-H), 3.15 (s, $CH(OCH_3)_2$), 3.20 (d, 2"-Heq), 3.25 (s, $CH(OCH_3)_2$), 3.59 (s, 4-$OCH_3$), 3.93 (br d, 5-H), 4.48 (dq, 5"-H), 4.57 (d, 4"-H), 4.68 (d, 1'-H), 4.80 (d, 1"-H), 4.92 (m, 9-H), 4.97 (dd, 2'-H), 5.08 (br dd, 3-H), 5.15 (m, 15-H), 6.37 (dt, CH═CH), 6.61 (d, CH═CH), 7.52 (ddd, quinoline), 7.67 (ddd, quinoline), 7.78 (br d, quinoline), 8.02 (d, quinoline), 8.06 (br d, quinoline), 8.95 (d, quinoline).

(b) In the same manner as in Example 2(c), 26 mg of a deacetyled compound (compound represented by the formula (25) mentioned in Preparation Scheme 8 wherein $R_2$ is hydrogen atom, $R_3$ is methyl group, $R_7$, $R_8$ and $R_{12}$ are hydrogen atoms, $R_{11}$ is trans-3-(quinolin-3-yl)-2-propenyl group, $R_{3''}$ is propionyl group, $R_{4''}$ is n-butyryl group, and X is oxygen atom) was obtained from 48 mg of the compound of Example 141(a).

Physicochemical Properties of this Compound (1) Molecular formula: $C_{58}H_{91}N_3O_{17}$ (2) Mass spectrum (FAB): m/z 1102 $(M+H)^+$ (3) Specific rotation: $[\alpha]_D^{24}$ −55° (c0.90, $CHCl_3$)

(4) $^1H$ NMR spectrum (300 MHz, $CDCl_3$) δ (ppm): 0.88 (d, 8-$CH_3$), 0.98 (t, 4"-OCO$(CH_2)_2CH_3$), 1.09 (d, 6"-H), 1.11 (t, 3-$OCOCH_2CH_3$), 1.13 (t, 3"-$OCOCH_2CH_3$), 1.21 (d, 6'-H), 1.42 (s, 3"-$CH_3$), 1.70 (t, 4"-OCO$(CH_2)_2CH_3$), 1.93 (m, 6-H), 2.34 (s, $NCH_3$), 2.53 (s, 3'-$N(CH_3)_2$), 2.62 (dd, 2-H), 2.82 (dd, 2-H), 3.15 (s, $CH(OCH_3)_2$), 3.17 (d, 2"-Heq), 3.25 (s, $CH(OCH_3)_2$), 3.34 (m, 9-H), 3.48 (dd, 2'-H), 3.65 (s, 4-$OCH_3$), 3.89 (br d, 5-H), 3.97 (br d, 4-H), 4.45 (d, 1'-H), 4.49 (dd, $CH(OCH_3)_2$), 4.57 (m, 4"-H), 4.57 (m, 5"-H), 4.82 (d, 1"-H), 5.14 (m, 15-H), 5.48 (br dd, 3-H), 6.35 (dt, CH═$CH_2$), 6.59 (d, CH═$CH_2$), 7.53 (ddd, quinoline), 7.66 (ddd, quinoline), 7.78 (br d, quinoline), 8.00 (d, quinoline), 8.06 (br d, quinoline), 8.94 (d, quinoline).

(c) In the same manner as in Example 2(d), 23 mg of the title compound was obtained from 25 mg of the compound of Example 141(b).

Physicochemical Properties of this Compound (1) Molecular formula: $C_{56}H_{85}N_3O_{16}$ (2) Mass spectrum (FAB): m/z 1056 $(M+H)^+$ (3) Specific rotation: $[\alpha]_D^{22}$ −60° (c0.80, $CHCl_3$)

(4) $^1H$ NMR spectrum (300 MHz, $CDCl_3$) δ (ppm): 0.90 (d, 8-$CH_3$), 0.98 (t, 4"-OCO$(CH_2)_2CH_3$)), 1.09 (d, 6"-H), 1.12 (t, 3-$OCOCH_2CH_3$), 1.14 (d, 6'-H), 1.16 (t, 3"-$OCOCH_2CH_3$), 1.35 (m, 8-H), 1.42 (s, 3"-$CH_3$), 2.32 (s, $NCH_3$), 2.53 (s, 3'-$N(CH_3)_2$), 2.64 (dd, 2-H), 2.68 (dd, 12-H), 2.84 (dd, 2-H), 2.89 (dd, 6-$CH_2$), 3.16 (m, 4'-H), 3.18 (m, 5'-H), 3.22 (d, 2"-Heq), 3.35 (m, 9-H), 3.40 (dd, 2'-H), 3.66 (s, 4-$OCH_3$), 3.87 (br d, 5-H), 3.98 (br d, 4-H), 4.38 (d, 1'-H), 4.52 (dq, 5"-H), 4.58 (d, 4"-H), 4.83 (d, 1"-H), 5.13 (m, 15-H), 5.57 (br dd, 3-H), 6.35 (dt, CH═$CH_2$), 6.59 (d, CH═$CH_2$), 7.53 (ddd, quinoline), 7.66 (ddd, quinoline), 7.78 (br d, quinoline), 8.00 (d, quinoline), 8.06 (br d, quinoline), 8.94 (d, quinoline), 9.65 (s, CHO).

Example 1

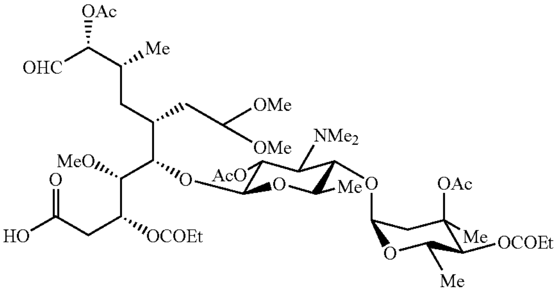

Example 2

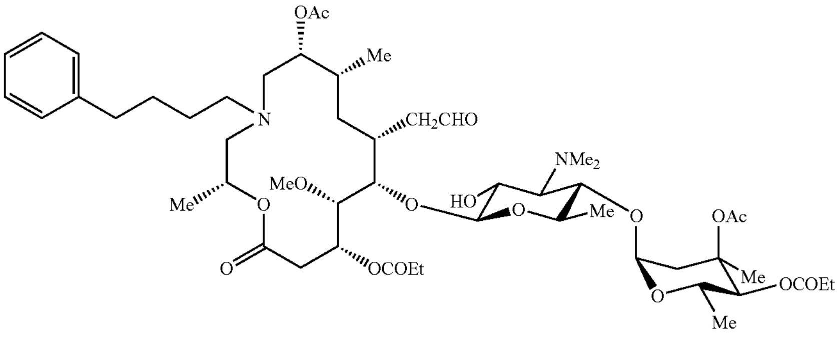

Example 3

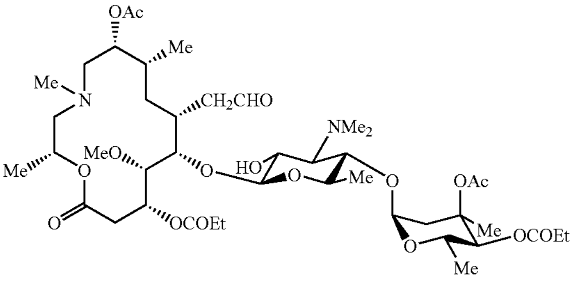

Example 4
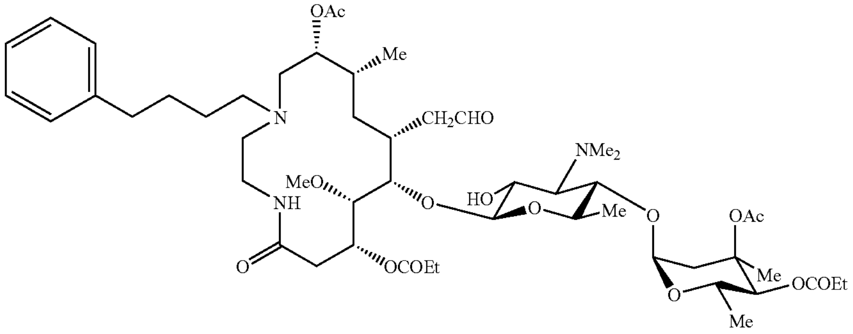
Example 5
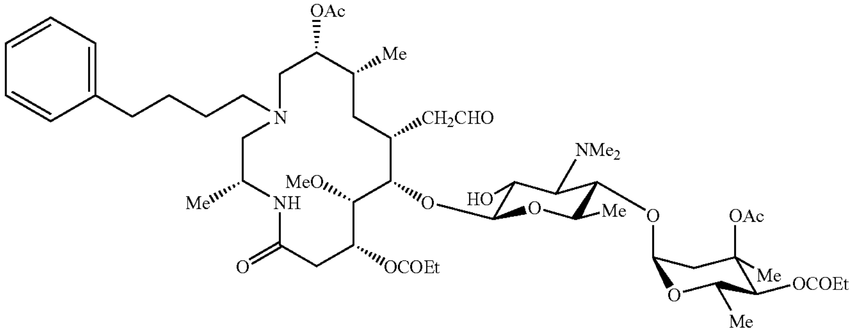
Example 6
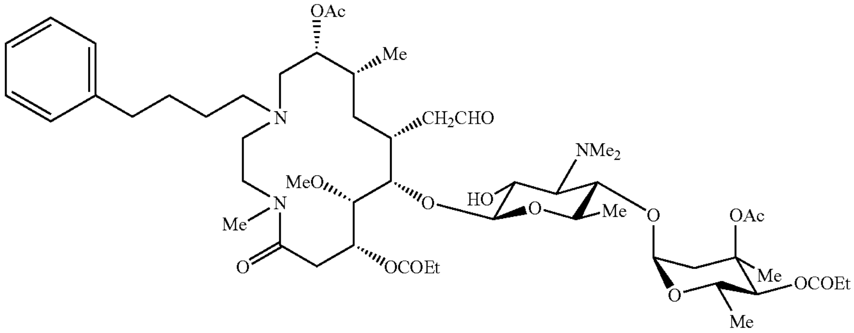
Example 7
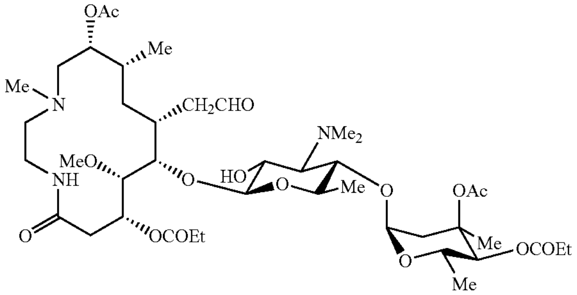
Example 8
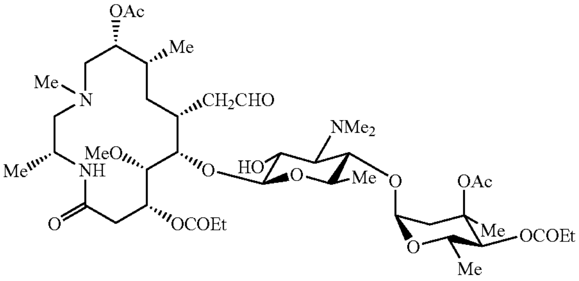

Example 9
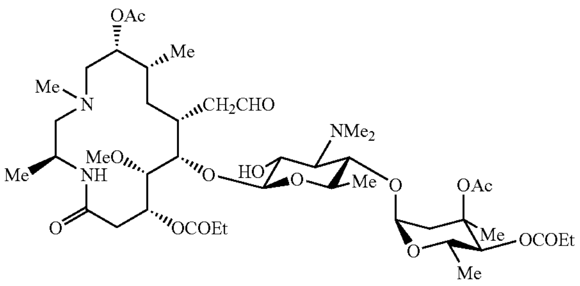
Example 10
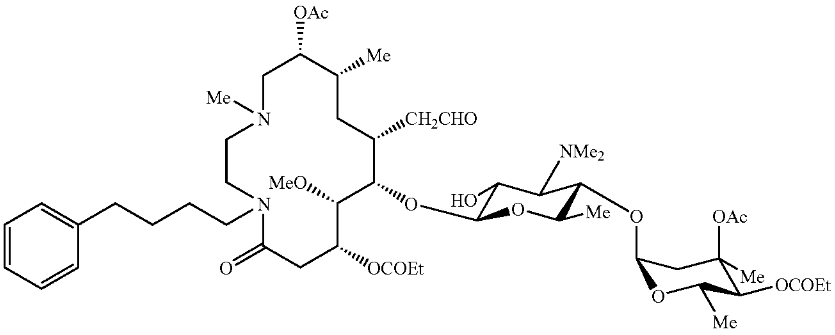
Example 11
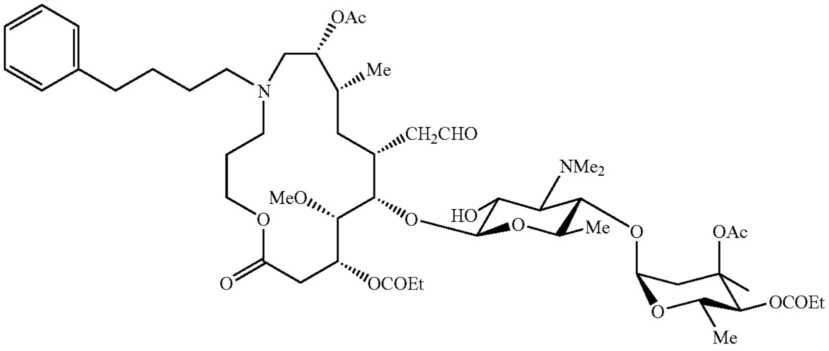
Example 12
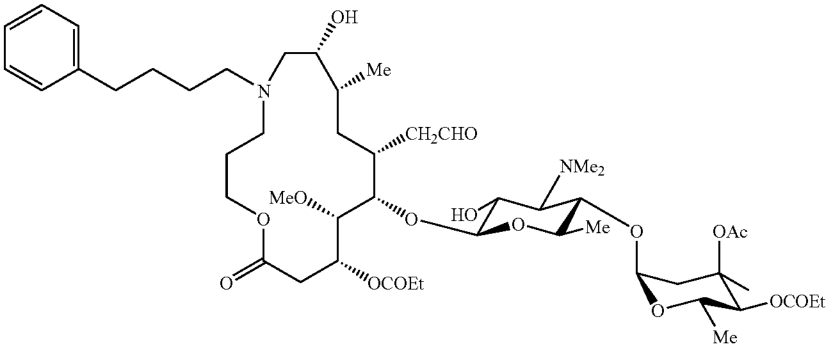

Example 13
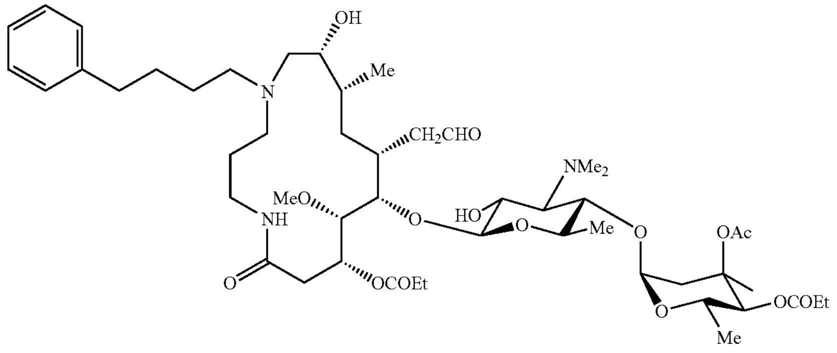
Example 14
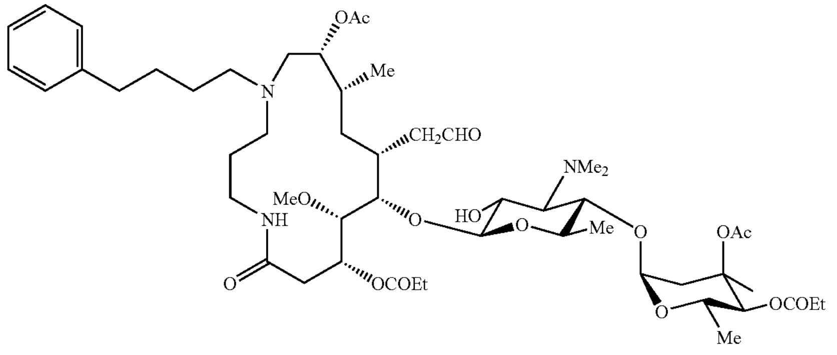
Example 15
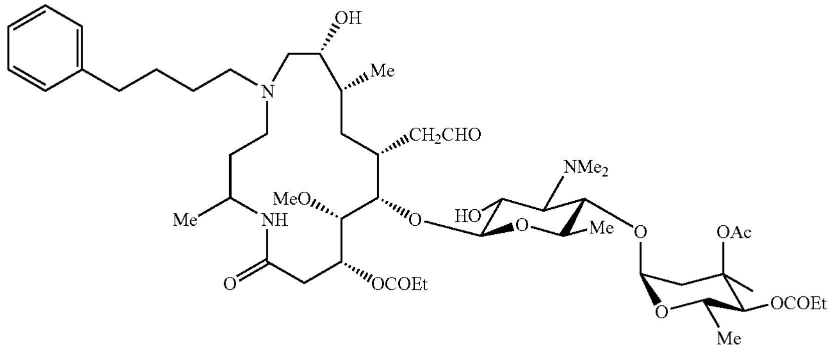

Example 16
Stereoisomer of the Compound of Example 15
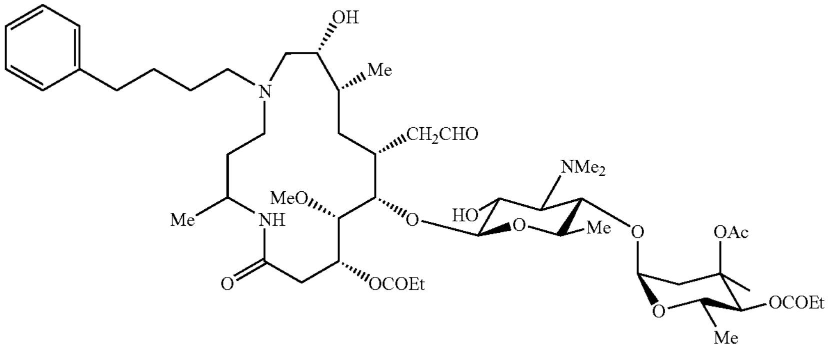
Example 17
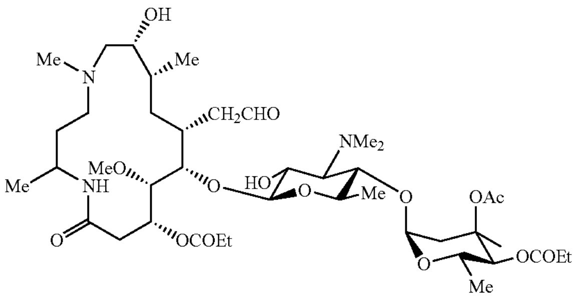
Example 18
Stereoisomer of the Compound of Example 17
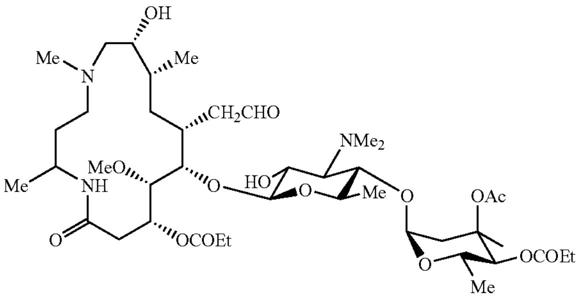
Example 19
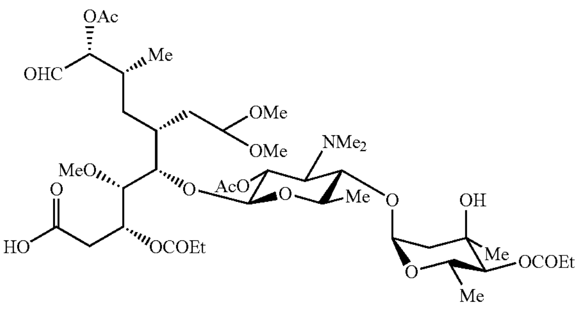

Example 20
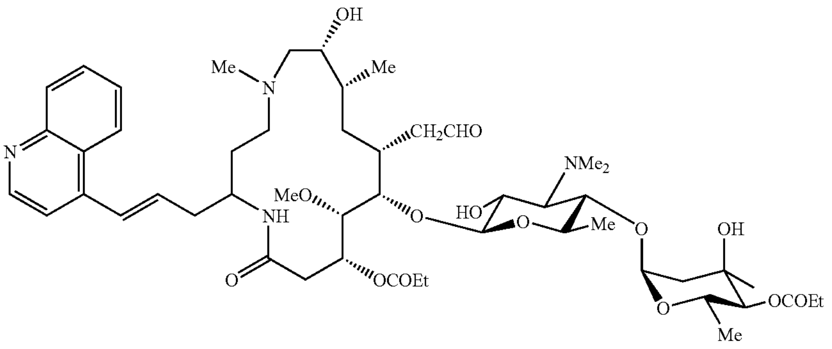
Example 21
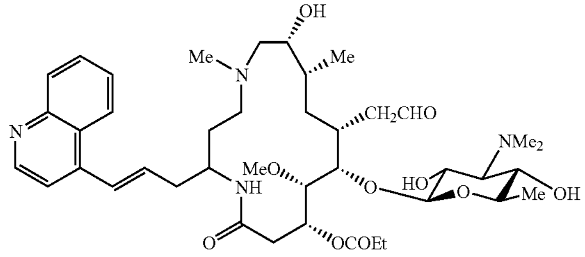
Example 22
Stereoisomer of the Compound of Example 20
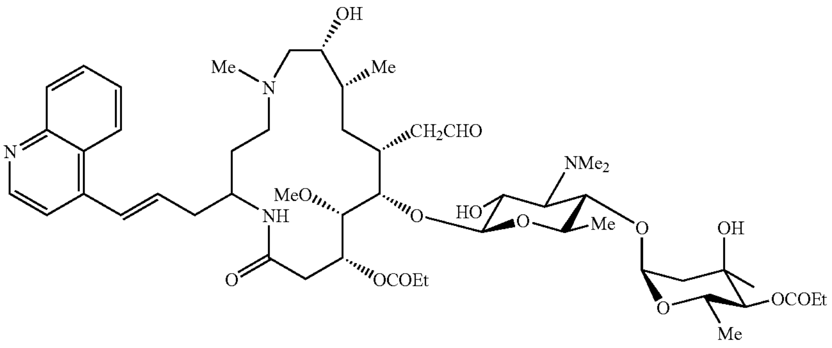

Example 23
Stereoisomer of the Compound of Example 21
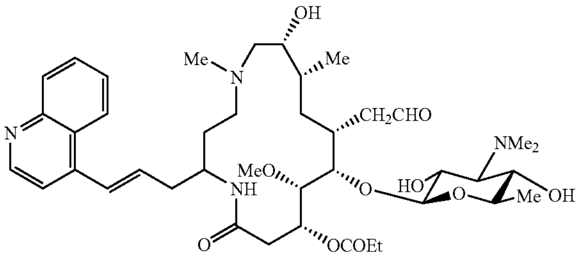
Example 24
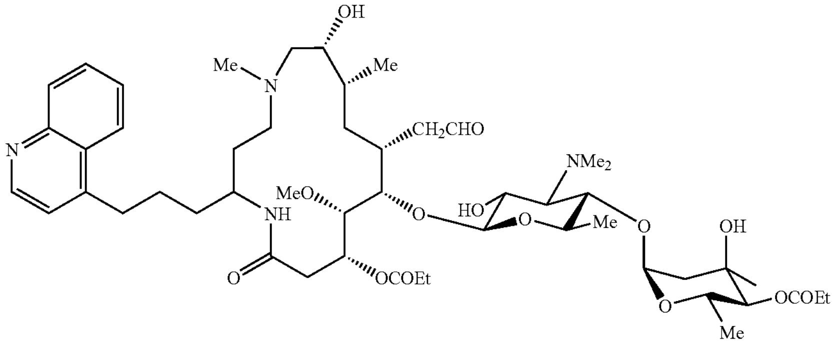
Example 25
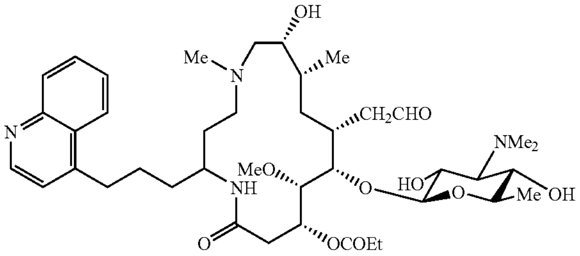
Example 26
Stereoisomer of the Compound of Example 24
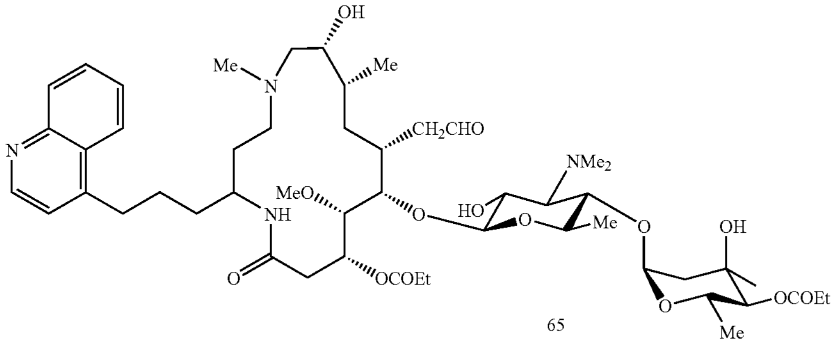

Example 27
Stereoisomer of the Compound of Example 25
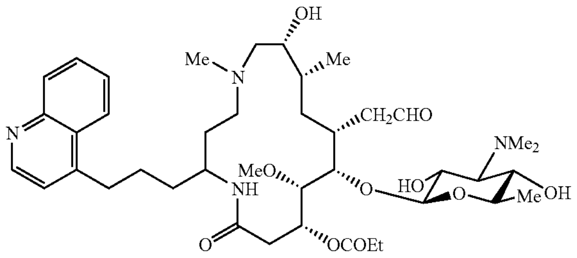
Example 28
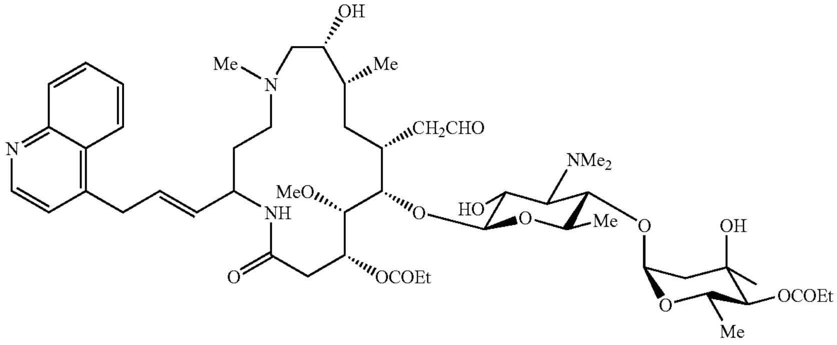
Example 29
Stereoisomer of the Compound of Example 28
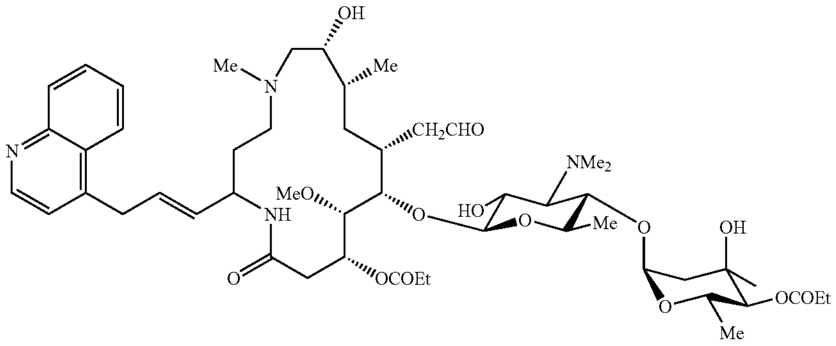

Example 30
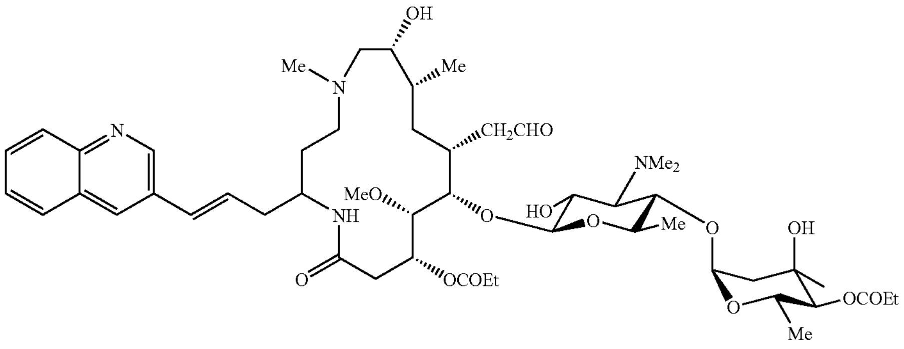
Example 31
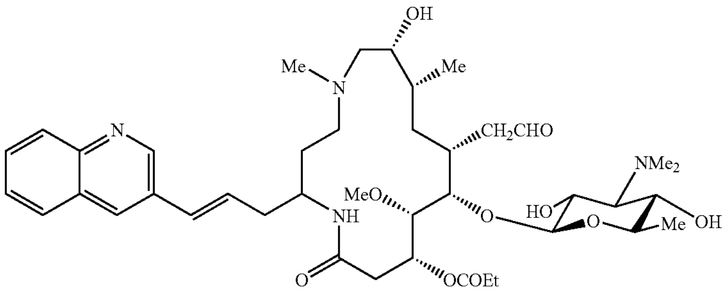
Example 32
Stereoisomer of the Compound of Example 30
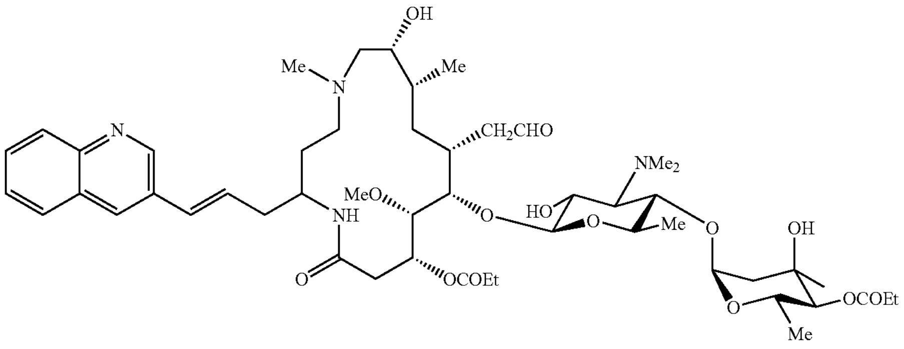

Example 33
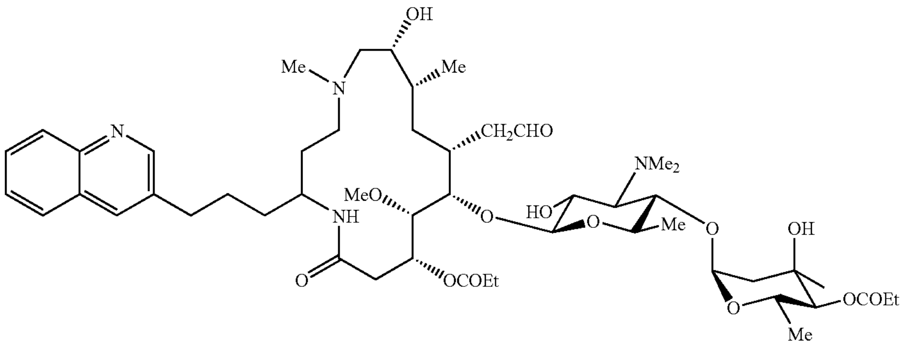
Example 34
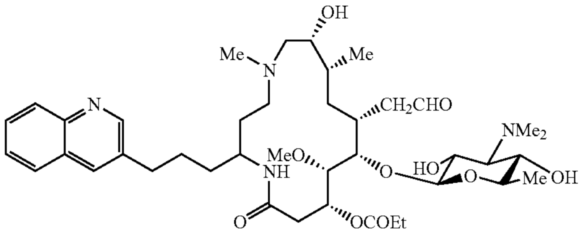
Example 35
Stereoisomer of the Compound of Example 33
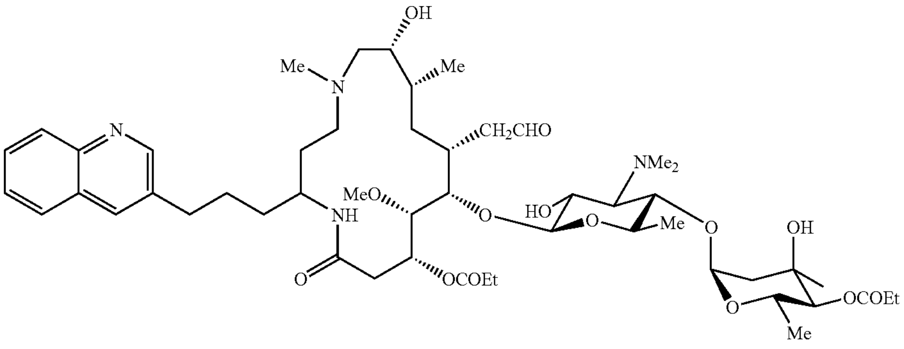

Example 36
Stereoisomer of the Compound of Example 34
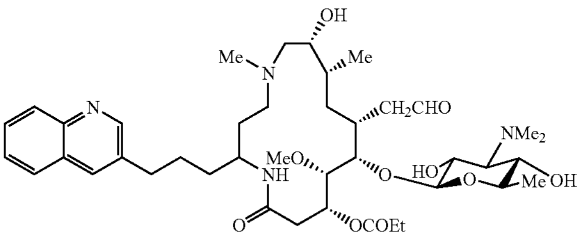
Example 37
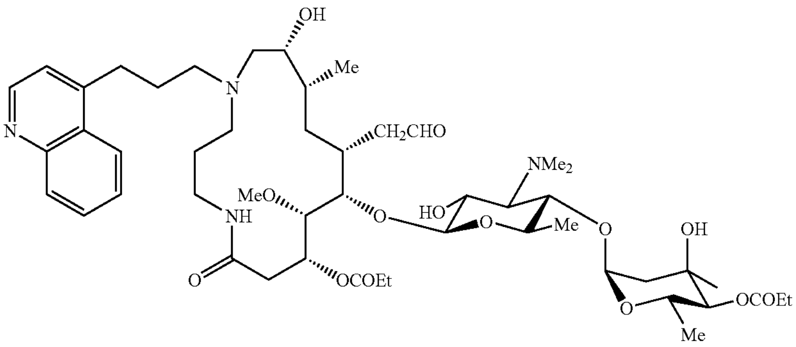
Example 38
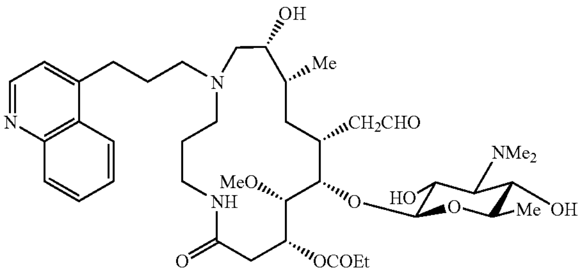
Example 39
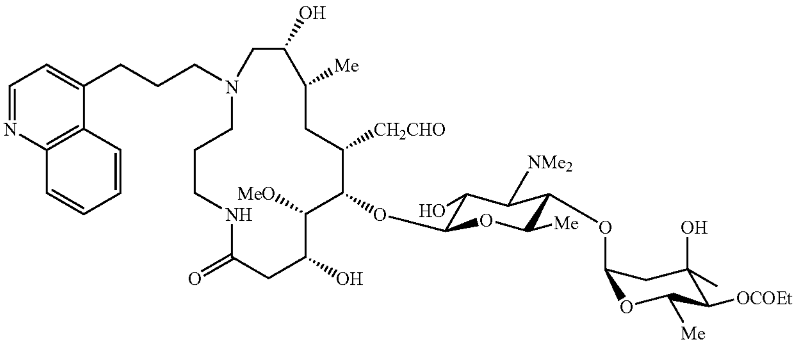

Example 40
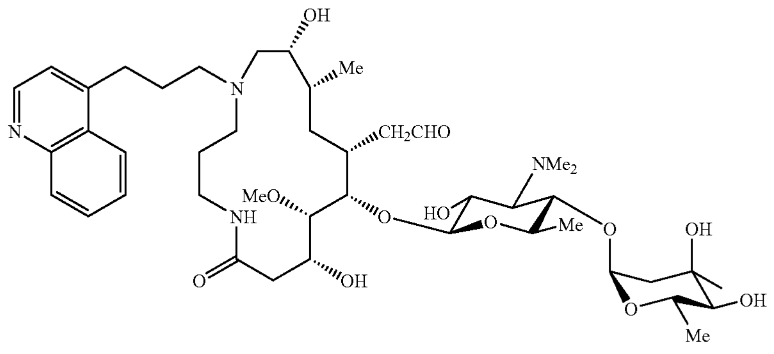
Example 41
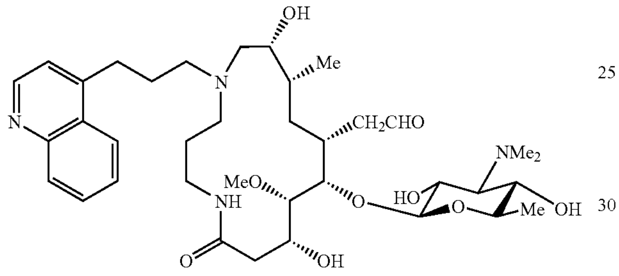
Example 42
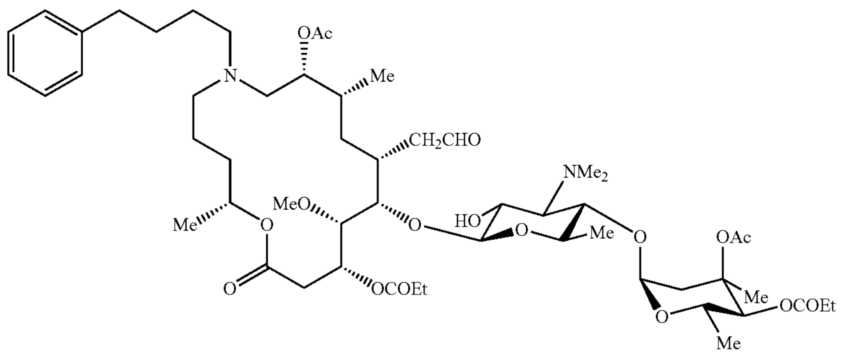

Example 43
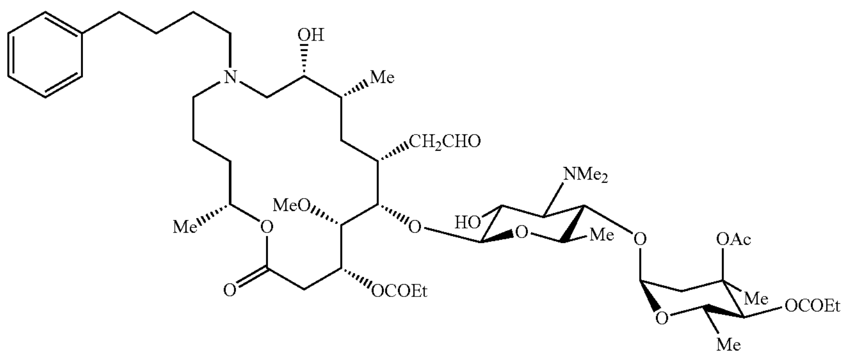
Example 44
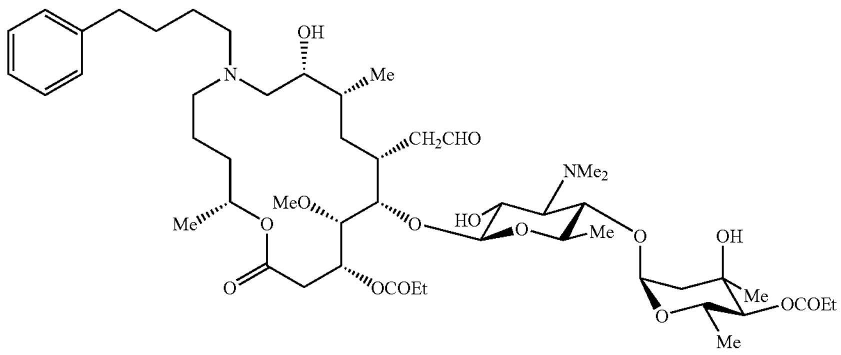
Example 45
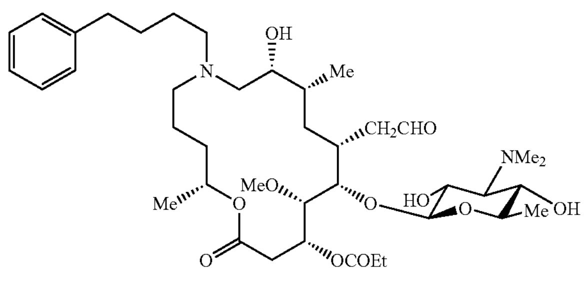

Example 46
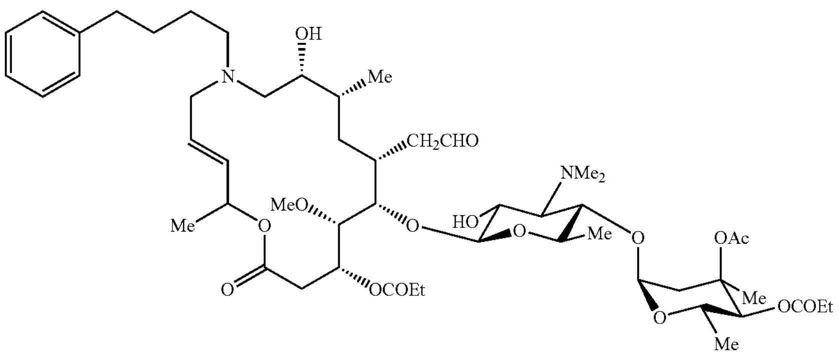
Example 47
Stereoisomer of the Compound of Example 46
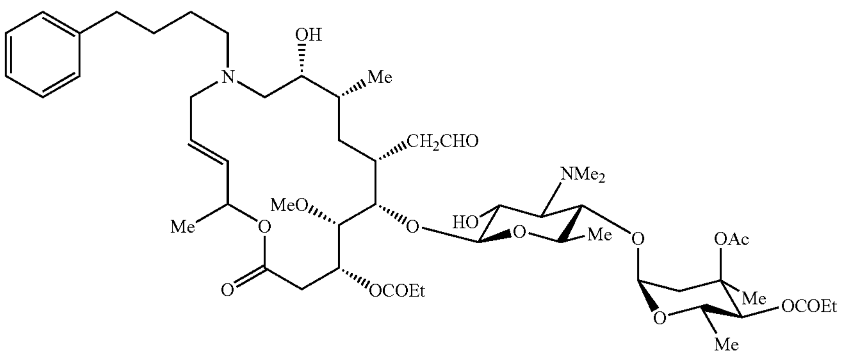
Example 48
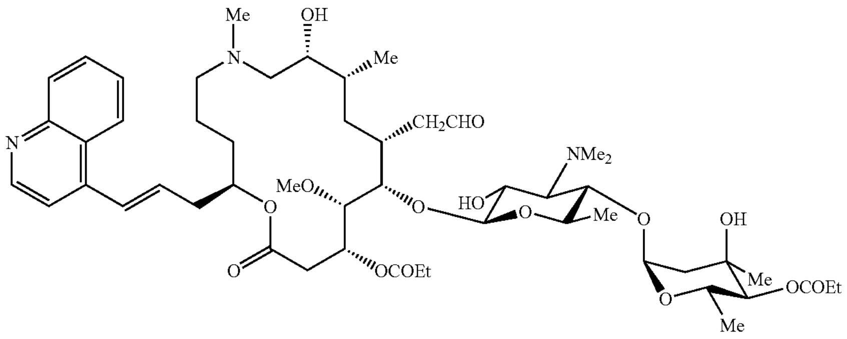

Example 49
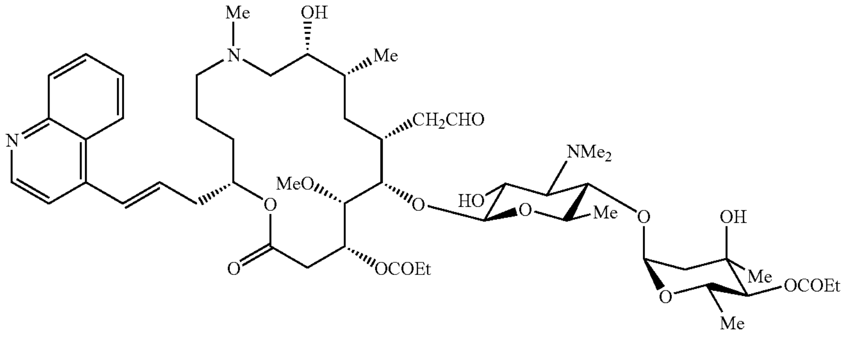
Example 50
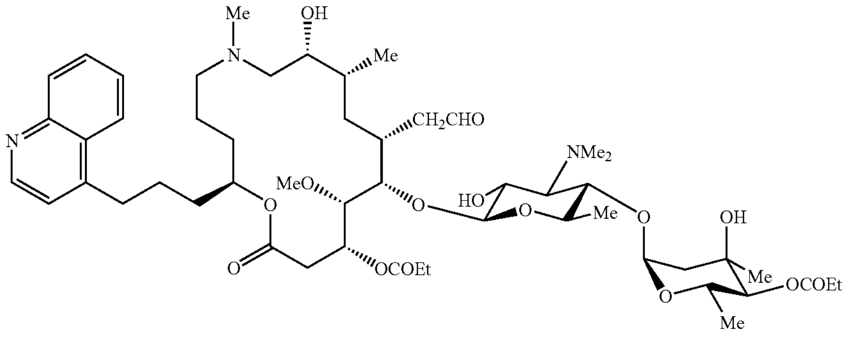
Example 51
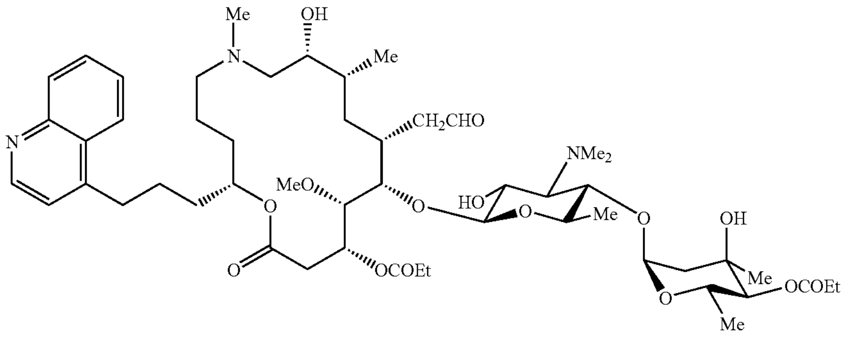

Example 52
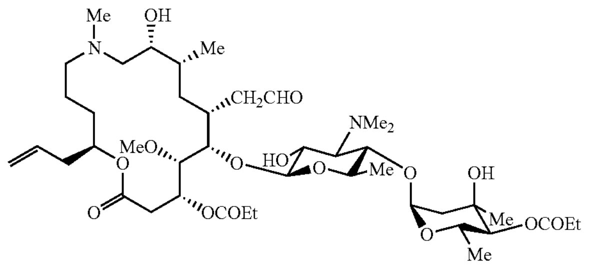
Example 53
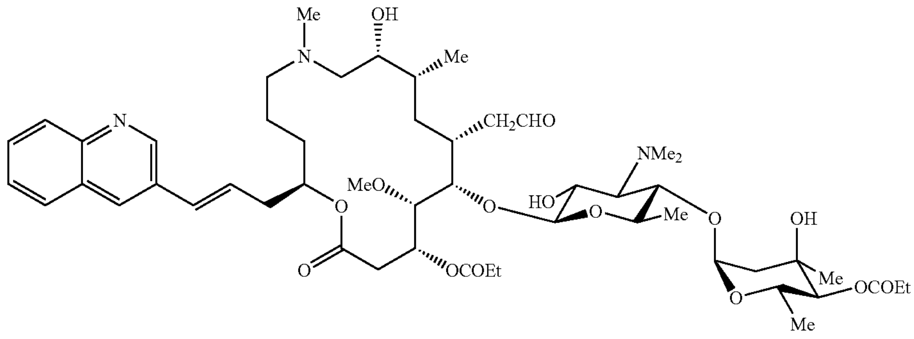
Example 54
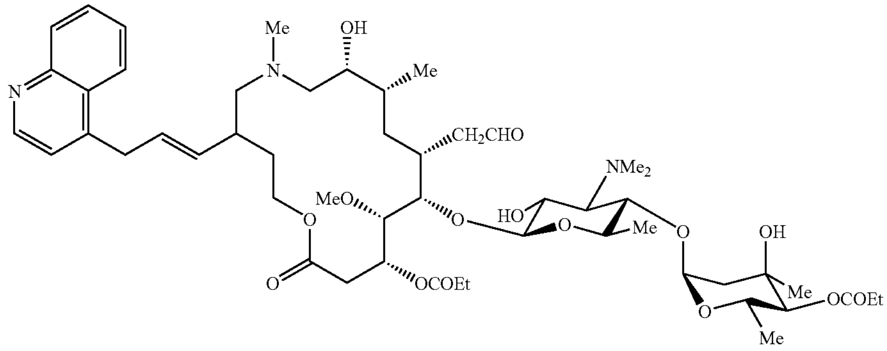

Example 55
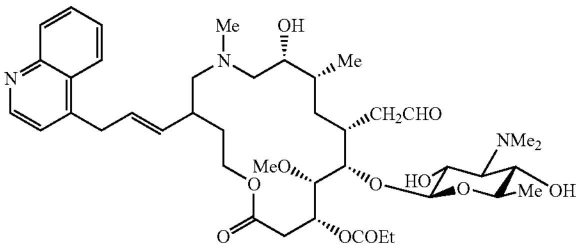
Example 56
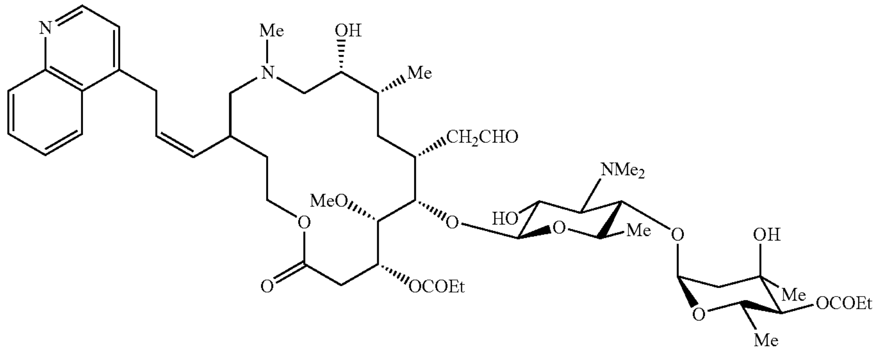
Example 57
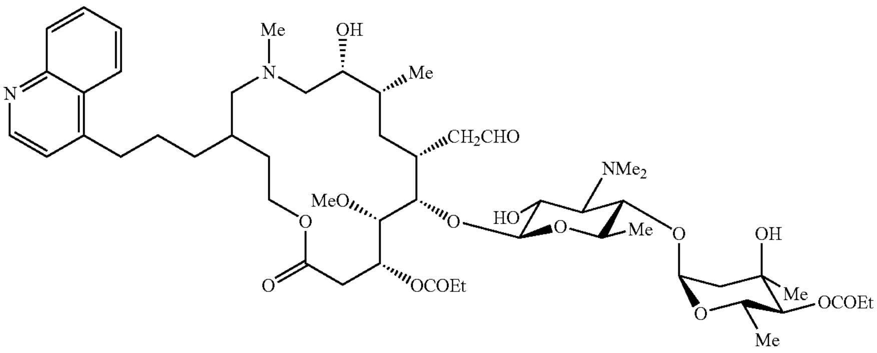
Example 58
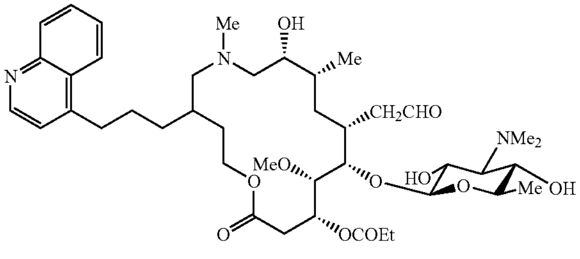

Example 59
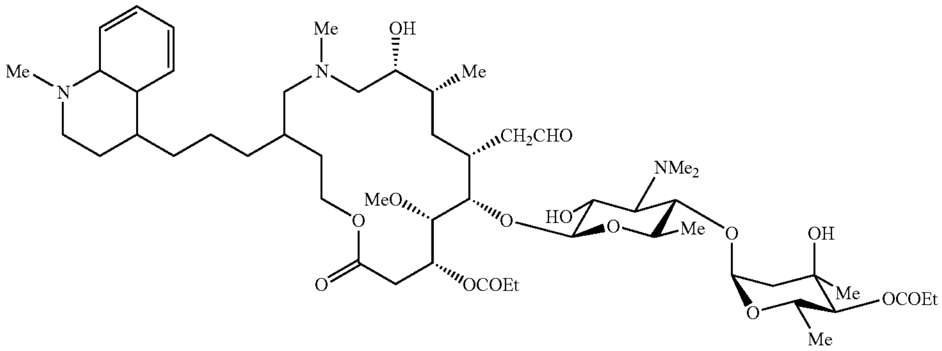
Example 60
Stereoisomer of the Compound of Example 54
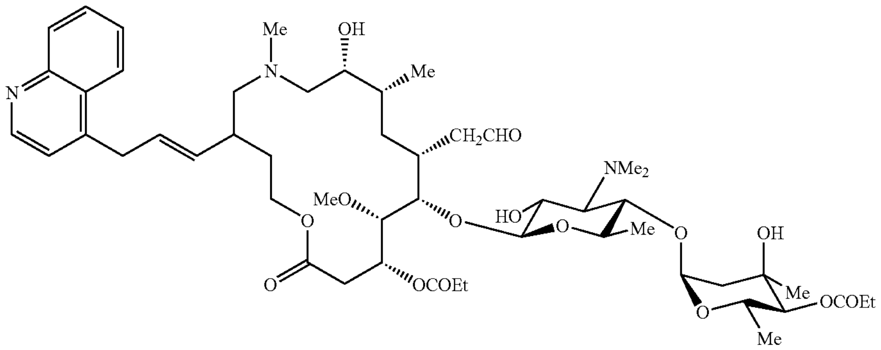
Example 61
Stereoisomer of the Compound of Example 55
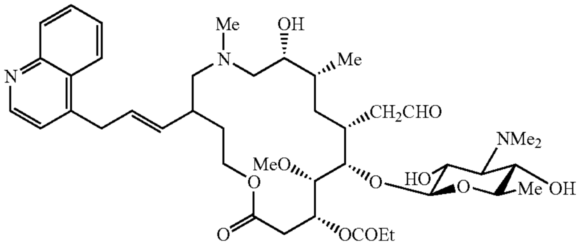

Example 62
Stereoisomer of the Compound of Example 56
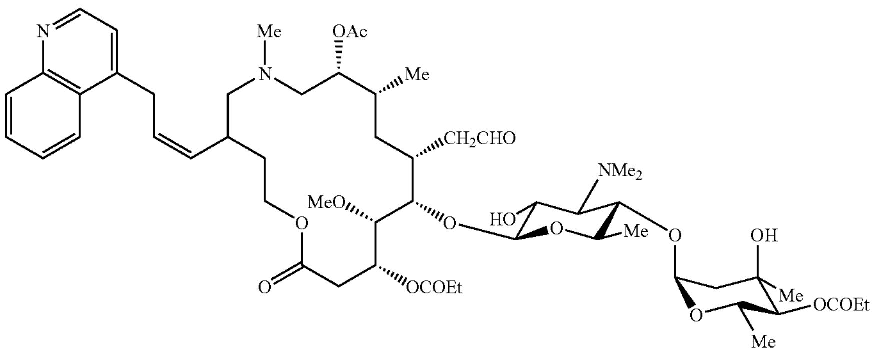
Example 63
Stereoisomer of the Compound of Example 57
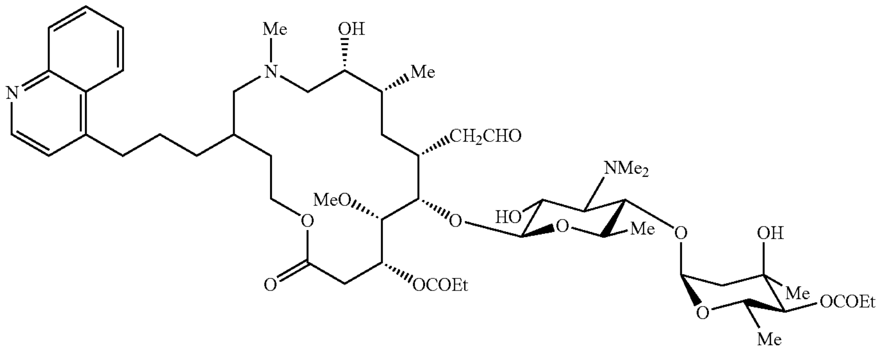
Example 64
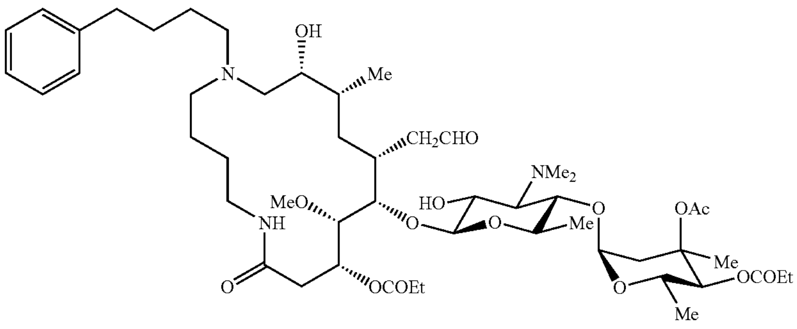

Example 65
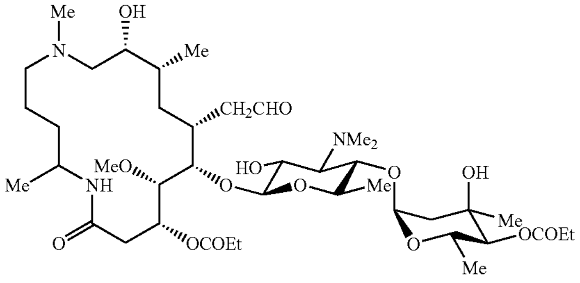
Example 66
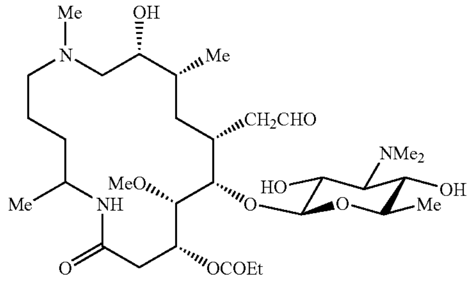
Example 67
Stereoisomer of the Compound of Example 65
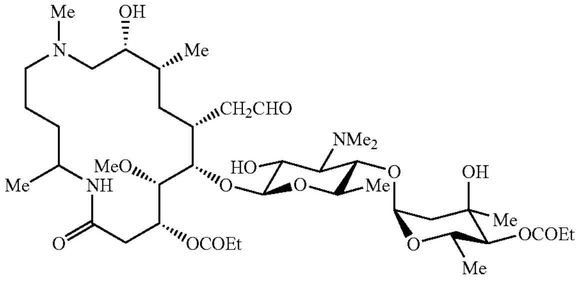
Example 68
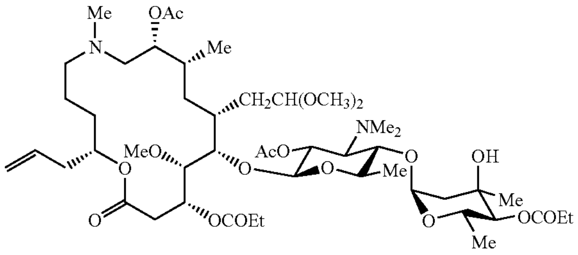
Example 69
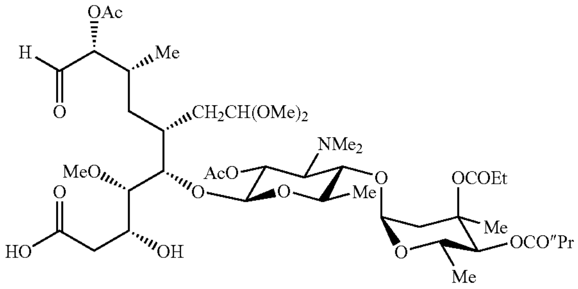
Example 70
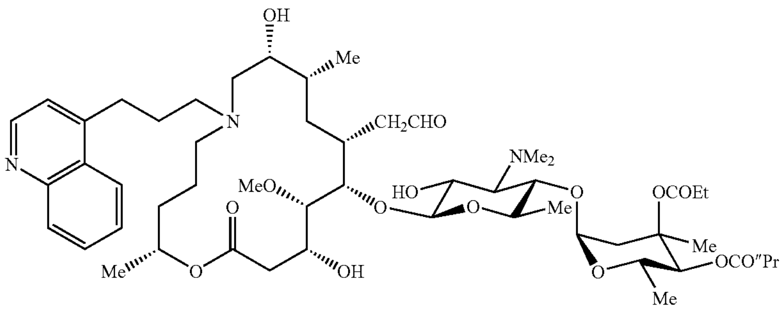

Example 71
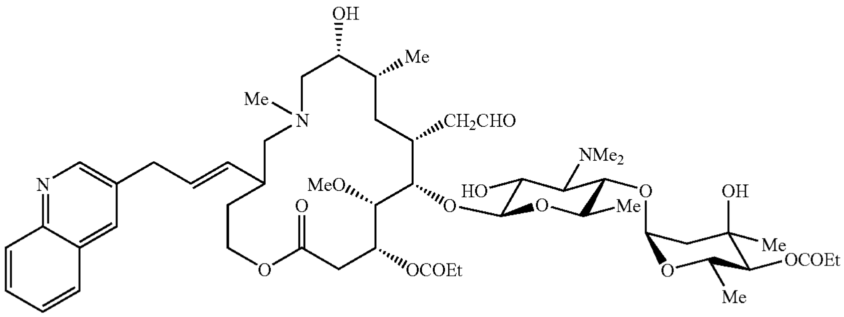
Example 72
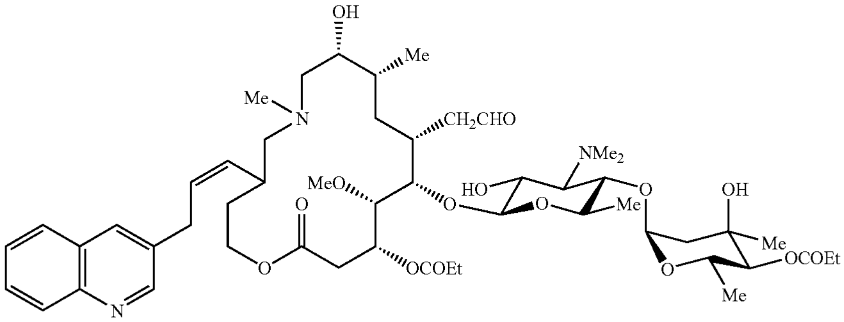
Example 73
Stereoisomer of the compound of Example 71
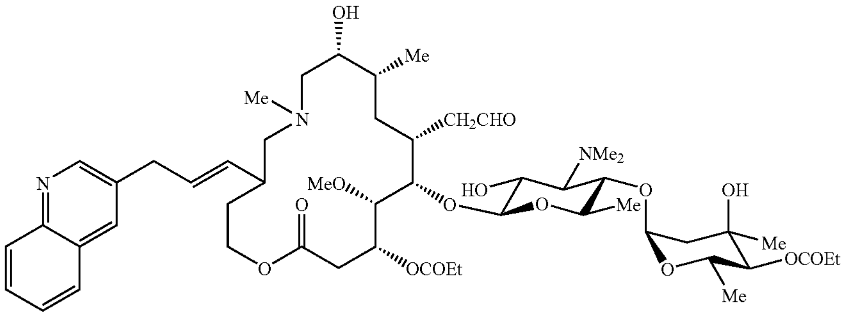

Example 74
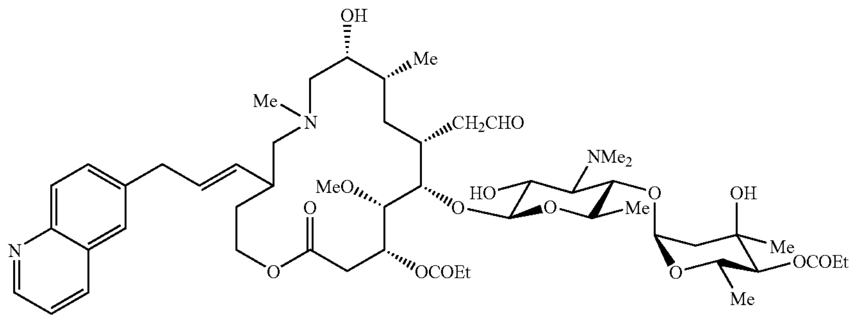
Example 75
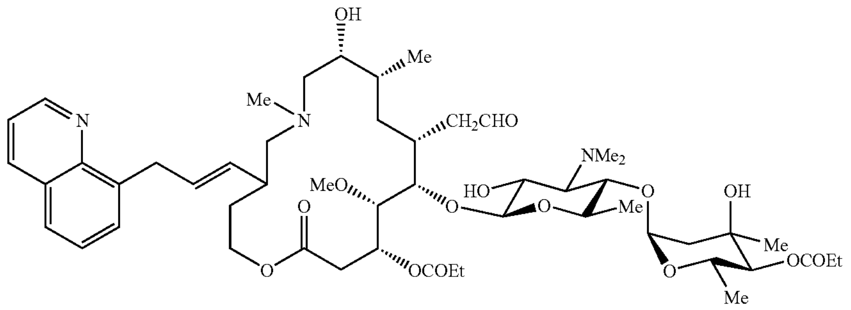
Example 76
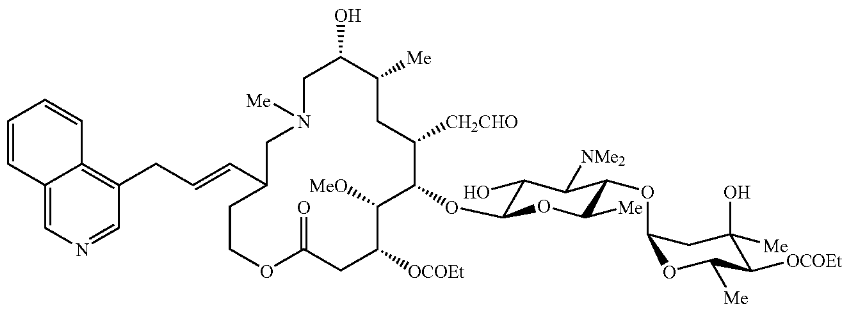

Example 77
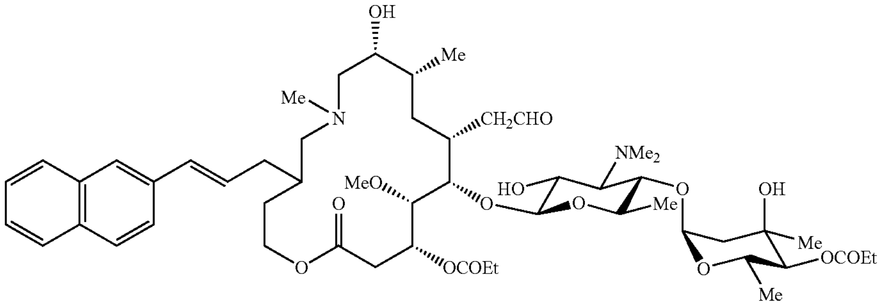
Example 78
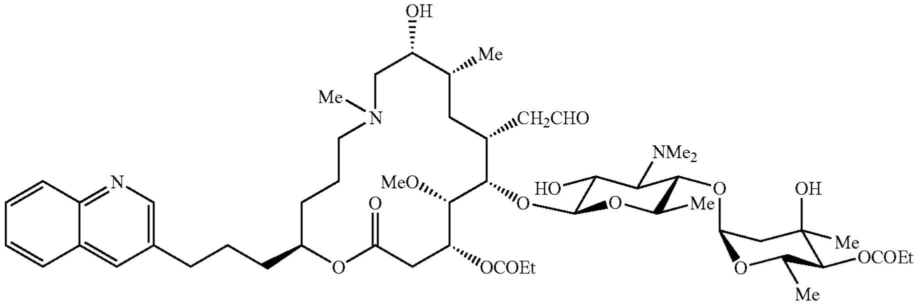
Example 79
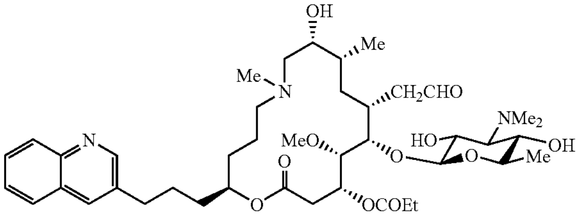

Example 80
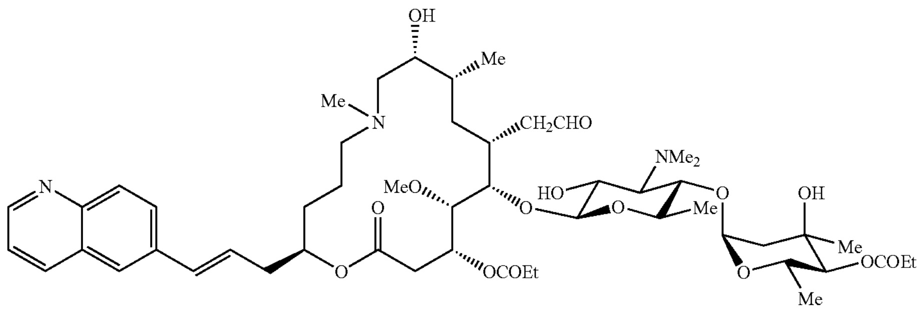
Example 81
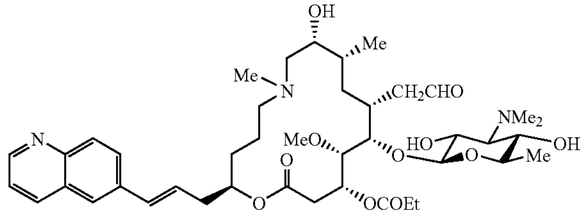
Example 82
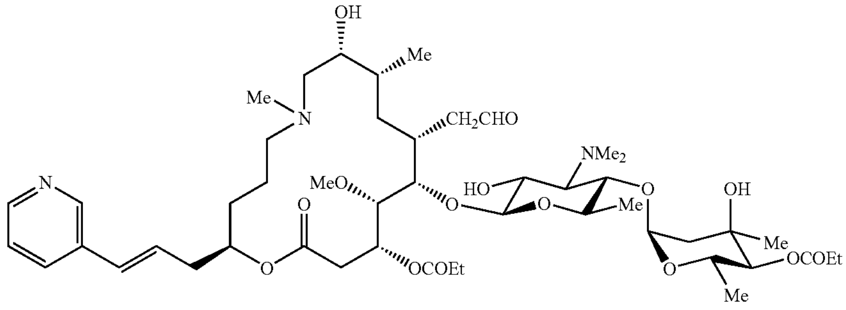

Example 83
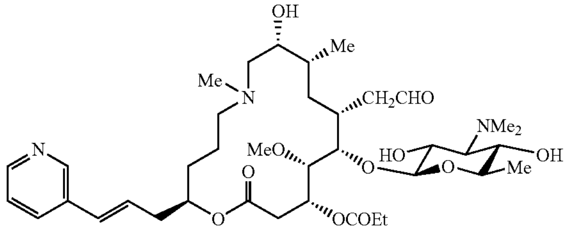
Example 84
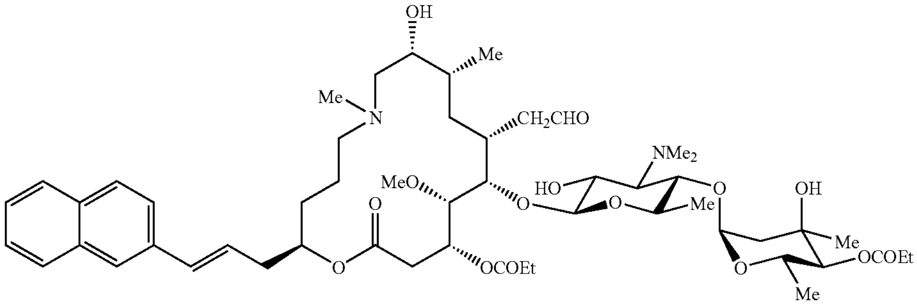
Example 85
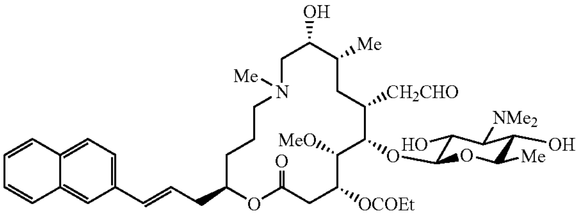
Example 86
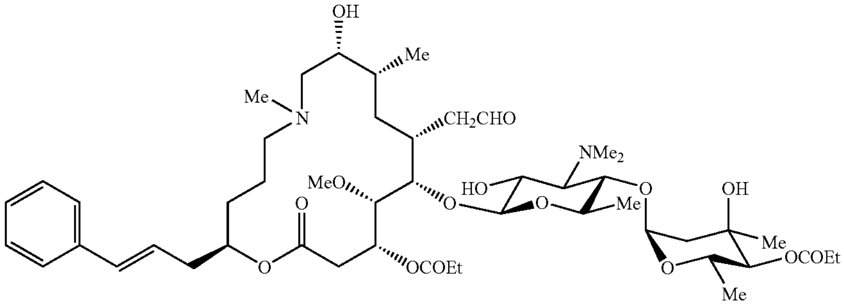

Example 87
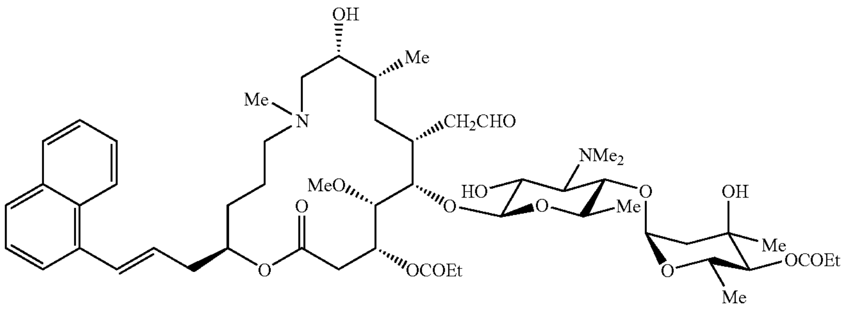
Example 88
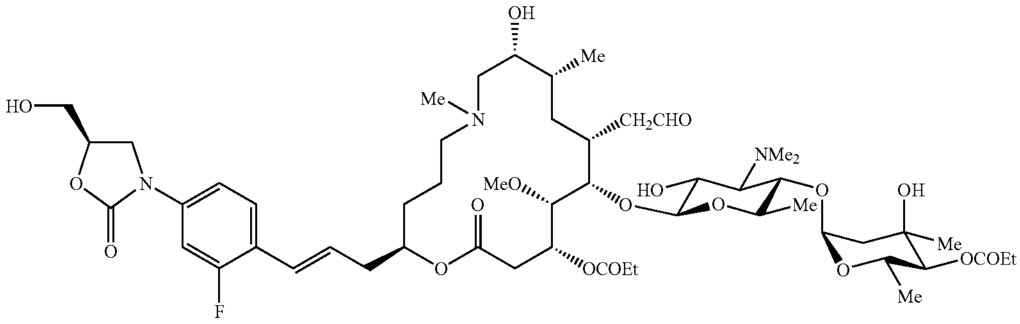
Example 89
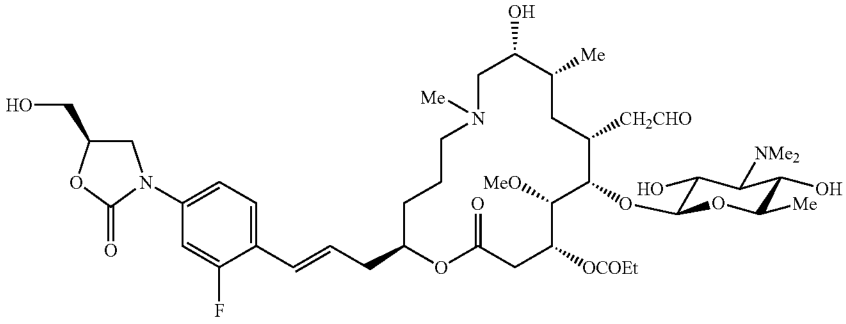

Example 90
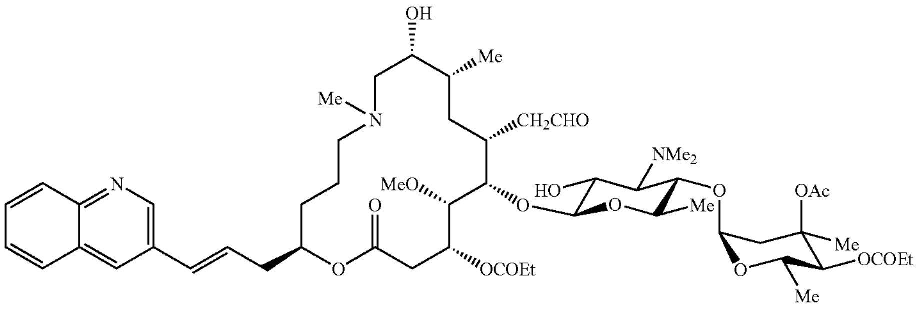
Example 91
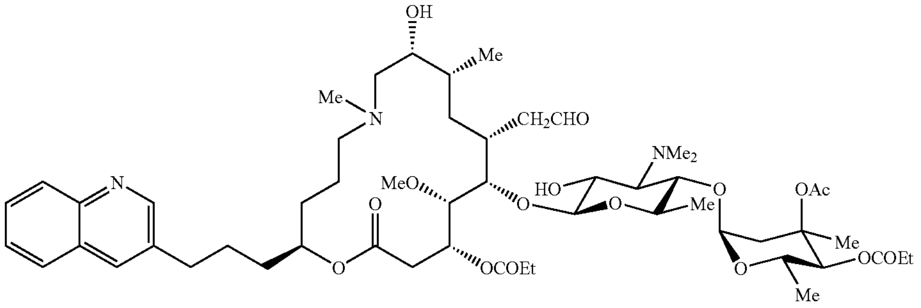
Example 92
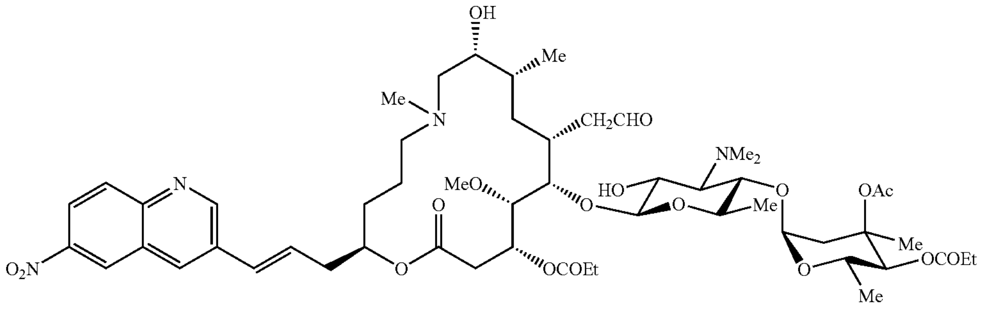

Example 93
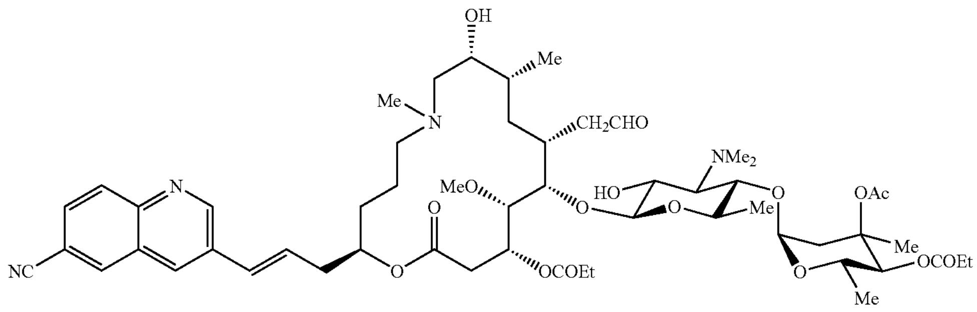
Example 94
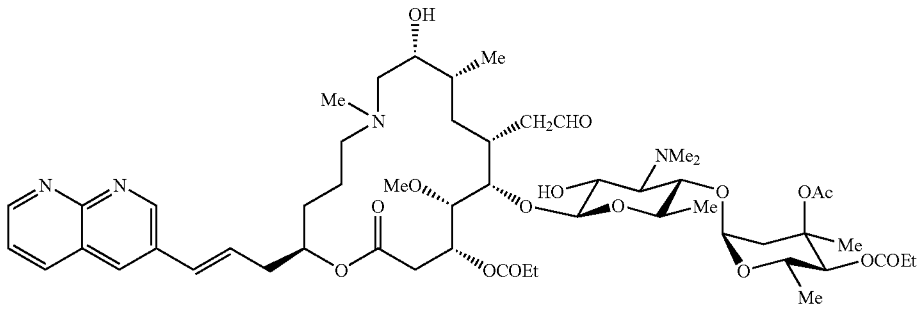
Example 95
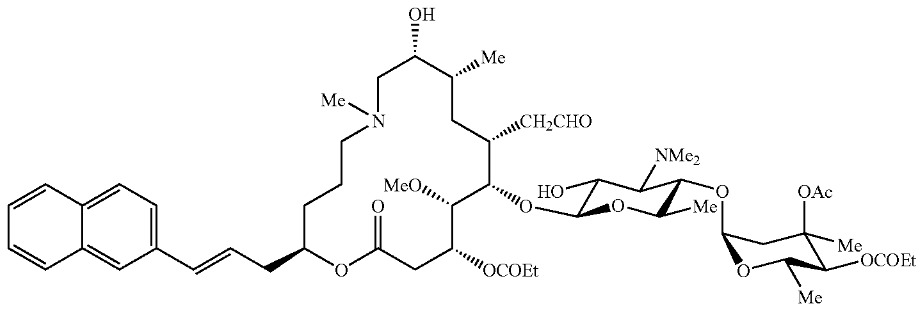

Example 96
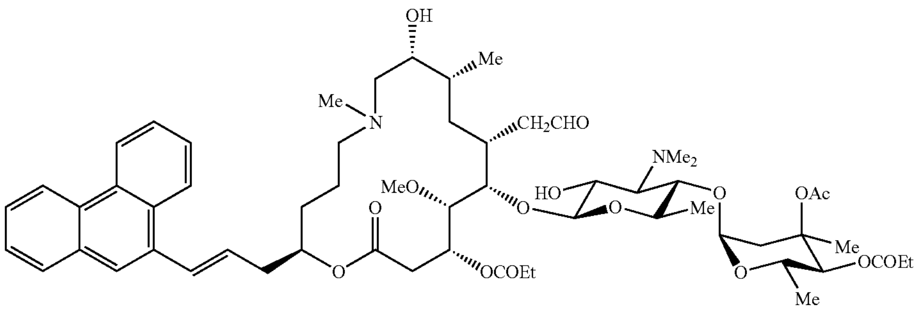
Example 97
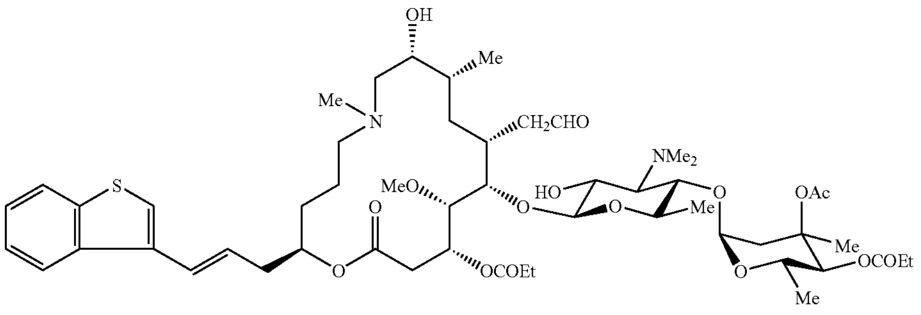
Example 98
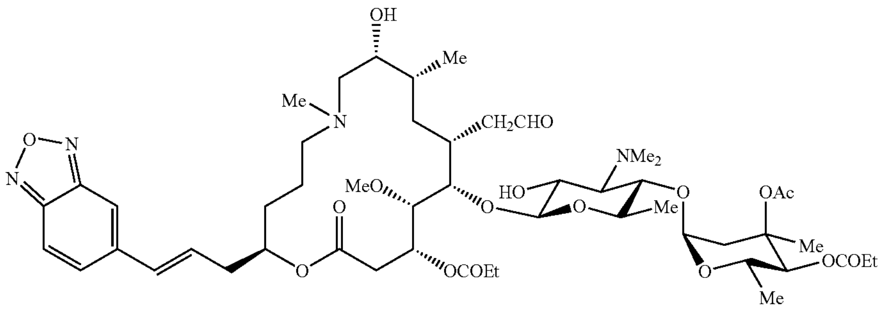

Example 99
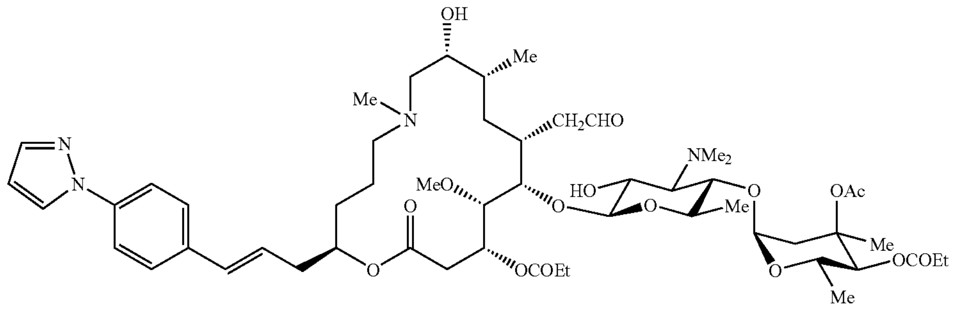
Example 100
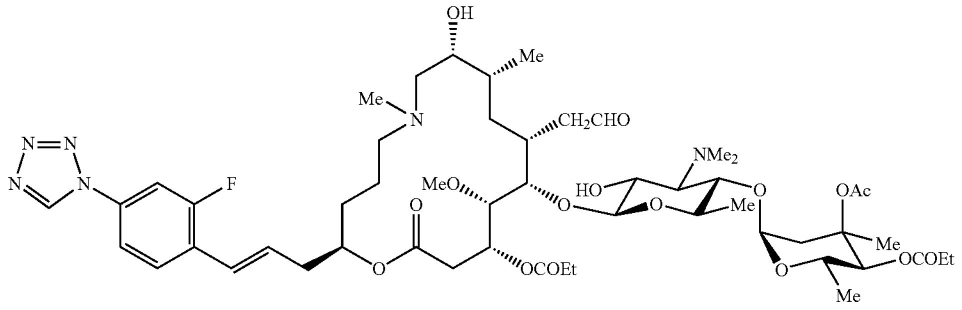
Example 101
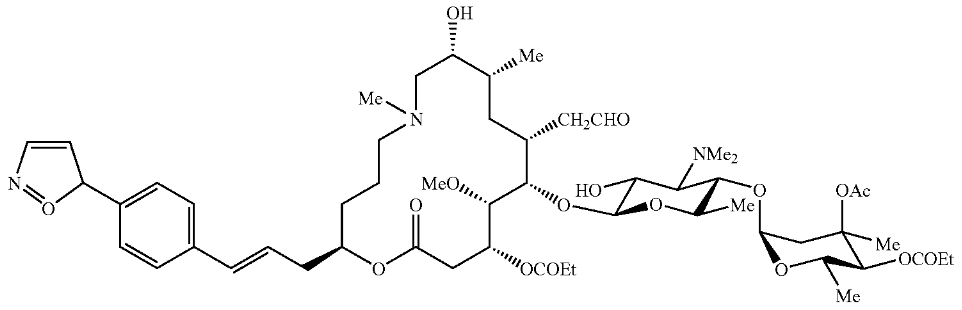

Example 102
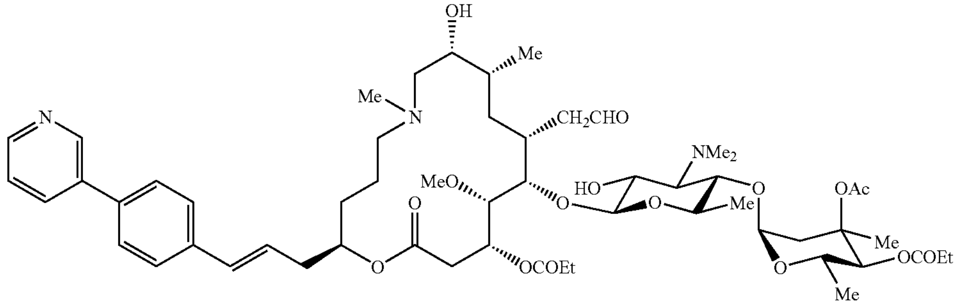
Example 103
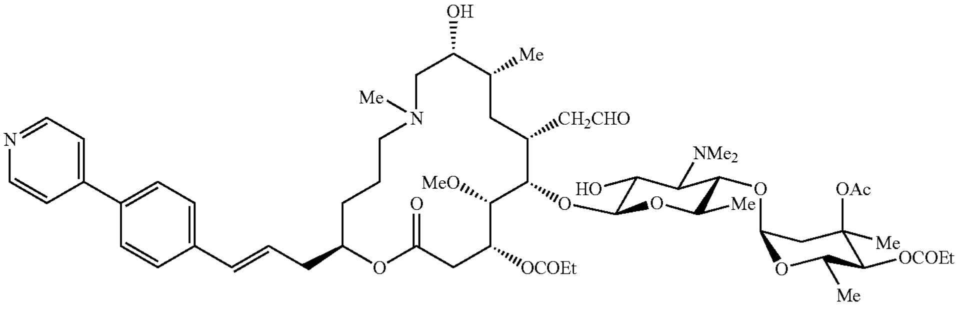
Example 104
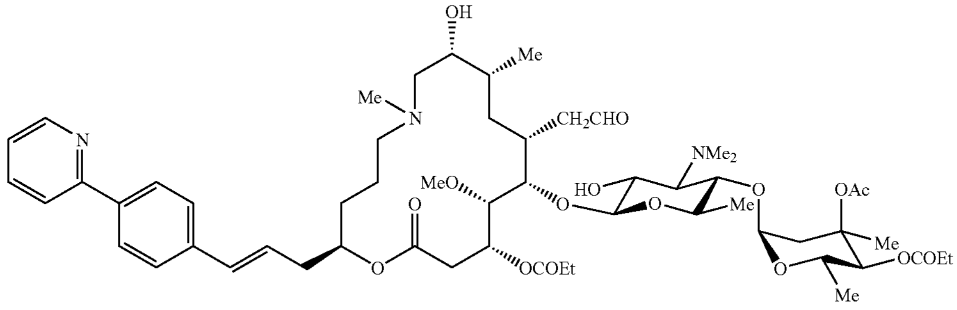

Example 105
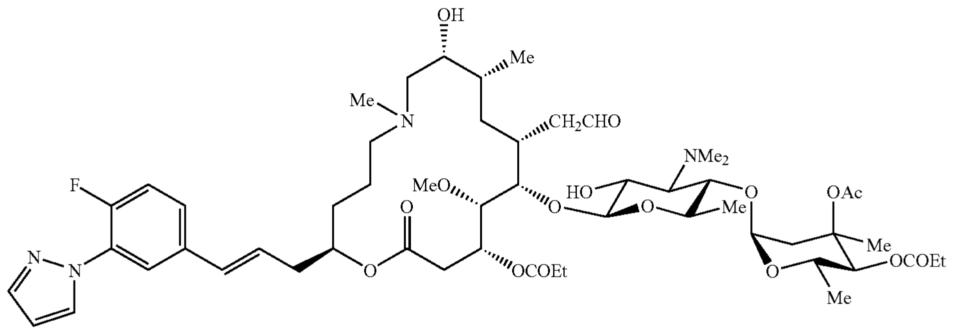
Example 106
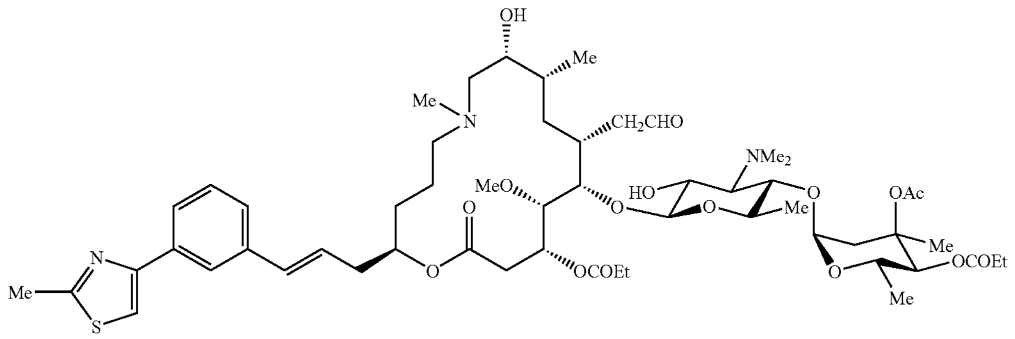
Example 107
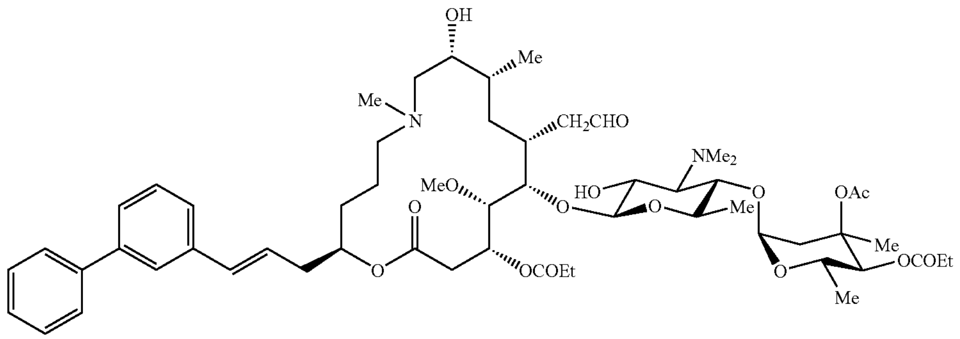

Example 108
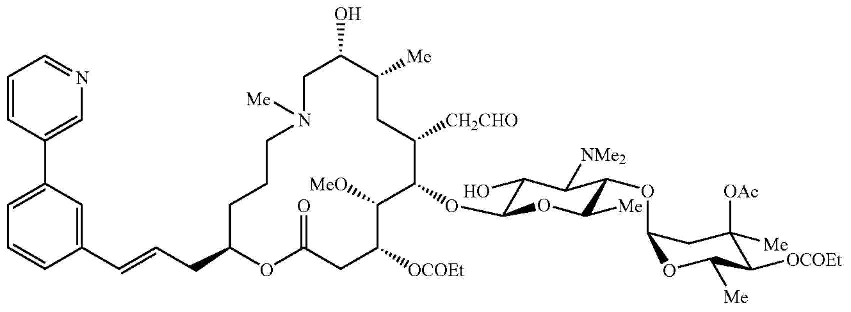
Example 109
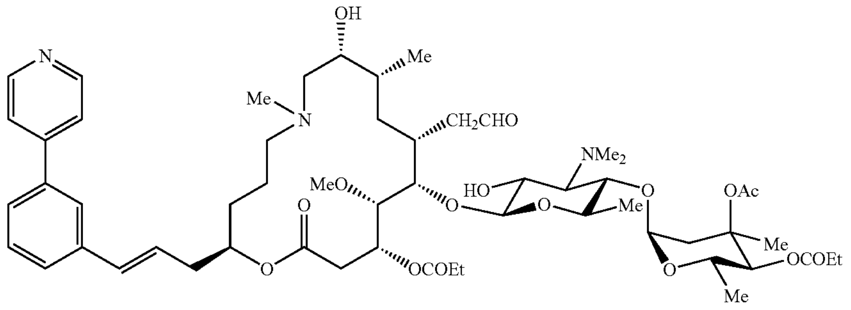
Example 110
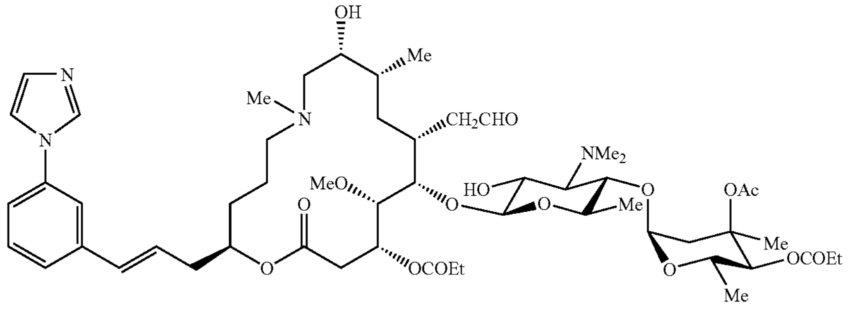

Example 111
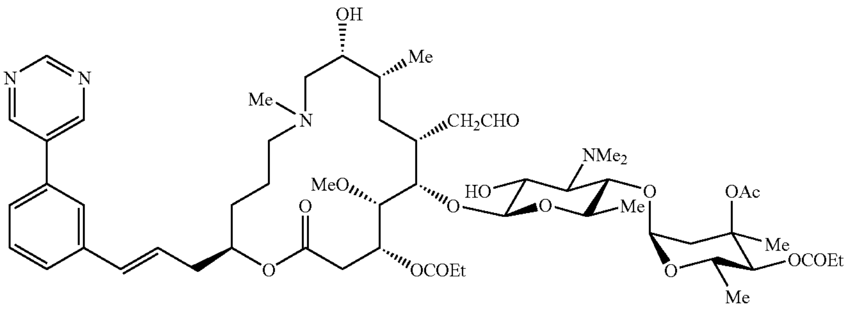
Example 112
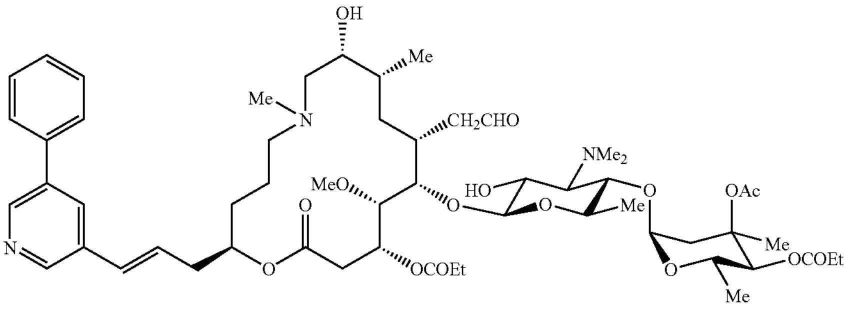
Example 113
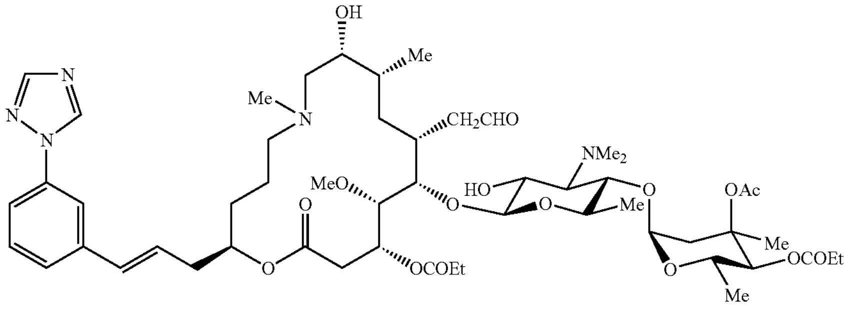

Example 114
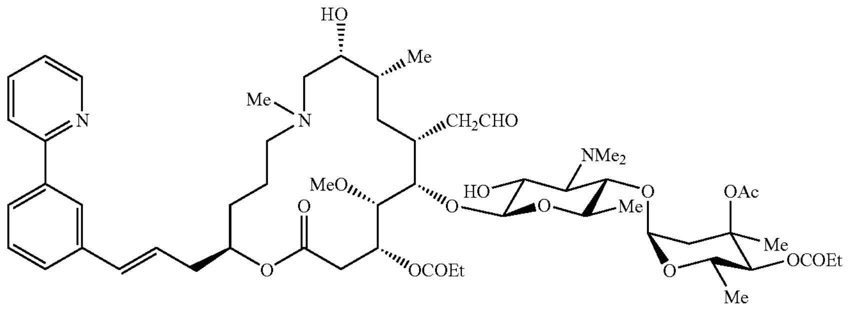
Example 115
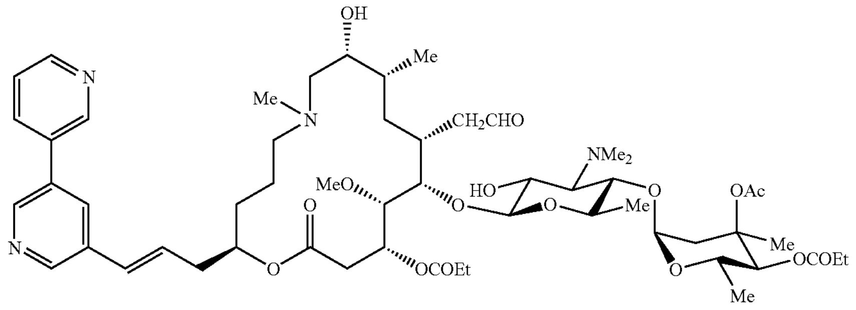
Example 116
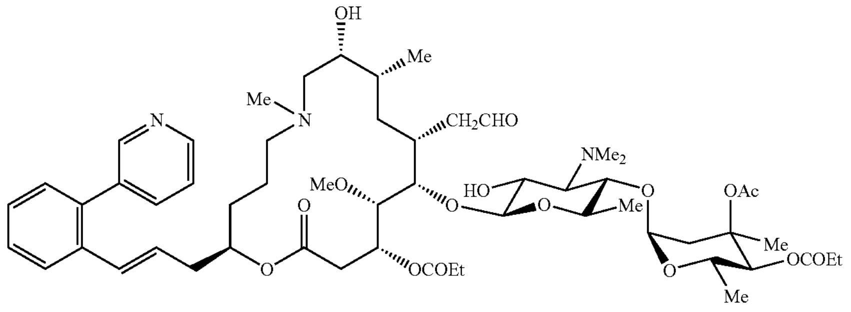

Example 117
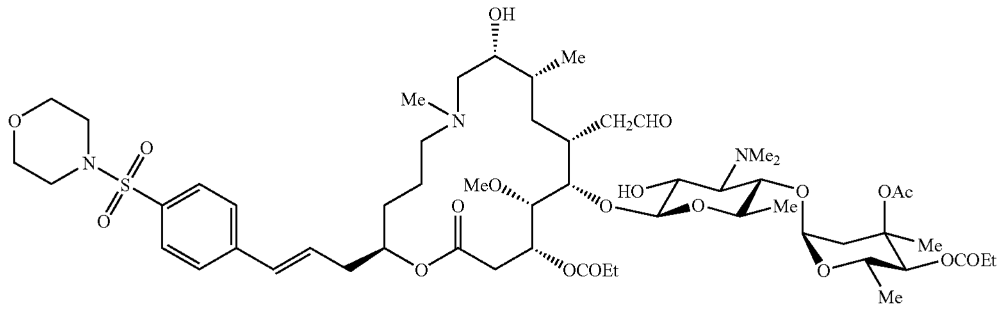
Example 118
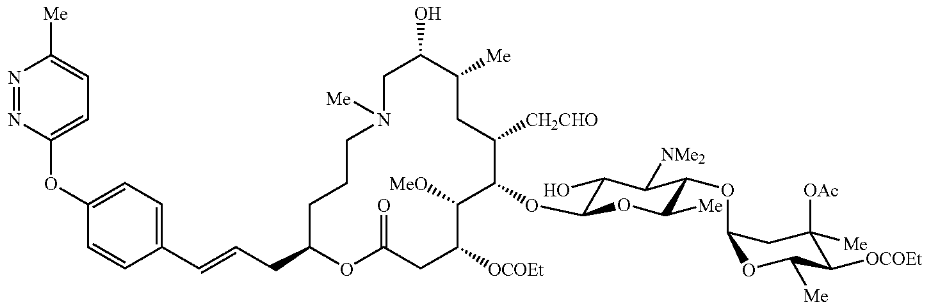
Example 119
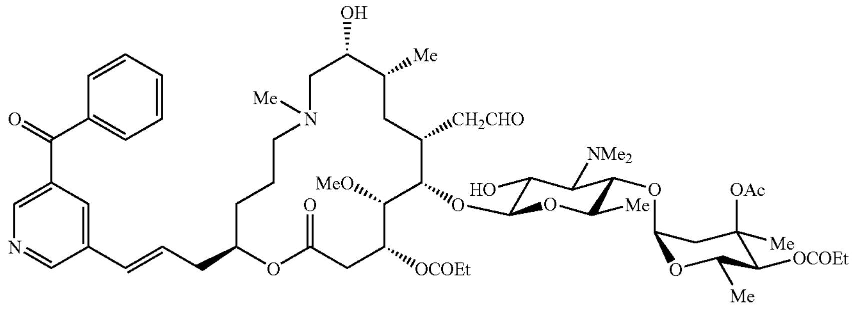

Example 120
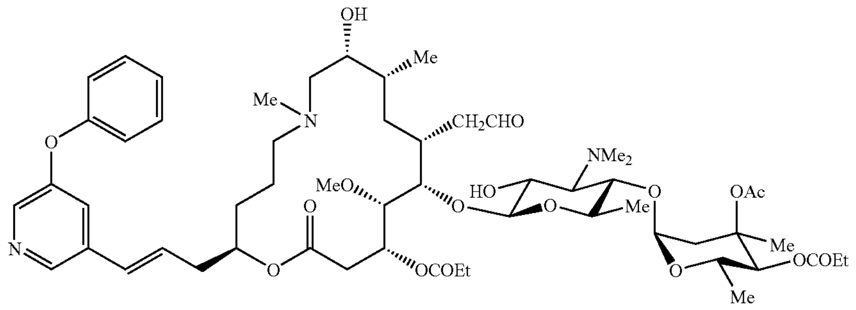
Example 121
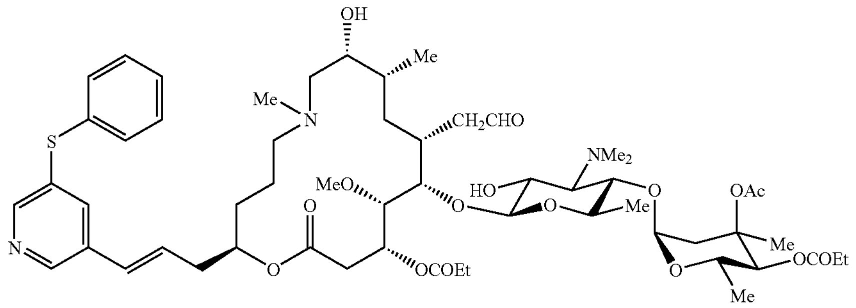
Example 122
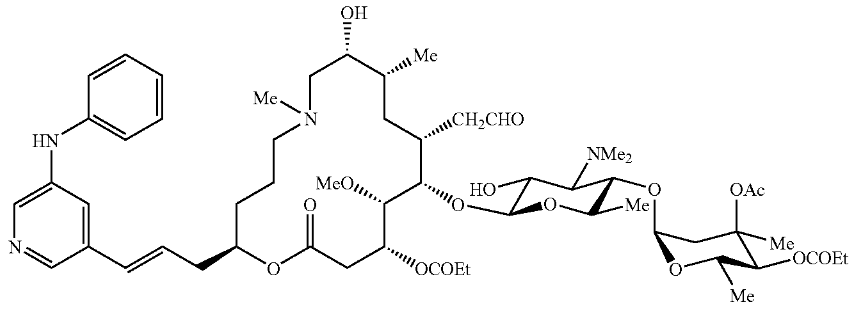

Example 123
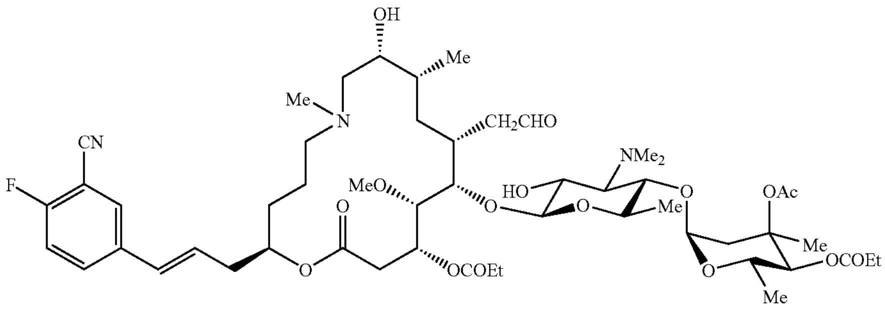
Example 124
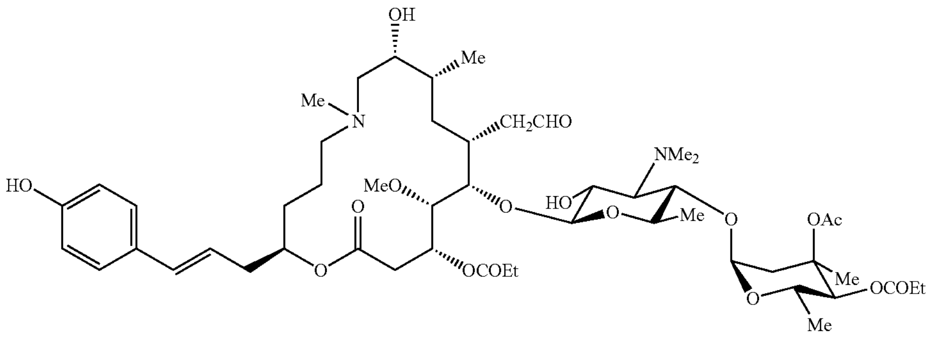
Example 125
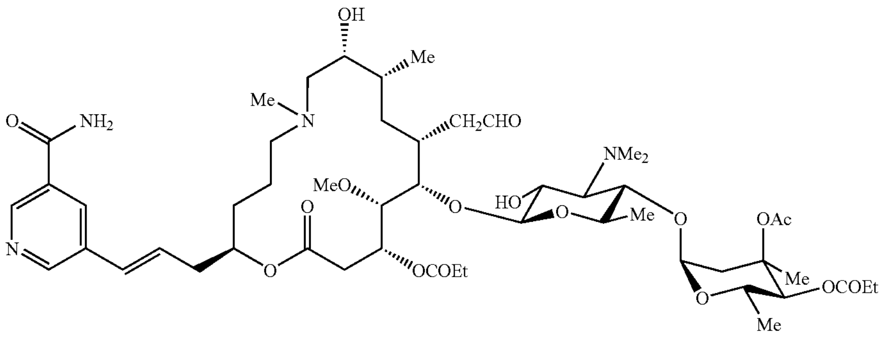

Example 126
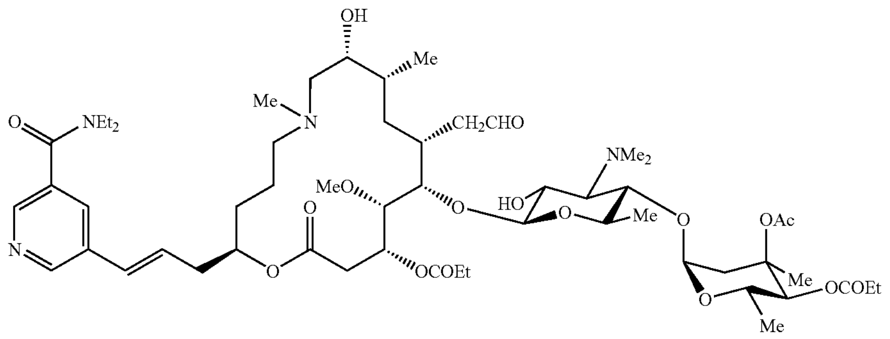
Example 127
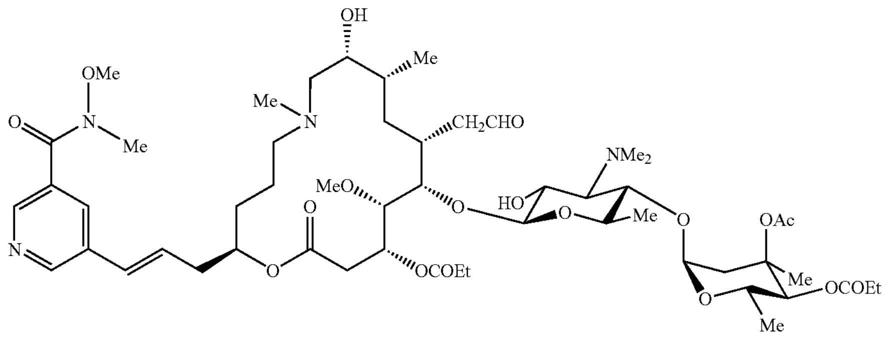
Example 128
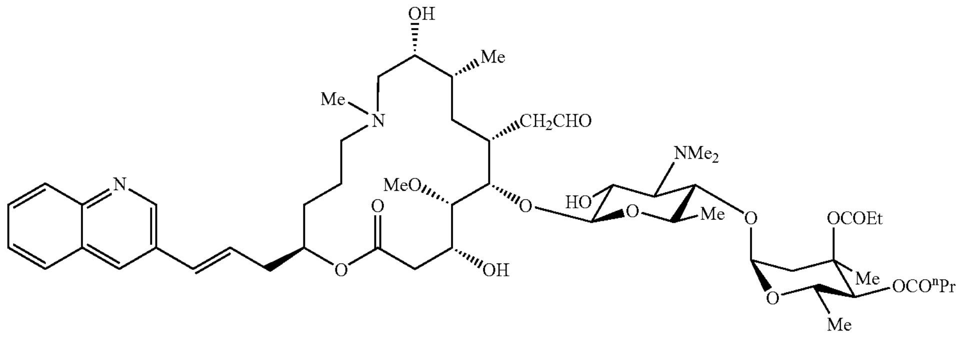

Example 129
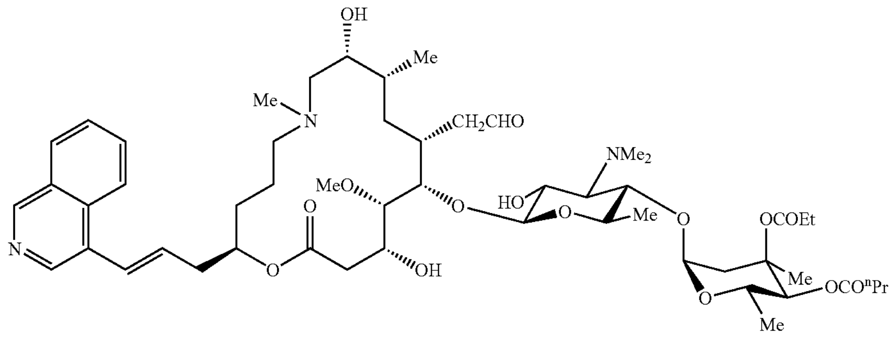
Example 130
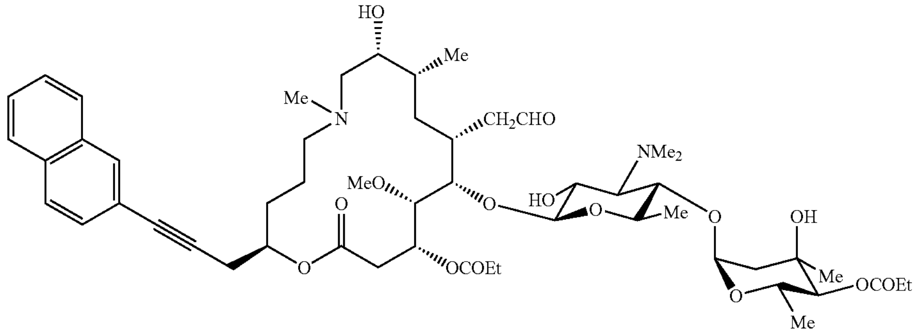
Example 131
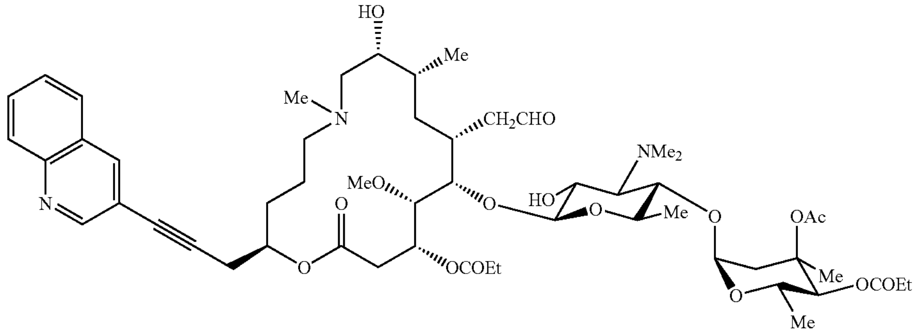

Example 132
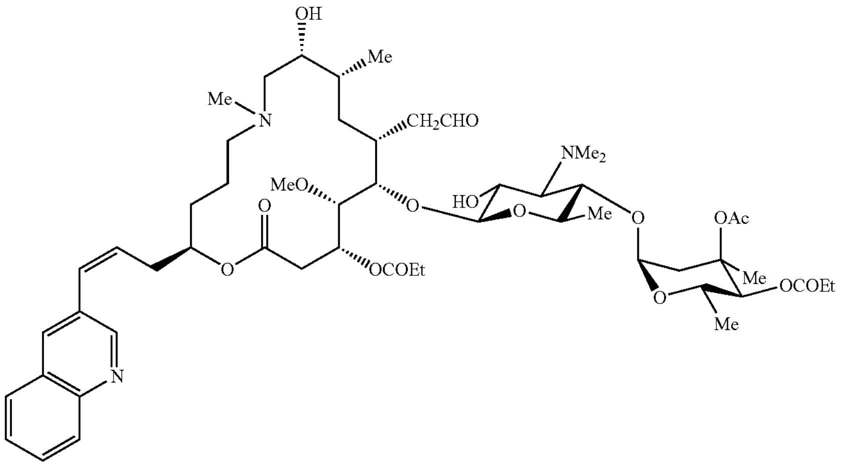
Example 133
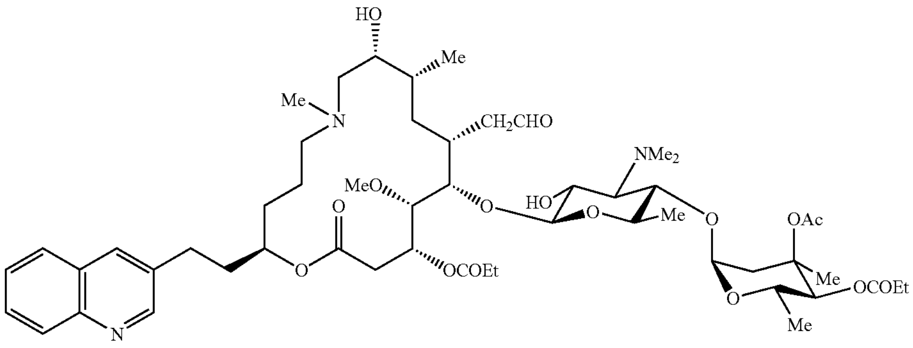
Example 134
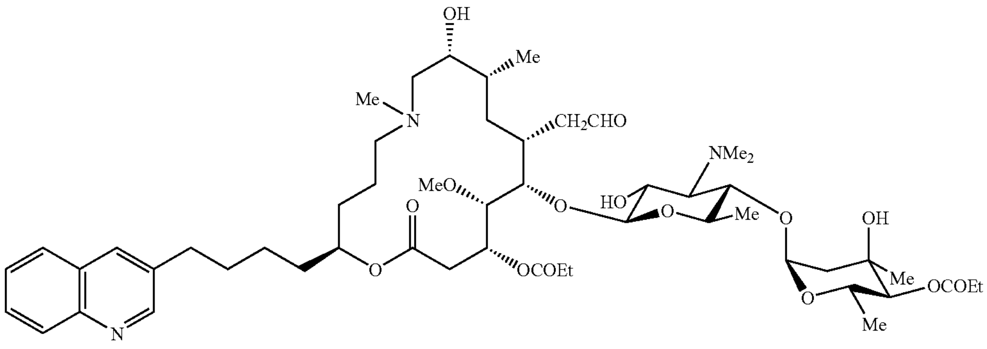

Example 135
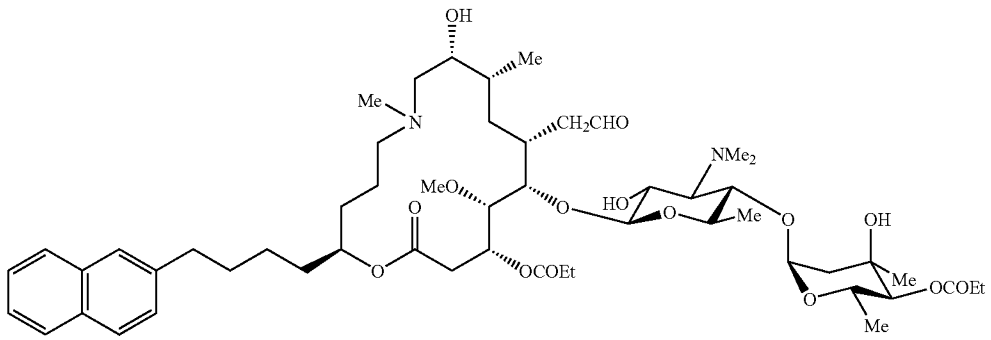
Example 136
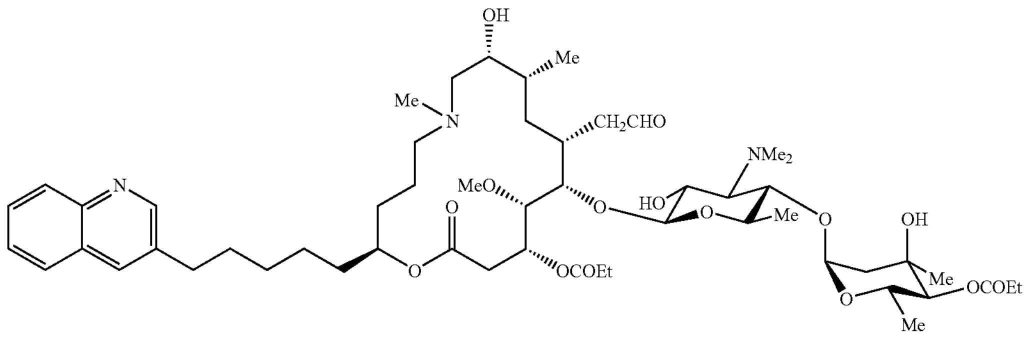
Example 137
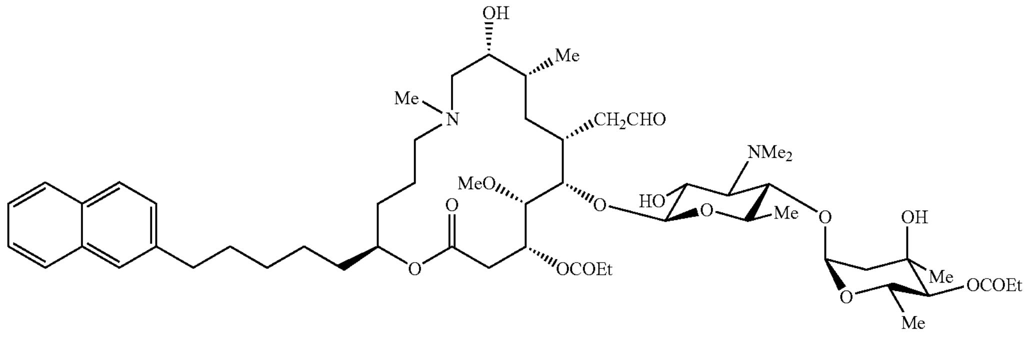

Example 138
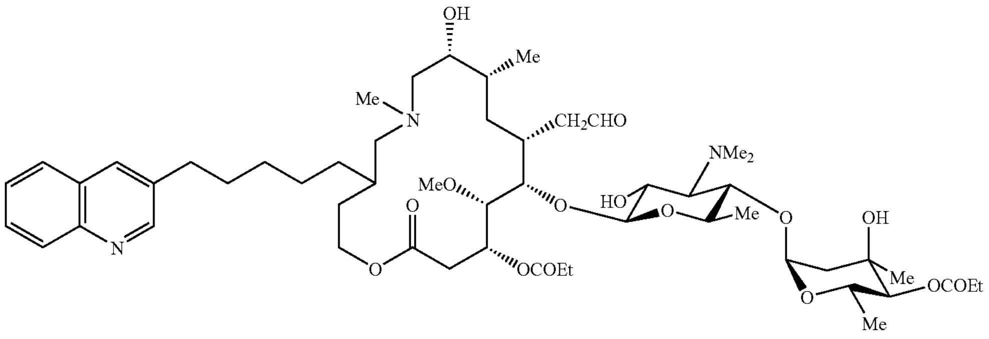
Example 139
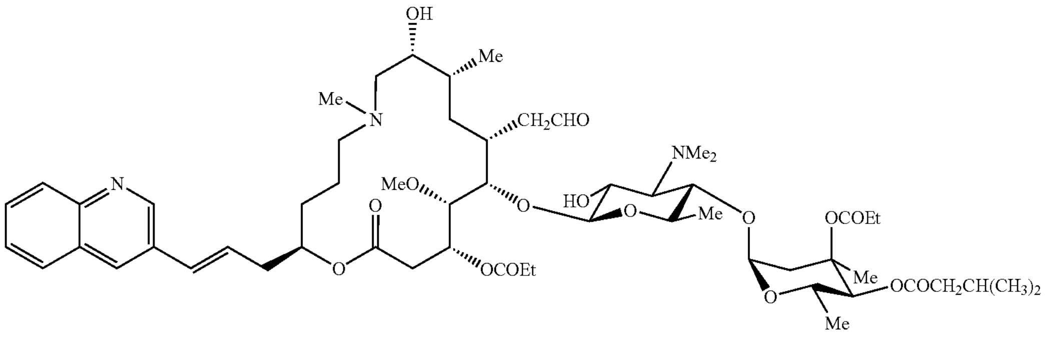
Example 140
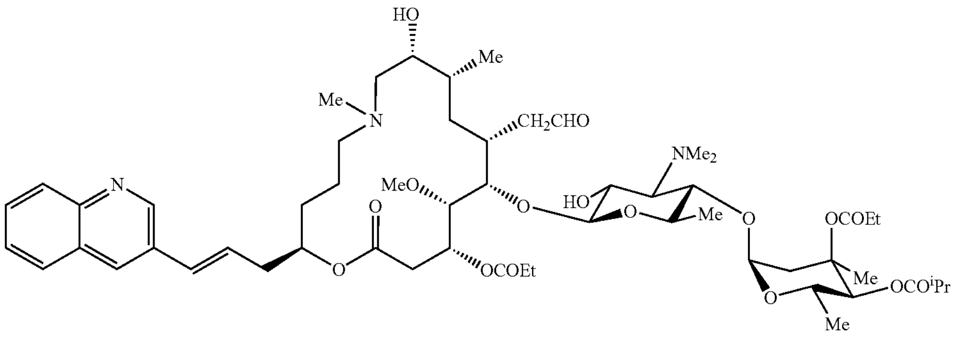

Example 141

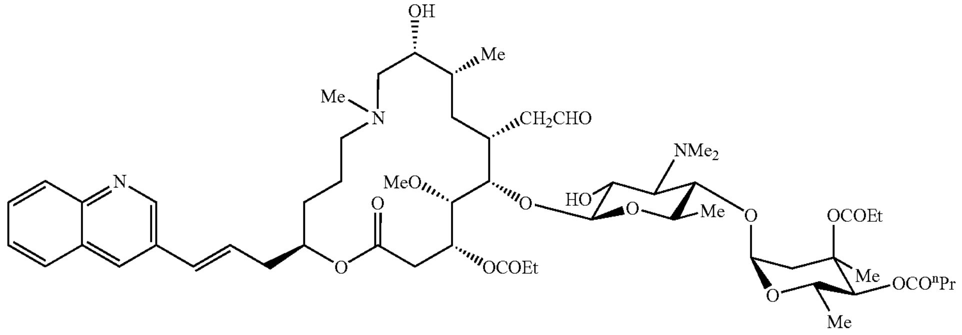

(Test Example) Antibacterial Activity Test

In vitro antibacterial activities of the compounds of Examples 13, 28, 35, 43, 53 to 55, 64, 70, 84, 90, 94, 95, 108, 128, and 129 were measured as follows by referring to the standard method of the Japanese Society of Chemotherapy (Chemotherapy, Vol. 29, pp. 76-79, 1981). The antibacterial activity of midecamycin (MDM) was similarly measured for comparison.

Using each solution of the test substance prepared in methanol at a concentration of 6400 μg/l, 2-fold serial dilutions were prepared by using methanol. Each of the prepared solutions of the test substances was put into a petri dish in a volume of 200 μl, added with 10 ml of agar medium for sensitivity measurement added with 5% horse sterile defibrinated blood, 15 μg/ml of β-nicotinamide-adenine dinucleotide, and 2.5 μg/ml of Hemin, and mixed for dilution to prepare an agar plate containing a test substance. A predetermined volume of a liquid medium for sensitivity measurement, prepared so as to contain a given number of test bactera, was inoculated on the agar plate containing a test substance by using a micro planter (Sakuma Seisakusho), and after the inoculation, the bacteria were cultured at 37° C. for about 20 hours. After the culture, presence or absence of growth of the test bacteria on the plate was observed by visual inspection, and the minimum concentration at which growth was not observed was determined as the minimum inhibitory concentration (MIC) of the test sustance. The results are shown in Table 2.

TABLE 1

| Test bacteria used for the experiments | |
|---|---|
| Test bacteria | Bacterium ID |
| *Staphylococcus aureus* 209P JC-1 | A |
| *Streptococcus pneumoniae* DP1 TypeI | B |
| *Streptococcus pneumoniae* IP692 | C |
| *Streptococcus pneumoniae* TH-662 | D |
| *Streptococcus pyogenes* Cook | E |
| *Moraxella catarrhalis* W-0506 | F |
| *Haemophilus influenzae* 9334 | G |

TABLE 2

| Minimum inhibitory concentration (MIC, μg/ml) | | | | | | | |
|---|---|---|---|---|---|---|---|
| Compound | A | B | C | D | E | F | G |
| MDM | 0.5 | 0.25 | 0.5 | >128 | 0.25 | 2 | 2 |
| Example 13 | 0.25 | 0.13 | 0.25 | 16 | 0.25 | 0.25 | 0.5 |
| Example 28 | 0.5 | 0.03 | 0.13 | 8 | 0.25 | 2 | 1 |
| Example 35 | 1 | 0.03 | 0.06 | 8 | 0.25 | 4 | 2 |
| Example 43 | 0.25 | 0.06 | 0.06 | 1 | 0.13 | 0.5 | 0.5 |
| Example 53 | 0.5 | 0.015 | 0.03 | 8 | 0.06 | 1 | 2 |
| Example 54 | 0.13 | 0.015 | 0.03 | 8 | 0.03 | 1 | NT |
| Example 55 | 0.5 | 0.03 | 0.03 | >128 | 0.06 | 0.25 | NT |
| Example 64 | 0.25 | 0.13 | 0.25 | 8 | 0.06 | 0.25 | 1 |
| Example 70 | 0.25 | 0.015 | 0.03 | 0.25 | 0.06 | 0.5 | 2 |
| Example 84 | 0.5 | 0.06 | 0.06 | 8 | 0.25 | 2 | 8 |
| Example 90 | 0.25 | 0.015 | 0.03 | 0.25 | 0.03 | 1 | 4 |
| Example 94 | 0.5 | 0.015 | 0.03 | 0.5 | 0.06 | 1 | 4 |
| Example 95 | 1 | 0.06 | 0.13 | 1 | 0.25 | 4 | 32 |
| Example 108 | 0.5 | 0.03 | 0.06 | 0.5 | 0.13 | 2 | 8 |
| Example 128 | 0.5 | 0.03 | 0.03 | 0.13 | 0.06 | 1 | 16 |
| Example 129 | 0.5 | 0.015 | 0.03 | 0.13 | 0.06 | 1 | 8 |

(Note)
Medium used: Blood agar medium using Sensitivity disk agar-N "Nissui" as a basal medium As for the antibacterial activities against gram positive bacteria, 2 to 16 times of improvements of antibacterial activities against the test bacteria B and C were observed for the compounds of Examples 13, 28, 35, 43, 53 to 55, 64, 70, 84, 90, 94, 95, 108, 128, and 129 as compared with MDM. The antibacterial activities of the compounds of Examples 13, 28, 35, 43, 53, 54, 64, 70, 84, 90, 94, 95, 108, 128, and 129 against the test bacterium D were improved 8 to 1024 times or more as compared with MDM.

As for the antibacterial activities against gram negative bacteria, the antibacterial activities against the test bacterium F of the compounds of Examples 13, 43, 53 to 55, 64, 70, 90, 94, 128, and 129 were improved 2 to 8 times as compared with MDM. The antibacterial activities against the test bacterium G of the compounds of Examples 13, 28, 43, and 64 were improved 2 to 4 times as compared with MDM.

INDUSTRIAL APPLICABILITY

The novel 14- to 16-membered ring azalide and 14- to 16-membered ring azalactam derivatives of the present invention have higher antibacterial activities against clinically important gram positive and gram negative bacteria than those of conventional antibacterial agents, and they are clinically highly useful as active ingredients of medicaments for prophylactic and/or therapeutic treatments of infectious diseases.

Further, by using the compounds of the present invention represented by the general formula (4), it becames possible to provide novel 14-, 15-, and 16-membered ring azalide and azalactam derivatives represented by the general formula (1), (2), or (3).

What is claimed is:

1. A compound represented by the following general formula (1) or a pharmaceutically acceptable salt thereof:

(1)

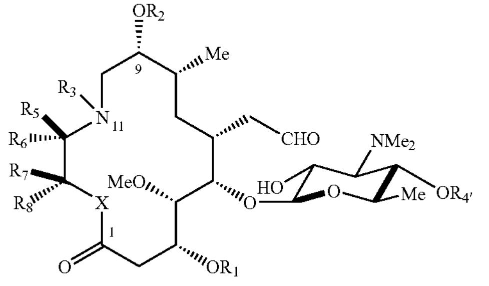

[wherein:

$R_1$ represents hydrogen atom, or a linear C1-6 alkylcarbonyl group, $R_2$ represents hydrogen atom, or a C1-6 alkylcarbonyl group, $R_3$ represents hydrogen atom, a C1-6 alkyl group, a C1-6 alkylcarbonyl group, a C1-6 alkenyl group, a C2-6 alkenylcarbonyl group, a C2-6 alkynyl group, or an Ar—B— group (wherein Ar represents an aryl group, or a heterocyclic group, and B represents a C1-6 alkyl group, a C1-6 alkylcarbonyl group, a C2-6 alkenyl group, a C2-6 alkenylcarbonyl group, or a C2-6 alkynyl group), $R_5$, $R_6$, $R_7$, and $R_8$ may be the same or different, and represent hydrogen atom, a C1-6 alkyl group, a C2-6 alkenyl group, a C2-6 alkynyl group, or an Ar—B'— group (wherein Ar has the same meaning as that defined above, and B' represents a C1-6 alkyl group, a C2-6 alkenyl group, or a C2-6 alkynyl group), X represents oxygen atom, or an —$NR_4$— group (wherein $R_4$ represents hydrogen atom, a C1-6 alkyl group, or a C1-6 alkyl group which may be substituted with an Ar group (wherein Ar has the same meaning as that defined above)), and $R_{4'}$ represents hydrogen atom, or a group represented by the following formula (a):

(a)

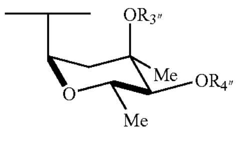

(wherein $R_{3''}$ and $R_{4''}$ may be the same or different, and represent hydrogen atom, or a linear or branched C1-6 alkylcarbonyl group)].

2. The compound or a pharmaceutically acceptable salt thereof according to claim 1, wherein $R_3$ represents a C1-6 alkyl group, a C2-6 alkenyl group, or an Ar—B— group (wherein Ar represents an aryl group, or a heterocyclic group, and B represents a C1-6 alkyl group, a C1-6 alkylcarbonyl group, a C2-6 alkenyl group, or a C2-6 alkenylcarbonyl group).

3. The compound or a pharmaceutically acceptable salt thereof according to claim 1, wherein $R_1$ is a linear C1-6 alkylcarbonyl group, $R_2$ is a C1-6 alkylcarbonyl group, $R_3$ is a C1-6 alkyl group, a C2-6 alkenyl group, or an Ar—B— group (wherein Ar represents an aryl group, or a heterocyclic group, and B represents a C1-6 alkyl group, a C1-6 alkylcarbonyl group, a C2-6 alkenyl group, or a C2-6 alkenylcarbonyl group), $R_5$ and $R_6$ are hydrogen atoms, one of $R_7$ and $R_8$ is hydrogen atom, the other is hydrogen atom, a C1-6 alkyl group, a C2-6 alkenyl group, a C2-6 alkynyl group, or an Ar—B'— group (wherein Ar has the same meaning as that defined above, and B' represents a C1-6 alkyl group, a C2-6 alkenyl group, or a C2-6 alkynyl group), X is oxygen atom, or an —$NR_4$— group (wherein $R_4$ represents hydrogen atom, a C1-6 alkyl group, or a C1-6 alkyl group which may be substituted with an Ar group (wherein Ar has the same meaning as that defined above)), and $R_{4'}$ is a group represented by the following formula (a)

(a)

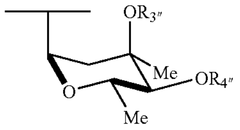

(wherein $R_{3''}$ and $R_{4''}$ may be the same or different, and represent hydrogen atom, or a linear or branched C1-6 alkylcarbonyl group).

4. The compound or a pharmaceutically acceptable salt thereof according to claim 1, wherein $R_3$ is methyl group, or 4-phenylbutyl group.

5. The compound or a pharmaceutically acceptable salt thereof according to claim 1, wherein $R_7$ and $R_8$ may be the same or different, and represent hydrogen atom, or methyl group.

6. The compound or a pharmaceutically acceptable salt thereof according to claim 1, wherein X is an —$NR_4$— group, and $R_4$ is hydrogen atom, methyl group, or 4-phenylbutyl group.

7. The compound or a pharmaceutically acceptable salt thereof according to claim 1, wherein X is oxygen atom.

8. The compound or a pharmaceutically acceptable salt thereof according to claim 1, wherein $R_3$ is methyl group, or 4-phenylbutyl group, $R_7$ and $R_8$ represent hydrogen atom, or methyl group, X is oxygen atom, or an —$NR_4$— group, and $R_4$ is hydrogen atom, methyl group, or 4-phenylbutyl group.

9. A compound represented by the following general formula (2) or a pharmaceutically acceptable salt thereof:

(2)

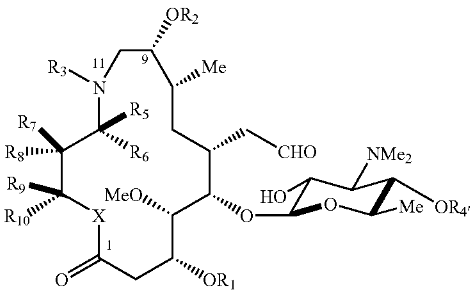

[wherein:

$R_1$ represents hydrogen atom, or a linear C1-6 alkylcarbonyl group, $R_2$ represents hydrogen atom, or a C1-6 alkylcarbonyl group, $R_3$ represents hydrogen atom, a C1-6 alkyl group, a C1-6 alkylcarbonyl group, a C2-6 alkenyl group, a C2-6 alkenylcarbonyl group, a C2-6 alkynyl group, or an Ar—B— group (wherein Ar represents an aryl group, or a heterocyclic group, and B represents a C1-6 alkyl group, a C1-6 alkylcarbonyl group, a C2-6 alkenyl group, a C2-6 alkenylcarbonyl group, or a C2-6 alkynyl group), $R_5$, $R_6$, $R_9$ and $R_{10}$ may be the same or different, and represent hydrogen atom, a C1-6 alkyl group, a C2-6 alkenyl group, a C2-6 alkynyl group, or an Ar—B'— group (wherein Ar has the same meaning as that defined above, and B' represents a C1-6 alkyl group, a C2-6 alkenyl group, or a C2-6 alkynyl group), $R_7$ and $R_8$ may be the same or different, and represent hydrogen atom, hydroxyl group, a C1-6 alkyl group, a C2-6 alkenyl group, a C2-6 alkynyl group, or an Ar—B'— group (wherein Ar has the same meaning as that defined above, and B' represents a C1-6 alkyl group, a C2-6 alkenyl group, or a C2-6 alkynyl group), X represents oxygen atom, or an —$NR_4$— group (wherein $R_4$ represents hydrogen atom, a C1-6 alkyl group, or an Ar—B"— group (wherein Ar has the same meaning as that defined above, and B" represents a C1-6 alkyl group)), and $R_{4'}$ represents hydrogen atom, or a group represented by the following formula (a)

(a)

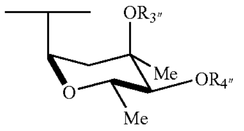

(wherein $R_{3''}$ and $R_{4''}$ may be the same or different, and represent hydrogen atom, or a linear or branched C1-6 alkylcarbonyl group), provided that a compound wherein X is oxygen atom, $R_5$, $R_6$, $R_7$, $R_8$ and $R_9$ are hydrogen atoms, and $R_{10}$ is methyl group is excluded].

10. The compound or a pharmaceutically acceptable salt thereof according to claim 9, wherein $R_3$ is a C1-6 alkyl group, a C2-6 alkenyl group, or an Ar—B— group (wherein Ar represents an aryl group, or a heterocyclic group, and B represents a C1-6 alkyl group, or a C2-6 alkenyl group), and $R_5$, $R_6$, $R_7$, $R_8$, $R_9$, and $R_{10}$ may be the same or different, and represent hydrogen atom, a C1-6 alkyl group, a C2-6 alkenyl group, or an Ar—B'— group (wherein Ar has the same meaning as that defined above, and B' represents a C1-6 alkyl group, or a C2-6 alkenyl group).

11. The compound or a pharmaceutically acceptable salt thereof according to claim 9, wherein $R_3$ is a C1-6 alkyl group, a C2-6 alkenyl group, or an Ar—B— group (wherein Ar represents an aryl group, or a heterocyclic group, and B represents a C1-6 alkyl group, or a C2-6 alkenyl group), $R_5$, $R_6$, $R_7$, and $R_8$ are hydrogen atoms, one of $R_9$ and $R_{10}$ is hydrogen atom, and the other is hydrogen atom, a C1-6 alkyl group, a C2-6 alkenyl group, or an Ar—B'— group (wherein Ar has the same meaning as that defined above, and B' represents a C1-6 alkyl group, or a C2-6 alkenyl group).

12. The compound or a pharmaceutically acceptable salt thereof according to claim 9, wherein $R_1$ is a linear C1-6 alkylcarbonyl group, $R_2$ is hydrogen atom, and $R_{3''}$ and $R_{4''}$ may be the same or different, and represent a linear or branched C1-6 alkylcarbonyl group.

13. The compound or a pharmaceutically acceptable salt thereof according to claim 9, wherein $R_1$ is a linear C1-6 alkylcarbonyl group, $R_2$ is hydrogen atom, $R_{3''}$ is hydrogen atom, and $R_{4''}$ is a linear or branched C1-6 alkylcarbonyl group.

14. The compound or a pharmaceutically acceptable salt thereof according to claim 9, wherein $R_1$, $R_2$, and $R_{3''}$ are hydrogen atoms, and $R_{4''}$ is hydrogen atom, or a linear or branched C1-6 alkylcarbonyl group.

15. The compound or a pharmaceutically acceptable salt thereof according to claim 9, wherein $R_{4'}$ is hydrogen atom.

16. The compound or a pharmaceutically acceptable salt thereof according to claim 9, wherein X is —NH— group.

17. The compound or a pharmaceutically acceptable salt thereof according to claim 9, wherein X is oxygen atom.

18. The compound or a pharmaceutically acceptable salt thereof according to claim 9, wherein $R_3$ is methyl group, 4-phenylbutyl group, or 3-(quinolin-4-yl)propyl group.

19. The compound or a pharmaceutically acceptable salt thereof according to claim 9, wherein one of $R_9$ and $R_{10}$ is hydrogen atom, and the other is hydrogen atom, methyl group, 3-(quinolin-4-yl)propyl group, trans-3-(quinolin-4-yl)-2-propenyl group, trans-3-(quinolin-4-yl)-1-propenyl group, 3-(quinolin-3-yl)propyl group, or trans-3-(quinolin-3-yl)-2-propenyl group.

20. The compound or a pharmaceutically acceptable salt thereof according to claim 9, wherein $R_3$ is methyl group, 4-phenylbutyl group, or 3-(quinolin-4-yl)propyl group, $R_5$, $R_6$, $R_7$, and $R_8$ are hydrogen atoms, one of $R_9$ and $R_{10}$ is hydrogen atom, the other is hydrogen atom, methyl group, 3-(quinolin-4-yl)propyl group, trans-3-(quinolin-4-yl)-2-propenyl group, trans-3-(quinolin-4-yl)-1-propenyl group, 3-(quinolin-3-yl)propyl group, or trans-3-(quinolin-3-yl)-2-propenyl group, and X is oxygen atom, or —NH— group.

21. A compound represented by the following general formula (3) or a pharmaceutically acceptable salt thereof:

(3)

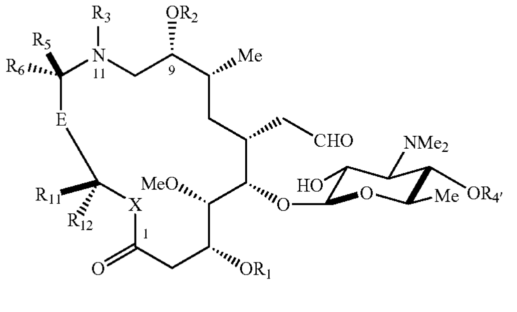

[wherein:

$R_1$ represents hydrogen atom, or a linear C1-6 alkylcarbonyl group, $R_2$ represents hydrogen atom, or acetyl group, $R_3$ represents hydrogen atom, a C1-6 alkyl group, a C1-6 alkylcarbonyl group, a C2-6 alkenyl group, a C2-6 alkenylcarbonyl group, a C2-6 alkynyl group, or an Ar—B— group (wherein Ar represents an aryl group, or a heterocyclic group, and B represents a C1-6 alkyl group, a C1-6 alkylcarbonyl group, a C2-6 alkenyl group, a C2-6 alkenylcarbonyl group, or a C2-6 alkynyl group), when E is a group represented by the following formula (b), (b)

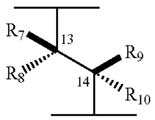

one of $R_5$, $R_6$, $R_7$, $R_8$, $R_9$, $R_{10}$, $R_{11}$ and $R_{12}$ represents hydrogen atom, a C1-6 alkyl group, a C2-6 alkenyl group, a C2-6 alkynyl group, or an Ar—B'— group (wherein Ar has the same meaning as that defined above, and B' represents a C1-6 alkyl group, a C2-6 alkenyl group, or a C2-6 alkynyl group), another represents hydrogen atom, hydroxyl group, or a C1-6 alkyl group, and all the remaining groups represent hydrogen atom, when E is a group represented by the following formula (c), (c)

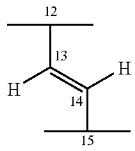

one of $R_5$, $R_6$, $R_{11}$ and $R_{12}$ represents hydrogen atom, a C1-6 alkyl group, a C2-6 alkenyl group, a C2-6 alkynyl group, or an Ar—B'— group (wherein Ar has the same meaning as that defined above, and B' represents a C1-6 alkyl group, a C2-6 alkenyl group, or a C2-6 alkynyl group), another represents hydrogen atom, or a C1-6 alkyl group, and all the remaining groups represent hydrogen atom, X represents oxygen atom, or an —$NR_4$— group (wherein $R_4$ represents hydrogen atom, a C1-6 alkyl group, or Ar—B"— group (wherein Ar has the same meaning as that defined above, and B" represents a C1-6 alkyl group)), and $R_{4'}$ represents hydrogen atom, or a group represented by the following formula (a)

(a)

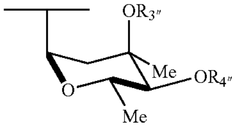

(wherein $R_{3''}$ and $R_{4''}$ may be the same or different, and represent hydrogen atom, or a linear or branched C1-6 alkylcarbonyl group)].

22. The compound or a pharmaceutically acceptable salt thereof according to claim 21, wherein $R_3$ is a C1-6 alkyl group, a C2-6 alkenyl group, or an Ar—B— group (wherein Ar represents an aryl group, or a heterocyclic group, and B represents a C1-6 alkyl group, or a C2-6 alkenyl group), when E is a group represented by the following formula (b), (b)

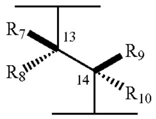

one of $R_5$, $R_6$, $R_7$, $R_8$, $R_9$, $R_{10}$, $R_{11}$ and $R_{12}$ is hydrogen atom, a C1-6 alkyl group, a C2-6 alkenyl group, or an Ar—B'— group (wherein Ar has the same meaning as that defined above, and B' represents a C1-6 alkyl group, a C2-6 alkenyl group, or a C2-6 alkynyl group), another is hydrogen atom, or a C1-6 alkyl group, and all the remaining groups are hydrogen atoms, and when E is a group represented by the following formula (c), (c)

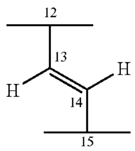

one of $R_5$, $R_6$, $R_{11}$ and $R_{12}$ is hydrogen atom, a C1-6 alkyl group, a C2-6 alkenyl group, or an Ar—B'— group (wherein Ar has the same meaning as that defined above, and B' represents a C1-6 alkyl group, or a C2-6 alkenyl group), another is hydrogen atom, or a C1-6 alkyl group, and all the remaining groups are hydrogen atoms.

23. The compound or a pharmaceutically acceptable salt thereof according to claim 21, wherein E is a group represented by the following formula (b), (b)

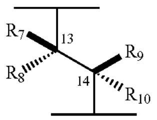

$R_5$, $R_6$, $R_9$, $R_{10}$, $R_{11}$ and $R_{12}$ are hydrogen atoms, one of $R_7$ and $R_8$ represents hydrogen atom, a C1-6 alkyl group, a C2-6 alkenyl group, or an Ar—B'— group (wherein Ar has the same meaning as that defined above, and B' represents a C1-6 alkyl group, or a C2-6 alkenyl group), and all the remaining groups are hydrogen atoms.

24. The compound or a pharmaceutically acceptable salt thereof according to claim 21, wherein E is a group represented by the following formula (b), (b)

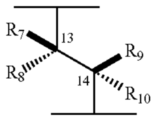

$R_5$, $R_6$, $R_7$, $R_8$, $R_9$ and $R_{10}$ are hydrogen atoms, one of $R_{11}$ and $R_{12}$ is hydrogen atom, a C1-6 alkyl group, a C2-6 alkenyl group, or an Ar—B'— group (wherein Ar has the same meaning as that defined above, and B' represents a C1-6 alkyl group, a C2-6 alkenyl group, or a C2-6 alkynyl group), and the other is hydrogen atom.

25. The compound or a pharmaceutically acceptable salt thereof according to claim 21, wherein E is a group represented by the following formula (c), (c)

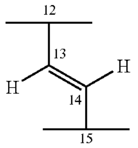

$R_5$ and $R_6$ are hydrogen atoms, one of $R_{11}$ and $R_{12}$ is hydrogen atom, a C1-6 alkyl group, a C2-6 alkenyl group, or an Ar—B'— group (wherein Ar has the same meaning as that defined above, and B' represents a C1-6 alkyl group, or a C2-6 alkenyl group), and the other is hydrogen atom.

26. The compound or a pharmaceutically acceptable salt thereof according to claim 21, wherein $R_1$ is a linear C1-6 alkylcarbonyl group, $R_2$ is hydrogen atom, or acetyl group, and $R_{3''}$ and $R_{4''}$ may be the same or different, and represent a linear or branched C1-6 alkylcarbonyl group.

27. The compound or a pharmaceutically acceptable salt thereof according to claim 21, wherein $R_1$ is a linear C1-6 alkylcarbonyl group, $R_2$ is hydrogen atom, or acetyl group, $R_{3''}$ is hydrogen atom, and $R_{4'}$ is a linear or branched C1-6 alkylcarbonyl group.

28. The compound or a pharmaceutically acceptable salt thereof according to claim 21, wherein $R_1$, $R_2$ and $R_{3''}$ are hydrogen atoms, and $R_{4''}$ is hydrogen atom, or a linear or branched C1-6 alkylcarbonyl group.

29. The compound or a pharmaceutically acceptable salt thereof according to claim 21, wherein $R_1$ is hydrogen atom, $R_2$ is hydrogen atom, or acetyl group, and $R_{3''}$ and $R_{4''}$ may be the same or different, and represent hydrogen atom, or a linear or branched C1-6 alkylcarbonyl group.

30. The compound or a pharmaceutically acceptable salt thereof according to claim 21, wherein $R_{4'}$ is hydrogen atom.

31. The compound or a pharmaceutically acceptable salt thereof according to claim 21, wherein X is —NH— group.

32. The compound or a pharmaceutically acceptable salt thereof according to claim 21, wherein X is oxygen atom.

33. The compound or a pharmaceutically acceptable salt thereof according to claim 21, wherein $R_3$ is methyl group, 4-phenylbutyl group, or 3-(quinolin-4-yl)propyl group.

34. The compound or a pharmaceutically acceptable salt thereof according to claim 21, wherein one of $R_7$ and $R_8$ is hydrogen atom, and the other is hydrogen atom, 3-(quinolin-4-yl)propyl group, trans-3-(quinolin-4-yl)-1-propenyl group, cis-3-(quinolin-4-yl)-1-propenyl group, 3-(1-methyl-1,2,3,4-tetrahydroquinolin-4-yl)propyl group, trans-3-(quinolin-3-yl)-1-propenyl group, cis-3-(quinolin-3-yl)-1-propenyl group, trans-3-(quinolin-6-yl)-1-propenyl group, trans-3-(quinolin-8-yl)-1-propenyl group, trans-3-(isoquinolin-4-yl)-1-propenyl group, trans-3-(naphthalen-2-yl)-2-propenyl group, or 5-(quinolin-3-yl)pentyl group.

35. The compound or a pharmaceutically acceptable salt thereof according to claim 21, wherein one of $R_{11}$ and $R_{12}$ is hydrogen atom, and the other is hydrogen atom, methyl group, 2-propenyl group, 3-(quinolin-4-yl)propyl group, trans-3-(quinolin-4-yl)-2-propenyl group, 3-(quinolin-3-yl) propyl group, trans-3-(quinolin-3-yl)-2-propenyl group, trans-3-(quinolin-6-yl)-2-propenyl group, trans-3-(pyridin-3-yl)-2-propenyl group, trans-3-(naphthalen-2-yl)-2-propenyl group, trans-3-phenyl-2-propenyl group, trans-3-(naphthalen-1-yl)-2-propenyl group, trans-3-(2-fluoro-4-((R)-5-(hydroxymethyl)oxazolidin-2-on-3-yl)phenyl)-2-propenyl group, trans-3-(6-nitroquinolin-3-yl)-2-propenyl group, trans-3-(6-cyanoquinolin-3-yl)-2-propenyl group, trans-3-(1,8-naphthyridin-3-yl)-2-propenyl group, trans-3-(phenanthren-9-yl)-2-propenyl group, trans-3-(benzothiophen-3-yl)-2-propenyl group, trans-3-(benzo[c][1,2,5]oxadiazol-5-yl)-2-propenyl group, trans-3-(4-(1H-pyrazol-1-yl)phenyl)-2-propenyl group, trans-3-(2-fluoro-4-(1H-tetrazol-1-yl) phenyl)-2-propenyl group, trans-3-(4-(isoxazol-5-yl) phenyl)-2-propenyl group, trans-3-(4-(pyridin-3-yl)phenyl)-2-propenyl group, trans-3-(4-(pyridin-4-yl)phenyl)-2-propenyl group, trans-3-(4-(pyridin-2-yl)phenyl)-2-propenyl group, trans-3-(4-fluoro-3-(1H-pyrazol-1-yl) phenyl)-2-propenyl group, trans-3-(3-(2-methylthiazol-4-yl) phenyl)-2-propenyl group, trans-3-(3-biphenyl)-2-propenyl group, trans-3-(3-(pyridin-3-yl)phenyl)-2-propenyl group, trans-3-(3-(pyridin-4-yl)phenyl)-2-propenyl group, trans-3-(3-(1H-imidazol-1-yl)phenyl)-2-propenyl group, trans-3-(3-(pyrimidin-5-yl)phenyl)-2-propenyl group, trans-3-(5-phenylpyridin-3-yl)-2-propenyl group, trans-3-(3-(1H-1,2,4-triazol-1-yl)phenyl)-2-propenyl group, trans-3-(3-(pyridin-2-yl)phenyl)-2-propenyl group, trans-3-(5-(pyridin-3-yl) pyridin-3-yl)-2-propenyl group, trans-3-(2-(pyridin-3-yl) phenyl)-2-propenyl group, trans-3-(4-(4-morpholinesulfonyl)phenyl)-2-propenyl group, trans-3-(4-(6-methylpyridazin-3-yloxy)phenyl)-2-propenyl group, trans-3-(5-benzoylpyridin-3-yl)-2-propenyl group, trans-3-(5-phenoxypyridin-3-yl)-2-propenyl group, trans-3-(5-phenylthiopyridin-3-yl)-2-propenyl group, trans-3-(5-phenylaminopyridin-3-yl)-2-propenyl group, trans-3-(3-cyano-4-fluorophenyl)-2-propenyl group, trans-3-(4-hydroxyphenyl)-2-propenyl group, trans-3-(5-aminocarbonylpyridin-3-yl)-2-propenyl group, trans-3-(5-diethylaminocarbonylpyridin-3-yl)-2-propenyl group, trans-3-(5-(N,O-dimethylhydroxyaminocarbonyl)pyridin-3-yl)-2-propenyl group, trans-3-(isoquinolin-4-yl)-2-propenyl group, 3-(naphthalen-2-yl)-2-propynyl group, 3-(quinolin-3-yl)-2-propynyl group, cis-3-(quinolin-3-yl)-2-propenyl group, 2-(quinolin-3-yl)ethyl group, 4-(quinolin-3-yl)butyl group, 4-(naphthalen-2-yl)butyl group, 5-(quinolin-3-yl) pentyl group, or 5-(naphthalen-2-yl)pentyl group.

36. The compound or a pharmaceutically acceptable salt thereof according to claim 21, wherein $R_3$ is methyl group, 4-phenylbutyl group, or 3-(quinolin-4-yl)propyl group, $R_5$ and $R_6$ are hydrogen atoms, $R_7$ and $R_8$ represent hydrogen atom, 3-(quinolin-4-yl)propyl group, trans-3-(quinolin-4-yl)-1-propenyl group, cis-3-(quinolin-4-yl)-1-propenyl group, 3-(1-methyl-1,2,3,4-tetrahydroquinolin-4-yl)propyl group, trans-3-(quinolin-3-yl)-1-propenyl group, cis-3-(quinolin-3-yl)-1-propenyl group, trans-3-(quinolin-6-yl)-1-propenyl group, trans-3-(quinolin-8-yl)-1-propenyl group, trans-3-(isoquinolin-4-yl)-1-propenyl group, trans-3-(naphthalen-2-yl)-2-propenyl group, or 5-(quinolin-3-yl)pentyl group, $R_9$ and $R_{10}$ are hydrogen atoms, $R_{11}$, and $R_{12}$ represents hydrogen atom, methyl group, 2-propenyl group, 3-(quinolin-4-yl)propyl group, trans-3-(quinolin-4-yl)-2-propenyl group, 3-(quinolin-3-yl)propyl group, trans-3-(quinolin-3-yl)-2-propenyl group, trans-3-(quinolin-6-yl)-2-propenyl group, trans-3-(pyridin-3-yl)-2-propenyl group, trans-3-(naphthalen-2-yl)-2-propenyl group, trans-3-phenyl-2-propenyl group, trans-3-(naphthalen-1-yl)-2-propenyl group, trans-3-(2-fluoro-4-((R)-5-(hydroxymethyl)oxazolidin-2-on-3-yl)phenyl)-2-propenyl group, trans-3-(6-nitroquinolin-3-yl)-2-propenyl group, trans-3-(6-cyanoquinolin-3-yl)-2-propenyl group, trans-3-(1,8-naphthyridin-3-yl)-2-propenyl group, trans-3-(phenanthren-9-yl)-2-propenyl group, trans-3-(benzothiophen-3-yl)-2-propenyl group, trans-3-(benzo[c][1,2,5]oxadiazol-5-yl)-2-propenyl group, trans-3-(4-(1H-pyrazol-1-yl)phenyl)-2-propenyl group, trans-3-(2-fluoro-4-(1H-tetrazol-1-yl)phenyl)-2-propenyl group, trans-3-(4-(isoxazol-5-yl)phenyl)-2-propenyl group, trans-3-(4-(pyridin-3-yl)phenyl)-2-propenyl group, trans-3-(4-(pyridin-4-yl)phenyl)-2-propenyl group, trans-3-(4-(pyridin-2-yl)phenyl)-2-propenyl group, trans-3-(4-fluoro-3-(1H-pyrazol-1-yl)phenyl)-2-propenyl group, trans-3-(3-(2-methylthiazol-4-yl)phenyl)-2-propenyl group, trans-3-(3-biphenyl)-2-propenyl group, trans-3-(3-(pyridin-3-yl) phenyl)-2-propenyl group, trans-3-(3-(pyridin-4-yl)phenyl)-2-propenyl group, trans-3-(3-(1H-imidazol-1-yl)phenyl)-2-propenyl group, trans-3-(3-(pyrimidin-5-yl)phenyl)-2-propenyl group, trans-3-(5-phenylpyridin-3-yl)-2-propenyl group, trans-3-(3-(1H-1,2,4-triazol-1-yl)phenyl)-2-propenyl group, trans-3-(3-(pyridin-2-yl)phenyl)-2-propenyl group, trans-3-(5-(pyridin-3-yl)pyridin-3-yl)-2-propenyl group, trans-3-(2-(pyridin-3-yl)phenyl)-2-propenyl group, trans-3-(4-(4-morpholinesulfonyl)phenyl)-2-propenyl group, trans-3-(4-(6-methylpyridazin-3-yloxy)phenyl)-2-propenyl group, trans-3-(5-benzoylpyridin-3-yl)-2-propenyl group, trans-3-(5-phenoxypyridin-3-yl)-2-propenyl group, trans-3-(5-phenylthiopyridin-3-yl)-2-propenyl group, trans-3-(5-phenylaminopyridin-3-yl)-2-propenyl group, trans-3-(3-cyano-4-fluorophenyl)-2-propenyl group, trans-3-(4-hydroxyphenyl)-2-propenyl group, trans-3-(5-aminocarbonylpyridin-3-yl)-2-propenyl group, trans-3-(5-diethylaminocarbonylpyridin-3-yl)-2-propenyl group, trans-3-(5-(N,O-dimethylhydroxyaminocarbonyl)pyridin-3-yl)-2-propenyl group, trans-3-(isoquinolin-4-yl)-2-propenyl group, 3-(naphthalen-2-yl)-2-propynyl group, 3-(quinolin-3-yl)-2-propynyl group, cis-3-(quinolin-3-yl)-2-propenyl group, 2-(quinolin-3-yl)ethyl group, 4-(quinolin-3-yl)butyl group, 4-(naphthalen-2-yl)butyl group, 5-(quinolin-3-yl) pentyl group, or 5-(naphthalen-2-yl)pentyl group, and X is oxygen atom, or —NH— group.

37. A compound represented by the following general formula (4) or a pharmaceutically acceptable salt thereof:

(4)

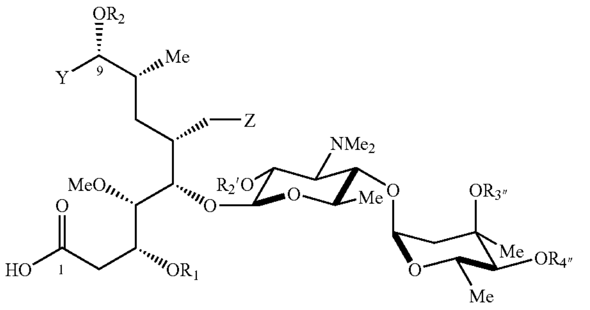

[wherein:

$R_1$ represents hydrogen atom, or a linear C1-6 alkylcarbonyl group, $R_2$ represents hydrogen atom, a C1-6 alkylcarbonyl group, or a silyl type protective group, $R_{3''}$ and $R_{4'}$ may be the same or different, and represent hydrogen atom, or a linear or branched C1-6 alkylcarbonyl group, $R_{2'}$ represents hydrogen atom, a linear C1-6 alkylcarbonyl group, a silyl type protective group, or benzyloxycarbonyl group, Z represents a —$CH(OR_{13})_2$ group (wherein $R_{13}$ represents a C1-6 alkyl group), or a group represented by the following formula (d)

(d)

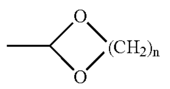

(wherein n represents an integer of 2 or 3), and

Y represents formyl group, or hydroxymethyl group].

38. The compound or a pharmaceutically acceptable salt thereof according to claim 37, wherein $R_2$ is a C1-6 alkylcarbonyl group, $R_{2'}$ is hydrogen atom, or a linear C1-6 alkylcarbonyl group, Z is —$CH(OCH_3)_2$ group, and Y is formyl group.

39. A method for producing the compound or a pharmaceutically acceptable salt thereof according to claim 1, which comprises cyclizing a compound represented by the following general formula (4) or a pharmaceutically acceptable salt thereof:

(4)

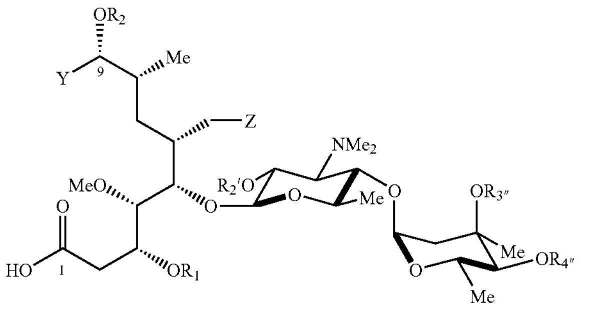

[wherein:

$R_1$ represents hydrogen atom, or a linear C1-6 alkylcarbonyl group, $R_2$ represents hydrogen atom, a C1-6 alkylcarbonyl group, or a silyl type protective group, $R_{3''}$ and $R_{4''}$ may be the same or different, and represent hydrogen atom, or a linear or branched C1-6 alkylcarbonyl group, $R_{2'}$ represents hydrogen atom, a linear C1-6 alkylcarbonyl group, a silyl type protective group, or benzyloxycarbonyl group, Z represents a —$CH(OR_{13})_2$ group (wherein $R_{13}$ represents a C1-6 alkyl group), or a group represented by the following formula (d)

(d)

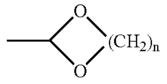

(wherein n represents an integer of 2 or 3), and

Y represents formyl group, or hydroxymethyl group].

40. A medicament comprising the compound or a pharmaceutically acceptable salt thereof according to claim 1 as an active ingredient.

41. The method according to claim 39, wherein $R_2$ is a C1-6 alkylcarbonyl group, $R_{2'}$ is hydrogen atom, or a linear C1-6 alkylcarbonyl group, Z is —$CH(OCH_3)_2$ group, and Y is formyl group.

* * * * *